(12) United States Patent
Narayanan et al.

(10) Patent No.: US 11,648,234 B2
(45) Date of Patent: *May 16, 2023

(54) SELECTIVE ANDROGEN RECEPTOR DEGRADER (SARD) LIGANDS AND METHODS OF USE

(71) Applicant: University of Tennessee Research Foundation, Knoxville, TN (US)

(72) Inventors: Ramesh Narayanan, Cordova, TN (US); Duane D. Miller, Collierville, TN (US); Thamarai Ponnusamy, Memphis, TN (US); Dong-Jin Hwang, Arlington, TN (US); Yali He, Germantown, TN (US)

(73) Assignee: University of Tennessee Research Foundation, Knoxville, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/007,143

(22) Filed: Aug. 31, 2020

(65) Prior Publication Data

US 2021/0161864 A1 Jun. 3, 2021

Related U.S. Application Data

(63) Continuation of application No. 15/981,892, filed on May 16, 2018, now Pat. No. 10,806,720, which is a continuation-in-part of application No. 15/331,777, filed on Oct. 21, 2016, now Pat. No. 10,035,763, which is a continuation-in-part of application No. 15/222,734, filed on Jul. 28, 2016, now Pat. No. 10,017,471, which is a continuation-in-part of application No. 15/135,334, filed on Apr. 21, 2016, now Pat. No. 9,814,698, said application No. 15/981,892 is a continuation-in-part of application No. 15/923,668, filed on Mar. 16, 2018, now Pat. No. 10,654,809, which is a continuation-in-part of application No. 15/620,761, filed on Jun. 12, 2017, now Pat. No. 10,314,797, said application No. 15/981,892 is a continuation-in-part of application No. 15/830,688, filed on Dec. 4, 2017, now Pat. No. 10,093,613, which is a continuation-in-part of application No. 15/331,751, filed on Oct. 21, 2016, now Pat. No. 9,834,507, which is a continuation-in-part of application No. 15/135,151, filed on Apr. 21, 2016, now Pat. No. 9,815,776.

(60) Provisional application No. 62/150,768, filed on Apr. 21, 2015, provisional application No. 62/241,532, filed on Oct. 14, 2015, provisional application No. 62/220,187, filed on Sep. 17, 2015, provisional application No. 62/219,859, filed on Sep. 17, 2015, provisional application No. 62/348,474, filed on Jun. 10, 2016, provisional application No. 62/455,397, filed on Feb. 6, 2017, provisional application No.

(Continued)

(51) Int. Cl.
| | |
|---|---|
| A61K 31/4164 | (2006.01) |
| A61K 31/40 | (2006.01) |
| A61K 31/415 | (2006.01) |
| A61P 35/00 | (2006.01) |
| A61K 31/4196 | (2006.01) |
| A61K 31/4439 | (2006.01) |
| A61K 31/5375 | (2006.01) |

(52) U.S. Cl.
CPC .......... *A61K 31/4164* (2013.01); *A61K 31/40* (2013.01); *A61K 31/415* (2013.01); *A61K 31/4196* (2013.01); *A61K 31/4439* (2013.01); *A61K 31/5375* (2013.01); *A61P 35/00* (2018.01)

(58) Field of Classification Search
CPC .. A61K 31/4164; A61K 31/40; A61K 31/415; A61K 31/4196; A61K 31/4439; A61K 31/5375; A61P 35/00
See application file for complete search history.

(56) References Cited

U.S. PATENT DOCUMENTS

| | | | |
|---|---|---|---|
| 5,480,656 | A | 1/1996 | Okada et al. |
| 5,575,987 | A | 11/1996 | Kamei et al. |

(Continued)

FOREIGN PATENT DOCUMENTS

| | | |
|---|---|---|
| CN | 1597662 A | 3/2005 |
| CN | 102884057 A | 1/2013 |

(Continued)

OTHER PUBLICATIONS

Aggarwal et al. "Androgens affect muscle, motor neuron, and survival in a mouse model of SOD1-related amyotrophic lateral sclerosis". Neurobiology of aging. Aug. 1, 2014;35(8):1929-38.

(Continued)

*Primary Examiner* — D Margaret M Seaman
(74) *Attorney, Agent, or Firm* — Knobbe, Martens, Olson & Bear, LLP

(57) ABSTRACT

This invention is directed to selective androgen receptor degrader (SARD) compounds pharmaceutical compositions and uses thereof in treating early prostate cancer, prostate cancer, advanced prostate cancer, castration resistant prostate cancer, triple negative breast cancer, other cancers expressing the androgen receptor, androgenic alopecia or other hyperandrogenic dermal diseases, Kennedy's disease, amyotrophic lateral sclerosis (ALS), abdominal aortic aneurysm (AAA), and uterine fibroids, and to methods for reducing the levels of androgen receptor-full length (AR-FL) including pathogenic or resistance mutations, AR-splice variants (AR-SV), and pathogenic polyglutamine (polyQ) polymorphisms of AR in a subject.

15 Claims, 149 Drawing Sheets

Related U.S. Application Data

62/482,036, filed on Apr. 5, 2017, provisional application No. 62/220,094, filed on Sep. 17, 2015, provisional application No. 62/150,768, filed on Apr. 21, 2015, provisional application No. 62/220,057, filed on Sep. 17, 2015.

(56) References Cited

U.S. PATENT DOCUMENTS

| | | | |
|---|---|---|---|
| 5,631,020 A | 5/1997 | Okada et al. | |
| 5,643,607 A | 7/1997 | Okada et al. | |
| 5,716,640 A | 2/1998 | Kamei et al. | |
| 5,814,342 A | 9/1998 | Okada et al. | |
| 6,036,976 A | 3/2000 | Takechi et al. | |
| 6,472,415 B1 | 10/2002 | Sovak et al. | |
| 7,022,870 B2 | 4/2006 | Dalton et al. | |
| 7,118,552 B2 | 10/2006 | Shaw et al. | |
| 7,186,854 B2 | 3/2007 | Thijs et al. | |
| 7,220,247 B2 | 5/2007 | Shaw et al. | |
| 7,500,964 B2 | 3/2009 | Shaw et al. | |
| 7,741,371 B2 | 6/2010 | Dalton et al. | |
| 8,735,440 B2 | 5/2014 | McKnight et al. | |
| 9,550,742 B2 | 1/2017 | Marugan et al. | |
| 9,814,698 B2* | 11/2017 | Narayanan | A61K 31/403 |
| 9,815,776 B2 | 11/2017 | Narayanan et al. | |
| 9,834,507 B2 | 12/2017 | Narayanan et al. | |
| 10,017,471 B2* | 7/2018 | Narayanan | C07D 215/00 |
| 10,035,763 B2* | 7/2018 | Narayanan | C07D 235/06 |
| 10,093,613 B2 | 10/2018 | Narayanan et al. | |
| 10,314,797 B2 | 6/2019 | Narayanan et al. | |
| 10,441,570 B2* | 10/2019 | Narayanan | A61K 31/437 |
| 10,597,354 B2 | 3/2020 | Narayanan et al. | |
| 10,654,809 B2* | 5/2020 | Narayanan | C07D 207/34 |
| 10,806,719 B2 | 10/2020 | Narayanan et al. | |
| 10,806,720 B2* | 10/2020 | Narayanan | A61K 31/415 |
| 10,865,184 B2* | 12/2020 | Narayanan | C07D 217/04 |
| 11,230,523 B2 | 1/2022 | Narayanan et al. | |
| 11,230,531 B2 | 1/2022 | Narayanan et al. | |
| 11,273,147 B2* | 3/2022 | Narayanan | A61K 31/47 |
| 2005/0101657 A1 | 5/2005 | Furuya et al. | |
| 2006/0142387 A1 | 6/2006 | Cadilla et al. | |
| 2006/0160845 A1 | 7/2006 | Schlienger et al. | |
| 2006/0173037 A1 | 8/2006 | Schlienger et al. | |
| 2006/0241180 A1 | 10/2006 | Dalton et al. | |
| 2007/0049629 A1 | 3/2007 | Scanlan et al. | |
| 2007/0123512 A1 | 5/2007 | Ratilainen | |
| 2007/0123563 A1 | 5/2007 | Dalton et al. | |
| 2007/0173546 A1 | 7/2007 | Dalton et al. | |
| 2007/0265290 A1 | 11/2007 | Dalton et al. | |
| 2008/0293766 A1 | 11/2008 | Diamond et al. | |
| 2009/0042844 A1 | 2/2009 | Labrie et al. | |
| 2009/0060873 A1 | 3/2009 | Sporn et al. | |
| 2009/0142323 A1 | 6/2009 | Quarles et al. | |
| 2010/0227846 A1 | 9/2010 | Ito et al. | |
| 2010/0331418 A1 | 12/2010 | Koh et al. | |
| 2011/0028719 A1 | 2/2011 | Slon-Usakiewicz | |
| 2013/0116258 A1 | 5/2013 | Smith et al. | |
| 2013/0253035 A1 | 9/2013 | McDonnell et al. | |
| 2014/0018433 A1 | 1/2014 | Dalton et al. | |
| 2014/0094474 A1 | 4/2014 | Törmakängas et al. | |
| 2015/0331777 A1 | 11/2015 | Lvin | |
| 2016/0264540 A1 | 9/2016 | Wipf et al. | |
| 2017/0029370 A1 | 2/2017 | Narayanan et al. | |
| 2017/0095446 A1 | 4/2017 | Narayanan et al. | |
| 2017/0166526 A1 | 6/2017 | Narayanan et al. | |
| 2018/0028521 A1 | 2/2018 | Gottardis et al. | |
| 2018/0118663 A1 | 5/2018 | Narayanan et al. | |
| 2018/0271849 A1 | 9/2018 | Ge et al. | |
| 2018/0273487 A1 | 9/2018 | Narayanna et al. | |
| 2018/0360805 A1 | 12/2018 | Narayanan et al. | |
| 2020/0222365 A1 | 7/2020 | Narayanan et al. | |
| 2021/0024458 A1 | 1/2021 | Ponnusamy et al. | |
| 2021/0196678 A1 | 7/2021 | Narayanan et al. | |
| 2021/0253525 A1 | 8/2021 | Narayanan et al. | |
| 2021/0340122 A1 | 11/2021 | Narayanan et al. | |

FOREIGN PATENT DOCUMENTS

| | | |
|---|---|---|
| CN | 106551934 A | 9/2016 |
| EP | 0253503 | 1/1988 |
| EP | 0524781 A1 | 1/1993 |
| EP | 100172 A1 | 2/2004 |
| EP | 2159049 A1 | 3/2010 |
| JP | 2008526888 A | 7/2008 |
| WO | WO 2001/058855 A1 | 8/2001 |
| WO | WO 2002/016310 A | 2/2002 |
| WO | WO 2002/016310 A1 | 2/2002 |
| WO | WO 2002/046164 A1 | 6/2002 |
| WO | WO 2003/074473 A2 | 9/2003 |
| WO | WO 2003/106401 A1 | 12/2003 |
| WO | WO 2004/035737 A2 | 4/2004 |
| WO | WO 2004/035738 A2 | 4/2004 |
| WO | WO 2005/000794 A1 | 1/2005 |
| WO | WO 2005000794 A1 | 1/2005 |
| WO | WO 2005/094531 A2 | 10/2005 |
| WO | WO 2005/120477 A2 | 12/2005 |
| WO | WO 2006/014420 A1 | 2/2006 |
| WO | WO 2006/044359 A2 | 4/2006 |
| WO | WO 2007/005887 A2 | 1/2007 |
| WO | WO 2007/126988 A2 | 11/2007 |
| WO | WO 2008/011072 A2 | 1/2008 |
| WO | WO 2008/044033 A1 | 4/2008 |
| WO | WO 2008/076918 A2 | 6/2008 |
| WO | WO 2008/124000 A2 | 10/2008 |
| WO | WO 2008/137038 A1 | 11/2008 |
| WO | WO 2009/010480 A1 | 1/2009 |
| WO | WO 2009/069736 A1 | 6/2009 |
| WO | WO 2009/082437 A2 | 7/2009 |
| WO | WO 2012/007644 A1 | 1/2012 |
| WO | WO 2013/064681 A1 | 5/2013 |
| WO | WO 2014/113260 A1 | 7/2014 |
| WO | WO 2015/042297 A1 | 3/2015 |
| WO | WO 2017/214634 A1 | 12/2017 |

OTHER PUBLICATIONS

Andersen et al. "Regression of castrate-recurrent prostate cancer by a small-molecule inhibitor of the amino-terminus domain of the androgen receptor" Cancer cell. Jun. 15, 2010;17(6):535-46.

Antonarakis et al. "AR-V7 and resistance to enzalutamide and abiraterone in prostate cancer" New England Journal of Medicine. Sep. 11, 2014;371(11):1028-38.

Antonarakis et al. "Clinical significance of androgen receptor splice variant-7 mRNA detection in circulating tumor cells of men with metastatic castration-resistant prostate cancer treated with first-and second-line abiraterone and enzalutamide" Journal of Clinical Oncology. Apr. 6, 2017;35(19):2149-56.

Aradi et al. "DFTB+, a sparse matrix-based implementation of the DFTB method" The Journal of Physical Chemistry A. Jul. 5, 2007;111 (26):5678-84.

Attard et al. "Selective inhibition of CYP17 with abiraterone acetate is highly active in the treatment of castration-resistant prostate cancer" Journal of clinical oncology. May 26, 2009;27(23):3742-8.

Baek et al. "Ligand-specific allosteric regulation of coactivator functions of androgen receptor in prostate cancer cells" Proceedings of the National Academy of Sciences of the United States of America. Feb. 28, 2006;103(9):3100-5.

Baniahmad A. "Inhibition of the androgen receptor by antiandrogens in spinobulbar muscle atrophy" Journal of Molecular Neuroscience. Mar. 1, 2016;58(3):343-7.

Berrevoets et al. "Effects of antiandrogens on transformation and transcription activation of wild-type and mutated (LNCaP) androgen receptors" The Journal of steroid biochemistry and molecular biology. Dec. 31, 1993;46(6):731-6.

Bohl et al. "Structural basis for antagonism and resistance of bicalutamide in prostate cancer" Proceedings of the National Academy of Sciences. Apr. 26, 2005;102(17):6201-6.

Bohl et al. "A ligand-based approach to identify quantitative structure-activity relationships for the androgen receptor" Journal of medicinal chemistry. Jul. 15, 2004;47(15):3765.

(56) References Cited

OTHER PUBLICATIONS

Bohl et al. "Structural basis for accommodation of nonsteroidal ligands in the androgen receptor" Journal of Biological Chemistry. Nov. 11, 2005;280(45):37747-54.

Bratenko et al. "Polyfunctional pyrazoies. 3.* Synthesis of 3-(3-aryl-4-formyl-1-pyrazolyl) propionic acids and their amides" Chemistry of Heterocyclic Compounds. Oct. 1, 2004;40(10):1279-82.

Bryce et al. "Androgen receptor splice variant 7 in castration-resistant prostate cancer: Clinical considerations" International Journal of Urology. Aug. 1, 2016;23(8):646-53.

Claessens et al. "Diverse roles of androgen receptor (AR) domains in AR-mediated signaling" Nuclear receptor signaling. Jun. 27, 2008;6:e008.

Clegg et al. "ARN-509: a novel antiandrogen for prostate cancer treatment" Cancer research. Mar. 15, 2012;72(6):1494-503.

Cochrane et al. "Role of the androgen receptor in breast cancer and preclinicai analysis of enzalutamide" Breast Cancer Research. Feb. 2014;16(1):R7.

Dalvit et al. "Identification of compounds with binding affinity to proteins via magnetization transfer from bulk water" Journal of biomolecular NMR. Sep. 1, 2000;18(1):65-8.

Danquah et al. "Combination therapy of antiandrogen and XIAP inhibitor for treating advanced prostate cancer" Pharmaceutical research. Aug. 1, 2012;29(8):2079-91.

DATABASE Caplus Chemical Abstracts Service; Database Accession No. 2005:14358, Abstract of WO 2005000794, published Jan. 6, 2005.

Davis et al. "Pharmacologic blockade and genetic deletion of androgen receptor attenuates aortic aneurysm formation" Journal of vascular surgery. Jun. 1, 2016;63(6):1602-12.

Dehm et al. "Alternatively spliced androgen receptor variants" Endocrine-related cancer. Oct. 1, 2011;18(5):R183-96.

Dehm et al. "Splicing of a novel androgen receptor exon generates a constitutively active androgen receceotor that mediates prostate cancer therapy resistance" Cancer research. Jun. 1, 2008;68(13):5469-77.

De Bono et al. "Abiraterone and increased survival in metastatic prostate cancer" New England Journal of Medicine. May 26, 2011;364(21):1995-2005.

Dias et al. "NMR approaches in structure-based lead discovery: recent developments and new frontiers for targeting multi-protein complexes" Progress in biophysics and molecular biology. Nov. 1, 2014;116(2-3):101-12.

Duke III, Charles B., et al. "Synthesis and biological studies of androgen receptor ligands: Towards mutation-resistant nonsteroidal antagonism." Abstracts of Papers of the American Chemical Society. vol. 240.

Elstner et al. "Self-consistent-charge density-functional tight-binding method for simulations of complex materials properties" Physical Review B. Sep. 15, 1998;58(11):7260.

Epps et al. "Determination of the affinity of drugs toward serum albumin by measurement of the quenching of the intrinsic tryptophan fluorescence of the protein" Journal of pharmacy and pharmacology. Jan. 1999;51(1):41-8.

Gal et al. "Efficient isothermal titration calorimetry technique identifies direct interaction of small molecule inhibitors with the target protein" Combinatorial chemistry & high throughput screening. Jan. 1, 2016;19(1):4-13.

Galbiati et al. "The anabolic/androgenic steroid nandrolone exacerbates gene expression modifications induced by mutant SOD1 in muscles of mice models of amyotrophic lateral sclerosis". Pharmacological research. Feb. 1, 2012;65(2):221-30.

Hara et al. "Novel mutations of androgen receptor: a possible mechanism of bicalutamide withdrawal syndrome" Cancer research. Jan. 1, 2003;63(1):149-53.

Hsieh et al. "Androgen receptor trinucleotide polymorphism in leiomyoma" Journal of assisted reproduction and genetics. Dec. 1, 2004;21(12):453-7.

Hu et al. "Distinct transcriptional programs mediated by the ligand-dependent full-length androgen receptor and its splice variants in castration-resistant prostate cancer" Cancer research. Jul. 15, 2012;72(14):3457-62.

Hwang et al. "Arylisothiocyanato selective androgen receptor modulators (SARMs) for prostate cancer" Bioorganic & medicinal chemistry. Oct. 1, 2006;14(19):6525-38.

Joseph et al. "A clinically relevant androgen receptor mutation confers resistance to second-generation antiandrogens enzalutamide and ARN-509" Cancer discovery. Sep. 1, 2013;3(9):1020-9.

Jin, et al. "Synthesis and biological evaluation of 1-substituted-3(5)-(6-methylpyridin-2-yl)-4-(quinoxalin-6-yl) pyrazoies as transforming growth factor-β type 1 receptor kinase inhibitors." European Journal of Medicinal Chemistry vol. 19, 2633-2640, 2011.

Jin, et al. "Synthesis and biological evaluation of 1-substituted-3(5)-(6-methylpyridin-2-yl)-4-(quinoxalin-6-yl) pyrazoies as transforming growth factor-β type 1 receptor kinase inhibitors." European Journal of Medicinal Chemistry 46.9 (2011): 3917-3925.

Kanda et al. "Androgen receptor signaling in hepatocellular carcinoma and pancreatic cancers" World Journal of Gastroenterology: WJG. Jul. 28, 2014;20(28):9229.

Kawahara et al. "ELK1 is up-regulated by androgen in bladder cancer cells and promotes tumor progression" Oncotarget. Oct. 6, 2015;6(30):29860.

Klotz L. "Maximal androgen blockade for advanced prostate cancer" Best Practice & Research Clinical Endocrinology & Metabolism. Apr. 30, 2008;22(2):331-40.

Lallous et al. "Functional analysis of androgen receptor mutations that confer anti-androgen resistance identified in circulating cell-free DNA from prostate cancer patients" Genome biology. Dec. 2016;17(1):10.

La Spada et al. "Androgen receptor gene mutations in X-linked spinal and bulbar muscular atrophy" Nature. Jul. 1991;352(6330):77.

Li et al. "Androgen receptor splice variants mediate enzalutamide resistance in castration-resistant prostate cancer cell lines" Cancer research. Jan. 15, 2013;73(2):483-9.

Li et al. "On the physical origin of blue-shifted hydrogen bonds" Journal of the American Chemical Society. Aug. 14, 2002;124(32):9639-47.

Lieberman et al. "Peripheral androgen receptor gene suppression rescues disease in mouse models of spinal and bulbar muscular atrophy" Cell reports. May 8, 2014;7(3):774-84.

Locati et al. "Clinical activity of androgen deprivation therapy in patients with metastatic/relapsed androgen receptor-positive salivary gland cancers" Head & neck. May 1, 2016;38(5):724-31.

Marhefka et al. "Homology modeling using multiple molecular dynamics simulations and docking studies of the human androgen receptor ligand binding domain bound to testosterone and nonsteroidal ligands" Journal of medicinal chemistry. May 24, 2001;44(11):1729-40.

Marhefka et al. "Design, synthesis, and biological characterization of metabolically stable selective androgen receptor modulators" Journal of medicinal chemistry. Feb. 12, 2004;47(4):993.

McBeth et al. "Involvement of the androgen and glucocorticoid receptors in bladder cancer" International journal of endocrinology. 2015;2015.

McGinley et al. "Circumventing anti-androgen resistance by molecular design" Journal of the American Chemical Society. Apr. 4, 2007;129(13):3822-3.

Miller Irreversible Nonsteroida SARMs for Prostate Cancer at http://grantome.com/grant/NIH/R01-DK065227-20, 2003.

Miller et al. "Phase III, randomized, placebo-controlled study of once-daily oral zibotentan (ZD4054) in patients with non-metastatic castration-resistant prostate cancer" Prostate cancer and prostatic diseases. Jun. 2013;16(2):187.

Mitsiades N. "A road map to comprehensive androgen receptor axis targeting for castration-resistant prostate cancer" Cancer research. Aug. 1, 2013;73(15):4599-605.

Monge et al. "Unfaithfulness and promiscuity of a mutant androgen receptor in a hormone-refractory prostate cancer" Cellular and molecular life sciences. Feb. 1, 2006;63(4):487-97.

(56) References Cited

OTHER PUBLICATIONS

Nagata et al. "Preparation and reactions of cyclic α-monocarbonyl azo-compounds: 1-pyrazolin-3-one derivatives" Journal of the Chemical Society C: Organic. 1970(4):540-50.

Narayanan et al. "Selective androgen receptor modulators (SARMs) negatively regulate triple-negative breast cancer growth and epithelial: mesenchymal stem cell signaling" PloS one. Jul. 29, 2014;9(7):e103202.

Narayanan et al. "Biological synthesis of metal nanoparticles by microbes" advances in colloid and interface science. Apr. 22, 2010;156(1-2):1-3.

Nazareth et al. "Activation of the human androgen receptor through a protein kinase A signaling pathway" Journal of Biological Chemistry. Aug. 16, 1996;271(33):19900-7.

Nyquist et al. "TALEN-engineered AR gene rearrangements reveal endocrine uncoupling of androgen receptor in prostate cancer" Proceedings of the National Academy of Sciences. Oct. 22, 2013;110(43):17492-7.

PUBMED, CID 20221988, Dec. 5, 2007, pp. 1-11; retrieved from the Internet <URL: https://pubchem.ncbi.nlm.nih.gov/compound/20221988>; p. 3, formula.

Rawel et al. "Determining the binding affinities of phenolic compounds to proteins by quenching of the intrinsic tryptophan fluorescence" Molecular nutrition & food research. Aug. 2006;50(8):705-13.

Renier et al. "Antiandrogen flutamide protects male mice from androgen-dependent toxicity in three models of spinal bulbar muscular atrophy" Endocrinology. Jul. 1, 2014;155(7):2624-34.

Rosa et al. "Polymorphisms of CYP17A1, CYP19, and androgen in Brazilian women with uterine leiomyomas" Clinical chemistry and laboratory medicine. Jun. 1, 2008;46(6):814-23.

Rygula et al. "Raman spectroscopy of proteins: a review" Journal of Raman Spectroscopy. Aug. 2013;44(8):1061-76.

Sadar Md. "Androgen-independent induction of prostate-specific antigen gene expression via crosstalk between the androgen receptor and protein kinase A signal transduction pathways" Journal of Biological Chemistry. Mar. 19, 1999;274(12):7777-83.

Sadar et al. "Ligand-independent activation of the androgen receptor by the differentiation agent butyrate in human prostate cancer cells" Cancer research. Oct. 15, 2000;60(20):5825-31.

Sartor et al. "Androgen receptor variant-7: an important predictive biomarker in castrate resistant prostate cancer" Asian journal of andrology. May 2015;17(3):439.

Scher et al. "Increased survival with enzalutamide in prostate cancer after chemotherapy" New England Journal of Medicine. Sep. 27, 2012;367(13):1187-97.

Shortridge et al. "Estimating protein—ligand binding affinity using high-throughput screening by NMR" Journal of combinatorial chemistry. Oct. 3, 2008;10(6):948-58.

Sieber PR. "Treatment of bicalutamide-induced breast events" Expert review of anticancer therapy. Dec. 1, 2007;7(12):1773-9.

Siegel et al. "Cancer statistics" CA Cancer. J. Clin. 2014;64:9-29.

Sun et al. "Castration resistance in human prostate cancer is conferred by a frequently occurring androgen receptor splice variant" The Journal of clinical investigation. Aug. 2, 2010;120(8):2715-30.

Tan et al. "Dehydroepiandrosterone activates mutant androgen receptors expressed in the androgendependent human prostate cancer xenograft CWR22 and LNCaP cells" Molecular endocrinology. Apr. 1, 1997;11(4):450-9.

Tran et al. "Development of a second-generation antiandrogen for treatment of advanced prostate cancer" Science. May 8, 2009;324(5928):787-90.

Ueda et al. Ligand-independent activation of the androgen receptor by interleukin-6 and the role of steroid receptor coactivator-1 in prostate cancer cells: Journal of Biological Chemistry. Oct. 11, 2002;277(41):38087-94.

Wang et al. "Small molecule inhibition of the steroid receptor coactivators, SRC-3 and SRC-1" Molecular endocrinology. Dec. 1, 2011;25(12):2041-53.

Wang et al. "Effects of hydrogen bond and solvent polarity on the C=O stretching of bis (2-thienyl) ketone in solution" The Journal of chemical physics. Mar. 28, 2012;136(12):03B614.

Watson et al. "Constitutively active androgen receptor splice variants expressed in castration-resistant prostate cancer require full-length androgen receptor" Proceedings of the national academy of sciences. Sep. 28, 2010;107(39):16759-65.

Weiner LP. "Possible role of androgen receptors in amyotrophic lateral sclerosis: a hypothesis" Archives of neurology. Mar. 1, 1980;37(3):129-31.

Wen et al. "LHRH-conjugated micelles for targeted delivery of antiandrogen to treat advanced prostate cancer" Pharmaceutical research. Oct. 1, 2014 ;31(10):2784-95.

Wen et al. "Targeting fatty acid synthase with ASC-J9 suppresses proliferation and invasion of prostate cancer cells" Molecular carcinogenesis. Dec. 2016;55(12):2278-90.

West AR. "Solid state chemistry and its applications" John Wiley & Sons; 1988; pp. 358, 365.

Yamashita et al. "ASC-J9 suppresses castration-resistant prostate cancer growth through degradation of full-length and splice variant androgen receptors" Neoplasia. Jan. 1, 2012; 14(1):74IN9-83IN12.

Yepuru et al. "Steroidogenic enzyme AKR1C3 is a novel androgen receptor-selective coactivator that promotes prostate cancer growth" Clinical Cancer Research. Oct. 15, 2013;19(20):5613-25.

Yoshida et al. "Antiandrogen bicalutamide promotes tumor growth in a novel androgen-dependent prostate cancer xenograft model derived from a bicalutamide-treated patient" Cancer Research. Nov.1, 2005;65(21):9611-6.

Aggarwal et al., "Androgens affect muscle, motor neuron, and survival in a mouse model of SOD1-related amyotrophic lateral sclerosis," Neurobiol Aging, 2014, 35: 1929-1938.

Andersen et al., "Regression of castrate-recurrent prostate cancer by a small-molecule inhibitor of the amino-terminus domain of the androgen receptor," Cancer cell, Jun. 15, 2010; 17(6): 535-546.

Antonarakis et al., "AR-V7 and resistance to enzalutamide and abiraterone in prostate cancer," New England Journal of Medicine, Sep. 11, 2014; 371(11): 1028-1038.

Antonarakis et al., Clinical significance of androgen receptor splice variant-y mRNA detection in circulating tumor cells of men with metastatic castration-resistant prostate cancer treated with first-and second-line abiraterone and enzalutamide. J Clin Oncol., Jul. 1, 2017;35(19): 2149-2156.

Aradi et al., "DFTB+, a sparse matrix-based implementation of the DFTB method", J Phys Chem. A. Jul. 5, 2007;111(26): 5678-5684.

Attard et al., "Selective inhibition of CYP17 with abiraterone acetate is highly active in the treatment of castration-resistant prostate cancer," Journal of clinical oncology, May 26, 2009; 27(23); 3742-3748.

Baek et al., "Ligand-specific allosteric regulation of coactivator functions of androgen receptor in prostate cancer cells" Proceedings of the National Academy of Sciences of the United States of America, Feb. 28, 2006; 103(9); 3100-3105.

Baniahmad A., "Inhibition of the androgen receptor by antiandrogens in spinobulbar muscle atrophy", J Mol Neurosci. Mar. 2016;58(3): 343-347.

Berrevoets et al., "Effects of antiandrogens on transformation and transcription activation of wild-type and mutated (LNCaP) androgen receptors," The Journal of steroid biochemistry and molecular biology, Dec. 31, 1993; 46(6): 731-736.

Bohl et al., "Structural basis for antagonism and resistance of bicalutamide in prostate cancer," Proceedings of the National Academy of Sciences, Apr. 26, 2005; 102(17): 6201-6206.

Bohl et al., "A ligand-based approach to identify quantitative structure-activity relationships for the androgen receptor," J Med Chem., Jul. 15, 2004; 47(15): 3765-3776.

Bohl et al., "Structural basis for accommodation of nonsteroidal ligands in the androgen receptor," J Biol. Chem., Nov. 11, 2005; 280(45): 37747-37754.

Bratenko et al., "Polyfunctional pyrazoles. 3.* Synthesis of 3-(3-aryl-4-formyl-1-pyrazolyl) propionic acids and their amides", Chem Heter Compounds. Oct. 2004;40(10): 1279-1282.

(56) References Cited

OTHER PUBLICATIONS

Bryce et al., "Androgen receptor splice variant 7 in castration-resistant prostate cancer: Clinical considerations", Int J Urology. Aug. 2016;23(8): 646-653.
Claessens et al., "Diverse roles of androgen receptor (AR) domains in AR-mediated signaling," J Nucl Recep Signal. Jun. 27, 2008; 6:e008 in 13 pages.
Clegg et al., "ARN-509: A novel antiandrogen for prostate cancer treatment," Cancer Res., Mar. 15, 2012; 72(6): 1494-1503.
Cochrane et al., "Role of the androgen receptor in breast cancer and preclinical analysis of enzalutamide", Breast Cancer Res. Feb. 2014;16(1): 1-9.
Dalvit et al., "Identification of compounds with binding affinity to proteins via magnetization transfer from bulk water", J Biomolecular NMR. Sep. 2000;18(1): 65-68.
Danquah et al., "Combination therapy of antiandrogen and XIAP inhibitor for treating advanced prostate cancer," Pharma Res., Aug. 1, 2012; 29(8): 2079-2091.
DATABASE Caplus Chemical Abstracts Service; Database Accession No. 2005:14358, Abstract of WO 2005000794, published, Jan. 6, 2005; in 9 pages.
Davis et al., "Pharmacologic blockade and genetic deletion of androgen receptor attenuates aortic aneurysm formation", J Vasc Surgery. Jun. 1, 2016;63(6): 1602-1612.
De Bono et al., "Abiraterone and increased survival in metastatic prostate cancer," N Eng J Med., May 26, 2011; 364(21): 1995-2005.
Dehm et al., "Alternatively spliced androgen receptor variants," Endocrine-related Cancer, Oct. 1, 2011; 18(5): R183-R196.
Dehm et al., "Splicing of a novel androgen receptor exon generates a constitutively active androgen receptor that mediates prostate cancer therapy resistance," Cancer Res., Jul. 1, 2008; 68(13): 5469-5477.
Dias et al., "NMR approaches in structure-based lead discovery: recent develpments and new frontiers for targeting multi-protein complexes", Prog Biophys Mol Biol. Nov. 1, 2014;116(2-3): 101-112.
Duke III, Charles B., et al., "Synthesis and biological studies of androgen receptor ligands: Towards mutation-resistant nonsteroidal antagonism," Abstract of Papers of the American Chemical Society, vol. 240, 1155; 16th St, NW, Washington, DC 20036 USA: Amer Chem Soc, 2010; 1 page.
Elstner et al., "Self-consistent-charge density-functional tight-binding method for simulations of complex materials properties", Phys Rev B. Sep. 15, 1998;58(11): 7260-7268.
Epps et al., "Determination of the affinity of drugs toward serum albumin by measurement of the quenching of the intrinsic tryptophan fluorescence of the protein", J Pharm Pharmacol. Jan. 1999;51(1): 41-48.
Gal et al., "Efficient isothermal titration calorimetry technique identifies direct interation of small molecule inhibitors with the target protein", Combin Chem High Throughput Screen. Jan. 1, 2016;19(1): 4-13.
Galbiati et al., "The anabolic/androgenic steroid nandrolone exacerbates gene expression modifications induced by mutant SOD1 in muscles of mice models of amyotrophic lateral sclerosis", Pharma Res. Feb. 1, 2012;65(2): 221-230.
Hara et al., "Novel mutations of androgen receptor: a possible mechanism of bicalutamide withdrawal syndrome", Cancer Res. Jan. 1, 2003;63(1): 149-153.
Hsieh et al., "Androgen receptor trinucleotide polymorphism in leiomyoma", J Ass Repro Genetics. Dec. 2004;21(12): 453-457.
Hu et al., "Distinct transcriptional programs mediated by the ligand-dependent full-length androgen receptor and its splice variants in castration-resistant prostate cancer," Cancer Res., Jul. 15, 2012;72(14): 3457-3462.
Hwang et al., "Arylisothiocyanato selective androgen receptor modulators (SARMs) for prostate cancer," Bioorg Med Chem., Oct. 1, 2006; 14(19): 6525-6538.

Jin et al., "Synthesis and biological evaluation of 1-substituted-3(5)-(6-methylpyridin-2-yl)-4-(quinoxalin-6-yl)pyrazoles as transforming growth factor-β type 1 receptor kinase inhibitors," Euro J Med Chem. (2011)46: 3917-3925.
Jin et al., "Synthesis and biological evaluation of 1-substituted-3(5)-(6-methylpyridin-2-yl)-4-(quinolin-6-yl)pyrazoles as transforming growth factor-β type 1 receptor kinase inhibitors", Bioorg Med Chem. 2011;19: 2633-2640.
Joseph et al., "A clinically relevant androgen receptor mutation confers resistance to second-generation antiandrogens enzalutamide and ARM-509", Cancer Discov. Sep. 1, 2013;3(9): 1020-1029.
Kanda et al., "Androgen receptor signaling in hepatocellular carcinoma and pancreatic cancers", World J Gastroenter.: WJG. Jul. 28, 2014;20(28): 9229-9236.
Kawahara et al., "ELK1 is up-regulated by androgen in bladder cancer cells and promotes tumor progression", Oncotarget. Oct. 6, 2015;6(30): 29860=29876.
Kim et al., "Ribosomal proteins as unrevealed caretakers for cellular stress and genomic instability," Oncotarget, Feb. 1, 2014; 5(4): 860-71.
Klotz L., "Maximal androgen blockade for advanced prostate cancer," Best Pract Res Clin Endocrin Metabol., Apr. 30, 2008; 22(2): 331-340.
Lallous et al., "Functional analysis of androgen receptor mutations that confer anti-androgen resistance identified in circulating cell-free DNA from prostate cancer patients", Gen Biol. Dec. 2016;17(1): 1-5.
La Spada et al., "Androgen receptor gene mutations in X-linked spinal and bulbar muscular atrophy", Nature. Jul. 1991;352(6330): 77-79.
Li et al., "On the physical origin of blue-shifted hydrogen bonds", J Am Chem Soc. Aug. 14, 2002;124(32): 9639-9647.
Li et al., "Androgen receptor splice variants mediate enzalutamide resistance in castration-resistant prostate cancer cell lines," Cancer Res., Jan. 15, 2012; 73(2): 483-489.
Lieberman et al., "Peripheral androgen receptor gene suppression rescues disease in mouse models of spinal and bulbar muscular atrophy", Cell Reports. May 8, 2014;7(3): 774-784.
Locati et al., "Clinical activity of androgen deprivation therapy in patients with metastatic/relapsed androgen receptor-positive salivary gland cancers", Head Neck. May 2016;38(5): 724-731.
MacLean et al., "Spinal and bulbar muscular atrophy: androgen receptor dysfunction caused by a trinucleotide repeat expansion," Journal of the neurological sciences, Feb. 29, 1996; 135(2): 149-57.
Marhefka et al., "Homology modeling using multiple molecular dynamics simulations and docking studies of the human androgen receptor ligand binding domain bound to testosterone and nonsteroidal ligands," J Med Chem., May 22, 2001; 44(11): 1729-1740.
Marhefka et al., "Design, synthesis, and biological characterization of metabolically stable selective androgen receptor modulators," J Med Chem., Feb. 12, 2004; 47(4): 993-998.
McBeth et al., "Involvement of the androgen and glucocorticoid receptors in bladder cancer", Int J Endocrin. Aug. 10, 2015;2015:Art. ID384860 in 10 pages.
McGinley et al., "Circumventing anti-androgen resistance by molecular design," J Am Chem Soc., Apr. 4, 2007; 129(13): 3822-3823.
Miller D.D., "Irreversible Nonsteroida SARMs for Prostate Cancer", Aug. 15, 2003;online at http://grantome.com/grant/NIH/R01-DK065227-20, 2003, 4 pages.
Miller et al., "Phase III, randomized, placebo-controlled study of once-daily oral zibotentan (ZD4054) in patients with non-metastatic castration-resistant prostate cancer", Prost Canc Prost Dis. Jun. 2013;16(2): 187-192.
Mitsiades N., "A road map to comprehensive androgen receptor axis targeting for castration-resistant prostate cancer," Cancer Res., Aug. 1, 2013; 73(15): 4599-4605.
Monge et al., "Unfaithfulness and promiscuity of a mutant androgen receptor in a hormone-refractory prostate cancer," Cell Mol Life Sci., Feb. 1, 2006; 63(4): 487-497.
Nagata et al., "Preparation and reactions of cyclic α-monocarbonyl azo-compounds: 1-pyrazolin-3-one derivatives", J Chem Soc. C: Organic. 1970(4): 540-550.

(56) References Cited

OTHER PUBLICATIONS

Narayanan et al., "Biological synthesis of metal nanoparticles by microbes", Adv Colloid Interface Science. Apr. 22, 2010;156(1-2): 1-3.
Narayanan et al., "Selective Androgen Receptor Modulators (SARMs) Negatively Regulate Triple-Negative Breast Cancer Growth and Epithelial: Mesenchymal Stem Cell Signaling," Plos One, Jul. 2014; 9(7): 1-12.
Nazareth et al., "Activation of the human androgen receptor through a protein kinase A signaling pathway," J Biol Chem., Aug. 16, 1996; 271(33): 19900-19907.
Nyquist et al., "TALEN-engineered AR gene rearrangements reveal endocrine uncoupling of androgen receptor in prostate cancer," Proc Nat Acad. Sci., Oct. 22, 2013; 110(43): 17492-17497.
PUBMED, CID 20221988, "Compound Summary for CID 20221988-C12H13N30"; Dec. 5, 2007, pp. 1-11; retrieved from the Internet <URL: https://pubchem.ncbi.nlm.nih.gov/compound/20221988>.
Rawel et al., "Determining the binding affinities of phenolic compounds to proteins by quenching of the intrinsic tryptophan fluorescence", Mol Nutri Food Res. Aug. 2006;50(8): 705-713.
Renier et al., "Antiandrogen flutamide protects male mice from androgen-dependent toxicity in three models of spinal bulbar muscular atrophy," Neuroendocrinol. Jul. 1, 2014; 155(7): 2624-2634.
Rosa et al., "Polymorphisms of CYP17A1, CYP19, and androgen in Brazilian women with uterine leiomyomas", Clin Chem Lab Med. Jun. 1, 2008;46(6): 814-823.
Rygula et al., "Raman spectroscopy of proteins: a review", J Raman Spectrosc. Aug. 2013;44(8): 1061-1076.
Sadar M.D., "Androgen-independent induction of prostate-specific antigen gene expression via cross-talk between the androgen receptor and protein kinase a signal transduction pathways," J Biol Chem., Mar. 19, 1999; 274(12): 7777-7783.
Sadar et al., "Ligand-independent activation of the androgen receptor by the differentiation agent butyrate in human prostate cancer cells," Cancer Res., Oct. 15, 2000; 60(20): 5825-5831.
Sartor et al., "Androgen receptor variant-7: an important predictive biomarker in castrate resistant prostate cancer," Asian J Andrology, May 2015; 17(3): 439-440.
Scher et al., "Increased survival with enzalutamide in prostate cancer after chemotherapy," N Eng J Med., Sep. 27, 2012; 367(13): 1187-1197.
Shortridge et al., "Estimating protein-ligand binding affinity using high-throughput screening by NMR", J Comb Chem. Nov. 10, 2008;10(6): 948-958.
Sieber PR., "Treatment of bicalutamide-induced breast events," Exp Review Anticancer Thera., Dec. 1, 2007; 7(12): 1773-1779.
Siegel et al., "Cancer statistics, 2014" CA Cancer. J. Clin., 2014; 64: 9-29.
Sun et al., Castration resistance in human prostate cancer is conferred by a frequently occurring androgen receptor splice variant, J Clin Invest. Aug. 2, 2010;120(8): 2715-2730.
Tan et al., "Dehydroepiandrosterone activates mutant androgen receptors expressed in the androgen-dependent human prostate cancer xenograft CWR22 and LNCaP cells", Mol Endocrin. Apr. 1, 1997 ;11(4): 450-459.
Tran et al., "Development of a second-generation antiandrogen for treatment of advanced prostate cancer," Science, May 8, 2009; 324(5928): 787-790.
Ueda et al., "Ligand-independent activation of the androgen receptor by interleukin-6 and the role of steroid receptor coactivator-1 in prostate cancer cells," J Biol Chem., Oct. 11, 2002; 277(41): 38087-38094.
Wang et al., "Small molecule inhibition of the steroid receptor coactivators, SRC-3 and SRC-1", Mol Endocrin. Dec. 1, 2011;25(12): 2041-2053.
Wang et al., "Effects of hydrogen bond and solvent polarity on the C=O stretching of bis (2-thienyl)ketone in solution", J Chem Physics. Mar. 28, 2012;136(12): 03B614.

Watson et al., "Constitutively active androgen receptor splice variants expressed in castration-resistant prostate cancer require full-length androgen receptor", PNAS. Sep. 28, 2010;107(39): 16759-16765.
Weiner L.P., "Possible role of androgen receptors in amyotrophic lateral sclerosis: a hypothesis," Arch Neurol. Mar. 1, 1980; 37(3): 129-131 (Abstract).
Wen et al., "LHRH-conjugated micelles for targeted delivery of antiandrogen to treat advanced prostate cancer," Pharma Res., Oct. 1, 2014; 31(10): 2784-2795.
Wen et al., "Targeting fatty acid synthase with ASC-J9 suppresses proliferation and invasion of prostate cancer cells", Mol Carcino. Dec. 2016;55(12): 2278-2290.
West A.R., "Solid state chemistry and its applications", John Wiley & Sons; 1988; Chapter 10; pp. 358, 365.
Xu et al., "hSSB1 binds and protects p21 from ubiquitin-mediated degradation and positively correlates with p21 in human hepatocellular carcinomas," Oncogene, May 12, 2011; 30(19): 2219-29.
Yamashita et al., "ASC-J9 suppresses castration-resistant prostate cancer growth through degradation of full-length and splice variant androgen receptors," Neoplasia, Jan. 1, 2012;14(1): 74-83.
Yepuru et al., "Steroidogenic enzyme AKR1C3 is a novel androgen receptor-selective coactivator that promotes prostate cancer growth", Clin Cancer Res. Oct. 15, 2013;19(20): 5613-5625.
Yoshida et al., "Antiandrogen bicalutamide promotes tumor growth in a novel androgen-dependent prostate cancer xenograft model derived from a bicalutamide-treated patient," Cancer Res., Nov. 1, 2005; 65(21): 9611-9616.
Zhou et al., "Study of the impact of the T877A mutation on ligand-induced helix-12 positioning of the androgen receptor resulted in design and synthesis of novel antiandrogens," Proteins: Structure, Function, and Bioinformatics, Feb. 15, 2010; 78(3): 623-37.
Arora et al., "Glucocorticoid receptor confers resistance to antiandrogens by bypassing androgen receptor blockage", Cell. Dec. 5, 2013;155(6): 1309-1322.
Bassetto et al., "Design and synthesis of novel bicalutamide and enzalutamide derivatives as antiproliferative agents for the treatment of prostate cancer", Eur J Med Chem. Aug. 8, 2016;118: 230-243.
CAS Registry No. 55734-18-4; STN Entry Date: Nov. 16, 1984.
CAS Registry No. 945553-38-8; STN Entry Date: Aug. 24, 2007.
CAS Registry No. 1349723-51-8; STN Entry Date: Dec. 6, 2011.
CAS Registry No. 1480139-15-8; STN Entry Date: Nov. 24, 2013.
CAS Registry No. 1526624-00-9; STN Entry Date: Jan. 21, 2014.
CAS Registry No. 1839720-91-0; STN Entry Date: Jan. 1, 2016.
CAS Registry No. 1919463-97-0; STN Entry Date: May 27, 2016.
CAS Registry No. 1928217-46-2; STN Entry Date: Nov. 16, 2016.
Choi et al., "Collision tumor of hepatocellular carcinoma and neuroendocrine carcinoma involving the liver: case report and review of the literature", World J Gastroenterol. Nov. 7, 2016;22(41): 9229-9234.
ClinicalTrials.gov; "Enzalutamide in patients with androgen receptor positive (AR+) ovarian, primary peritoneal or fallopian tube cancer and one, two or three prior therapies", Study Sponsor: Memorial Sloan Kettering Cancer Center/Medivation, Inc., last update: Jun. 2017 in 6 pages.
Colin et al., "New Access to fluorinated ketoglycolic acid derivatives from trifluoropyruvamides", Tetrahe Letts. Jul. 12, 2004;45(29): 5611-5613.
Gibson et al., "Evidence of androgen action in endometrial and ovarian cancers", Endocrine-related cancer. Aug. 1, 2014;21(4): T203-T218.
Gottlieb et al., "Androgen insensitivity syndrome", University of Washington, Seattle (WA) Publication, initial Posting: Mar. 24, 1999; last Update: May 11, 2017, in 15 pages.
He et al., "ASC-J9 suppresses renal cell carcinoma progression by targeting an androgen receptor-dependent HIF2α/VEGF Signaling Pathway", Cancer Res. Aug. 2014;74(16): 4420-4430.
Hebenbrock K-F., "Preparation and reaction of 1-aryl-3-hydroxy-3-methyl-2,5-pyrrolidinediones", Justus Liebig's Annals of Chemistry, Aug. 1, 1978; vol. 2, pp. 320-336 (Abstract).

(56) References Cited

OTHER PUBLICATIONS

Isikbay et al., "Glucocorticoid receptor activity contributes to resistance to androgen-targeted therapy in prostate cancer", Horm Cancer. Apr. 2014;5(2): 72-89.
Kamal et al., "Androgen receptors are acquired by healthy postmenopausal endometrial epithelium and their subsequent loss in endometrial cancer is associated with poor survival", Br J Cancer. Mar. 2016;114(6): 688-696.
Kominea et al., "Androgen receptor (AR) expression is an independent unfavorable prognostic factor in gastric cancer", J Cancer Res Clin Oncol. May 2004;130(5): 253-258.
Lazar et al., "Hyperandrogenism as a cause of early polycystic ovary syndrome (PCOS) in girls with central precocious puberty (CPP)", Pediatric Research. May 1993;33(5): S14; Abstract 64.
Lieberman et al., [Eds.] Pharmaceutical Dosage Forms: Tablets; Marcel Dekker, 1989, TOC in 11 pages.
Mayo Clinic, "Uterine Fibroids—Overview", Mayo Clinic Staff; printed Aug. 7, 2017; 2 pages.
Mikkonen et al., "Androgen receptor and androgen-dependent gene expression in lung", Mol Cell Endocrinol. Apr. 12, 2010;317(1-2): 14-24.
Mohler et al., "Nonsteroidal selective androgen receptor modulators (SARMs): Dissociating the anabolic and androgenic activities of the androgen receptor for therapeutic benefit", J Med Chem., Jun. 2009;52(12): 3597-3617.
Mohler et al., "Androgen receptor antagonists: a patent review (2008-2011)," Expert Opinion Ther. Patents, (2012): 22(5): 541-565.
Morris et al., "Non-steroidal antiandrogens. Design of novel compounds based on an infrared study of the dominant conformation and hydrogen-bonding properties of a series of anilide antiandrogens", J Med Chem. Jan. 1991;34(1): 447-455.
Morvillo et al., "Androgen receptors in human melonoma cell lines IIB-MEL-LES and IIB-MEL-IAN and in human melanoma metastases", Melanomoa Res. Dec. 2002;12(6): 529-538 [Abstract].
Mostaghel et al., "Androgen receptor expression in mantle cell lymphoma: Potential novel therapeutic implications", Exp Hematol. May 2017;49: 34-38.e2.
Munoz et al., "Androgen receptors beyond prostate cancer: An old marker as a new target", Oncotarget. Jan. 2015;6(2): 592-603.
Park et al., "Expression of DBC1 and androgen receptor predict poor prognosis in diffuse large B cell lymphoma", Transl Oncol. Jun. 1, 2013;6(3): 370-381.
Ponnusamy et al., "Novel Selective Agents for the Degradation of Androgen Receptor Variants to Treat Castration-Resistant Prostate Cancer," Cancer Res. (2017); 77(22): 6282-6298.
PUBCHEM, CID 3145286.09, Aug. 9, 2005, pp. 1-12; retrieved from the Internet <URL: https:llpubchem.ncbl.nlm.nih.gov/compound/3145286> in 12 pages.

Gennaro A.R. [Ed.], "Remington's pharmaceutical sciences", Mack Publishing Company, 18th Edition; 1990, TOC in 6 pages.
Rowe R.C. [Ed.], "Handbook Of Pharmaceutical Excipients", American Pharmaceutical Association; Fifth Edition, 2006, TOC in 6 pages.
Schragl et al., "Novel pathway for the synthesis of arylpropionamide-derived selective androgen receptor modulator (SARM) metabolites of andarine and ostarine", Tetra Lettrs. May 1, 2013;54(18): 2239-2242.
Seligson et al., "Development of Fluridil, a topical suppressor of the androgen receptor in androgenetic alopecia", Drug Devel Res. Jul. 2003;59(3): 292-306.
Simanainen et al., "Androgen receptor actions modify skin structure and chemical carcinogen-induced skin cancer susceptibility in mice", Hormones and Cancer. Feb. 2015;6(1): 45-53.
Soper et al., "Definitive treatment of androgen receptor-positive salivary duct carcinoma with androgen deprivation therapy and external beam radiotherapy", Head Neck. Jan. 2014;36(1): E4-E7.
Sukocheva et al., "Androgens and esophageal cancer: What do we know?" World J Gastroenterol. May 28, 2015;21(20): 6146-6156.
Tangen et al., "Androgen receptor as potential therapeutic target in metastatic endometrial cancer", Oncotarget. Aug. 2, 2016;7(31): 49289-49298.
Tarikogullari et al., "Synthesis and anticonvulsant activity of some alkanamide derivatives", Arzneimittelforschung. Oct. 2010;60(10): 593-598 (Abstract).
Tucker et al., "Nonsteroidal antiandrogens. Synthesis and structure-activity relationships of 3-substituted derivatives of 2-hydroxypropionanilides", J Med Chem. May 1988;31(5): 954-959.
Tutton et al., "The influence of androgens, anti-androgens, and castration on cell proliferation in the jejunal and colonic crypt epithelia, and in dimehylhydrazine-induced adenocarcinoma of rat colon", Virchows Arch B Cell Pathol Incl Mol Pathol. 1982;38(3): 351-356 [Abstract].
Wikipedia, "Hyperandrogenism", downloaded Aug. 7, 2017 in 8 pages.
Wong et al., "Circulating sex hormones and risk of uterine fibroids: Study of women's health across the nation (SWAN)," J Clin Endocrinol. Jan. 1, 2016;101(1): 123-130.
Yu et al., "Androgen receptor signaling regulates growth of glioblastoma multiforme in men", Tumour Biol. Feb. 2015;36(2): 967-972 [Abstract].
International Search Report and Written Opinion for PCT Application No. PCT/US2016/028674, dated Sep. 6, 2016.
Supplementary EP Search Report for corresponding EP Application No. 16783866.3, dated Nov. 7, 2018.
International Search Report and Written Opinion for PCT Application No. PCT/US2019/049618, dated Dec. 19, 2019.

* cited by examiner

Compound 17

Figure 14:

Phase I (MLM)

| Time | Anal/IS | % remaining |
|------|---------|-------------|
| 0    | 0.242   | 100%        |
| 5    | 0.245   | 101%        |
| 10   | 0.216   | 90%         |
| 30   | 0.139   | 58%         |
| 60   | 0.079   | 33%         |

Half-life (min)   36.53
Clearance   1.89

Phase II (MLM)

| Time | Anal/IS | % remaining |
|------|---------|-------------|
| 0    | 0.221   | 100%        |
| 5    | 0.195   | 88%         |
| 10   | 0.240   | 109%        |
| 30   | 0.176   | 80%         |
| 60   | 0.125   | 57%         |

Half-life (min) 77.96
Clearance   0.88

| Time | Anal/IS | % remaining |
|---|---|---|
| 0 | 1.291 | 100% |
| 5 | 1.484 | 115% |
| 10 | 1.126 | 87% |
| 30 | 1.294 | 100% |
| 60 | 1.079 | 84% |

| Time | Anal/IS | % remaining |
|---|---|---|
| 0 | 1.332 | 100% |
| 5 | 1.277 | 96% |
| 10 | 1.132 | 85% |
| 30 | 1.094 | 82% |
| 60 | 1.045 | 78% |

| Time | Anal/IS | % remaining |
|---|---|---|
| 0 | 2.074 | 100% |
| 5 | 2.089 | 101% |
| 10 | 2.488 | 120% |
| 30 | 2.238 | 108% |
| 60 | 2.510 | 121% |

| Time | Anal/IS | % remaining |
|---|---|---|
| 0 | 2.256 | 100% |
| 5 | 2.349 | 104% |
| 10 | 2.664 | 118% |
| 30 | 2.473 | 110% |
| 60 | 2.467 | 109% |

| Time | Anal/IS | % remaining |
|------|---------|-------------|
| 0    | 4.543   | 100%        |
| 5    | 3.694   | 81%         |
| 10   | 3.500   | 77%         |
| 30   | 1.751   | 39%         |
| 60   | 0.810   | 18%         |

** p<0.01
*** p<0.001

\* = p<0.001

36

34

Experiment 1 (21 day duration)

*** p<0.001

Experiment 2 (14 day duration)

*** p<0.001

36

LNCaP

Compound 11

LNCaP

Compound 1002

ZR-75-1

Compound 1002

FIGURE 43A
FIGURE 43B
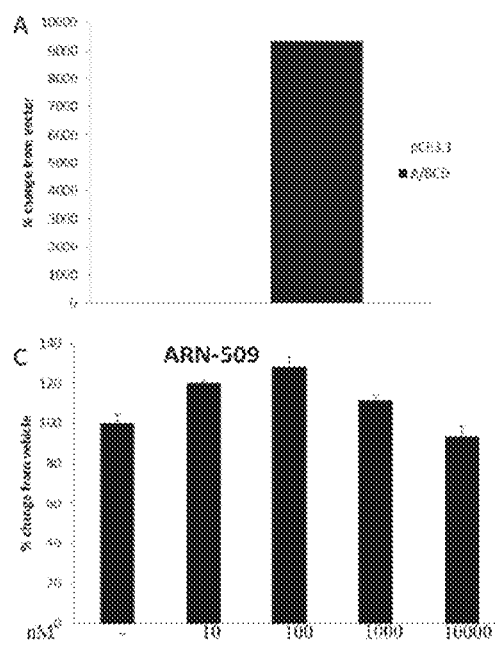
FIGURE 43C
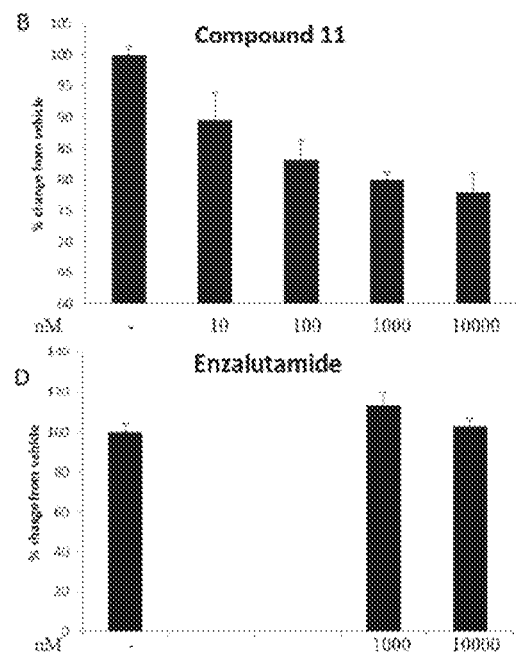
FIGURE 43D

All these data were generated in LNCaP cells

All these data were generated in 22RV-1 cells

All experiments in this figure were done in LNCaP cells.

This experiment was done in 22RV-1 cells.

All experiments in this figure were done in LNCaP cells.

All experiments in this figure were done in 22RV-1 cells.

LNCaP

134

130

22RV-1

LNCaP

40

FIGURE 65III
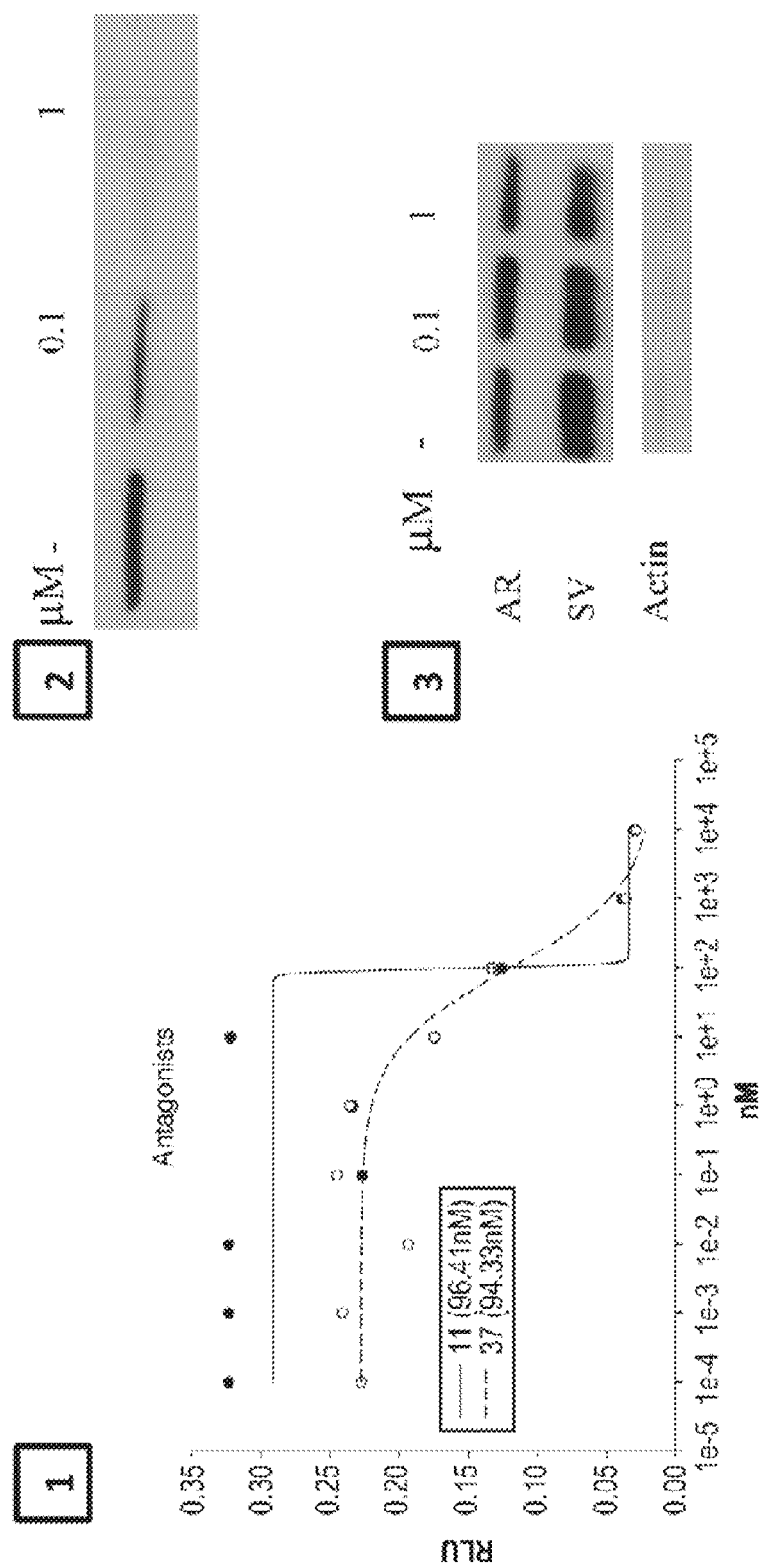
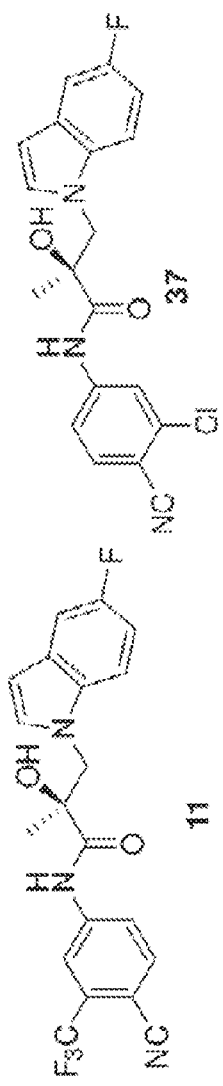

LNCaP

LNCaP

22RV1

LNCaP

22RV1

| | $K_i$ | $IC_{50}$ |
|---|---|---|
| 76 | 1588.62 | 1023.94 |

| | $K_i$ | $IC_{50}$ |
|---|---|---|
| 75 | 913.45 | 371.21 |

| | $K_i$ | $IC_{50}$ | MLM |
|---|---|---|---|
| 96 | 1006.38 | 372.87 | 53.71 / 12.91 |

| | $K_i$ | $IC_{50}$ | MLM |
|---|---|---|---|
| 97 | 1232.45 | 208.78 | 35.46 / 19.55 |

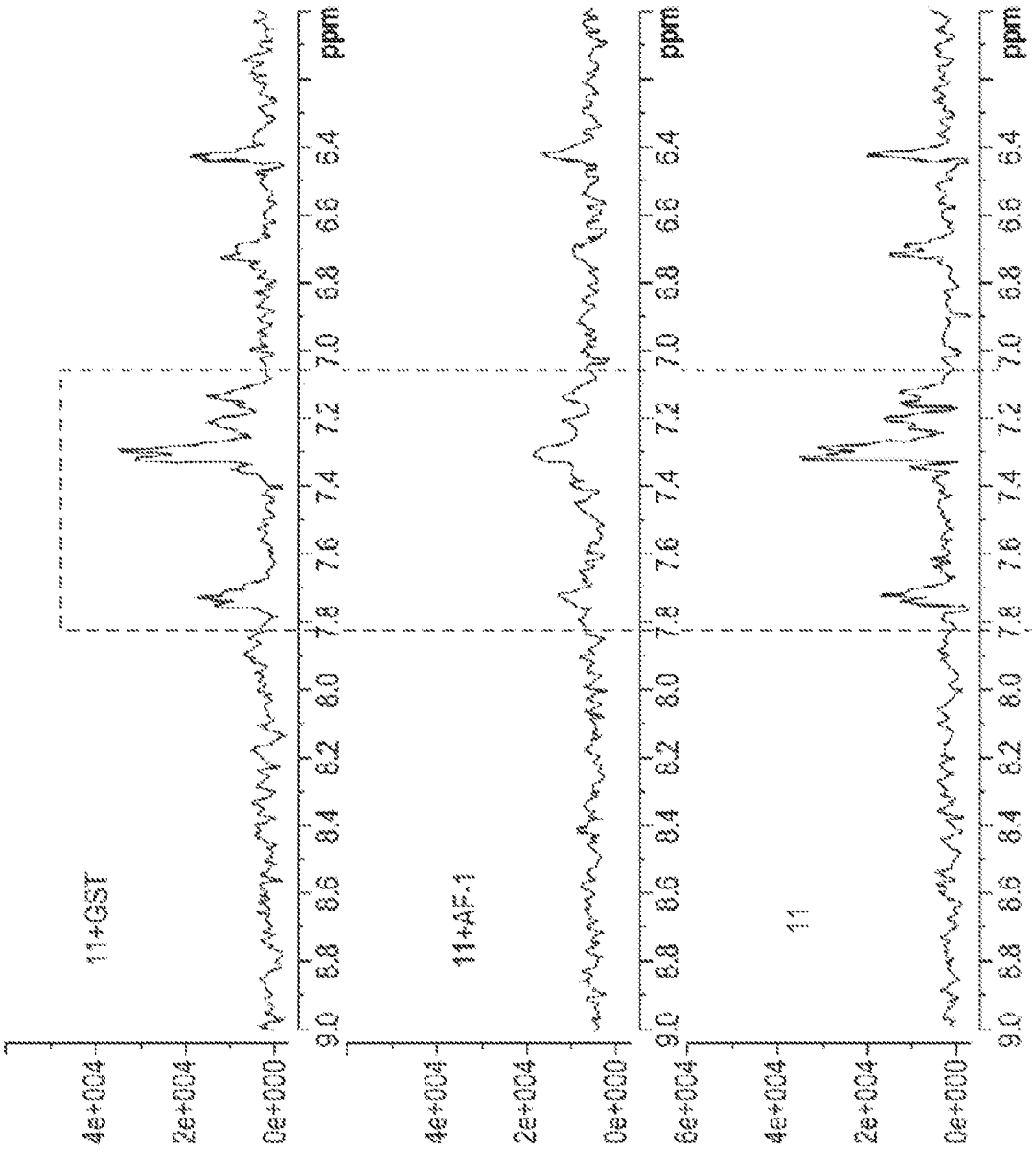

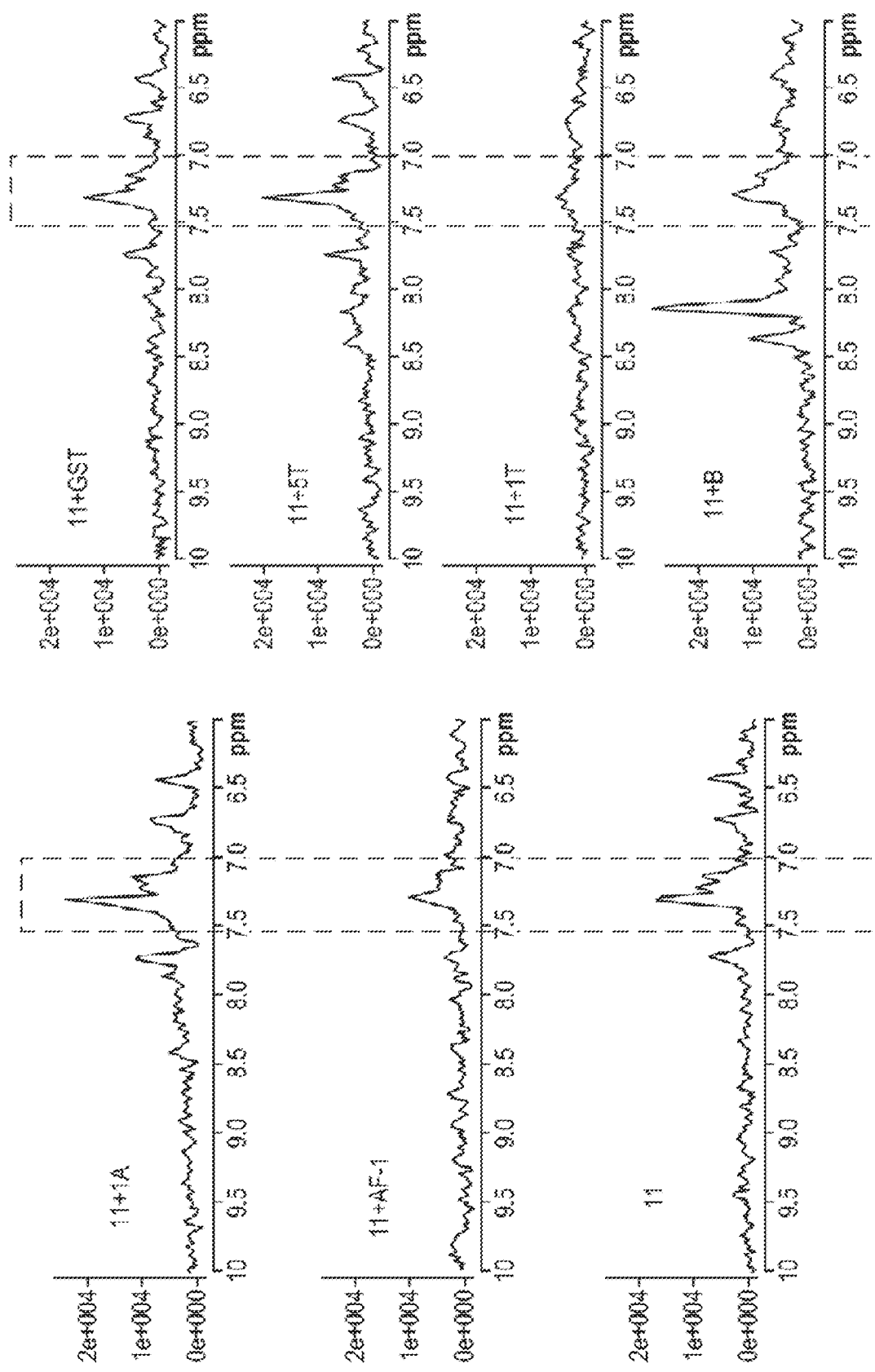

B (continued)

BINDING ENERGY

| Amino Acid | Drug U155 cis binding (eV) | Drug U155 trans binding (eV) |
|---|---|---|
| Glycine | 0.500 | 0.484 |
| Alanine | 0.515 | 0.483 |
| Leucine | 0.530 | 0.490 |
| Valine | 0.488 | 0.454 |
| Histidine | 0.475 | 0.454 |
| Proline | 0.548 | 0.473 |
| Tryosine | 0.500 | 0.474 |
| Phenylalanine | 0.502 | 0.470 |
| Serine | 0.516 | 0.495 |
| Cystine | 0.525 | 0.706 |

BINDING ENERGY

| Amino Acid | Drug YH34 cis binding (ev) | Drug YH34 trans binding (ev) |
|---|---|---|
| Glycine | 0.500 | 0.382 |
| Alanine | 0.512 | 0.384 |
| Leucine | 0.527 | 0.413 |
| Valine | 0.450 | 0.324 |
| Histidine | 0.494 | 0.358 |
| Proline | 0.490 | 0.256 |
| Tryosine | 0.483 | 0.418 |
| Phenylalanine | 0.490 | 0.408 |
| Serine | 0.512 | 0.435 |
| Cystine | 0.567 | 0.361 |

SELECTIVE ANDROGEN RECEPTOR DEGRADER (SARD) LIGANDS AND METHODS OF USE

CROSS REFERENCE TO RELATED APPLICATIONS

This application is a Continuation of U.S. patent application Ser. No. 15/981,892, filed May 16, 2018, which is a Continuation-in-Part Application of U.S. patent application Ser. No. 15/331,777, filed Oct. 21, 2016, which is a Continuation-in-Part Application of U.S. patent application Ser. No. 15/222,734, filed Jul. 28, 2016, which is a Continuation-in-Part Application of U.S. patent application Ser. No. 15/135,334, filed Apr. 21, 2016, which is now U.S. Pat. No. 9,814,698, which claims the benefit of U.S. Provisional Ser. No. 62/150,768, filed Apr. 21, 2015, U.S. Provisional Ser. No. 62/220,057, filed Sep. 17, 2015, U.S. Provisional Ser. No. 62/241,532, filed Oct. 14, 2015, U.S. Provisional Ser. No. 62/220,187, filed Sep. 17, 2015 and 62/219,859 filed Sep. 17, 2015, which are incorporated in their entirety herein by reference. U.S. patent application Ser. No. 15/981,892, filed May 16, 2018, is also a Continuation-in-Part Application of U.S. patent application Ser. No. 15/923,668, filed on Mar. 16, 2018, which is a Continuation-in-Part Application of U.S. patent application Ser. No. 15/620,761, filed on Jun. 12, 2017, which claims the benefit of U.S. Provisional Ser. No. 62/348,474, filed on Jun. 10, 2016, U.S. Provisional Ser. No. 62/455,397, filed on Feb. 6, 2017, and U.S. Provisional Ser. No. 62/482,036, filed on Apr. 5, 2017, which are incorporated in their entirety herein by reference. U.S. patent application Ser. No. 15/981,892, filed May 16, 2018, is also a Continuation-in-Part Application of U.S. patent application Ser. No. 15/830,688, filed Dec. 4, 2017, which is a Continuation-in-Part Application of U.S. patent application Ser. No. 15/331,751, filed on Oct. 21, 2016, which is now U.S. Pat. No. 9,834,507, which is a Continuation-in-Part application of U.S. patent application Ser. No. 15/135,151, filed on Apr. 21, 2016, now U.S. Pat. No. 9,815,776, which claims the benefit of U.S. Provisional Application Ser. No. 62/220,094, filed on Sep. 17, 2015, and U.S. Provisional Application Ser. No. 62/150,768, filed on Apr. 21, 2015, which are incorporated in their entirety herein by reference.

FIELD OF THE INVENTION

This invention is directed to selective androgen receptor degrader (SARD) compounds pharmaceutical compositions and uses thereof in treating early prostate cancer, advanced prostate cancer, castration resistant prostate cancer, triple negative breast cancer, other cancers expressing the androgen receptor, androgenic alopecia or other hyperandrogenic dermal diseases, Kennedy's disease, amyotrophic lateral sclerosis (ALS), abdominal aortic aneurysm (AAA), and uterine fibroids, and to methods for reducing the levels of androgen receptor-full length (AR-FL) including pathogenic or resistance mutations, AR-splice variants (AR-SV), and pathogenic polyglutamine (polyQ) polymorphisms of AR in a subject.

BACKGROUND OF THE INVENTION

Prostate cancer (PCa) is one of the most frequently diagnosed noncutaneous cancers among men in the US and is the second most common cause of cancer deaths with more than 200,000 new cases and over 30,000 deaths each year in the United States. PCa therapeutics market is growing at an annual rate of 15-20% globally.

Androgen-deprivation therapy (ADT) is the standard of treatment for advanced PCa. Patients with advanced prostate cancer undergo ADT, either by luteinizing hormone releasing hormone (LHRH) agonists, LHRH antagonists or by bilateral orchiectomy. Despite initial response to ADT, disease progression is inevitable and the cancer emerges as castration-resistant prostate cancer (CRPC). Up to 30% of patients with prostate cancer that undergo primary treatment by radiation or surgery will develop metastatic disease within 10 years of the primary treatment. Approximately 50,000 patients a year will develop metastatic disease, which is termed metastatic CRPC (mCRPC).

Patients with CRPC have a median survival of 12-18 months. Though castration-resistant, CRPC is still dependent on the androgen receptor (AR) signaling axis for continued growth. The primary reason for CRPC re-emergence is re-activation of AR by alternate mechanisms such as: 1) intracrine androgen synthesis, 2) AR splice variants (AR-SV), e.g., that lack ligand binding domain (LBD), 3) AR-LBD mutations with potential to resist AR antagonists (i.e., mutants that are not sensitive to inhibition by AR antagonists, and in some cases AR antagonists act as agonists of the AR bearing these LBD mutations), and 4) amplifications of the AR gene within the tumor. A critical barrier to progress in treating CRPC is that AR signaling inhibitors such as enzalutamide, bicalutamide, and abiraterone, acting through the LBD, fail to inhibit growth driven by the N-terminal domain (NTD)-dependent constitutively active AR-SV such as AR-V7, the most prominent AR-SV. Recent high-impact clinical trials with enzalutamide and abiraterone in CRPC patients demonstrated that just 13.9% of AR-V7-positive patients among 202 patients starting treatment with enzalutamide (Xtandi) or abiraterone acetate (Zytiga) had PSA responses to either of the treatments (Antonarakis E S, Lu C, Luber B, et al. *J. Gun. Oncol.* 2017 Apr. 6. doi: 10.1200/JCO.2016.70.1961), indicating the requirement for next generation AR antagonists that target AR-SVs. In addition, a significant number of CRPC patients are becoming refractory to abiraterone or enzalutamide, emphasizing the need for next generation AR antagonists.

Current evidences demonstrate that CRPC growth is dependent on constitutively active AR including AR-SV's that lack the LBD such as AR-V7 and therefore cannot be inhibited by conventional antagonists. AR inhibition and degradation through binding to a domain that is distinct from the AR LBD provides alternate strategies to manage CRPC.

Molecules that degrade the AR prevent any inadvertent AR activation through growth factors or signaling pathways, or promiscuous ligand-dependent activation. In addition, molecules that inhibit the constitutive activation of AR-SVs are extremely important to provide extended benefit to CRPC patients.

Currently only a few chemotypes are known to degrade AR which include the SARDs ARN-509, AZD-3514, and ASC-J9. However, these molecules degrade AR indirectly at much higher concentrations than their binding coefficient and they fail to degrade the AR-SVs that have become in recent years the primary reason for resurgence of treatment-resistant CRPC.

This invention describes novel AR antagonists with unique pharmacology that strongly (high potency and efficacy) and selectively bind AR (better than known antagonists in some cases; bind to LBD and/or NTD), antagonize AR, and degrade AR full length (AR-FL) and AR-SV. Selective androgen receptor degrader (SARD) compounds possess dual degradation and AR-SV inhibitory functions and hence are distinct from any available CRPC therapeutics. These novel selective androgen receptor degrader (SARD) compounds inhibit the growth of PCa cells and tumors that are dependent on AR-FL and AR-SV for proliferation. SARDs have the potential to evolve as new therapeutics to treat CRPCs that are untreatable with any other antagonists. This unique property of degrading AR-SV has extremely important health consequences for prostate cancer. Till date only one series of synthetic molecules (EPI-001, EPI-506, etc.) and some marine natural products such as the sinkotamides and glycerol ether Naphetenone B, are reported to bind to AR-NTD and inhibit AR function and PCa cell growth, albeit at lower affinity and inability to degrade the receptor. The SARDs reported herein also bind to AR-NTD and inhibit NTD-driven (e.g., ligand independent) AR activity.

The positive correlation between AR and PCa and the lack of a fail-safe AR antagonist, emphasizes the need for molecules that inhibit AR function through novel or alternate mechanisms and/or binding sites, and that can elicit antagonistic activities within an altered cellular environment.

Although traditional antiandrogens such as enzalutamide, bicalutamide and flutamide and androgen deprivation therapies (ADT) were approved for use in prostate cancer, there is significant evidence that antiandrogens could also be used in a variety of other hormone dependent and hormone independent cancers. For example, antiandrogens have been tested in breast cancer (enzalutamide; Breast Cancer Res. (2014) 16(1): R7), non-small cell lung cancer (shRNAi AR), renal cell carcinoma (ASC-J9), partial androgen insensitivity syndrome (PAIS) associated malignancies such as gonadal tumors and seminoma, advanced pancreatic cancer (*World J. Gastroenterology* 20(29), 9229), cancer of the ovary, fallopian tubes, or peritoneum, cancer of the salivary gland (*Head and Neck* (2016) 38, 724-731; ADT was tested in AR-expressing recurrent/metastatic salivary gland cancers and was confirmed to have benefit on progression free survival and overall survival endpoints), bladder cancer (*Oncotarget* 6(30), 29860-29876); *Int J. Endocrinol* (2015), Article ID 384860), pancreatic cancer, lymphoma (including mantle cell), and hepatocellular carcinoma. Use of a more potent antiandrogen such as a SARD in these cancers may more efficaciously treat the progression of these and other cancers. Other cancers may also benefit from SARD treatment such as breast cancer (e.g., triple negative breast cancer (TNBC)), testicular cancer, cancers associated with partial androgen insensitivity syndromes (PAIS) such as gonadal tumors and seminoma, uterine cancer, ovarian cancer, cancer of the fallopian tubes or peritoneum, salivary gland cancer, bladder cancer, urogenital cancer, brain cancer, skin cancer, lymphoma, mantle cell lymphoma, liver cancer, hepatocellular carcinoma, renal cancer, renal cell carcinoma, osteosarcoma, pancreatic cancer, endometrial cancer, lung cancer, non-small cell lung cancer (NSCLC), gastric cancer, colon cancer, perianal adenoma, or central nervous system cancer.

Triple negative breast cancer (TNBC) is a type of breast cancer lacking the expression of the estrogen receptor (ER), progesterone receptor (PR), and HER2 receptor kinase. As such, TNBC lacks the hormone and kinase therapeutic targets used to treat other types of primary breast cancers. Correspondingly, chemotherapy is often the initial pharmacotherapy for TNBC. Interestingly, AR is often still expressed in TNBC and may offer a hormone targeted therapeutic alternative to chemotherapy. In ER-positive breast cancer, AR is a positive prognostic indicator as it is believed that activation of AR limits and/or opposes the effects of the ER in breast tissue and tumors. However, in the absence of ER, it is possible that AR actually supports the growth of breast cancer tumors. Though the role of AR is not fully understood in TNBC, we have evidence that certain TNBC's may be supported by androgen independent activation of AR-SVs lacking the LBD or androgen-dependent activation of AR full length. As such, enzalutamide and other LBD-directed traditional AR antagonists would not be able to antagonize AR-S Vs in these TNBC's. However, SARDs of this invention which are capable of destroying AR-S Vs (see Table 1 and Example 5) through a binding site in the NTD of AR (see Example 9) would be able to antagonize AR including AR-SV observed in TNBC patient derived xenografts and provide an anti-tumor effect, as shown in Example 8.

Traditional antiandrogens such as bicalutamide and flutamide were approved for use in prostate cancer. Subsequent studies have demonstrated the utility of antiandrogens (e.g., flutamide, spironolactone, cyproterone acetate, finasteride and chlormadinone acetate) in androgen-dependent dermatological conditions such as androgenic alopecia (male pattern baldness), acne vulgaris, and hirsutism (e.g., in female facial hair). Prepubertal castration prevents sebum production and androgenic alopecia but this can be reversed by use of testosterone, suggesting its androgen-dependence.

The AR gene has a polymorphism of glutamine repeats (polyQ) within exon 1 which when shortened may augment AR transactivation (i.e., hyperandrogenism). It has been found that shortened polyQ polymorphisms are more common in people with alopecia, hirsutism, and acne. Classic antiandrogens are undesirable for these purposes because they are ineffective through dermal dosing and their long-term systemic use raises the risks of untoward sexual effects such as gynecomastia and impotence. Further, similar to CPRC discussed above, inhibition of ligand-dependent AR activity alone may not be sufficient as AR can be activated by various cellular factors other than the endogeneous androgens testosterone (T) and dihydrotestosterone (DHT), such as growth factors, kinases, co-activator overexpression and/or promiscuous activation by other hormones (e.g., estrogens or glucocorticoids). Consequently, blocking the binding of T and DHT to AR with a classical antiandrogen may not be sufficient to have the desired efficacy.

An emerging concept is the topical application of a SARD to destroy the AR locally to the affected areas of the skin or other tissue without exerting any systemic antiandrogenism. For this use, a SARD that does not penetrate the skin or is rapidly metabolized would be preferable.

Supporting this approach is the observation that cutaneous wound healing has been demonstrated to be suppressed by androgens. Castration of mice accelerates cutaneous wound healing while attenuating the inflammation in the wounds. The negative correlation between androgen levels and cutaneous healing and inflammation, in part, explains another mechanism by which high levels of endogenous androgens exacerbate hyperandrogenic dermatological conditions.

Further, it provides a rationale for the treatment of wounds such as diabetic ulcers or even trauma, or skin disorders with an inflammatory component such as acne or psoriasis, with a topical SARD.

Androgenic alopecia occurs in ~50% of Caucasian males by midlife and up to 90% by 80 years old. Minoxidil (a topical vasodilator) and finasteride (a systemic 5alpha reductase type II inhibitor) are FDA approved for alopecia but require 4-12 months of treatment to produce a therapeutic effect and only arrest hair loss in most with mild to moderate hair regrowth in 30-60%. Since currently available treatments have slow and limited efficacy that varies widely between individuals, and produce unwanted sexual side effects, it is important to find a novel approach to treat androgenic alopecia and other hyperandrogenic dermatologic diseases.

Amyotrophic lateral sclerosis (ALS) is a fatal neurodegenerative disease characterized by selective loss of upper and lower motor neurons and skeletal muscle atrophy. Epidemiologic and experimental evidence suggest the involvement of androgens in ALS pathogenesis ("Anabolic/androgenic steroid nandrolone exacerbates gene expression modifications induced by mutant SOD1 in muscles of mice models of amyotrophic lateral sclerosis." Galbiati M, Onesto E, Zito A, Crippa V, Rusmini P, Mariotti R, Bentivoglio M, Bendotti C, Poletti A. *Pharmacol. Res.* 2012, 65(2), 221-230), but the mechanism through which androgens modify the ALS phenotype is unknown. A transgenic animal model of ALS demonstrated improved survival upon surgical castration (i.e., androgen ablation). Treatment of these castrated animals with the androgen agonist nandrolone decanoate worsened disease manifestations. Castration reduces the AR level, which may be the reason for extended survival. The survival benefit is reversed by androgen agonist ("Androgens affect muscle, motor neuron, and survival in a mouse model of SOD1-related amyotrophic lateral sclerosis." Aggarwal T, Polanco M J, Scaramuzzino C, Rocchi A, Milioto C, Emionite L, Ognio E, Sambataro F, Galbiati M, Poletti A, Pennuto M. *Neurobiol. Aging.* 2014 35(8), 1929-1938). Notably, stimulation with nandrolone decanoate promoted the recruitment of endogenous androgen receptor into biochemical complexes that were insoluble in sodium dodecyl sulfate, a finding consistent with protein aggregation. Overall, these results shed light on the role of androgens as modifiers of ALS pathogenesis via dysregulation of androgen receptor homeostasis. Antiandrogens should block the effects of nandrolone undecanoate or endogeneous androgens and reverse the toxicities due to AR aggregation. Further, an antiandrogen that can block action of LBD-dependent AR agonists and concomitantly lower AR protein levels, such as the SARDs of this invention, would be therapeutic in ALS. Riluzole is an available drug for ALS treatment, however, it only provides short-term effects. There is an urgent need for drugs that extend the survival of ALS patients.

Androgen receptor action promotes uterine proliferation. Hyperandrogenicity of the short polyQ AR has been associated with increased leiomyoma or uterine fibroids. (Hsieh Y Y, Chang C C, Tsai F J, Lin C C, Yeh L S, Peng C T. *J. Assist. Reprod. Genet.* 2004, 21(12), 453-457). A separate study of Brazilian women found that shorter and longer [CAG](n) repeat alleles of AR were exclusive to the leiomyoma group in their study (Rosa F E, Canevari Rde A, Ambrosio E P, Ramos Cirilo P D, Pontes A, Rainho C A, Rogatto S R. *Clin. Chem. Lab. Med.* 2008, 46(6), 814-823). Similarly, in Asian Indian women long polyQ AR was associated with endometriosis and leiomyoma and can be regarded as high-risk markers. SARDs could be used in women with uterine fibroids, especially those expressing shorter and longer [CAG](n) repeat alleles, to treat existing uterine fibroids, prevent worsening of fibroids and/or ameliorate carcinogenicity associated with fibroids.

An abdominal aortic aneurysm (AAA) is an enlarged area in the lower part of the aorta, the major blood vessel that supplies blood to the body. The aorta, about the thickness of a garden hose, runs from your heart through the center of your chest and abdomen. Because the aorta is the body's main supplier of blood, a ruptured abdominal aortic aneurysm can cause life-threatening bleeding. Depending on the size and the rate at which your abdominal aortic aneurysm is growing, treatment may vary from watchful waiting to emergency surgery. Once an abdominal aortic aneurysm is found, doctors will closely monitor it so that surgery can be planned if it is necessary. Emergency surgery for a ruptured abdominal aortic aneurysm can be risky. AR blockade (pharmacologic or genetic) reduces AAA. Davis et al. (Davis J P, Salmon M, Pope N H, Lu G, Su G, Meher A, Ailawadi G, Upchurch G R Jr. J Vasc Surg (2016) 63(6): 1602-1612) showed that flutamide (50 mg/kg) or ketoconazole (150 mg/kg) attenuated porcine pancreatic elastase (0.35 U/mL) induced AAA by 84.2% and 91.5% compared to vehicle (121%). Further AR −/− mice showed attenuated AAA growth (64.4%) compared to wildtype (both treated with elastase). Correspondingly, administration of a SARD to a patient suffering from an AAA may help reverse, treat or delay progression of AAA to the point where surgery is needed.

X-linked spinal-bulbar muscular atrophy (SBMA—also known as Kennedy's disease) is a muscular atrophy that arises from a defect in the androgen receptor gene on the X chromosome. Proximal limb and bulbar muscle weakness results in physical limitations including dependence on a wheelchair in some cases. The mutation results in a protracted polyglutamine tract added to the N-terminal domain of the androgen receptor (polyQ AR). Binding and activation of this lengthened polyQ AR by endogeneous androgens (testosterone and DHT) results in unfolding and nuclear translocation of the mutant androgen receptor. The androgen-induced toxicity and androgen-dependent nuclear accumulation of polyQ AR protein seems to be central to the pathogenesis. Therefore, the inhibition of the androgen-activated polyQ AR might be a therapeutic option (A. Baniahmad. Inhibition of the androgen receptor by antiandrogens in spinobulbar muscle atrophy. *J. Mol. Neurosci.* 2016 58(3), 343-347). These steps are required for pathogenesis and result in partial loss of transactivation function (i.e., an androgen insensitivity) and a poorly understood neuromuscular degeneration. Support of use antiandrogen comes in a report in which the antiandrogen flutamide protects male mice from androgen-dependent toxicity in three models of spinal bulbar muscular atrophy (Renier K J, Troxell-Smith S M, Johansen J A, Katsuno M, Adachi H, Sobue G, Chua J P, Sun Kim H, Lieberman A P, Breedlove S M, Jordan C L. *Endocrinology* 2014, 155(7), 2624-2634). Currently there are no disease-modifying treatments but rather only symptom directed treatments. Efforts to target the polyQ AR of Kennedy's disease as the proximal mediator of toxicity by harnessing cellular machinery to promote its degradation, i.e., through the use of a SARD, hold promise for therapeutic intervention. Selective androgen receptor degraders such as those reported herein bind to and degrade all androgen receptors tested (full length, splice variant, antiandrogen resistance mutants, etc.) so degradation of polyQ AR polymorphism is also expected, indicating that they are promising leads for treatment of SBMA.

Here we describe, inter alia, pyrrole, pyrazole, triazole, imidazole, and morpholine based selective androgen receptor degrader (SARD) compounds that may bind to the LBD and/or an alternate binding and degradation domain (BDD) located in the NTD, antagonize AR, and degrade AR thereby blocking ligand-dependent and ligand-independent AR activities. This novel mechanism produces improved efficacy when dosed systemically (e.g., for prostate cancer) or topically (e.g., dermatological diseases).

SUMMARY OF THE INVENTION

In one embodiment this invention provides a method of treating prostate cancer in a subject in need thereof, comprising administering to the subject a therapeutically effective amount of a compound that binds to the N-terminal domain (NTD) of androgen receptor (AR).

In one embodiment this invention provides a method of treating prostate cancer in a subject in need thereof, comprising administering to the subject a therapeutically effective amount of a compound of this invention (of formula I-XXXIII) that binds to the N-terminal domain (NTD) of androgen receptor (AR).

In another embodiment, the NTD binding site for the compound is TAU-5.

In another embodiment, the NTD binding site for the compound binds between amino acid 380 and amino acid 529.

In another embodiment, the prostate cancer is advanced prostate cancer, castration resistant prostate cancer (CRPC), metastatic CRPC (mCRPC), non-metastatic CRPC (nm-CRPC), high-risk nmCRPC or any combination thereof.

In another embodiment, the subject has normal or high levels of endogenous androgens or irrespective of androgen levels.

In one embodiment, this invention provides a method of adjuvant therapy of prostate cancer (PCa), and/or of neoadjuvant therapy of prostate cancer (PCa), and/or of treatment of early disease prostate cancer (PCa), and/or of treatment of prostate cancer (PCa) in intact males, and/or of treatment of prostate cancer (PCa) prior to androgen deprivation therapy (ADT) or castration, and/or of first line therapy of PCa, comprising administering to a subject in need thereof, a therapeutically effective amount of a compound that binds to the N-terminal domain (NTD) of androgen receptor (AR).

In one embodiment, this invention provides a method of adjuvant therapy of prostate cancer (PCa), and/or of neoadjuvant therapy of prostate cancer (PCa), and/or of treatment of early disease prostate cancer (PCa), and/or of treatment of prostate cancer (PCa) in intact males, and/or of treatment of prostate cancer (PCa) prior to androgen deprivation therapy (ADT) or castration, and/or of first line therapy of PCa, comprising administering to a subject in need thereof, a therapeutically effective amount of a compound of this invention (of formula I-XXXIII) that binds to the N-terminal domain (NTD) of androgen receptor (AR).

In another embodiment, the NTD binding site for the compound is TAU-5.

In another embodiment, the NTD binding site for the compound binds between amino acid 380 and amino acid 529.

In another embodiment, the prostate cancer is advanced prostate cancer, castration resistant prostate cancer (CRPC), metastatic CRPC (mCRPC), non-metastatic CRPC (nm-CRPC), high-risk nmCRPC or any combination thereof.

In one embodiment, this invention provides a method of adjuvant therapy of prostate cancer (PCa), and/or of neoadjuvant therapy of prostate cancer (PCa), and/or of treatment of early disease prostate cancer (PCa), and/or of treatment of prostate cancer (PCa) in intact males, and/or of treatment of prostate cancer (PCa) prior to androgen deprivation therapy (ADT) or castration, and/or of first line therapy of PCa, comprising administering to a subject in need thereof, a therapeutically effective amount of a selective androgen receptor degrader (SARD) compound of this invention of formula I to XXXIII

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings.

FIG. 1A plotted the results with RLU reported on the y-axis and SARD concentration on the x-axis, where the antagonist mode was reported in closed dots. A curve was fitted to the closed dots. FIG. 1B illustrates the Western blot of the androgen receptor degradation assay with AD1 cells and the results were reported in Table 1, under SARD Activity: Full Length % Inhibition. FIG. 1C illustrates the Western blot of the androgen receptor degradation splice variant assay with D567es cells. (The results in 22RV1 cells were reported in Table 1, under 'SARD Activity: S.V. % Inhibition'.)

FIG. 2A plotted the results with RLU reported on the y-axis and SARD concentration on the x-axis, where the antagonist mode was reported for 11 and 1002. Compound 11 is represented in closed dots and solid line and 1002 is represented in open dots and dashed line. A curve was fitted to the open and closed dots for 1002 and 11, respectively. FIG. 2B illustrates the Western blots of an AR degradation assay with AD1 cells (Full Length AR) and a splice variant assay with 22RV1 cells for 11,11R (R-isomer of 11), 1002, and 1020 (R-isomer of 1002). The results were reported in Table 1 in columns labeled 'SARD Activity: Full Length % Inhibition' and 'SARD Activity: S.V. % Inhibition', respectively. In short, the R-isomer of indole and pyrazole SARDs retained SARD activity, in contrast to LBD-dependent inhibitors.

FIG. 3A plotted the results with RLU reported on the y-axis and SARD concentration on the x-axis, where the agonist mode was reported in closed dots and the antagonist mode was reported in open dots. A curve was fitted to the open dots. FIG. 3B illustrates the Western blot of the full length androgen receptor degradation assay and the results were reported in Table 1, under SARD Activity: Full Length % Inhibition.

FIG. 4A plotted the results with RLU reported on the y-axis and SARD concentration on the x-axis, where the agonist mode was reported in closed dots and antagonist mode was reported in open dots. A curve was fitted to the open dots. FIG. 4B illustrates the Western blot of the full length androgen receptor degradation assay and the results were reported in Table 1, under SARD Activity: Full Length % Inhibition. The numbers under the Western blot indicate the ratio of AR to actin in each lane.

FIG. 5A plotted the results with RLU reported on the y-axis and SARD concentration on the x-axis, where the agonist mode was reported in closed dots and antagonist mode was reported in open. A curve was fitted to the open dots. FIG. 5B illustrates the Western blot of the full length androgen receptor degradation assay and the results were reported in Table 1, under SARD Activity: Full Length % Inhibition.

FIG. 6A plotted the results with RLU reported on the y-axis and SARD concentration on the x-axis, where the agonist mode was reported in closed dots and antagonist mode was reported in open dots. A curve was fitted to the open dots. FIG. 6B illustrates the Western blot of the full length androgen receptor degradation assay and the results were reported in Table 1, under SARD Activity: Full Length % Inhibition.

FIG. 8 plotted the results with RLU reported on the y-axis and SARD concentration on the x-axis, where the antagonist mode was reported in closed dots. A curve was fitted to the closed dots.

FIG. 9 plotted the results with RLU reported on the y-axis and SARD concentration on the x-axis, where the antagonist mode was reported in closed dots. A curve was fitted to the closed dots.

FIG. 10 plotted the results with RLU reported on the y-axis and SARD concentration on the x-axis, where the antagonist mode was reported in closed dots. A curve was fitted to the closed dots.

FIG. 11 plotted the results with RLU reported on the y-axis and SARD concentration on the x-axis, where the antagonist mode was reported in closed dots. A curve was fitted to the closed dots.

FIG. 12 plotted the results with RLU reported on the y-axis and SARD concentration on the x-axis, where the antagonist mode was reported in closed dots. A curve was fitted to the closed dots.

FIG. 13A plotted the results with RLU reported on the y-axis and SARD concentration on the x-axis, where the antagonist mode was reported in closed dots. A curve was fitted to the closed dots. FIG. 13B illustrates the Western blot of the full length androgen receptor degradation assay and the results were reported in Table 1, under SARD Activity: Full Length % Inhibition. FIG. 13C illustrates the Western blot of the androgen receptor degradation splice variant assay with 22RV1 cells and the results were reported in Table 1, under SARD Activity: S.V. % Inhibition.

FIG. 14: FIG. 14 illustrates the phase I and phase I & II data as a raw data table for the determination of metabolic stability for 1002 in mouse liver microsomes (MLM) and the $T_{1/2}$ (half-life in minutes) and $CL_{int}$ (clearance in µL/min/mg protein) values calculated therefrom.

FIG. 15A reports phase I data as a raw data table and graphed data for one experiment for 1002 in mouse liver microsomes (MLM). FIG. 15B reports phase I & II data as a raw data table and graphed data for one experiment for 1002 in mouse liver microsomes (MLM). Value for $T_{1/2}$ was 224 min. $CL_{int}$ was 3.12 µL/min/mg.

FIG. 16A reports phase I data for human liver microsomes (HLM). FIG. 16B reports phase I & II data as a raw data table and graphed data for one experiment for 1002 in human liver microsomes (HLM). For this experiment, the caluculated value for $T_{1/2}$ was infinity and $CL_{int}$ was 0. Suggesting greater stability for 1002 in HLM than MLM.

FIG. 17 reports phase I data as a raw data table and graphed data for one experiment for 1001 in mouse liver microsomes (MLM). Value for $T_{1/2}$ was 23.5 min and $CL_{int}$ was 29.5 µL/min/mg. Results depict relatively poor stability for 1001, but still an improvement compared to 11.

FIG. 19A reports weights organs in intact Sprague Dawley rats with body weights of 165-180 grams treated daily with vehicle, 40 mg/kg 1002, 60 mg/kg 1002, or 20 mg/kg enzalutamide orally. After 13 days of treatment, the rats were sacrificed and the weights of prostate, seminal vesicles, and levator ani were measured. FIG. 19B reports the same data as a % decrease from vehicle. Bottom right pane illustrates intact vs. castrated % organ weights for vehicle treated rats.

FIG. 20A illustrates for each compound the Western blot of the full length androgen receptor degradation assay. The results were reported in Table 1, under SARD Activity: Full Length % Inhibition. FIG. 20B illustrates the Western blot of the androgen receptor degradation splice variant assay with D567es.

FIG. 27A depicts the perturbation of the fluorescent signal of AR-NTD and AR-AF1 in the presence of urea (denaturant), TMAO (folding stabilizer), and buffer, but no SARD. FIGS. 27B-27D depict the perturbations of AR-NTD and AR-AF1 fluorescence associated with the titrations of 1002 (FIG. 27B), 1010 (FIG. 27C), and 36 (FIG. 27D), respectively.

FIGS. 28A, 28C, and 28D illustrate the Western blots of the full length androgen receptor degradation assay. The results were reported in Table 1, under SARD Activity: Full Length % Inhibition. FIG. 28B illustrates the Western blots of the androgen receptor degradation splice variant assay with 22RV1 cells which are represented in Table 1 in the column labeled 'SARD Activity: S.V. % Inhibition'.

(FIG. 29A) Enzalutamide inhibited F876L AR at doses more potent than wildtype AR but was a weaker antagonist of W741L AR (FIG. 29B). However, when the assay was run in agonist mode (FIG. 29C), enzalutamide, at higher doses acted as an agonist of F876L AR. This is characteristic of agonist switch mutations in which AR antagonists of wildtype AR become AR agonists in due to the AR mutation. By comparison, SARDs like 1002 possess no intrinsic transcriptional agonist activity on wildtype AR or F876L AR, suggesting that tumors possessing agonist switch mutations can be inhibited by SARDs of this invention. Similarly, W741L is an agonist switch mutation conferring resistance to bicalutamide, which is inhibited by SARDs.

FIGS. 30A-30E: SARDs degrade the AR, AR-SV, and AR-F876L (MR49F), but not PR and ER (see ZR-75-1 cells). FIG. 30A: LNCaP (compound 11); FIG. 30B: LNCaP (compound 1002); FIG. 30C: ZR-75-1 (compound 1002); FIG. 30D: LNCaP-AR-V7 (compounds 11 and 1002); and FIG. 30E: MR49F (compound 1002). LNCaP cells possess the T877A mutation which confers resistance to flutamide (or hydroxyflutamide, the active metabolite) which demonstrates that SARDs will degrade an agonist switch mutant AR. Likewise, the F876L AR mutation confers resistance to enzalutamide and abiraterone and FIG. 30E demonstrates the ability to degrade this mutant. Cumulatively, this is good evidence that agonist switch mutations to current anti-androgens can be overcome with the SARDs of this invention.

FIG. 31A: compounds 11 and 1002; and FIG. 31B: compound 1002 and bortezomib. The FIG. 31A shows an immunoblot in which a fusion protein with AR connected to hemagglutinin (HA) is expressed in cells. Then the cells are treated with the indicated SARDs or untreated, the AR complex is immunoprecipitated with anti-HA, and run on a Western blot and visualized with anti-ubiquitin antibody (anti-Ub). In the untreated lane, there is no observed ubiquitination of AR, whereas there is various degrees of ubiquitination of AR in the SARD (11 and 1002) treated lanes which are apparent as a smear of AR molecular weights extending up from the fusion protein molecular weight. This indicated that the SARDs induced the ubiquitination of AR. Relative AR levels are shown under each lane (10% input:AR). FIG. 31B indicates that 1002 degrades AR at 10 micromolar in the presence of 50 micromolar cycloheximide. Further, bortezomib, a protease inhibitor, does not induce AR expression at 1, 5 and 10 micromolar. However, co-treatment of cells with 1002 and 1, 5 and 10 micromolar resulted in a dose responsive reversal of the SARD activity of 1002. Reversal of SARD activity by a proteasome inhibitor indicates that the 1002 and other SARDs of this invention work by a proteasome-dependent protein degradation pathway.

FIG. 34A: FKBP5 expression in LNCaP cells; FIG. 34B: Growth inhibition of LNCaP cells; FIG. 34C: FKBP5 expression in enzalutamide resistant (EnzR)LNCaP cells; and FIG. 34D: Growth inhibition in LNCaP-EnzR cells. 1002 inhibited the AR-dependent gene FKBP5 in either LNCaP and LNCaP-EnzR cells demonstrating the ability to inhibit the AR-axis in either CRPC's such as LNCaP (T877A) or enzalutamide resistant prostate cancers, and, correspondingly, to also inhibit cell growth in these AR-dependent cell lines whereas enzalutamide was unable to significantly inhibit FKBP5 or growth in the LNCaP-EnzR cell line.

(FIG. 37A) 14, 18, and 20; (FIG. 37B) 11 and 12; and (FIG. 37C) 11, 23 and 27; of this invention. (Example 21)

FIGS. 43A-43D present that 11 inhibits transactivation of AR-NTD-DBD-hinge (A/BCD) AR construct which lacks the LBD. (FIG. 43A) AR A/BCD increases GRE-LUC reporter activity. AR A/BCD construct that lacks the ligand binding domain or empty vector was transfected into HEK-293 cells along with GRE-LUC and CMV-renilla LUC. Forty eight hours after transfection cells were harvested and luciferase assay performed. (FIG. 43B) AR A/BCD activity was inhibited by 11. The A/BCD AR construct that lacks the ligand binding domain (LBD) was transfected along with GRE-LUC and CMV-LUC. Cells were treated 24 hrs after transfection as indicated in the figure and luciferase assay performed 48 hrs after transfection. 11 (a SARD) inhibited the activity of construct lacking LBD confirming the binding to an alternate site in addition to the LBD. (FIG. 43C) and (FIG. 43D) Non-SARD antagonists ARN-509 and enzalutamide did not inhibit the activity of this AR construct lacking the LBD, suggesting that of the compounds tested, only SARDs of this invention have the ability to inhibit ligand independent AR activity. (Example 25)

(FIG. 44A) 11, 12, and 14, galeterone, EPI-001, and enzalutamide; and (FIG. 44B) 11, galeterone, and enzalutamide. SARDs of this invention more potently inhibited (AR-FL) transactivation. (Example 26)

(FIG. 45A) 11 significantly reduced tumor volume and (FIG. 45B) tumor weight in a 22RV-1 xenograft tumor study, whereas AR antagonist enzalutamide did not have any effect compared to vehicle. (FIG. 45C) shows tumor expressed levels of AR-FL and AR-V7 were decreased by 11 but not enzalutamide, demonstrating that in vivo activity correlated with AR degradation in the tumors; and (FIG. 45D) demonstrates an in vivo antiandrogenic tone in gene expression as the serum PSA in these animals was decreased by 11 but not enzalutamide in this 22RV-1 xenograft study. (Example 27)

(FIG. 53A) A dose-dependent shift in the fluorescence intensity, i.e., fluorescent quenching, was observed with 11 when incubated with AR AF-1. (FIG. 53B) The fluorescence shoulder observed at 307 nm, which corresponds to tyrosine residues in the AF-1, is shifted by 11. The overall fluorescence is also markedly altered by 11. (FIG. 53C) Data shown was plotted as difference in fluorescence between control and 11 treated samples (fluorescence in the absence of compound–fluorescence in the presence of compound), a dose dependent increase was observed in the presence of 11. Cumulatively, these data suggest a direct interaction between 11 and AR AF-1. (Example 28)

(FIG. 65A) presents transactivation data for 42 ($IC_{50}$=1015 nM) and binding ($K_i$=86.1 nM). (Example 21) (FIG. 65B) presents transactivation data for 41 ($IC_{50}$=>10,000 nM) and binding ($K_i$=84.3 nM). (Example 21) (FIG. 65C) presents (1) transactivation data for 132 ($IC_{50}$=978.1 nM) and binding ($K_i$=353.2 nM), (2) AR full length degradation for 132, and (3) AR splice variant degradation for 132. (Example 22) (FIG. 65D) presents transactivation data for 40 ($IC_{50}$=1032.1 nM) and binding ($K_i$=134.9 nM). (Example 21) (FIG. 65E) presents (1) transactivation data for 92 ($IC_{50}$=946.8 nM) and binding ($K_i$=nM), (2) AR full length degradation for 92, and (3) AR splice variant D567es degradation for 92. (Example 21) (FIG. 65F) presents (1) transactivation data for 39 ($IC_{50}$=233.8 nM) and binding ($K_i$=719.9 nM), (2) AR full length degradation for 39. (Example 21) (FIG. 65G) presents (1) transactivation data for 38 ($IC_{50}$=318.4 nM) and binding ($K_i$=331.8 nM), (2) AR full length degradation for 38, and (3) AR splice variant AR-V7 degradation for 38. (Example 21) (FIG. 65H) presents (1) transactivation data for 11 ($IC_{50}$=96.4 nM) and 37 ($IC_{50}$=94.0 nM) and binding ($K_i$=252.6 nM), (2) AR full length degradation for 37, and (3) AR splice variant degradation for 37. (Example 21) (FIG. 65I) presents (1) transactivation data for 36 ($IC_{50}$=1142.0 nM) and binding ($K_i$=315.3 nM), (2) AR full length degradation for 36. (Example 21) (FIG. 65J) presents (1) transactivation data for 115 ($IC_{50}$=244.4 nM) and binding ($K_i$=71.5 nM), (2) AR full length degradation for 115, and (3) AR splice variant AR-V7 degradation for 115. (Example 22) (FIG. 65K) presents (1) transactivation data for 35 ($IC_{50}$=98.47 nM) and binding ($K_i$=155.7 nM) and (2) AR full length degradation for 35. (Example 21) (FIG. 65L) presents (1) transactivation data for 205 ($IC_{50}$=1079.1 nM) and binding ($K_i$=90.7 nM), (2) AR full length degradation for 205, and (3) AR splice variant AR-V7 degradation for 205. (Example 29) (FIG. 65M) presents (1) transactivation data for 114 ($IC_{50}$=834.7 nM) and binding ($K_i$=204.4 nM), (2) AR full length degradation for 114, and (3) AR splice variant AR-V7 degradation for 114. (Example 22) (FIG. 65N) presents transactivation data for 204 ($IC_{50}$=1025.4 nM) and binding ($K_i$=809.6 nM). (Example 29) (FIG. 65O) presents (1) transactivation data for 34 ($IC_{50}$=nM) and binding ($K_i$=nM), (2) AR full length degradation for 34, and (3) AR splice variant degradation for 34. (Example 21)

(FIG. 66A) and (FIG. 66D) SARDs demonstrated various degrees of decreased seminal vesicles (S.V.) weight, (FIG. 66B) increased in body weight (B.Wt.), and (FIG. 66C) decreased prostate weight. This behavior is consistent with an in vivo antiandrogenic effect exerted by SARDs of this invention. (Example 32)

FIGS. 69A-69D present binding ($K_i$), transactivation ($IC_{50}$), half-life in liver microsomes (MLM; $t_{1/2}$ (minutes)) and full-length AR degradation via Western blot of the androgen receptor with AD1 cells treated with: (FIG. 69A) 76, (FIG. 69B) 75, (FIG. 69C) 96, and (FIG. 69D) 97. (Example 23)

(FIG. 73E).

(FIG. 77A). 11 inhibits D567es-AR-transactivation and cell growth. AR transactivation was performed by transfecting human GRE-LUC and CMV-renilla LUC into D567es cells. Cells were treated with vehicle, 10 µM 11, or enzalutamide 24 hrs after transfection and luciferase assay was performed 48 hrs after transfection (left panel). Right: D567es cells plated in growth medium were treated with vehicle, 10 µM 11 or enzalutamide (FIG. 77B). Left: Cells were re-treated three days later and the cell viability was measured after 6 days of treatment using SRB assay (FIG. 77B).

(FIG. 78A). 11 inhibits nuclear translocation of enzalutamide-resistant AR (EnzR AR). EnzR LNCaP cells were maintained in charcoal-stripped serum (CSS) containing medium and treated with 10 µM 11 in the presence or absence of 0.1 nM R1881 for 4 hours. Translocation of the AR into nucleus was measured by immunofluorescence and quantified (FIG. 78B). Ligand binding of SARDs was critical for transactivation, but not for degradation. Molecular modeling shows the critical amino acids in the AR-LBD interacting with 11. The amino acids with which 11 forms hydrogen bond were mutated and transactivation assay was performed in HEK-293 cells. Left panel: shows that the mutants have weakened the R1881-induced transactivation. Right panel: was performed with a dose response of 11 in combination with 0.1 nM R1881 for wildtype AR, 10 nM R1881 for Q711A, R752L, and L704A, and 1 µM for N705A (FIG. 78C). Degradation of the wildtype and mutant AR by 11 was evaluated by transfecting the AR constructs in HeLa cells and treated as indicated in panel 42C for transactivation (FIG. 78D). Values in the graphs are $IC_{50}$. Enh—enhancer. ARE—Androgen Responsive Element. SRB—Sulforhodamine B. CSS—charcoal-stripped serum. DFCI—Dana-Farber Cancer Institute.

FIGS. 82A-82D: 11 binds to the AR Activation Function Domain 1 (AF-1) between amino acids 244 and 360. Nuclear magnetic resonance (NMR) studies confirm the binding to AR-AF-1. 11 or enzalutamide (500 µM) dissolved in deuterated-DMSO were either added to an NMR tube alone or in combination with 5 µM GST (negative control) or GST-AF-1 purified protein. The intensity of nuclear spin was measured at different magnetic fields (6 ppm). The peaks between 7 and 8 ppm (shown in box) correspond to the aromatic rings of 11 and enzalutamide (FIG. 82A). Waterlogsy experiment with 11 (200 µM) alone or in combination with 2 µM purified GST-AR-AF-1 was performed as a confirmation for binding (FIG. 82B). Map of various N-terminal domain fragments cloned, expressed, and corresponding proteins purified. Purified proteins and molecular weight markers are shown (M.Wt. of fragments=M.Wt.+ GST M.Wt. of 26 KDa) (FIG. 82C). NMR studies were performed with 11 (500 µM) was performed with 5 µM of various N-terminal domain fragments as described in panel 46C (FIG. 82D).

FIG. 86A: AR with phenylalanine 876 mutated to leucine (F876L), GRE-LUC, and CMV-renilla LUC were transfected in COS cells. Cells were treated 24 h after transfection with 0.1 nM R1881 (agonist) and a dose response of antagonists. Luciferase assay was performed 48 h after transfection. FIG. 86B: Enzalutamide-resistant LNCaP cells (MR49F) were maintained in charcoal-stripped, serum containing medium for 2 d and treated with 0.1 nM R1881 (agonist) and a titration of the SARD as indicated in the figure.

FIG. 88A: Mice (left) or rats (right) were treated with vehicle or indicated SARDs (40 mg/kg/day left panel) orally (n=5/group). Animals were sacrificed 14 d after treatment and weights of prostate and seminal vesicles were measured and normalized to body weight. FIG. 88B: Enzalutamide resistant LNCaP cells (5 million/mouse) were implanted subcutaneously in male NOD SCID Gamma (NSG) mice (n=7-9 per group). Animals were castrated when the tumors reached 100-200 mm$^3$ and allowed to regrow as castration-resistant tumors. Animals were treated orally with vehicle (DMSO:PEG-300 15:85) or 100 mg/kg/day of SARD. Tumor volume was measured twice weekly and represented as percent change. Values are expressed as average ±S.E. *=p<0.05.

(FIG. 90A) LNCaP cells were plated in serum free medium and treated with the indicated concentrations of compound 17 and ARN-509 in the presence or absence of R1881. Cells were harvested, protein extracted and Western blotted for AR and actin. (FIG. 90B) LNCaP cells were plated in 96 well plates at 10,000 cells/well in RPMI+1% csFBS without phenol red. Cells were treated as indicated above in combination with 0.1 nM R1881 for 6 days with medium change on day 3. At the end of 6 days, the cells were fixed and stained with sulphorhodamine blue stain to measure cell growth. Enzalutamide and ARN-509 are other AR antagonists reported to degrade AR.

FIG. 99A: There are two tryptophan residues and up to 12 tyrosine residues. This has allowed us to study the folding properties of this domain using intrinsic steady state fluorescence emission spectra. Excitation at 287 nm excites both tyrosine and tryptophan residues. The emission maximum ($\lambda_{max}$) for the tryptophan is sensitive to the exposure to solvent. In the presence of the natural osmolyte TMAO (AF1+TMAO) there is a characteristic 'blue shift' consistent with the tryptophan residues being less solvent exposed and a loss of the shoulder (~307 nm; see solid black trace as compared to AF1 (alone) which is the $2^{nd}$ to top trace at 300 nm in the left panel and top trace at 300 nm in the right panel) for tyrosine as there is increased energy transfer to tryptophan as the polypeptide folds. In contrast in the presence of urea (causes unfolding) there is a 'red shift' as the tryptophan residues become more solvent exposed and a defined peak for tyrosine emission appears. To test if the compounds (enobosarm (E) and 17) interact with AF-1 and/or alter the folding of this domain we measured the steady state fluorescence for each compound with AR-AF1 alone or the presence of TMAO (3 M) or urea (4 or 6 M). Enobosarm was used as a negative control (should not interact) while TMAO serves as a positive control (should promote folding). We used 1 μM of AR-AF1 and 5 μM of the individual compounds and preincubated for at least 30 minutes prior to measuring the emission spectra. The emission spectra were all corrected for buffer alone or buffer with TMAO/urea/compounds as necessary. There was no dramatic effect of enobosarm (left panel) on the $\lambda_{max}$ for tryptophan, while 17 (right panel) reduces the wavelength (i.e., a 'blue shift'), indicating that 17 binds to the AF-1 and enobosarm does not bind to AF-1. Also, the shoulder is missing on the AF1+TMAO+17 trace. FIG. 99B: Left Panel: A dose-dependent shift in the fluorescence intensity (i.e., quenching) by 17 was observed when incubated with AR AF-1. The fluorescence shoulder observed at 307 nm, which corresponds to tyrosine residues in the AF-1, is shifted by 17. The overall fluorescence is also markedly altered by 17. This indicates that 17 interacts with the AR AF-1 (in addition to the LBD binding demonstrated in other experiments). Right Panel. Data shown in the left panel was plotted as a difference in fluorescence plot between control and 17 treated samples (fluorescence in the absence of compound–fluorescence in the presence of compound), a dose dependent increase was observed in the presence of 17, again supporting that 17 interacts with the AR AF-1. AF1—activation function-1 which is a domain in the NTD of AR; TMAO—trimethylamine-N-oxide; E—enobosarm which is a selective androgen receptor modulator which does not bind NTD; 17—a selective androgen receptor degrader (SARD) of this invention.

(FIG. 101A). 17 comparably inhibited transactivation of wildtype and LBD-mutant AR. Transactivation assay with 17 was performed with wildtype AR or AR carrying commonly known LBD mutants. (FIG. 101B). 17 does not cross-react with mineralocorticoid receptor (MR) or glucocorticoid receptor (GR). Transactivation was performed by transfecting human AR, GR, or MR cDNA, GRE-LUC, and CMV-renilla LUC into HEK-293 cells. Cells were treated 24 hrs after transfection with indicated doses of 17 in combination with 0.1 nM R1881 (AR), dexamethasone (GR) and aldosterone (MR) and luciferase assay was performed 48 hrs after transfection. (FIG. 101C). 17 potently inhibited the expression of AR-target genes in LNCaP cells. LNCaP cells were maintained in charcoal stripped serum containing medium for two days and treated with vehicle or indicated compounds (17 or enzalutamide with concentration range between 1 and 10,000 nM) in the presence of 0.1 nM R1881. RNA was isolated and expression of PSA (not shown) or FKBP5 was quantified and normalized to GAPDH by real-time PCR (FIG. 101D).

FIG. 107A—left demonstrates that pyrazole 1002 and indole 11 degrade an AR construct lacking the ligand binding domain (LBD) (Ga14-AR-NTD-DBD), which is an evidence that the SARD bind to AR and induce its degradation via a region outside of the LBD. In an effort to determine which local domain(s) of AR-NTD are required for SARD activity, deletion mutation constructs were created in which amino acids 141-338 or 380-529 of hAR were deleted corresponding to Tau-1 and Tau-5 regions, respectively. In the right pane of FIG. 107A-107D, it is shown that deletion of Tau-5 region (AR-Tau5 (Del) or dtau5) prevented the degradation by pyrazole 1002 and indole 11. Whereas in FIGS. 107B-107D Tau-1 deletion mutant were degraded by pyrazole 1002. These domain deletion experiments provide evidence for the necessity of Tau-5 for SARD activity.

FIG. 110 demonstrates that enzalutamide resistant (MDVR) VCaP xenografts were regressed when treated with 1002 whereas to enzalutamide growth in intact animals was comparable to vehicle (i.e., MDVR is enzalutamide resistant in this model).

Figure 1A:
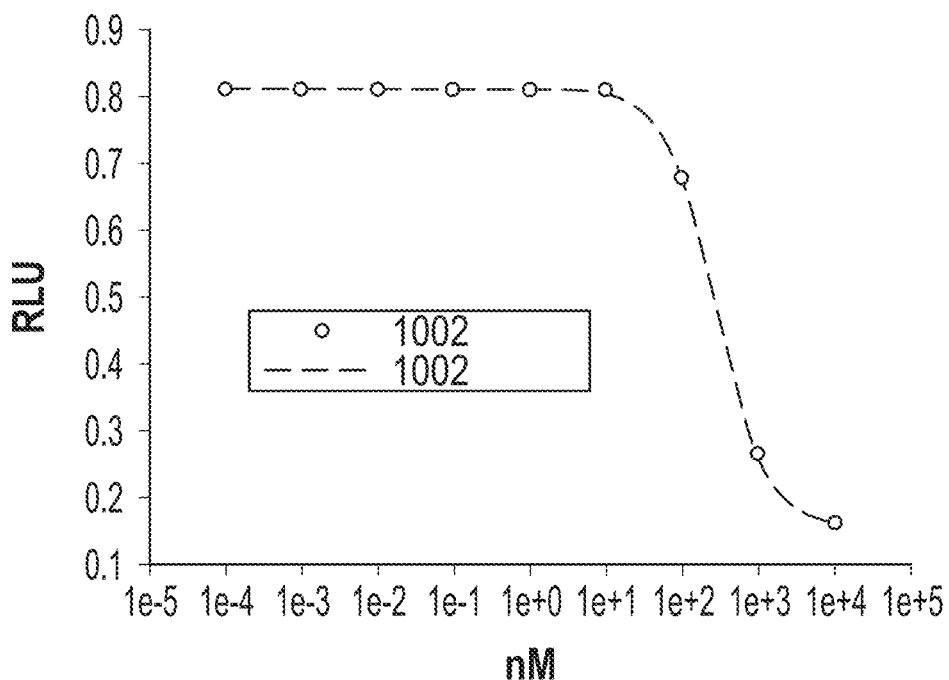
FIGS. 1A-1C: The transactivation result of 1002 was reported based on measured luciferase light emissions and reported as relative light unit intensity (RLU).

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Androgens act in cells by binding to the AR, a member of the steroid receptor superfamily of transcription factors. As the growth and maintenance of prostate cancer (PCa) is largely controlled by circulating androgens, treatment of PCa heavily relies on therapies that target AR. Treatment with AR antagonists such as enzalutamide, bicalutamide or hydroxyflutamide to disrupt receptor activation has been successfully used in the past to reduce PCa growth. All currently available AR antagonists competitively bind AR and recruit corepressors such as NCoR and SMRT to repress transcription of target genes. However, altered intracellular signaling, AR mutations, and increased expression of coactivators lead to functional impairment of antagonists or even transformation of antagonists into agonists. Studies have demonstrated that mutation of W741 and T877 within AR converts bicalutamide and hydroxyflutamide, respectively, to agonists. Similarly, increased intracellular cytokines recruit coactivators instead of corepressors to AR-responsive promoters subsequently converting bicalutamide to an agonist. Similarly, mutations that have been linked to enzalutamide resistance include F876, H874, T877, and di-mutants T877/S888, T877/D890, F876/T877 (i.e., MR49 cells), and H874/T877 (*Genome Biol.* (2016) 17:10 (doi: 10.1186/s13059-015-0864-1)). Abiraterone resistance mutations include L702H mutations which results in activation of the AR by glucocorticoids such as prednisone, causing resistance to abiraterone because abiraterone is usually prescribed in combination with prednisone. If resistance develops to enzalutamide then often the patient is refractory to abiraterone also and vice versa; or the duration of response is very short. This situation highlights the need for a definitive androgen ablation therapy to prevent AR reactivation in advanced prostate cancers.

Despite initial response to androgen deprivation therapy (ADT), PCa disease progression is inevitable and the cancer emerges as castration-resistant prostate cancer (CRPC). The primary reason for castration resistant prostate cancer (CRPC) re-emergence is re-activation of androgen receptor (AR) by alternate mechanisms such as:
  (a) intracrine androgen synthesis;
  (b) expression of AR splice variants (AR-SV), e.g., that lack ligand binding domain (LBD);
  (c) AR-LBD mutations with potential to resist antagonists;
  (d) hyper-sensitization of AR to low androgen levels, e.g., due to AR gene amplification or AR mutation;
  (e) amplification of the AR gene within the tumor; and
  (f) over expression of coactivators and/or altered intracellular signal transduction.

The invention encompasses selective androgen receptor degrader (SARD) compounds, which inhibit the growth of prostate cancer (PCa) cells and tumors that are dependent on AR full length (AR-FL) including pathogenic and resistance mutations and wildtype, and/or AR splice variants (AR-SV) for proliferation.

As used herein, unless otherwise defined, a "selective androgen receptor degrader" (SARD) compound is an androgen receptor antagonist capable of inhibiting the growth of PCa cells and tumors that are dependent on AR-full length (AR-FL) and/or AR splice variants (AR-SV) for proliferation. Alternatively, a "selective androgen receptor degrader" (SARD) compound is an androgen receptor antagonist capable of causing degradation of a variety of pathogenic mutant variant AR's and wildtype AR and hence are capable of exerting anti-androgenism is a wide variety of pathogenic altered cellular environments found in the disease states embodied in this invention. In one embodiment, the SARD is orally active. In another embodiment, the SARD is applied topically to the site of action.

The SARD compound may bind to the N-terminal domain (NTD) of the AR; to an alternate binding and degradation domain (BDD) of the AR; to both the AR ligand binding domain (LBD) and to an alternate binding and degradation domain (BDD); or to both the N-terminal domain (NTD) and to the ligand binding domain (LBD) of the AR. In one embodiment, the BDD may be located in the NTD. In one embodiment, the BDD is located in the AF-1 region of the NTD. Alternatively, the SARD compound may be capable of: inhibiting growth driven by the N-terminal domain (NTD)-dependent constitutively active AR-SV; or inhibiting the AR through binding to a domain that is distinct from the AR LBD. Also, the SARD compound may be a strong (i.e., highly potent and highly efficacious) selective androgen receptor antagonist, which antagonizes the AR stronger than other known AR antagonists (e.g., enzalutamide, bicalutamide and abiraterone).

The SARD compound may be a selective androgen receptor antagonist, which targets AR-SVs, which cannot be inhibited by conventional antagonists. The SARD compound may exhibit any one of several activities including, but not limited to: AR-SV degradation activity; AR-FL degradation activity; AR-SV inhibitory activity (i.e., is an AR-SV antagonist); AR-FL inhibitory activity (i.e., is an AR-FL antagonist); inhibition of the constitutive activation of AR-SVs; or inhibition of the constitutive activation of AR-FLs. Alternatively, the SARD compound may possess dual AR-SV degradation and AR-SV inhibitory functions, and/or dual AR-FL degradation and AR-FL inhibitory functions; or alternatively possess all four of these activities.

The SARD compound may also degrade AR-FL and AR-SV. The SARD compound may degrade the AR through binding to a domain that is distinct from the AR LBD. The SARD compound may possess dual degradation and AR-SV inhibitory functions that are distinct from any available CRPC therapeutics. The SARD compound may inhibit the re-activation of the AR by alternate mechanisms such as: intracrine androgen synthesis, expression of AR-SV that lack ligand binding domain (LBD) and AR-LBD mutations with potential to resist antagonists, or inhibit re-activated androgen receptors present in pathogenic altered cellular environments.

Examples of AR-splice variants include, but are not limited to, AR-V7 and ARv567es (a.k.a. AR-V12; S. Sun, et al. Castration resistance in human prostate cancer is conferred by a frequently occurring androgen receptor splice variant. *J. Clin Invest.* (2010) 120(8), 2715-2730). Nonlimiting examples of AR mutations conferring antiandrogen resistance are: W741L, T877A, and F876L (J. D. Joseph et al. A clinically relevant androgen receptor mutation confers resistance to second-generation antiandrogens enzalutamide and ARN-509. *Cancer Discov.* (2013) 3(9), 1020-1029) mutations. Many other LBD resistance conferring mutations are known in the art and will continue to be discovered. AR-V7 is a splice variant of AR that lacks the LBD (A. H. Bryce & E. S. Antonarakis. Androgen receptor splice variant 7 in castration-resistant prostate cancer: Clinical considerations. *Int J Urol.* (2016 Jun. 3) 23(8), 646-53. doi: 10.1111/iju.13134). It is constitutively active and has been demonstrated to be responsible for aggressive PCa and resistance to endocrine therapy.

In one embodiment this invention provides a method of treating prostate cancer in a subject in need thereof, comprising administering to the subject a therapeutically effective amount of a compound that binds to the N-terminal domain (NTD) of androgen receptor (AR).

In one embodiment this invention provides a method of treating prostate cancer in a subject in need thereof, comprising administering to the subject a therapeutically effective amount of a compound of this invention (of formula I-XXXIII) that binds to the N-terminal domain (NTD) of androgen receptor (AR).

In another embodiment, the NTD binding site for the compound is TAU-5.

In another embodiment, the NTD binding site for the compound binds between amino acid 380 and amino acid 529.

In another embodiment, the prostate cancer is advanced prostate cancer, castration resistant prostate cancer (CRPC), metastatic CRPC (mCRPC), non-metastatic CRPC (nm-CRPC), high-risk nmCRPC or any combination thereof.

In another embodiment, the subject has normal or high levels of endogenous androgens or irrespective of androgen levels.

The SARD compounds may be used in treating CRPC that cannot be treated with any other antagonist. The SARD compounds may treat CRPC by degrading AR-SVs. The SARD compounds may maintain their antagonistic activity in AR mutants that normally convert AR antagonists to agonists. For instance, the SARD compounds maintain their antagonistic activity to AR mutants W741L, T877A, and F876L (J. D. Joseph et al. A clinically relevant androgen receptor mutation confers resistance to second-generation antiandrogens enzalutamide and ARN-509. *Cancer Discov.* (2013) 3(9), 1020-1029). Alternatively, the SARD compounds elicit antagonistic activity within an altered cellular environment in which LBD-targeted agents are not effective or in which NTD-dependent AR activity is constitutively active.

In one embodiment, this invention provides a method of adjuvant therapy of prostate cancer (PCa), and/or of neoadjuvant therapy of prostate cancer (PCa), and/or of treatment of early disease prostate cancer (PCa), and/or of treatment of prostate cancer (PCa) in intact males, and/or of treatment of prostate cancer (PCa) prior to androgen deprivation therapy (ADT) or castration, and/or of first line therapy of PCa, comprising administering to a subject in need thereof, a therapeutically effective amount of a compound that binds to the N-terminal domain (NTD) of androgen receptor (AR).

In one embodiment, this invention provides a method of adjuvant therapy of prostate cancer (PCa), and/or of neoadjuvant therapy of prostate cancer (PCa), and/or of treatment of early disease prostate cancer (PCa), and/or of treatment of prostate cancer (PCa) in intact males, and/or of treatment of prostate cancer (PCa) prior to androgen deprivation therapy (ADT) or castration, and/or of first line therapy of PCa, comprising administering to a subject in need thereof, a therapeutically effective amount of a compound of this invention (of formula I-XXXIII) that binds to the N-terminal domain (NTD) of androgen receptor (AR).

In another embodiment, the NTD binding site for the compound is TAU-5.

In another embodiment, the NTD binding site for the compound binds between amino acid 380 and amino acid 529.

In another embodiment, the prostate cancer is advanced prostate cancer, castration resistant prostate cancer (CRPC), metastatic CRPC (mCRPC), non-metastatic CRPC (nm-CRPC), high-risk nmCRPC or any combination thereof.

In one embodiment, this invention provides a method of adjuvant therapy of prostate cancer (PCa), and/or of neoadjuvant therapy of prostate cancer (PCa), and/or of treatment of early disease prostate cancer (PCa), and/or of treatment of prostate cancer (PCa) in intact males, and/or of treatment of prostate cancer (PCa) prior to androgen deprivation therapy (ADT) or castration, and/or of first line therapy of PCa, comprising administering to a subject in need thereof, a therapeutically effective amount of a selective androgen receptor degrader (SARD) compound of this invention of formula I to XXXIII.

Selective Androgen Receptor Degrader (SARD) Compounds

The invention encompasses selective androgen receptor degrader (SARD) compounds represented by the structure of formula I:

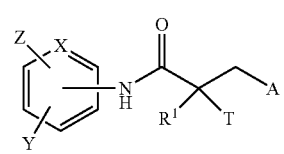

I wherein
T is H, OH, OR, OCOR, $CH_3$, —$NHCOCH_3$, or NHCOR;
$R^1$ is H, $CH_3$, $CH_2F$, $CHF_2$, $CF_3$, $CH_2CH_3$, or $CF_2CF_3$;
or T and $R^1$ form a 3-8 carbocyclic or heterocyclic ring;
Y is H, $CF_3$, F, I, Br, Cl, CN, or $C(R)_3$;
Z is H, $NO_2$, CN, halide, COOH, COR, NHCOR, CONHR,
or Y and Z form a 5 to 8 membered fused ring;
X is CH or N;
R is H, alkyl, alkenyl, haloalkyl, alcohol, $CH_2CH_2OH$, $CF_3$, $CH_2Cl$, $CH_2CH_2Cl$, aryl, F, Cl, Br, I, or OH;
A is $R^2$ or $R^3$;
$R^2$ is a five or six-membered saturated or unsaturated ring having at least one nitrogen atom and 0, 1, or 2 double bonds, optionally substituted with at least one of $Q^1$, $Q^2$, $Q^3$, or $Q^4$, each independently selected from hydrogen, keto, substituted or unsubstituted linear or branched alkyl, substituted or unsubstituted cycloalkyl, substituted or unsubstituted heterocycloalkyl, haloalkyl, $CF_3$, substituted or unsubstituted aryl, substituted or unsubstituted phenyl, F, Cl, Br, I, CN, $NO_2$, hydroxyl, alkoxy, OR, arylalkyl, NCS, maleimide, NHCOOR, $N(R)_2$, NHCOR, CONHR, COOR or COR;
$R^3$ is $NHR^2$, halide, N3, $OR^4$, $CF_3$, $COR^4$, COCl, COO-$COR^4$, $COOR^4$, $OCOR^4$, $OCONHR^4$, $NHCOOR^4$, $NHCONHR^4$, $OCOOR^4$, CN, $CONH_2$, $CONH(R^4)$, $CON(R^4)_2$, $SR^4$, $SO_2R^4$, $SOR^4$ $SO_3H$, $SO_2NH_2$, $SO_2NH(R^4)$, $SO_2N(R^4)_2$, $NH_2$, $NH(R^4)$, $N(R^4)_2$, CO(N-heterocycle), $NO_2$, cyanate, isocyanate, thiocyanate, isothiocyanate, mesylate, tosylate, triflate, $PO(OH)_2$ or $OPO(OH)_2$; and
$R^4$ is H, alkyl, haloalkyl, cycloalkyl, aryl or heteroaryl, wherein said alkyl, haloalkyl, cycloalkyl, aryl or heteroaryl groups are optionally substituted;
or its optical isomer, isomer, pharmaceutically acceptable salt, pharmaceutical product, polymorph, hydrate or any combination thereof;
wherein if A is Br or I, $R^1$ is $CH_3$, and T is OH, then X is N or the aniline ring forms a fused heterocyclic ring.

In various embodiments, the SARD compound of formula I has a chiral carbon. In other embodiments, the SARD compound of formula I is a racemic mixture. In other embodiments, the SARD compound of formula I is an (S) isomer. In other embodiments, the SARD compound of formula I is an (R) isomer.

The invention encompasses selective androgen receptor degrader (SARD) compounds represented by the structure of formula IA:

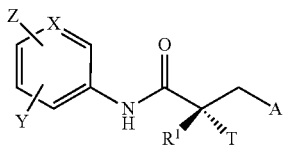

IA wherein
T is H, OH, OR, OCOR, $CH_3$, —$NHCOCH_3$, or NHCOR;
$R^1$ is H, $CH_3$, $CH_2F$, $CHF_2$, $CF_3$, $CH_2CH_3$, or $CF_2CF_3$;
or T and $R^1$ form a 3-8 carbocyclic or heterocyclic ring;
Y is H, $CF_3$, F, I, Br, Cl, CN, or $C(R)_3$;
Z is H, $NO_2$, CN, halide, COOH, COR, NHCOR, CONHR,
or Y and Z form a 5 to 8 membered fused ring;
X is CH or N;
R is H, alkyl, alkenyl, haloalkyl, alcohol, $CH_2CH_2OH$, $CF_3$, $CH_2Cl$, $CH_2CH_2Cl$, aryl, F, Cl, Br, I, or OH;
A is $R^2$ or $R^3$;
$R^2$ is a five or six-membered saturated or unsaturated ring having at least one nitrogen atom and 0, 1, or 2 double bonds, optionally substituted with at least one of $Q^1$, $Q^2$, $Q^3$, or $Q^4$, each independently selected from hydrogen, keto, substituted or unsubstituted linear or branched alkyl, substituted or unsubstituted cycloalkyl, substituted or unsubstituted heterocycloalkyl, haloalkyl, $CF_3$, substituted or unsubstituted aryl, substituted or unsubstituted phenyl, F, Cl, Br, I, CN, $NO_2$, hydroxyl, alkoxy, OR, arylalkyl, NCS, maleimide, NHCOOR, $N(R)_2$, NHCOR, CONHR, COOR or COR;
$R^3$ is $NHR^2$, halide, $N_3$, $OR^4$, $CF_3$, $COR^4$, COCl, $COOCOR^4$, $COOR^4$, $OCOR^4$, $OCONHR^4$, $NHCOOR^4$, $NHCONHR^4$, $OCOOR^4$, CN, $CONH_2$, $CONH(R^4)$, $CON(R^4)_2$, $SR^4$, $SO_2R^4$, $SOR^4$ $SO_3H$, $SO_2NH_2$, $SO_2NH(R^4)$, $SO_2N(R^4)_2$, $NH_2$, $NH(R^4)$, $N(R^4)_2$, CO(N-heterocycle), $NO_2$, cyanate, isocyanate, thiocyanate, isothiocyanate, mesylate, tosylate, triflate, $PO(OH)_2$ or $OPO(OH)_2$; and
$R^4$ is H, alkyl, haloalkyl, cycloalkyl, aryl or heteroaryl, wherein said alkyl, haloalkyl, cycloalkyl, aryl or heteroaryl groups are optionally substituted;

or its isomer, pharmaceutically acceptable salt, pharmaceutical product, polymorph, hydrate or any combination thereof;
wherein if A is Br or I, $R^1$ is $CH_3$, and T is OH, then X is N or the aniline ring forms a fused heterocyclic ring.

The invention encompasses selective androgen receptor degrader (SARD) compounds represented by the structure of formula IB:

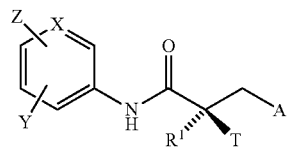

IB wherein
T is H, OH, OR, OCOR, $CH_3$, —$NHCOCH_3$, or NHCOR;
$R^1$ is H, $CH_3$, $CH_2F$, $CHF_2$, $CF_3$, $CH_2CH_3$, or $CF_2CF_3$;
or T and $R^1$ form a 3-8 carbocyclic or heterocyclic ring;
Y is H, $CF_3$, F, I, Br, Cl, CN, or $C(R)_3$;
Z is H, $NO_2$, CN, halide, COOH, COR, NHCOR, CONHR,
or Y and Z form a 5 to 8 membered fused ring;
X is CH or N;
R is H, alkyl, alkenyl, haloalkyl, alcohol, $CH_2CH_2OH$, $CF_3$, $CH_2Cl$, $CH_2CH_2Cl$, aryl, F, Cl, Br, I, or OH;
A is $R^2$ or $R^3$;
$R^2$ is a five or six-membered saturated or unsaturated ring having at least one nitrogen atom and 0, 1, or 2 double bonds, optionally substituted with at least one of $Q^1$, $Q^2$, $Q^3$, or $Q^4$, each independently selected from hydrogen, keto, substituted or unsubstituted linear or branched alkyl, substituted or unsubstituted cycloalkyl, substituted or unsubstituted heterocycloalkyl, haloalkyl, $CF_3$, substituted or unsubstituted aryl, substituted or unsubstituted phenyl, F, Cl, Br, I, CN, $NO_2$, hydroxyl, alkoxy, OR, arylalkyl, NCS, maleimide, NHCOOR, $N(R)_2$, NHCOR, CONHR, COOR or COR;
$R^3$ is $NHR^2$, halide, $N_3$, $OR^4$, $CF_3$, $COR^4$, COCl, $COOCOR^4$, $COOR^4$, $OCOR^4$, $OCONHR^4$, $NHCOOR^4$, $NHCONHR^4$, $OCOOR^4$, CN, $CONH_2$, $CONH(R^4)$, $CON(R^4)_2$, $SR^4$, $SO_2R^4$, $SOR^4$ $SO_3H$, $SO_2NH_2$, $SO_2NH(R^4)$, $SO_2N(R^4)_2$, $NH_2$, $NH(R^4)$, $N(R^4)_2$, CO(N-heterocycle), $NO_2$, cyanate, isocyanate, thiocyanate, isothiocyanate, mesylate, tosylate, triflate, $PO(OH)_2$ or $OPO(OH)_2$; and
$R^4$ is H, alkyl, haloalkyl, cycloalkyl, aryl or heteroaryl, wherein said alkyl, haloalkyl, cycloalkyl, aryl or heteroaryl groups are optionally substituted;

or its isomer, pharmaceutically acceptable salt, pharmaceutical product, polymorph, hydrate or any combination thereof;
wherein if A is Br or I, $R^1$ is $CH_3$, and T is OH, then X is N or the aniline ring forms a fused heterocyclic ring.

The invention encompasses selective androgen receptor degrader (SARD) compounds represented by the structure of formula IC:

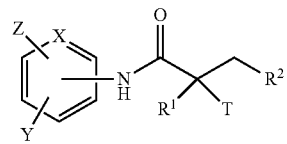

IC wherein
T is H, OH, OR, OCOR, $CH_3$, —$NHCOCH_3$, or NHCOR;
$R^1$ is H, $CH_3$, $CH_2F$, $CHF_2$, $CF_3$, $CH_2CH_3$, or $CF_2CF_3$;
or T and $R^1$ form a 3-8 carbocyclic or heterocyclic ring;
Y is H, $CF_3$, F, I, Br, Cl, CN, or $C(R)_3$;

Z is H, NO$_2$, CN, halide, COOH, COR, NHCOR, CONHR, or Y and Z form a 5 to 8 membered fused ring;

X is CH or N;

R is H, alkyl, alkenyl, haloalkyl, alcohol, CH$_2$CH$_2$OH, CF$_3$, CH$_2$Cl, CH$_2$CH$_2$Cl, aryl, F, Cl, Br, I, or OH;

R$^2$ is a five or six-membered saturated or unsaturated ring having at least one nitrogen atom and 0, 1, or 2 double bonds, optionally substituted with at least one of Q$^1$, Q$^2$, Q$^3$, or Q$^4$, each independently selected from hydrogen, keto, substituted or unsubstituted linear or branched alkyl, substituted or unsubstituted cycloalkyl, substituted or unsubstituted heterocycloalkyl, haloalkyl, CF$_3$, substituted or unsubstituted aryl, substituted or unsubstituted phenyl, F, Cl, Br, I, CN, NO$_2$, hydroxyl, alkoxy, OR, arylalkyl, NCS, maleimide, NHCOOR, N(R)$_2$, NHCOR, CONHR, COOR or COR;

or its optical isomer, isomer, pharmaceutically acceptable salt, pharmaceutical product, polymorph, hydrate or any combination thereof.

The invention encompasses selective androgen receptor degrader (SARD) compounds represented by the structure of formula ID:

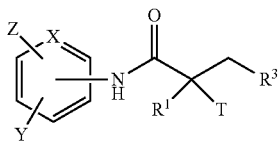

ID wherein

T is H, OH, OR, OCOR, CH$_3$, —NHCOCH$_3$, or NHCOR;

R$^1$ is H, CH$_3$, CH$_2$F, CHF$_2$, CF$_3$, CH$_2$CH$_3$, or CF$_2$CF$_3$;

or T and R$^1$ form a 3-8 carbocyclic or heterocyclic ring;

Y is H, CF$_3$, F, I, Br, Cl, CN, or C(R)$_3$;

Z is H, NO$_2$, CN, halide, COOH, COR, NHCOR, CONHR, or Y and Z form a 5 to 8 membered fused ring;

X is CH or N;

R is H, alkyl, alkenyl, haloalkyl, alcohol, CH$_2$CH$_2$OH, CF$_3$, CH$_2$Cl, CH$_2$CH$_2$Cl, aryl, F, Cl, Br, I, or OH;

R$^3$ is NHR$^2$, halide, N$_3$, OR$^4$, CF$_3$, COR$^4$, COCl, COO-COR$^4$, COOR$^4$, OCOR$^4$, OCONHR$^4$, NHCOOR$^4$, NHCONHR$^4$, OCOOR$^4$, CN, CONH$_2$, CONH(R$^4$), CON(R$^4$)$_2$, SR$^4$, SO$_2$R$^4$, SOR$^4$ SO$_3$H, SO$_2$NH$_2$, SO$_2$NH(R$^4$), SO$_2$N(R$^4$)$_2$, NH$_2$, NH(R$^4$), N(R$^4$)$_2$, CO(N-heterocycle), NO$_2$, cyanate, isocyanate, thiocyanate, isothiocyanate, mesylate, tosylate, triflate, PO(OH)$_2$ or OPO(OH)$_2$; and R$^4$ H, is alkyl, haloalkyl, cycloalkyl, aryl or heteroaryl, wherein said alkyl, haloalkyl, cycloalkyl, aryl or heteroaryl groups are optionally substituted;

or its optical isomer, isomer, pharmaceutically acceptable salt, pharmaceutical product, polymorph, hydrate or any combination thereof;

wherein if R$^3$ is Br or I, R$^1$ is CH$_3$, and T is OH, then X is N or the aniline ring forms a fused heterocyclic ring.

The invention encompasses a SARD compound represented by the structure of formula II:

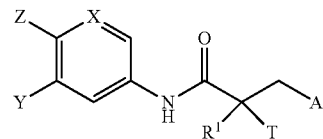

II wherein

T is H, OH, OR, OCOR, CH$_3$, —NHCOCH$_3$, or NHCOR;

R$^1$ is H, CH$_3$, CH$_2$F, CHF$_2$, CF$_3$, CH$_2$CH$_3$, or CF$_2$CF$_3$;

or T and R$^1$ form a 3-8 carbocyclic or heterocyclic ring;

Y is H, CF$_3$, F, I, Br, Cl, CN, or C(R)$_3$;

Z is H, NO$_2$, CN, halide, COOH, COR, NHCOR, CONHR, or Y and Z form a 5 to 8 membered fused ring;

X is CH or N;

R is H, alkyl, alkenyl, haloalkyl, alcohol, CH$_2$CH$_2$OH, CF$_3$, CH$_2$Cl, CH$_2$CH$_2$Cl, aryl, F, Cl, Br, I, or OH;

A is R$^2$ or R$^3$;

R$^2$ is a pyrrole, pyrroline, pyrrolidine, pyrazole, pyrazoline, pyrazolidine, triazole, imidazole, imidazoline, imidazolidine, or morpholine ring, said ring optionally substituted with at least one of Q$^1$, Q$^2$, Q$^3$, or Q$^4$, each independently selected from hydrogen, keto, substituted or unsubstituted linear or branched alkyl, substituted or unsubstituted cycloalkyl, substituted or unsubstituted heterocycloalkyl, haloalkyl, CF$_3$, substituted or unsubstituted aryl, substituted or unsubstituted phenyl, F, Cl, Br, I, CN, NO$_2$, hydroxyl, alkoxy, OR, arylalkyl, NCS, maleimide, NHCOOR, N(R)$_2$, NHCOR, CONHR, COOR or COR;

R$^3$ is NHR$^2$, halide, N$_3$, OR$^4$, CF$_3$, COR$^4$, COCl, COO-COR$^4$, COOR$^4$, OCOR$^4$, OCONHR$^4$, NHCOOR$^4$, NHCONHR$^4$, OCOOR$^4$, CN, CONH$_2$, CONH(R$^4$), CON(R$^4$)$_2$, SR$^4$, SO$_2$R$^4$, SOR$^4$ SO$_3$H, SO$_2$NH$_2$, SO$_2$NH(R$^4$), SO$_2$N(R$^4$)$_2$, NH$_2$, NH(R$^4$), N(R$^4$)$_2$, CO(N-heterocycle), NO$_2$, cyanate, isocyanate, thiocyanate, isothiocyanate, mesylate, tosylate, triflate, PO(OH)$_2$ or OPO(OH)$_2$; and R$^4$ is H, alkyl, haloalkyl, cycloalkyl, aryl or heteroaryl, wherein said alkyl, haloalkyl, cycloalkyl, aryl or heteroaryl groups are optionally substituted;

or its optical isomer, isomer, pharmaceutically acceptable salt, pharmaceutical product, polymorph, hydrate or any combination thereof;

wherein if A is Br or I, R$^1$ is CH$_3$, and T is OH, then X is N or the aniline ring forms a fused heterocyclic ring.

In various embodiments, the SARD compound of formula II has a chiral carbon. In other embodiments, the SARD compound of formula II is a racemic mixture. In other embodiments, the SARD compound of formula II is an (S) isomer. In other embodiments, the SARD compound of formula II is an (R) isomer.

The invention encompasses a SARD compound represented by the structure of formula IIA:

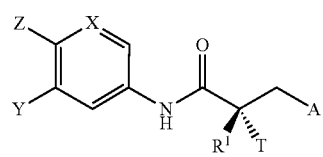

IIA wherein
T is H, OH, OR, OCOR, CH₃, —NHCOCH₃, or NHCOR;
R¹ is H, CH₃, CH₂F, CHF₂, CF₃, CH₂CH₃, or CF₂CF₃;
or T and R¹ form a 3-8 carbocyclic or heterocyclic ring;
Y is H, CF₃, F, I, Br, Cl, CN, or C(R)₃;
Z is H, NO₂, CN, halide, COOH, COR, NHCOR, CONHR,
or Y and Z form a 5 to 8 membered fused ring;
X is CH or N;
R is H, alkyl, alkenyl, haloalkyl, alcohol, CH₂CH₂OH, CF₃, CH₂Cl, CH₂CH₂Cl, aryl, F, Cl, Br, I, or OH;
A is R² or R³;
R² is a pyrrole, pyrroline, pyrrolidine, pyrazole, pyrazoline, pyrazolidine, triazole, imidazole, imidazoline, imidazolidine, or morpholine ring, said ring optionally substituted with at least one of Q¹, Q², Q³, or Q⁴, each independently selected from hydrogen, keto, substituted or unsubstituted linear or branched alkyl, substituted or unsubstituted cycloalkyl, substituted or unsubstituted heterocycloalkyl, haloalkyl, CF₃, substituted or unsubstituted aryl, substituted or unsubstituted phenyl, F, Cl, Br, I, CN, NO₂, hydroxyl, alkoxy, OR, arylalkyl, NCS, maleimide, NHCOOR, N(R)₂, NHCOR, CONHR, COOR or COR;
R³ is NHR², halide, N₃, OR⁴, CF₃, COR⁴, COCl, COOCOR⁴, COOR⁴, OCOR⁴, OCONHR⁴, NHCOOR⁴, NHCONHR⁴, OCOOR⁴, CN, CONH₂, CONH(R⁴), CON(R⁴)₂, SR⁴, SO₂R⁴, SOR⁴ SO₃H, SO₂NH₂, SO₂NH(R⁴), SO₂N(R⁴)₂, NH₂, NH(R⁴), N(R⁴)₂, CO(N-heterocycle), NO₂, cyanate, isocyanate, thiocyanate, isothiocyanate, mesylate, tosylate, triflate, PO(OH)₂ or OPO(OH)₂; and
R⁴ is H, alkyl, haloalkyl, cycloalkyl, aryl or heteroaryl, wherein said alkyl, haloalkyl, cycloalkyl, aryl or heteroaryl groups are optionally substituted;
or its isomer, pharmaceutically acceptable salt, pharmaceutical product, polymorph, hydrate or any combination thereof;
wherein if A is Br or I, R¹ is CH₃, and T is OH, then X is N or the aniline ring forms a fused heterocyclic ring.

The invention encompasses a SARD compound represented by the structure of formula JIB:

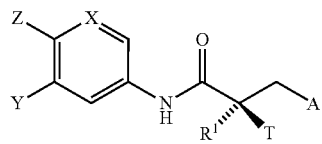

IIB wherein
R¹ is H, CH₃, CH₂F, CHF₂, CF₃, CH₂CH₃, or CF₂CF₃;
or T and R¹ form a 3-8 carbocyclic or heterocyclic ring;
T is H, OH, OR, OCOR, CH₃, —NHCOCH₃, or NHCOR;
Y is H, CF₃, F, I, Br, Cl, CN, or C(R)₃;
Z is H, NO₂, CN, halide, COOH, COR, NHCOR, CONHR,
or Y and Z form a 5 to 8 membered fused ring;
X is CH or N;
R is H, alkyl, alkenyl, haloalkyl, alcohol, CH₂CH₂OH, CF₃, CH₂Cl, CH₂CH₂Cl, aryl, F, Cl, Br, I, or OH;
A is R² or R³;
R² a pyrrole, pyrroline, pyrrolidine, pyrazole, pyrazoline, pyrazolidine, triazole, imidazole, imidazoline, imidazolidine, or morpholine ring, said ring optionally substituted with at least one of Q¹, Q², Q³ or Q⁴, each independently selected from hydrogen, keto, substituted or unsubstituted linear or branched alkyl, substituted or unsubstituted cycloalkyl, substituted or unsubstituted heterocycloalkyl, haloalkyl, CF₃, substituted or unsubstituted aryl, substituted or unsubstituted phenyl, F, Cl, Br, I, CN, NO₂, hydroxyl, alkoxy, OR, arylalkyl, NCS, maleimide, NHCOOR, N(R)₂, NHCOR, CONHR, COOR or COR;
R³ is NHR², halide, N₃, OR⁴, CF₃, COR⁴, COCl, COOCOR⁴, COOR⁴, OCOR⁴, OCONHR⁴, NHCOOR⁴, NHCONHR⁴, OCOOR⁴, CN, CONH₂, CONH(R⁴), CON(R⁴)₂, SR⁴, SO₂R⁴, SOR⁴ SO₃H, SO₂NH₂, SO₂NH(R⁴), SO₂N(R⁴)₂, NH₂, NH(R⁴), N(R⁴)₂, CO(N-heterocycle), NO₂, cyanate, isocyanate, thiocyanate, isothiocyanate, mesylate, tosylate, triflate, PO(OH)₂ or OPO(OH)₂; and
R⁴ is H, alkyl, haloalkyl, cycloalkyl, aryl or heteroaryl, wherein said alkyl, haloalkyl, cycloalkyl, aryl or heteroaryl groups are optionally substituted;
or its isomer, pharmaceutically acceptable salt, pharmaceutical product, polymorph, hydrate or any combination thereof;
wherein if A is Br or I, R¹ is CH₃, and T is OH, then X is N or the aniline ring forms a fused heterocyclic ring.

The invention encompasses a SARD compound represented by the structure of formula III:

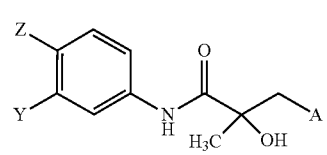

III wherein
Y is H, CF₃, F, I, Br, Cl, CN, or C(R)₃;
Z is H, NO₂, CN, halide, COOH, COR, NHCOR, CONHR,
or Y and Z form a 5 to 8 membered fused ring;
R is H, alkyl, alkenyl, haloalkyl, alcohol, CH₂CH₂OH, CF₃, CH₂Cl, CH₂CH₂Cl, aryl, F, Cl, Br, I, or OH;
A is R² or R³;
R² is a pyrrole, pyrroline, pyrrolidine, pyrazole, pyrazoline, pyrazolidine, triazole, imidazole, imidazoline, imidazolidine, or morpholine ring, said ring optionally substituted with at least one of Q¹, Q², Q³, or Q⁴, each independently selected from hydrogen, keto, substituted or unsubstituted linear or branched alkyl, substituted or unsubstituted cycloalkyl, substituted or unsubstituted heterocycloalkyl, haloalkyl, CF₃, substituted or unsubstituted aryl, substituted or unsubstituted phenyl, F, Cl, Br, I, CN, NO₂, hydroxyl, alkoxy, OR, arylalkyl, NCS, maleimide, NHCOOR, N(R)₂, NHCOR, CONHR, COOR or COR;
R³ is NHR², halide, N₃, OR⁴, CF₃, COR⁴, COCl, COOCOR⁴, COOR⁴, OCOR⁴, OCONHR⁴, NHCOOR⁴, NHCONHR⁴, OCOOR⁴, CN, CONH₂, CONH(R⁴), CON(R⁴)₂, SR⁴, SO₂R⁴, SOR⁴ SO₃H, SO₂NH₂, SO₂NH(R⁴), SO₂N(R⁴)₂, NH₂, NH(R⁴), N(R⁴)₂, CO(N-heterocycle), NO₂, cyanate, isocyanate, thiocyanate, isothiocyanate, mesylate, tosylate, triflate, PO(OH)₂ or OPO(OH)₂; and
R⁴ is H, alkyl, haloalkyl, cycloalkyl, aryl or heteroaryl, wherein said alkyl, haloalkyl, cycloalkyl, aryl or heteroaryl groups are optionally substituted;

or its optical isomer, isomer, pharmaceutically acceptable salt, pharmaceutical product, polymorph, hydrate or any combination thereof;

wherein if A is Br or I, then the aniline ring forms a fused heterocyclic ring.

In various embodiments, the SARD compound of formula III has a chiral carbon. In other embodiments, the SARD compound of formula III is a racemic mixture. In other embodiments, the SARD compound of formula III is an (S) isomer. In other embodiments, the SARD compound of formula III is an (R) isomer.

The invention encompasses a selective androgen receptor degrader compound represented by the structure of formula IV:

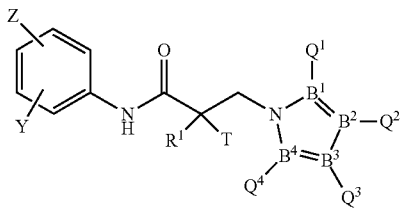

IV wherein $B^1$, $B^2$, $B^3$, and $B^4$ are each independently carbon or nitrogen;

Y is H, $CF_3$, F, I, Br, Cl, CN, or $C(R)_3$;

Z is H, $NO_2$, CN, halide, COOH, COR, NHCOR, CONHR, or Y and Z form a 5 to 8 membered fused ring;

$R^1$ is H, $CH_3$, $CH_2F$, $CHF_2$, $CF_3$, $CH_2CH_3$, or $CF_2CF_3$;

T is H, OH, OR, OCOR, $CH_3$, —$NHCOCH_3$, or NHCOR;

or T and $R^1$ form a 3-8 carbocyclic or heterocyclic ring;

R is H, alkyl, alkenyl, haloalkyl, alcohol, $CH_2CH_2OH$, $CF_3$, $CH_2Cl$, $CH_2CH_2Cl$, aryl, F, Cl, Br, I, or OH; and $Q^1$, $Q^2$, $Q^3$ or $Q^4$ are each independently selected from hydrogen, keto, substituted or unsubstituted linear or branched alkyl, substituted or unsubstituted cycloalkyl, substituted or unsubstituted heterocycloalkyl, haloalkyl, $CF_3$, substituted or unsubstituted aryl, substituted or unsubstituted phenyl, F, Cl, Br, I, CN, $NO_2$, hydroxyl, alkoxy, OR, arylalkyl, NCS, maleimide, NHCOOR, $N(R)_2$, NHCOR, CONHR, COOR or COR; wherein if $B^1$, $B^2$, $B^3$, or $B^4$ is nitrogen then $Q^1$, $Q^2$, $Q^3$, or $Q^4$, respectively, is nothing; or its optical isomer, isomer, pharmaceutically acceptable salt, pharmaceutical product, polymorph, hydrate or any combination thereof.

In various embodiments, the SARD compound of formula IV has a chiral carbon. In other embodiments, the SARD compound of formula IV is a racemic mixture. In other embodiments, the SARD compound of formula IV is an (S) isomer. In other embodiments, the SARD compound of formula IV is an (R) isomer.

The invention encompasses a selective androgen receptor degrader compound represented by the structure of formula V:

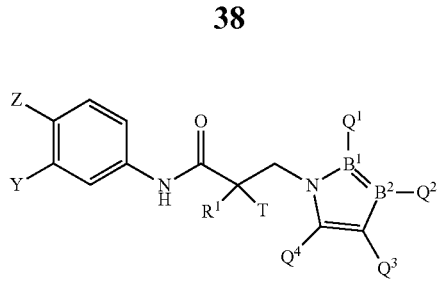

V wherein $B^1$ and $B^2$ are each independently carbon or nitrogen;

Y is H, $CF_3$, F, I, Br, Cl, CN, or $C(R)_3$;

Z is H, $NO_2$, CN, halide, COOH, COR, NHCOR, CONHR, or Y and Z form a 5 to 8 membered fused ring;

$R^1$ is H, $CH_3$, $CH_2F$, $CHF_2$, $CF_3$, $CH_2CH_3$, or $CF_2CF_3$;

T is H, OH, OR, OCOR, $CH_3$, —$NHCOCH_3$, or NHCOR;

or T and $R^1$ form a 3-8 carbocyclic or heterocyclic ring;

R is H, alkyl, alkenyl, haloalkyl, alcohol, $CH_2CH_2OH$, $CF_3$, $CH_2Cl$, $CH_2CH_2Cl$, aryl, F, Cl, Br, I, or OH; and $Q^1$, $Q^2$, $Q^3$ or $Q^4$ are each independently selected from hydrogen, keto, substituted or unsubstituted linear or branched alkyl, substituted or unsubstituted cycloalkyl, substituted or unsubstituted heterocycloalkyl, haloalkyl, $CF_3$, substituted or unsubstituted aryl, substituted or unsubstituted phenyl, F, Cl, Br, I, CN, $NO_2$, hydroxyl, alkoxy, OR, arylalkyl, NCS, maleimide, NHCOOR, $N(R)_2$, NHCOR, CONHR, COOR or COR; wherein if $B^1$ or $B^2$ is nitrogen then $Q^1$ or $Q^2$, respectively, is nothing; or its optical isomer, isomer, pharmaceutically acceptable salt, pharmaceutical product, polymorph, hydrate or any combination thereof.

In various embodiments, the SARD compound of formula V has a chiral carbon. In other embodiments, the SARD compound of formula V is a racemic mixture. In other embodiments, the SARD compound of formula V is an (S) isomer. In other embodiments, the SARD compound of formula V is an (R) isomer.

The invention encompasses a selective androgen receptor degrader compound represented by the structure of formula VI:

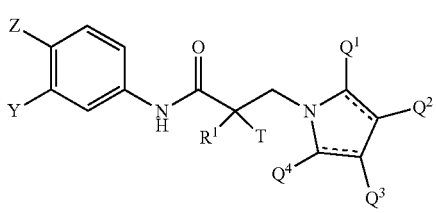

VI wherein $\text{-----}$ is a single or double bond;

Y is H, $CF_3$, F, I, Br, Cl, CN, or $C(R)_3$;

Z is H, $NO_2$, CN, halide, COOH, COR, NHCOR, CONHR, or Y and Z form a 5 to 8 membered fused ring;

$R^1$ is H, $CH_3$, $CH_2F$, $CHF_2$, $CF_3$, $CH_2CH_3$, or $CF_2CF_3$;

T is H, OH, OR, OCOR, $CH_3$, —$NHCOCH_3$, or NHCOR;

or T and $R^1$ form a 3-8 carbocyclic or heterocyclic ring;

R is H, alkyl, alkenyl, haloalkyl, alcohol, $CH_2CH_2OH$, $CF_3$, $CH_2Cl$, $CH_2CH_2Cl$, aryl, F, Cl, Br, I, or OH; and Q¹, Q², Q³, or Q⁴ are each independently selected from hydrogen, keto, substituted or unsubstituted linear or branched alkyl, substituted or unsubstituted cycloalkyl, substituted or unsubstituted heterocycloalkyl, haloalkyl, CF₃, substituted or unsubstituted aryl, substituted or unsubstituted phenyl, F, Cl, Br, I, CN, NO₂, hydroxyl, alkoxy, OR, arylalkyl, NCS, maleimide, NHCOOR, N(R)₂, NHCOR, CONHR, COOR or COR; or its optical isomer, isomer, pharmaceutically acceptable salt, pharmaceutical product, polymorph, hydrate or any combination thereof.

In various embodiments, the SARD compound of formula VI has a chiral carbon. In other embodiments, the SARD compound of formula VI is a racemic mixture. In other embodiments, the SARD compound of formula VI is an (S) isomer. In other embodiments, the SARD compound of formula VI is an (R) isomer.

The invention encompasses a selective androgen receptor degrader compound represented by the structure of formula VII:

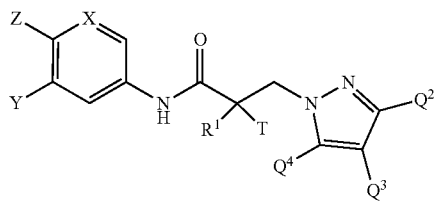

wherein
X is CH or N;
Y is H, CF₃, F, I, Br, Cl, CN, or C(R)₃;
Z is H, NO₂, CN, halide, COOH, COR, NHCOR, CONHR,
or Y and Z form a 5 to 8 membered fused ring;
R¹ is H, CH₃, CH₂F, CHF₂, CF₃, CH₂CH₃, or CF₂CF₃;
T is H, OH, OR, OCOR, CH₃, —NHCOCH₃, or NHCOR;
or T and R¹ form a 3-8 carbocyclic or heterocyclic ring;
R is H, alkyl, alkenyl, haloalkyl, alcohol, CH₂CH₂OH, CF₃, CH₂Cl, CH₂CH₂Cl, aryl, F, Cl, Br, I, or OH; and
Q², Q³, or Q⁴ are each independently selected from hydrogen, keto, substituted or unsubstituted linear or branched alkyl, substituted or unsubstituted cycloalkyl, substituted or unsubstituted heterocycloalkyl, haloalkyl, CF₃, substituted or unsubstituted aryl, substituted or unsubstituted phenyl, F, Cl, Br, I, CN, NO₂, hydroxyl, alkoxy, OR, arylalkyl, NCS, maleimide, NHCOOR, N(R)₂, NHCOR, CONHR, COOR or COR; or its optical isomer, isomer, pharmaceutically acceptable salt, pharmaceutical product, polymorph, hydrate or any combination thereof.

In various embodiments, the SARD compound of formula VII has a chiral carbon. In other embodiments, the SARD compound of formula VII is a racemic mixture. In other embodiments, the SARD compound of formula VII is an (S) isomer. In other embodiments, the SARD compound of formula VII is an (R) isomer.

The invention encompasses a selective androgen receptor degrader compound represented by the structure of formula VIIA:

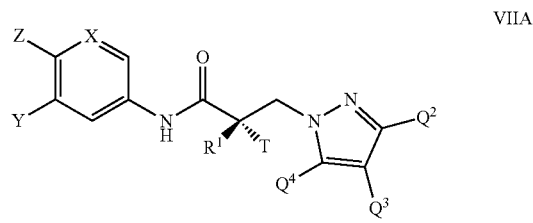

wherein
X is CH or N;
Y is H, CF₃, F, I, Br, Cl, CN, or C(R)₃;
Z is H, NO₂, CN, halide, COOH, COR, NHCOR, CONHR,
or Y and Z form a 5 to 8 membered fused ring;
R¹ is H, CH₃, CH₂F, CHF₂, CF₃, CH₂CH₃, or CF₂CF₃;
T is H, OH, OR, OCOR, CH₃, —NHCOCH₃, or NHCOR;
or T and R¹ form a 3-8 carbocyclic or heterocyclic ring;
R is H, alkyl, alkenyl, haloalkyl, alcohol, CH₂CH₂OH, CF₃, CH₂Cl, CH₂CH₂Cl, aryl, F, Cl, Br, I, or OH; and
Q², Q³, or Q⁴ are each independently selected from hydrogen, keto, substituted or unsubstituted linear or branched alkyl, substituted or unsubstituted cycloalkyl, substituted or unsubstituted heterocycloalkyl, haloalkyl, CF₃, substituted or unsubstituted aryl, substituted or unsubstituted phenyl, F, Cl, Br, I, CN, NO₂, hydroxyl, alkoxy, OR, arylalkyl, NCS, maleimide, NHCOOR, N(R)₂, NHCOR, CONHR, COOR or COR; or its isomer, pharmaceutically acceptable salt, pharmaceutical product, polymorph, hydrate or any combination thereof.

The invention encompasses a selective androgen receptor degrader compound represented by the structure of formula VIIB:

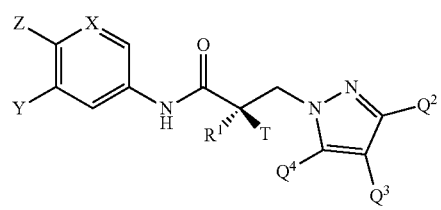

wherein
X is CH or N;
Y is H, CF₃, F, I, Br, Cl, CN, or C(R)₃;
Z is H, NO₂, CN, halide, COOH, COR, NHCOR, CONHR,
or Y and Z form a 5 to 8 membered fused ring;
R¹ is H, CH₃, CH₂F, CHF₂, CF₃, CH₂CH₃, or CF₂CF₃;
T is H, OH, OR, OCOR, CH₃, —NHCOCH₃, or NHCOR;
or T and R¹ form a 3-8 carbocyclic or heterocyclic ring;
R is H, alkyl, alkenyl, haloalkyl, alcohol, CH₂CH₂OH, CF₃, CH₂Cl, CH₂CH₂Cl, aryl, F, Cl, Br, I, or OH; and
Q², Q³, or Q⁴ are each independently selected from hydrogen, keto, substituted or unsubstituted linear or branched alkyl, substituted or unsubstituted cycloalkyl, substituted or unsubstituted heterocycloalkyl, haloalkyl, CF₃, substituted or unsubstituted aryl, substituted or unsubstituted phenyl, F, Cl, Br, I, CN, NO₂, hydroxyl, alkoxy, OR, arylalkyl, NCS, maleimide, NHCOOR, N(R)₂, NHCOR, CONHR, COOR or COR;

or its isomer, pharmaceutically acceptable salt, pharmaceutical product, polymorph, hydrate or any combination thereof.

In another embodiment, the invention encompasses a selective androgen receptor degrader compound represented by the structure of formula VIII:

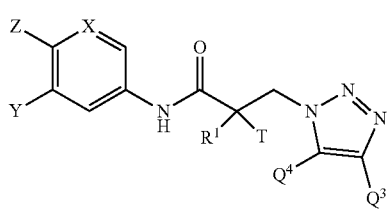

VIII wherein
X is CH or N;
Y is H, CF$_3$, F, I, Br, Cl, CN, or C(R)$_3$;
Z is H, NO$_2$, CN, halide, COOH, COR, NHCOR, CONHR,
or Y and Z form a 5 to 8 membered fused ring;
R$^1$ is H, CH$_3$, CH$_2$F, CHF$_2$, CF$_3$, CH$_2$CH$_3$, or CF$_2$CF$_3$;
T is H, OH, OR, OCOR, CH$_3$, —NHCOCH$_3$, or NHCOR;
or T and R$^1$ form a 3-8 carbocyclic or heterocyclic ring;
R is H, alkyl, alkenyl, haloalkyl, alcohol, CH$_2$CH$_2$OH, CF$_3$, CH$_2$Cl, CH$_2$CH$_2$Cl, aryl, F, Cl, Br, I, or OH; and
Q$^2$, Q$^3$ and Q$^4$ are each independently selected from hydrogen, keto, substituted or unsubstituted linear or branched alkyl, substituted or unsubstituted cycloalkyl, substituted or unsubstituted heterocycloalkyl, haloalkyl, CF$_3$, substituted or unsubstituted aryl, substituted or unsubstituted phenyl, F, Cl, Br, I, CN, NO$_2$, hydroxyl, alkoxy, OR, arylalkyl, NCS, maleimide, NHCOOR, N(R)$_2$, NHCOR, CONHR, COOR or COR;
or its optical isomer, isomer, pharmaceutically acceptable salt, pharmaceutical product, polymorph, hydrate or any combination thereof.

In another embodiment, the invention encompasses a selective androgen receptor degrader compound represented by the structure of formula VIIIA:

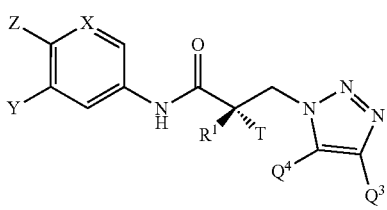

VIIIA wherein
X is CH or N;
Y is H, CF$_3$, F, I, Br, Cl, CN, or C(R)$_3$;
Z is H, NO$_2$, CN, halide, COOH, COR, NHCOR, CONHR,
or Y and Z form a 5 to 8 membered fused ring;
R$^1$ is H, CH$_3$, CH$_2$F, CHF$_2$, CF$_3$, CH$_2$CH$_3$, or CF$_2$CF$_3$;
T is H, OH, OR, OCOR, CH$_3$, —NHCOCH$_3$, or NHCOR;
or T and R$^1$ form a 3-8 carbocyclic or heterocyclic ring;
R is H, alkyl, alkenyl, haloalkyl, alcohol, CH$_2$CH$_2$OH, CF$_3$, CH$_2$Cl, CH$_2$CH$_2$Cl, aryl, F, Cl, Br, I, or OH; and
Q$^3$ and Q$^4$ are each independently selected from hydrogen, keto, substituted or unsubstituted linear or branched alkyl, substituted or unsubstituted cycloalkyl, substituted or unsubstituted heterocycloalkyl, haloalkyl, CF$_3$, substituted or unsubstituted aryl, substituted or unsubstituted phenyl, F, Cl, Br, I, CN, NO$_2$, hydroxyl, alkoxy, OR, arylalkyl, NCS, maleimide, NHCOOR, N(R)$_2$, NHCOR, CONHR, COOR or COR;
or its isomer, pharmaceutically acceptable salt, pharmaceutical product, polymorph, hydrate or any combination thereof.

In another embodiment, the invention encompasses a selective androgen receptor degrader compound represented by the structure of formula VIIIB:

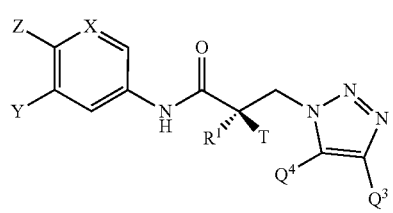

VIIIB wherein
X is CH or N;
Y is H, CF$_3$, F, I, Br, Cl, CN, or C(R)$_3$;
Z is H, NO$_2$, CN, halide, COOH, COR, NHCOR, CONHR,
or Y and Z form a 5 to 8 membered fused ring;
R$^1$ is H, CH$_3$, CH$_2$F, CHF$_2$, CF$_3$, CH$_2$CH$_3$, or CF$_2$CF$_3$;
T is H, OH, OR, OCOR, CH$_3$, —NHCOCH$_3$, or NHCOR;
or T and R$^1$ form a 3-8 carbocyclic or heterocyclic ring;
R is H, alkyl, alkenyl, haloalkyl, alcohol, CH$_2$CH$_2$OH, CF$_3$, CH$_2$Cl, CH$_2$CH$_2$Cl, aryl, F, Cl, Br, I, or OH; and
Q$^3$ and Q$^4$ are each independently selected from hydrogen, keto, substituted or unsubstituted linear or branched alkyl, substituted or unsubstituted cycloalkyl, substituted or unsubstituted heterocycloalkyl, haloalkyl, CF$_3$, substituted or unsubstituted aryl, substituted or unsubstituted phenyl, F, Cl, Br, I, CN, NO$_2$, hydroxyl, alkoxy, OR, arylalkyl, NCS, maleimide, NHCOOR, N(R)$_2$, NHCOR, CONHR, COOR or COR;
or its isomer, pharmaceutically acceptable salt, pharmaceutical product, polymorph, hydrate or any combination thereof.

In another embodiment, the invention encompasses a selective androgen receptor degrader compound represented by the structure of formula IX:

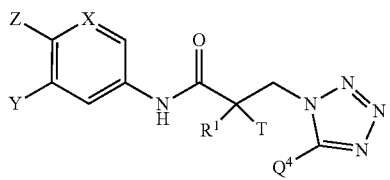

IX wherein
X is CH or N;
Y is H, CF$_3$, F, I, Br, Cl, CN, or C(R)$_3$;
Z is H, NO$_2$, CN, halide, COOH, COR, NHCOR, CONHR, or Y and Z form a 5 to 8 membered fused ring;
R¹ is H, CH₃, CH₂F, CHF₂, CF₃, CH₂CH₃, or CF₂CF₃;
T is H, OH, OR, OCOR, CH₃, —NHCOCH₃, or NHCOR;
or T and R¹ form a 3-8 carbocyclic or heterocyclic ring;
R is H, alkyl, alkenyl, haloalkyl, alcohol, CH₂CH₂OH, CF₃, CH₂Cl, CH₂CH₂Cl, aryl, F, Cl, Br, I, or OH; and
Q⁴ is selected from hydrogen, keto, substituted or unsubstituted linear or branched alkyl, substituted or unsubstituted cycloalkyl, substituted or unsubstituted heterocycloalkyl, haloalkyl, CF₃, substituted or unsubstituted aryl, substituted or unsubstituted phenyl, F, Cl, Br, I, CN, NO₂, hydroxyl, alkoxy, OR, arylalkyl, NCS, maleimide, NHCOOR, N(R)₂, NHCOR, CONHR, COOR or COR; or its optical isomer, isomer, pharmaceutically acceptable salt, pharmaceutical product, polymorph, hydrate or any combination thereof.

In another embodiment, the invention encompasses a selective androgen receptor degrader compound represented by the structure of formula IXA:

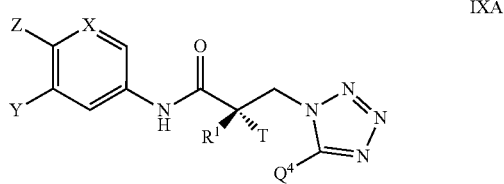

IXA wherein
X is CH or N;
Y is H, CF₃, F, I, Br, Cl, CN, or C(R)₃;
Z is H, NO₂, CN, halide, COOH, COR, NHCOR, CONHR,
or Y and Z form a 5 to 8 membered fused ring;
R¹ is H, CH₃, CH₂F, CHF₂, CF₃, CH₂CH₃, or CF₂CF₃;
T is H, OH, OR, OCOR, CH₃, —NHCOCH₃, or NHCOR;
or T and R¹ form a 3-8 carbocyclic or heterocyclic ring;
R is H, alkyl, alkenyl, haloalkyl, alcohol, CH₂CH₂OH, CF₃, CH₂Cl, CH₂CH₂Cl, aryl, F, Cl, Br, I, or OH; and
Q⁴ is selected from hydrogen, keto, substituted or unsubstituted linear or branched alkyl, substituted or unsubstituted cycloalkyl, substituted or unsubstituted heterocycloalkyl, haloalkyl, CF₃, substituted or unsubstituted aryl, substituted or unsubstituted phenyl, F, Cl, Br, I, CN, NO₂, hydroxyl, alkoxy, OR, arylalkyl, NCS, maleimide, NHCOOR, N(R)₂, NHCOR, CONHR, COOR or COR; or its isomer, pharmaceutically acceptable salt, pharmaceutical product, polymorph, hydrate or any combination thereof.

In another embodiment, the invention encompasses a selective androgen receptor degrader compound represented by the structure of formula IXB:

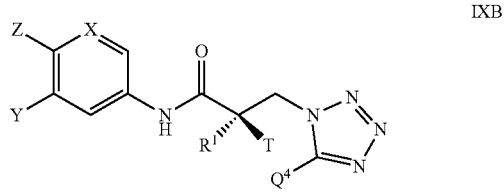

IXB wherein
X is CH or N;
Y is H, CF₃, F, I, Br, Cl, CN, or C(R)₃;
Z is H, NO₂, CN, halide, COOH, COR, NHCOR, CONHR,
or Y and Z form a 5 to 8 membered fused ring;
R¹ is H, CH₃, CH₂F, CHF₂, CF₃, CH₂CH₃, or CF₂CF₃;
T is H, OH, OR, OCOR, CH₃, —NHCOCH₃, or NHCOR;
or T and R¹ form a 3-8 carbocyclic or heterocyclic ring;
R is H, alkyl, alkenyl, haloalkyl, alcohol, CH₂CH₂OH, CF₃, CH₂Cl, CH₂CH₂Cl, aryl, F, Cl, Br, I, or OH;
and
Q⁴ is selected from hydrogen, keto, substituted or unsubstituted linear or branched alkyl, substituted or unsubstituted cycloalkyl, substituted or unsubstituted heterocycloalkyl, haloalkyl, CF₃, substituted or unsubstituted aryl, substituted or unsubstituted phenyl, F, Cl, Br, I, CN, NO₂, hydroxyl, alkoxy, OR, arylalkyl, NCS, maleimide, NHCOOR, N(R)₂, NHCOR, CONHR, COOR or COR; or its isomer, pharmaceutically acceptable salt, pharmaceutical product, polymorph, hydrate or any combination thereof.

In some embodiments, the compounds of formula I-IX are represented by the following structures:

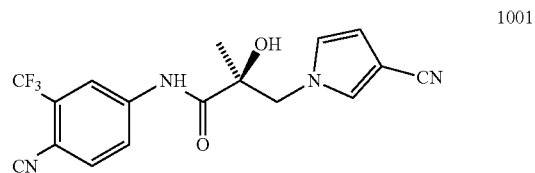

1001

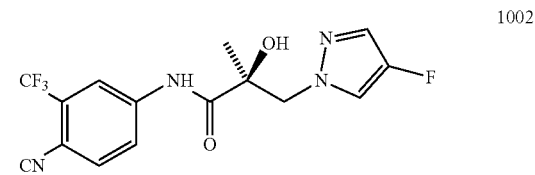

1002

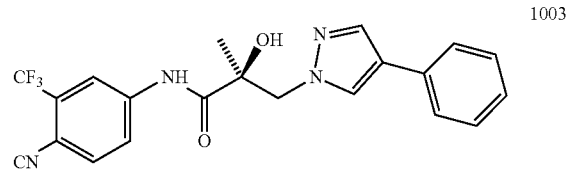

1003

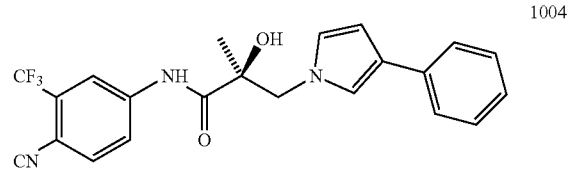

1004

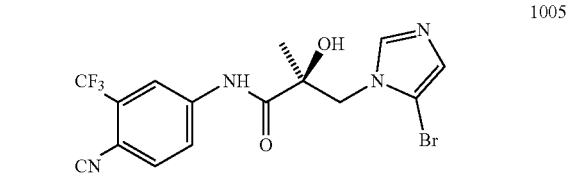

1005

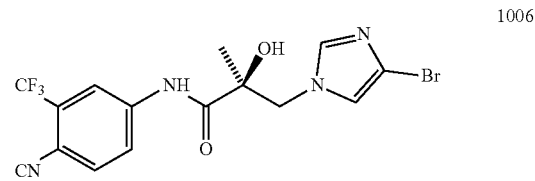

1006

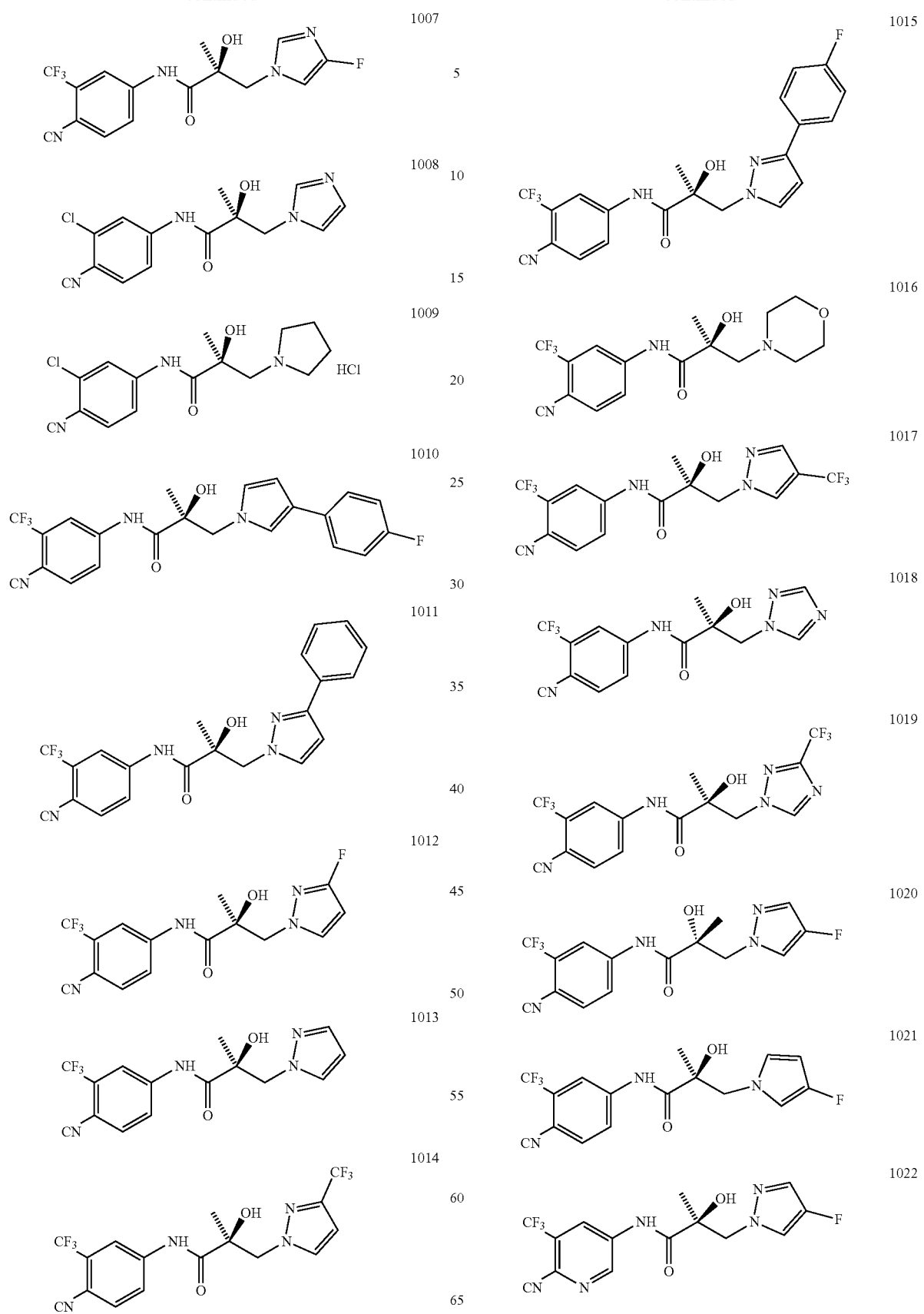

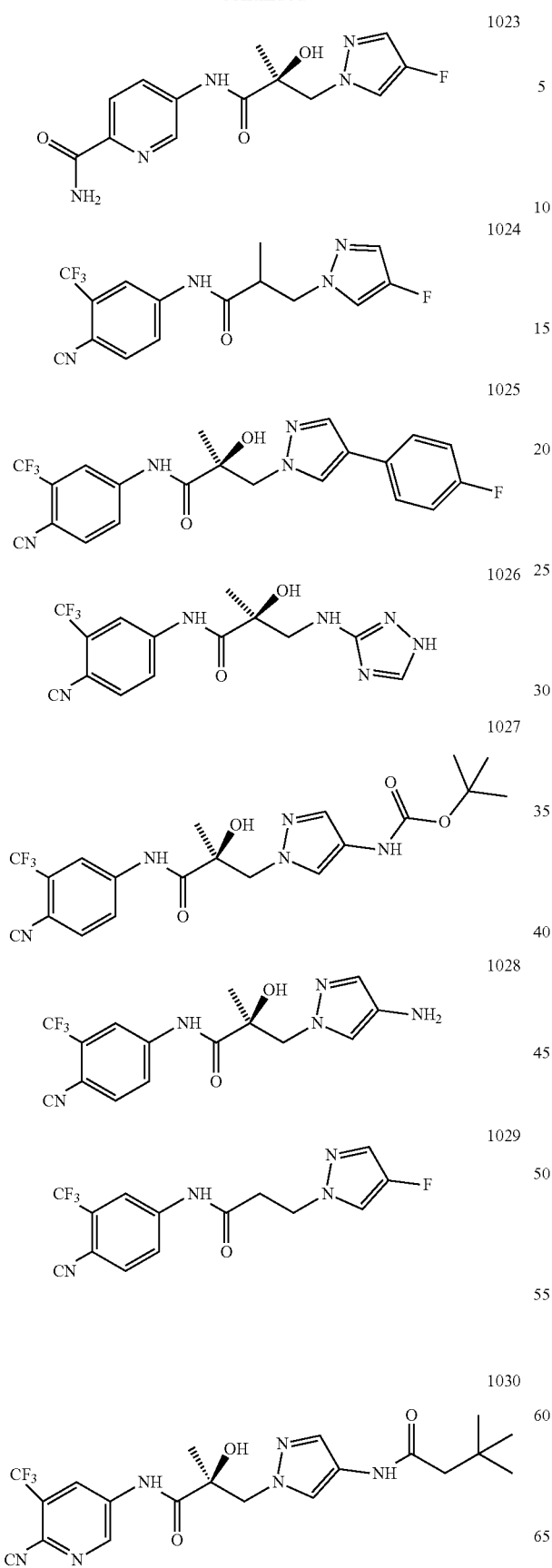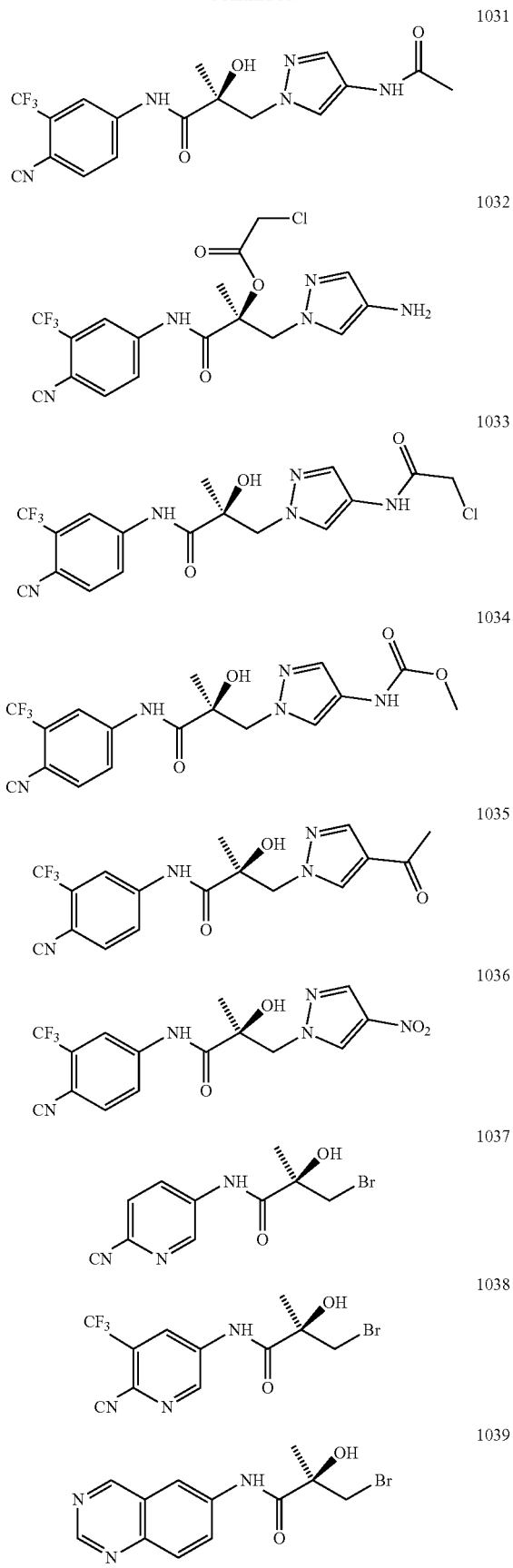

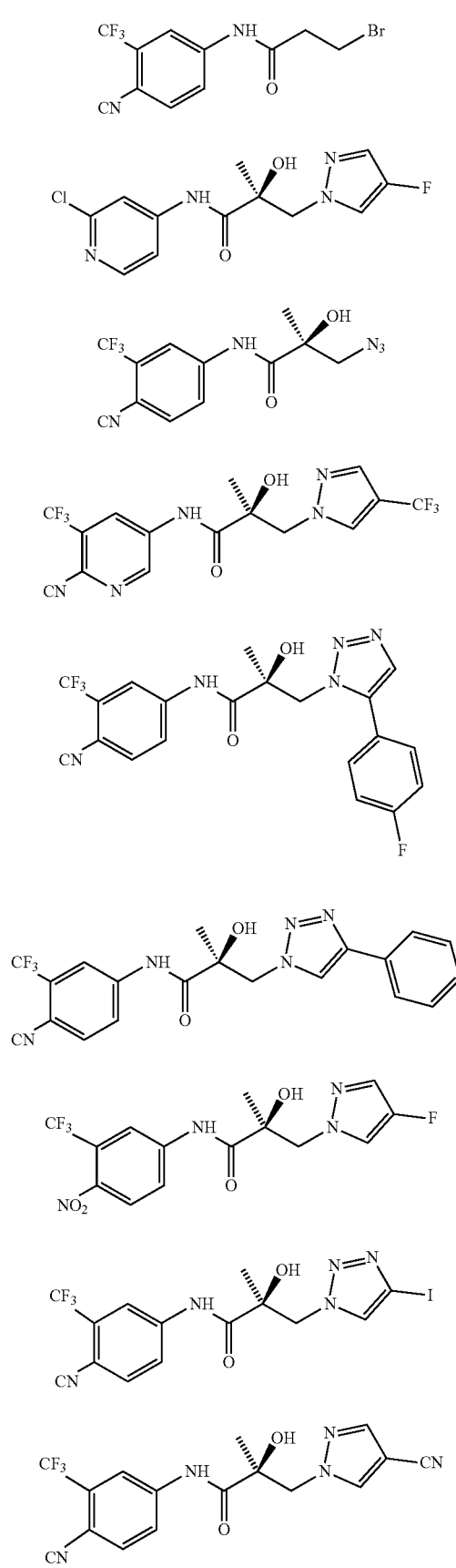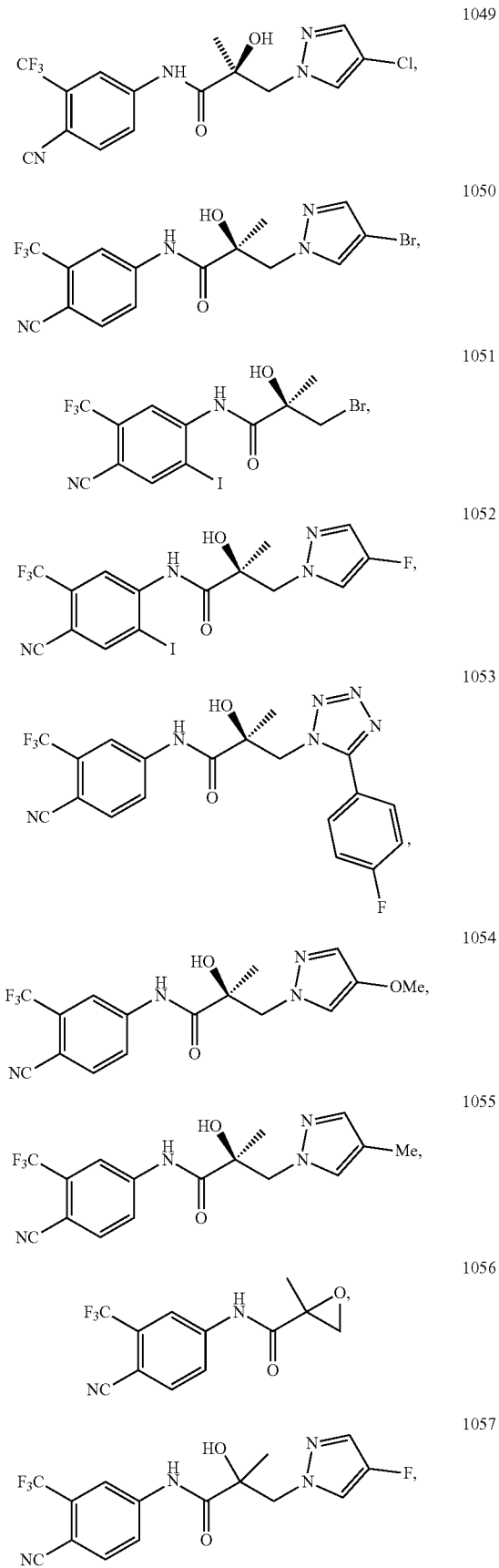

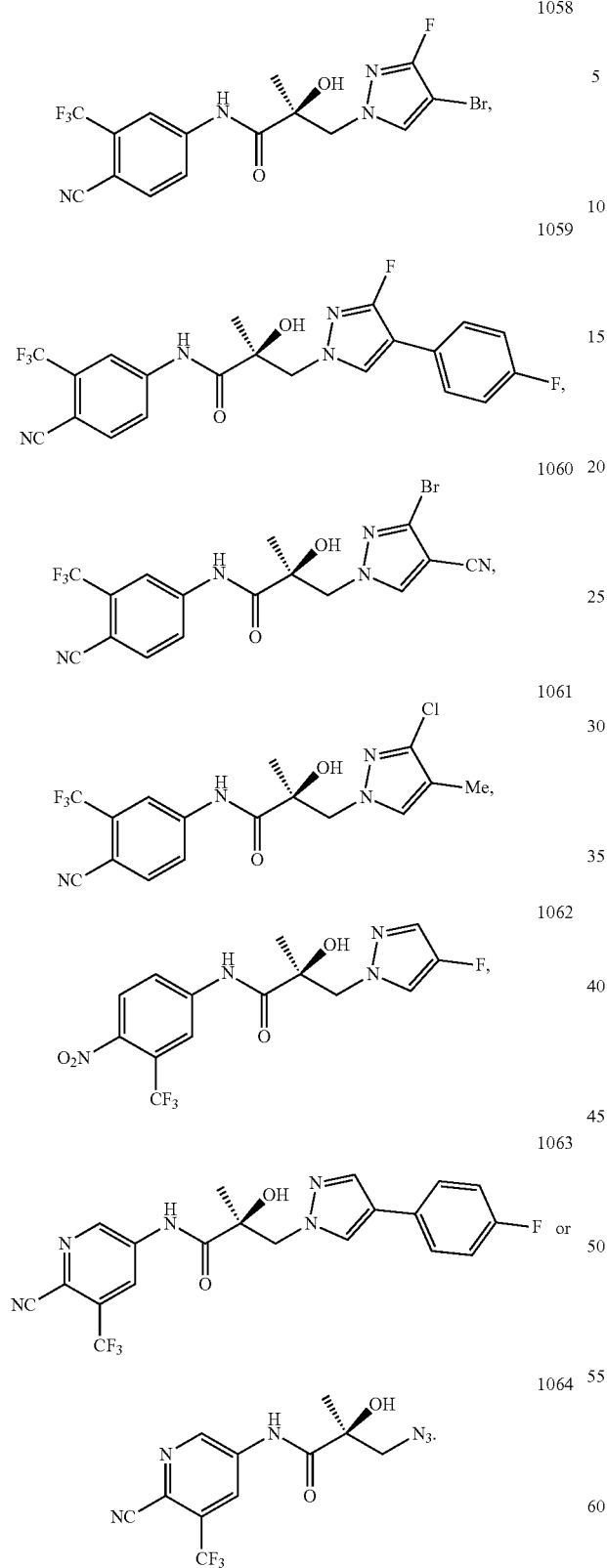

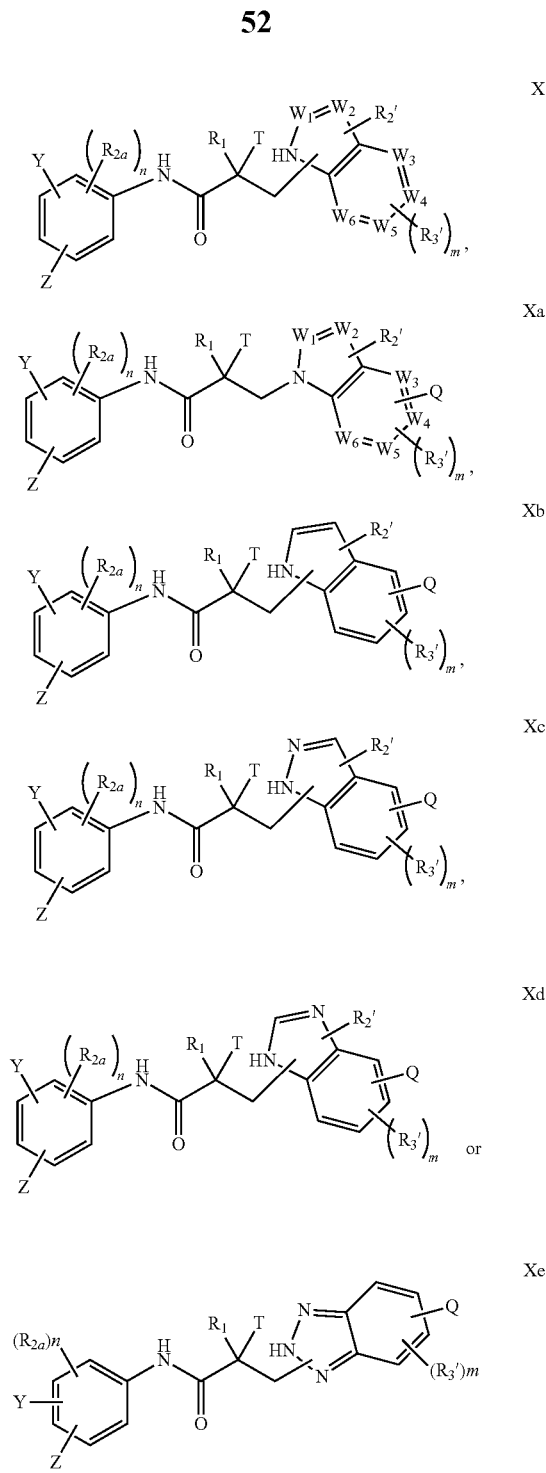

In another embodiment, the invention encompasses a selective androgen receptor degrader compound represented by the structure of formula X or Xa-Xe:

wherein $W_1$ and $W_2$ are each independently selected from N or CH;

$W_3$, $W_4$, $W_5$ and $W_6$ are each independently selected from CH or N;

wherein if any one of $W_1$, $W_2$, $W_3$, $W_4$, $W_5$, and $W_6$ is CH, then the H is optionally replaced with $R_4$, Q or $R_3$ in the respective position, and if any one of $W_1$, $W_2$, $W_3$, $W_4$, $W_5$, and $W_6$ is not CH, then the respective position is unsubstituted;

T is OH, OR, —NHCOCH$_3$, NHCOR or

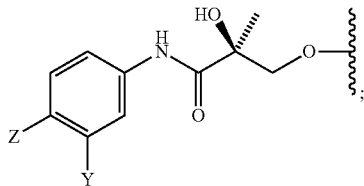

Z is H, NO$_2$, CN, halide, COOH, COR, NHCOR or CONHR;

Y is H, CF$_3$, F, I, Br, Cl, CN, Sn(R)$_3$, C(R)$_3$ or Y and Z form a 5 to 8 membered fused ring;

R is H, alkyl, haloalkyl, alcohol, CH$_2$CH$_2$OH, CH$_2$F, CHF$_2$, CF$_3$, CF$_2$CF$_3$, CH$_2$Cl, CH$_2$CH$_2$Cl, aryl, phenyl, F, Cl, Br, I, alkenyl or OH;

R$_1$ is H, CH$_3$, CH$_2$F, CHF$_2$, CF$_3$, CH$_2$CH$_3$, or CF$_2$CF$_3$;

R$_{2a}$ is hydrogen, halogen, CN, NO$_2$, COOH, COOR, COR, NHCOR, CONHR, OH, OR, SH, SR, NH$_2$, NHR, NR$_2$, C$_1$-C$_{12}$-alkyl, C$_1$-C$_{12}$-haloalkyl, O—C$_1$-C$_{12}$-alkyl, O—C$_1$-C$_{12}$-haloalkyl, —SO$_2$-aryl, —SO$_2$-phenyl, —CO-aryl, arylalkyl, benzyl, aryl, or C$_3$-C$_7$-cycloalkyl;

Q is hydrogen, F, Cl, Br, I, CF$_3$, CN, NO$_2$, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;

R$_3'$ and R$_4'$ are independently selected from hydrogen, F, Cl, Br, I, CF$_3$, CN, NO$_2$, NH$_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;

n is an integer between 1-3; and m is an integer between 1-3;

or its isomer, pharmaceutically acceptable salt, pharmaceutical product, polymorph, hydrate or any combination thereof.

In another embodiment, W$_1$, W$_2$, W$_3$, W$_4$, W$_5$, and W$_6$ of formula I or Ia, are each independently CH. In another embodiment, W$_1$ is N. In another embodiment, W$_2$ is N. In another embodiment, W$_1$ is CH. In another embodiment, W$_2$ is CH. In another embodiment, W$_3$ is N. In another embodiment, W$_4$ is N. In another embodiment, W$_5$ is N. In another embodiment, W$_6$ is N.

In another embodiment, W$_1$ is N and W$_1$, W$_3$, W$_4$, W$_5$, and W$_6$ are CH. In another embodiment, W$_2$ is N and W$_1$, W$_3$, W$_4$, W$_5$, and W$_6$ are CH. In another embodiment, W$_3$ is N and W$_1$, W$_2$, W$_4$, W$_5$, and W$_6$ are CH. In another embodiment, W$_4$ is N and W$_1$, W$_2$, W$_3$, W$_5$, and W$_6$ are CH. In another embodiment, W$_5$ is N and W$_1$, W$_2$, W$_3$, W$_4$, and W$_6$ are CH. In another embodiment, W$_6$ is N and W$_1$, W$_2$, W$_3$, W$_4$, and W$_5$ are CH.

In one embodiment, this invention is directed to a selective androgen receptor degrader (SARD) compound represented by the structure of formula X(1), Xa(1), Xb(1), Xc(1), or Xd(1):

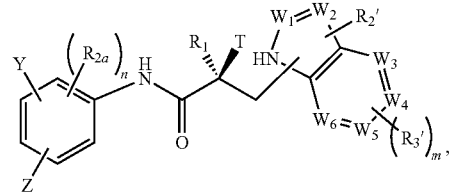

X(1)

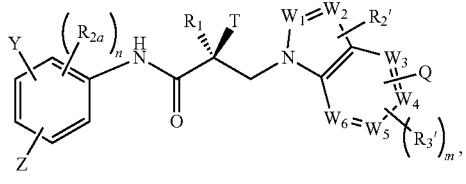

Xa(1)

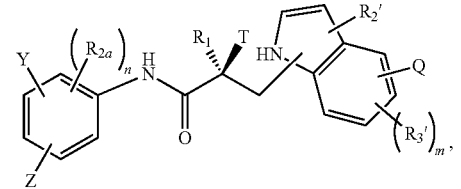

Xb(1)

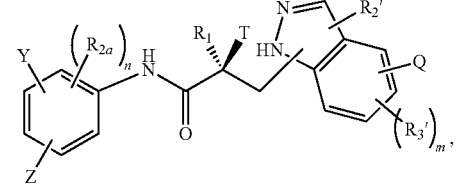

Xc(1)

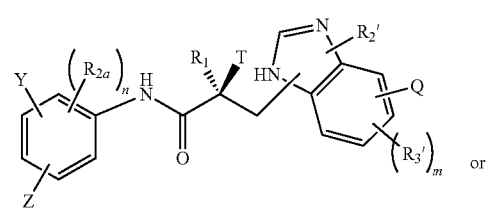

Xd(1) or

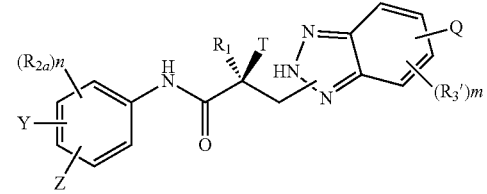

Xe(1)

wherein

W$_1$ and W$_2$ are each independently selected from N or CH;

W$_3$, W$_4$, W$_5$ and W$_6$ are each independently selected from CH or N;

wherein if any one of W$_1$, W$_2$, W$_3$, W$_4$, W$_5$, and W$_6$ is CH, then the H is optionally replaced with R$_4'$, Q or R$_3'$ in the respective position, and if any one of $W_1$, $W_2$, $W_3$, $W_4$, $W_5$, and $W_6$ is not CH, then the respective position is unsubstituted;

T is H, OH, OR, OCOR, $CH_3$, —$NHCOCH_3$, NHCOR or

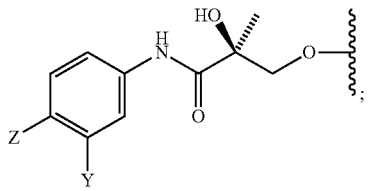

Z is H, $NO_2$, CN, halide, COOH, COR, NHCOR or CONHR;

Y is H, $CF_3$, F, I, Br, Cl, CN, $Sn(R)_3$, $C(R)_3$ or Y and Z form a 5 to 8 membered fused ring;

R is H, alkyl, haloalkyl, alcohol, $CH_2CH_2OH$, $CH_2F$, $CHF_2$, $CF_3$, $CF_2CF_3$, $CH_2Cl$, $CH_2CH_2Cl$, aryl, phenyl, F, Cl, Br, I, alkenyl or OH;

$R_1$ is H, $CH_3$, $CH_2F$, $CHF_2$, $CF_3$, $CH_2CH_3$, or $CF_2CF_3$;

$R_{2a}$ is hydrogen, halogen, CN, $NO_2$, COOH, COOR, COR, NHCOR, CONHR, OH, OR, SH, SR, $NH_2$, NHR, $NR_2$, $C_1$-$C_{12}$-alkyl, $C_1$-$C_{12}$-haloalkyl, O—$C_1$-$C_{12}$-alkyl, O—$C_1$-$C_{12}$-haloalkyl, —$SO_2$-aryl, —$SO_2$-phenyl, —CO-aryl, arylalkyl, benzyl, aryl, or $C_3$-$C_7$-cycloalkyl;

Q is hydrogen, F, Cl, Br, I, $CF_3$, CN, $NO_2$, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;

$R_{3'}$ and $R_{4'}$ are independently selected from hydrogen, F, Cl, Br, I, $CF_3$, CN, $NO_2$, $NH_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;

n is an integer between 1-3; and
m is an integer between 1-3;

or its isomer, pharmaceutically acceptable salt, pharmaceutical product, polymorph, hydrate or any combination thereof.

In another embodiment, $W_1$, $W_2$, $W_3$, $W_4$, $W_5$, and $W_6$ of formula I(1) or Ia(1), are each independently CH. In another embodiment, $W_1$ is N. In another embodiment, $W_2$ is N. In another embodiment, $W_1$ is CH. In another embodiment, $W_2$ is CH. In another embodiment, $W_3$ is N. In another embodiment, $W_4$ is N. In another embodiment, $W_5$ is N. In another embodiment, $W_6$ is N.

In another embodiment, $W_1$ is N and $W_1$, $W_3$, $W_4$, $W_5$, and $W_6$ are CH. In another embodiment, $W_2$ is N and $W_1$, $W_3$, $W_4$, $W_5$, and $W_6$ are CH. In another embodiment, $W_3$ is N and $W_1$, $W_2$, $W_4$, $W_5$, and $W_6$ are CH. In another embodiment, $W_4$ is N and $W_1$, $W_2$, $W_3$, $W_5$, and $W_6$ are CH. In another embodiment, $W_5$ is N and $W_1$, $W_2$, $W_3$, $W_4$, and $W_6$ are CH. In another embodiment, $W_6$ is N and $W_1$, $W_2$, $W_3$, $W_4$, and $W_5$ are CH.

In one embodiment, this invention is directed to a selective androgen receptor degrader (SARD) compound represented by the structure of formula X(2), Xa(2), Xb(2), Xc(2), or Xd(2):

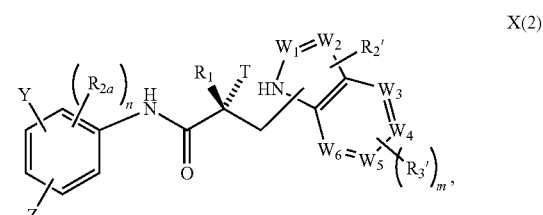
X(2)

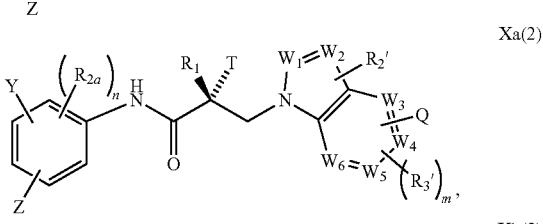
Xa(2)

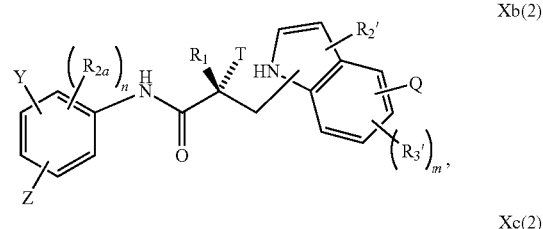
Xb(2)

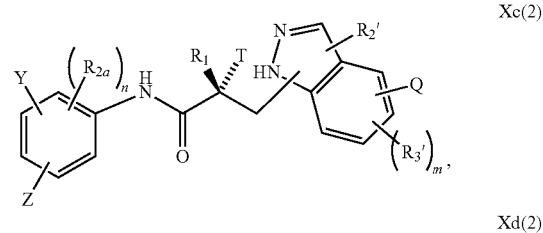
Xc(2)

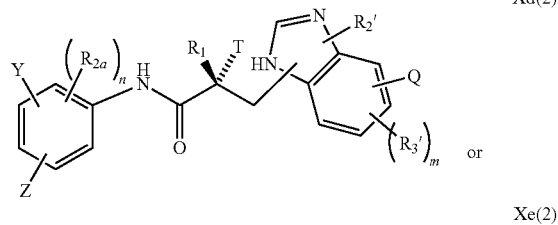
Xd(2)

or

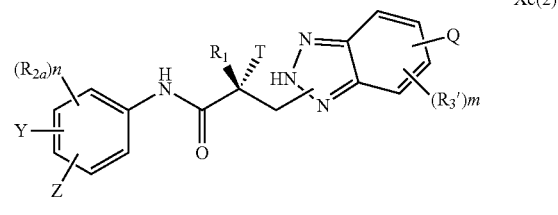
Xe(2)

wherein $W_1$ and $W_2$ are each independently selected from N or CH;

$W_3$, $W_4$, $W_5$ and $W_6$ are each independently selected from CH or N;

wherein if any one of $W_1$, $W_2$, $W_3$, $W_4$, $W_5$, and $W_6$ is CH, then the H is optionally replaced with $R_4$, Q or $R_3$ in the respective position, and if any one of $W_1$, $W_2$, $W_3$, $W_4$, $W_5$, and $W_6$ is not CH, then the respective position is unsubstituted;

T is H, OH, OR, OCOR, $CH_3$, —$NHCOCH_3$, NHCOR or

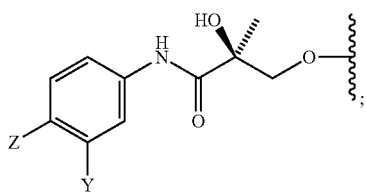

Z is H, $NO_2$, CN, halide, COOH, COR, NHCOR or CONHR;

Y is H, $CF_3$, F, I, Br, Cl, CN, $Sn(R)_3$, $C(R)_3$ or Y and Z form a 5 to 8 membered fused ring;

R is H, alkyl, haloalkyl, alcohol, $CH_2CH_2OH$, $CH_2F$, $CHF_2$, $CF_3$, $CF_2CF_3$, $CH_2Cl$, $CH_2CH_2Cl$, aryl, phenyl, F, Cl, Br, I, alkenyl or OH;

$R_1$ is H, $CH_3$, $CH_2F$, $CHF_2$, $CF_3$, $CH_2CH_3$, or $CF_2CF_3$;

$R_{2a}$ is hydrogen, halogen, CN, $NO_2$, COOH, COOR, COR, NHCOR, CONHR, OH, OR, SH, SR, $NH_2$, NHR, $NR_2$, $C_1$-$C_{12}$-alkyl, $C_1$-$C_{12}$-haloalkyl, O—$C_1$-$C_{12}$-alkyl, O—$C_1$-$C_{12}$-haloalkyl, —$SO_2$-aryl, —$SO_2$-phenyl, —CO-aryl, arylalkyl, benzyl, aryl, or $C_3$-$C_7$-cycloalkyl;

Q is hydrogen, F, Cl, Br, I, $CF_3$, CN, $NO_2$, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;

$R_{3'}$ and $R_{4'}$ are independently selected from hydrogen, F, Cl, Br, I, $CF_3$, CN, $NO_2$, $NH_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;

n is an integer between 1-3; and m is an integer between 1-3;

or its isomer, pharmaceutically acceptable salt, pharmaceutical product, polymorph, hydrate or any combination thereof.

In another embodiment, $W_1$, $W_2$, $W_3$, $W_4$, $W_5$, and $W_6$ of formula I or Ia, are each independently CH. In another embodiment, $W_1$ is N. In another embodiment, $W_2$ is N. In another embodiment, $W_1$ is CH. In another embodiment, $W_2$ is CH. In another embodiment, $W_3$ is N. In another embodiment, $W_4$ is N. In another embodiment, $W_5$ is N. In another embodiment, $W_6$ is N. In another embodiment, $W_1$ is N and $W_1$, $W_3$, $W_4$, $W_5$, and $W_6$ are CH. In another embodiment, $W_2$ is N and $W_1$, $W_3$, $W_4$, $W_5$, and $W_6$ are CH. In another embodiment, $W_3$ is N and $W_1$, $W_2$, $W_4$, $W_5$, and $W_6$ are CH. In another embodiment, $W_4$ is N and $W_1$, $W_2$, $W_3$, $W_5$, and $W_6$ are CH. In another embodiment, $W_5$ is N and $W_1$, $W_2$, $W_3$, $W_4$, and $W_6$ are CH. In another embodiment, $W_6$ is N and $W_1$, $W_2$, $W_3$, $W_4$, and $W_5$ are CH.

In one embodiment, this invention is directed to a selective androgen receptor degrader (SARD) compound represented by the structure of formula XI:

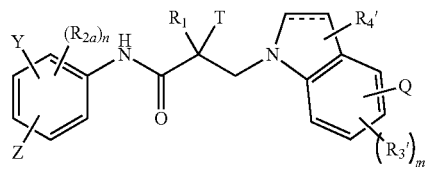

XI wherein

------ is a single or double bond;

T is H, OH, OR, OCOR, $CH_3$, —$NHCOCH_3$, NHCOR or

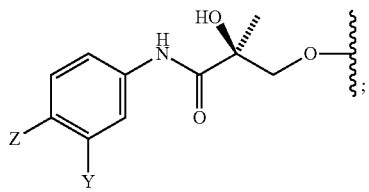

Z is H, $NO_2$, CN, halide, COOH, COR, NHCOR or CONHR;

Y is H, $CF_3$, F, I, Br, Cl, CN, $Sn(R)_3$, $C(R)_3$ or Y and Z form a 5 to 8 membered fused ring;

R is H, alkyl, haloalkyl, alcohol, $CH_2CH_2OH$, $CH_2F$, $CHF_2$, $CF_3$, $CF_2CF_3$, $CH_2Cl$, $CH_2CH_2Cl$, aryl, phenyl, F, Cl, Br, I, alkenyl or OH;

$R_1$ is H, $CH_3$, $CH_2F$, $CHF_2$, $CF_3$, $CH_2CH_3$, or $CF_2CF_3$;

$R_{2a}$ is hydrogen, halogen, CN, $NO_2$, COOH, COOR, COR, NHCOR, CONHR, OH, OR, SH, SR, $NH_2$, NHR, $NR_2$, $C_1$-$C_{12}$-alkyl, $C_1$-$C_{12}$-haloalkyl, O—$C_1$-$C_{12}$-alkyl, O—$C_1$-$C_{12}$-haloalkyl, —$SO_2$-aryl, —$SO_2$-phenyl, —CO-aryl, arylalkyl, benzyl, aryl, or $C_3$-$C_7$-cycloalkyl;

Q is hydrogen, F, Cl, Br, I, $CF_3$, CN, $NO_2$, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;

$R_{3'}$ is hydrogen, F, Cl, Br, I, $CF_3$, CN, $NO_2$, $NH_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;

R$_{4'}$ is hydrogen, F, Cl, Br, I, CF$_3$, CN, NO$_2$, NH$_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;

n is an integer between 1-3; and m is an integer between 1-3 or its isomer, pharmaceutically acceptable salt, pharmaceutical product, polymorph, hydrate or any combination thereof.

In one embodiment, this invention is directed to a selective androgen receptor degrader (SARD) compound represented by the structure of formula XI(1):

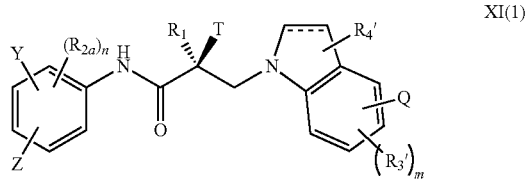

wherein

----- is a single or double bond;

T is H, OH, OR, OCOR, CH$_3$, —NHCOCH$_3$, NHCOR or

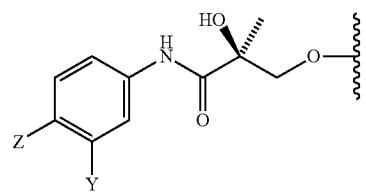

Z is H, NO$_2$, CN, halide, COOH, COR, NHCOR or CONHR;

Y is H, CF$_3$, F, I, Br, Cl, CN, Sn(R)$_3$, C(R)$_3$ or Y and Z form a 5 to 8 membered fused ring;

R is H, alkyl, haloalkyl, alcohol, CH$_2$CH$_2$OH, CH$_2$F, CHF$_2$, CF$_3$, CF$_2$CF$_3$, CH$_2$Cl, CH$_2$CH$_2$Cl, aryl, phenyl, F, Cl, Br, I, alkenyl or OH;

R$_1$ is H, CH$_3$, CH$_2$F, CHF$_2$, CF$_3$, CH$_2$CH$_3$, or CF$_2$CF$_3$;

R$_{2a}$ is hydrogen, halogen, CN, NO$_2$, COOH, COOR, COR, NHCOR, CONHR, OH, OR, SH, SR, NH$_2$, NHR, NR$_2$, C$_1$-C$_{12}$-alkyl, C$_1$-C$_{12}$-haloalkyl, O—C$_1$-C$_{12}$-alkyl, O—C$_1$-C$_{12}$-haloalkyl, —SO$_2$-aryl, —SO$_2$-phenyl, —CO-aryl, arylalkyl, benzyl, aryl, or C$_3$-C$_7$-cycloalkyl;

Q is hydrogen, F, Cl, Br, I, CF$_3$, CN, NO$_2$, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;

R$_{3'}$ is hydrogen, F, Cl, Br, I, CF$_3$, CN, NO$_2$, NH$_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;

R$_{4'}$ is hydrogen, F, Cl, Br, I, CF$_3$, CN, NO$_2$, NH$_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;

n is an integer between 1-3; and m is an integer between 1-3;

or its isomer, pharmaceutically acceptable salt, pharmaceutical product, polymorph, hydrate or any combination thereof.

In one embodiment, this invention is directed to a selective androgen receptor degrader (SARD) compound represented by the structure of formula XII:

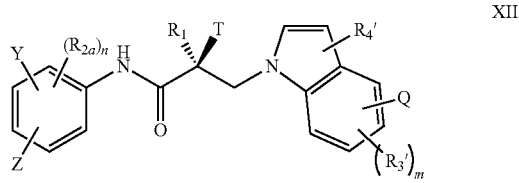

wherein

T is H, OH, OR, OCOR, CH$_3$, —NHCOCH$_3$, or NHCOR;

Z is H, NO$_2$, CN, halide, COOH, COR, NHCOR or CONHR;

Y is H, CF$_3$, F, I, Br, Cl, CN, Sn(R)$_3$, C(R)$_3$ or Y and Z form a 5 to 8 membered fused ring;

R is H, alkyl, haloalkyl, alcohol, CH$_2$CH$_2$OH; CH$_2$F, CHF$_2$, CF$_3$, CF$_2$CF$_3$, CH$_2$Cl, CH$_2$CH$_2$Cl, aryl, phenyl, F, Cl, Br, I, alkenyl or OH;

R$_1$ is H, CH$_3$, CH$_2$F, CHF$_2$, CF$_3$, CH$_2$CH$_3$, or CF$_2$CF$_3$;

R$_{2a}$ is hydrogen, halogen, CN, NO$_2$, COOH, COOR, COR, NHCOR, CONHR, OH, OR, SH, SR, NH$_2$, NHR, NR$_2$, C$_1$-C$_{12}$-alkyl, C$_1$-C$_{12}$-haloalkyl, O—C$_1$-C$_{12}$-alkyl, O—C$_1$-C$_{12}$-haloalkyl, —SO$_2$-aryl, —SO$_2$-phenyl, —CO-aryl, arylalkyl, benzyl, aryl, or C$_3$-C$_7$-cycloalkyl;

Q is hydrogen, F, Cl, Br, I, CF$_3$, CN, NO$_2$, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;

R$_3$' is hydrogen, F, Cl, Br, I, CF$_3$, CN, NO$_2$, NH$_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;

R$_4$' is hydrogen, F, Cl, Br, I, CF$_3$, CN, NO$_2$, NH$_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;

n is an integer between 1-3; and
m is an integer between 1-3
or its isomer, pharmaceutically acceptable salt, pharmaceutical product, polymorph, hydrate or any combination thereof.

In one embodiment, this invention is directed to a selective androgen receptor degrader (SARD) compound represented by the structure of formula XIII;

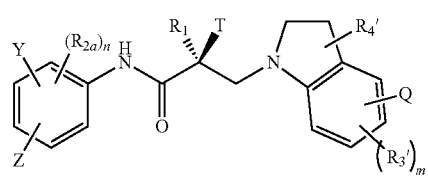

XIII wherein
T is H, OH, OR, OCOR, CH$_3$, —NHCOCH$_3$, or NHCOR:
Z is H, NO$_2$, CN, halide, COOH, COR, NHCOR or CONHR;
Y is H, CF$_3$, F, I, Br, Cl, CN, Sn(R)$_3$, C(R)$_3$ or Y and Z form a 5 to 8 membered fused ring;
R is H, alkyl, haloalkyl, alcohol, CH$_2$CH$_2$OH;

CH$_2$F, CHF$_2$, CF$_3$, CF$_2$CF$_3$, CH$_2$Cl, CH$_2$CH$_2$Cl, aryl, phenyl, F, Cl, Br, I, alkenyl or OH;
R$_1$ is H, CH$_3$, CH$_2$F, CHF$_2$, CF$_3$, CH$_2$CH$_3$, or CF$_2$CF$_3$;
R$_{2a}$ is hydrogen, halogen, CN, NO$_2$, COOH, COOR, COR, NHCOR, CONHR, OH, OR, SH, SR, NH$_2$, NHR, NR$_2$, C$_1$-C$_{12}$-alkyl, C$_1$-C$_{12}$-haloalkyl, O—C$_1$-C$_{12}$-alkyl, O—C$_1$-C$_{12}$-haloalkyl, —SO$_2$-aryl, —SO$_2$-phenyl, —CO-aryl, arylalkyl, benzyl, aryl, or C$_3$-C$_7$-cycloalkyl;

Q is hydrogen, F, Cl, Br, I, CF$_3$, CN, NO$_2$, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;

R$_3$' is hydrogen, F, Cl, Br, I, CF$_3$, CN, NO$_2$, NH$_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;

R$_4$' is hydrogen, F, Cl, Br, I, CF$_3$, CN, NO$_2$, NH$_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;

n is an integer between 1-3; and
m is an integer between 1-3;
or its isomer, pharmaceutically acceptable salt, pharmaceutical product, polymorph, hydrate or any combination thereof.

In one embodiment, this invention is directed to a selective androgen receptor degrader (SARD) compound represented by the structure of formula XIV:

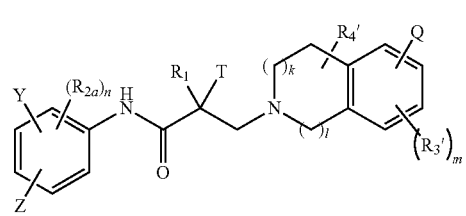

XIV wherein

T is H, OH, OR, OCOR, CH₃, —NHCOCH₃ or NHCOR;

Z is H, NO₂, CN, halide, COOH, COR, NHCOR or CONHR;

Y is H, CF₃, F, I, Br, Cl, CN, Sn(R)₃, C(R)₃ or Y and Z form a 5 to 8 membered fused ring;

R is H, alkyl, haloalkyl, alcohol, CH₂CH₂OH, CH₂F, CHF₂, CF₃, CF₂CF₃, CH₂Cl, CH₂CH₂Cl, aryl, phenyl, F, Cl, Br, I, alkenyl or OH;

R₁ is H, CH₃, CH₂F, CHF₂, CF₃, CH₂CH₃, or CF₂CF₃;

R₂ₐ is hydrogen, halogen, CN, NO₂, COOH, COOR, COR, NHCOR, CONHR, OH, OR, SH, SR, NH₂, NHR, NR₂, C₁-C₁₂-alkyl, C₁-C₁₂-haloalkyl, O—C₁-C₁₂-alkyl, O—C₁-C₁₂-haloalkyl, —SO₂-aryl, —SO₂-phenyl, —CO-aryl, arylalkyl, benzyl, aryl, or C₃-C₇-cycloalkyl;

Q is hydrogen, F, Cl, Br, I, CF₃, CN, NO₂, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)₃, N(R)₂, NHCOCH₃, NHCOCF₃, NHCOR, NHCONHR, NHCOOR, OCONHR, CONHR, NHCSCH₃, NHCSCF₃, NHCSR, NHSO₂CH₃, NHSO₂R, OR, COR, OCOR, OSO₂R, SO₂R, SR, NCS, SCN, NCO or OCN;

R₃· is hydrogen, F, Cl, Br, I, CF₃, CN, NO₂, NH₂, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)₃, N(R)₂, NHCOCH₃, NHCOCF₃, NHCOR, NHCONHR, NHCOOR, OCONHR, CONHR, NHCSCH₃, NHCSCF₃, NHCSR, NHSO₂CH₃, NHSO₂R, OR, COR, OCOR, OSO₂R, SO₂R, SR, NCS, SCN, NCO or OCN;

R₄· is hydrogen, F, Cl, Br, I, CF₃, CN, NO₂, NH₂, SH, COOH, COOR, keto (=O), alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)₃, N(R)₂, NHCOCH₃, NHCOCF₃, NHCOR, NHCONHR, NHCOOR, OCONHR, CONHR, NHCSCH₃, NHCSCF₃, NHCSR, NHSO₂CH₃, NHSO₂R, OR, COR, OCOR, OSO₂R, SO₂R, SR, NCS, SCN, NCO or OCN;

n is an integer between 1-3;

m is an integer between 1-3;

l is 0 or 1; and k is 0, 1 or 2;

or its isomer, pharmaceutically acceptable salt, pharmaceutical product, polymorph, hydrate or any combination thereof.

In one embodiment, this invention is directed to a selective androgen receptor degrader (SARD) compound represented by the structure of formula XIV(1):

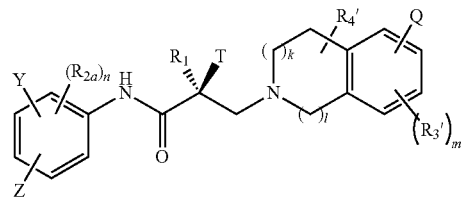

wherein

T is H, OH, OR, OCOR, CH₃, —NHCOCH₃ or NHCOR;

Z is H, NO₂, CN, halide, COOH, COR, NHCOR or CONHR;

Y is H, CF₃, F, I, Br, Cl, CN, Sn(R)₃, C(R)₃ or Y and Z form a 5 to 8 membered fused ring;

R is H, alkyl, haloalkyl, alcohol, CH₂CH₂OH, CH₂F, CHF₂, CF₃, CF₂CF₃, CH₂Cl, CH₂CH₂Cl, aryl, phenyl, F, Cl, Br, I, alkenyl or OH;

R₁ is H, CH₃, CH₂F, CHF₂, CF₃, CH₂CH₃, or CF₂CF₃;

R₂ₐ is hydrogen, halogen, CN, NO₂, COOH, COOR, COR, NHCOR, CONHR, OH, OR, SH, SR, NH₂, NHR, NR₂, C₁-C₁₂-alkyl, C₁-C₁₂-haloalkyl, O—C₁-C₁₂-alkyl, O—C₁-C₁₂-haloalkyl, —SO₂-aryl, —SO₂-phenyl, —CO-aryl, arylalkyl, benzyl, aryl, or C₃-C₇-cycloalkyl;

Q is hydrogen, F, Cl, Br, I, CF₃, CN, NO₂, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)₃, N(R)₂, NHCOCH₃, NHCOCF₃, NHCOR, NHCONHR, NHCOOR, OCONHR, CONHR, NHCSCH₃, NHCSCF₃, NHCSR, NHSO₂CH₃, NHSO₂R, OR, COR, OCOR, OSO₂R, SO₂R, SR, NCS, SCN, NCO or OCN;

R₃· is hydrogen, F, Cl, Br, I, CF₃, CN, NO₂, NH₂, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)₃, N(R)₂, NHCOCH₃, NHCOCF₃, NHCOR, NHCONHR, NHCOOR, OCONHR, CONHR, NHCSCH₃, NHCSCF₃, NHCSR, NHSO₂CH₃, NHSO₂R, OR, COR, OCOR, OSO₂R, SO₂R, SR, NCS, SCN, NCO or OCN;

R₄· is hydrogen, F, Cl, Br, I, CF₃, CN, NO₂, NH₂, SH, COOH, COOR, keto (=O), alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)₃, N(R)₂, NHCOCH₃, NHCOCF₃, NHCOR, NHCONHR, NHCOOR, OCONHR, CONHR, NHCSCH₃, NHCSCF₃, NHCSR, NHSO₂CH₃, NHSO₂R, OR, COR, OCOR, OSO₂R, SO₂R, SR, NCS, SCN, NCO or OCN;

n is an integer between 1-3;

m is an integer between 1-3;

l is 0 or 1; and k is 0, 1 or 2;

or its isomer, pharmaceutically acceptable salt, pharmaceutical product, polymorph, hydrate or any combination thereof.

In one embodiment, this invention is directed to a selective androgen receptor degrader (SARD) compound represented by the structure of formula XIV(2):

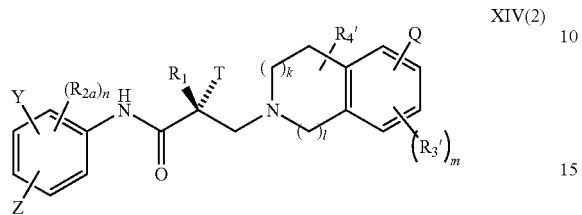

XIV(2)

wherein

T is H, OH, OR, OCOR, CH$_3$, —NHCOCH$_3$, NHCOR or

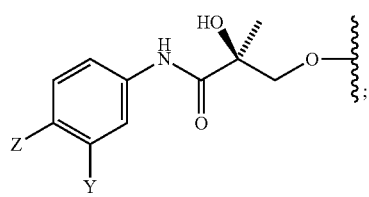

Z is H, NO$_2$, CN, halide, COOH, COR, NHCOR or CONHR;
Y is H, CF$_3$, F, I, Br, Cl, CN, Sn(R)$_3$, C(R)$_3$ or Y and Z form a 5 to 8 membered fused ring;
R is H, alkyl, haloalkyl, alcohol, CH$_2$CH$_2$OH, CH$_2$F, CHF$_2$, CF$_3$, CF$_2$CF$_3$, CH$_2$Cl, CH$_2$CH$_2$Cl, aryl, phenyl, F, Cl, Br, I, alkenyl or OH;
R$_1$ is H, CH$_3$, CH$_2$F, CHF$_2$, CF$_3$, CH$_2$CH$_3$, or CF$_2$CF$_3$;
R$_{2a}$ is hydrogen, halogen, CN, NO$_2$, COOH, COOR, COR, NHCOR, CONHR, OH, OR, SH, SR, NH$_2$, NHR, NR$_2$, C$_1$-C$_{12}$-alkyl, C$_1$-C$_{12}$-haloalkyl, O—C$_1$-C$_{12}$-alkyl, O—C$_1$-C$_{12}$-haloalkyl, —SO$_2$-aryl, —SO$_2$-phenyl, —CO-aryl, arylalkyl, benzyl, aryl, or C$_3$-C$_7$-cycloalkyl;
Q is hydrogen, F, Cl, Br, I, CF$_3$, CN, NO$_2$, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;
R$_{3'}$ is hydrogen, F, Cl, Br, I, CF$_3$, CN, NO$_2$, NH$_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;
R$_{4'}$ is hydrogen, F, Cl, Br, I, CF$_3$, CN, NO$_2$, NH$_2$, SH, COOH, COOR, keto (=O), alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;
n is an integer between 1-3;
m is an integer between 1-3;
l is 0 or 1; and
k is 0, 1 or 2;
or its isomer, pharmaceutically acceptable salt, pharmaceutical product, polymorph, hydrate or any combination thereof.

In one embodiment, this invention is directed to a selective androgen receptor degrader (SARD) compound represented by the structure of formula XV:

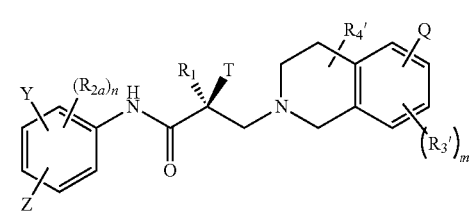

XV wherein

T is H, OH, OR, OCOR, CH$_3$, —NHCOCH$_3$, NHCOR or

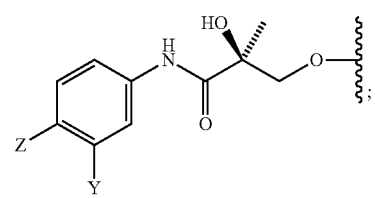

Z is H, NO$_2$, CN, halide, COOH, COR, NHCOR or CONHR;
Y is H, CF$_3$, F, I, Br, Cl, CN, Sn(R)$_3$, C(R)$_3$ or Y and Z form a 5 to 8 membered fused ring;
R is H, alkyl, haloalkyl, alcohol, CH$_2$CH$_2$OH, CH$_2$F, CHF$_2$, CF$_3$, CF$_2$CF$_3$, CH$_2$Cl, CH$_2$CH$_2$Cl, aryl, phenyl, F, Cl, Br, I, alkenyl or OH;
R$_1$ is H, CH$_3$, CH$_2$F, CHF$_2$, CF$_3$, CH$_2$CH$_3$, or CF$_2$CF$_3$;
R$_{2a}$ is hydrogen, halogen, CN, NO$_2$, COOH, COOR, COR, NHCOR, CONHR, OH, OR, SH, SR, NH$_2$, NHR, NR$_2$, C$_1$-C$_{12}$-alkyl, C$_1$-C$_{12}$-haloalkyl, O—C$_1$-C$_{12}$-alkyl, O—C$_1$-C$_{12}$-haloalkyl, —SO$_2$-aryl, —SO$_2$-phenyl, —CO-aryl, arylalkyl, benzyl, aryl, or C$_3$-C$_7$-cycloalkyl;
Q is hydrogen, F, Cl, Br, I, CF$_3$, CN, NO$_2$, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)₃, N(R)₂, NHCOCH₃, NHCOCF₃, NHCOR, NHCONHR, NHCOOR, OCONHR, CONHR, NHCSCH₃, NHCSCF₃, NHCSR, NHSO₂CH₃, NHSO₂R, OR, COR, OCOR, OSO₂R, SO₂R, SR, NCS, SCN, NCO or OCN;

$R_{3'}$ is hydrogen, F, Cl, Br, I, CF₃, CN, NO₂, NH₂, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)₃, N(R)₂, NHCOCH₃, NHCOCF₃, NHCOR, NHCONHR, NHCOOR, OCONHR, CONHR, NHCSCH₃, NHCSCF₃, NHCSR, NHSO₂CH₃, NHSO₂R, OR, COR, OCOR, OSO₂R, SO₂R, SR, NCS, SCN, NCO or OCN;

$R_{4'}$ is hydrogen, F, Cl, Br, I, CF₃, CN, NO₂, NH₂, SH, COOH, COOR, keto (=O), alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)₃, N(R)₂, NHCOCH₃, NHCOCF₃, NHCOR, NHCONHR, NHCOOR, OCONHR, CONHR, NHCSCH₃, NHCSCF₃, NHCSR, NHSO₂CH₃, NHSO₂R, OR, COR, OCOR, OSO₂R, SO₂R, SR, NCS, SCN, NCO or OCN;

n is an integer between 1-3; and m is an integer between 1-3;

or its isomer, pharmaceutically acceptable salt, pharmaceutical product, polymorph, hydrate or any combination thereof.

In one embodiment, this invention is directed to a selective androgen receptor degrader (SARD) compound represented by the structure of formula XVI:

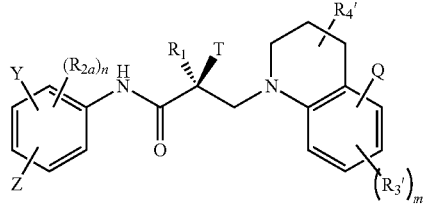

XVI wherein

T is H, OH, OR, OCOR, CH₃, —NHCOCH₃, NHCOR or

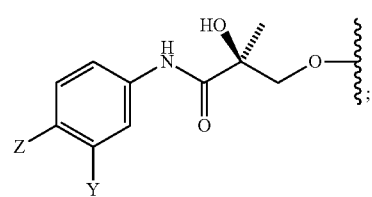

Z is H, NO₂, CN, halide, COOH, COR, NHCOR or CONHR;

Y is H, CF₃, F, I, Br, Cl, CN, Sn(R)₃, C(R)₃ or Y and Z form a 5 to 8 membered fused ring;

R is H, alkyl, haloalkyl, alcohol, CH₂CH₂OH, CH₂F, CHF₂, CF₃, CF₂CF₃, CH₂Cl, CH₂CH₂Cl, aryl, phenyl, F, Cl, Br, I, alkenyl or OH;

$R_1$ is H, CH₃, CH₂F, CHF₂, CF₃, CH₂CH₃, or CF₂CF₃;

$R_{2a}$ is hydrogen, halogen, CN, NO₂, COOH, COOR, COR, NHCOR, CONHR, OH, OR, SH, SR, NH₂, NHR, NR₂, C₁-C₁₂-alkyl, C₁-C₁₂-haloalkyl, O—C₁-C₁₂-alkyl, O—C₁-C₁₂-haloalkyl, —SO₂-aryl, —SO₂-phenyl, —CO-aryl, arylalkyl, benzyl, aryl, or C₃-C₇-cycloalkyl;

Q is hydrogen, F, Cl, Br, I, CF₃, CN, NO₂, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)₃, N(R)₂, NHCOCH₃, NHCOCF₃, NHCOR, NHCONHR, NHCOOR, OCONHR, CONHR, NHCSCH₃, NHCSCF₃, NHCSR, NHSO₂CH₃, NHSO₂R, OR, COR, OCOR, OSO₂R, SO₂R, SR, NCS, SCN, NCO or OCN;

$R_{3'}$ is hydrogen, F, Cl, Br, I, CF₃, CN, NO₂, NH₂, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)₃, N(R)₂, NHCOCH₃, NHCOCF₃, NHCOR, NHCONHR, NHCOOR, OCONHR, CONHR, NHCSCH₃, NHCSCF₃, NHCSR, NHSO₂CH₃, NHSO₂R, OR, COR, OCOR, OSO₂R, SO₂R, SR, NCS, SCN, NCO or OCN;

$R_{4'}$ is hydrogen, F, Cl, Br, I, CF₃, CN, NO₂, NH₂, SH, COOH, COOR, keto (=O), alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)₃, N(R)₂, NHCOCH₃, NHCOCF₃, NHCOR, NHCONHR, NHCOOR, OCONHR, CONHR, NHCSCH₃, NHCSCF₃, NHCSR, NHSO₂CH₃, NHSO₂R, OR, COR, OCOR, OSO₂R, SO₂R, SR, NCS, SCN, NCO or OCN;

n is an integer between 1-3; and m is an integer between 1-3;

or its isomer, pharmaceutically acceptable salt, pharmaceutical product, polymorph, hydrate or any combination thereof.

In one embodiment, this invention is directed to a selective androgen receptor degrader (SARD) compound represented by the structure of formula XVII:

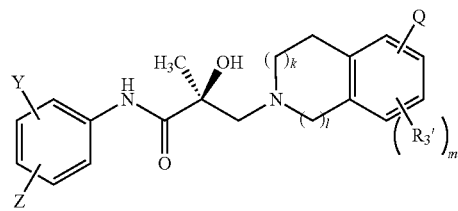

XVII wherein
Z is H, NO$_2$, CN, halide, COOH, COR, NHCOR or CONHR;
Y is H, CF$_3$, F, I, Br, Cl, CN, Sn(R)$_3$, C(R)$_3$ or Y and Z form a 5 to 8 membered fused ring;
R is H, alkyl, haloalkyl, alcohol, CH$_2$CH$_2$OH, CH$_2$F, CHF$_2$, CF$_3$, CF$_2$CF$_3$, CH$_2$Cl, CH$_2$CH$_2$Cl, aryl, phenyl, F, Cl, Br, I, alkenyl or OH;
Q is hydrogen, F, Cl, Br, I, CF$_3$, CN, NO$_2$, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;
R$_{3'}$ is hydrogen, F, Cl, Br, I, CF$_3$, CN, NO$_2$, NH$_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;
m is an integer between 1-3;
l is 0 or 1; and
k is 0, 1 or 2;
or its isomer, pharmaceutically acceptable salt, pharmaceutical product, polymorph, hydrate or any combination thereof.

In one embodiment, this invention is directed to a selective androgen receptor degrader (SARD) compound represented by the structure of formula XVIIIa, XVIIIb, XVIIIc, XVIIId, XVIIIe, XVIIIf, XVIIIg or XVIIIh:

XVIIIa

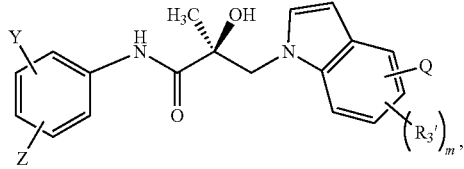

XVIIIb

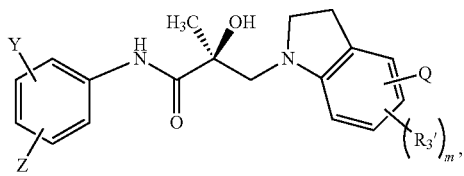

XVIIIc

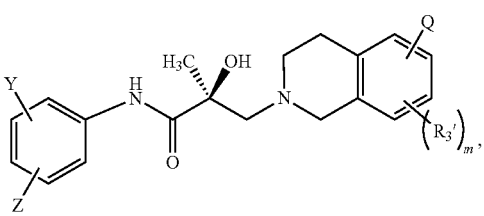

XVIIId

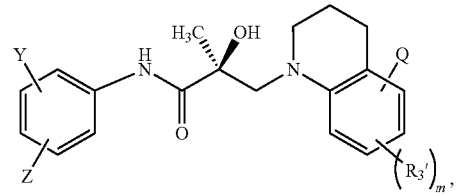

XVIIIe

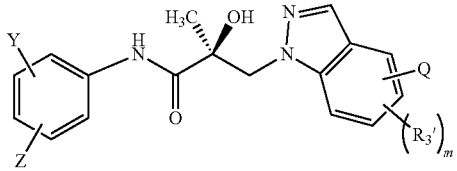

XVIIIf

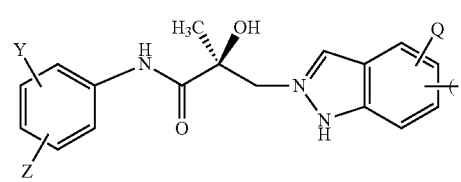

XVIIIg

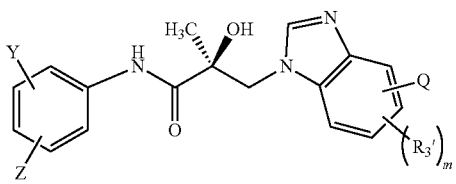

XVIIIh

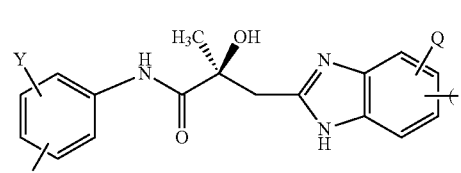

XVIIIi

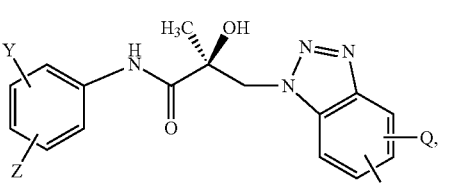

, or

XVIIIj

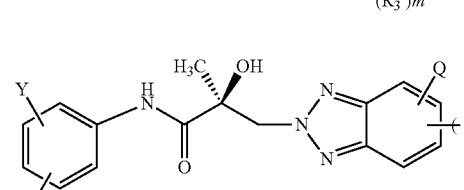

wherein
Z is H, NO$_2$, CN, halide, COOH, COR, NHCOR or CONHR;
Y is H, CF$_3$, F, I, Br, Cl, CN, Sn(R)$_3$, C(R)$_3$ or Y and Z form a 5 to 8 membered fused ring;
R is H, alkyl, haloalkyl, alcohol, CH$_2$CH$_2$OH, CH$_2$F, CHF$_2$, CF$_3$, CF$_2$CF$_3$, CH$_2$Cl, CH$_2$CH$_2$Cl, aryl, phenyl, F, Cl, Br, I, alkenyl or OH;
Q is hydrogen, F, Cl, Br, I, CF$_3$, CN, NO$_2$, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;

R$_{3'}$ is hydrogen, F, Cl, Br, I, CF$_3$, CN, NO$_2$, NH$_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN; and m is an integer between 1-3;

or its isomer, pharmaceutically acceptable salt, pharmaceutical product, polymorph, hydrate or any combination thereof.

In one embodiment, this invention is directed to a selective androgen receptor degrader (SARD) compound represented by the structure of formula XIX:

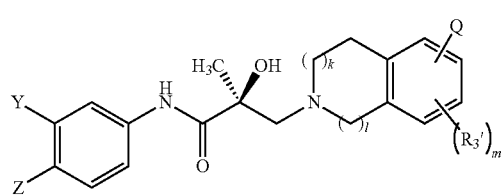

XIX wherein

Z is H, NO$_2$, CN, halide, COOH, COR, NHCOR or CONHR;

Y is H, CF$_3$, F, I, Br, Cl, CN, Sn(R)$_3$, C(R)$_3$ or Y and Z form a 5 to 8 membered fused ring;

R is H, alkyl, haloalkyl, alcohol, CH$_2$CH$_2$OH, CH$_2$F, CHF$_2$, CF$_3$, CF$_2$CF$_3$, CH$_2$Cl, CH$_2$CH$_2$Cl, aryl, phenyl, F, Cl, Br, I, alkenyl or OH;

Q is hydrogen, F, Cl, Br, I, CF$_3$, CN, NO$_2$, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;

R$_{3'}$ is hydrogen, F, Cl, Br, I, CF$_3$, CN, NO$_2$, NH$_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;

m is an integer between 1-3;

l is 0 or 1; and k is 0, 1 or 2;

or its isomer, pharmaceutically acceptable salt, pharmaceutical product, polymorph, hydrate or any combination thereof.

In one embodiment, this invention is directed to a selective androgen receptor degrader (SARD) compound represented by the structure of formula XXa, XXb, XXc, XXd, XXe, XXf, XXg, or XXh:

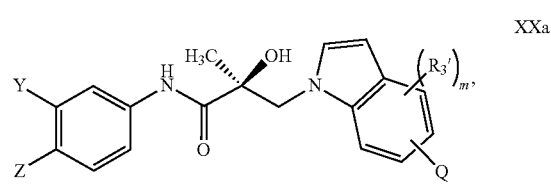

XXa

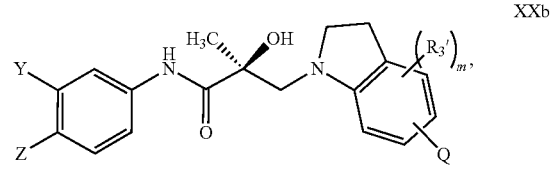

XXb

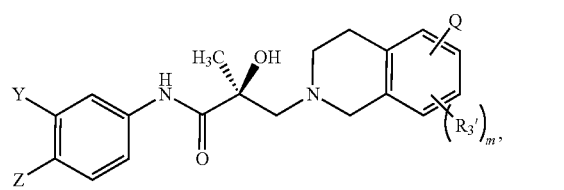

XXc

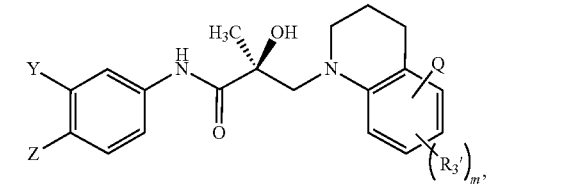

XXd

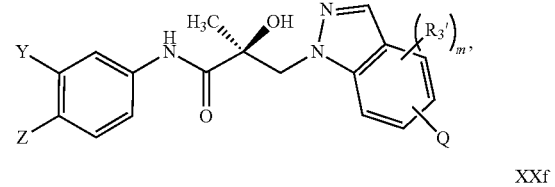

XXe

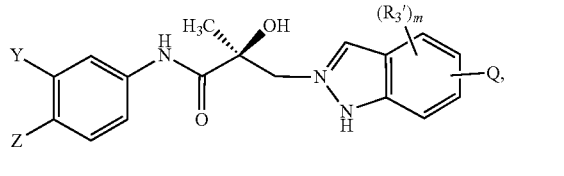

XXf

-continued

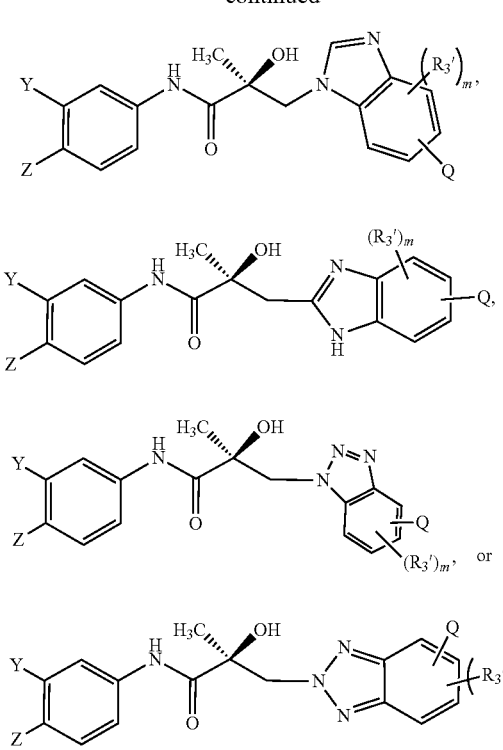

wherein
Z is H, NO₂, CN, halide, COOH, COR, NHCOR or CONHR;
Y is H, CF₃, F, I, Br, Cl, CN, Sn(R)₃, C(R)₃ or Y and Z form a 5 to 8 membered fused ring;
R is H, alkyl, haloalkyl, alcohol, CH₂CH₂OH, CH₂F, CHF₂, CF₃, CF₂CF₃, CH₂Cl, CH₂CH₂Cl, aryl, phenyl, F, Cl, Br, I, alkenyl or OH;
Q is hydrogen, F, Cl, Br, I, CF₃, CN, NO₂, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)₃, N(R)₂, NHCOCH₃, NHCOCF₃, NHCOR, NHCONHR, NHCOOR, OCONHR, CONHR, NHCSCH₃, NHCSCF₃, NHCSR, NHSO₂CH₃, NHSO₂R, OR, COR, OCOR, OSO₂R, SO₂R, SR, NCS, SCN, NCO or OCN;
R₃' is hydrogen, F, Cl, Br, I, CF₃, CN, NO₂, NH₂, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)₃, N(R)₂, NHCOCH₃, NHCOCF₃, NHCOR, NHCONHR, NHCOOR, OCONHR, CONHR, NHCSCH₃, NHCSCF₃, NHCSR, NHSO₂CH₃, NHSO₂R, OR, COR, OCOR, OSO₂R, SO₂R, SR, NCS, SCN, NCO or OCN; and
m is an integer between 1-3;
or its isomer, pharmaceutically acceptable salt, pharmaceutical product, polymorph, hydrate or any combination thereof.

In one embodiment, this invention is directed to a selective androgen receptor degrader (SARD) compound represented by the structure of formula XXI:

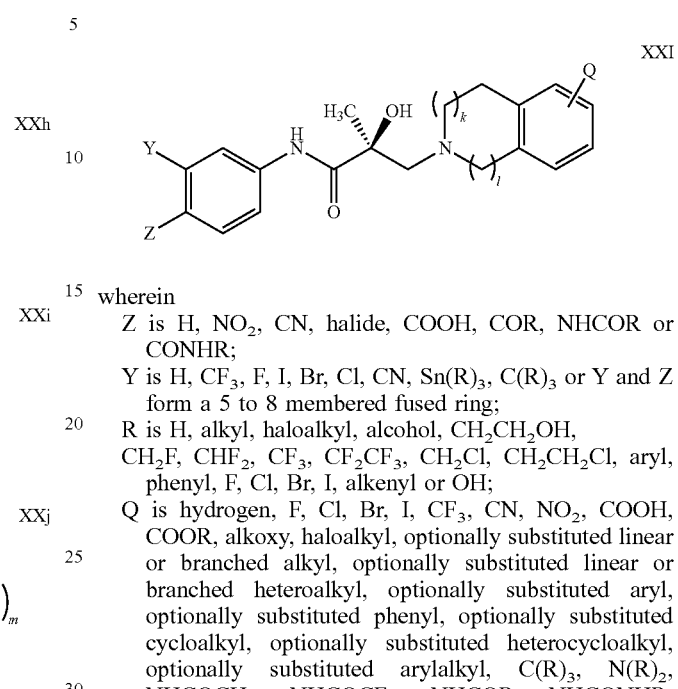

wherein
Z is H, NO₂, CN, halide, COOH, COR, NHCOR or CONHR;
Y is H, CF₃, F, I, Br, Cl, CN, Sn(R)₃, C(R)₃ or Y and Z form a 5 to 8 membered fused ring;
R is H, alkyl, haloalkyl, alcohol, CH₂CH₂OH, CH₂F, CHF₂, CF₃, CF₂CF₃, CH₂Cl, CH₂CH₂Cl, aryl, phenyl, F, Cl, Br, I, alkenyl or OH;
Q is hydrogen, F, Cl, Br, I, CF₃, CN, NO₂, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)₃, N(R)₂, NHCOCH₃, NHCOCF₃, NHCOR, NHCONHR, NHCOOR, OCONHR, CONHR, NHCSCH₃, NHCSCF₃, NHCSR, NHSO₂CH₃, NHSO₂R, OR, COR, OCOR, OSO₂R, SO₂R, SR, NCS, SCN, NCO or OCN;
l is 0 or 1; and
k is 0, 1 or 2;
or its isomer, pharmaceutically acceptable salt, pharmaceutical product, polymorph, hydrate or any combination thereof.

In one embodiment, this invention is directed to a selective androgen receptor degrader (SARD) compound represented by the structure of formula XXIIa, XXIIb, XXIIc, XXIId, XXIIe, XXIIf, XXIIg, or XXIIh:

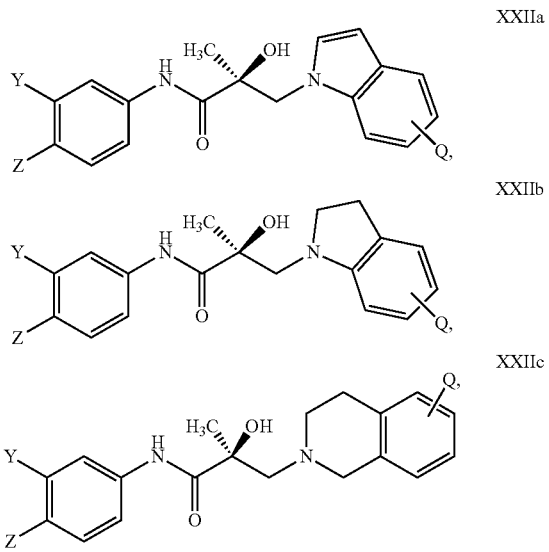

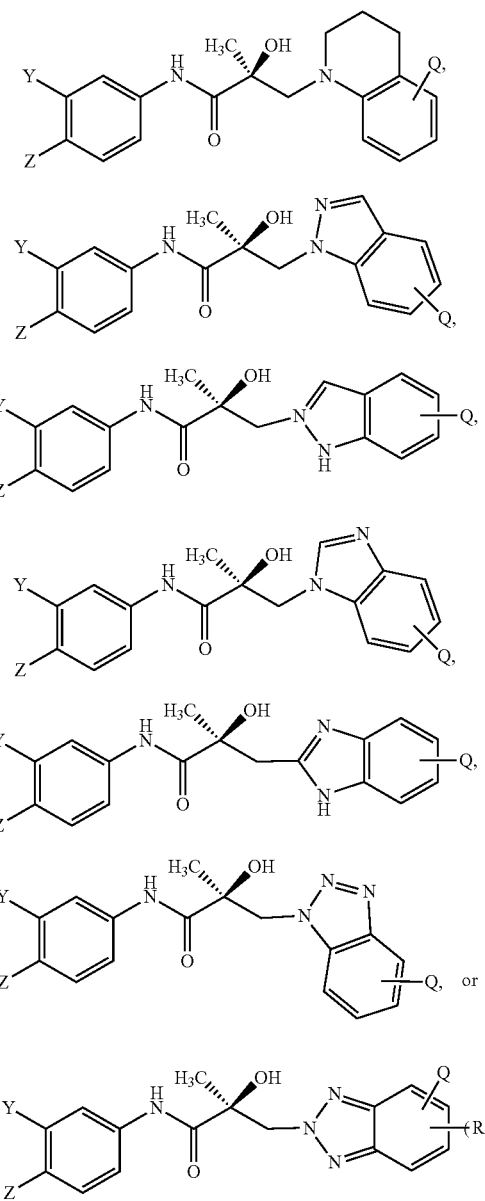

wherein
- Z is H, NO₂, CN, halide, COOH, COR, NHCOR or CONHR;
- Y is H, CF₃, F, I, Br, Cl, CN, Sn(R)₃, C(R)₃ or Y and Z form a 5 to 8 membered fused ring;
- R is H, alkyl, haloalkyl, alcohol, CH₂CH₂OH, CH₂F, CHF₂, CF₃, CF₂CF₃, CH₂Cl, CH₂CH₂Cl, aryl, phenyl, F, Cl, Br, I, alkenyl or OH;
- Q is hydrogen, F, Cl, Br, I, CF₃, CN, NO₂, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)₃, N(R)₂, NHCOCH₃, NHCOCF₃, NHCOR, NHCONHR, NHCOOR, OCONHR, CONHR, NHCSCH₃, NHCSCF₃, NHCSR, NHSO₂CH₃, NHSO₂R, OR, COR, OCOR, OSO₂R, SO₂R, SR, NCS, SCN, NCO or OCN;

or its isomer, pharmaceutically acceptable salt, pharmaceutical product, polymorph, hydrate or any combination thereof.

In one embodiment, this invention is directed to a selective androgen receptor degrader (SARD) compound represented by the structure of formula XXIII:

XXIII wherein
- T is H, OH, OR, OCOR, CH₃, —NHCOCH₃, or NHCOR;
- Z is H, NO₂, CN, halide, COOH, COR, NHCOR or CONHR;
- Y is H, CF₃, F, I, Br, Cl, CN, Sn(R)₃, C(R)₃ or Y and Z form a 5 to 8 membered fused ring;
- R is H, alkyl, haloalkyl, alcohol, CH₂CH₂OH, CH₂F, CHF₂, CF₃, CF₂CF₃, CH₂Cl, CH₂CH₂Cl, aryl, phenyl, F, Cl, Br, I, alkenyl or OH;
- R₁ is H, CH₃, CH₂F, CHF₂, CF₃, CH₂CH₃, or CF₂CF₃;
- R₂ₐ is hydrogen, halogen, CN, NO₂, COOH, COOR, COR, NHCOR, CONHR, OH, OR, SH, SR, NH₂, NHR, NR₂, C₁-C₁₂-alkyl, C₁-C₁₂-haloalkyl, O—C₁-C₁₂-alkyl, O—C₁-C₁₂-haloalkyl, —SO₂-aryl, —SO₂-phenyl, —CO-aryl, arylalkyl, benzyl, aryl, or C₃-C₇-cycloalkyl;
- Q is hydrogen, F, Cl, Br, I, CF₃, CN, NO₂, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)₃, N(R)₂, NHCOCH₃, NHCOCF₃, NHCOR, NHCONHR, NHCOOR, OCONHR, CONHR, NHCSCH₃, NHCSCF₃, NHCSR, NHSO₂CH₃, NHSO₂R, OR, COR, OCOR, OSO₂R, SO₂R, SR, NCS, SCN, NCO or OCN;
- R₃' is hydrogen, F, Cl, Br, I, CF₃, CN, NO₂, NH₂, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)₃, N(R)₂, NHCOCH₃, NHCOCF₃, NHCOR, NHCONHR, NHCOOR, OCONHR, CONHR, NHCSCH₃, NHCSCF₃, NHCSR, NHSO₂CH₃, NHSO₂R, OR, COR, OCOR, OSO₂R, SO₂R, SR, NCS, SCN, NCO or OCN;
- R₄' is hydrogen, F, Cl, Br, I, CF₃, CN, NO₂, NH₂, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;

n is an integer between 1-3; and m is an integer between 1-3;

or its isomer, pharmaceutically acceptable salt, pharmaceutical product, polymorph, hydrate or any combination thereof.

In one embodiment, this invention is directed to a selective androgen receptor degrader (SARD) compound represented by the structure of formula XXIII(1):

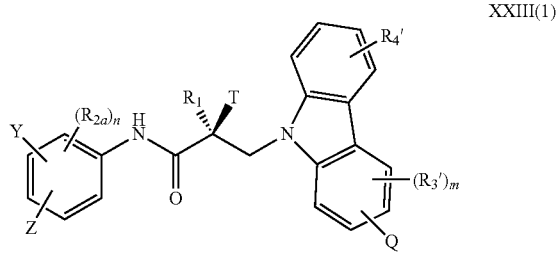

XXIII(1)

wherein

T is H, OH, OR, OCOR, CH$_3$, —NHCOCH$_3$ or NHCOR;

Z is H, NO$_2$, CN, halide, COOH, COR, NHCOR or CONHR;

Y is H, CF$_3$, F, I, Br, Cl, CN, Sn(R)$_3$, C(R)$_3$ or Y and Z form a 5 to 8 membered fused ring;

R is H, alkyl, haloalkyl, alcohol, CH$_2$CH$_2$OH, CH$_2$F, CHF$_2$, CF$_3$, CF$_2$CF$_3$, CH$_2$Cl, CH$_2$CH$_2$Cl, aryl, phenyl, F, Cl, Br, I, alkenyl or OH;

R$_1$ is H, CH$_3$, CH$_2$F, CHF$_2$, CF$_3$, CH$_2$CH$_3$, or CF$_2$CF$_3$;

R$_{2a}$ is hydrogen, halogen, CN, NO$_2$, COOH, COOR, COR, NHCOR, CONHR, OH, OR, SH, SR, NH$_2$, NHR, NR$_2$, C$_1$-C$_{12}$-alkyl, C$_1$-C$_{12}$-haloalkyl, O—C$_1$-C$_{12}$-alkyl, O—C$_1$-C$_{12}$-haloalkyl, —SO$_2$-aryl, —SO$_2$-phenyl, —CO-aryl, arylalkyl, benzyl, aryl, or C$_3$-C$_7$-cycloalkyl;

Q is hydrogen, F, Cl, Br, I, CF$_3$, CN, NO$_2$, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;

R$_{3'}$ is hydrogen, F, Cl, Br, I, CF$_3$, CN, NO$_2$, NH$_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;

R$_{4'}$ is hydrogen, F, Cl, Br, I, CF$_3$, CN, NO$_2$, NH$_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;

n is an integer between 1-3; and m is an integer between 1-3;

or its isomer, pharmaceutically acceptable salt, pharmaceutical product, polymorph, hydrate or any combination thereof.

In one embodiment, this invention is directed to a selective androgen receptor degrader (SARD) compound represented by the structure of formula XXIII(2):

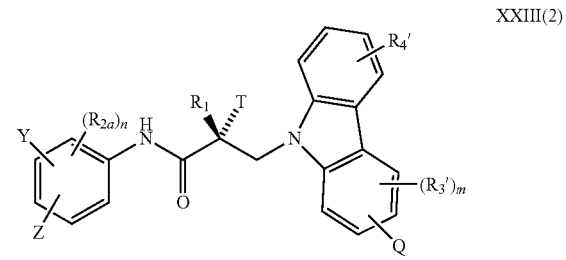

XXIII(2)

wherein

T is H, OH, OR, OCOR, CH$_3$, —NHCOCH$_3$ or NHCOR;

Z is H, NO$_2$, CN, halide, COOH, COR, NHCOR or CONHR;

Y is H, CF$_3$, F, I, Br, Cl, CN, Sn(R)$_3$, C(R)$_3$ or Y and Z form a 5 to 8 membered fused ring;

R is H, alkyl, haloalkyl, alcohol, CH$_2$CH$_2$OH, CH$_2$F, CHF$_2$, CF$_3$, CF$_2$CF$_3$, CH$_2$Cl, CH$_2$CH$_2$Cl, aryl, phenyl, F, Cl, Br, I, alkenyl or OH;

R$_1$ is H, CH$_3$, CH$_2$F, CHF$_2$, CF$_3$, CH$_2$CH$_3$, or CF$_2$CF$_3$;

R$_{2a}$ is hydrogen, halogen, CN, NO$_2$, COOH, COOR, COR, NHCOR, CONHR, OH, OR, SH, SR, NH$_2$, NHR, NR$_2$, C$_1$-C$_{12}$-alkyl, C$_1$-C$_{12}$-haloalkyl, O—C$_1$-C$_{12}$-alkyl, O—C$_1$-C$_{12}$-haloalkyl, —SO$_2$-aryl, —SO$_2$-phenyl, —CO-aryl, arylalkyl, benzyl, aryl, or C$_3$-C$_7$-cycloalkyl;

Q is hydrogen, F, Cl, Br, I, CF$_3$, CN, NO$_2$, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;

R$_{3'}$ is hydrogen, F, Cl, Br, I, CF$_3$, CN, NO$_2$, NH$_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;

$R_{4'}$ is hydrogen, F, Cl, Br, I, $CF_3$, CN, $NO_2$, $NH_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;

n is an integer between 1-3; and m is an integer between 1-3;

or its isomer, pharmaceutically acceptable salt, pharmaceutical product, polymorph, hydrate or any combination thereof.

In one embodiment, this invention is directed to a selective androgen receptor degrader (SARD) compound represented by the structure of formula XXIV:

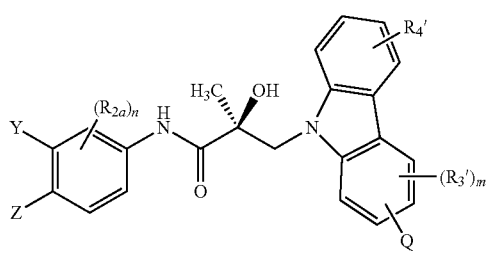

XXIV wherein

T is H, OH, OR, OCOR, $CH_3$, —$NHCOCH_3$ or NHCOR;

Z is H, $NO_2$, CN, halide, COOH, COR, NHCOR or CONHR;

Y is H, $CF_3$, F, I, Br, Cl, CN, $Sn(R)_3$, $C(R)_3$ or Y and Z form a 5 to 8 membered fused ring;

R is H, alkyl, haloalkyl, alcohol, $CH_2CH_2OH$, $CH_2F$, $CHF_2$, $CF_3$, $CF_2CF_3$, $CH_2Cl$, $CH_2CH_2Cl$, aryl, phenyl, F, Cl, Br, I, alkenyl or OH;

$R_{2a}$ is hydrogen, halogen, CN, $NO_2$, COOH, COOR, COR, NHCOR, CONHR, OH, OR, SH, SR, $NH_2$, NHR, $NR_2$, $C_1$-$C_{12}$-alkyl, $C_1$-$C_{12}$-haloalkyl, O—$C_1$-$C_{12}$-alkyl, O—$C_1$-$C_{12}$-haloalkyl, —$SO_2$-aryl, —$SO_2$-phenyl, —CO-aryl, arylalkyl, benzyl, aryl, or $C_3$-$C_7$-cycloalkyl;

Q is hydrogen, F, Cl, Br, I, $CF_3$, CN, $NO_2$, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;

$R_{3'}$ is hydrogen, F, Cl, Br, I, $CF_3$, CN, $NO_2$, $NH_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;

$R_{4'}$ is hydrogen, F, Cl, Br, I, $CF_3$, CN, $NO_2$, $NH_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;

n is an integer between 1-3; and m is an integer between 1-3;

or its isomer, pharmaceutically acceptable salt, pharmaceutical product, polymorph, hydrate or any combination thereof.

In another embodiment, compounds of formula XXIII, XXIII(1), XXIII(20 and XXIV are represented by the following structures:

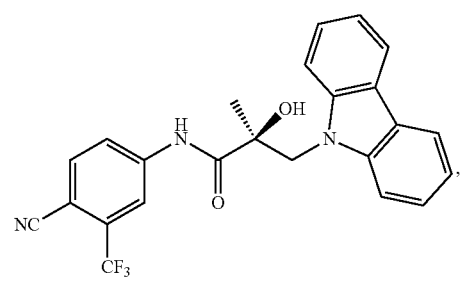

200

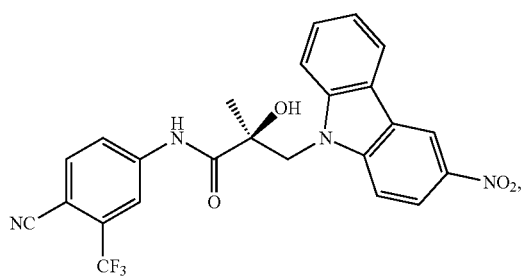

201

-continued

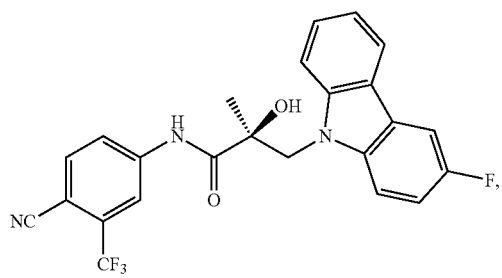
202

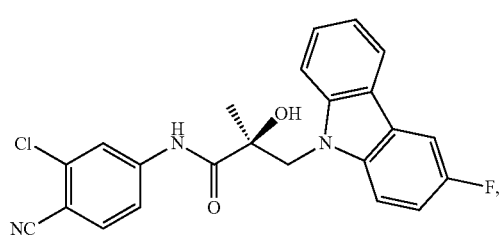
203

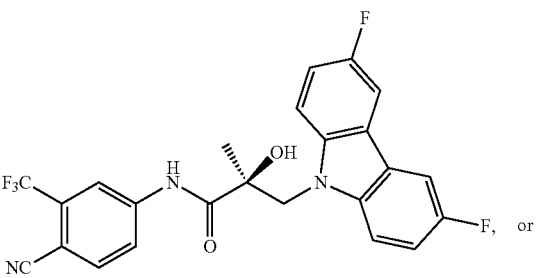
204

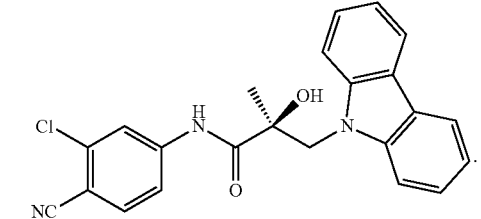
, or

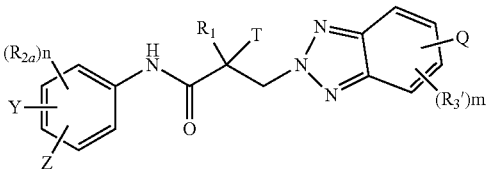
205

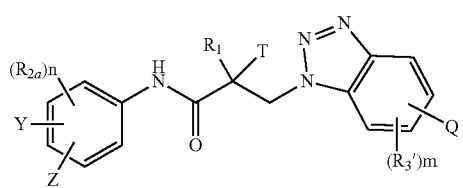

In one embodiment, this invention is directed to a selective androgen receptor degrader (SARD) compound represented by the structure of formula XXVa, XXVb, XXVa(1), XXVb(1), XXVa(2), XXVb(2):

XXVa

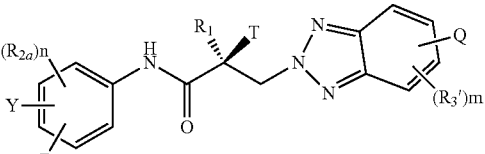

XXVb

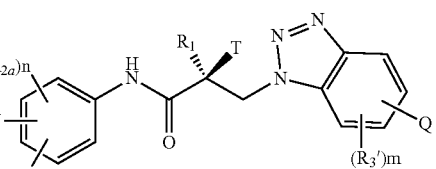

-continued

XXVa(1)

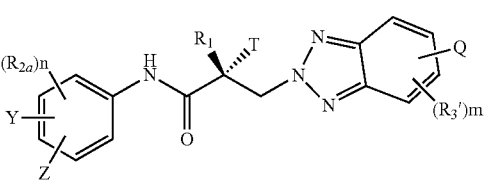

XXVb(1)

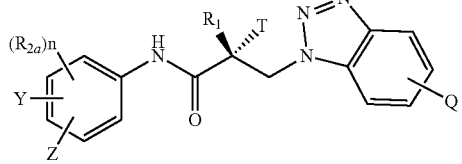

XXVa(2)

XXVb(2)

wherein

T is H, OH, OR, OCOR, $CH_3$, —$NHCOCH_3$ or NHCOR;

Z is H, $NO_2$, CN, halide, COOH, COR, NHCOR or CONHR;

Y is H, $CF_3$, F, I, Br, Cl, CN, $Sn(R)_3$, $C(R)_3$ or Y and Z form a 5 to 8 membered fused ring;

R is H, alkyl, haloalkyl, alcohol, $CH_2CH_2OH$, $CH_2F$, $CHF_2$, $CF_3$, $CF_2CF_3$, $CH_2Cl$, $CH_2CH_2Cl$, aryl, phenyl, F, Cl, Br, I, alkenyl or OH;

$R_{2a}$ is hydrogen, halogen, CN, $NO_2$, COOH, COOR, COR, NHCOR, CONHR, OH, OR, SH, SR, $NH_2$, NHR, $NR_2$, $C_1$-$C_{12}$-alkyl, $C_1$-$C_{12}$-haloalkyl, O—$C_1$-$C_{12}$-alkyl, O—$C_1$-$C_{12}$-haloalkyl, —$SO_2$-aryl, —$SO_2$-phenyl, —CO-aryl, arylalkyl, benzyl, aryl, or $C_3$-$C_7$-cycloalkyl Q is hydrogen, F, Cl, Br, I, $CF_3$, CN, $NO_2$, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;

$R_{3'}$ is hydrogen, F, Cl, Br, I, $CF_3$, CN, $NO_2$, $NH_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)₃, N(R)₂, NHCOCH₃, NHCOCF₃, NHCOR, NHCONHR, NHCOOR, OCONHR, CONHR, NHCSCH₃, NHCSCF₃, NHCSR, NHSO₂CH₃, NHSO₂R, OR, COR, OCOR, OSO₂R, SO₂R, SR, NCS, SCN, NCO or OCN;

n is an integer between 1-3; and m is an integer between 1-3;

or its isomer, pharmaceutically acceptable salt, pharmaceutical product, polymorph, hydrate or any combination thereof.

In some embodiments, the compounds of formula X-XXV are represented by the following structures:

indoles:

11

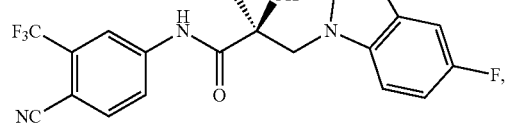

11R

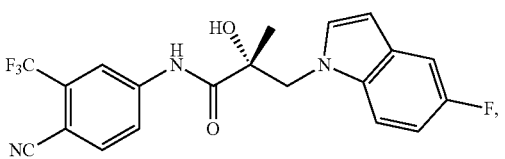

12

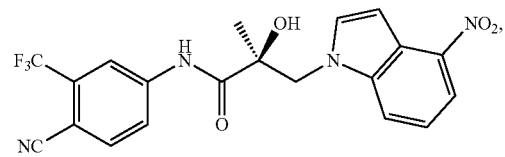

13

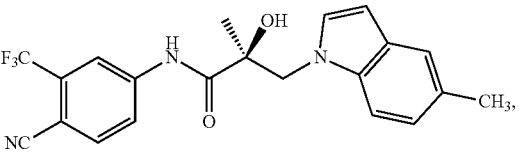

14

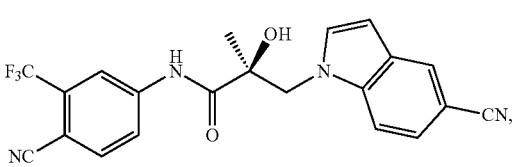

15

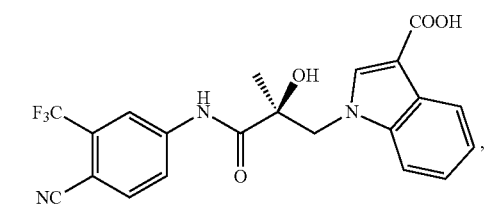

-continued

16

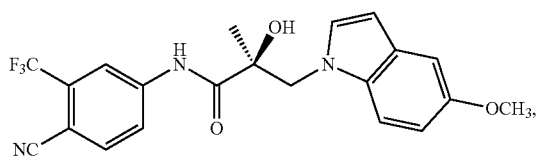

17

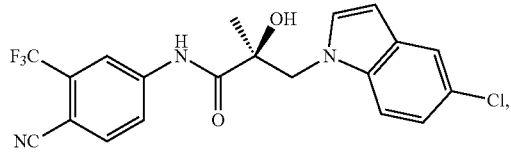

18

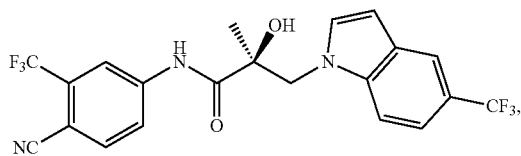

19

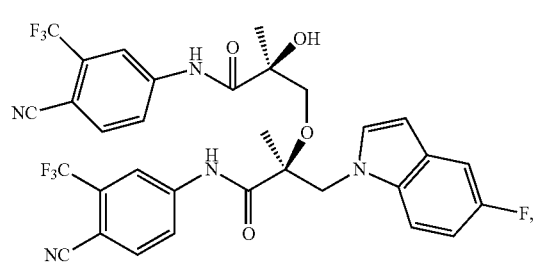

20

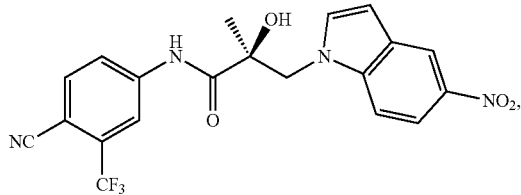

21

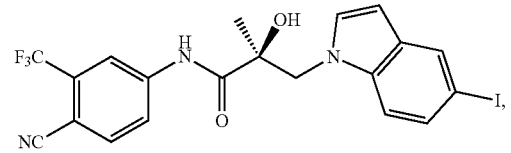

22

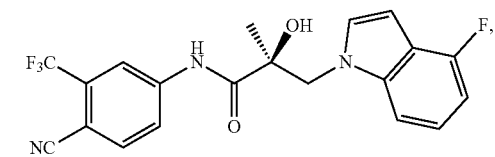

23

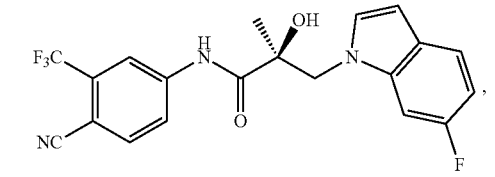

85
-continued
24
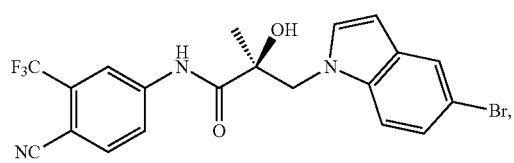
25
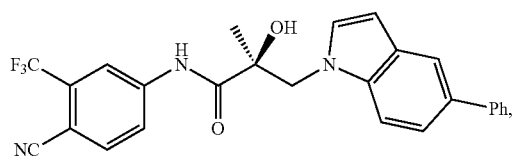
26
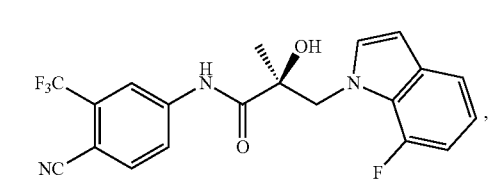
27
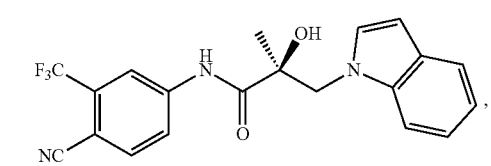
30
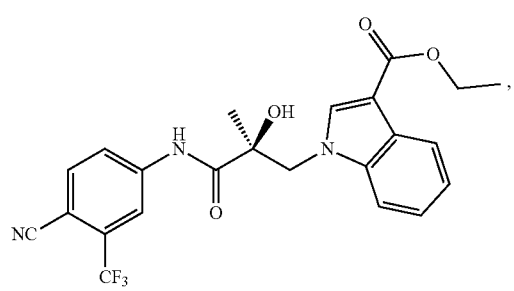
31
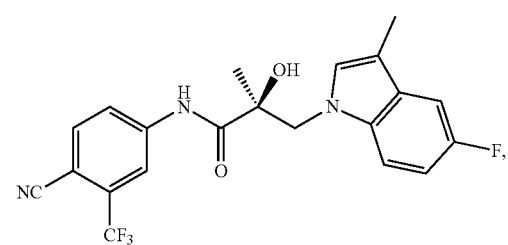
32
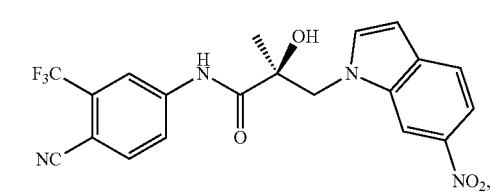
86
-continued
33
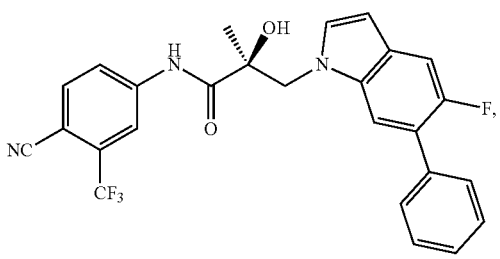
34
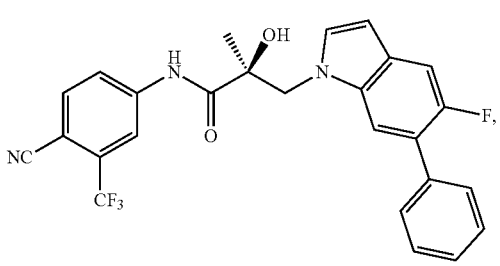
35
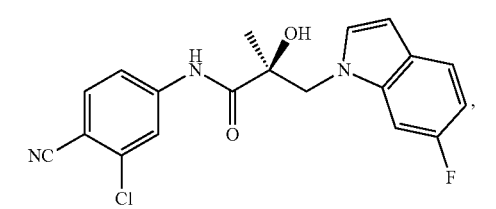
36
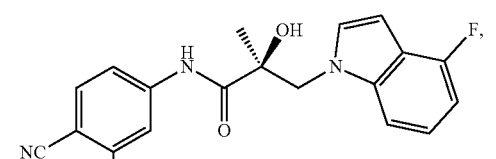
37
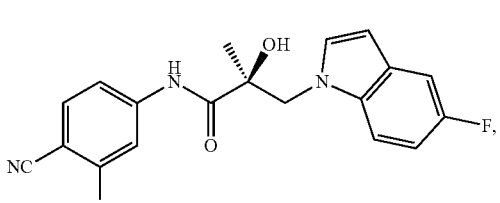
38
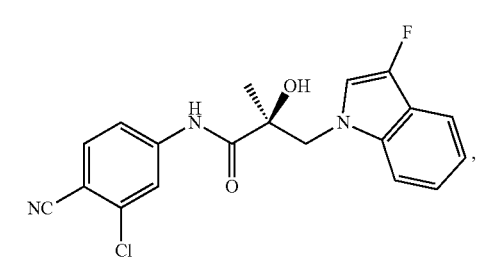
39
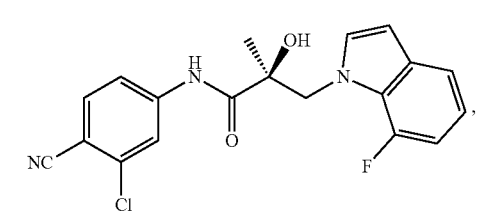

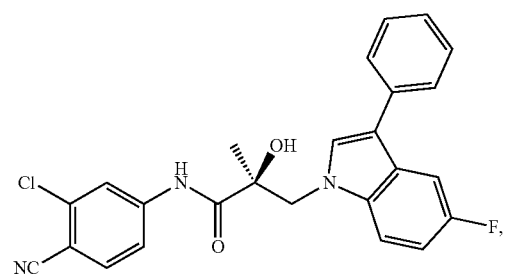
40
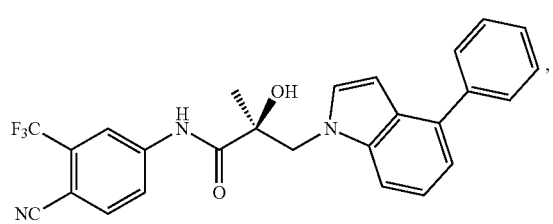
41
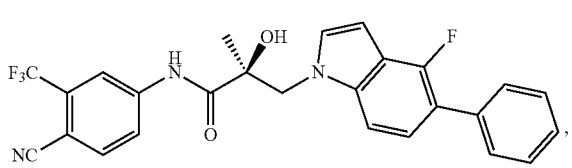
42
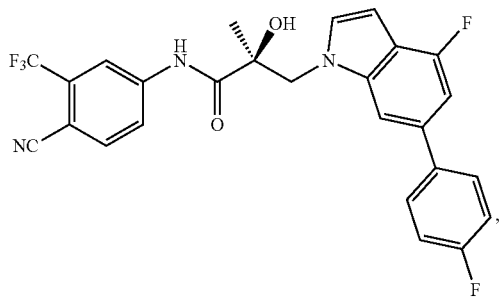
43
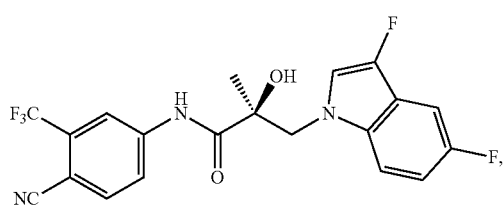
44
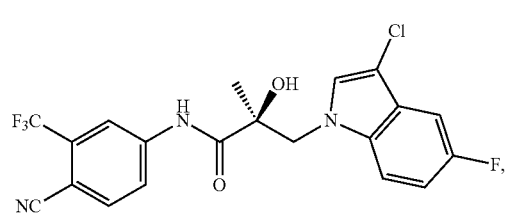
45
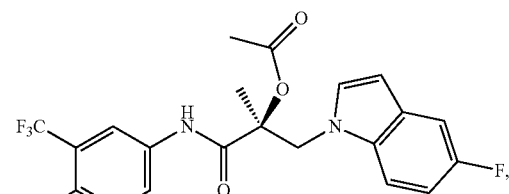
46
benzimidazoles:
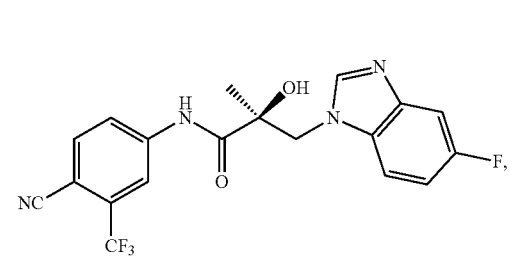
70
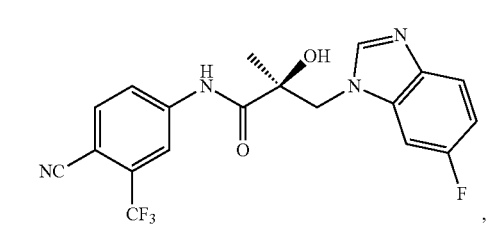
71
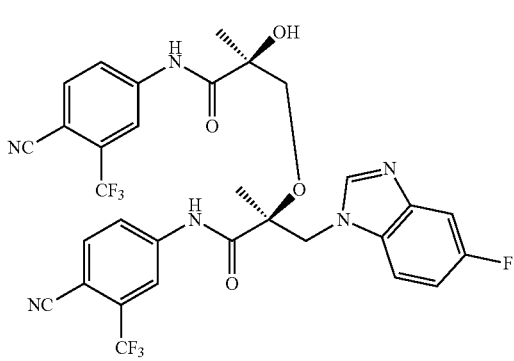
72
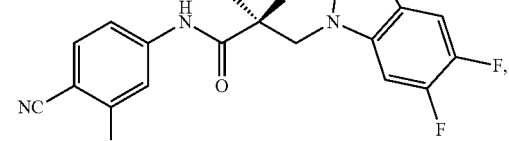
73
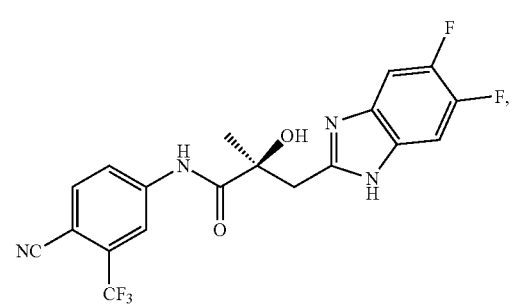
74

-continued
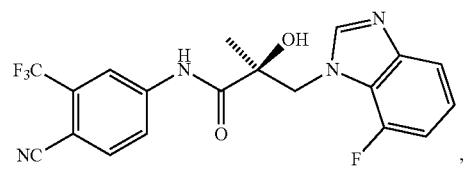
75
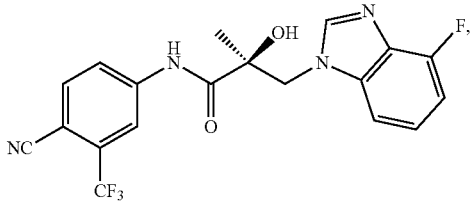
76
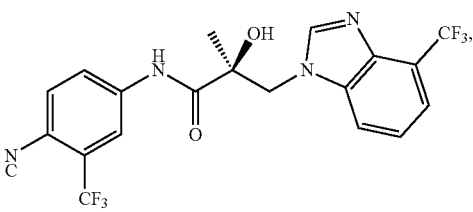
77
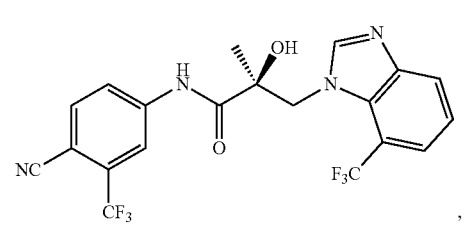
78
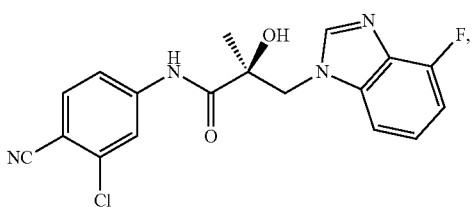
79
pyrrolo-pyridine:
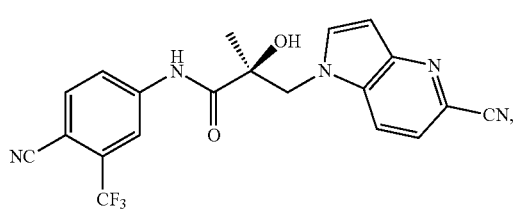
80
indazoles:
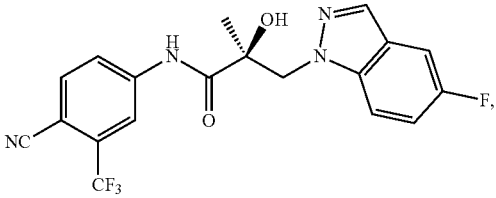
90
91
92
93
94
95
96

97 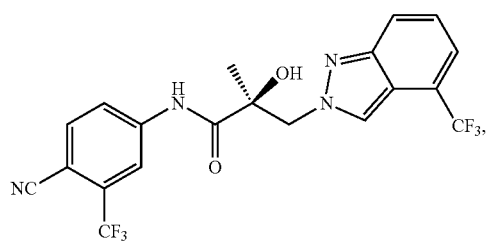
98 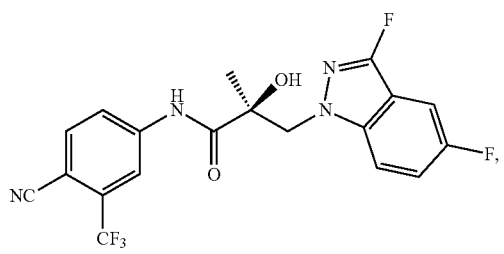
benzotriazoles:
300 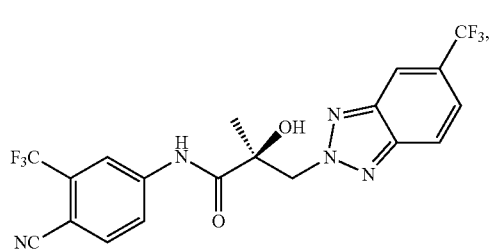
301 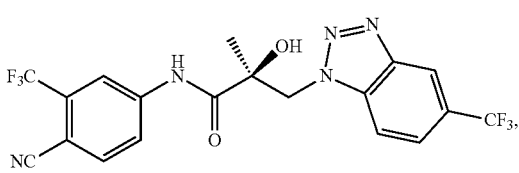
302 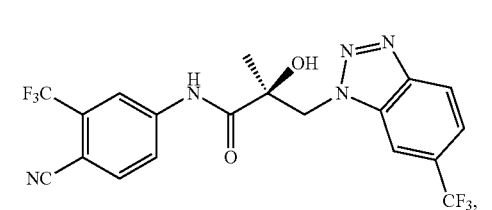
303
304 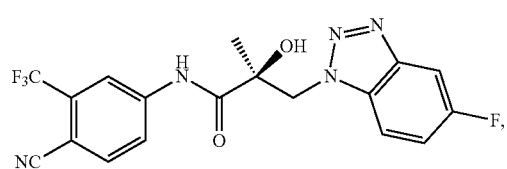
305 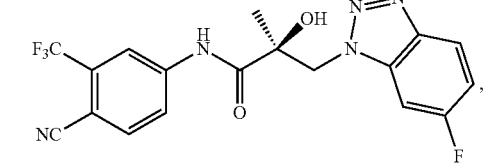
306 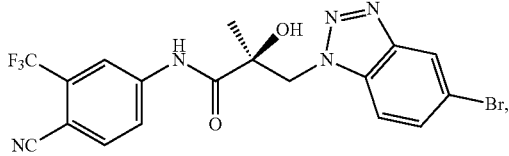
307 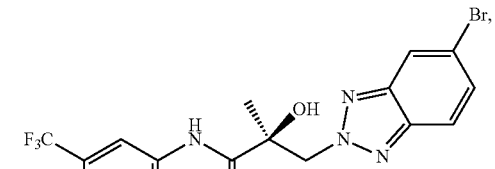
308 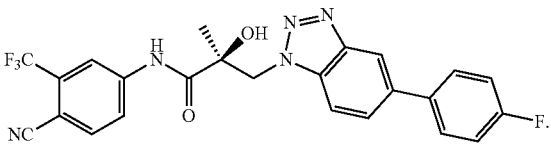
Indolines:
100 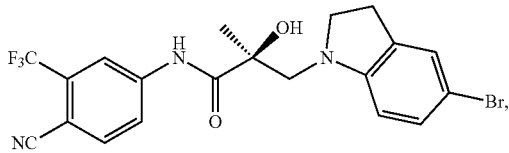
101 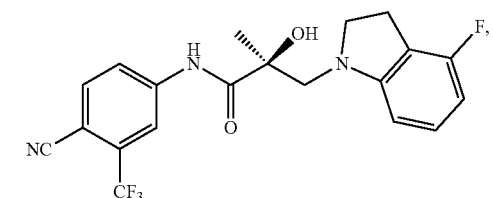
102 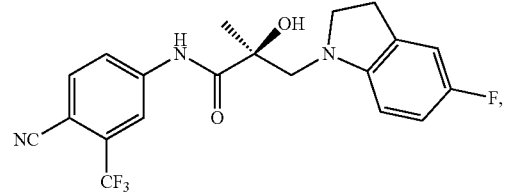

-continued
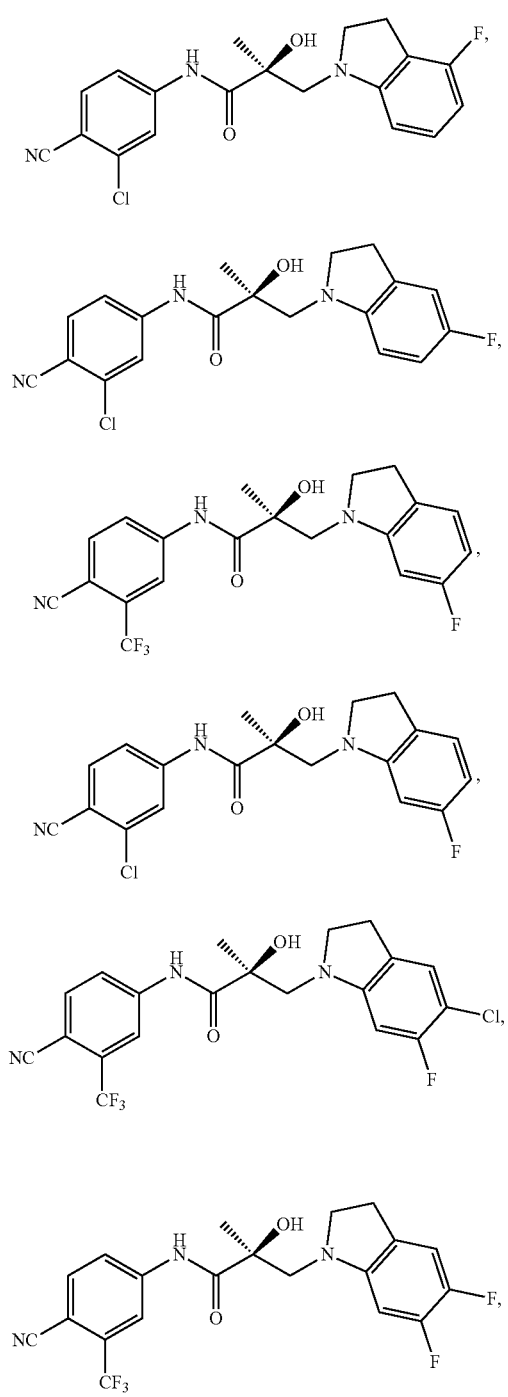
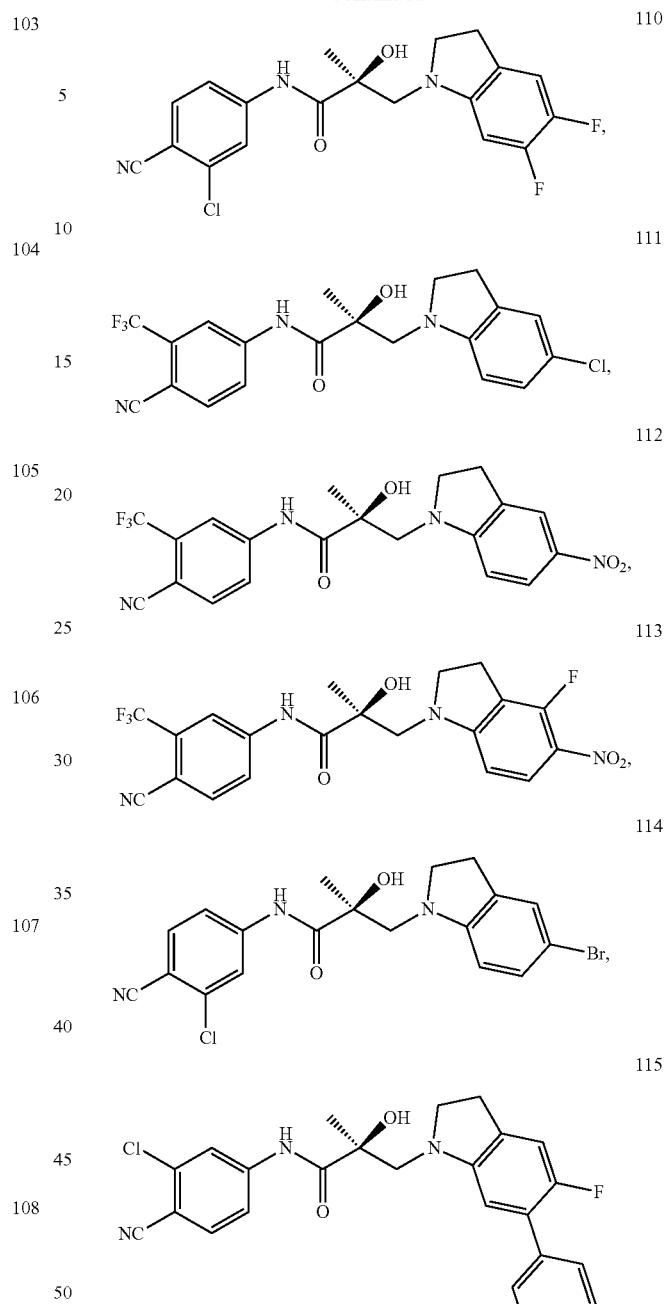
isoquinolines and quinolines:
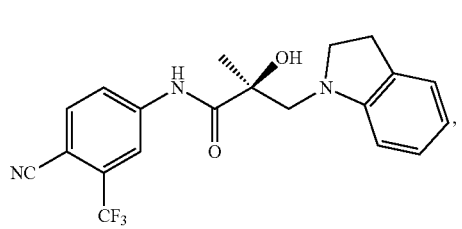
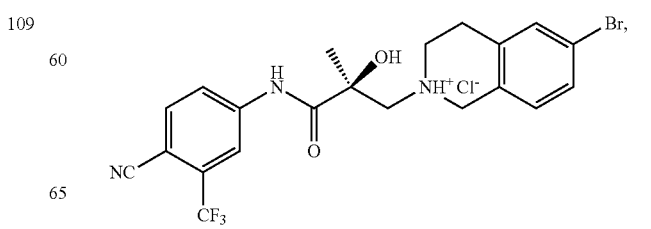

In one embodiment, this invention is directed to a selective androgen receptor degrader (SARD) compound represented by the structure of formula XXVI:

$$XXVI$$

wherein
T is OH, OR, —NHCOCH$_3$, or NHCOR;
Z is H, NO$_2$, CN, halide, COOH, COR, NHCOR or CONHR;
Y is H, CF$_3$, F, I, Br, Cl, CN, C(R)$_3$, Sn(R)$_3$ or Y and Z form
a 5 to 8 membered fused ring;
R is H, alkyl, haloalkyl, alcohol, CH$_2$CH$_2$OH, CH$_2$F, CHF$_2$, CF$_3$, CF$_2$CF$_3$, CH$_2$Cl, CH$_2$CH$_2$Cl, aryl, phenyl, F, Cl, Br, I, alkenyl or OH;
R$_1$ is H, CH$_3$, CH$_2$F, CHF$_2$, CF$_3$, CH$_2$CH$_3$, or CF$_2$CF$_3$;
R$_{2b}$ is hydrogen, C$_1$-C$_{12}$-alkyl, —SO$_2$-aryl, —SO$_2$-phenyl, —CO-aryl, arylalkyl, benzyl, aryl, or C$_3$-C$_7$-cycloalkyl;
Q$_{1a}$, Q$_{2a}$, Q$_{3a}$, Q$_{4a}$, and Q$_{5a}$ are each independently selected from hydrogen, substituted or unsubstituted linear or branched alkyl, substituted or unsubstituted aryl, substituted or unsubstituted phenyl, F, Cl, Br, I, CF$_3$, CN, NO$_2$, substituted or unsubstituted cycloalkyl, substituted or unsubstituted heterocycloalkyl, substituted or unsubstituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO, or OCN; or its isomer, pharmaceutically acceptable salt, pharmaceutical product, polymorph, hydrate or any combination thereof;
wherein at least two of Q$_{1a}$, Q$_{2a}$, Q$_{3a}$, Q$_{4a}$, and Q$_{5a}$ are not hydrogens; or
Q$_{1a}$ and Q$_{2a}$ are joined together to form a substituted or unsubstituted C$_5$-C$_8$ carbocyclic or heterocyclic ring, and Q$_{3a}$, Q$_{4a}$, and Q$_{5a}$ are as defined above; or
Q$_{2a}$ and Q$_{3a}$ are joined together to form a substituted or unsubstituted C$_5$-C$_8$ carbocyclic or heterocyclic ring, and Q$_{1a}$, Q$_{4a}$, and Q$_{5a}$ are as defined above; and
wherein said formed carbocyclic or heterocyclic ring is not dihydropyridin-2(1H)-one, pyridin-2(1H)-one or 1H-pyrrole.

In one embodiment, this invention is directed to a selective androgen receptor degrader (SARD) compound represented by the structure of formula XXVIIA:

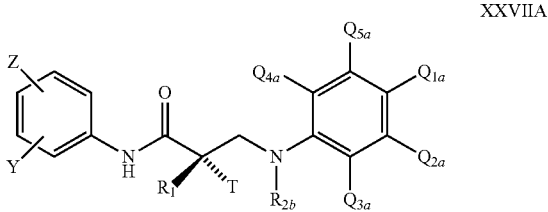

XXVIIA wherein
T is H, OH, OR, OCOR, CH$_3$, —NHCOCH$_3$ or NHCOR;
Z is H, NO$_2$, CN, halide, COOH, COR, NHCOR or CONHR;
Y is H, CF$_3$, F, I, Br, Cl, CN, C(R)$_3$, Sn(R)$_3$ or Y and Z form a 5 to 8 membered fused ring;
R is H, alkyl, haloalkyl, alcohol, CH$_2$CH$_2$OH, CH$_2$F, CHF$_2$, CF$_3$, CF$_2$CF$_3$, CH$_2$Cl, CH$_2$CH$_2$Cl, aryl, phenyl, F, Cl, Br, I, alkenyl or OH;
R$_1$ is H, CH$_3$, CH$_2$F, CHF$_2$, CF$_3$, CH$_2$CH$_3$, or CF$_2$CF$_3$;
R$_{2b}$ is hydrogen, C$_1$-C$_{12}$-alkyl, —SO$_2$-aryl, —SO$_2$-phenyl, —CO-aryl, arylalkyl, benzyl, aryl, or C$_3$-C$_7$-cycloalkyl;
Q$_{1a}$, Q$_{2a}$, Q$_{3a}$, Q$_{4a}$, and Q$_{5a}$ are each independently selected from hydrogen, substituted or unsubstituted linear or branched alkyl, substituted or unsubstituted aryl, substituted or unsubstituted phenyl, F, Cl, Br, I, CF$_3$, CN, NO$_2$, substituted or unsubstituted cycloalkyl, substituted or unsubstituted heterocycloalkyl, substituted or unsubstituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO, or OCN; or its isomer, pharmaceutically acceptable salt, pharmaceutical product, polymorph, hydrate or any combination thereof;
wherein at least two of Q$_{1a}$, Q$_{2a}$, Q$_{3a}$, Q$_{4a}$, and Q$_{5a}$ are not hydrogens; or
Q$_{1a}$ and Q$_{2a}$ are joined together to form a substituted or unsubstituted C$_5$-C$_8$ carbocyclic or heterocyclic ring, and Q$_{3a}$, Q$_{4a}$, and Q$_{5a}$ are as defined above; or
Q$_{2a}$ and Q$_{3a}$ are joined together to form a substituted or unsubstituted C$_5$-C$_8$ carbocyclic or heterocyclic ring, and Q$_{1a}$, Q$_{4a}$, and Q$_{5a}$ are as defined above; and
wherein said formed carbocyclic or heterocyclic ring is not dihydropyridin-2(1H)-one, pyridin-2(1H)-one or 1H-pyrrole.

In one embodiment, this invention is directed to a selective androgen receptor degrader (SARD) compound represented by the structure of formula XVIIB:

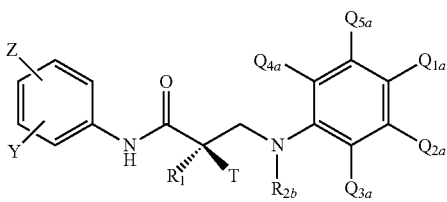

XXVIIB wherein
T is H, OH, OR, OCOR, CH$_3$, —NHCOCH$_3$ or NHCOR;
Z is H, NO$_2$, CN, halide, COOH, COR, NHCOR or CONHR;
Y is H, CF$_3$, F, I, Br, Cl, CN, C(R)$_3$, Sn(R)$_3$ or Y and Z form a 5 to 8 membered fused ring;
R is H, alkyl, haloalkyl, alcohol, CH$_2$CH$_2$OH, CH$_2$F, CHF$_2$, CF$_3$, CF$_2$CF$_3$, CH$_2$Cl, CH$_2$CH$_2$Cl, aryl, phenyl, F, Cl, Br, I, alkenyl or OH;
R$_1$ is H, CH$_3$, CH$_2$F, CHF$_2$, CF$_3$, CH$_2$CH$_3$, or CF$_2$CF$_3$;
R$_{2b}$ is hydrogen, C$_1$-C$_{12}$-alkyl, —SO$_2$-aryl, —SO$_2$-phenyl, —CO-aryl, arylalkyl, benzyl, aryl, or C$_3$-C$_7$-cycloalkyl;
Q$_{1a}$, Q$_{2a}$, Q$_{3a}$, Q$_{4a}$, and Q$_{5a}$ are each independently selected from hydrogen, substituted or unsubstituted linear or branched alkyl, substituted or unsubstituted aryl, substituted or unsubstituted phenyl, F, Cl, Br, I, CF$_3$, CN, NO$_2$, substituted or unsubstituted cycloalkyl, substituted or unsubstituted heterocycloalkyl, substituted or unsubstituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO, or OCN; or its isomer, pharmaceutically acceptable salt, pharmaceutical product, polymorph, hydrate or any combination thereof;
wherein at least two of Q$_{1a}$, Q$_{2a}$, Q$_{3a}$, Q$_{4a}$, and Q$_{5a}$ are not hydrogens; or
Q$_{1a}$ and Q$_{2a}$ are joined together to form a substituted or unsubstituted C$_5$-C$_8$ carbocyclic or heterocyclic ring, and Q$_{3a}$, Q$_{4a}$, and Q$_{5a}$ are as defined above; or
Q$_{2a}$ and Q$_{3a}$ are joined together to form a substituted or unsubstituted C$_5$-C$_8$ carbocyclic or heterocyclic ring, and Q$_{1a}$, Q$_{4a}$, and Q$_{5a}$ are as defined above; and
wherein said formed carbocyclic or heterocyclic ring is not dihydropyridin-2(1H)-one, pyridin-2(1H)-one or 1H-pyrrole.

In one embodiment, this invention provides a selective androgen receptor degrader (SARD) compound represented by the structure of formula XXVIII:

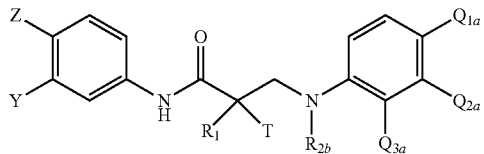

XXVIII wherein
T is H, OH, OR, OCOR, CH$_3$, —NHCOCH$_3$, or NHCOR;
Z is H, NO$_2$, CN, halide, COOH, COR, NHCOR or CONHR;
Y is H, CF$_3$, F, I, Br, Cl, CN, C(R)$_3$, Sn(R)$_3$ or Y and Z form a 5 to 8 membered fused ring;
R is H, alkyl, haloalkyl, alcohol, CH$_2$CH$_2$OH, CH$_2$F, CHF$_2$, CF$_3$, CF$_2$CF$_3$, CH$_2$Cl, CH$_2$CH$_2$Cl, aryl, phenyl, F, Cl, Br, I, alkenyl or OH;
R$_1$ is H, CH$_3$, CH$_2$F, CHF$_2$, CF$_3$, CH$_2$CH$_3$, or CF$_2$CF$_3$;
R$_{2b}$ is hydrogen, C$_1$-C$_{12}$-alkyl, —SO$_2$-aryl, —SO$_2$-phenyl, —CO-aryl, arylalkyl, benzyl, aryl, or C$_3$-C$_7$-cycloalkyl;

$Q_{1a}$, $Q_{2a}$, $Q_{3a}$, $Q_{4a}$, and $Q_{5a}$ are each independently selected from hydrogen, substituted or unsubstituted linear or branched alkyl, substituted or unsubstituted aryl, substituted or unsubstituted phenyl, F, Cl, Br, I, $CF_3$, CN, $NO_2$, substituted or unsubstituted cycloalkyl, substituted or unsubstituted heterocycloalkyl, substituted or unsubstituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO, or OCN; or its isomer, pharmaceutically acceptable salt, pharmaceutical product, polymorph, hydrate or any combination thereof;

wherein at least two of $Q_{1a}$, $Q_{2a}$, $Q_{3a}$, $Q_{4a}$, and $Q_{5a}$ are not hydrogens; or $Q_{1a}$ and $Q_{2a}$ are joined together to form a substituted or unsubstituted $C_5$-$C_8$ carbocyclic or heterocyclic ring, and $Q_{3a}$, $Q_{4a}$, and $Q_{5a}$ are as defined above; or $Q_{2a}$ and $Q_{3a}$ are joined together to form a substituted or unsubstituted $C_5$-$C_8$ carbocyclic or heterocyclic ring, and $Q_{1a}$, $Q_{4a}$, and $Q_{5a}$ are as defined above; and wherein said formed carbocyclic or heterocyclic ring is not dihydropyridin-2(1H)-one, pyridin-2(1H)-one or 1H-pyrrole.

In one embodiment, this invention is directed to a selective androgen receptor degrader (SARD) compound represented by the structure of formula XXVIIIA:

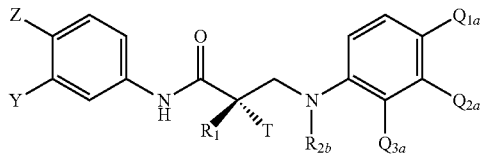

XXVIIIA wherein

T is H, OH, OR, OCOR, $CH_3$, —$NHCOCH_3$, or NHCOR;

Z is H, $NO_2$, CN, halide, COOH, COR, NHCOR or CONHR;

Y is H, $CF_3$, F, I, Br, Cl, CN, $C(R)_3$, $Sn(R)_3$ or Y and Z form a 5 to 8 membered fused ring;

R is H, alkyl, haloalkyl, alcohol, $CH_2CH_2OH$, $CH_2F$, $CHF_2$, $CF_3$, $CF_2CF_3$, $CH_2Cl$, $CH_2CH_2Cl$, aryl, phenyl, F, Cl, Br, I, alkenyl or OH;

$R_1$ is H, $CH_3$, $CH_2F$, $CHF_2$, $CF_3$, $CH_2CH_3$, or $CF_2CF_3$;

$R_{2b}$ is hydrogen, $C_1$-$C_{12}$-alkyl, —$SO_2$-aryl, —$SO_2$-phenyl, —CO-aryl, arylalkyl, benzyl, aryl, or $C_3$-$C_7$-cycloalkyl;

$Q_{1a}$ is hydrogen, substituted or unsubstituted linear or branched alkyl, substituted or unsubstituted aryl, substituted or unsubstituted phenyl, F, Cl, Br, I, $CF_3$, CN, $NO_2$, substituted or unsubstituted cycloalkyl, substituted or unsubstituted heterocycloalkyl, substituted or unsubstituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO, or OCN;

$Q_{2a}$ is hydrogen, substituted or unsubstituted linear or branched alkyl, substituted or unsubstituted aryl, substituted or unsubstituted phenyl, F, Cl, Br, I, $CF_3$, CN, $NO_2$, substituted or unsubstituted cycloalkyl, substituted or unsubstituted heterocycloalkyl, substituted or unsubstituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO, or OCN;

$Q_{3a}$ is hydrogen, substituted or unsubstituted linear or branched alkyl, substituted or unsubstituted aryl, substituted or unsubstituted phenyl, F, Cl, Br, I, $CF_3$, CN, $NO_2$, substituted or unsubstituted cycloalkyl, substituted or unsubstituted heterocycloalkyl, substituted or unsubstituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO, or OCN; or its isomer, pharmaceutically acceptable salt, pharmaceutical product, polymorph, hydrate or any combination thereof;

wherein at least two of $Q_{1a}$, $Q_{2a}$ and $Q_{3a}$ are not hydrogens; or $Q_{1a}$ and $Q_{2a}$ are joined together to form a substituted or unsubstituted $C_5$-$C_8$ carbocyclic or heterocyclic ring and $Q_{3a}$ is as defined above; or $Q_{2a}$ and $Q_{3a}$ are joined together to form a substituted or unsubstituted $C_5$-$C_8$ carbocyclic or heterocyclic ring and $Q_{1a}$ is as defined above; and wherein said formed carbocyclic or heterocyclic ring is not dihydropyridin-2(1H)-one, pyridin-2(1H)-one or 1H-pyrrole.

In one embodiment, this invention is directed to a selective androgen receptor degrader (SARD) compound represented by the structure of formula XXVIIIB:

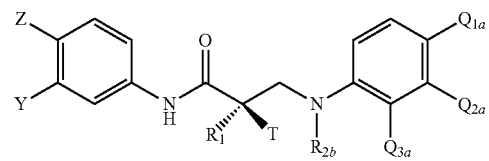

XXVIIIB wherein

T is H, OH, OR, OCOR, $CH_3$, —$NHCOCH_3$, or NHCOR;

Z is H, $NO_2$, CN, halide, COOH, COR, NHCOR or CONHR;

Y is H, $CF_3$, F, I, Br, Cl, CN, $C(R)_3$, $Sn(R)_3$ or Y and Z form a 5 to 8 membered fused ring;

R is H, alkyl, haloalkyl, alcohol, $CH_2CH_2OH$, $CH_2F$, $CHF_2$, $CF_3$, $CF_2CF_3$, $CH_2Cl$, $CH_2CH_2Cl$, aryl, phenyl, F, Cl, Br, I, alkenyl or OH;

$R_1$ is H, $CH_3$, $CH_2F$, $CHF_2$, $CF_3$, $CH_2CH_3$, or $CF_2CF_3$;

$R_{2b}$ is hydrogen, $C_1$-$C_{12}$-alkyl, —$SO_2$-aryl, —$SO_2$-phenyl, —CO-aryl, arylalkyl, benzyl, aryl, or $C_3$-$C_7$-cycloalkyl;

$Q_{1a}$ is hydrogen, substituted or unsubstituted linear or branched alkyl, substituted or unsubstituted aryl, substituted or unsubstituted phenyl, F, Cl, Br, I, $CF_3$, CN, $NO_2$, substituted or unsubstituted cycloalkyl, substituted or unsubstituted heterocycloalkyl, substituted or unsubstituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO, or OCN;

$Q_{2a}$ is hydrogen, substituted or unsubstituted linear or branched alkyl, substituted or unsubstituted aryl, substituted or unsubstituted phenyl, F, Cl, Br, I, CF$_3$, CN, NO$_2$, substituted or unsubstituted cycloalkyl, substituted or unsubstituted heterocycloalkyl, substituted or unsubstituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO, or OCN;

Q$_{3a}$ is hydrogen, substituted or unsubstituted linear or branched alkyl, substituted or unsubstituted aryl, substituted or unsubstituted phenyl, F, Cl, Br, I, CF$_3$, CN, NO$_2$, substituted or unsubstituted cycloalkyl, substituted or unsubstituted heterocycloalkyl, substituted or unsubstituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO, or OCN; or its isomer, pharmaceutically acceptable salt, pharmaceutical product, polymorph, hydrate or any combination thereof;

wherein at least two of Q$_{1a}$, Q$_{2a}$ and Q$_{3a}$ are not hydrogens; or

Q$_{1a}$ and Q$_{2a}$ are joined together to form a substituted or unsubstituted C$_5$-C$_8$ carbocyclic or heterocyclic ring and Q$_{3a}$ is as defined above; or Q$_{2a}$ and Q$_{3a}$ are joined together to form a substituted or unsubstituted C$_5$-C$_8$ carbocyclic or heterocyclic ring and Q$_{1a}$ is as defined above; and wherein said formed carbocyclic or heterocyclic ring is not dihydropyridin-2(1H)-one, pyridin-2(1H)-one or 1H-pyrrole.

In one embodiment, this invention is directed to a selective androgen receptor degrader (SARD) compound represented by the structure of formula XXIX:

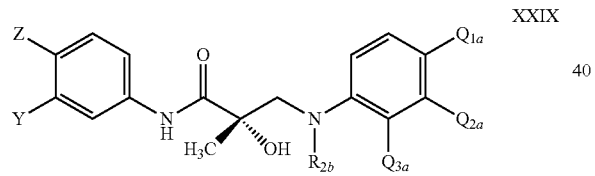

XXIX wherein

Z is NO$_2$ or CN;

Y is CF$_3$, F, I, Br, Cl, or CN;

R$_{2b}$ is hydrogen, C$_1$-C$_{12}$-alkyl, —SO$_2$-aryl, —SO$_2$-phenyl, —CO-aryl, arylalkyl, benzyl, aryl, or C$_3$-C$_7$-cycloalkyl;

Q$_{1a}$ is substituted or unsubstituted aryl, substituted or unsubstituted phenyl, substituted or unsubstituted arylalkyl, CN, or NO$_2$;

Q$_{2a}$ is hydrogen, substituted or unsubstituted aryl, substituted or unsubstituted phenyl, F, Cl, Br, I, CF$_3$, CN, NO$_2$, substituted or unsubstituted cycloalkyl, substituted or unsubstituted heterocycloalkyl, or substituted or unsubstituted arylalkyl;

Q$_{3a}$ is hydrogen, substituted or unsubstituted aryl, substituted or unsubstituted phenyl, F, Cl, Br, I, CF$_3$, CN, NO$_2$, substituted or unsubstituted cycloalkyl, substituted or unsubstituted heterocycloalkyl, or substituted or unsubstituted arylalkyl;

wherein at least one of Q$_{2a}$ and Q$_{3a}$ is a substituted or unsubstituted aryl, substituted or unsubstituted phenyl or substituted or unsubstituted arylalkyl; or Q$_{2a}$ and Q$_{3a}$ are joined together to form a substituted or unsubstituted C$_5$-C$_8$ carbocyclic or heterocyclic ring and Q$_{1a}$ is as defined above; or its isomer, pharmaceutically acceptable salt, pharmaceutical product, polymorph, hydrate or any combination thereof.

In one embodiment, this invention is directed to a selective androgen receptor degrader (SARD) compound represented by the structure of formula XXX:

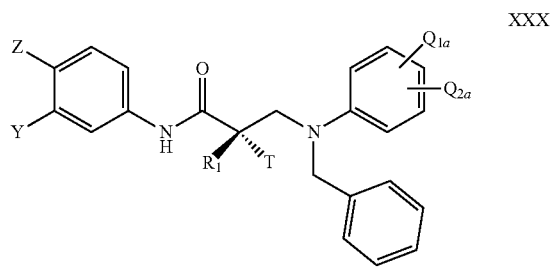

XXX wherein

T is H, OH, OR, OCOR, CH$_3$, —NHCOCH$_3$, or NHCOR;

Z is H, NO$_2$, CN, halide, COOH, COR, NHCOR or CONHR;

Y is H, CF$_3$, F, I, Br, Cl, CN, C(R)$_3$, Sn(R)$_3$ or Y and Z form a 5 to 8 membered fused ring;

R is H, alkyl, haloalkyl, alcohol, CH$_2$CH$_2$OH, CH$_2$F, CHF$_2$, CF$_3$, CF$_2$CF$_3$, CH$_2$Cl, CH$_2$CH$_2$Cl, aryl, phenyl, F, Cl, Br, I, alkenyl or OH;

R$_1$ is H, CH$_3$, CH$_2$F, CHF$_2$, CF$_3$, CH$_2$CH$_3$, or CF$_2$CF$_3$;

Q$_{1a}$ is hydrogen, substituted or unsubstituted linear or branched alkyl, substituted or unsubstituted aryl, substituted or unsubstituted phenyl, F, Cl, Br, I, CF$_3$, CN, NO$_2$, substituted or unsubstituted cycloalkyl, substituted or unsubstituted heterocycloalkyl, substituted or unsubstituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO, or OCN;

Q$_{2a}$ is hydrogen, substituted or unsubstituted linear or branched alkyl, substituted or unsubstituted aryl, substituted or unsubstituted phenyl, F, Cl, Br, I, CF$_3$, CN, NO$_2$, substituted or unsubstituted cycloalkyl, substituted or unsubstituted heterocycloalkyl, substituted or unsubstituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO, or OCN; or Q$_{1a}$ and Q$_{2a}$ are joined together to form a substituted or unsubstituted C$_5$-C$_8$ carbocyclic or heterocyclic ring; or its isomer, pharmaceutically acceptable salt, pharmaceutical product, polymorph, hydrate or any combination thereof.

In one embodiment, this invention is directed to a selective androgen receptor degrader (SARD) compound represented by the structure of formula XXXI:

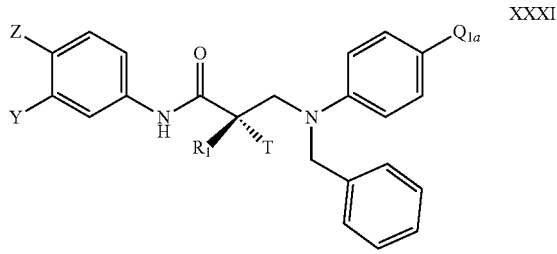

XXXI wherein

T is H, OH, OR, OCOR, CH$_3$, —NHCOCH$_3$, or NHCOR;

Z is H, NO$_2$, CN, halide, COOH, COR, NHCOR or CONHR;

Y is H, CF$_3$, F, I, Br, Cl, CN, C(R)$_3$, Sn(R)$_3$ or Y and Z form a 5 to 8 membered fused ring;

R is H, alkyl, haloalkyl, alcohol, CH$_2$CH$_2$OH, CH$_2$F, CHF$_2$, CF$_3$, CF$_2$CF$_3$, CH$_2$Cl, CH$_2$CH$_2$Cl, aryl, phenyl, F, Cl, Br, I, alkenyl or OH;

R$_1$ is H, CH$_3$, CH$_2$F, CHF$_2$, CF$_3$, CH$_2$CH$_3$, or CF$_2$CF$_3$;

Q$_{1a}$ is hydrogen, substituted or unsubstituted linear or branched alkyl, substituted or unsubstituted aryl, substituted or unsubstituted phenyl, F, Cl, Br, I, CF$_3$, CN, NO$_2$, substituted or unsubstituted cycloalkyl, substituted or unsubstituted heterocycloalkyl, substituted or unsubstituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO, or OCN; or its isomer, pharmaceutically acceptable salt, pharmaceutical product, polymorph, hydrate or any combination thereof.

In one embodiment, this invention is directed to a selective androgen receptor degrader (SARD) compound represented by the structure of formula XXXII:

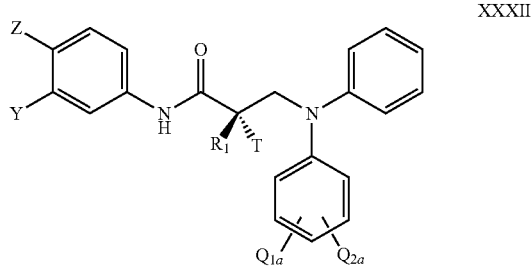

XXXII wherein

T is H, OH, OR, OCOR, CH$_3$, —NHCOCH$_3$, or NHCOR;

Z is H, NO$_2$, CN, halide, COOH, COR, NHCOR or CONHR;

Y is H, CF$_3$, F, I, Br, Cl, CN, C(R)$_3$, Sn(R)$_3$ or Y and Z form a 5 to 8 membered fused ring;

R is H, alkyl, haloalkyl, alcohol, CH$_2$CH$_2$OH, CH$_2$F, CHF$_2$, CF$_3$, CF$_2$CF$_3$, CH$_2$Cl, CH$_2$CH$_2$Cl, aryl, phenyl, F, Cl, Br, I, alkenyl or OH;

R$_1$ is H, CH$_3$, CH$_2$F, CHF$_2$, CF$_3$, CH$_2$CH$_3$, or CF$_2$CF$_3$;

Q$_{1a}$ is hydrogen, substituted or unsubstituted linear or branched alkyl, substituted or unsubstituted aryl, substituted or unsubstituted phenyl, F, Cl, Br, I, CF$_3$, CN, NO$_2$, substituted or unsubstituted cycloalkyl, substituted or unsubstituted heterocycloalkyl, substituted or unsubstituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO, or OCN;

Q$_{2a}$ is hydrogen, substituted or unsubstituted linear or branched alkyl, substituted or unsubstituted aryl, substituted or unsubstituted phenyl, F, Cl, Br, I, CF$_3$, CN, NO$_2$, substituted or unsubstituted cycloalkyl, substituted or unsubstituted heterocycloalkyl, substituted or unsubstituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO, or OCN;

or

Q$_{1a}$ and Q$_{2a}$ are joined together to form a substituted or unsubstituted C$_5$-C$_8$ carbocyclic or heterocyclic ring; or its isomer, pharmaceutically acceptable salt, pharmaceutical product, polymorph, hydrate or any combination thereof.

In one embodiment, this invention is directed to a selective androgen receptor degrader (SARD) compound represented by the structure of formula XXXIII:

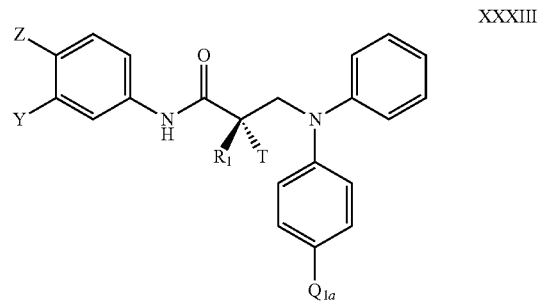

XXXIII wherein

T is H, OH, OR, OCOR, CH$_3$, —NHCOCH$_3$, or NHCOR;

Z is H, NO$_2$, CN, halide, COOH, COR, NHCOR or CONHR;

Y is H, CF$_3$, F, I, Br, Cl, CN, C(R)$_3$, Sn(R)$_3$ or Y and Z form a 5 to 8 membered fused ring;

R is H, alkyl, haloalkyl, alcohol, CH$_2$CH$_2$OH, CH$_2$F, CHF$_2$, CF$_3$, CF$_2$CF$_3$, CH$_2$Cl, CH$_2$CH$_2$Cl, aryl, phenyl, F, Cl, Br, I, alkenyl or OH;

R$_1$ is H, CH$_3$, CH$_2$F, CHF$_2$, CF$_3$, CH$_2$CH$_3$, or CF$_2$CF$_3$;

Q$_{1a}$ is hydrogen, substituted or unsubstituted linear or branched alkyl, substituted or unsubstituted aryl, substituted or unsubstituted phenyl, F, Cl, Br, I, CF$_3$, CN, NO$_2$, substituted or unsubstituted cycloalkyl, substituted or unsubstituted heterocycloalkyl, substituted or unsubstituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO, or OCN; or its isomer, pharmaceutically acceptable salt, pharmaceutical product, polymorph, hydrate or any combination thereof.

In another embodiment, the compounds of formula XXVI-XXXIII are represented by the following compounds:

13

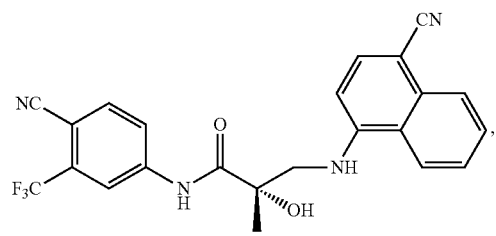

14

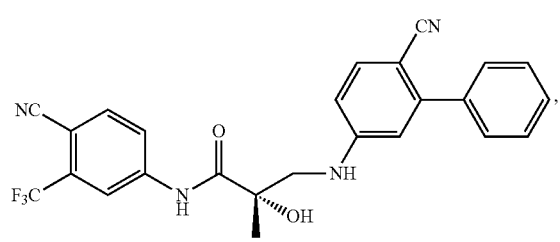

15

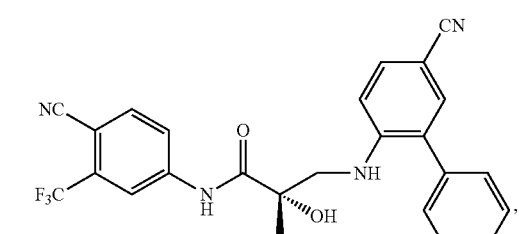

16

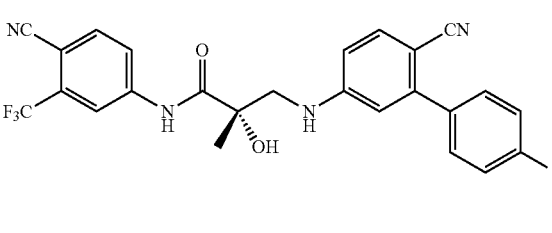

17

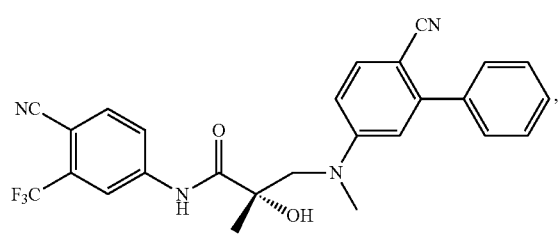

17a

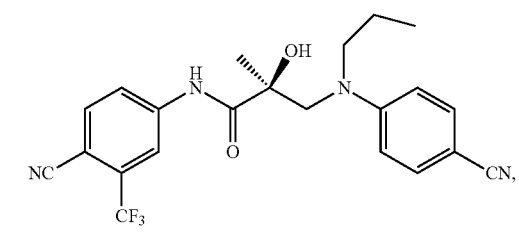

18

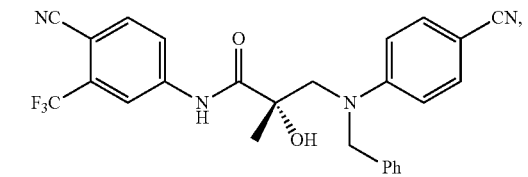

19

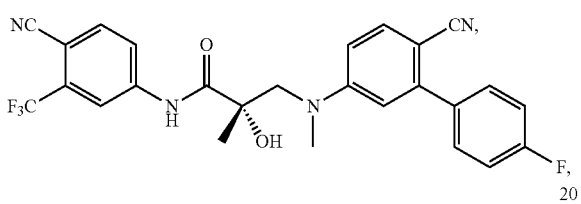

20

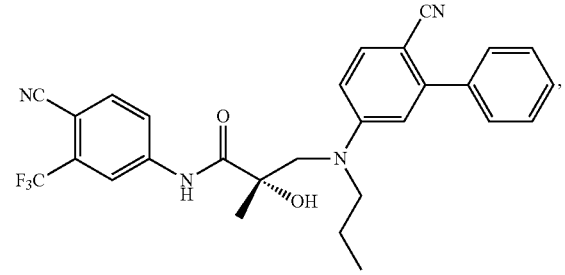

21

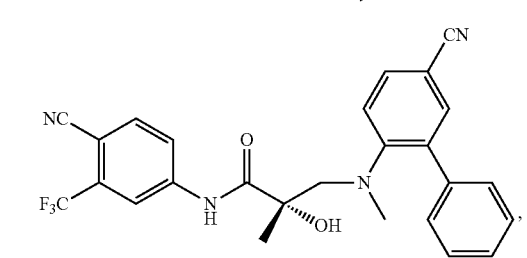

49

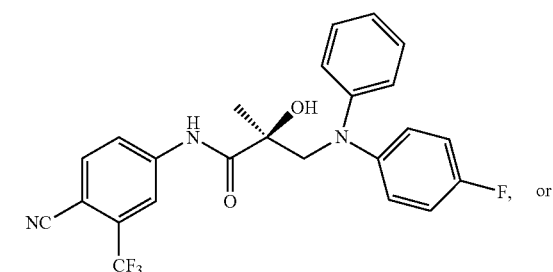

or

50

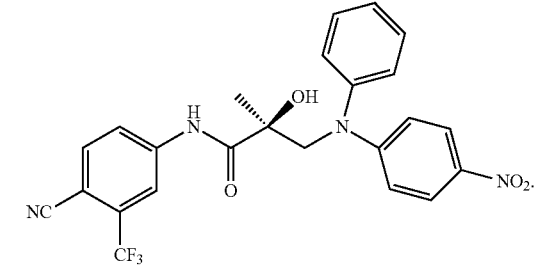

In one embodiment, A of formula I-III, IA, IB, IIA, and IIB and $R^2$ of formula IC is a five or six-membered saturated or unsaturated ring having at least one nitrogen atom. In another embodiment, A is a substituted or unsubstituted pyrrole, pyrroline, pyrrolidine, pyrazole, pyrazoline, pyrazolidine, imidazole, imidazoline, imidazolidine, triazole, tetrazole, pyridine, morpholine, or other heterocyclic ring. Each represents a separate embodiment of this invention. In another embodiment, A is a five or six-membered heterocyclic ring. In another embodiment, a nitrogen atom of the five or six membered saturated or unsaturated ring is attached to the backbone structure of the molecule. In another embodiment, a carbon atom of the five or six membered saturated or unsaturated ring is attached to the backbone structure of the molecule.

In one embodiment, A of formula I-III, IA, IB, IIA, and IIB and $R^3$ of formula ID is $NHR^2$, halide, $N_3$, $OR^4$, $CF_3$, $COR^4$, $COCl$, $COOCOR^4$, $COOR^4$, $OCOR^4$, $OCONHR^4$, $NHCOOR^4$, $NHCONHR^4$, $OCOOR^4$, $CN$, $CONH_2$, $CONH(R^4)$, $CON(R^4)_2$, $SR^4$, $SO_2R^4$, $SOR^4$ $SO_3H$, $SO_2NH_2$, $SO_2NH(R^4)$, $SO_2N(R^4)_2$, $NH_2$, $NH(R^4)$, $N(R^4)_2$, CO(N-heterocycle), $NO_2$, cyanate, isocyanate, thiocyanate, isothiocyanate, mesylate, tosylate, triflate, $PO(OH)_2$ or $OPO(OH)_2$; wherein $R^4$ is H, alkyl, haloalkyl, cycloalkyl, aryl or heteroaryl, wherein said alkyl, haloalkyl, cycloalkyl, aryl or heteroaryl groups are optionally substituted.

In one embodiment, A of formula I-III, IA, IB, IIA, and IIB and $R^3$ of formula ID is $NHR^2$. In one embodiment, A of formula I-III, IA, IB, IIA, and IIB and $R^3$ of formula ID is halide. In one embodiment, A of formula I-III, IA, IB, IIA, and IIB and $R^3$ of formula ID is F. In one embodiment, A of formula I-III, IA, IB, IIA, and IIB and $R^3$ of formula ID is Br. In one embodiment, A of formula I-III, IA, IB, IIA, and IIB and $R^3$ of formula ID is Cl. In one embodiment, A of formula I-III, IA, IB, IIA, and IIB and $R^3$ of formula ID is I. In one embodiment, A of formula I-III, IA, IB, IIA, and IIB and $R^3$ of formula ID is $N_3$. In one embodiment, A of formula I-III, IA, IB, IIA, and IIB and $R^3$ of formula ID is $OR^4$. In one embodiment, A of formula I-III, IA, IB, IIA, and IIB and $R^3$ of formula ID is $CF_3$. In one embodiment, A of formula I-III, IA, IB, IIA, and IIB and $R^3$ of formula ID is $COR^4$. In one embodiment, A of formula I-III, IA, IB, IIA, and IIB and $R^3$ of formula ID is $COCl$. In one embodiment, A of formula I-III, IA, IB, IIA, and IIB and $R^3$ of formula ID is $COOCOR^4$. In one embodiment, A of formula I-III, IA, IB, IIA, and IIB and $R^3$ of formula ID is $COOR^4$. In one embodiment, A of formula I-III, IA, IB, IIA, and IIB and $R^3$ of formula ID is $OCOR^4$. In one embodiment, A of formula I-III, IA, IB, IIA, and IIB and $R^3$ of formula ID is $OCONHR^4$. In one embodiment, A of formula I-III, IA, IB, IIA, and IIB and $R^3$ of formula ID is $NHCOOR^4$. In one embodiment, A of formula I-III, IA, IB, IIA, and JIB and $R^3$ of formula ID is $NHCONHR^4$. In one embodiment, A of formula I-III, IA, IB, IIA, and IIB and $R^3$ of formula ID is $OCOOR^4$. In one embodiment, A of formula I-III, IA, IB, IIA, and IIB and $R^3$ of formula ID is CN.

In one embodiment, A of formula I-III, IA, IB, IIA, and IIB and $R^3$ of formula ID is $CON(R^4)_2$. In one embodiment, A of formula I-III, IA, IB, IIA, and IIB and $R^3$ of formula ID is $SR^4$. In one embodiment, A of formula I-III, IA, IB, IIA, and IIB and $R^3$ of formula ID is $SO_2R^4$. In one embodiment, A of formula I-III, IA, IB, IIA, and IIB and $R^3$ of formula ID is $SOR^4$. In one embodiment, A of formula I-III, IA, IB, IIA, and IIB and $R^3$ of formula ID is $SO_3H$. In one embodiment, A of formula I-III, IA, IB, IIA, and IIB and $R^3$ of formula ID is $SO_2NH_2$. In one embodiment, A of formula I-III, IA, IB, IIA, and IIB and $R^3$ of formula ID is $SO_2NH(R^4)$. In one embodiment, A of formula I-III, IA, IB, IIA, and IIB and $R^3$ of formula ID is $SO_2N(R^4)_2$. In one embodiment, A of formula I-III, IA, IB, IIA, and IIB and $R^3$ of formula ID is $NH_2$. In one embodiment, A of formula I-III, IA, IB, IIA, and IIB and $R^3$ of formula ID is $NH(R^4)$. In one embodiment, A of formula I-III, IA, IB, IIA, and IIB and $R^3$ of formula ID is $N(R^4)_2$. In one embodiment, A of formula I-III, IA, IB, IIA, and IIB and $R^3$ of formula ID is $CONH_2$. In one embodiment, A of formula I-III, IA, IB, IIA, and IIB and $R^3$ of formula ID is $CONH(R^4)$. In one embodiment, A of formula I-III, IA, IB, IIA, and IIB and $R^3$ of formula ID is CO(N-heterocycle). In one embodiment, A of formula I-III, IA, IB, IIA, and IIB and $R^3$ of formula ID is $NO_2$. In one embodiment, A of formula I-III, IA, IB, IIA, and IIB and $R^3$ of formula ID is cyanate. In one embodiment, A of formula I-III, IA, IB, IIA, and IIB and $R^3$ of formula ID is isocyanate. In one embodiment, A of formula I-III, IA, IB, IIA, and IIB and $R^3$ of formula ID is thiocyanate. In one embodiment, A of formula I-III, IA, IB, IIA, and IIB and $R^3$ of formula ID is isothiocyanate. In one embodiment, A of formula I-III, IA, IB, IIA, and IIB and $R^3$ of formula ID is mesylate. In one embodiment, A of formula I-III, IA, IB, IIA, and IIB and $R^3$ of formula ID is tosylate. In one embodiment, A of formula I-III, IA, IB, IIA, and IIB and $R^3$ of formula ID is triflate. In one embodiment, A of formula I-III, IA, IB, IIA, and IIB and $R^3$ of formula ID is $PO(OH)_2$. In one embodiment, A of formula I-III, IA, IB, IIA, and IIB and $R^3$ of formula ID is $OPO(OH)_2$.

In some embodiments, wherein if A or $R^3$ is Br or I, $R^1$ is $CH_3$, and T is OH, then X is N or the aniline ring forms a fused heterocyclic ring.

In a particular embodiment Y is H. In a particular embodiment of formulas Y is $CF_3$. In a particular embodiment Y is F. In a particular embodiment Y is I. In a particular embodiment Y is Br. In a particular embodiment Y is Cl. In a particular embodiment Y is CN. In a particular embodiment Y is $C(R)_3$.

In a particular embodiment Z is H. In a particular embodiment Z is $NO_2$. In a particular embodiment Z is CN. In a particular embodiment Z is a halide. In a particular embodiment Z is F. In a particular embodiment Z is Cl. In a particular embodiment Z is Br. In a particular embodiment Z is I. In a particular embodiment Z is COOH. In a particular embodiment Z is COR. In a particular embodiment Z is NHCOR. In a particular embodiment Z is CONHR.

In a particular embodiment of formulas Y and Z forms a fused ring with the phenyl. In other embodiments, the fused ring with the phenyl is a 5 to 8 membered ring. In other embodiments, the fused ring with the phenyl is a 5 or 6 membered ring. In other embodiments, the ring is a carbocyclic or heterocyclic. In other embodiments, Y and Z form together with the phenyl to form a naphthyl, quinolinyl, benzimidazolyl, indazolyl, indolyl, isoindolyl, indenyl, or quinazolinyl. In a particular embodiment, Y and Z form together with the phenyl to form a quinazolin-6-yl ring system.

In a particular embodiment $R^1$ is H. In a particular embodiment $R^1$ is $CH_3$. In a particular embodiment $R^1$ is $CH_2F$. In a particular embodiment $R^1$ is $CHF_2$. In a particular embodiment $R_1$ is $CF_3$. In a particular embodiment $R^1$ is $CH_2CH_3$. In a particular embodiment $R^1$ is $CF_2CF_3$.

In a particular embodiment T is H. In a particular embodiment of T is OH. In a particular embodiment T is OR. In a particular embodiment T is OCOR In a particular embodiment T is $CH_3$. In a particular T is —$NHCOCH_3$. In a particular embodiment T is NHCOR.

In a particular embodiment of T and $R^1$ form a 3-8 carbocyclic or heterocyclic ring. In other embodiments, T and $R^1$ form a 3, 4, 5, 6, 7, or 8 membered carbocyclic or heterocyclic ring. Each represents a separate embodiment of this invention. In some embodiments T and $R^1$ form a carbocyclic ring such as cyclopropyl, cyclobutyl, cyclopentyl, cyclohexyl, etc. In some embodiments T and $R^1$ form a heterocyclic ring such as piperidine, pyridine, furan, thiophene, pyrrole, pyrazole, pyrimidine, etc.

In a particular embodiment of formulas R is H. In a particular embodiment R is alkyl. In a particular embodiment R is alkenyl. In a particular embodiment R is haloalkyl. In a particular embodiment R is alcohol. In a particular embodiment R is CH$_2$CH$_2$OH. In a particular embodiment R is CF$_3$. In a particular embodiment R is CH$_2$Cl. In a particular embodiment of R is CH$_2$CH$_2$Cl. In a particular embodiment R is aryl. In a particular embodiment R is F. In a particular embodiment R is Cl. In a particular embodiment R is Br. In a particular embodiment R is I. In a particular embodiment R is OH.

In a particular embodiment of formula IV, Q$^1$ is H, CN, CF$_3$, phenyl, 4-fluorophenyl, F, Br, Cl, I, COMe, NHCOOMe, NHCOMe or NHCOOC(CH$_3$)$_3$.

In a particular embodiment of formula V, Q$^1$ is H, CN, CF$_3$, phenyl, 4-fluorophenyl, F, Br, Cl, I, COMe, NHCOOMe, NHCOMe or NHCOOC(CH$_3$)$_3$.

In a particular embodiment of formula VI, Q$^1$ is H, CN, CF$_3$, phenyl, 4-fluorophenyl, F, Br, Cl, I, COMe, NHCOOMe, NHCOMe or NHCOOC(CH$_3$)$_3$.

In a particular embodiment of formula IV, Q$^2$ is H, CN, CF$_3$, phenyl, 4-fluorophenyl, F, Br, Cl, I, COMe, NHCOOMe, NHCOMe or NHCOOC(CH$_3$)$_3$.

In a particular embodiment of formula V, Q$^2$ is H, CN, CF$_3$, phenyl, 4-fluorophenyl, F, Br, Cl, I, COMe, NHCOOMe, NHCOMe or NHCOOC(CH$_3$)$_3$.

In a particular embodiment of formula VI, Q$^2$ is H, CN, CF$_3$, phenyl, 4-fluorophenyl, F, Br, Cl, I, COMe, NHCOOMe, NHCOMe or NHCOOC(CH$_3$)$_3$.

In a particular embodiment of formula VII, Q$^2$ is H, CN, CF$_3$, phenyl, 4-fluorophenyl, F, Br, Cl, I, COMe, NHCOOMe, NHCOMe or NHCOOC(CH$_3$)$_3$.

In a particular embodiment of formula VIIA, Q$^2$ is H, CN, CF$_3$, phenyl, 4-fluorophenyl, F, Br, Cl, I, COMe, NHCOOMe, NHCOMe or NHCOOC(CH$_3$)$_3$.

In a particular embodiment of formula VIIB, Q$^2$ is H, CN, CF$_3$, phenyl, 4-fluorophenyl, F, Br, Cl, I, COMe, NHCOOMe, NHCOMe or NHCOOC(CH$_3$)$_3$.

In a particular embodiment of formula IV, Q$^3$ is H, CN, CF$_3$, phenyl, 4-fluorophenyl, F, Br, Cl, I, COMe, NHCOOMe, NHCOMe or NHCOOC(CH$_3$)$_3$.

In a particular embodiment of formula V, Q$^3$ is H, CN, CF$_3$, phenyl, 4-fluorophenyl, F, Br, Cl, I, COMe, NHCOOMe, NHCOMe or NHCOOC(CH$_3$)$_3$.

In a particular embodiment of formula VI, Q$^3$ is H, CN, CF$_3$, phenyl, 4-fluorophenyl, F, Br, Cl, I, COMe, NHCOOMe, NHCOMe or NHCOOC(CH$_3$)$_3$.

In a particular embodiment of formula VII, Q$^3$ is H, CN, CF$_3$, phenyl, 4-fluorophenyl, F, Br, Cl, I, COMe, NHCOOMe, NHCOMe or NHCOOC(CH$_3$)$_3$.

In a particular embodiment of formula VIII, Q$^3$ is H, CN, CF$_3$, phenyl, 4-fluorophenyl, F, Br, Cl, I, COMe, NHCOOMe, NHCOMe or NHCOOC(CH$_3$)$_3$.

In a particular embodiment of formula IV, Q$^4$ is H, CN, CF$_3$, phenyl, 4-fluorophenyl, F, Br, Cl, I, COMe, NHCOOMe, NHCOMe or NHCOOC(CH$_3$)$_3$.

In a particular embodiment of formula V, Q$^4$ is H, CN, CF$_3$, phenyl, 4-fluorophenyl, F, Br, Cl, I, COMe, NHCOOMe, NHCOMe or NHCOOC(CH$_3$)$_3$.

In a particular embodiment of formula VI, Q$^4$ is H, CN, CF$_3$, phenyl, 4-fluorophenyl, F, Br, Cl, I, COMe, NHCOOMe, NHCOMe or NHCOOC(CH$_3$)$_3$.

In a particular embodiment of formula VII, Q$^4$ is H, CN, CF$_3$, phenyl, 4-fluorophenyl, F, Br, Cl, I, COMe, NHCOOMe, NHCOMe or NHCOOC(CH$_3$)$_3$.

In a particular embodiment of formula VIIA, Q$^4$ is H, CN, CF$_3$, phenyl, 4-fluorophenyl, F, Br, Cl, I, COMe, NHCOOMe, NHCOMe or NHCOOC(CH$_3$)$_3$.

In a particular embodiment of formula VIIB, Q$^4$ is H, CN, CF$_3$, phenyl, 4-fluorophenyl, F, Br, Cl, I, COMe, NHCOOMe, NHCOMe or NHCOOC(CH$_3$)$_3$.

In a particular embodiment of formula VIII, VIIIA, or VIIIB, Q$^4$ is H, CN, CF$_3$, phenyl, 4-fluorophenyl, F, Br, Cl, I, COMe, NHCOOMe, NHCOMe or NHCOOC(CH$_3$)$_3$.

In a particular embodiment of formula IX, IXA, or IXB, Q$^4$ is H, CN, CF$_3$, phenyl, 4-fluorophenyl, F, Br, Cl, I, COMe, NHCOOMe, NHCOMe or NHCOOC(CH$_3$)$_3$.

As used herein, the term "heterocycle" or "heterocyclic ring" group refers to a ring structure comprising in addition to carbon atoms, at least one atom of sulfur, oxygen, nitrogen or any combination thereof, as part of the ring. The heterocycle may be a 3-12 membered ring; 4-8 membered ring; a 5-7 membered ring; or a 6 membered ring. Preferably, the heterocycle is a 5 to 6 membered ring. Typical examples of heterocycles include, but are not limited to, piperidine, pyridine, furan, thiophene, pyrrole, pyrrolidine, pyrazole, pyrazine, piperazine or pyrimidine. Examples of C$_5$-C$_8$ heterocyclic rings include pyran, dihydropyran, tetrahydropyran, dihydropyrrole, tetrahydropyrrole, pyrazine, dihydropyrazine, tetrahydropyrazine, pyrimidine, dihydropyrimidine, tetrahydropyrimidone, pyrazole, dihydropyrazole, tetrahydropyrazole, triazole, tetrazole, piperidine, piperazine, pyridine, dihydropyridine, tetrahydropyridine, morpholine, thiomorpholine, furan, dihydrofuran, tetrahydrofuran, thiophene, dihydrothiophene, tetrahydrothiophene, thiazole, imidazole, isoxazole, and the like. The heterocycle ring may be fused to another saturated or unsaturated cycloalkyl or a saturated or unsaturated heterocyclic ring. When the heterocycle ring is substituted, the substituents include at least one of halogen, haloalkyl, hydroxyl, alkoxy, carbonyl, amido, alkylamido, dialkylamido, cyano, nitro, CO$_2$H, amino, alkylamino, dialkylamino, carboxyl, thiol, or thioalkyl.

The term "aniline ring system" refers to the conserved ring represented to the left of the structures in this document which is substituted by X, Y, and/or Z.

The term "cycloalkyl" refers to a non-aromatic, monocyclic or polycyclic ring comprising carbon and hydrogen atoms. A cycloalkyl group can have one or more carbon-carbon double bonds in the ring so long as the ring is not rendered aromatic by their presence. Examples of cycloalkyl groups include, but are not limited to, (C$_3$-C$_7$) cycloalkyl groups, such as cyclopropyl, cyclobutyl, cyclopentyl, cyclohexyl, and cycloheptyl, and saturated cyclic and bicyclic terpenes and (C$_3$-C$_7$) cycloalkenyl groups, such as cyclopropenyl, cyclobutenyl, cyclopentenyl, cyclohexenyl, and cycloheptenyl, and unsaturated cyclic and bicyclic terpenes. Examples of C$_5$-C$_8$ carbocyclic include cyclopentane, cyclopentene, cyclohexane, and cyclohexene rings. A cycloalkyl group can be unsubstituted or substituted by at least one substituent. Preferably, the cycloalkyl group is a monocyclic ring or bicyclic ring.

The term "alkyl" refers to a saturated aliphatic hydrocarbon, including straight-chained and branched-chained. Typically, the alkyl group has 1-12 carbons, 1-7 carbons, 1-6 carbons, or 1-4 carbon atoms. A branched alkyl is an alkyl substituted by alkyl side chains of 1 to 5 carbons. The branched alkyl may have an alkyl substituted by a C$_1$-C$_5$haloalkyl. Additionally, the alkyl group may be substituted by at least one of halogen, haloalkyl, hydroxyl, alkoxy carbonyl, amido, alkylamido, dialkylamido, nitro, CN, amino, alkylamino, dialkylamino, carboxyl, thio or thioalkyl.

An "arylalkyl" group refers to an alkyl bound to an aryl, wherein alkyl and aryl are as defined herein. An example of an arylalkyl group is a benzyl group.

An "alkenyl" group refers to an unsaturated hydrocarbon, including straight chain and branched chain having one or more double bonds. The alkenyl group may have 2-12 carbons, preferably the alkenyl group has 2-6 carbons or 2-4 carbons. Examples of alkenyl groups include, but are not limited to, ethenyl, propenyl, butenyl, cyclohexenyl, etc. The alkenyl group may be substituted by at least one halogen, hydroxy, alkoxy carbonyl, amido, alkylamido, dialkylamido, nitro, amino, alkylamino, dialkylamino, carboxyl, thio, or thioalkyl.

As used herein the term "aryl" group refers to an aromatic group having at least one carbocyclic aromatic group or heterocyclic aromatic group, which may be unsubstituted or substituted. When present, substituents include, but are not limited to, at least one halogen, haloalkyl, hydroxy, alkoxy carbonyl, amido, alkylamido, dialkylamido, nitro, amino, alkylamino, dialkylamino, carboxy or thio or thioalkyl. Nonlimiting examples of aryl rings are phenyl, naphthyl, pyranyl, pyrrolyl, pyrazinyl, pyrimidinyl, pyrazolyl, pyridinyl, furanyl, thiophenyl, thiazolyl, imidazolyl, isoxazolyl, and the like. The aryl group may be a 4-12 membered ring, preferably the aryl group is a 4-8 membered ring. Also the aryl group may be a 6 or 5 membered ring.

The term "heteroaryl" refers to an aromatic group having at least one heterocyclic aromatic ring. In one embodiment, the heteroaryl comprises at least one heteroatom such as sulfur, oxygen, nitrogen, silicon, phosphorous or any combination thereof, as part of the ring. In another embodiment, the heteroaryl may be unsubstituted or substituted by one or more groups selected from halogen, aryl, heteroaryl, cyano, haloalkyl, hydroxy, alkoxy carbonyl, amido, alkylamido, dialkylamido, nitro, amino, alkylamino, dialkylamino, carboxy or thio or thioalkyl. Nonlimiting examples of heteroaryl rings are pyranyl, pyrrolyl, pyrazinyl, pyrimidinyl, pyrazolyl, pyridinyl, furanyl, thiophenyl, thiazolyl, indolyl, imidazolyl, isoxazolyl, and the like. In one embodiment, the heteroaryl group is a 5-12 membered ring. In one embodiment, the heteroaryl group is a five membered ring. In one embodiment, the heteroaryl group is a six membered ring. In another embodiment, the heteroaryl group is a 5-8 membered ring. In another embodiment, the heteroaryl group comprises of 1-4 fused rings. In one embodiment, the heteroaryl group is 1,2,3-triazole. In one embodiment the heteroaryl is a pyridyl. In one embodiment the heteroaryl is a bipyridyl. In one embodiment the heteroaryl is a terpyridyl.

As used herein, the term "haloalkyl" group refers to an alkyl group that is substituted by one or more halogen atoms, e.g. by F, Cl, Br or I.

A "hydroxyl" group refers to an OH group. It is understood by a person skilled in the art that when T, $Q^1$, $Q^2$, $Q^3$, or $Q^4$, in the compounds of the present invention is OR, then R is not OH.

The term "halogen" or "halo" or "halide" refers to a halogen; F, Cl, Br or I.

In one embodiment, this invention provides the compounds and/or its use and/or, its derivative, optical isomer, isomer, metabolite, pharmaceutically acceptable salt, pharmaceutical product, hydrate, N-oxide, prodrug, polymorph, crystal or combinations thereof.

In one embodiment, the methods of this invention make use of "pharmaceutically acceptable salts" of the compounds, which may be produced, by reaction of a compound of this invention with an acid or base.

The compounds of the invention may be converted into pharmaceutically acceptable salts. A pharmaceutically acceptable salt may be produced by reaction of a compound with an acid or base.

Suitable pharmaceutically acceptable salts of amines may be prepared from an inorganic acid or from an organic acid. Examples of inorganic salts of amines include, but are not limited to, bisulfates, borates, bromides, chlorides, hemisulfates, hydrobromates, hydrochlorates, 2-hydroxyethylsulfonates (hydroxyethanesulfonates), iodates, iodides, isothionates, nitrates, persulfates, phosphates, sulfates, sulfamates, sulfanilates, sulfonic acids (alkylsulfonates, arylsulfonates, halogen substituted alkylsulfonates, halogen substituted arylsulfonates), sulfonates, or thiocyanates.

Examples of organic salts of amines may be selected from aliphatic, cycloaliphatic, aromatic, aralphatic, heterocyclic, carboxylic and sulfonic classes of organic acids, examples of which are acetates, arginines, aspartates, ascorbates, adipates, anthranilates, algenates, alkane carboxylates, substituted alkane carboxylates, alginates, benzenesulfonates, benzoates, bisulfates, butyrates, bicarbonates, bitartrates, carboxylates, citrates, camphorates, camphorsulfonates, cyclohexylsulfamates, cyclopentanepropionates, calcium edetates, camsylates, carbonates, clavulanates, cinnamates, dicarboxylates, digluconates, dodecylsulfonates, dihydrochlorides, decanoates, enanthuates, ethanesulfonates, edetates, edisylates, estolates, esylates, fumarates, formates, fluorides, galacturonates, gluconates, glutamates, glycolates, glucorates, glucoheptanoates, glycerophosphates, gluceptates, glycollylarsanilates, glutarates, glutamates, heptanoates, hexanoates, hydroxymaleates, hydroxycarboxlic acids, hexylresorcinates, hydroxybenzoates, hydroxynaphthoates, hydrofluorates, lactates, lactobionates, laurates, malates, maleates, methylenebis(beta-oxynaphthoate), malonates, mandelates, mesylates, methane sulfonates, methylbromides, methylnitrates, methylsulfonates, monopotassium maleates, mucates, monocarboxylates, nitrates, naphthalenesulfonates, 2-naphthalenesulfonates, nicotinates, napsylates, N-methylglucamines, oxalates, octanoates, oleates, pamoates, phenylacetates, picrates, phenylbenzoates, pivalates, propionates, phthalates, pectinates, phenylpropionates, palmitates, pantothenates, polygalacturates, pyruvates, quinates, salicylates, succinates, stearates, sulfanilates, subacetates, tartarates, theophyllineacetates, p-toluenesulfonates (tosylates), trifluoroacetates, terephthalates, tannates, teoclates, trihaloacetates, triethiodide, tricarboxylates, undecanoates and valerates. Examples of inorganic salts of carboxylic acids or phenols may be selected from ammonium, alkali metals, and alkaline earth metals. Alkali metals include, but are not limited to, lithium, sodium, potassium, or cesium Alkaline earth metals include, but are not limited to, calcium, magnesium, aluminium; zinc, barium, cholines, or quaternary ammoniums. Examples of organic salts of carboxylic acids or phenols may be selected from arginine, organic amines to include aliphatic organic amines, alicyclic organic amines, aromatic organic amines, benzathines, t-butylamines, benethamines (N-benzylphenethylamine), dicyclohexylamines, dimethylamines, diethanolamines, ethanolamines, ethylenediamines, hydrabamines, imidazoles, lysines, methylamines, meglamines, N-methyl-D-glucamines, N,N'-dibenzylethylenediamines, nicotinamides, organic amines, ornithines, pyridines, picolines, piperazines, procaine, tris(hydroxymethyl)methylamines, triethylamines, triethanolamines, trimethylamines, tromethamines and ureas.

In various embodiments, the pharmaceutically acceptable salts of the compounds of this invention include: HCl salt, oxalic acid salt, L-(+)-tartaric acid salt, HBr salt and succinic acid salt. Each represents a separate embodiment of this invention.

Salts may be formed by conventional means, such as by reacting the free base or free acid form of the product with one or more equivalents of the appropriate acid or base in a solvent or medium in which the salt is insoluble or in a solvent such as water, which is removed in vacuo or by freeze drying or by exchanging the ions of a existing salt for another ion or suitable ion-exchange resin.

The methods of the invention may use an uncharged compound or a pharmaceutically acceptable salt of the compound of formula I-XXXIII The pharmaceutically acceptable salt may be an amine salt or a salt of a phenol.

In one embodiment, the methods of this invention make use of a free base, free acid, non charged or non-complexed compounds of formula I-XXXIII, and/or its isomer, pharmaceutical product, hydrate, polymorph, or combinations thereof.

In one embodiment, the methods of this invention make use of an optical isomer of a compound of formulas I-XXXIII In one embodiment, the methods of this invention make use of an isomer of a compound of formulas I-XXXIII In one embodiment, the methods of this invention make use of a pharmaceutical product of a compound of formulas I-XXXIII In one embodiment, the methods of this invention make use of a hydrate of a compound of I-XXXIII In one embodiment, the methods of this invention make use of a polymorph of a compound of formulas I-XXXIII In one embodiment, the methods of this invention make use of a metabolite of a compound of formulas I-XXXIII In another embodiment, the methods of this invention make use of a composition comprising a compound of formulas I-XXXIII as described herein, or, in another embodiment, a combination of isomer, metabolite, pharmaceutical product, hydrate, polymorph of a compound of formulas I-XXXIII As used herein, the term "isomer" includes, but is not limited to, optical isomers, structural isomers, or conformational isomers.

The term "isomer" is meant to encompass optical isomers of the SARD compound. It will be appreciated by those skilled in the art that the SARDs of the present invention contain at least one chiral center. Accordingly, the compounds may exist as optically-active (such as an (R) isomer or (S) isomer) or racemic forms. Optically active compounds may exist as enantiomerically enriched mixtures. Some compounds may also exhibit polymorphism. It is to be understood that the present invention encompasses any racemic, optically active, polymorphic, or stereroisomeric form, or mixtures thereof. Thus, the invention may encompass SARD compounds as pure (R)-isomers or as pure (S)-isomers. It is known in the art how to prepare optically active forms. For example, by resolution of the racemic form by recrystallization techniques, by synthesis from optically active starting materials, by chiral synthesis, or by chromatographic separation using a chiral stationary phase.

Compounds of the invention may be hydrates of the compounds. As used herein, the term "hydrate" includes, but is not limited to, hemihydrate, monohydrate, dihydrate, or trihydrate. The invention also includes use of N-oxides of the amino substituents of the compounds described herein.

This invention provides, in other embodiments, use of metabolites of the compounds as herein described. In one embodiment, "metabolite" means any substance produced from another substance by metabolism or a metabolic process.

In one embodiment, the compounds of this invention are prepared according to Example 1.

Biological Activity of Selective Androgen Receptor Degraders

A method of treating prostate cancer (PCa) or increasing the survival of a male subject suffering from prostate cancer comprising administering to the subject a therapeutically effective amount of a compound or its pharmaceutically acceptable salt, of compound I-XXXIII In one embodiment this invention provides a method of treating prostate cancer (PCa) or increasing the survival of a male subject suffering from prostate cancer comprising administering to the subject a therapeutically effective amount of a compound or its pharmaceutically acceptable salt, or isomer, represented by a compound of formulas I-XXXIII.

The prostate cancer may be advanced prostate cancer, refractory prostate cancer, castration resistant prostate cancer (CRPC), metastatic CRPC (mCRPC), non-metastatic CRPC (nmCRPC), high-risk nmCRPC or any combination thereof.

The prostate cancer may depend on AR-FL and/or AR-SV for proliferation. The prostate or other cancer may be resistant to treatment with an androgen receptor antagonist. The prostate or other cancer may be resistant to treatment with enzalutamide, bicalutamide, abiraterone, ARN-509, ODM-201, EPI-001, EPI-506, AZD-3514, galeterone, ASC-J9, flutamide, hydroxyflutamide, nilutamide, cyproterone acetate, ketoconazole, spironolactone, or any combination thereof. The method may also reduce the levels of AR, AR-FL, AR-FL with antiandrogen resistance-conferring AR-LBD mutations, AR-SV, gene-amplified AR, or any combination thereof.

In one embodiment, this invention provides a method of treating enzalutamide resistant prostate cancer comprising administering to the subject a therapeutically effective amount of a compound of this invention, or its optical isomer, isomer, pharmaceutically acceptable salt, pharmaceutical product, polymorph, hydrate or any combination thereof.

In one embodiment, this invention provides a method of treating abiraterone resistant prostate cancer comprising administering to the subject a therapeutically effective amount of a compound of this invention, or its optical isomer, isomer, pharmaceutically acceptable salt, pharmaceutical product, polymorph, hydrate or any combination thereof.

In one embodiment, this invention provides a method of treating triple negative breast cancer (TNBC) comprising administering to the subject a therapeutically effective amount of a compound of this invention, or its optical isomer, isomer, pharmaceutically acceptable salt, pharmaceutical product, polymorph, hydrate or any combination thereof.

The method may further comprise a second therapy such as androgen deprivation therapy (ADT) or LHRH agonist or antagonist. LHRH agonists include, but are not limited to, leuprolide acetate.

The invention encompasses a method of treating or inhibiting the progression of prostate cancer (PCa) or increasing the survival of a male subject suffering from prostate cancer comprising administering to the subject a therapeutically effective amount of a SARD compound or pharmaceutically acceptable salt, wherein the compound is at least one of compounds described herein.

The invention encompasses a method of treating or inhibiting the progression of refractory prostate cancer (PCa) or increasing the survival of a male subject suffering from refractory prostate cancer comprising administering to the subject a therapeutically effective amount of a SARD compound or pharmaceutically acceptable salt, wherein the compound is a compound of formula I-XXXIII, as described herein.

The invention encompasses a method of treating or increasing the survival of a male subject suffering from castration resistant prostate cancer (CRPC) comprising administering to the subject a therapeutically effective amount of a SARD wherein the compound is a compound of formulas I-XXXIII.

The method may further comprise administering androgen deprivation therapy to the subject.

The invention encompasses a method of treating or inhibiting the progression of enzalutamide resistant prostate cancer (PCa) or increasing the survival of a male subject suffering from enzalutamide resistant prostate cancer comprising administering to the subject a therapeutically effective amount of a SARD compound or pharmaceutically acceptable salt, wherein the compound is represented by a compound of formula I-XXXIII.

The method may further comprise administering androgen deprivation therapy to the subject.

The invention encompasses a method of treating or inhibiting the progression of triple negative breast cancer (TNBC) or increasing the survival of a female subject suffering from triple negative breast cancer comprising administering to the subject a therapeutically effective amount of a SARD compound or pharmaceutically acceptable salt, wherein the compound is represented by a compound of formula I-XXXIII.

The invention encompasses a method of treating breast cancer in a subject in need thereof, wherein said subject has AR expressing breast cancer, AR-SV expressing breast cancer, and/or AR-V7 expressing breast cancer, comprising administering to the subject a therapeutically effective amount of a selective androgen receptor degrader (SARD) compound, or its isomer, pharmaceutically acceptable salt, pharmaceutical product, polymorph, hydrate or any combination thereof, wherein said SARD compound is represented by the structure of formula I-XXXIII.

The invention encompasses a method of treating AR expressing breast cancer in a subject in need thereof, comprising administering to the subject a therapeutically effective amount of a selective androgen receptor degrader (SARD) compound, or its isomer, pharmaceutically acceptable salt, pharmaceutical product, polymorph, hydrate or any combination thereof, wherein said SARD compound is represented by the structure of formula I-XXXIII The invention encompasses a method of treating AR-SV expressing breast cancer in a subject in need thereof, comprising administering to the subject a therapeutically effective amount of a selective androgen receptor degrader (SARD) compound, or its isomer, pharmaceutically acceptable salt, pharmaceutical product, polymorph, hydrate or any combination thereof, wherein said SARD compound is represented by the structure of formula I-XXXIII The invention encompasses a method of treating AR-V7 expressing breast cancer in a subject in need thereof, comprising administering to the subject a therapeutically effective amount of a selective androgen receptor degrader (SARD) compound, or its isomer, pharmaceutically acceptable salt, pharmaceutical product, polymorph, hydrate or any combination thereof, wherein said SARD compound is represented by the structure of formula I-XXXIII In one embodiment this invention provides a method of treating prostate cancer in a subject in need thereof, comprising administering to the subject a therapeutically effective amount of a compound that binds to the N-terminal domain (NTD) of androgen receptor (AR).

In one embodiment this invention provides a method of treating prostate cancer in a subject in need thereof, comprising administering to the subject a therapeutically effective amount of a compound of this invention (of formula I-XXXIII) that binds to the N-terminal domain (NTD) of androgen receptor (AR).

In another embodiment, the NTD binding site for the compound is TAU-5.

In another embodiment, the NTD binding site for the compound binds between amino acid 380 and amino acid 529.

In another embodiment, the prostate cancer is advanced prostate cancer, castration resistant prostate cancer (CRPC), metastatic CRPC (mCRPC), non-metastatic CRPC (nm-CRPC), high-risk nmCRPC or any combination thereof.

In another embodiment, the subject has normal or high levels of endogenous androgens or irrespective of androgen levels.

In one embodiment, this invention provides a method of adjuvant therapy of prostate cancer (PCa), and/or of neoadjuvant therapy of prostate cancer (PCa), and/or of treatment of early disease prostate cancer (PCa), and/or of treatment of prostate cancer (PCa) in intact males, and/or of treatment of prostate cancer (PCa) prior to androgen deprivation therapy (ADT) or castration, and/or of first line therapy of PCa, comprising administering to a subject in need thereof, a therapeutically effective amount of a compound that binds to the N-terminal domain (NTD) of androgen receptor (AR).

In one embodiment, this invention provides a method of adjuvant therapy of prostate cancer (PCa), and/or of neoadjuvant therapy of prostate cancer (PCa), and/or of treatment of early disease prostate cancer (PCa), and/or of treatment of prostate cancer (PCa) in intact males, and/or of treatment of prostate cancer (PCa) prior to androgen deprivation therapy (ADT) or castration, and/or of first line therapy of PCa, comprising administering to a subject in need thereof, a therapeutically effective amount of a compound of this invention (of formula I-XXXIII) that binds to the N-terminal domain (NTD) of androgen receptor (AR).

In another embodiment, the NTD binding site for the compound is TAU-5.

In another embodiment, the NTD binding site for the compound binds between amino acid 380 and amino acid 529.

In another embodiment, the prostate cancer is advanced prostate cancer, castration resistant prostate cancer (CRPC), metastatic CRPC (mCRPC), non-metastatic CRPC (nm-CRPC), high-risk nmCRPC or any combination thereof.

In one embodiment, this invention provides a method of adjuvant therapy of prostate cancer (PCa), and/or of neoadjuvant therapy of prostate cancer (PCa), and/or of treatment of early disease prostate cancer (PCa), and/or of treatment of prostate cancer (PCa) in intact males, and/or of treatment of prostate cancer (PCa) prior to androgen deprivation therapy (ADT) or castration, and/or of first line therapy of PCa, comprising administering to a subject in need thereof, a therapeutically effective amount of a selective androgen receptor degrader (SARD) compound of this invention of formula I to XXXIII.

As used herein, the term "increase the survival" refers to a lengthening of time when describing the survival of a subject. Thus in this context, the compounds of the invention may be used to increase the survival of men with advanced prostate cancer, refractory prostate cancer, castration resistant prostate cancer (CRPC); metastatic CRPC (mCRPC); non-metastatic CRPC (nmCRPC); or high-risk nmCRPC; or women with TNBC.

Alternatively, as used herein, the terms "increase", "increasing", or "increased" may be used interchangeably and refer to an entity becoming progressively greater (as in size, amount, number, or intensity), wherein for example the entity is sex hormone-binding globulin (SHBG) or prostate-specific antigen (PSA).

The compounds and compositions of the invention may be used for increasing metastasis-free survival (MFS) in a subject suffering from non-metastatic prostate cancer. The non-metastatic prostate cancer may be non-metastatic advanced prostate cancer, non-metastatic CRPC (nmCRPC), or high-risk nmCRPC.

The SARD compounds described herein may be used to provide a dual action. For example, the SARD compounds may treat prostate cancer and prevent metastasis. The prostate cancer may be refractory prostate cancer; advanced prostate cancer; castration resistant prostate cancer (CRPC); metastatic CRPC (mCRPC); non-metastatic CRPC (nmCRPC); or high-risk nmCRPC.

The SARD compounds described herein may be used to provide a dual action. For example, the SARD compounds may treat TNBC and prevent metastasis.

Men with advanced prostate cancer who are at high risk for progression to castration resistant prostate cancer (CRPC) are men on ADT with serum total testosterone concentrations greater than 20 ng/dL or men with advanced prostate cancer who at the time of starting ADT had either (1) confirmed Gleason pattern 4 or 5 prostate cancer, (2) metastatic prostate cancer, (3) a PSA doubling time <3 months, (4) a PSA ≥20 ng/mL, or (5) a PSA relapse in <3 years after definitive local therapy (radical prostatectomy or radiation therapy).

Normal levels of prostate specific antigen (PSA) are dependent on several factors, such as age and the size of a male subject's prostate, among others. PSA levels in the range between 2.5-10 ng/mL are considered "borderline high" while levels above 10 ng/mL are considered "high." A rate change or "PSA velocity" greater than 0.75/year is considered high. PSA levels may increase despite ongoing ADT or a history of ADT, surgical castration or despite treatment with antiandrogens and/or LHRH agonist.

Men with high risk non-metastatic castration resistant prostate cancer (high-risk nmCRPC) may include those with rapid PSA doubling times, having an expected progression-free survival of approximately 18 months or less (Miller K, Moul J W, Gleave M, et al. 2013. "Phase III, randomized, placebo-controlled study of once-daily oral zibotentan (ZD4054) in patients with non-metastatic castration-resistant prostate cancer," *Prostate Canc Prost Dis*. February; 16:187-192). This relatively rapid progression of their disease underscores the importance of novel therapies for these individuals.

The methods of the invention may treat subjects with PSA levels greater than 8 ng/mL where the subject suffers from high-risk nmCRPC. The patient population includes subjects suffering from nmCRPC where PSA doubles in less than 8 months or less than 10 months. The method may also treat patient populations where the total serum testosterone levels are greater than 20 ng/mL in a subject suffering from high-risk nmCRPC. In one case, the serum free testosterone levels are greater than those observed in an orchiectomized male in a subject suffering from high-risk nmCRPC.

The pharmaceutical compositions of the invention may further comprise at least one LHRH agonist or antagonist, antiandrogen, anti-programmed death receptor 1 (anti-PD-1) drug or anti-PD-L1 drug. LHRH agonists include, but are not limited to, leuprolide acetate (Lupron®) (U.S. Pat. Nos. 5,480,656; 5,575,987; 5,631,020; 5,643,607; 5,716,640; 5,814,342; 6,036,976 hereby incorporated by reference) or goserelin acetate (Zoladex®) (U.S. Pat. Nos. 7,118,552; 7,220,247; 7,500,964 hereby incorporated by reference). LHRH antagonists include, but are not limited to, degarelix or abarelix. Antiandrogens include, but are not limited to, bicalutamide, flutamide, apalutamide, finasteride, dutasteride, enzalutamide, nilutamide, chlormadinone, abiraterone, or any combination thereof.

Anti-PD-1 drugs include, but are not limited to, AMP-224, nivolumab, pembrolizumab, pidilizumab, and AMP-554. Anti-PD-L1 drugs include, but are not limited to, BMS-936559, atezolizumab, durvalumab, avelumab, and MPDL3280A. Anti-CTLA-4 drugs include, but are not limited to, ipilimumab and tremelimumab.

Treatment of prostate cancer, advanced prostate cancer, CRPC, mCRPC and/or nmCRPC may result in clinically meaningful improvement in prostate cancer related symptoms, function and/or survival. Clinically meaningful improvement can be determined by an increase in radiographic progression free survival (rPFS) if cancer is metastatic, or an increase metastasis-free survival (MFS) if cancer is non-metastatic, among others.

The invention encompasses methods of lowering serum prostate specific antigen (PSA) levels in a male subject suffering from prostate cancer, advanced prostate cancer, metastatic prostate cancer or castration resistant prostate cancer (CRPC) comprising administering a therapeutically effective amount of a SARD compound, wherein the compound is represented by the structure of formulas I-XXXIII.

The invention encompasses a method of secondary hormonal therapy that reduces serum PSA in a male subject suffering from castration resistant prostate cancer (CRPC) comprising administering a therapeutically effective amount of a compound of formulas I-XXXIII that reduces serum PSA in a male subject suffering from castration resistant prostate cancer.

The invention encompasses a method of reducing levels of AR, AR-full length (AR-FL), AR-FL with antiandrogen resistance-conferring AR-LBD mutations, AR-splice variant (AR-SV), and/or amplifications of the AR gene within the tumor in the subject in need thereof comprising administering a therapeutically effective amount of a compound of formulas I-XXXIII to reduce the level of AR, AR-full length (AR-FL), AR-FL with antiandrogen resistance-conferring AR-LBD or other AR mutations, AR-splice variant (AR-SV), and/or amplifications of the AR gene within the tumor.

The method may increase radiographic progression free survival (rPFS) or metastasis-free survival (MFS).

Subjects may have non-metastatic cancer; failed androgen deprivation therapy (ADT), undergone orchidectomy, or have high or increasing prostate specific antigen (PSA) levels; subjects may be a patient with prostate cancer, advanced prostate cancer, refractory prostate cancer, CRPC patient, metastatic castration resistant prostate cancer (mCRPC) patient, or non-metastatic castration resistant prostate cancer (nmCRPC) patient. In these subjects, the refractory may be enzalutamide resistant prostate cancer. In these subjects, the nmCRPC may be high-risk nmCRPC. Further the subject may be on androgen deprivation therapy (ADT) with or without castrate levels of total T.

As used herein, the phrase "a subject suffering from castration resistant prostate cancer" refers to a subject with at least one of the following characteristics: has been previously treated with androgen deprivation therapy (ADT); has responded to the ADT and currently has a serum PSA >2 ng/mL or >2 ng/mL and representing a 25% increase above the nadir achieved on the ADT; a subject which despite being maintained on androgen deprivation therapy is diagnosed to have serum PSA progression; a castrate level of serum total testosterone (<50 ng/dL) or a castrate level of serum total testosterone (<20 ng/dL). The subject may have rising serum PSA on two successive assessments at least 2 weeks apart; been effectively treated with ADT; or has a history of serum PSA response after initiation of ADT.

As used herein, the term "serum PSA progression" refers to a 25% or greater increase in serum PSA and an absolute increase of 2 ng/ml or more from the nadir; or to serum PSA >2 ng/mL, or >2 ng/mL and a 25% increase above the nadir after the initiation of androgen deprivation therapy (ADT). The term "nadir" refers to the lowest PSA level while a patient is undergoing ADT.

The term "serum PSA response" refers to at least one of the following: at least 90% reduction in serum PSA value prior to the initiation of ADT; to <10 ng/mL undetectable level of serum PSA (<0.2 ng/mL) at any time; at least 50% decline from baseline in serum PSA; at least 90% decline from baseline in serum PSA; at least 30% decline from baseline in serum PSA; or at least 10% decline from baseline in serum PSA.

The methods of this invention comprise administering a combination of forms of ADT and a compound of this invention. Forms of ADT include a LHRH agonist. LHRH agonist includes, but is not limited to, leuprolide acetate (Lupron®)(U.S. Pat. Nos. 5,480,656; 5,575,987; 5,631,020; 5,643,607; 5,716,640; 5,814,342; 6,036,976 hereby incorporated by reference) or goserelin acetate (Zoladex®) (U.S. Pat. Nos. 7,118,552; 7,220,247; 7,500,964 hereby incorporated by reference). Forms of ADT include, but are not limited to LHRH antagonists, reversible antiandrogens, or bilateral orchidectomy. LHRH antagonists include, but are not limited to, degarelix and abarelix. Antiandrogens include, but are not limited to, bicalutamide, flutamide, apalutamide, finasteride, dutasteride, enzalutamide, EPI-001, EPI-506, ARN-509, ODM-201, nilutamide, chlormadinone, abiraterone, or any combination thereof.

The methods of the invention encompass administering at least one compound of the invention and a lyase inhibitor (e.g., abiraterone).

The term "advanced prostate cancer" refers to metastatic cancer having originated in the prostate, and having widely metastasized to beyond the prostate such as the surrounding tissues to include the seminal vesicles the pelvic lymph nodes or bone, or to other parts of the body. Prostate cancer pathologies are graded with a Gleason grading from 1 to 5 in order of increasing malignancy. Patients with significant risk of progressive disease and/or death from prostate cancer should be included in the definition and any patient with cancer outside the prostate capsule with disease stages as low as IIB clearly has "advanced" disease. "Advanced prostate cancer" can refer to locally advanced prostate cancer. Similarly, "advanced breast cancer" refers to metastatic cancer having originated in the breast, and having widely metastasized to beyond the breast to surrounding tissues or other parts of the body such as the liver, brain, lungs, or bone.

The term "refractory" may refer to cancers that do not respond to treatment. E.g., prostate or breast cancer may be resistant at the beginning of treatment or it may become resistant during treatment. "Refractory cancer" may also be referred to herein as "resistant cancer".

The term "castration resistant prostate cancer" (CRPC) refers to advanced prostate cancer that is worsening or progressing while the patient remains on ADT or other therapies to reduce testosterone, or prostate cancer which is considered hormone refractory, hormone naïve, androgen independent or chemical or surgical castration resistant. CRPC may be the result of AR activation by intracrine androgen synthesis; expression of AR splice variants (AR-SV) that lack ligand binding domain (LBD); or expression of AR-LBD or other AR mutations with potential to resist antagonists. Castration resistant prostate cancer (CRPC) is an advanced prostate cancer which developed despite ongoing ADT and/or surgical castration. Castration resistant prostate cancer is defined as prostate cancer that continues to progress or worsen or adversely affect the health of the patient despite prior surgical castration, continued treatment with gonadotropin releasing hormone agonists (e.g., leuprolide) or antagonists (e.g., degarelix or abarelix), antiandrogens (e.g., bicalutamide, flutamide, apalutamide, enzalutamide, ketoconazole, aminoglutethimide), chemotherapeutic agents (e.g., docetaxel, paclitaxel, cabazitaxel, adriamycin, mitoxantrone, estramustine, cyclophosphamide), kinase inhibitors (imatinib (Gleevec®) or gefitinib (Iressa®), cabozantinib (Cometrig™, also known as XL184)) or other prostate cancer therapies (e.g., vaccines (sipuleucel-T (Provenge®), GVAX, etc.), herbal (PC-SPES) and lyase inhibitor (abiraterone)) as evidenced by increasing or higher serum levels of prostate specific antigen (PSA), metastasis, bone metastasis, pain, lymph node involvement, increasing size or serum markers for tumor growth, worsening diagnostic markers of prognosis, or patient condition.

Castration resistant prostate cancer may be defined as hormone naïve prostate cancer. In men with castration resistant prostate cancer, the tumor cells may have the ability to grow in the absence of androgens (hormones that promote the development and maintenance of male sex characteristics).

Many early prostate cancers require androgens for growth, but advanced prostate cancers are androgen-independent, or hormone naïve.

The term "androgen deprivation therapy" (ADT) may include orchiectomy; administering luteinizing hormone-releasing hormone (LHRH) analogs; administering luteinizing hormone-releasing hormone (LHRH) antagonists; administering 5α-reductase inhibitors; administering antiandrogens; administering inhibitors of testosterone biosynthesis; administering estrogens; or administering 17α-hydroxylase/C17,20 lyase (CYP17A1) inhibitors. LHRH drugs lower the amount of testosterone made by the testicles. Examples of LHRH analogs available in the United States include leuprolide (Lupron®, Viadur®, Eligard®), goserelin (Zoladex®), triptorelin (Trelstar®), and histrelin (Vantas®). Antiandrogens block the body's ability to use any androgens. Examples of antiandrogens drugs include enzalutamide (Xtandi®), flutamide (Eulexin®), apalutamide (Erleada®), bicalutamide (Casodex®), and nilutamide (Nilandron®). Luteinizing hormone-releasing hormone (LHRH) antagonists include abarelix (Plenaxis®) or degarelix (Firmagon®) (approved for use by the FDA in 2008 to treat advanced prostate cancer). 5α-Reductase inhibitors block the body's ability to convert testosterone to the more active androgen, 5α-dihydrotestosterone (DHT) and include drugs such as finasteride (Proscar®) and dutasteride (Avodart®). Inhibitors of testosterone biosynthesis include drugs such as ketoconazole (Nizoral®). Estrogens include diethylstilbestrol or 17β-estradiol. 17α-Hydroxylase/C17,20 lyase (CYP17A1) inhibitors include abiraterone (Zytiga®).

The invention encompasses a method of treating antiandrogen-resistant prostate cancer. The antiandrogen may include, but is not limited to, bicalutamide, hydroxyflutamide, flutamide, apalutamide, enzalutamide or abiraterone.

The invention encompasses a method of treating prostate cancer in a subject in need thereof, wherein said subject has AR overexpressing prostate cancer, castration-resistant prostate cancer, castration-sensitive prostate cancer, AR-V7 expressing prostate cancer, or d567ES expressing prostate cancer, comprising administering to the subject a therapeutically effective amount of a selective androgen receptor degrader (SARD) compound, or its isomer, pharmaceutically acceptable salt, pharmaceutical product, polymorph, hydrate or any combination thereof, wherein said SARD compound is represented by the structure of formula I-XXXIII.

In one embodiment, the castration-resistant prostate cancer is AR overexpressing castration-resistant prostate cancer, F876L mutation expressing castration-resistant prostate cancer, F876L_T877A double mutation expressing castration-resistant prostate cancer, AR-V7 expressing castration-resistant prostate cancer, d567ES expressing castration-resistant prostate cancer, and/or expressing castration-resistant prostate cancer.

In one embodiment, the castration-sensitive prostate cancer is F876L mutation expressing castration-sensitive prostate cancer, F876L_T877A double mutation castration-sensitive prostate cancer, and/or expressing castration-sensitive prostate cancer.

In one embodiment, the treating of castration-sensitive prostate cancer is conducted in a non-castrate setting, or as monotherapy, or when castration-sensitive prostate cancer tumor is resistant to enzalutamide, apalutamide, and/or abiraterone.

The invention encompasses a method of treating AR overexpressing prostate cancer in a subject in need thereof, comprising administering to the subject a therapeutically effective amount of a selective androgen receptor degrader (SARD) compound, or its isomer, pharmaceutically acceptable salt, pharmaceutical product, polymorph, hydrate or any combination thereof, wherein said SARD compound is represented by the structure of formula I-XXXIII.

The invention encompasses a method of treating castration-resistant prostate cancer in a subject in need thereof, comprising administering to the subject a therapeutically effective amount of a selective androgen receptor degrader (SARD) compound, or its isomer, pharmaceutically acceptable salt, pharmaceutical product, polymorph, hydrate or any combination thereof, wherein said SARD compound is represented by the structure of formula I-XXXIII In one embodiment, the castration-resistant prostate cancer is AR overexpressing castration-resistant prostate cancer, F876L mutation expressing castration-resistant prostate cancer, F876L_T877A double mutation expressing castration-resistant prostate cancer, AR-V7 expressing castration-resistant prostate cancer, d567ES expressing castration-resistant prostate cancer, expressing castration-resistant prostate cancer.

The invention encompasses a method of treating castration-sensitive prostate cancer in a subject in need thereof, comprising administering to the subject a therapeutically effective amount of a selective androgen receptor degrader (SARD) compound, or its isomer, pharmaceutically acceptable salt, pharmaceutical product, polymorph, hydrate or any combination thereof, wherein said SARD compound is represented by the structure of formula I-XXXIII. In one embodiment, the castration-sensitive prostate cancer is F876L mutation expressing castration-sensitive prostate cancer, F876L_T877A double mutation castration-sensitive prostate cancer, and/or expressing castration-sensitive prostate cancer. In one embodiment, the treating of castration-sensitive prostate cancer is conducted in a non-castrate setting, or as monotherapy, or when castration-sensitive prostate cancer tumor is resistant to enzalutamide, apalutamide, and/or abiraterone.

The invention encompasses a method of treating AR-V7 expressing prostate cancer in a subject in need thereof, comprising administering to the subject a therapeutically effective amount of a selective androgen receptor degrader (SARD) compound, or its isomer, pharmaceutically acceptable salt, pharmaceutical product, polymorph, hydrate or any combination thereof, wherein said SARD compound is represented by the structure of formula I-XXXIII.

The invention encompasses a method of treating d567ES expressing prostate cancer in a subject in need thereof, comprising administering to the subject a therapeutically effective amount of a selective androgen receptor degrader (SARD) compound, or its isomer, pharmaceutically acceptable salt, pharmaceutical product, polymorph, hydrate or any combination thereof, wherein said SARD compound is represented by the structure of formula I-XXXIII.

Treatment of Triple Negative Breast Cancer (TNBC)

Triple negative breast cancer (TNBC) is a type of breast cancer lacking the expression of the estrogen receptor (ER), progesterone receptor (PR), and HER2 receptor kinase. As such, TNBC lacks the hormone and kinase therapeutic targets used to treat other types of primary breast cancers. Correspondingly, chemotherapy is often the initial pharmacotherapy for TNBC. Interestingly, AR is often still expressed in TNBC and may offer a hormone targeted therapeutic alternative to chemotherapy. In ER-positive breast cancer, AR is a positive prognostic indicator as it is believed that activation of AR limits and/or opposes the effects of the ER in breast tissue and tumors. However, in the absence of ER, it is possible that AR actually supports the growth of breast cancer tumors. Though the role of AR is not fully understood in TNBC, we have evidence that certain TNBC's may be supported by androgen independent activation of AR-SVs lacking the LBD or androgen-dependent activation of AR full length. As such, enzalutamide and other LBD-directed traditional AR antagonists would not be able to antagonize AR-S Vs in these TNBC's. However, SARDs of this invention which are capable of destroying AR-S Vs (see Table 1 and Example 5) through a binding site in the NTD of AR (see Example 9) would be able to antagonize AR in these TNBC's and provide an anti-tumor effect, as shown in Example 8.

Treatment of Kennedy's Disease

Muscle atrophy (MA) is characterized by wasting away or diminution of muscle and a decrease in muscle mass. For example, post-polio MA is muscle wasting that occurs as part of the post-polio syndrome (PPS). The atrophy includes weakness, muscle fatigue, and pain. Another type of MA is X-linked spinal-bulbar muscular atrophy (SBMA—also known as Kennedy's Disease). This disease arises from a defect in the androgen receptor gene on the X chromosome, affects only males, and its onset is in late adolescence to adulthood. Proximal limb and bulbar muscle weakness results in physical limitations including dependence on a wheelchair in some cases. The mutation results in an extended polyglutamine tract at the N-terminal domain of the androgen receptor (polyQ AR).

Binding and activation of the polyQ AR by endogenous androgens (testosterone and DHT) results in unfolding and nuclear translocation of the mutant androgen receptor. The androgen-induced toxicity and androgen-dependent nuclear accumulation of polyQ AR protein seems to be central to the pathogenesis. Therefore, the inhibition of the androgen-activated polyQ AR might be a therapeutic option (A. Baniahmad. Inhibition of the androgen receptor by antiandrogens in spinobulbar muscle atrophy. *J. Mol. Neurosci.* 2016 58(3), 343-347). These steps are required for pathogenesis and result in partial loss of transactivation function (i.e., an androgen insensitivity) and a poorly understood neuromuscular degeneration. Peripheral polyQ AR antisense therapy rescues disease in mouse models of SBMA (*Cell Reports* 7, 774-784, May 8, 2014). Further support of use antiandrogen comes in a report in which the antiandrogen flutamide protects male mice from androgen-dependent toxicity in three models of spinal bulbar muscular atrophy (Renier K J, Troxell-Smith S M, Johansen J A, Katsuno M, Adachi H, Sobue G, Chua J P, Sun Kim H, Lieberman A P, Breedlove S M, Jordan C L. *Endocrinology* 2014, 155(7), 2624-2634). These steps are required for pathogenesis and result in partial loss of transactivation function (i.e., an androgen insensitivity) and a poorly understood neuromuscular degeneration. Currently there are no disease-modifying treatments but rather only symptom directed treatments. Efforts to target the polyQ AR as the proximal mediator of toxicity by harnessing cellular machinery to promote its degradation hold promise for therapeutic intervention.

Selective androgen receptor degraders such as those reported herein bind to, inhibit transactivation, and degrade all androgen receptors tested to date (full length, splice variant, antiandrogen resistance mutants, etc.), indicating that they are promising leads for treatment diseases whose pathogenesis is androgen-dependent such as SBMA.

The invention encompasses methods of treating Kennedy's disease comprising administering a therapeutically effective amount of a compound of formulas I-XXXIII.

As used herein, the term "androgen receptor associated conditions" or "androgen sensitive diseases or disorders" or "androgen-dependent diseases or disorders" are conditions, diseases, or disorders that are modulated by or whose pathogenesis is dependent upon the activity of the androgen receptor. The androgen receptor is expressed in most tissues of the body however it is overexpressed in, inter alia, the prostate and skin. ADT has been the mainstay of prostate cancer treatment for many years, and SARDs may also be useful in treating various prostate cancers, benign prostatic hypertrophy, prostamegaly, and other maladies of the prostate.

The invention encompasses methods of treating benign prostatic hypertrophy comprising administering a therapeutically effective amount of at least one compound of formulas I-XXXIII.

The invention encompasses methods of treating prostamegaly comprising administering a therapeutically effective amount of at least one compound of formulas I-XXXIII.

The invention encompasses methods of treating hyperproliferative prostatic disorders and diseases comprising administering a therapeutically effective amount of a compound of formulas I-XXXIII.

The effect of the AR on the skin is apparent in the gender dimorphism and puberty related dermatological problems common to teens and early adults. The hyperandrogenism of puberty stimulates terminal hair growth, sebum production, and predisposes male teens to acne, acne vulgaris, seborrhea, excess sebum, hidradenitis suppurativa, hirsutism, hypertrichosis, hyperpilosity, androgenic alopecia, male pattern baldness, and other dermatological maladies. Although antiandrogens theoretically should prevent the hyperandrogenic dermatological diseases discussed, they are limited by toxicities, sexual side effects, and lack of efficacy when topically applied. The SARDs of this invention potently inhibit ligand-dependent and ligand-independent AR activation, and (in some cases) have short biological half-lives in the serum, suggesting that topically formulated SARDs of this invention could be applied to the areas affected by acne, seborrheic dermatitis, and/or hirsutism without risk of systemic side effects.

The invention encompasses methods of treating acne, acne vulgaris, seborrhea, seborrheic dermatitis, hidradenitis supporativa, hirsutism, hypertrichosis, hyperpilosity, or alopecia comprising administering a therapeutically effective amount of a compound of formulas I-XXXIII.

The compounds and/or compositions described herein may be used for treating hair loss, alopecia, androgenic alopecia, alopecia areata, alopecia secondary to chemotherapy, alopecia secondary to radiation therapy, alopecia induced by scarring or alopecia induced by stress. Generally "hair loss" or "alopecia" refers to baldness as in the very common type of male-pattern baldness. Baldness typically begins with patch hair loss on the scalp and sometimes progresses to complete baldness and even loss of body hair. Hair loss affects both males and females.

The invention encompasses methods of treating androgenic alopecia comprising administering a therapeutically effective amount of a compound of formula I-XXXIII.

The invention encompasses methods of treating, suppressing, reducing the incidence, reducing the severity, or inhibiting the progression of a hormonal condition in a male in need thereof, comprising administering to the subject a therapeutically effective amount of a selective androgen receptor degrader (SARD) compound, or its isomer, pharmaceutically acceptable salt, pharmaceutical product, polymorph, hydrate or any combination thereof, wherein said SARD compound is represented by the structure of formula I-XXXIII.

In one embodiment, the condition is sexual dysfunction, decreased sexual libido, erectile dysfunction, hypogonadism, sarcopenia, osteopenia, osteoporosis, alterations in cognition and mood, depression, anemia, hair loss, obesity, benign prostate hyperplasia and/or prostate cancer.

SARDs of this invention may also be useful in the treatment of hormonal conditions in females which can have hyperandrogenic pathogenesis such as precocious puberty, early puberty, dysmenorrhea, amenorrhea, multilocular uterus syndrome, endometriosis, hysteromyoma, abnormal uterine bleeding, early menarche, fibrocystic breast disease, fibroids of the uterus, ovarian cysts, polycystic ovary syndrome, pre-eclampsia, eclampsia of pregnancy, preterm labor, premenstrual syndrome, and/or vaginal dryness.

The invention encompasses methods of treating precocious puberty or early puberty, dysmenorrhea or amenorrhea, multilocular uterus syndrome, endometriosis, hysteromyoma, abnormal uterine bleeding, hyper-androgenic diseases (such as polycystic ovary syndrome (PCOS)), fibrocystic breast disease, fibroids of the uterus, ovarian cysts, polycystic ovary syndrome, pre-eclampsia, eclampsia of pregnancy, preterm labor, premenstrual syndrome, or vaginal dryness comprising administering a therapeutically effective amount of a compound of formulas I-XXXIII.

SARDs of this invention may also find utility in treatment of sexual perversion, hypersexuality, paraphilias, androgen psychosis, virilization, androgen insensitivity syndromes (AIS) (such as complete AIS (CAIS) and partial AIS (PAIS)), and improving ovulation in an animal.

The invention encompasses methods of treating sexual perversion, hypersexuality, paraphilias, androgen psychosis, virilization androgen, insensitivity syndromes, increasing or modulating or improving ovulation comprising administering a therapeutically effective amount of a compound of formulas I-XXXIII.

SARDs of this invention may also be useful for treating hormone-dependent cancers such as prostate cancer, breast cancer, testicular cancer, ovarian cancer, hepatocellular carcinoma, urogenital cancer, etc. In another embodiment, the breast cancer is triple negative breast cancer. Further, local or systemic SARD administration may be useful for treatment of precursors of hormone-dependent cancers such as prostatic intraepithelial neoplasia (PIN) and atypical small acinar proliferation (ASAP).

The invention encompasses methods of treating breast cancer, testicular cancer, uterine cancer, ovarian cancer, urogenital cancer, precursors of prostate cancer, or AR related or AR expressing solid tumors, comprising administering a therapeutically effective amount of a compound of formulas I-XXXIII. A precursor of prostate cancers may be prostatic intraepithelial neoplasia (PIN) or atypical small acinar proliferation (ASAP). The tumor may be hepatocellular carcinoma (HCC) or bladder cancer. Serum testosterone may be positively linked to the development of HCC. Based on epidemiologic, experimental observations, and notably the fact that men have a substantially higher risk of bladder cancer than women, androgens and/or the AR may also play a role in bladder cancer initiation.

Although traditional antiandrogens such as enzalutamide, bicalutamide and flutamide and androgen deprivation therapies (ADT) such as leuprolide were approved for use in prostate cancer, there is significant evidence that antiandrogens could also be used in a variety of other hormone-dependent and hormone-independent cancers. For example, antiandrogens have been successfully tested in breast cancer (enzalutamide; Breast Cancer Res (2014) 16(1): R7), non-small cell lung cancer (shRNAi AR), renal cell carcinoma (ASC-J9), partial androgen insensitivity associated malignancies such as gonadal tumors and seminoma, advanced pancreatic cancer (World J Gastroenterology 20(29):9229), cancer of the ovary, fallopian tubes, or peritoneum, cancer of the salivary gland (Head and Neck (2016) 38: 724-731; ADT was tested in AR-expressing recurrent/metastatic salivary gland cancers and was confirmed to have benefit on progression free survival and overall survival endpoints), bladder cancer (Oncotarget 6 (30): 29860-29876); Int J Endocrinol (2015), Article ID 384860), pancreatic cancer, lymphoma (including mantle cell), and hepatocellular carcinoma. Use of a more potent antiandrogen such as a SARD in these cancers may treat the progression of these and other cancers. Other cancers may also benefit from SARD treatment such as testicular cancer, uterine cancer, ovarian cancer, urogenital cancer, breast cancer, brain cancer, skin cancer, lymphoma, liver cancer, renal cancer, osteosarcoma, pancreatic cancer, endometrial cancer, lung cancer, non-small cell lung cancer (NSCLC), colon cancer, perianal adenoma, or central nervous system cancer.

SARDs of this invention may also be useful for treating other cancers containing AR such as breast, brain, skin, ovarian, bladder, lymphoma, liver, kidney, pancreas, endometrium, lung (e.g., NSCLC), colon, perianal adenoma, osteosarcoma, CNS, melanoma, hypercalcemia of malignancy and metastatic bone disease, etc.

Thus, the invention encompasses methods of treating hypercalcemia of malignancy, metastatic bone disease, brain cancer, skin cancer, bladder cancer, lymphoma, liver cancer, renal cancer, osteosarcoma, pancreatic cancer, endometrial cancer, lung cancer, central nervous system cancer, gastric cancer, colon cancer, melanoma, amyotrophic lateral sclerosis (ALS), and/or uterine fibroids comprising administering a therapeutically effective amount of a compound of formulas I-XXXIII. The lung cancer may be non-small cell lung cancer (NSCLC).

SARDs of this invention may also be useful for the treating of non-hormone-dependent cancers. Non-hormone-dependent cancers include liver, salivary duct, etc.

In another embodiment, the SARDs of this invention are used for treating gastric cancer. In another embodiment, the SARDs of this invention are used for treating salivary duct carcinoma. In another embodiment, the SARDs of this invention are used for treating bladder cancer. In another embodiment, the SARDs of this invention are used for treating esophageal cancer. In another embodiment, the SARDs of this invention are used for treating pancreatic cancer. In another embodiment, the SARDs of this invention are used for treating colon cancer. In another embodiment, the SARDs of this invention are used for treating non-small cell lung cancer. In another embodiment, the SARDs of this invention are used for treating renal cell carcinoma.

AR plays a role in cancer initiation in hepatocellular carcinoma (HCC). Therefore, targeting AR may be an appropriate treatment for patients with early stage HCC. In late-stage HCC disease, there is evidence that metastasis is suppressed by androgens. In another embodiment, the SARDs of this invention are used for treating hepatocellular carcinoma (HCC).

Locati et al. in Head & Neck, 2016, 724-731 demonstrated the use of androgen deprivation therapy (ADT) in AR-expressing recurrent/metastatic salivary gland cancers and confirmed improved progression free survival and overall survival endpoints with ADT. In another embodiment, the SARDs of this invention are used for treating salivary gland cancer.

Kawahara et al. in Oncotarget, 2015, Vol 6 (30), 29860-29876 demonstrated that ELK1 inhibition, together with AR inactivation, has the potential of being a therapeutic approach for bladder cancer. McBeth et al. Int J Endocrinology, 2015, Vol 2015, Article ID 384860 suggested that the combination of antiandrogen therapy plus glucocorticoids as treatment of bladder cancer as this cancer is believed to have an inflammatory etiology. In another embodiment, the SARDs of this invention are used for treating bladder cancer, optionally in combination with glucocorticoids.

Abdominal Aortic Aneurysm (AAA)

An abdominal aortic aneurysm (AAA) is an enlarged area in the lower part of the aorta, the major blood vessel that supplies blood to the body. The aorta, about the thickness of a garden hose, runs from your heart through the center of your chest and abdomen. Because the aorta is the body's main supplier of blood, a ruptured abdominal aortic aneurysm can cause life-threatening bleeding. Depending on the size and the rate at which your abdominal aortic aneurysm is growing, treatment may vary from watchful waiting to emergency surgery. Once an abdominal aortic aneurysm is found, doctors will closely monitor it so that surgery can be planned if it is necessary. Emergency surgery for a ruptured abdominal aortic aneurysm can be risky. AR blockade (pharmacologic or genetic) reduces AAA. Davis et al. (Davis J P, Salmon M, Pope N H, Lu G, Su G, Meher A, Ailawadi G, Upchurch G R Jr. J Vasc Surg (2016) 63(6): 1602-1612) showed that flutamide (50 mg/kg) or ketoconazole (150 mg/kg) attenuated AAA induced by porcine pancreatic elastase (0.35 U/mL) by 84.2% and 91.5% compared to vehicle (121%). Further AR −/− mice showed attenuated AAA growth (64.4%) compared to wildtype (both treated with elastase). Correspondingly, administration of a SARD to a patient suffering from an AAA may help reverse, treat or delay progression of AAA to the point where surgery is needed.

Treatment of Wounds

Wounds and/or ulcers are normally found protruding from the skin or on a mucosal surface or as a result of an infarction in an organ. A wound may be a result of a soft tissue defect or a lesion or of an underlying condition. The term "wound" denotes a bodily injury with disruption of the normal integrity of tissue structures, sore, lesion, necrosis, and/or ulcer. The term "sore" refers to any lesion of the skin or mucous membranes and the term "ulcer" refers to a local defect, or excavation, of the surface of an organ or tissue, which is produced by the sloughing of necrotic tissue. "Lesion" generally includes any tissue defect. "Necrosis" refers to dead tissue resulting from infection, injury, inflammation, or infarctions. All of these are encompassed by the term "wound," which denotes any wound at any particular stage in the healing process including the stage before any healing has initiated or even before a specific wound like a surgical incision is made (prophylactic treatment).

Examples of wounds which can be treated in accordance with the present invention are aseptic wounds, contused wounds, incised wounds, lacerated wounds, non-penetrating wounds (i.e. wounds in which there is no disruption of the skin but there is injury to underlying structures), open wounds, penetrating wounds, perforating wounds, puncture wounds, septic wounds, subcutaneous wounds, etc. Examples of sores include, but are not limited to, bed sores, canker sores, chrome sores, cold sores, pressure sores, etc. Examples of ulcers include, but are not limited to, peptic ulcer, duodenal ulcer, gastric ulcer, gouty ulcer, diabetic ulcer, hypertensive ischemic ulcer, stasis ulcer, ulcus cruris (venous ulcer), sublingual ulcer, submucous ulcer, symptomatic ulcer, trophic ulcer, tropical ulcer, veneral ulcer, e.g., caused by gonorrhoea (including urethritis, endocervicitis and proctitis). Conditions related to wounds or sores which may be successfully treated according to the invention include, but are not limited to, burns, anthrax, tetanus, gas gangrene, scalatina, erysipelas, sycosis barbae, folliculitis, impetigo contagiosa, impetigo bullosa, etc. It is understood, that there may be an overlap between the use of the terms "wound" and "ulcer," or "wound" and "sore" and, furthermore, the terms are often used at random.

The kinds of wounds to be treated according to the invention include also: i) general wounds such as, e.g., surgical, traumatic, infectious, ischemic, thermal, chemical and bullous wounds; ii) wounds specific for the oral cavity such as, e.g., post-extraction wounds, endodontic wounds especially in connection with treatment of cysts and abscesses, ulcers and lesions of bacterial, viral or autoimmunological origin, mechanical, chemical, thermal, infectious and lichenoid wounds; herpes ulcers, stomatitis aphthosa, acute necrotising ulcerative gingivitis and burning mouth syndrome are specific examples; and iii) wounds on the skin such as, e.g., neoplasm, burns (e.g. chemical, thermal), lesions (bacterial, viral, autoimmunological), bites and surgical incisions. Another way of classifying wounds is by tissue loss, where: i) small tissue loss (due to surgical incisions, minor abrasions, and minor bites) or ii) significant tissue loss. The latter group includes ischemic ulcers, pressure sores, fistulae, lacerations, severe bites, thermal burns and donor site wounds (in soft and hard tissues) and infarctions. Other wounds include ischemic ulcers, pressure sores, fistulae, severe bites, thermal burns, or donor site wounds.

Ischemic ulcers and pressure sores are wounds, which normally only heal very slowly and especially in such cases an improved and more rapid healing is of great importance to the patient. Furthermore, the costs involved in the treatment of patients suffering from such wounds are markedly reduced when the healing is improved and takes place more rapidly.

Donor site wounds are wounds which e.g. occur in connection with removal of hard tissue from one part of the body to another part of the body e.g. in connection with transplantation. The wounds resulting from such operations are very painful and an improved healing is therefore most valuable.

In one case, the wound to be treated is selected from the group consisting of aseptic wounds, infarctions, contused wounds, incised wounds, lacerated wounds, non-penetrating wounds, open wounds, penetrating wounds, perforating wounds, puncture wounds, septic wounds, and subcutaneous wounds.

The invention encompasses methods of treating a subject suffering from a wound comprising administering to the subject a therapeutically effective amount of a compound of formulas I-XXXIII, pharmaceutically acceptable salt thereof, or a pharmaceutical composition thereof.

The invention encompasses methods of treating a subject suffering from a burn comprising administering to the subject a therapeutically effective amount of a compound of formulas I-XXXIII, pharmaceutically acceptable salt thereof, or a pharmaceutical composition thereof.

The term "skin" is used in a very broad sense embracing the epidermal layer of the skin and in those cases where the skin surface is more or less injured also the dermal layer of the skin. Apart from the stratum corneum, the epidermal layer of the skin is the outer (epithelial) layer and the deeper connective tissue layer of the skin is called the dermis.

Since the skin is the most exposed part of the body, it is particularly susceptible to various kinds of injuries such as, e.g., ruptures, cuts, abrasions, burns and frostbites or injuries arising from various diseases. Furthermore, much skin is often destroyed in accidents. However, due to the important barrier and physiologic function of the skin, the integrity of the skin is important to the well-being of the individual, and any breach or rupture represents a threat that must be met by the body in order to protect its continued existence.

Apart from injuries on the skin, injuries may also be present in all kinds of tissues (i.e. soft and hard tissues). Injuries on soft tissues including mucosal membranes and/or skin are especially relevant in connection with the present invention.

Healing of a wound on the skin or on a mucosal membrane undergoes a series of stages that results either in repair or regeneration of the skin or mucosal membrane. In recent years, regeneration and repair have been distinguished as the two types of healing that may occur. Regeneration may be defined as a biological process whereby the architecture and function of lost tissue are completely renewed. Repair, on the other hand, is a biological process whereby continuity of disrupted tissue is restored by new tissues which do not replicate the structure and function of the lost ones.

The majority of wounds heal through repair, meaning that the new tissue formed is structurally and chemically unlike the original tissue (scar tissue). In the early stage of the tissue repair, one process which is almost always involved is the formation of a transient connective tissue in the area of tissue injury. This process starts by formation of a new extracellular collagen matrix by fibroblasts. This new extracellular collagen matrix is then the support for a connective tissue during the final healing process. The final healing is, in most tissues, a scar formation containing connective tissue. In tissues which have regenerative properties, such as, e.g., skin and bone, the final healing includes regeneration of the original tissue. This regenerated tissue has frequently also some scar characteristics, e.g. a thickening of a healed bone fracture.

Under normal circumstances, the body provides mechanisms for healing injured skin or mucosa in order to restore the integrity of the skin barrier or the mucosa. The repair process for even minor ruptures or wounds may take a period of time extending from hours and days to weeks. However, in ulceration, the healing can be very slow and the wound may persist for an extended period of time, i.e. months or even years.

Burns are associated with reduced testosterone levels, and hypogonadism is associated with delayed wound healing. The invention encompasses methods for treating a subject suffering from a wound or a burn by administering at least one SARD compound according to this invention. The SARD may promote resolving of the burn or wound, participates in the healing process of a burn or a wound, or, treats a secondary complication of a burn or a wound.

The treatment of burns or wounds may further use at least one growth factor such as epidermal growth factor (EGF), transforming growth factor-α (TGF-α), platelet derived growth factor (PDGF), fibroblast growth factors (FGFs) including acidic fibroblast growth factor (α-FGF) and basic fibroblast growth factor (β-FGF), transforming growth factor-β (TGF-β) and insulin like growth factors (IGF-1 and IGF-2), or any combination thereof, which promote wound healing.

Wound healing may be measured by many procedures known in the art, including, but not limited to, wound tensile strength, hydroxyproline or collagen content, procollagen expression, or re-epithelialization. As an example, a SARD as described herein may be administered orally or topically at a dosage of about 0.1-100 mg per day. Therapeutic effectiveness is measured as effectiveness in enhancing wound healing as compared to the absence of the SARD compound. Enhanced wound healing may be measured by known techniques such as decrease in healing time, increase in collagen density, increase in hydroxyproline, reduction in complications, increase in tensile strength, and increased cellularity of scar tissue.

The term "reducing the pathogenesis" is to be understood to encompass reducing tissue damage, or organ damage associated with a particular disease, disorder or condition. The term may include reducing the incidence or severity of an associated disease, disorder or condition, with that in question or reducing the number of associated diseases, disorders or conditions with the indicated, or symptoms associated thereto.

Pharmaceutical Compositions

The compounds of the invention may be used in pharmaceutical compositions. As used herein, "pharmaceutical composition" means either the compound or pharmaceutically acceptable salt of the active ingredient with a pharmaceutically acceptable carrier or diluent. A "therapeutically effective amount" as used herein refers to that amount which provides a therapeutic effect for a given indication and administration regimen.

As used herein, the term "administering" refers to bringing a subject in contact with a compound of the present invention. As used herein, administration can be accomplished in vitro, i.e. in a test tube, or in vivo, i.e. in cells or tissues of living organisms, for example humans. The subjects may be a male or female subject or both.

Numerous standard references are available that describe procedures for preparing various compositions or formulations suitable for administration of the compounds of the invention. Examples of methods of making formulations and preparations can be found in the Handbook of Pharmaceutical Excipients, American Pharmaceutical Association (current edition); Pharmaceutical Dosage Forms: Tablets (Lieberman, Lachman and Schwartz, editors) current edition, published by Marcel Dekker, Inc., as well as Remington's Pharmaceutical Sciences (Arthur Osol, editor), 1553-1593 (current edition).

The mode of administration and dosage form are closely related to the therapeutic amounts of the compounds or compositions which are desirable and efficacious for the given treatment application.

The pharmaceutical compositions of the invention can be administered to a subject by any method known to a person skilled in the art. These methods include, but are not limited to, orally, parenterally, intravascularly, paracancerally, transmucosally, transdermally, intramuscularly, intranasally, intravenously, intradermally, subcutaneously, sublingually, intraperitoneally, intraventricularly, intracranially, intravaginally, by inhalation, rectally, or intratumorally. These methods include any means in which the composition can be delivered to tissue (e.g., needle or catheter). Alternatively, a topical administration may be desired for application to dermal, ocular, or mucosal surfaces. Another method of administration is via aspiration or aerosol formulation. The pharmaceutical compositions may be administered topically to body surfaces, and are thus formulated in a form suitable for topical administration. Suitable topical formulations include gels, ointments, creams, lotions, drops and the like. For topical administrations, the compositions are prepared and applied as solutions, suspensions, or emulsions in a physiologically acceptable diluent with or without a pharmaceutical carrier.

Suitable dosage forms include, but are not limited to, oral, rectal, sub-lingual, mucosal, nasal, ophthalmic, subcutaneous, intramuscular, intravenous, transdermal, spinal, intrathecal, intra-articular, intra-arterial, sub-arachinoid, bronchial, lymphatic, and intra-uterile administration, and other dosage forms for systemic delivery of active ingredients. Depending on the indication, formulations suitable for oral or topical administration are preferred.

Topical Administration: The compounds of formulas I-XXXIII may be administered topically. As used herein, "topical administration" refers to application of the compounds of formulas I-XXXIII (and optional carrier) directly to the skin and/or hair. The topical composition can be in the form of solutions, lotions, salves, creams, ointments, liposomes, sprays, gels, foams, roller sticks, and any other formulation routinely used in dermatology.

Topical administration is used for indications found on the skin, such as hirsutism, alopecia, acne, and excess sebum. The dose will vary, but as a general guideline, the compound will be present in a dermatologically acceptable carrier in an amount of from about 0.01 to 50 w/w %, and more typically from about 0.1 to 10 w/w %. Typically, the dermatological preparation will be applied to the affected area from 1 to 4 times daily. "Dermatologically acceptable" refers to a carrier which may be applied to the skin or hair, and which will allow the drug to diffuse to the site of action. More specifically "site of action", it refers to a site where inhibition of androgen receptor or degradation of the androgen receptor is desired.

The compounds of formulas I-XXXIII, may be used topically to relieve alopecia, especially androgenic alopecia. Androgens have a profound effect on both hair growth and hair loss. In most body sites, such as the beard and pubic skin, androgens stimulate hair growth by prolonging the growth phase of the hair cycle (anagen) and increasing follicle size. Hair growth on the scalp does not require androgens but, paradoxically, androgens are necessary for the balding on the scalp in genetically predisposed individuals (androgenic alopecia) where there is a progressive decline in the duration of anagen and in hair follicle size. Androgenic alopecia is also common in women where it usually presents as a diffuse hair loss rather than showing the patterning seen in men.

While the compounds of formulas I-XXXIII will most typically be used to alleviate androgenic alopecia, the compounds may be used to alleviate any type of alopecia. Examples of non-androgenic alopecia include, but are not limited to, alopecia areata, alopecia due to radiotherapy or chemotherapy, scarring alopecia, or stress related alopecia.

The compounds of formulas I-XXXIII can be applied topically to the scalp and hair to prevent, or treat balding. Further, the compound of formulas I-XXXIII can be applied topically in order to induce or promote the growth or regrowth of hair on the scalp.

The invention also encompasses topically administering a compound of formula I-XXXIII to treat or prevent the growth of hair in areas where such hair growth in not desired. One such use will be to alleviate hirsutism. Hirsutism is excessive hair growth in areas that typically do not have hair (e.g., a female face). Such inappropriate hair growth occurs most commonly in women and is frequently seen at menopause. The topical administration of the compounds of formulas I-XXXIII will alleviate this condition leading to a reduction, or elimination of this inappropriate, or undesired, hair growth.

The compounds of formulas I-XXXIII may also be used topically to decrease sebum production. Sebum is composed of triglycerides, wax esters, fatty acids, sterol esters and squalene. Sebum is produced in the acinar cells of the sebaceous glands and accumulates as these cells age. At maturation, the acinar cells lyse, releasing sebum into the luminal duct so that it may be deposited on the surface of the skin.

In some individuals, an excessive quantity of sebum is secreted onto the skin. This can have a number of adverse consequences. It can exacerbate acne, since sebum is the primary food source for *Propionibacterium acnes*, the causative agent of acne. It can cause the skin to have a greasy appearance, typically considered cosmetically unappealing.

Formation of sebum is regulated by growth factors and a variety of hormones including androgens. The cellular and molecular mechanism by which androgens exert their influence on the sebaceous gland has not been fully elucidated. However, clinical experience documents the impact androgens have on sebum production. Sebum production is significantly increased during puberty, when androgen levels are their highest. The compounds of formulas I-XXXIII inhibit the secretion of sebum and thus reduce the amount of sebum on the surface of the skin. The compounds of formulas I-XXXIII can be used to treat a variety of dermal diseases such as acne or seborrheic dermatitis.

In addition to treating diseases associated with excess sebum production, the compounds of formulas I-XXXIII can also be used to achieve a cosmetic effect. Some consumers believe that they are afflicted with overactive sebaceous glands. They feel that their skin is oily and thus unattractive. These individuals may use the compounds of formulas I-XXXIII to decrease the amount of sebum on their skin. Decreasing the secretion of sebum will alleviate oily skin in individuals afflicted with such conditions.

To treat these topical indications, the invention encompasses cosmetic or pharmaceutical compositions (such as dermatological compositions), comprising at least one of the compounds of formulas I-XXXIII Such dermatological compositions will contain from 0.001% to 10% w/w % of the compound(s) in admixture with a dermatologically acceptable carrier, and more typically, from 0.1 to 5 w/w % of the compounds. Such compositions will typically be applied from 1 to 4 times daily. The reader's attention is directed to Remington's Pharmaceutical Science, Edition 17, Mark Publishing Co., Easton, Pa. for a discussion of how to prepare such formulations.

The compositions of the invention may also include solid preparations such as cleansing soaps or bars. These compositions are prepared according to methods known in the art.

Formulations such as aqueous, alcoholic, or aqueous-alcoholic solutions, or creams, gels, emulsions or mousses, or aerosol compositions with a propellant may be used to treat indications that arise where hair is present. Thus, the composition can also be a hair care composition. Such hair care compositions include, but are not limited to, shampoo, a hair-setting lotion, a treating lotion, a styling cream or gel, a dye composition, or a lotion or gel for preventing hair loss. The amounts of the various constituents in the dermatological compositions are those conventionally used in the fields considered.

Medicinal and cosmetic agents containing the compounds of formulas I-XXXIII will typically be packaged for retail distribution (i.e., an article of manufacture). Such articles will be labeled and packaged in a manner to instruct the patient how to use the product. Such instructions will include the condition to be treated, duration of treatment, dosing schedule, etc.

Antiandrogens, such as finasteride or flutamide, have been shown to decrease androgen levels or block androgen action in the skin to some extent but suffer from undesirable systemic effects. An alternative approach is to topically apply a selective androgen receptor degrader (SARD) compound to the affected areas. Such SARD compound would exhibit potent but local inhibition of AR activity, and local degradation of the AR, would not penetrate to the systemic circulation of the subject, or would be rapidly metabolized upon entry into the blood, limiting systemic exposure.

To prepare such pharmaceutical dosage forms, the active ingredient may be mixed with a pharmaceutical carrier according to conventional pharmaceutical compounding techniques. The carrier may take a wide variety of forms depending on the form of preparation desired for administration.

As used herein "pharmaceutically acceptable carriers or diluents" are well known to those skilled in the art. The carrier or diluent may be a solid carrier or diluent for solid formulations, a liquid carrier or diluent for liquid formulations, or mixtures thereof.

Solid carriers/diluents include, but are not limited to, a gum, a starch (e.g. corn starch, pregelatinized starch), a sugar (e.g., lactose, mannitol, sucrose, dextrose), a cellulosic material (e.g. microcrystalline cellulose), an acrylate (e.g. polymethylacrylate), calcium carbonate, magnesium oxide, talc, or mixtures thereof.

Oral and Parenteral Administration: In preparing the compositions in oral dosage form, any of the usual pharmaceutical media may be employed. Thus, for liquid oral preparations, such as, suspensions, elixirs, and solutions, suitable carriers and additives include water, glycols, oils, alcohols, flavoring agents, preservatives, coloring agents, and the like. For solid oral preparations such as, powders, capsules, and tablets, suitable carriers and additives include starches, sugars, diluents, granulating agents, lubricants, binders, disintegrating agents, and the like. Due to their ease in administration, tablets and capsules represent the most advantageous oral dosage unit form. If desired, tablets may be sugar coated or enteric coated by standard techniques.

For parenteral formulations, the carrier will usually comprise sterile water, though other ingredients may be included, such as ingredients that aid solubility or for preservation. Injectable solutions may also be prepared in which case appropriate stabilizing agents may be employed.

In some applications, it may be advantageous to utilize the active agent in a "vectorized" form, such as by encapsulation of the active agent in a liposome or other encapsulant medium, or by fixation of the active agent, e.g., by covalent bonding, chelation, or associative coordination, on a suitable biomolecule, such as those selected from proteins, lipoproteins, glycoproteins, and polysaccharides.

Methods of treatment using formulations suitable for oral administration may be presented as discrete units such as capsules, cachets, tablets, or lozenges, each containing a predetermined amount of the active ingredient. Optionally, a suspension in an aqueous liquor or a non-aqueous liquid may be employed, such as a syrup, an elixir, an emulsion, or a draught.

A tablet may be made by compression or molding, or wet granulation, optionally with one or more accessory ingredients. Compressed tablets may be prepared by compressing in a suitable machine, with the active compound being in a free-flowing form such as a powder or granules which optionally is mixed with, for example, a binder, disintegrant, lubricant, inert diluent, surface active agent, or discharging agent. Molded tablets comprised of a mixture of the powdered active compound with a suitable carrier may be made by molding in a suitable machine.

A syrup may be made by adding the active compound to a concentrated aqueous solution of a sugar, for example sucrose, to which may also be added any accessory ingredient(s). Such accessory ingredient(s) may include flavorings, suitable preservative, agents to retard crystallization of the sugar, and agents to increase the solubility of any other ingredient, such as a polyhydroxy alcohol, for example glycerol or sorbitol.

Formulations suitable for parenteral administration may comprise a sterile aqueous preparation of the active compound, which preferably is isotonic with the blood of the recipient (e.g., physiological saline solution). Such formulations may include suspending agents and thickening agents and liposomes or other microparticulate systems which are designed to target the compound to blood components or one or more organs. The formulations may be presented in unit-dose or multi-dose form.

Parenteral administration may comprise any suitable form of systemic delivery. Administration may for example be intravenous, intra-arterial, intrathecal, intramuscular, subcutaneous, intramuscular, intra-abdominal (e.g., intraperitoneal), etc., and may be effected by infusion pumps (external or implantable) or any other suitable means appropriate to the desired administration modality.

Nasal and other mucosal spray formulations (e.g. inhalable forms) can comprise purified aqueous solutions of the active compounds with preservative agents and isotonic agents. Such formulations are preferably adjusted to a pH and isotonic state compatible with the nasal or other mucous membranes. Alternatively, they can be in the form of finely divided solid powders suspended in a gas carrier. Such formulations may be delivered by any suitable means or method, e.g., by nebulizer, atomizer, metered dose inhaler, or the like.

Formulations for rectal administration may be presented as a suppository with a suitable carrier such as cocoa butter, hydrogenated fats, or hydrogenated fatty carboxylic acids.

Transdermal formulations may be prepared by incorporating the active agent in a thixotropic or gelatinous carrier such as a cellulosic medium, e.g., methyl cellulose or hydroxyethyl cellulose, with the resulting formulation then being packed in a transdermal device adapted to be secured in dermal contact with the skin of a wearer.

In addition to the aforementioned ingredients, formulations of this invention may further include one or more ingredient selected from diluents, buffers, flavoring agents, binders, disintegrants, surface active agents, thickeners, lubricants, preservatives (including antioxidants), and the like.

The formulations may be of immediate release, sustained release, delayed-onset release or any other release profile known to one skilled in the art.

For administration to mammals, and particularly humans, it is expected that the physician will determine the actual dosage and duration of treatment, which will be most suitable for an individual and can vary with the age, weight, genetics and/or response of the particular individual.

The methods of the invention comprise administration of a compound at a therapeutically effective amount. The therapeutically effective amount may include various dosages.

In one embodiment, a compound of this invention is administered at a dosage of 1-3000 mg per day. In additional embodiments, a compound of this invention is administered at a dose of 1-10 mg per day, 3-26 mg per day, 3-60 mg per day, 3-16 mg per day, 3-30 mg per day, 10-26 mg per day, 15-60 mg, 50-100 mg per day, 50-200 mg per day, 100-250 mg per day, 125-300 mg per day, 20-50 mg per day, 5-50 mg per day, 200-500 mg per day, 125-500 mg per day, 500-1000 mg per day, 200-1000 mg per day, 1000-2000 mg per day, 1000-3000 mg per day, 125-3000 mg per day, 2000-3000 mg per day, 300-1500 mg per day or 100-1000 mg per day. In one embodiment, a compound of this invention is administered at a dosage of 25 mg per day. In one embodiment, a compound of this invention is administered at a dosage of 40 mg per day. In one embodiment, a compound of this invention is administered at a dosage of 50 mg per day. In one embodiment, a compound of this invention is administered at a dosage of 67.5 mg per day. In one embodiment, a compound of this invention is administered at a dosage of 75 mg per day. In one embodiment, a compound of this invention is administered at a dosage of 80 mg per day. In one embodiment, a compound of this invention is administered at a dosage of 100 mg per day. In one embodiment, a compound of this invention is administered at a dosage of 125 mg per day. In one embodiment, a compound of this invention is administered at a dosage of 250 mg per day. In one embodiment, a compound of this invention is administered at a dosage of 300 mg per day. In one embodiment, a compound of this invention is administered at a dosage of 500 mg per day. In one embodiment, a compound of this invention is administered at a dosage of 600 mg per day. In one embodiment, a compound of this invention is administered at a dosage of 1000 mg per day. In one embodiment, a compound of this invention is administered at a dosage of 1500 mg per day. In one embodiment, a compound of this invention is administered at a dosage of 2000 mg per day. In one embodiment, a compound of this invention is administered at a dosage of 2500 mg per day. In one embodiment, a compound of this invention is administered at a dosage of 3000 mg per day.

The methods may comprise administering a compound at various dosages. For example, the compound may be administered at a dosage of 3 mg, 10 mg, 30 mg, 40 mg, 50 mg, 80 mg, 100 mg, 120 mg, 125 mg, 200 mg, 250 mg, 300 mg, 450 mg, 500 mg, 600 mg, 900 mg, 1000 mg, 1500 mg, 2000 mg, 2500 mg or 3000 mg.

Alternatively, the compound may be administered at a dosage of 0.1 mg/kg/day. The compound may administered at a dosage between 0.2 to 30 mg/kg/day, or 0.2 mg/kg/day, 0.3 mg/kg/day, 1 mg/kg/day, 3 mg/kg/day, 5 mg/kg/day, 10 mg/kg/day, 20 mg/kg/day, 30 mg/kg/day, 50 mg/kg/day or 100 mg/kg/day.

The pharmaceutical composition may be a solid dosage form, a solution, or a transdermal patch. Solid dosage forms include, but are not limited to, tablets and capsules.

The following examples are presented in order to more fully illustrate the preferred embodiments of the invention. They should in no way, however, be construed as limiting the broad scope of the invention.

EXAMPLES

Example 1

Synthesis of SARDs

Synthesis of Intermediates 9-10

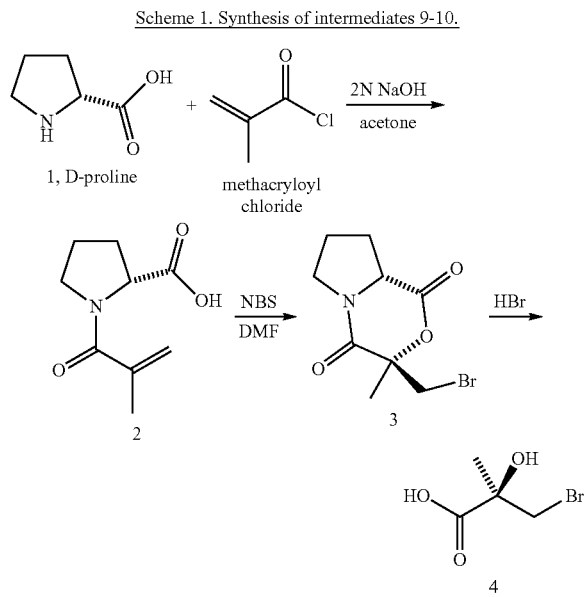

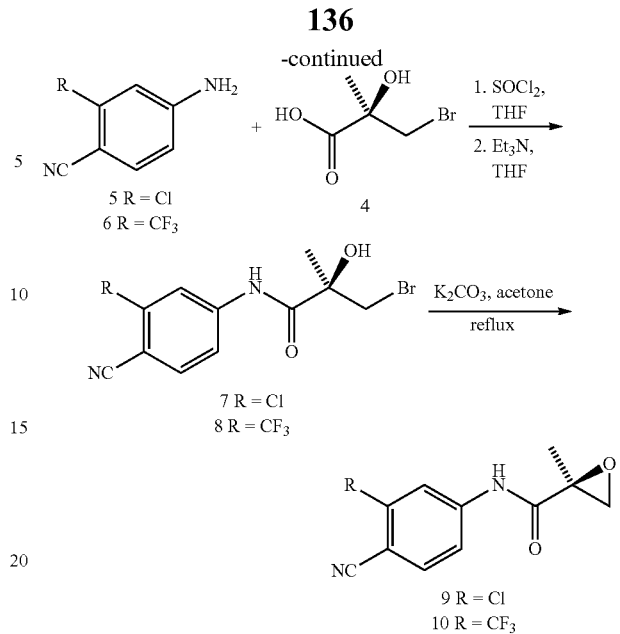

(2R)-1-Methacryloylpyrrolidin-2-carboxylic acid (2)

D-Proline (1, 14.93 g, 0.13 mol) was dissolved in 71 mL of 2 N NaOH and cooled in an ice bath. The resulting alkaline solution was diluted with acetone (71 mL). An acetone solution (71 mL) of methacryloyl chloride (13.56 g, 0.13 mol) and 2 N NaOH solution (71 mL) were simultaneously added over 40 min to the aqueous solution of D-proline in an ice bath. The temperature of the mixture was kept at 10-11° C. during the addition of the methacryloyl chloride. After stirring (3 hours (h), room temperature (RT)), the mixture was evaporated in vacuo at a temperature of 35-45° C. to remove acetone. The resulting solution was washed with ethyl ether and was acidified to pH 2 with concentrated HCl. The acidic mixture was saturated with NaCl and was extracted with EtOAc (100 mL×3). The combined extracts were dried over $Na_2SO_4$, filtered through Celite®, and evaporated in vacuo to give the crude product as a colorless oil. Recrystallization of the oil from ethyl ether and hexanes afforded 16.2 g (68%) of the desired compound as colorless crystals: mp 102.1-103.4° C. (lit. mp 102.5-103.5° C.); the NMR spectrum of this compound demonstrated the existence of two rotamers of the title compound.
$^1$H NMR (300 MHz, DMSO-$d_6$) δ 5.28 (s) and 5.15 (s) for the first rotamer, 5.15 (s) and 5.03 (s) for the second rotamer (totally 2H for both rotamers, vinyl $CH_2$), 4.48-4.44 for the first rotamer, 4.24-4.20 (m) for the second rotamer (totally 1H for both rotamers, CH at the chiral center), 3.57-3.38 (m, 2H, $CH_2$), 2.27-2.12 (1H, CH), 1.97-1.72 (m, 6H, $CH_2$, CH, Me); $^{13}$C NMR (75 MHz, DMSO-$d_6$) δ for major rotamer 173.3, 169.1, 140.9, 116.4, 58.3, 48.7, 28.9, 24.7, 19.5: for minor rotamer 174.0, 170.0, 141.6, 115.2, 60.3, 45.9, 31.0, 22.3, 19.7; IR (KBr) 3437 (OH), 1737 (=O), 1647 (CO, COOH), 1584, 1508, 1459, 1369, 1348, 1178 $cm^{-1}$; $[α]_D^{26}$+ 80.8° (c=1, MeOH); Anal. Calcd. for $C_9H_{13}NO_3$: C, 59.00, H, 7.15, N, 7.65. Found: C, 59.13, H, 7.19, N, 7.61.

(3R,8aR)-3-Bromomethyl-3-methyl-tetrahydro-pyrrolo[2,1-c][1,4]oxazine-1,4-dione (3)

A solution of NBS (23.5 g, 0.132 mol) in 100 mL of DMF was added dropwise to a stirred solution of the (methylacryloyl)-pyrrolidine (16.1 g, 88 mmol) in 70 mL of DMF under argon at RT, and the resulting mixture was stirred 3 days. The solvent was removed in vacuo, and a yellow solid was precipitated. The solid was suspended in water, stirred overnight at RT, filtered, and dried to give 18.6 g (81%) (smaller weight when dried ~34%) of the titled compound as a yellow solid: mp 158.1-160.3° C.;

$^1$H NMR (300 MHz, DMSO-d$_6$) δ 4.69 (dd, J=9.6 Hz, J=6.7 Hz, 1H, CH at the chiral center), 4.02 (d, J=11.4 Hz, 1H, CHH$_a$), 3.86 (d, J=11.4 Hz, 1H, CHH$_b$), 3.53-3.24 (m, 4H, CH$_2$), 2.30-2.20 (m, 1H, CH), 2.04-1.72 (m, 3H, CH$_2$ and CH), 1.56 (s, 2H, Me); $^{13}$C NMR (75 MHz, DMSO-d$_6$) δ 167.3, 163.1, 83.9, 57.2, 45.4, 37.8, 29.0, 22.9, 21.6; IR (KBr) 3474, 1745 (=O), 1687 (=O), 1448, 1377, 1360, 1308, 1227, 1159, 1062 cm$^{-1}$; [α]$_D^{26}$+124.5° (c=1.3, chloroform); Anal. Calcd. for C$_9$H$_{12}$BrNO$_3$: C, 41.24, H, 4.61, N, 5.34. Found: C, 41.46, H, 4.64, N, 5.32.

(2R)-3-Bromo-2-hydroxy-2-methylpropanoic acid (4)

A mixture of bromolactone (18.5 g, 71 mmol) in 300 mL of 24% HBr was heated at reflux for 1 h. The resulting solution was diluted with brine (200 mL), and was extracted with ethyl acetate (100 mL×4). The combined extracts were washed with saturated NaHCO$_3$ (100 mL×4). The aqueous solution was acidified with concentrated HCl to pH=1, which, in turn, was extracted with ethyl acetate (100 mL×4). The combined organic solution was dried over Na$_2$SO$_4$, filtered through Celite®, and evaporated in vacuo to dryness. Recrystallization from toluene afforded 10.2 g (86%) of the desired compound as colorless crystals: mp 110.3-113.8° C.;

$^1$H NMR (300 MHz, DMSO-d$_6$) δ 3.63 (d, J=10.1 Hz, 1H, CHH$_a$), 3.52 (d, J=10.1 Hz, 1H, CHH$_b$), 1.35 (s, 3H, Me); IR (KBr) 3434 (OH), 3300-2500 (COOH), 1730 (C=O), 1449, 1421, 1380, 1292, 1193, 1085 cm$^{-1}$; [α]$_D^{26}$+10.5° (c=2.6, MeOH); Anal. Calcd. for C$_4$H$_7$BrO$_3$: C, 26.25, H, 3.86. Found: C, 26.28, H, 3.75.

(2R)-3-Bromo-N-[4-cyano-3-(trifluoromethyl)phenyl]-2-hydroxy-2-methylpropanamide (8)

Thionyl chloride (46.02 g, 0.39 mol) was added dropwise to a cooled solution (less than 4° C.) of (R)-3-bromo-2-hydroxy-2-methylpropanoic acid (4, 51.13 g, 0.28 mol) in 300 mL of THF under an argon atmosphere. The resulting mixture was stirred for 3 h under the same condition. To this was added Et$_3$N (39.14 g, 0.39 mol) and stirred for 20 min under the same condition. After 20 min, 5-amino-2-cyanobenzotrifluoride (6, 40.0 g, 0.21 mol), 400 mL of THF were added and then the mixture was allowed to stir overnight at RT. The solvent was removed under reduced pressure to give a solid which was treated with 300 mL of H$_2$O, and extracted with EtOAc (2×400 mL). The combined organic extracts were washed with saturated NaHCO$_3$ solution (2×300 mL) and brine (300 mL). The organic layer was dried over MgSO$_4$ and concentrated under reduced pressure to give a solid which was purified from column chromatography using CH$_2$Cl$_2$/EtOAc (80:20) to give a solid. This solid was recrystallized from CH$_2$Cl$_2$/hexane to give 55.8 g (73.9%) of (2R)-3-bromo-N-[4-cyano-3-(trifluoromethyl)phenyl]-2-hydroxy-2-methylpropanamide as a light-yellow solid.

$^1$H NMR (CDCl$_3$/TMS) δ 1.66 (s, 3H, CH$_3$), 3.11 (s, 1H, OH), 3.63 (d, J=10.8 Hz, 1H, CH$_2$), 4.05 (d, J=10.8 Hz, 1H, CH$_2$), 7.85 (d, J=8.4 Hz, 1H, ArH), 7.99 (dd, J=2.1, 8.4 Hz, 1H, ArH), 8.12 (d, J=2.1 Hz, 1H, ArH), 9.04 (bs, 1H, NH). MS (ESI) 349.0 [M−H]$^−$; mp 124-126° C.

(2R)-3-Bromo-N-(4-cyano-3-chlorophenyl)-2-hydroxy-2-methylpropanamide (7)

Under an argon atmosphere, thionyl chloride (15 mL, 0.20 mol) was added dropwise to a cooled solution (less than 4° C.) of (R)-3-bromo-2-hydroxy-2-methylpropanoic acid (4, 24.3 g, 0.133 mol) in 300 mL of THF at ice-water bath. The resulting mixture stirred for 3 h under the same condition. To this was added Et$_3$N (35 mL, 0.245 mol) and stirred for 20 min under the same condition. After 20 min, a solution of 4-amino-2-chlorobenzonitrile (5, 15.6 g, 0.10 mol) in 100 mL of THF were added and then the mixture was allowed to stir overnight at RT. The solvent removed under reduced pressure to give a solid, which treated with 300 mL of H$_2$O, and extracted with EtOAc (2×150 mL). The combined organic extracts washed with saturated NaHCO$_3$ solution (2×150 mL) and brine (300 mL). The organic layer was dried over MgSO$_4$ and concentrated under reduced pressure to give a solid, which purified by flash column chromatography using CH$_2$Cl$_2$/EtOAc (80:20) to give a solid. This solid was recrystallized from CH$_2$Cl$_2$/hexane to give 31.8 g (73%) of (2R)-3-bromo-N-(4-cyano-3-chlorophenyl)-2-hydroxy-2-methylpropanamide (7) as a light-yellow solid.

$^1$H NMR (CDCl$_3$, 400 MHz) δ 1.7 (s, 3H, CH$_3$), 3.0 (s, 1H, OH), 3.7 (d, 1H, CH), 4.0 (d, 1H, CH), 7.5 (d, 1H, ArH), 7.7 (d, 1H, ArH), 8.0 (s, 1H, ArH), 8.8 (s, 1H, NH). MS: 342 (M+23); mp 129° C.

(S)—N-(3-Chloro-4-cyanophenyl)-2-methyloxirane-2-carboxamide (9)

A mixture of 3-bromo-N-(4-cyano-3-chlorophenyl)-2-hydroxy-2-methylpropanamide (7, 0.84 mmol) and potassium carbonate (1.68 mmol) in 10 mL acetone was heated to reflux for 30 min. After complete conversion of starting bromide 7 to desired epoxide 9 as monitored by TLC, the solvent was evaporated under reduced pressure to give yellowish residue, which was poured into 10 mL of anhydrous EtOAc. The solution was filtered through Celite® pad to remove K$_2$CO$_3$ residue and condensed under reduced pressure to give epoxide 9 as a light yellowish solid.

$^1$H NMR (CDCl$_3$, 400 MHz) δ 8.41 (bs, NH), 8.02 (d, J=2.0 Hz, 1H, ArH), 7.91 (dd, J=2.0, 8.4 Hz, 1H, ArH), 7.79 (d, J=2.0 Hz, 1H, ArH), 3.01 (s, 2H), 1.69 (s, 3H). MS (ESI) m/z 235.0 [M−H]$^−$.

5-Membered Ring Compounds

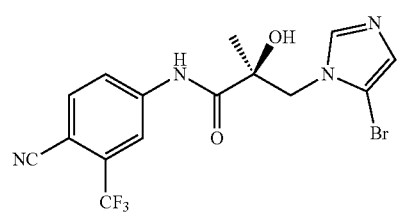

1005

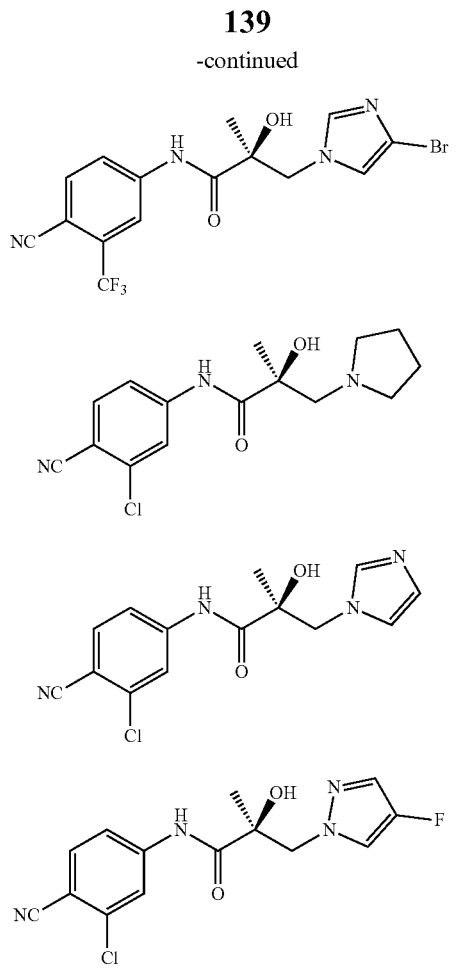

Five membered ring compounds of the invention were made using the following general synthetic routes (Method A and Method B) where m=0. Variables X and Y are defined as necessary to obtain the desired compound.

Method A:

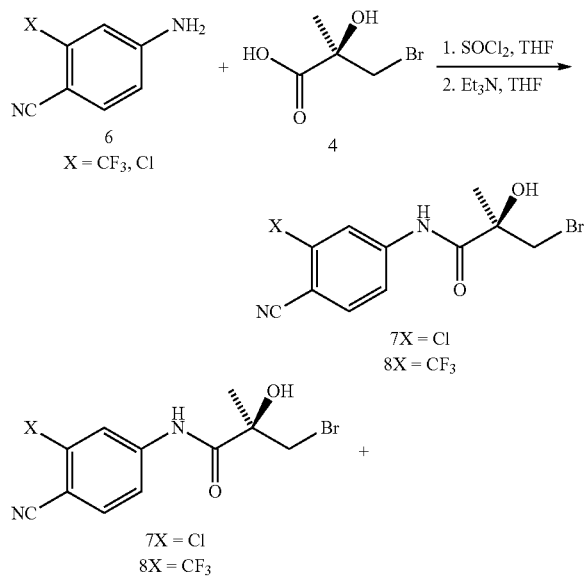

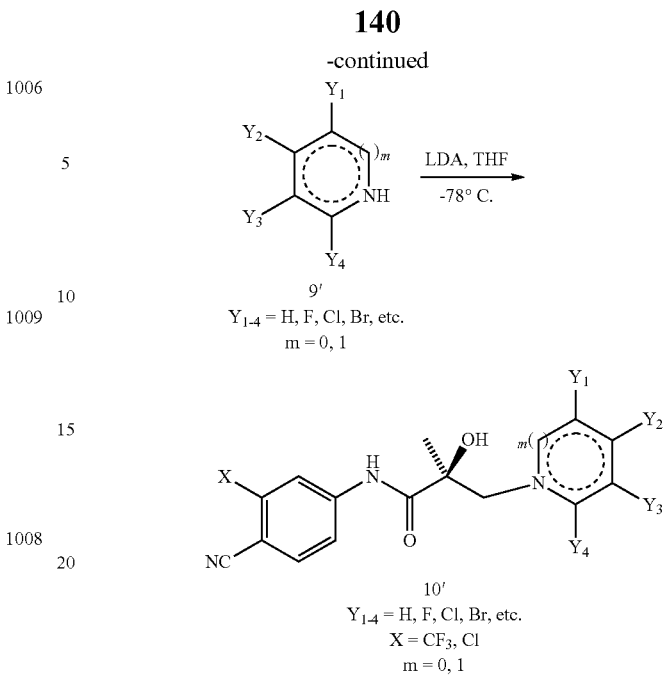

Preparation of lithium diisopropylamide (LDA) solution in THF: To a stirred solution of freshly distilled diisopropylamine (0.14 mL, 1.2 mmol) in anhydrous 5 mL of THF was added a solution of n-butyllithium (0.53 mL, 1.32 mmol, 2.5 M solution in hexane) at −78° C. under argon atmosphere. The prepared solution of LDA or commercial 2.0 M LDA was slowly warmed to 0° C. and stirred for 10 min and cooled again to −78° C. To the LDA solution was added dropwise a solution of 9' (1.0 mmol) in 5 mL of THF for 20 min. Compound 7 or 8 in THF was added dropwise through dropping funnel under argon atmosphere at −78° C. The reaction mixture was stirred at the same temperature for 30 min and quenched by addition of sat. NH$_4$Cl. The solution was concentrated under reduced pressure and dispersed into excess EtOAc and dried over Na$_2$SO$_4$. The solution was concentrated and the resulting solid was recrystallized from EtOAc/hexane or DCM/hexane to give designed compound 10'. The mother liquor was concentrated and purified by flash column chromatography (EtOAc/hexane) to give a second crop of 10'.

Method B:

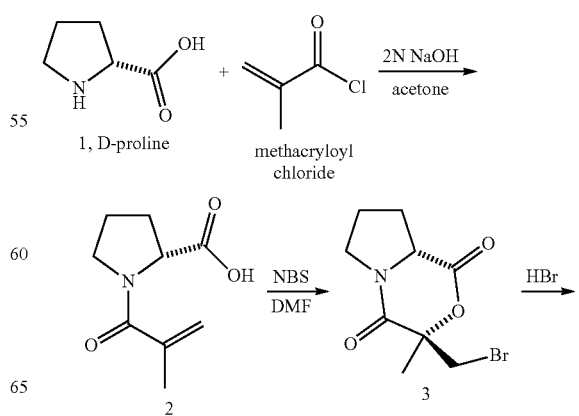

-continued

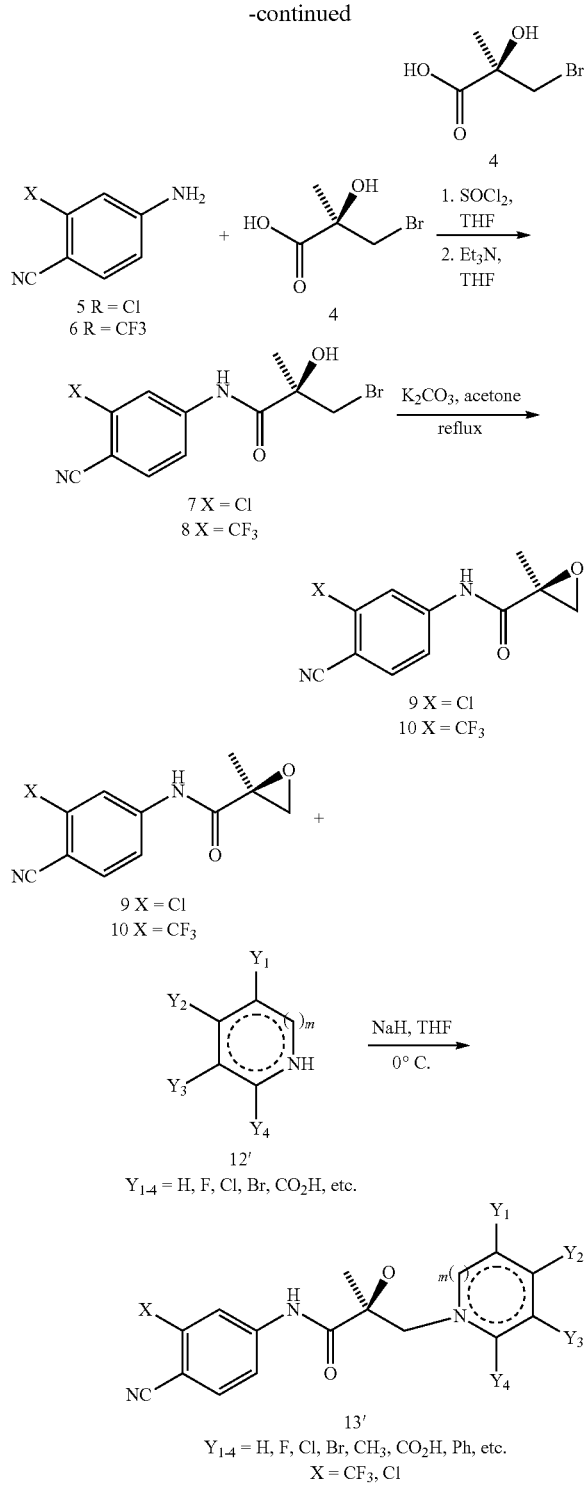

$Y_{1-4}$ = H, F, Cl, Br, CO$_2$H, etc.

$Y_{1-4}$ = H, F, Cl, Br, CH$_3$, CO$_2$H, Ph, etc.
X = CF$_3$, Cl

The steps through the synthesis of the oxiranes 9 and 10 are the same as above for Scheme 1. NaH of 60% dispersion in mineral oil (228 mg, 5.7 mmol) was added in 20 mL of anhydrous THF solvent into a 100 mL dried two necked round bottom flask equipped with a dropping funnel. A compound of general structure 12' (2.84 mmol) was added to the solution under argon atmosphere in ice-water bath, and the resulting solution was stirred for 30 min at the ice-water bath. Into the flask, epoxide 9 or 10 (2.84 mmol in THF) was added through dropping funnel under argon atmosphere at the ice-water bath and stirred overnight at RT. After adding 1 mL of H$_2$O, the reaction mixture was condensed under reduced pressure, and then dispersed into 50 mL of EtOAc, washed with 50 mL (×2) water, brine, dried over anhydrous MgSO$_4$, and evaporated to dryness. The mixture was purified with flash column chromatography with an eluent of EtOAc/hexane, and the condensed compounds were then recrystallized in EtOAc/hexane to give a product of general structure 13'.

The synthetic procedure for 1001 as an example:

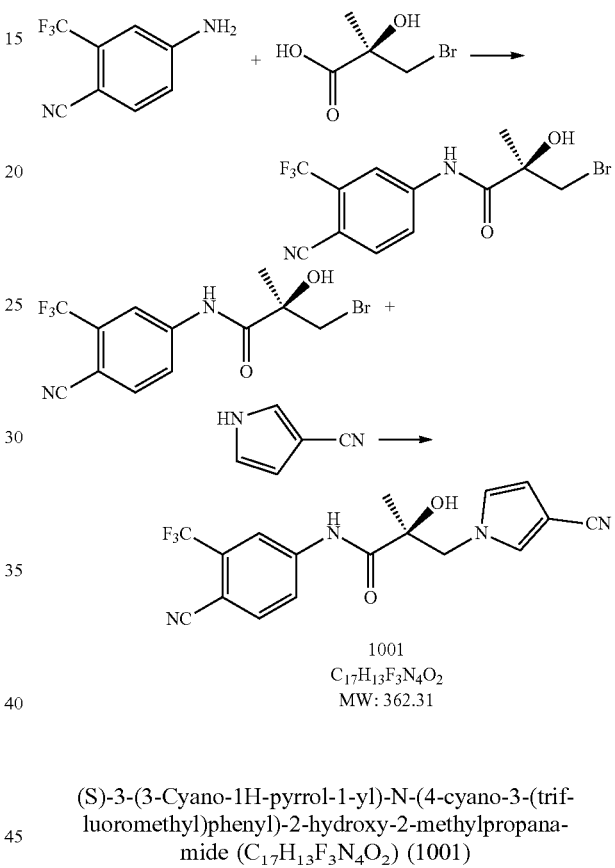

1001
C$_{17}$H$_{13}$F$_3$N$_4$O$_2$
MW: 362.31

(S)-3-(3-Cyano-1H-pyrrol-1-yl)-N-(4-cyano-3-(trifluoromethyl)phenyl)-2-hydroxy-2-methylpropanamide (C$_{17}$H$_{13}$F$_3$N$_4$O$_2$) (1001)

To a solution of 1H-pyrrole-3-carbonitrile (0.10 g, 0.00108 mol) in anhydrous THF (10 mL), which was cooled in an ice water bath under an argon atmosphere, was added sodium hydride (60% dispersion in oil, 0.090 g, 0.00217 mol). After addition, the resulting mixture was stirred for 3 h. (R)-3-Bromo-N-(4-cyano-3-(trifluoromethyl)phenyl)-2-hydroxy-2-methylpropanamide (8, 0.38 g, 0.00108 mol) was added to above solution, and the resulting reaction mixture was allowed to stir overnight at RT under argon. The reaction was quenched by water, and extracted with ethyl acetate. The organic layer was washed with brine, dried with MgSO₄, filtered, and concentrated under vacuum. The product was purified by a silica gel column using ethyl acetate and hexanes (1:1) as eluent to afford 0.26 g of the titled compound as pinkish solid.

Compound 1001 was characterized as follows: ¹H NMR (400 MHz, DMSO-d₆) δ 10.44 (s, 1H, NH), 8.44 (s, 1H, ArH), 8.24 (d, J=8.8 Hz, 1H, ArH), 8.10 (d, J=8.8 Hz, 1H, ArH), 7.49 (s, 1H, Pyrrole-H), 6.38 (t, J=2.0 Hz, 1H, Pyrrole-H), 6.41-6.40 (m, 2H, OH and Pyrrole-H), 4.30 (d, J=14.0 Hz, 1H, CH), 4.14 (d, J=14.0 Hz, 1H, CH), 1.34 (s, 3H, CH₃); (ESI, Positive): 363.1079 [M+H]⁺.

(S)—N-(4-Cyano-3-(trifluoromethyl)phenyl)-3-(4-fluoro-1H-pyrazol-1-yl)-2-hydroxy-2-methylpropanamide (C₁₅H₁₂F₄N₄O₂) (1002)

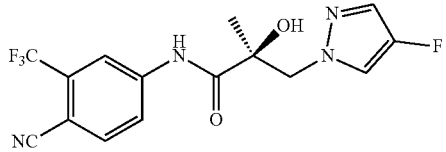 [SMILES: C[C@](O)(Cn1cc(F)cn1)C(=O)Nc1ccc(C#N)c(C(F)(F)F)c1]

To a solution of 4-fluoro-pyrazole (0.10 g, 0.00116 mol) in anhydrous THF (10 mL), which was cooled in an ice water bath under an argon atmosphere, was added sodium hydride (60% dispersion in oil, 0.12 g, 0.00291 mol). After addition, the resulting mixture was stirred for 3 h. (R)-3-Bromo-N-(4-cyano-3-(trifluoromethyl)phenyl)-2-hydroxy-2-methylpropanamide (8) (0.41 g, 0.00116 mol) was added to the above solution, and the resulting reaction mixture was allowed to stir overnight at RT under argon. The reaction was quenched by water, and extracted with ethyl acetate. The organic layer was washed with brine, dried with MgSO₄, filtered, and concentrated under vacuum. The product was purified by a silica gel column using ethyl acetate and hexanes (1:1) as eluent to afford 0.13 g of the titled compound as white solid.

Compound 1002 was characterized as follows: ¹H NMR (400 MHz, DMSO-d₆) δ 10.39 (s, 1H, NH), 8.47 (d, J=1.6 Hz, 1H, ArH), 8.24 (dd, J=8.4 Hz, J=2.0 Hz, 1H, ArH), 8.10 (d, J=8.4 Hz, 1H, ArH), 7.73 (d, J=4.4 Hz, 1H, Pyrazole-H), 7.41 (d, J=4.4 Hz, 1H, Pyrazole-H), 6.31 (s, 1H, OH), 4.38 (d, J=14.0 Hz, 1H, CH), 4.21 (d, J=14.0 Hz, 1H, CH), 1.34 (s, 3H, CH₃); Mass (ESI, Positive): 357.0966 [M+H]⁺; mp 109-111° C.

(S)—N-(4-Cyano-3-(trifluoromethyl)phenyl)-3-(4-fluoro-1H-pyrazol-1-yl)-2-hydroxy-2-methylpropanamide hydrochloride (C₁₅H₁₃ClF₄NO₂) (1002-HCl)

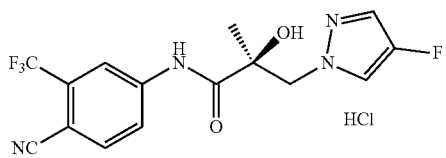 [SMILES: C[C@](O)(Cn1cc(F)cn1)C(=O)Nc1ccc(C#N)c(C(F)(F)F)c1 ; Cl]

To a solution of (S)—N-(4-cyano-3-(trifluoromethyl)phenyl)-3-(4-fluoro-1H-pyrazol-1-yl)-2-hydroxy-2-methylpropanamide (0.100 g, 0.2807 mmol) in 3 mL of methanol was added hydrochloride (2 M HCl in ether, 0.15 mL, 0.2947 mol). After addition, the resulting mixture was stirred for 1-2 h at RT. Solvent was removed under vacuum, and dried to afford 0.11 g (99%) of the titled compound as white foam.

(S)—N-(4-Cyano-3-(trifluoromethyl)phenyl)-3-(4-fluoro-1H-pyrazol-1-yl)-2-hydroxy-2-methylpropanamide oxalate (C₁₇H₁₄F₄N₄O₆) (1002-oxalic acid salt)

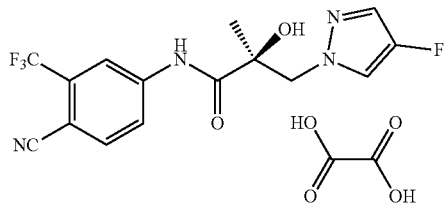

To a solution of (S)—N-(4-cyano-3-(trifluoromethyl)phenyl)-3-(4-fluoro-1H-pyrazol-1-yl)-2-hydroxy-2-methylpropanamide (0.050 g, 0.14034 mmol) in 2 mL of methanol was added oxalic acid (0.0177 g, 0.14034 mol). After addition, the resulting mixture was stirred for 1-2 h at RT. Diethyl ether was added to above solution, and the solid was filtered, and dried under vacuum to afford 0.058 g (92%) of the titled compound as white solid.

Compound 1002-oxalate was characterized as follows: ¹H NMR (400 MHz, DMSO-d₆) δ 14.02 (bs, 2H), 10.38 (s, 1H, NH), 8.46 (s, 1H, ArH), 8.24 (d, J=8.4 Hz, 1H, ArH), 8.10 (d, J=8.4 Hz, 1H, ArH), 7.73 (d, J=4.8 Hz, 1H, Pyrazole-H), 7.41 (d, J=4.0 Hz, 1H, Pyrazole-H), 6.30 (s, 1H, OH), 4.38 (d, J=14.0 Hz, 1H, CH), 4.31 (s, 2H), 4.21 (d, J=14.0 Hz, 1H, CH), 2.42 (s, 4H), 1.34 (s, 3H, CH₃).

(S)—N-(4-Cyano-3-(trifluoromethyl)phenyl)-3-(4-fluoro-1H-pyrazol-1-yl)-2-hydroxy-2-methylpropanamide 2,3-dihydroxysuccinate (C₁₉H₁₈F₄N₄O₈) (1002-tartaric acid salt)

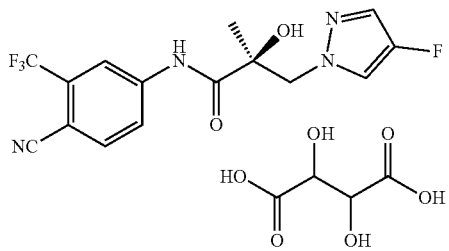

To a solution of (S)—N-(4-cyano-3-(trifluoromethyl)phenyl)-3-(4-fluoro-1H-pyrazol-1-yl)-2-hydroxy-2-methylpropanamide (0.050 g, 0.14034 mmol) in 2 mL of methanol was added L-(+)-tartaric acid (0.021 g, 0.14034 mol). After addition, the resulting mixture was stirred for 1-2 h at RT. Diethyl ether was added to above solution, and the solid was filtered and dried under vacuum to afford 0.067 g (94%) of the titled compound as white solid.

Compound 1002—tartaric acid salt was characterized as follows: ¹H NMR (400 MHz, DMSO-d₆) δ 12.69 (s, 2H), 10.38 (s, 1H, NH), 8.46 (s, 1H, ArH), 8.24 (d, J=8.4 Hz, 1H, ArH), 8.10 (d, J=8.4 Hz, 1H, ArH), 7.73 (d, J=4.4 Hz, 1H, Pyrazole-H), 7.41 (d, J=4.0 Hz, 1H, Pyrazole-H), 6.30 (s, 1H, OH), 5.08 (s, 2H, OH), 4.38 (d, J=14.0 Hz, 1H, CH), 4.31 (s, 2H), 4.21 (d, J=14.0 Hz, 1H, CH), 2.42 (s, 4H), 1.34 (s, 3H, CH₃).

(S)—N-(4-Cyano-3-(trifluoromethyl)phenyl)-3-(4-fluoro-1H-pyrazol-1-yl)-2-hydroxy-2-methylpropanamide hydrobromide ($C_{15}H_{13}BrF_4N_4O_2$) (1002-HBr)

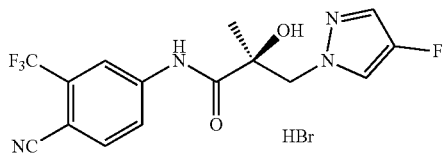

To a solution of (S)—N-(4-cyano-3-(trifluoromethyl)phenyl)-3-(4-fluoro-1H-pyrazol-1-yl)-2-hydroxy-2-methylpropanamide (0.050 g, 0.1403 mmol) in 2 mL of methanol was added hydrobromide (48% w/w aqueous solution, 0.0159 mL, 0.1403 mol). After addition, the resulting mixture was stirred for 1-2 h at RT. Solvent was removed under vacuum, and dried to afford 0.061 g (99%) of the titled compound as yellowish foam.

(S)—N-(4-Cyano-3-(trifluoromethyl)phenyl)-3-(4-fluoro-1H-pyrazol-1-yl)-2-hydroxy-2-methylpropanamide succinate (1002-succinic acid salt) ($C_{19}H_{18}F_4N_4O_6$)

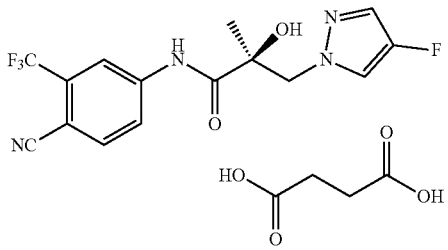

To a solution of (S)—N-(4-cyano-3-(trifluoromethyl)phenyl)-3-(4-fluoro-1H-pyrazol-1-yl)-2-hydroxy-2-methylpropanamide (0.050 g, 0.14034 mmol) in 2 mL of methanol was added succinic acid (0.0166 g, 0.14034 mol). After addition, the resulting mixture was stirred for 1-2 h at RT. Diethyl ether was added to above solution, and the solid was filtered and dried under vacuum to afford 0.063 g (95%) of the titled compound as white solid.

Compound 1002—tartaric acid salt was characterized as follows: ¹H NMR (400 MHz, DMSO-d₆) δ 12.14 (s, 2H), 10.39 (s, 1H, NH), 8.46 (s, 1H, ArH), 8.24 (d, J=8.8 Hz, 1H, ArH), 8.10 (d, J=8.8 Hz, 1H, ArH), 7.73 (d, J=4.4 Hz, 1H, Pyrazole-H), 7.41 (d, J=4.4 Hz, 1H, Pyrazole-H), 6.30 (s, 1H, OH), 4.39 (d, J=14.0 Hz, 1H, CH), 4.21 (d, J=14.0 Hz, 1H, CH), 2.42 (s, 4H), 1.34 (s, 3H, CH₃).

(S)—N-(4-Cyano-3-(trifluoromethyl)phenyl)-2-hydroxy-2-methyl-3-(4-phenyl-1H-pyrazol-1-yl)propanamide ($C_{21}H_{17}F_3N_4O_2$) (1003)

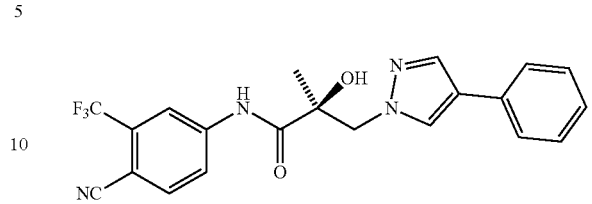

To a solution of 4-phenyl-pyrazole (0.50 g, 0.003468 mol) in anhydrous THF (10 mL), which was cooled in an ice water bath under an argon atmosphere, was added sodium hydride (60% dispersion in oil (0.35 g, 0.00867 mol). After addition, the resulting mixture was stirred for 3 h. (R)-3-Bromo-N-(4-cyano-3-(trifluoromethyl)phenyl)-2-hydroxy-2-methylpropanamide (8, 1.22 g, 0.003468 mol) was added to above solution, and the resulting reaction mixture was allowed to stir overnight at RT under argon. The reaction was quenched by water, and extracted with ethyl acetate. The organic layer was washed with brine, dried with MgSO₄, filtered, and concentrated under vacuum. The product was purified by a silica gel column using ethyl acetate and hexanes (1:2) as eluent to afford 0.90 g of the titled compound as white needles.

Compound 1003 was characterized as follows: ¹H NMR (400 MHz, DMSO-d₆) δ 10.40 (s, 1H, NH), 8.46 (d, J=2.0 Hz, 1H, ArH), 8.24 (dd, J=8.4 Hz, J=2.0 Hz, 1H, ArH), 8.09 (d, J=8.4 Hz, 1H, ArH), 8.05 (s, 1H, Pyrazole-H), 7.82 (s, 1H, Pyrazole-H), 7.52-7.45 (m, 2H, ArH), 7.35-7.31 (m, 2H, ArH), 7.20-7.16 (m, 1H, ArH), 6.33 (s, 1H, OH), 4.50 (d, J=14.0 Hz, 1H, CH), 4.30 (d, J=14.0 Hz, 1H, CH), 1.40 (s, 3H, CH₃); Mass (ESI, Positive): 415.1455 [M+H]⁺.

(S)—N-(4-Cyano-3-(trifluoromethyl)phenyl)-2-hydroxy-2-methyl-3-(3-phenyl-1H-pyrrol-1-yl)propanamide ($C_{22}H_{18}F_3N_3O_2$) (1004)

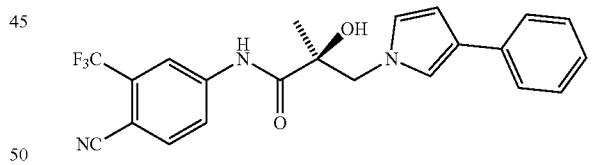

To a solution of 3-phenyl-pyrrole (0.50 g, 0.00349 mol) in anhydrous THF (10 mL), which was cooled in an ice water bath under an argon atmosphere, was added sodium hydride (60% dispersion in oil, 0.35 g, 0.00873 mol). After addition, the resulting mixture was stirred for 3 h. (R)-3-Bromo-N-(4-cyano-3-(trifluoromethyl)phenyl)-2-hydroxy-2-methylpropanamide (8, 1.23 g, 0.00349 mol) was added to above solution, and the resulting reaction mixture was allowed to stir overnight at RT under argon. The reaction was quenched by water, and extracted with ethyl acetate. The organic layer was washed with brine, dried with MgSO₄, filtered, and concentrated under vacuum. The product was purified by a silica gel column using ethyl acetate and hexanes (1:2) as eluent to afford 0.90 g of the titled compound as pink solid.

Compound 1004 was characterized as follows: ¹H NMR (400 MHz, DMSO-d₆) δ 10.41 (s, 1H, NH), 8.24 (d, J=1.6

Hz, 1H, ArH), 8.17 (dd, J=8.4 Hz, J=2.0 Hz, 1H, ArH), 8.07 (d, J=8.4 Hz, 1H, ArH), 7.38-7.33 (m, 4H, ArH), 7.28-7.24 (m, 1H, ArH), 6.96 (t, J=3.0 Hz, 1H, Pyrrole-H), 6.28 (s, 1H, OH), 6.07 (t, J=3.5 Hz, 1H, Pyrrole-H), 6.03 (m, 1H, Pyrrole-H), 4.30-4.22 (m, 2H, CH$_2$), 1.01 (s, 3H, CH$_3$); Mass (ESI, Positive): 414.1432 [M+H]$^+$.

Bromo-1H-imidazol-1-yl)-N-(4-cyano-3-(trifluoromethyl)phenyl)-2-hydroxy-2-methylpropanamides (1005 and 1006)

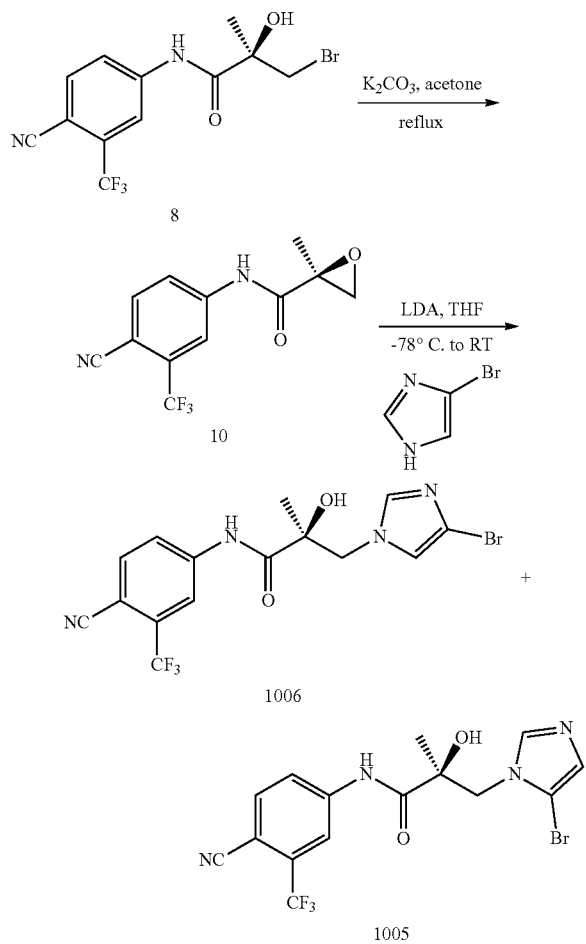

Lithium diisopropylamide solution (2.0 M) in THF/heptane/ethylbenzene (1 mL) was slowly added to a solution of 4-bromo-1H-imidazole (1.0 mmol, 2 mmol) in 5 mL of anhydrous THF at −78° C. and warmed to 0° C. and stirred for 10 min and cooled again to −78° C. To the solution was added dropwise a solution of (S)—N-(4-cyano-3-(trifluoromethyl)phenyl)-2-methyloxirane-2-carboxamide (10, 1 mmol) prepared from 8 (1 mmol) and the reaction mixture was stirred for overnight. After quenching by addition of sat. NH$_4$Cl, the solution was concentrated under reduced pressure and dispersed into excess EtOAc and dried over Na$_2$SO$_4$. The solution was concentrated and purified by flash column chromatography (EtOAc/hexane) to give the desired products as total yield of 69% (37% for 1005 and 32% for 1006) as white solids.

The compounds were characterized as follows:

(S)-3-(5-Bromo-1H-imidazol-1-yl)-N-(4-cyano-3-(trifluoromethyl)phenyl)-2-hydroxy-2-methylpropanamide (C$_{15}$H$_{12}$BrF$_3$N$_4$O$_2$) (1005)

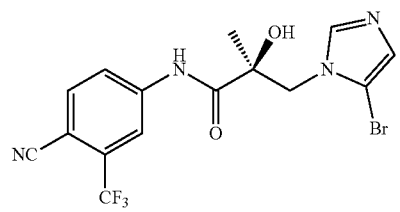

Method A (using bromoamide 8 and 4-bromo-1H-imidazole instead of general structure 9') gave a white solid; $^1$H NMR (acetone-d$_6$, 400 MHz) δ 9.93 (bs, 1H, NH), 8.44 (d, J=2.0 Hz, 1H), 8.26 (dd, J=8.6, 2.0 Hz, 1H), 8.03 (d, J=8.6 Hz, 1H), 7.47 (s, 1H), 7.11 (s, 1H), 5.83 (s, 1H, OH), 4.50 (d, J=14.0 Hz, 1H), 4.23 (d, J=14.0 Hz, 1H), 1.55 (s, 3H); $^{19}$F NMR (acetone-d$_6$, 400 MHz) δ 114.69; MS (ESI): 415.0 [M−H]$^-$; LCMS (ESI) m/z calcd for C$_{15}$H$_{11}$N$_4$O$_2$F$_3$Br: 415.0088. Found: 415.0017 [M−H]$^-$.

(S)-3-(4-Bromo-1H-imidazol-1-yl)-N-(4-cyano-3-(trifluoromethyl)phenyl)-2-hydroxy-2-methylpropanamide (C$_{15}$H$_{12}$BrF$_3$N$_4$O$_2$) (1006)

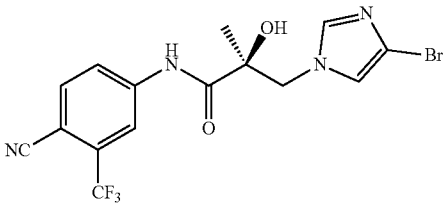

Method A (using bromoamide 8 and 4-bromo-1H-imidazole instead of general structure 9') gave a white solid; $^1$H NMR (CDCl$_3$, 400 MHz) δ 9.48 (bs, 1H, NH), 8.15 (s, 1H), 7.97 (d, J=8.6 Hz, 1H), 7.83 (d, J=8.6 Hz, 1H), 7.71 (s, 1H), 6.75 (s, 1H), 4.53 (d, J=14.4 Hz, 1H), 4.09 (d, J=14.4 Hz, 1H), 2.84 (s, 1H, OH), 1.45 (s, 3H); $^{19}$F NMR (CDCl$_3$, 400 MHz) δ −62.19; MS (ESI): 415.0 [M−H]$^-$.

(S)—N-(3-Chloro-4-cyanophenyl)-2-hydroxy-3-(1H-imidazol-1-yl)-2-methylpropanamide (C$_{14}$H$_{13}$ClN$_4$O$_2$) (1008)

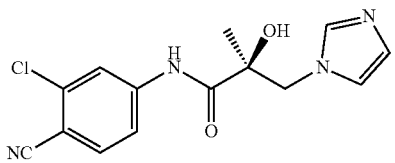

Method A (using bromoamide 7 and 1H-imidazole instead of general structure 9') gave a yellowish solid. Yield 53%; $^1$H NMR (DMSO-d$_6$, 400 MHz) δ 10.24 (bs, 1H, NH), 8.19 (s, 1H), 7.90 (m, 2H), 7.53 (s, 1H), 7.05 (s, 1H), 6.83 (s, 1H), 6.40 (bs, 1H, OH), 4.31 (d, J=14.4 Hz, 1H), 4.11 (d, J=14.4

Hz, 1H), 1.34 (s, 3H); LCMS (ESI) m/z calcd for $C_{14}H_{14}ClN_4O_2$: 305.0805. Found: 305.0809 [M+H]$^+$.

(S)—N-(3-Chloro-4-cyanophenyl)-2-hydroxy-2-methyl-3-(pyrrolidin-1-yl)propanamide ($C_{15}H_{18}ClN_3O_2$) (1009)

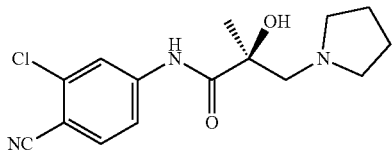

Method A (using bromoamide 7 and pyrrolidine instead of general structure 9') gave a yield of 89%; $^1$H NMR (CDCl$_3$, 400 MHz) δ 9.41 (bs, 1H, NH), 7.98 (d, J=2.0 Hz, 1H), 7.62 (d, J=8.8 Hz, 1H), 7.51 (dd, J=8.8, 2.0 Hz, 1H), 5.20 (s, 1H), 3.15 (d, J=12.4 Hz, 1H), 2.72 (d, J=12.4 Hz, 1H), 2.64-2.58 (m, 4H), 1.76 (m, 4H), 1.41 (s, 3H); $^{13}$C NMR (CDCl$_3$, 100 MHz) δ 175.6 (—NHCO—), 142.5, 137.9, 134.6, 119.9, 117.3, 116.1, 108.0, 72.9, 62.3, 54.6 (2C), 25.5, 24.0; LCMS (ESI) m/z calcd for $C_{15}H_{19}ClN_3O_2$: 308.1166. Found: 308.1173 [M+H]$^+$.

Preparation of HCl salt type of (S)—N-(3-chloro-4-cyanophenyl)-2-hydroxy-2-methyl-3-(pyrrolidin-1-yl)propanamide To a solution of 1009 in EtOH (20 mL) was added dropwise acetyl chloride (1 mL) at 0° C. and further stirred at RT overnight and removed the solvent to gain target salt of 1009.

(S)—N-(3-Chloro-4-cyanophenyl)-3-(4-fluoro-1H-pyrazol-1-yl)-2-hydroxy-2-methylpropanamide ($C_{14}H_{12}ClFN_4O_2$) (1007)

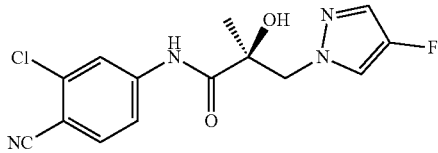

Method B (using oxirane 9 and 4-fluoro-1H-pyrazole instead of general structure 12') gave a yellowish solid; yield 72%; $^1$H NMR (CDCl$_3$, 400 MHz) δ 8.97 (bs, 1H, NH), 7.88 (d, J=2.0 Hz, 1H), 7.60 (d, J=8.4 Hz, 1H), 7.45 (dd, J=8.4, 2.0 Hz, 1H), 7.36 (d, J=4.0 Hz, 1H), 7.35 (d, J=4.4 Hz, 1H), 5.86 (bs, 1H, OH), 4.54 (d, J=14.0 Hz, 1H), 4.15 (d, J=14.0 Hz, 1H), 1.46 (s, 3H); $^{19}$F NMR (CDCl$_3$, 400 MHz) δ −176.47; LCMS (ESI) m/z calcd for $C_{14}H_{13}ClFN_4O_2$: 323.0711. Found: 323.0710 [M+H]$^+$.

(S)—N-(4-Cyano-3-(trifluoromethyl)phenyl)-3-(3-(4-fluorophenyl)-1H-pyrrol-1-yl)-2-hydroxy-2-methylpropanamide ($C_{22}H_{17}F_4N_3O_2$) (1010)

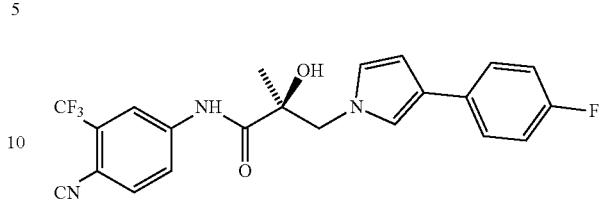

To a solution of 3-(4-fluorophenyl)-pyrrole (0.50 g, 0.003102 mol) in anhydrous THF (10 mL), which was cooled in an ice water bath under an argon atmosphere, was added sodium hydride (60% dispersion in oil, 0.37 g, 0.009306 mol). After addition, the resulting mixture was stirred for 3 h. (R)-3-Bromo-N-(4-cyano-3-(trifluoromethyl)phenyl)-2-hydroxy-2-methylpropanamide (8) (1.09 g, 0.003102 mol) was added to the above solution, and the resulting reaction mixture was allowed to stir overnight at RT under argon. The reaction was quenched by water, and extracted with ethyl acetate. The organic layer was washed with brine, dried with MgSO$_4$, filtered, and concentrated under vacuum. The product was purified by a silica gel column using ethyl acetate and hexanes (1:2 to 1:1) as eluent to afford 0.60 g (45%) of the compound as yellowish solid.

Compound 1010 was characterized as follows: $^1$H NMR (400 MHz, DMSO-d$_6$) δ 10.40 (s, 1H, NH), 8.42 (d, J=2.0 Hz, 1H, ArH), 8.24 (dd, J=8.8 Hz, J=2.0 Hz, 1H, ArH), 8.07 (d, J=8.8 Hz, 1H, ArH), 7.43-7.38 (m, 2H, ArH), 7.11-7.05 (m, 3H, ArH), 6.73 (t, J=2.0 Hz, 1H, Pyrrole-H), 6.33 (s, 1H, OH), 4.24 (d, J=14.0 Hz, 1H, CH), 4.05 (d, J=14.0 Hz, 1H, CH), 1.37 (s, 3H, CH$_3$); Mass (ESI, Positive): 432.1352 [M+H]$^+$; mp 187-189° C.

(S)—N-(4-Cyano-3-(trifluoromethyl)phenyl)-2-hydroxy-2-methyl-3-(3-phenyl-1H-pyrazol-1-yl)propanamide ($C_{21}H_{17}F_3N_4O_2$) (1011)

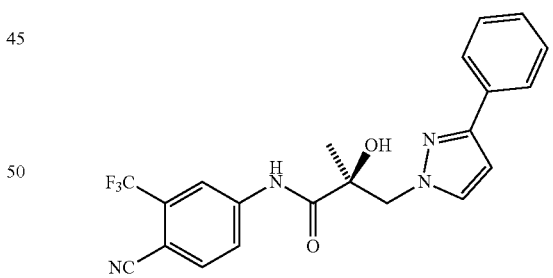

To a solution of 3-phenyl-pyrazole (0.50 g, 0.003468 mol) in anhydrous THF (10 mL), which was cooled in an ice water bath under an argon atmosphere, was added sodium hydride (60% dispersion in oil, 0.35 g, 0.00867 mol). After addition, the resulting mixture was stirred for 3 h. (R)-3-Bromo-N-(4-cyano-3-(trifluoromethyl)phenyl)-2-hydroxy-2-methylpropanamide (8, 1.22 g, 0.003468 mol) was added to above solution, and the resulting reaction mixture was allowed to stir overnight at RT under argon. The reaction was quenched by water, and extracted with ethyl acetate. The organic layer was washed with brine, dried with MgSO$_4$, filtered, and concentrated under vacuum. The product was purified by a silica gel column using ethyl acetate and hexanes (1:3 to 1:2) as eluent to afford 0.60 g of the titled compound as white needles.

Compound 1011 was characterized as follows: $^1$H NMR (400 MHz, DMSO-$d_6$) δ 10.33 (s, 1H, NH), 8.48 (d, J=2.0 Hz, 1H, ArH), 8.22 (dd, J=8.2 Hz, J=2.0 Hz, 1H, ArH), 8.05 (d, J=8.2 Hz, 1H, ArH), 7.69 (d, J=2.0 Hz, 1H, ArH), 7.60-7.57 (m, 2H, ArH), 7.28-7.21 (m, 3H, ArH), 6.66 (d, J=3.0 Hz, 1H, ArH), 6.31 (s, 1H, OH), 4.52 (d, J=14.6 Hz, 1H, CH), 4.32 (d, J=14.6 Hz, 1H, CH), 1.43 (s, 3H, CH$_3$).

(S)—N-(4-Cyano-3-(trifluoromethyl)phenyl)-3-(3-fluoro-1H-pyrazol-1-yl)-2-hydroxy-2-methylpropanamide ($C_{15}H_{12}F_4N_4O_2$) (1012)

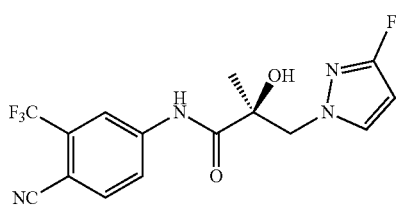

To a solution of 3-fluoro-pyrazole (0.20 g, 0.00232 mol) in anhydrous THF (10 mL), which was cooled in an ice water bath under an argon atmosphere, was added sodium hydride (60% dispersion in oil, 0.24 g, 0.00582 mol). After addition, the resulting mixture was stirred for 3 h. (R)-3-Bromo-N-(4-cyano-3-(trifluoromethyl)phenyl)-2-hydroxy-2-methylpropanamide (8, 0.82 g, 0.00232 mol) was added to above solution, and the resulting reaction mixture was allowed to stir overnight at RT under argon. The reaction was quenched by water, and extracted with ethyl acetate. The organic layer was washed with brine, dried with MgSO$_4$, filtered, and concentrated under vacuum. The product was purified by a silica gel column using ethyl acetate and hexanes (2:1) as eluent to afford 0.36 g of the compound as white needles.

Compound 1012 was characterized as follows: $^1$H NMR (400 MHz, DMSO-$d_6$) δ 10.39 (s, 1H, NH), 8.47 (d, J=2.0 Hz, 1H, ArH), 8.24 (dd, J=8.8 Hz, J=2.0 Hz, 1H, ArH), 8.11 (d, J=8.8 Hz, 1H, ArH), 7.55 (t, J=3.0 Hz, 1H, Pyrazole-H), 6.29 (s, 1H, OH), 5.93-5.91 (m, 1H, Pyrazole-H), 4.34 (d, J=13.6 Hz, 1H, CH), 4.15 (d, J=13.6 Hz, 1H, CH), 1.36 (s, 3H, CH$_3$); Mass (ESI, Positive): 357.0966 [M+H]$^+$.

(S)—N-(4-Cyano-3-(trifluoromethyl)phenyl)-2-hydroxy-2-methyl-3-(1H-pyrazol-1-yl)propanamide ($C_{15}H_{13}F_3N_4O_2$) (1013)

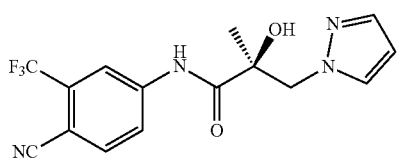

To a solution of 1H-pyrazole (0.20 g, 0.002938 mol) in anhydrous THF (10 mL), which was cooled in an ice water bath under an argon atmosphere, was added sodium hydride (60% dispersion in oil, 0.29 g, 0.007344 mol). After addition, the resulting mixture was stirred for 3 h. (R)-3-Bromo-N-(4-cyano-3-(trifluoromethyl)phenyl)-2-hydroxy-2-methylpropanamide (8, 1.03 g, 0.002938 mol) was added to above solution, and the resulting reaction mixture was allowed to stir overnight at RT under argon. The reaction was quenched by water, and extracted with ethyl acetate. The organic layer was washed with brine, dried with MgSO$_4$, filtered, and concentrated under vacuum. The product was purified by a silica gel column using ethyl acetate and hexanes (2:1) as eluent to afford 0.52 g of the compound as white solid.

Compound 1013 was characterized as follows: $^1$H NMR (400 MHz, DMSO-$d_6$) δ 10.39 (s, 1H, NH), 8.48 (d, J=2.0 Hz, 1H, ArH), 8.22 (dd, J=8.2 Hz, J=2.0 Hz, 1H, ArH), 8.08 (d, J=8.2 Hz, 1H, ArH), 7.66-7.65 (m, 1H, Pyrazole-H), 7.39-7.38 (m, 1H, Pyrazole-H), 6.28 (s, 1H, OH), 6.25-6.23 (m, 1H, Pyrazole-H), 4.50 (d, J=13.6 Hz, 1H, CH), 4.29 (d, J=13.6 Hz, 1H, CH), 1.35 (s, 3H, CH$_3$); Mass (ESI, Positive): 339.1105 [M+H]$^+$.

(S)—N-(4-Cyano-3-(trifluoromethyl)phenyl)-2-hydroxy-2-methyl-3-(3-(trifluoromethyl)-1H-pyrazol-1-yl)propanamide ($C_{16}H_{12}F_6N_4O_2$) (1014)

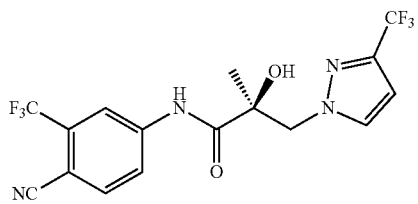 [SMILES: C[C@](O)(Cn1ccc(C(F)(F)F)n1)C(=O)Nc1ccc(C#N)c(C(F)(F)F)c1]

To a solution of 3-trifluoromethyl-pyrazole (0.20 g, 0.00147 mol) in anhydrous THF (10 mL), which was cooled in an ice water bath under an argon atmosphere, was added sodium hydride (60% dispersion in oil, 0.15 g, 0.003674 mol). After addition, the resulting mixture was stirred for 3 h. (R)-3-Bromo-N-(4-cyano-3-(trifluoromethyl)phenyl)-2-hydroxy-2-methylpropanamide (8) (0.516 g, 0.00147 mol) was added to above solution, and the resulting reaction mixture was allowed to stir overnight at RT under argon. The reaction was quenched by water, and extracted with ethyl acetate. The organic layer was washed with brine, dried with MgSO$_4$, filtered, and concentrated under vacuum. The product was purified by a silica gel column using ethyl acetate and hexanes (2:1) as eluent to afford the titled compound (103 mg, 70%) as a white solid.

Compound 1014 was characterized as follows: $^1$H NMR (400 MHz, DMSO-$d_6$) δ 10.31 (bs, 1H, NH), 8.42 (d, J=2.0 Hz, 1H, ArH), 8.19 (dd, J=8.8, 2.0 Hz, 1H, ArH), 8.09 (d, J=8.8 Hz, 1H, ArH), 7.83 (d, J=1.2 Hz, 1H, ArH), 6.67 (d, J=2.0 Hz, 1H, ArH), 6.41 (bs, OH), 4.56 (d, J=14.0 Hz, 1H, CHH), 4.37 (d, J=14.0 Hz, 1H, CHH), 1.41 (s, 3H, CH$_3$); $^{19}$F NMR (CDCl$_3$, decoupling) δ −60.44, −61.25; HRMS (ESI) m/z calcd for $C_{16}H_{12}F_6N_4O_2$: 407.0943 [M+H]$^+$; Found: 407.0943 [M+H]$^+$; mp 153-155° C.

(S)—N-(4-Cyano-3-(trifluoromethyl)phenyl)-3-(3-(4-fluorophenyl)-1H-pyrazol-1-yl)-2-hydroxy-2-methylpropanamide ($C_{21}H_{16}F_4N_4O_2$) (1015)

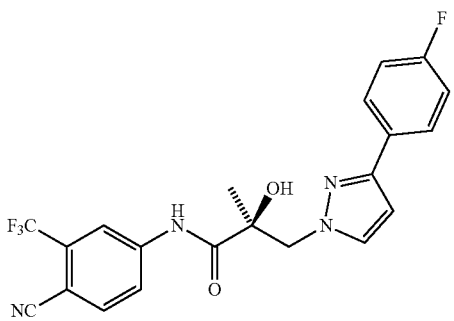 [SMILES: C[C@](O)(Cn1ccc(-c2ccc(F)cc2)n1)C(=O)Nc1ccc(C#N)c(C(F)(F)F)c1]

To a solution of 3-(4-fluorophenyl)-pyrazole (0.30 g, 0.00185 mol) in anhydrous THF (10 mL), which was cooled in an ice water bath under an argon atmosphere, was added sodium hydride (60% dispersion in oil, 0.22 g, 0.00555 mol). After addition, the resulting mixture was stirred for 3 h. (R)-3-Bromo-N-(4-cyano-3-(trifluoromethyl)phenyl)-2-hydroxy-2-methylpropanamide (8) (0.65 g, 0.00185 mol) was added to above solution, and the resulting reaction mixture was allowed to stir overnight at RT under argon. The reaction was quenched by water, and extracted with ethyl acetate. The organic layer was washed with brine, dried with $MgSO_4$, filtered, and concentrated under vacuum. The product was purified by a silica gel column using ethyl acetate and hexanes (2:1) as eluent to afford 0.32 g (40%) of the titled compound as pinkish solid.

Compound 1015 was characterized as follows: $^1H$ NMR (400 MHz, DMSO-$d_6$) δ 10.30 (s, 1H, NH), 8.41 (d, J=2.0 Hz, 1H, ArH), 8.21 (dd, J=8.2 Hz, J=2.0 Hz, 1H, ArH), 8.05 (d, J=8.2 Hz, 1H, ArH), 7.68 (d, J=2.0 Hz, 1H, ArH), 7.64-7.59 (m, 2H, ArH), 7.11-7.05 (m, 2H, ArH), 6.65 (d, J=3.0 Hz, 1H, ArH), 6.31 (s, 1H, OH), 4.50 (d, J=13.6 Hz, 1H, CH), 4.30 (d, J=13.6 Hz, 1H, CH), 1.42 (s, 3H, $CH_3$); Mass (ESI, Positive): 433.1312 [M+H]$^+$.

(S)—N-(4-Cyano-3-(trifluoromethyl)phenyl)-2-hydroxy-2-methyl-3-morpholinopropanamide ($C_{16}H_{18}F_3N_3O_3$) (1016)

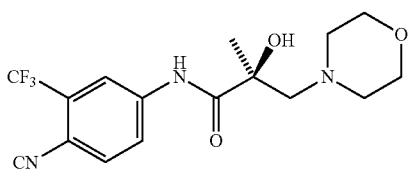

Under an argon atmosphere, 1.0 mL of lithium bis(trimethylsilyl)amide in THF (1 mmol, Aldrich, 1 M solution in THF) was slowly added to a solution of 0.09 mL of morpholine (0.67 mmol) in THF (10 mL) at −78° C. and stirred for 30 min at that temperature. A solution of 8 (234 mg, 0.67 mmol) in 5 mL of THF was added dropwise to the solution. The reaction mixture was stirred at the same temperature for 30 min, then stirred overnight at RT, and quenched by an addition of sat. $NH_4Cl$ solution. The mixture was concentrated under reduced pressure, dispersed into excess EtOAc, dried over $Na_2SO_4$, concentrated and purified by flash column chromatography (EtOAc/hexane) to give the target compound (209 mg, yield 88%) as white solid.

Compound 1016 was characterized as follows: $^1H$ NMR ($CDCl_3$, 400 MHz) δ 9.36 (bs, 1H, NH), 8.08 (d, J=1.6 Hz, 1H), 7.94 (dd, J=8.4, 1.6 Hz, 1H), 7.80 (d, J=8.4 Hz, 1H), 3.68 (m, 4H), 3.28 (d, J=13.2 Hz, 1H), 2.55 (m, 4H), 2.42 (d, J=13.2 Hz, 1H), 1.50 (bs, 1H, OH), 1.42 (s, 3H); $^{19}F$ NMR (acetone-$d_6$, 400 MHz) δ−62.20; LCMS (ESI) m/z calcd for $C_{16}H_{19}F_3N_3O_3$: 358.1379. Found: 358.1383 [M+H]$^+$.

(S)—N-(4-Cyano-3-(trifluoromethyl)phenyl)-2-hydroxy-2-methyl-3-(4-(trifluoromethyl)-1H-pyrazol-1-yl)propanamide ($C_{16}H_{12}F_6N_4O_2$) (1017)

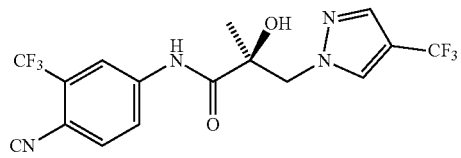

To a solution of 4-trifluoromethyl-pyrazole (0.20 g, 0.00147 mol) in anhydrous THF (10 mL), which was cooled in an ice water bath under an argon atmosphere, was added sodium hydride (60% dispersion in oil, 0.18 g, 0.004409 mol). After addition, the resulting mixture was stirred for 3 h. (R)-3-Bromo-N-(4-cyano-3-(trifluoromethyl)phenyl)-2-hydroxy-2-methylpropanamide (8) (0.516 g, 0.00147 mol) was added to above solution, and the resulting reaction mixture was allowed to stir overnight at RT under argon. The reaction was quenched by water, and extracted with ethyl acetate. The organic layer was washed with brine, dried with $MgSO_4$, filtered, and concentrated under vacuum. The product was purified by a silica gel column using DCM and ethyl acetate (19:1) as eluent to afford 0.30 g (50%) of the titled compound as white foam.

Compound 1017 was characterized as follows: $^1H$ NMR (400 MHz, DMSO-$d_6$) δ 10.38 (s, 1H, NH), 8.45 (d, J=2.0 Hz, 1H, ArH), 8.25-8.22 (m, 2H, ArH & Pyrazole-H), 8.11 (d, J=8.2 Hz, 1H, ArH), 7.82 (s, 1H, Pyrazole-H), 6.39 (s, 1H, OH), 4.55 (d, J=14.0 Hz, 1H, CH), 4.37 (d, J=14.0 Hz, 1H, CH), 1.40 (s, 3H, $CH_3$); Mass (ESI, Positive): 407.0945 [M+H]$^+$.

Triazoles 1018 and 1019:

(S)—N-(4-Cyano-3-(trifluoromethyl)phenyl)-2-hydroxy-2-methyl-3-(1H-1,2,4-triazol-1-yl)propanamide ($C_{14}H_{12}F_3N_5O_2$) (1018)

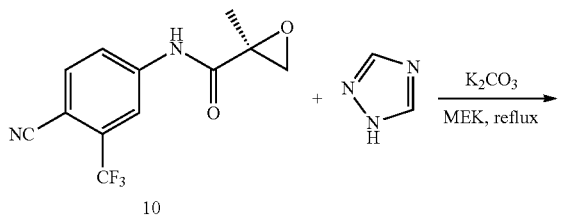

-continued

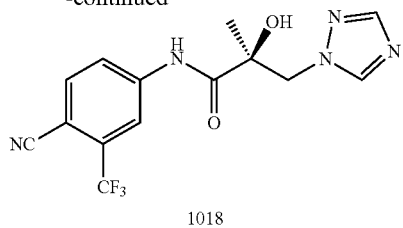

1018

To a dry, nitrogen-purged 50 mL round-bottom flask, epoxide (10, 270 mg, 1 mmol), 1,2,4-triazole (69 mg, 1 mmol) and $K_2CO_3$ (268 mg, 2 mmol) were dispersed into 10 mL of 2-butanone (methylethylketone (MEK)). The mixture was heated to reflux for 12 h. The resulting mixture was cooled down to RT. The volume of mixture was reduced under reduced pressure, poured into water, and extracted with ethyl acetate (3 times). The organic layer was dried over $MgSO_4$, concentrated and purified by flash column chromatography (ethyl acetate/hexane 2:3 v/v) on silica gel to produce target product (143 mg, 43% yield). Compound 1018 was characterized as follows: $^1$H NMR (CDCl$_3$, 400 MHz) δ 9.10 (bs, 1H, NH), 8.15 (s, 1H), 8.02 (d, J=2.0 Hz, 1H), 7.88 (dd, J=8.4, 2.0 Hz, 1H), 7.78 (d, J=8.4 Hz, 1H), 5.70 (bs, 1H, OH), 4.79 (d, J=14.0 Hz, 1H), 4.35 (d, J=14.0 Hz, 1H), 1.53 (s, 3H); $^{19}$F NMR (CDCl$_3$, 400 MHz) δ −62.22; HRMS (ESI) m/z calcd for $C_{14}H_{12}F_3N_5O_2$ Exact Mass: 340.1021 [M+H]$^+$. Found: 340.1067 [M+H]$^+$.

(S)—N-(4-Cyano-3-(trifluoromethyl)phenyl)-2-hydroxy-2-methyl-3-(3-(trifluoromethyl)-1H-1,2,4-triazol-1-yl)propanamide ($C_{15}H_{11}F_6N_5O_2$) (1019)

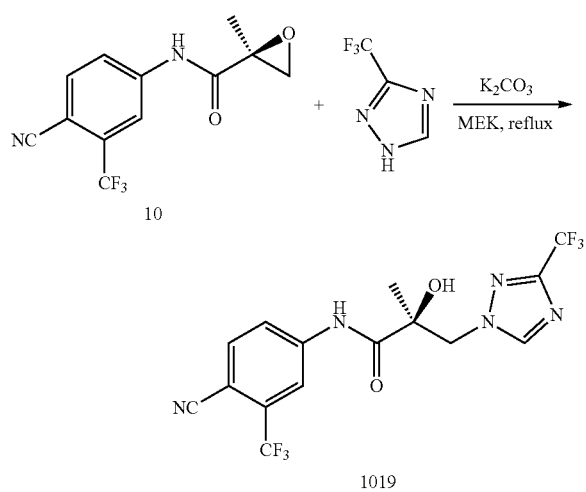

To a dry, nitrogen-purged 50 mL round-bottom flask, epoxide (10, 270 mg, 1 mmol), 3-(trifluoromethyl)-1H-1,2,4-triazole (137 mg, 1 mmol) and $K_2CO_3$ (268 mg, 2 mmol) were dispersed into 10 mL of 2-butanone (methylethylketone or MEK). The mixture was heated to reflux for 12 h. The resulting mixture was cooled down to RT. The volume of mixture was reduced under reduced pressure, poured into water, and extracted with ethyl acetate (3 times). The organic layer was dried over $MgSO_4$, concentrated and purified by flash column chromatography (ethyl acetate/hexane 2:3 v/v) on silica gel to produce target product (213 mg, 53% yield).

Compound 1019 was characterized as follows: $^1$H NMR (acetone-d$_6$, 400 MHz) δ 9.88 (bs, 1H, NH), 9.44 (s, 1H), 8.44 (s, 1H), 8.25 (d, J=8.4 Hz, 1H), 8.04 (d, J=8.4 Hz, 1H), 4.82 (d, J=14.4 Hz, 1H), 4.61 (d, J=14.4 Hz, 1H), 2.88 (bs, 1H, OH), 1.61 (s, 3H); $^{19}$F NMR (CDCl$_3$, 400 MHz) δ −62.26, −65.25; HRMS (ESI) m/z calcd for $C_{15}H_{11}F_6N_5O_2$ Exact Mass: 408.0895 [M+H]$^+$. Found: 408.0898 [M+H]$^+$.

(R)—N-(4-Cyano-3-(trifluoromethyl)phenyl)-3-(4-fluoro-1H-pyrazol-1-yl)-2-hydroxy-2-methylpropanamide ($C_{15}H_{12}F_4N_4O_2$) (1020)

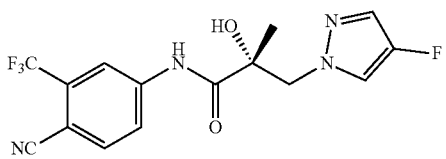 [SMILES: C[C@@](O)(Cn1cc(F)cn1)C(=O)Nc1ccc(C#N)c(C(F)(F)F)c1]

To a solution of 4-fluoro-1H-pyrazole (0.1 g, 1.16 mmol) in anhydrous THF (10 mL), which was cooled in an ice bath under an argon atmosphere, was added sodium hydride (60% dispersion in mineral oil, 0.12 g, 2.91 mmol). After addition, the resulting mixture was stirred for 3 h. (S)-3-Bromo-N-(4-cyano-3-(trifluoromethyl)phenyl)-2-hydroxy-2-methylpropanamide (S-isomer of 8 (8S)*; 0.41 g, 1.16 mmol) was added to the above solution, and the resulting reaction mixture was allowed to stir overnight at RT under argon atmosphere. The reaction was quenched by water and extracted with ethyl acetate. The organic layer was washed with brine, dried with anhydrous $MgSO_4$, filtered, and concentrated under reduced pressure. The mixture was purified by flash column chromatography using ethyl acetate and hexanes (2/3, v/v) as eluent to afford the titled compound (127 mg, 71%) as white solid.

Compound 1020 was characterized as follows: $^1$H NMR (400 MHz, CDCl$_3$) δ 9.07 (bs, 1H, NH), 8.01 (d, J=2.0 Hz, 1H), 7.95 (dd, J=8.4, 2.0 Hz, 1H), 7.78 (d, J=8.4 Hz, 1H), 7.38 (d, J=4.0 Hz, 1H), 7.34 (d, J=4.4 Hz, 1H), 5.92 (s, OH), 4.54 (d, J=14.0 Hz, 1H), 4.16 (d, J=14.4 Hz, 1H), 1.47 (s, 3H); $^{19}$F NMR (CDCl$_3$, decoupling) δ −62.23, −176.47; HRMS (ESI) m/z calcd for $C_{15}H_{12}F_4N_4O_2$: 357.0975 [M+H]$^+$; Found: 357.0984 [M+H]$^+$; $[α]_D^{24}$+126.7° (c=1.0, MeOH) (compared with S-isomer: $[α]_D^{24}$−136.0° (c=0.5, MeOH)).

*: 8S was synthesized from L-proline using the same procedure as for 8 (i.e., the R-isomer), as outlined in Scheme 1.

(S)—N-(4-Cyano-3-(trifluoromethyl)phenyl)-3-(3-fluoro-1H-pyrrol-1-yl)-2-hydroxy-2-methylpropanamide ($C_{16}H_{13}F_4N_3O_2$) (1021)

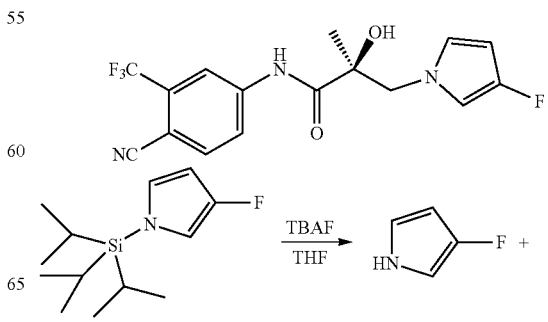

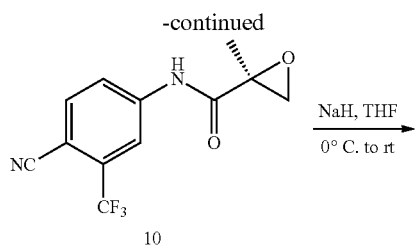

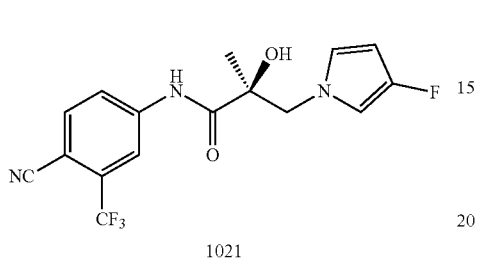

To a solution of 3-fluoro-1-(triisopropylsilyl)-1H-pyrrole (1.21 g, 5 mmol) in 20 mL of anhydrous THF, n-tetrabutylammonium fluoride trihydrate in tetrahydrofuran (7.5 mL, 7.5 mmol; 1M) was added at RT under argon atmosphere. The solution was stirred for 1 h. Without work-up procedure, the flask was cooled down to 0° C. at ice-water bath. To the solution, NaH of 60% in mineral oil (133 mg, 3.33 mmol) was added. The reaction mixture was stirred for 30 min and epoxide 10 (450 mg, 1.67 mmol) in anhydrous THF was added through dropping funnel under argon atmosphere at the ice-water bath and stirred overnight at RT. After quenching with 1 mL of H₂O, the reaction was condensed under reduced pressure, and then dispersed into 50 mL of EtOAc, washed with water, evaporated, dried over anhydrous MgSO₄, and evaporated to dryness. The mixture was purified with flash column chromatography by EtOAc/hexane=1/1 as eluent, and then the condensed compounds were recrystallized with EtOAc/hexane to give a target product 1021 (181 mg, 31%) as white solid.

Compound 1021 was characterized as follows: $^1$H NMR (400 MHz, CDCl$_3$) δ 8.91 (bs, 1H, NH), 8.03 (d, J=2.0 Hz, 1H), 7.90 (dd, J=8.4, 2.0 Hz, 1H), 7.81 (d, J=8.4 Hz, 1H), 6.47 (m, 1H), 6.41 (m, 1H), 5.91 (dd, J=2.8, 2.0 Hz, 1H), 4.36 (d, J=14.4 Hz, 1H), 3.98 (d, J=14.4 Hz, 1H), 1.54 (s, 3H); $^{19}$F NMR (CDCl$_3$, decoupling) δ−62.18, −164.26; HRMS (ESI) m/z calcd for C$_{16}$H$_{14}$F$_4$N$_3$O$_2$: 356.1022 [M+H]$^+$, Found: 356.1021 [M+H]$^+$; 378.0839 [H+Na]$^+$.

(S)—N-(6-Cyano-5-(trifluoromethyl)pyridin-3-yl)-3-(4-fluoro-1H-pyrazol-1-yl)-2-hydroxy-2-methylpropanamide (C$_{14}$H$_{11}$F$_4$N$_5$O$_2$) (1022)

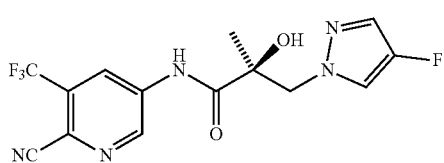 [SMILES: C[C@](O)(Cn1cc(F)cn1)C(=O)Nc1cnc(C#N)c(C(F)(F)F)c1]

(R)-3-Bromo-N-(6-cyano-5-(trifluoromethyl)pyridin-3-yl)-2-hydroxy-2-methylpropanamide (R)-3-Bromo-2-hydroxy-2-methylpropanoic acid (4, 1.03 g, 0.005625 mol) reacted with thionyl chloride (0.80 g, 0.006751 mol), trimethylamine (0.74 g, 0.007313 mol), and 5-amino-3-(trifluoromethyl)picolinonitrile (1.00 g, 0.005344 mol) to afford the titled compound. The product was purified by a silica gel column using hexanes and ethyl acetate (2:1) as eluent to afford 1.70 g (90%) of the titled compound as a yellowish solid.

$^1$H NMR (400 MHz, DMSO-d$_6$) δ 10.82 (s, 1H, NH), 9.41 (d, J=2.0 Hz, 1H, ArH), 8.90 (d, J=2.0 Hz, 1H, ArH), 6.51 (s, 1H, OH), 3.84 (d, J=10.4 Hz, 1H, CH), 3.61 (d, J=10.4 Hz, 1H, CH), 1.50 (s, 3H, CH$_3$); Mass (ESI, Positive): 351.9915 [M+H]$^+$.

(S)—N-(6-Cyano-5-(trifluoromethyl)pyridin-3-yl)-3-(4-fluoro-1H-pyrazol-1-yl)-2-hydroxy-2-methylpropanamide To a solution of 4-fluoro-pyrazole (0.20 g, 0.0023237 mol) in anhydrous THF (5 mL), which was cooled in an ice water bath under an argon atmosphere, was added sodium hydride (60% dispersion in oil, 0.28 g, 0.0069711 mol). After addition, the resulting mixture was stirred for 3 h. (R)-3-Bromo-N-(6-cyano-5-(trifluoromethyl)pyridin-3-yl)-2-hydroxy-2-methylpropanamide (0.82 g, 0.0023237 mol) was added to above solution, and the resulting reaction mixture was allowed to stir overnight at RT under argon. The reaction was quenched by water, and extracted with ethyl acetate. The organic layer was washed with brine, dried with MgSO$_4$, filtered, and concentrated under vacuum. The product was purified by a silica gel column using hexanes and ethyl acetate (1:1) as eluent to afford 0.50 g (60.2%) of the titled compound as white solid.

Compound 1022 was characterized as follows: $^1$H NMR (400 MHz, DMSO-d$_6$) δ 10.64 (s, 1H, NH), 9.32 (d, J=2.0 Hz, 1H, ArH), 8.82 (d, J=2.0 Hz, 1H, ArH), 7.75 (d, J=4.8 Hz, 1H, Pyrazole-H), 7.40 (d, J=4.0 Hz, 1H, Pyrazole-H), 6.41 (s, 1H, OH), 4.39 (d, J=14.0 Hz, 1H, CH), 4.22 (d, J=14.0 Hz, 1H, CH), 1.36 (s, 3H, CH$_3$); (ESI, Positive): 358.0939 [M+H]$^+$, 380.0749 [M+Na]$^+$.

(S)-5-(3-(4-Fluoro-1H-pyrazol-1-yl)-2-hydroxy-2-methylpropanamido)picolinamide ($C_{13}H_{14}FN_5O_3$) (1023)

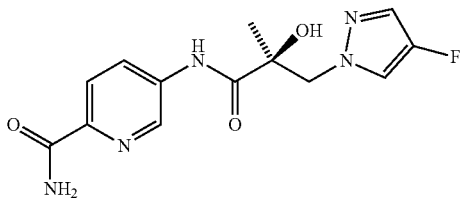 [SMILES: C[C@](O)(Cn1cc(F)cn1)C(=O)Nc1ccc(C(N)=O)nc1]

(R)-3-Bromo-N-(6-cyanopyridin-3-yl)-2-hydroxy-2-methylpropanamide

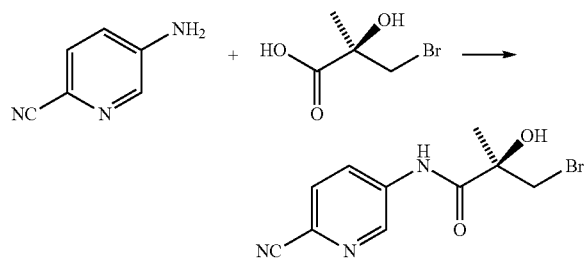

(R)-3-Bromo-2-hydroxy-2-methylpropanoic acid (4, 3.24 g, 0.017674 mol) reacted with thionyl chloride (2.53 g, 0.021208 mol), trimethylamine (2.33 g, 0.022976 mol), and 5-aminopicolinonitrile (2.00 g, 0.01679 mol) to afford the titled compound. The product was purified by a silica gel column using dichloromethane (DCM) and methanol (19:1) as eluent to afford 4.40 g (92%) of the titled compound as yellowish solid.

$^1$H NMR (400 MHz, DMSO-$d_6$) δ 10.42 (s, 1H, NH), 9.12 (d, J=2.4 Hz, 1H, ArH), 8.44 (dd, J=8.8 Hz, J=2.4 Hz, 1H, ArH), 8.00 (d, J=8.8 Hz, 1H, ArH), 6.40 (s, 1H, OH), 3.83 (d, J=10.4 Hz, 1H, CH), 3.59 (d, J=10.4 Hz, 1H, CH), 1.49 (s, 3H, $CH_3$); Mass (ESI, Positive): 284.0042 [M+H]$^+$.

(S)-5-(3-(4-Fluoro-1H-pyrazol-1-yl)-2-hydroxy-2-methylpropanamido)picolinamide To a solution of 4-fluoro-pyrazole (0.20 g, 0.0023237 mol) in anhydrous THF (5 mL), which was cooled in an ice water bath under an argon atmosphere, was added sodium hydride (60% dispersion in oil, 0.28 g, 0.0069711 mol). After addition, the resulting mixture was stirred for 3 h. (R)-3-Bromo-N-(6-cyanopyridin-3-yl)-2-hydroxy-2-methylpropanamide (0.66 g, 0.0023237 mol) was added to above solution, and the resulting reaction mixture was allowed to stir overnight at RT under argon. The reaction was quenched by water, and extracted with ethyl acetate. The organic layer was washed with brine, dried with $MgSO_4$, filtered, and concentrated under vacuum. The product was purified by a silica gel column using DCM and methanol (9:1) as eluent to afford 0.10 g (15%) of the titled compound as white solid.

Compound 1023 was characterized as follows: $^1$H NMR (400 MHz, DMSO-$d_6$) δ 10.08 (s, 1H, NH), 8.89 (d, J=2.4 Hz, 1H, ArH), 8.30 (dd, J=8.2 Hz, J=2.4 Hz, 1H, ArH), 8.01 (s, 1H, NH), 7.98 (d, J=8.2 Hz, 1H, ArH), 7.73 (d, J=4.4 Hz, 1H, Pyrazole-H), 7.51 (s, 1H, NH), 7.42 (d, J=4.0 Hz, 1H, Pyrazole-H), 6.24 (s, 1H, OH), 4.38 (d, J=14.0 Hz, 1H, CH), 4.42 (d, J=14.0 Hz, 1H, CH), 1.34 (s, 3H, $CH_3$); Mass (ESI, Positive): 308.1177 [M+H]$^+$, 330.0987 [M+Na]$^+$.

N-(4-Cyano-3-(trifluoromethyl)phenyl)-3-(4-fluoro-1H-pyrazol-1-yl)-2-methylpropanamide ($C_{15}H_{12}F_4N_4O$) (1024)

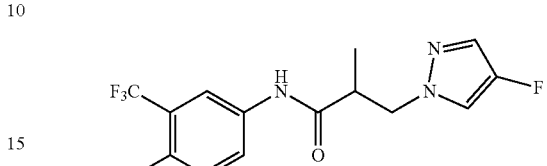

3-Bromo-N-(4-cyano-3-(trifluoromethyl)phenyl)-2-methylpropanamide

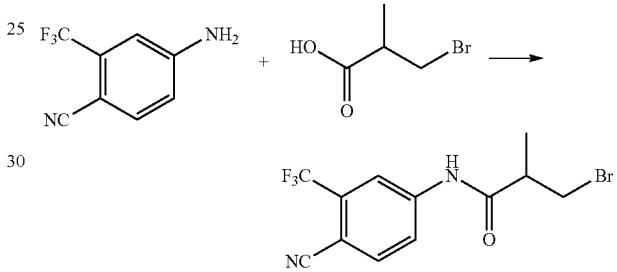

3-Bromo-2-methylpropanoic acid (2.00 g, 0.011976 mol) reacted with thionyl chloride (1.71 g, 0.014371 mol), trimethylamine (1.58 g, 0.015569 mol), and 4-amino-2-(trifluoromethyl)benzonitrile (2.12 g, 0.011377 mol) to afford the titled compound. The product was purified by a silica gel column using hexanes and ethyl acetate (2:1) as eluent to afford 3.50 g (91%) of the titled compound as a yellow to light brown solid.

$^1$H NMR (400 MHz, DMSO-$d_6$) δ 10.85 (s, 1H, NH), 8.30 (s, 1H, ArH), 8.12 (d, J=8.2 Hz, 1H, ArH), 8.03 (d, J=8.2 Hz, 1H, ArH), 3.72-3.67 (m, 1H, CH), 3.63-3.59 (m, 1H, CH), 3.03-2.97 (m, 1H, CH), 1.24 (d, J=6.8 Hz, 3H, $CH_3$); Mass (ESI, Negative): 334.85 [M–H]$^-$.

N-(4-Cyano-3-(trifluoromethyl)phenyl)-3-(4-fluoro-1H-pyrazol-1-yl)-2-methylpropanamide To a solution of 4-fluoro-pyrazole (0.20 g, 0.0023237 mol) in anhydrous THF (5 mL), which was cooled in an ice water bath under an argon atmosphere, was added sodium hydride (60% dispersion in oil, 0.28 g, 0.0069711 mol). After addition, the resulting mixture was stirred for 3 h. 3-Bromo-N-(4-cyano-3-(trifluoromethyl)phenyl)-2-methylpropanamide (0.78 g, 0.0023237 mol) was added to above solution, and the resulting reaction mixture was allowed to stir overnight at RT under argon. The reaction was quenched by water, and extracted with ethyl acetate. The organic layer was washed with brine, dried with $MgSO_4$, filtered, and concentrated under vacuum. The product was purified by a silica gel column using hexanes and ethyl acetate (1:1) as eluent to afford 0.050 g of the titled compound as yellowish solid.

Compound 1024 was characterized as follows: ¹H NMR (400 MHz, DMSO-d₆) δ 10.77 (s, 1H, NH), 8.25 (s, 1H, ArH), 8.10 (d, J=8.2 Hz, 1H, ArH), 7.96 (d, J=8.2 Hz, 1H, ArH), 7.85 (d, J=4.4 Hz, 1H, Pyrazole-H), 7.47 (d, J=4.4 Hz, 1H, Pyrazole-H), 4.35-4.30 (m, 1H, CH), 4.12-4.07 (m, 1H, CH), 3.12-3.10 (m, 1H, CH), 1.22 (d, J=6.8 Hz, 3H, CH₃).

(S)—N-(4-Cyano-3-(trifluoromethyl)phenyl)-3-(4-(4-fluorophenyl)-1H-pyrazol-1-yl)-2-hydroxy-2-methylpropanamide (C₂₁H₁₆F₄N₄O₂) (1025)

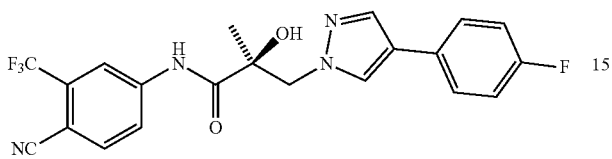

To a solution of 4-(4-fluorophenyl)-1H-pyrazole (0.20 g, 0.0012334 mol) in anhydrous THF (10 mL), which was cooled in an ice water bath under an argon atmosphere, was added sodium hydride (60% dispersion in oil, 0.15 g, 0.0037001 mol). After addition, the resulting mixture was stirred for 3 h. (R)-3-Bromo-N-(4-cyano-3-(trifluoromethyl)phenyl)-2-hydroxy-2-methylpropanamide (0.43 g, 0.0012334 mol) was added to the above solution, and the resulting reaction mixture was allowed to stir overnight at RT under argon. The reaction was quenched by water, and extracted with ethyl acetate. The organic layer was washed with brine, dried with MgSO₄, filtered, and concentrated under vacuum. The product was purified by a silica gel column using DCM and ethyl acetate (19:1) as eluent to afford 0.33 g (62%) of the titled compound as white solid.

Compound 1025 was characterized as follows: ¹H NMR (400 MHz, DMSO-d₆) δ 10.29 (s, 1H, NH), 8.41 (s, 1H, ArH), 8.21 (d, J=8.8 Hz, 1H, ArH), 8.05 (d, J=8.8 Hz, 1H, ArH), 7.68 (s, 1H, Pyrazole-H), 7.61 (t, J=6.4 Hz, 2H, ArH), 7.08 (t, J=8.4 Hz, 2H, ArH), 6.65 (s, 1H, Pyrazole-H), 6.30 (s, 1H, OH), 4.51 (d, J=14.0 Hz, 1H, CH), 4.31 (d, J=14.0 Hz, 1H, CH), 1.42 (s, 3H, CH₃); Mass (ESI, Negative): 431.12 [M−H]⁻.

(S)-3-((1H-1,2,4-Triazol-3-yl)amino)-N-(4-cyano-3-(trifluoromethyl)phenyl)-2-hydroxy-2-methylpropanamide (C₁₄H₁₃F₃N₆O₂) (1026)

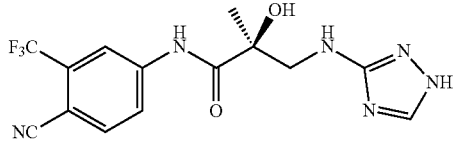 [SMILES: C[C@](O)(CNc1nc[nH]n1)C(=O)Nc1ccc(C#N)c(C(F)(F)F)c1]

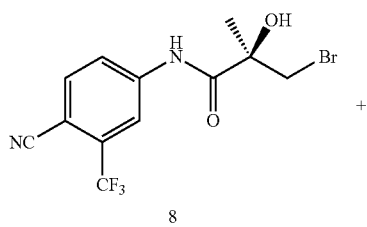

+

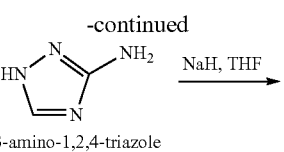

3-amino-1,2,4-triazole

NaH, THF →

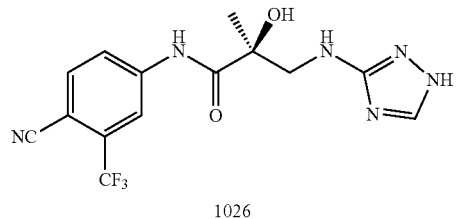

1026

Under argon atmosphere, 100 mL round bottom flask was cooled down to 0° C. at ice-water bath. NaH of 60% in mineral oil (265 mg, 6.6 mmol) was added to the flask at the ice-water bath and anhydrous THF (20 mL) was poured into the flask at that temperature. Into the flask, 3-amino-1,2,4-triazole (164 mg, 2 mmol) was added into the flask at that temperature and the reaction mixture was stirred for 30 min. Then, a prepared solution of (R)-3-bromo-N-(4-cyano-3-(trifluoromethyl)phenyl)-2-hydroxy-2-methylpropanamide (8, 702 mg, 2 mmol) in anhydrous THF (10 mL) was added through dropping funnel under argon atmosphere at the ice-water bath and stirred overnight at RT. After quenching with 1 mL of H₂O, the reaction mixture was condensed under reduced pressure, and then dispersed into 50 mL of EtOAc, washed with water, evaporated, dried over anhydrous MgSO₄, and evaporated to dryness. The mixture was purified with flash column chromatography with an eluent of EtOAc/hexane (2:1 v/v) to give a target product as brown solid.

Compound 1026 was characterized as follows: ¹H NMR (CDCl₃, 400 MHz) δ 9.10 (bs, 1H,C(O)NH), 8.01 (m, 1H, ArH), 7.87 and 7.81 (dd, J=8.4, 2.0 Hz, 1H, ArH), 7.78 (d, J=8.4 Hz, 1H, ArH), 7.72 and 7.51 (s, 1H, ArH), 5.90 and 5.65 (bs, 1H, NH), 4.74 (bs, 1H, NH), 4.56 and 4.55 (d, J=14.4 and 13.6 Hz, 1H, CH₂), 4.24 (bs, 1H, OH), 4.07 and 3.97 (d, J=13.6 and 14.4 Hz, 1H, CH₂), 1.56 and 1.48 (s, 3H, CH₃); ¹⁹F NMR (acetone-d₆, 400 MHz) δ −62.24; MS (ESI) m/z 353.03 [M−H]⁻; 355.10 [M+H]⁺; HRMS (ESI) m/z calcd for C₁₄H₁₃F₃N₆O₂: 355.1130 [M+H]⁺, Found: 355.1128 [M+H]⁺.

tert-Butyl (S)-(1-(3-((4-cyano-3-(trifluoromethyl)phenyl)amino)-2-hydroxy-2-methyl-3-oxopropyl)-1H-pyrazol-4-yl)carbamate (C₂₀H₂₂F₃N₅O₄) (1027)

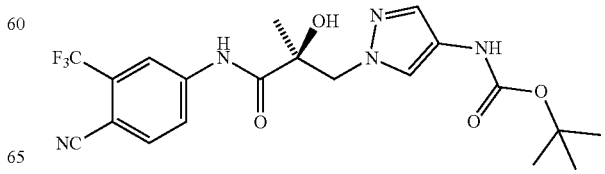

tert-Butyl-1H-pyrazol-4-ylcarbamate (1027a)

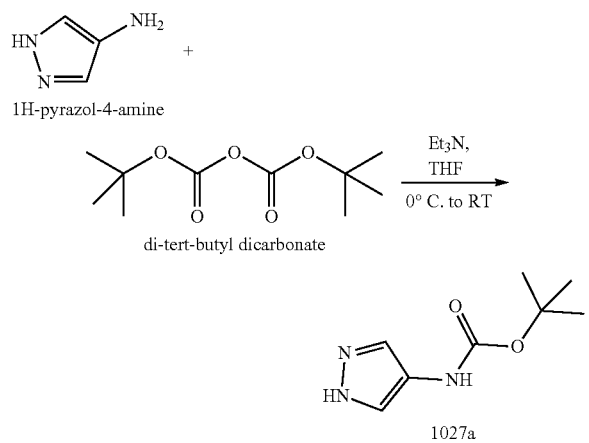

Under argon atmosphere, to a solution of 1H-pyrazol-4-amine (2 g, 28.9 mmol) and di-tert-butyl dicarbonate (6.3 g, 28.9 mmol) in 100 mL of anhydrous THF was added triethylamine (1.68 mL, 12 mmol) at 0° C. After stirring for 30 min, the temperature was raised to RT and the mixture was stirred for 2 h. The reaction mixture was condensed under reduced pressure, and then dispersed into 50 mL of EtOAc, washed with water, evaporated, dried over anhydrous MgSO$_4$, and evaporated to dryness. The mixture was purified with flash column chromatography with an eluent of EtOAc/hexane in a 1:1 v/v ratio, and then the condensed compounds were then recrystallized using EtOAc/hexane (1:1 v/v) to give a target product. $^1$H NMR (CDCl$_3$, 400 MHz) δ 7.63 (s, 2H, ArH), 6.29 (bs, 1H, NH), 1.51 (s, 9H, C(CH$_3$)$_3$); MS (ESI) m/z 182.1 [M–H]$^-$.

(S)-tert-Butyl (1-(3-((4-cyano-3-(trifluoromethyl)phenyl)amino)-2-hydroxy-2-methyl-3-oxopropyl)-1H-pyrazol-4-yl)carbamate

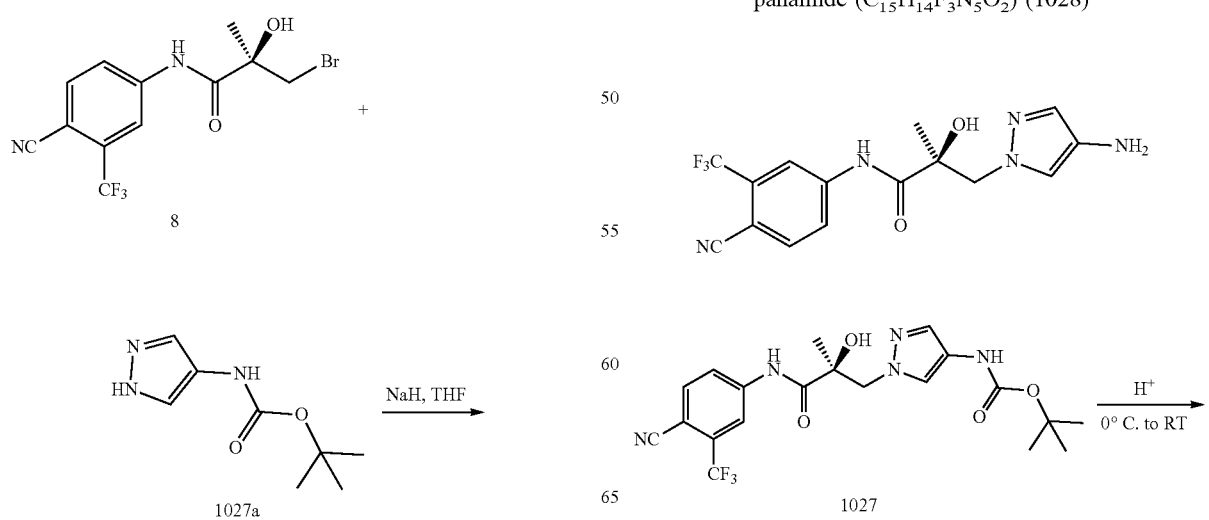

Under argon atmosphere, a 100 mL round bottom flask was cooled down to 0° C. at ice-water bath. NaH of 60% in mineral oil (160 mg, 4 mmol) was added to the flask at the ice-water bath and anhydrous THF (20 mL) was poured into the flask at that temperature. Into the flask, tert-butyl-1H-pyrazol-4-ylcarbamate (1027a, 366 mg, 2 mmol) was added at that temperature and the reaction mixture was stirred for 30 min, then a prepared solution of (R)-3-bromo-N-(4-cyano-3-(trifluoromethyl)phenyl)-2-hydroxy-2-methylpropanamide (8, 702 mg, 2 mmol) in anhydrous THF was added through a dropping funnel under argon atmosphere at the ice-water bath and stirred overnight at RT. After quenching with 1 mL of H$_2$O, the reaction was condensed under reduced pressure, and then dispersed into 50 mL of EtOAc, washed with water, evaporated, dried over anhydrous MgSO$_4$, and evaporated to dryness. The mixture was purified with flash column chromatography using EtOAc/hexane (2:1 v/v) as an eluent to give a target product (563 mg, 62%) as yellowish solid.

Compound 1027 was characterized as follows: $^1$H NMR (CDCl$_3$, 400 MHz) δ 9.13 (bs, 1H,C(O)NH), 8.01 (d, 1H, J=8.4 Hz, ArH), 7.85 (dd, J=8.4, 1.6 Hz, 1H, ArH), 7.76 (d, J=8.4 Hz, 1H, ArH), 7.63 (s, 1H, ArH), 7.43 (s, 1H, ArH), 6.21 (bs, 1H, C(O)NH), 6.17 (bs, 1H, OH), 4.54 (d, J=14.0 Hz, 1H, CH$_2$), 4.17 (d, J=14.0 Hz, 1H, CH$_2$), 1.47 (s, 9H, C(CH$_3$)$_3$), 1.45 (s, 3H, CH$_3$); $^{19}$F NMR (acetone-d$_6$, 400 MHz) δ −62.10; MS (ESI) m/z 452.11 [M–H]$^-$; 454.06 [M+H]$^+$.

(S)-3-(4-Amino-1H-pyrazol-1-yl)-N-(4-cyano-3-(trifluoromethyl)phenyl)-2-hydroxy-2-methylpropanamide (C$_{15}$H$_{14}$F$_3$N$_5$O$_2$) (1028)

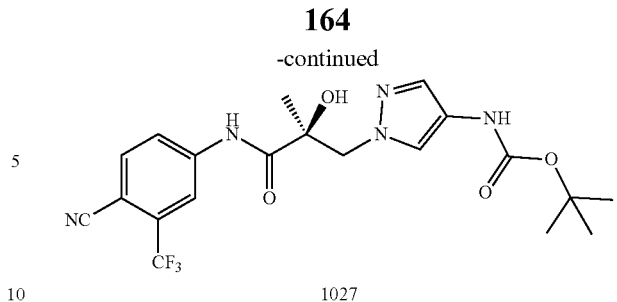

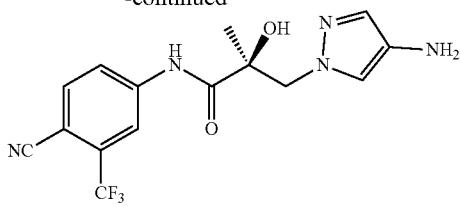

1028

Under argon atmosphere, a 100 mL round bottom flask was cooled down to 0° C. at ice-water bath. 5 mL of acetyl chloride was added dropwise to the solution of 1027 (815 mg, 1.80 mmol) of anhydrous EtOH (20 mL) at the ice-water bath. The reaction mixture was stirred for 30 min at that temperature. The solvent was concentrated under reduced pressure, and then dispersed into 50 mL of EtOAc, washed with water, evaporated, dried over anhydrous MgSO$_4$, and evaporated to dryness. The mixture was purified with flash column chromatography EtOAc/hexane (using 3:1 to 6:1 v/v ratios) as an eluent to give the target product (583 mg, 92%) as brown solid.

Compound 1028 was characterized as follows: $^1$H NMR (acetone-d$_6$, 400 MHz) δ 10.07 (bs, 1H,C(O)NH), 8.50 (s, 1H, ArH), 8.46 (s, 1H, ArH), 8.26 (d, J=8.0 Hz, 1H, ArH), 8.01 (d, J=8.0 Hz, 1H, ArH), 7.83 (s, 1H, ArH), 4.73 (d, J=14.0 Hz, 1H, CH$_2$), 4.53 (d, J=14.0 Hz, 1H, CH$_2$), 2.95 (bs, 1H, OH), 1.51 (s, 3H, CH$_3$); $^{19}$F NMR (acetone-d$_6$, 400 MHz) δ 114.77; MS (ESI) m/z 351.98 [M−H]$^-$; 354.08 [M+H]$^+$.

N-(4-Cyano-3-(trifluoromethyl)phenyl)-3-(4-fluoro-1H-pyrazol-1-yl)propanamide (C$_{14}$H$_{10}$F$_4$N$_4$O) (1029)

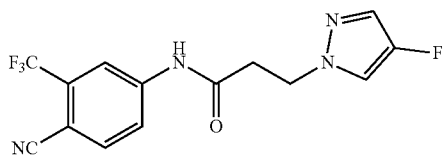 [SMILES: N#Cc1ccc(NC(=O)CCn2cc(F)cn2)cc1C(F)(F)F]

3-Bromo-N-(4-cyano-3-(trifluoromethyl)phenyl) propanamide (C$_{11}$H$_8$BrF$_3$N$_2$O)

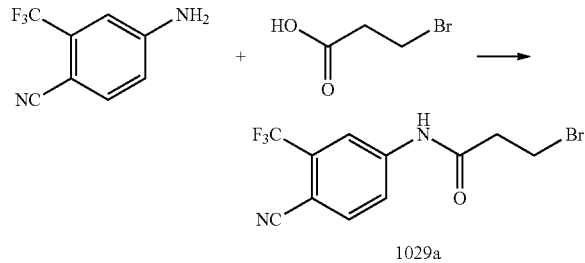

1029a

3-Bromopropanoic acid (2.00 g, 0.0130745 mol) reacted with thionyl chloride (1.87 g, 0.0156894 mol), trimethylamine (1.72 g, 0.0169968 mol), and 4-amino-2-(trifluoromethyl)benzonitrile (2.31 g, 0.0124207 mol) to afford the titled compound. The product was purified by a silica gel column using DCM and methanol (19:1) as eluent to afford 2.31 g (55%) of the titled compound as yellowish solid. $^1$H NMR (400 MHz, DMSO-d$_6$) δ 10.85 (s, 1H, NH), 8.28 (d, J=2.4 Hz, 1H, ArH), 8.12 (dd, J=8.8 Hz, J=2.4 Hz, 1H, ArH), 7.99 (d, J=8.8 Hz, 1H, ArH), 3.76 (t, J=6.0 Hz, 2H, CH$_2$), 3.06 (t, J=6.0 Hz, 2H, CH$_2$).

N-(4-Cyano-3-(trifluoromethyl)phenyl)-3-(4-fluoro-1H-pyrazol-1-yl)propanamide (C$_{14}$H$_{10}$F$_4$N$_4$O)

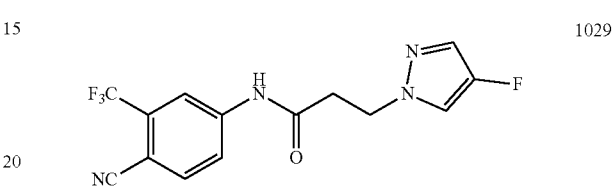

1029

To a solution of 4-fluoro-pyrazole (0.20 g, 0.0023237 mol) in anhydrous THF (5 mL), which was cooled in an ice water bath under an argon atmosphere, was added sodium hydride (60% dispersion in oil, 0.28 g, 0.0069711 mol). After addition, the resulting mixture was stirred for 3 h. 3-Bromo-N-(4-cyano-3-(trifluoromethyl)phenyl)propanamide (1029a, 0.75 g, 0.0023237 mol) was added to above solution, and the resulting reaction mixture was allowed to stir overnight at RT under argon. The reaction was quenched by water, and extracted with ethyl acetate. The organic layer was washed with brine, dried with MgSO$_4$, filtered, and concentrated under vacuum. The product was purified by a silica gel column using DCM and methanol (19:1) as eluent to afford 0.75 mg (10%) of the titled compound as white solid.

Compound 1029 was characterized as follows: $^1$H NMR (400 MHz, DMSO-d$_6$) δ 10.81 (s, 1H, NH), 8.25 (d, J=2.4 Hz, 1H, ArH), 8.10 (dd, J=8.8 Hz, J=2.4 Hz, 1H, ArH), 7.95 (d, J=8.8 Hz, 1H, ArH), 7.88 (s, 1H, Pyrazole-H), 7.46 (s, 1H, Pyrazole-H), 4.35 (t, J=6.0 Hz, 2H, CH$_2$), 2.79 (t, J=6.0 Hz, 2H, CH$_2$); Mass (ESI, Negative): 325.03 [M−H]$^-$.

(S)-tert-Butyl (1-(3-((6-cyano-5-(trifluoromethyl) pyridin-3-yl)amino)-2-hydroxy-2-methyl-3-oxopropyl)-1H-pyrazol-4-yl)carbamate (C$_{19}$H$_{21}$F$_3$N$_6$O$_4$) (1030)

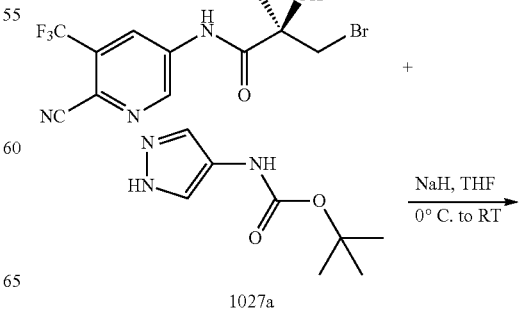

1027a

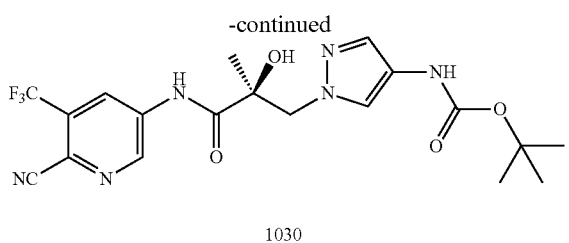

1030

Under argon atmosphere, a 50 mL round bottom flask was cooled down to 0° C. at an ice-water bath. NaH of 60% in mineral oil (160 mg, 4 mmol) was added to the flask at the ice-water bath and anhydrous THF (10 mL) was poured into the flask at that temperature. Tert-butyl-1H-pyrazol-4-ylcarbamate (1027a, 183 mg, 1 mmol) was added into the flask at that temperature and the reaction mixture was stirred for 30 min. Then a prepared solution of (R)-3-bromo-N-(6-cyano-5-(trifluoromethyl)pyridin-3-yl)-2-hydroxy-2-methylpropanamide (352 mg, 1 mmol) in anhydrous THF was added through dropping funnel under argon atmosphere at the ice-water bath and stirred overnight at RT. After quenching with 1 mL of H₂O, the reaction was condensed under reduced pressure, and then dispersed into 30 mL of EtOAc, washed with water, evaporated, dried over anhydrous MgSO₄, and evaporated to dryness. The mixture was purified with flash column chromatography as an eluent EtOAc/hexane to give the target product (273 mg, 60%) as yellowish solid.

Compound 1030 was characterized as follows: $^1$H NMR (CDCl₃, 400 MHz) δ 9.28 (bs, 1H,C(O)NH), 8.80 (s, 1H, ArH), 8.67 (s, 1H, ArH), 7.63 (bs, 1H,C(O)NH), 7.43 (s, 1H, ArH), 6.29 (bs, 1H, OH), 6.21 (s, 1H, ArH), 4.55 (d, J=14.0 Hz, 1H, CH₂), 4.18 (d, J=14.0 Hz, 1H, CH₂), 1.51 (s, 3H, CH₃) 1.47 (s, 9H, C(CH₃)₃); $^{19}$F NMR (CDCl₃, 400 MHz) δ −62.11; MS (ESI) m/z 453.16 [M−H]⁻; 477.16 [M+Na]⁺.

(S)-3-(4-Acetamido-1H-pyrazol-1-yl)-N-(4-cyano-3-(trifluoromethyl)phenyl)-2-hydroxy-2-methylpropanamide (C₁₇H₁₆F₃N₅O₃) (1031)

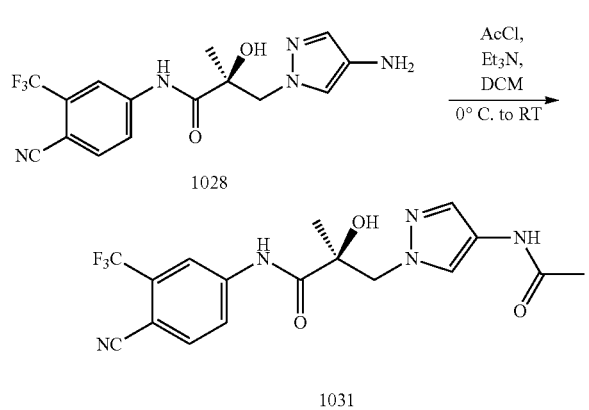

Under argon atmosphere, to a solution of 1028 (150 mg, 0.43 mmol) and triethyl amine (0.09 mL, 0.64 mmol) in 10 mL of anhydrous DCM was added acetyl chloride (AcCl, 0.038 mL, 0.53 mmol) at an ice-water bath. After stirring for 30 min, the temperature was raised to RT and the mixture was stirred for 2 h. The reaction mixture was condensed under reduced pressure, and then dispersed into 10 mL of EtOAc, washed with water, evaporated, dried over anhydrous MgSO₄, and evaporated to dryness. The mixture was purified with flash column chromatography as an eluent acetone/hexane (1/2, v/v) to produce 1031 (150 mg, 89%) as white solids.

Compound 1031 was characterized as follows: $^1$H NMR (CDCl₃, 400 MHz) δ 9.08 (bs, 1H,C(O)NH), 7.92 (bs, 1H,C(O)NH), 7.82-7.80 (m, 2H, ArH), 7.69 (d, J=8.4 Hz, 1H, ArH), 7.44 (s, 1H, ArH), 7.15 (s, 1H, ArH), 6.10 (bs, 1H, OH), 4.49 (d, J=13.6 Hz, 1H, CH₂), 4.13 (d, J=13.6 Hz, 1H, CH₂), 2.04 (s, 3H, NH(CO)CH₃), 1.39 (s, 3H, CH₃); $^{19}$F NMR (CDCl₃, 400 MHz) δ −62.20; MS (ESI) m/z 394.06 [M−H]⁻; 396.11 [M+H]⁺.

(S)-3-(4-Amino-1H-pyrazol-1-yl)-1-((4-cyano-3-(trifluoromethyl)phenyl)amino)-2-methyl-1-oxopropan-2-yl 2-chloroacetate (C₁₇H₁₅ClF₃N₅O₃) (1032); and (S)-3-(4-(2-Chloroacetamido)-1H-pyrazol-1-yl)-N-(4-cyano-3-(trifluoromethyl)phenyl)-2-hydroxy-2-methylpropanamide (C₁₇H₁₅ClF₃N₅O₃) (1033)

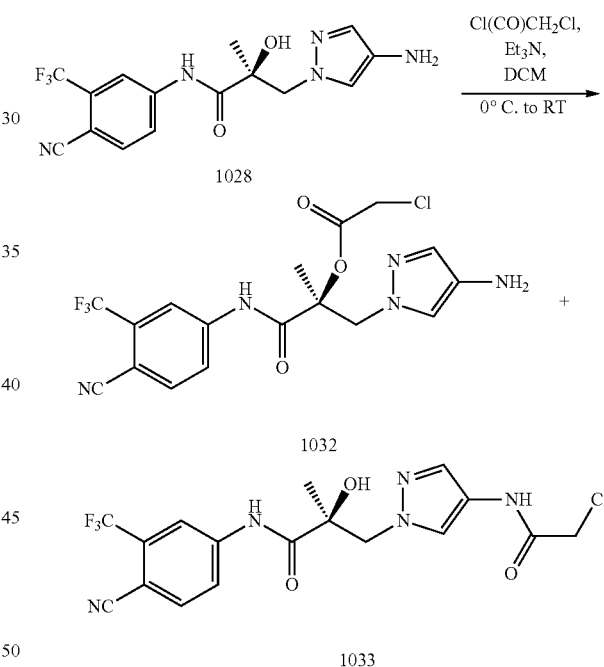

Under argon atmosphere, to a solution of 1028 (263 mg, 0.75 mmol) and triethyl amine (0.16 mL, 1.12 mmol) in 50 mL of anhydrous DCM was added chloroacetyl chloride (0.074 mL, 0.94 mmol) at an ice-water bath. After stirring for 30 min, the temperature was raised to RT and the mixture was stirred for 2 h. The reaction mixture was condensed under reduced pressure, and then dispersed into 30 mL of EtOAc, washed with water, evaporated, dried over anhydrous MgSO₄, and evaporated to dryness. The mixture was purified with flash column chromatography as an eluent EtOAc/hexane (3/1, v/v) to produce 1032 (105 mg, 33%) and 1033 (117 mg, 36%) as yellowish solids. Total yield 70%.

Compound 1032 was characterized as follows: $^1$H NMR (CDCl₃, 400 MHz) δ 9.22 (bs, NH₂), 8.10 (bs, 1H,C(O)NH), 7.93 (d, J=1.8 Hz, 1H, ArH), 7.86 (d, J=1.8 Hz, 1H, ArH), 7.79 (d, J=8.4 Hz, 1H, ArH), 5.16 (d, J=14.8 Hz, 1H, CH$_2$), 4.62 (d, J=14.8 Hz, 1H, CH$_2$), 4.11 (s, 2H, CH$_2$Cl), 1.77 (s, 3H, CH$_3$); $^{19}$F NMR (CDCl$_3$, 400 MHz) δ 114.77; MS (ESI) m/z 428.03 [M−H]$^-$; 452.02 [M+Na]$^+$.

Compound 1033 was characterized as follows: $^1$H NMR (CDCl$_3$, 400 MHz) δ 9.12 (bs, 1H,C(O)NH), 8.12 (bs, 1H,C(O)NH), 7.99 (d, J=1.6 Hz, 1H, ArH), 7.92 (s, 1H, ArH), 7.87 (dd, J=8.8, 1.6 Hz, 1H, ArH), 7.76 (d, J=8.8 Hz, 1H, ArH), 7.61 (s, 1H, ArH), 6.11 (bs, 1H, OH), 4.60 (d, J=13.6 Hz, 1H, CH$_2$), 4.22 (d, J=13.6 Hz, 1H, CH$_2$), 4.17 (s, 2H, CH$_2$Cl), 1.47 (s, 3H, CH$_3$); $^{19}$F NMR (CDCl$_3$, 400 MHz) δ −62.19; MS (ESI) m/z 428.00 [M−H]$^-$; 452.01 [M+Na]$^+$.

(S)-Methyl (1-(3-((4-cyano-3-(trifluoromethyl)phenyl)amino)-2-hydroxy-2-methyl-3-oxopropyl)-1H-pyrazol-4-yl)carbamate (C$_{17}$H$_{16}$F$_3$N$_5$O$_4$) (1034)

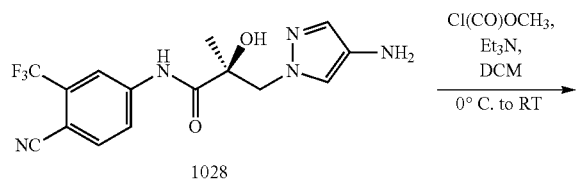

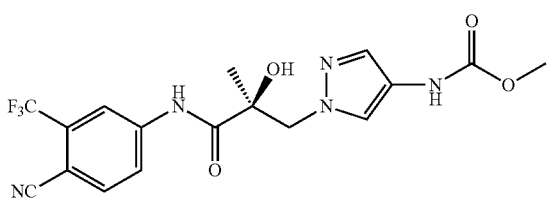

Under argon atmosphere, to a solution of 1028 (170 mg, 0.48 mmol) and triethyl amine (0.16 mL, 1.15 mmol) in 10 mL of anhydrous DCM was added methyl carbonochloridate (0.04 mL, 0.58 mmol) at ice-water bath. After stirring for 30 min, the temperature was raised to RT and the mixture stirred for 2 h. The reaction mixture was condensed under reduced pressure, and then dispersed into 10 mL of EtOAc, washed with water, evaporated, dried over anhydrous MgSO$_4$, and evaporated to dryness. The mixture was purified with flash column chromatography as an eluent EtOAc/hexane (2/1, v/v) to produce 1034 (141 mg, 71%) as white solids.

Compound 1034 was characterized as follows: $^1$H NMR (CDCl$_3$, 400 MHz) δ 9.07 (bs, 1H,C(O)NH), 7.91 (s, 1H, ArH), 7.79 (d, J=7.2 Hz, 1H, ArH), 7.69 (d, J=7.2 Hz, 1H, ArH), 7.57 (s, 1H, ArH), 7.40 (s, 1H, ArH), 6.33 (bs, 1H, NH), 6.08 (bs, 1H, OH), 4.50 (d, J=13.6 Hz, 1H, CH$_2$), 4.12 (d, J=13.6 Hz, 1H, CH$_2$), 3.67 (s, 3H, NH(CO)OCH$_3$), 1.39 (s, 3H, CH$_3$); $^{19}$F NMR (CDCl$_3$, 400 MHz) δ −62.21; MS (ESI) m/z 410.30 [M−H]$^-$; 413.21 [M+H]$^+$.

(S)-3-(4-Acetyl-1H-pyrazol-1-yl)-N-(4-cyano-3-(trifluoromethyl)phenyl)-2-hydroxy-2-methylpropanamide (C$_{17}$H$_{15}$F$_3$N$_4$O$_3$) (1035)

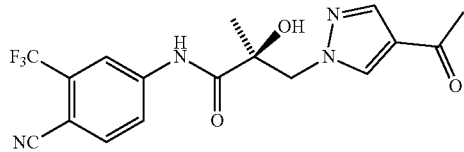 [SMILES: CC(=O)c1cnn(C[C@](C)(O)C(=O)Nc2ccc(C#N)c(C(F)(F)F)c2)c1]

To a solution of 1-(1H-pyrazol-4-yl)ethanone (0.10 g, 0.000908 mol) in anhydrous THF (5 mL), which was cooled in an ice water bath under an argon atmosphere, was added sodium hydride (60% dispersion in oil, 0.11 g, 0.002725 mol). After addition, the resulting mixture was stirred for 3 h. (R)-3-Bromo-N-(4-cyano-3-(trifluoromethyl)phenyl)-2-hydroxy-2-methylpropanamide (8, 0.32 g, 0.000908 mol) was added to the above solution, and the resulting reaction mixture was allowed to stir overnight at RT under argon. The reaction was quenched by water, and extracted with ethyl acetate. The organic layer was washed with brine, dried with MgSO$_4$, filtered, and concentrated under vacuum. The product was purified by a silica gel column using DCM and ethyl acetate (19:1) as eluent to afford 70 mg (20%) of the titled compound as yellowish solid.

Compound 1035 was characterized as follows: $^1$H NMR (400 MHz, DMSO-d$_6$) δ 10.37 (s, 1H, NH), 8.45 (d, J=1.2 Hz, 1H, ArH), 8.25 (s, 1H, Pyrazole-H), 8.23 (d, J=8.2 Hz, J=1.2 Hz, 1H, ArH), 8.10 (d, J=8.2 Hz, 1H, ArH), 7.86 (s, 1H, Pyrazole-H), 6.37 (s, 1H, OH), 4.50 (d, J=14.0 Hz, 1H, CH), 4.33 (d, J=14.0 Hz, 1H, CH), 2.34 (s, 3H, CH$_3$), 1.39 (s, 3H, CH$_3$); mass (ESI, Negative): 379.14 [M−H]$^-$; (ESI, Positive): 413.18 [M+Na]$^+$.

(S)—N-(4-Cyano-3-(trifluoromethyl)phenyl)-2-hydroxy-2-methyl-3-(4-nitro-1H-pyrazol-1-yl)propanamide (C$_{15}$H$_{12}$F$_3$N$_5$O$_4$) (1036)

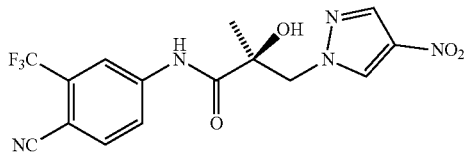 [SMILES: C[C@](O)(Cn1cc([N+](=O)[O-])cn1)C(=O)Nc1ccc(C#N)c(C(F)(F)F)c1]

To a solution of 4-nitro-1H-pyrazole (0.10 g, 0.0008844 mol) in anhydrous THF (5 mL), which was cooled in an ice water bath under an argon atmosphere, was added sodium hydride (60% dispersion in oil, 0.106 g, 0.002653 mol). After addition, the resulting mixture was stirred for 3 h. (R)-3-Bromo-N-(4-cyano-3-(trifluoromethyl)phenyl)-2-hydroxy-2-methylpropanamide (8, 0.31 g, 0.0008844 mol) was added to the above solution, and the resulting reaction mixture was allowed to stir overnight at RT under argon. The reaction was quenched by water, and extracted with ethyl acetate. The organic layer was washed with brine, dried with MgSO$_4$, filtered, and concentrated under vacuum. The product was purified by a silica gel column using hexanes and ethyl acetate (1:1) as eluent to afford 0.15 g (44%) of the titled compound as off-white solid.

Compound 1036 was characterized as follows: $^1$H NMR (400 MHz, DMSO-$d_6$) δ 10.36 (s, 1H, NH), 8.69 (s, 1H, Pyrazole-H), 8.45 (d, J=1.2 Hz, 1H, ArH), 8.23 (d, J=8.8 Hz, J=1.2 Hz, 1H, ArH), 8.19 (s, 1H, Pyrazole-H), 8.11 (d, J=8.8 Hz, 1H, ArH), 6.47 (s, 1H, OH), 4.56 (d, J=14.0 Hz, 1H, CH), 4.38 (d, J=14.0 Hz, 1H, CH), 1.41 (s, 3H, CH$_3$); mass (ESI, Negative): 382.13 [M−H]$^−$.

(R)-3-Bromo-N-(6-cyanopyridin-3-yl)-2-hydroxy-2-methylpropanamide ($C_{10}H_{10}BrN_3O_2$) (1037)

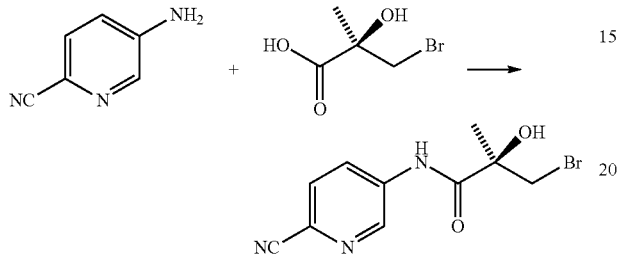

(R)-3-Bromo-2-hydroxy-2-methylpropanoic acid (4, 3.24 g, 0.017674 mol) reacted with thionyl chloride (2.53 g, 0.021208 mol), trimethylamine (2.33 g, 0.022976 mol), and 5-aminopicolinonitrile (2.00 g, 0.01679 mol) to afford the titled compound. The product was purified by a silica gel column using DCM and methanol (19:1) as eluent to afford 4.40 g (92%) of the titled compound as yellowish solid.

Compound 1037 was characterized as follows: $^1$H NMR (400 MHz, DMSO-$d_6$) δ 10.42 (s, 1H, NH), 9.12 (d, J=2.4 Hz, 1H, ArH), 8.44 (dd, J=8.8 Hz, J=2.4 Hz, 1H, ArH), 8.00 (d, J=8.8 Hz, 1H, ArH), 6.40 (s, 1H, OH), 3.83 (d, J=10.4 Hz, 1H, CH), 3.59 (d, J=10.4 Hz, 1H, CH), 1.49 (s, 3H, CH$_3$); mass (ESI, Positive): 284.0042 [M+H]$^+$.

(R)-3-Bromo-N-(6-cyano-5-(trifluoromethyl)pyridin-3-yl)-2-hydroxy-2-methylpropanamide ($C_{11}H_9BrF_3N_3O_2$) (1038)

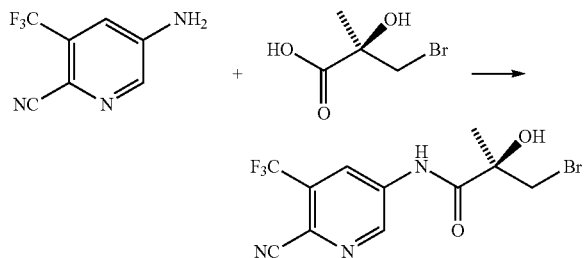

(R)-3-Bromo-2-hydroxy-2-methylpropanoic acid (4, 1.03 g, 0.005625 mol) reacted with thionyl chloride (0.80 g, 0.006751 mol), trimethylamine (0.74 g, 0.007313 mol), and 5-amino-3-(trifluoromethyl)picolinonitrile (1.00 g, 0.005344 mol) to afford the titled compound. The product was purified by a silica gel column using hexanes and ethyl acetate (2:1) as eluent to afford 1.70 g (90%) of the titled compound as yellowish solid.

Compound 1038 was characterized as follows: $^1$H NMR (400 MHz, DMSO-$d_6$) δ 10.82 (s, 1H, NH), 9.41 (d, J=2.0 Hz, 1H, ArH), 8.90 (d, J=2.0 Hz, 1H, ArH), 6.51 (s, 1H, OH), 3.84 (d, J=10.4 Hz, 1H, CH), 3.61 (d, J=10.4 Hz, 1H, CH), 1.50 (s, 3H, CH$_3$); mass (ESI, Positive): 351.9915 [M+H]$^+$.

(R)-3-Bromo-2-hydroxy-2-methyl-N-(quinazolin-6-yl)propanamide ($C_{12}H_{12}BrN_3O_2$) (1039)

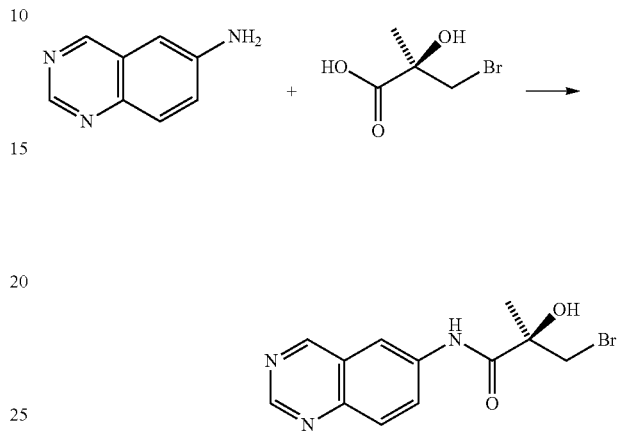

(R)-3-Bromo-2-hydroxy-2-methylpropanoic acid (2.65 g, 0.014503 mol) was reacted with thionyl chloride (2.07 g, 0.017404 mol), trimethylamine (1.91 g, 0.018854 mol), and quinazolin-6-amine (2.00 g, 0.013778 mol) to afford the titled compound. The product was purified by a silica gel column using hexanes and ethyl acetate (3:1 to 2:1) as eluent to afford 0.71 g of the titled compound as yellowish solid.

Compound 1039 was characterized as follows: Mass (ESI, Positive) 309.98 [M+H]$^+$.

3-Bromo-N-(4-cyano-3-(trifluoromethyl)phenyl)propanamide ($C_{11}H_8BrF_3N_2O$) (1040)

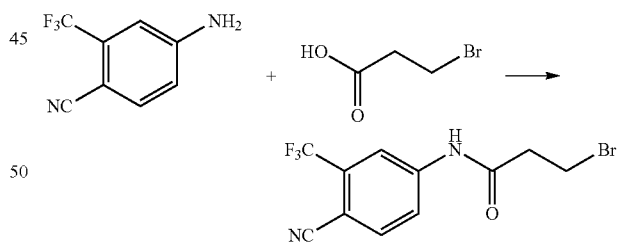

3-Bromopropanoic acid (2.00 g, 0.0130745 mol) reacted with thionyl chloride (1.87 g, 0.0156894 mol), trimethylamine (1.72 g, 0.0169968 mol), and 4-amino-2-(trifluoromethyl)benzonitrile (2.31 g, 0.0124207 mol) to afford the titled compound. The product was purified by a silica gel column using DCM and methanol (19:1) as eluent to afford 2.31 g (55%) of the titled compound as yellowish solid.

Compound 1040 was characterized as follows: $^1$H NMR (400 MHz, DMSO-$d_6$) δ 10.85 (s, 1H, NH), 8.28 (d, J=2.4 Hz, 1H, ArH), 8.12 (dd, J=8.8 Hz, J=2.4 Hz, 1H, ArH), 7.99 (d, J=8.8 Hz, 1H, ArH), 3.76 (t, J=6.0 Hz, 2H, CH$_2$), 3.06 (t, J=6.0 Hz, 2H, CH$_2$).

173

(S)—N-(2-Chloropyridin-4-yl)-3-(4-fluoro-1H-pyrazol-1-yl)-2-hydroxy-2-methylpropanamide (C₁₂H₁₂ClFN₄O₂) (1041)

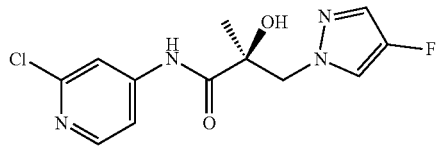 [SMILES: C[C@](O)(Cn1cc(F)cn1)C(=O)Nc1ccnc(Cl)c1]

(R)-3-Bromo-N-(2-chloropyridin-4-yl)-2-hydroxy-2-methylpropanamide

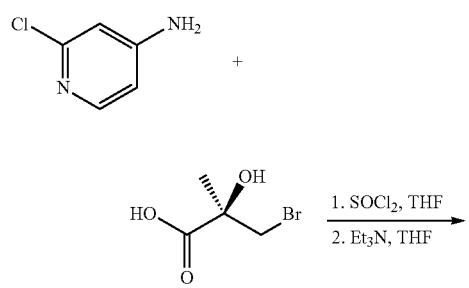

Thionyl chloride (11.2 mL, 0.154 mol) was added dropwise to a cooled solution (less than 4° C.) of (R)-3-bromo-2-hydroxy-2-methylpropanoic acid (4, 18.3 g, 0.100 mol) in 100 mL of THF under an argon atmosphere. The resulting mixture stirred for 3 h under the same condition. To this was added Et₃N (25.7 mL, 0.185 mol) and then stirred for 20 min under the same condition. After 20 min, 2-chloropyridin-4-amine (9.89 g, 0.077 mol), 100 mL of THF were added and then the mixture was allowed to stir overnight at RT. The solvent was removed under reduced pressure to give a solid, which was treated with 100 mL of H₂O, and extracted with EtOAc (2×50 mL). The combined organic extracts were washed with saturated NaHCO₃ solution (2×100 mL) and brine (100 mL). The organic layer was dried over MgSO₄ and concentrated under reduced pressure to give a solid, which was dissolved and purified by column chromatography using CH₂Cl₂/EtOAc (80:20) to give a solid. This solid recrystallized from CH₂Cl₂/hexane to give 12.6 g (43%) of (R)-3-bromo-N-(2-chloropyridin-4-yl)-2-hydroxy-2-methylpropanamide as a light-yellow solid. ¹H NMR (400 MHz, CDCl₃) δ 9.06 (bs, 1H, NH), 8.31 (d, J=5.6 Hz, 1H), 7.77 (d, J=0.8 Hz, 1H), 7.45 (dd, J=5.6, 0.8 Hz, 1H), 4.81 (bs, 1H, OH), 3.97 (d, J=10.6 Hz, 1H), 3.60 (d, J=10.6 Hz, 1H), 1.64 (s, 3H); MS (ESI) m/z 295.28 [M+H]⁺.

174

(S)—N-(2-Chloropyridin-4-yl)-3-(4-fluoro-1H-pyrazol-1-yl)-2-hydroxy-2-methylpropanamide (C₁₂H₁₂ClFN₄O₂)

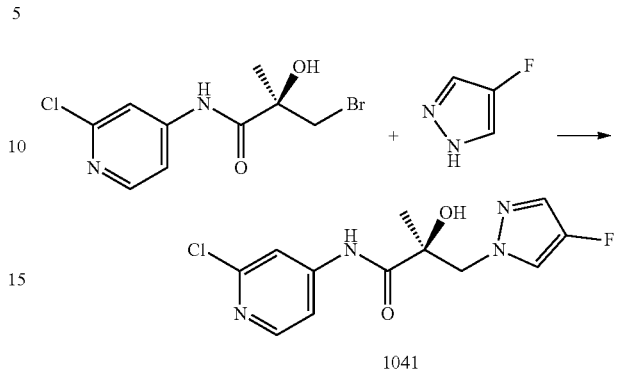

To a dry, nitrogen-purged 100 mL round-bottom flask equipped with a dropping funnel under argon atmosphere, NaH of 60% dispersion in mineral oil (96 mg, 2.4 mmol) was added in 10 mL of anhydrous THF solvent at ice-water bath. 4-Fluoro-1H-pyrazole (103 mg, 1.2 mmol) was added and the solution stirred 30 min at the ice-water bath. Into the flask, the solution of (R)-3-bromo-N-(2-chloropyridin-4-yl)-2-hydroxy-2-methylpropanamide (293 mg, 1.0 mmol) in 5 mL of anhydrous THF was added through dropping funnel under argon atmosphere at the ice-water bath and stirred overnight at RT. After adding 1 mL of H₂O, the reaction mixture was condensed under reduced pressure, and then dispersed into 50 mL of EtOAc, washed with 50 mL (×2) water, evaporated, dried over anhydrous MgSO₄, and evaporated to dryness. The mixture was purified with flash column chromatography using as an eluent EtOAc/hexane as a 1:2 ratio to produce compounds to produce the titled compound (55%) as a white solid.

Compound 1041 was characterized as follows: ¹H NMR (400 MHz, CDCl₃) δ 8.90 (bs, 1H, NH), 8.26 (d, J=5.6 Hz, 1H), 7.63 (s, 1H), 7.75 (d, J=4.2 Hz, 1H), 7.33 (d, J=4.2 Hz, 1H), 7.31 (dd, J=5.6, 1.2 Hz, 1H), 5.88 (s, 1H, OH), 4.53 (d, J=13.6 Hz, 1H), 4.14 (d, J=13.6 Hz, 1H), 1.45 (s, 3H); ¹⁹F NMR (CDCl₃, decoupled) δ −176.47; MS (ESI) m/z 298.98 [M+H]⁺; 296.96 [M−H]⁻.

(S)-3-Azido-N-(4-cyano-3-(trifluoromethyl)phenyl)-2-hydroxy-2-methylpropanamide (C₁₂H₁₀F₃N₅O₂) (1042)

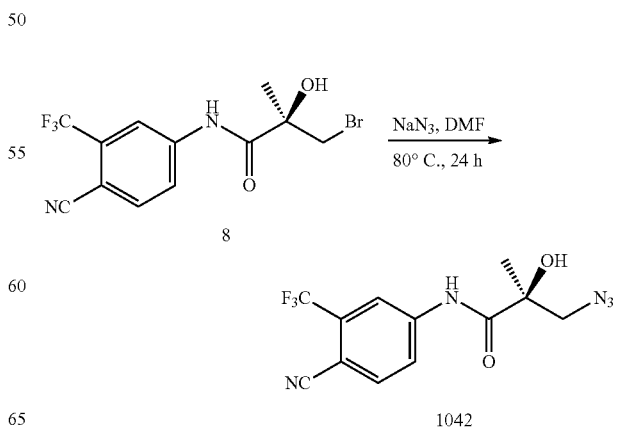

A solution of 8 (351 mg, 1 mmol) in DMF (10 mL) was treated with NaN₃ (325 mg, 5 mmol) under argon at 80° C. for 24 h. The reaction mixture was then, cooled and extracted with CH₂Cl₂ (3×20 mL). The combined organic layers were washed with H₂O (3×20 mL) and brine, dried and evaporated to give a crude oil, which was purified by silica gel chromatography (EtOAc/n-hexane=1:2, v/v) to afford the titled compound as a yellow solid (224 mg, 72%).

Compound 1042 was characterized as follows: $^1$H NMR (400 MHz, CDCl₃) δ 9.00 (bs, 1H, NH), 8.08 (s, 1H), 7.95 (d, J=8.4 Hz, 1H), 7.81 (d, J=8.4 Hz, 1H), 3.92 (d, J=12.4 Hz, 1H), 3.50 (d, J=12.4 Hz, 1H), 2.96 (s, 1H, OH), 1.54 (s, 3H); $^{19}$F NMR (CDCl₃, decoupled) δ− 62.21; MS (ESI) m/z 314.03 [M+H]⁺; 312.18 [M−H]⁻.

(S)—N-(6-Cyano-5-(trifluoromethyl)pyridin-3-yl)-2-hydroxy-2-methyl-3-(4-(trifluoromethyl)-1H-pyrazol-1-yl)propanamide (C₁₅H₁₁F₆N₅O₂) (1043)

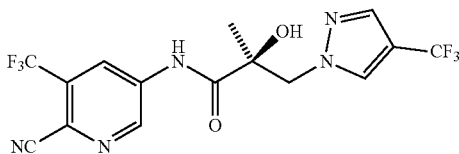 [SMILES: C[C@](O)(Cn1cc(C(F)(F)F)cn1)C(=O)Nc1cnc(C#N)c(C(F)(F)F)c1]

To a solution of 4-trifluoromethyl-pyrazole (0.10 g, 0.0007349 mol) in anhydrous THF (5 mL), which was cooled in an ice water bath under an argon atmosphere, was added sodium hydride (60% dispersion in oil, 0.09 g, 0.002025 mol). After addition, the resulting mixture was stirred for 3 h. (R)-3-Bromo-N-(6-cyano-5-(trifluoromethyl)pyridin-3-yl)-2-hydroxy-2-methylpropanamide (0.26 g, 0.0007349 mol) was added to the above solution, and the resulting reaction mixture was allowed to stir overnight at RT under argon. The reaction was quenched by water, and extracted with ethyl acetate. The organic layer was washed with brine, dried with MgSO₄, filtered, and concentrated under vacuum. The product was purified by a silica gel column using DCM and ethyl acetate (19:1) as eluent to afford 0.18 g (60%) of the titled compound as white solid.

Compound 1043 was characterized as follows: $^1$H NMR (400 MHz, DMSO-d₆) δ 10.63 (s, 1H, NH), 9.31 (s, 1H, ArH), 8.80 (s, 1H, ArH), 8.32 (s, 1H, Pyrazole-H), 7.81 (s, 1H, Pyrazole-H), 6.48 (s, 1H, OH), 4.55 (d, J=14.0 Hz, 1H, CH), 4.37 (d, J=14.0 Hz, 1H, CH), 1.42 (s, 3H, CH₃); mass (ESI, Negative): 406.08 [M−H]⁻; (ESI, Positive): [M+H]⁺, 430.13 [M+Na]⁺.

(S)—N-(4-Cyano-3-(trifluoromethyl)phenyl)-3-(5-(4-fluorophenyl)-1H-1,2,3-triazol-1-yl)-2-hydroxy-2-methylpropanamide (C₂₀H₁₅F₄N₅O₂) (1044)

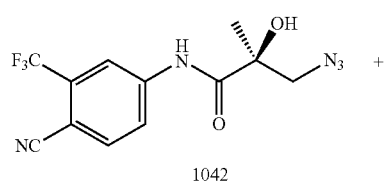

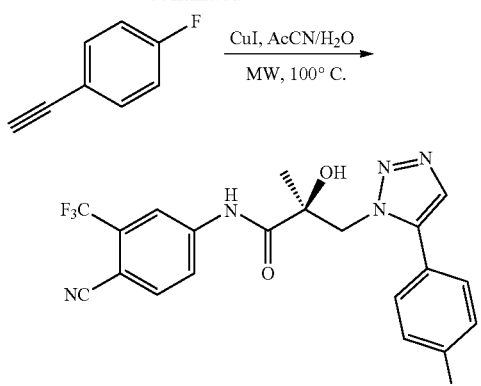

A mixture of 1042 (57 mg, 0.18 mmol), 1-ethynyl-4-fluorobenzene (0.015 mL, 0.18 mmol), and copper iodide (11 mg, 0.055 mmol) in AcCN/H₂O (1/0.5 mL) were loaded into a vessel with a cap. The reaction vessels were placed in a reactor block in the microwave reactor. A programmable microwave (MW) irradiation cycle of 30 min on (300 W) at 100° C. and 25 min off (fan-cooled) was executed twice because starting materials were shown on TLC after the first cycle (total irradiation time, 60 min). The mixture was transferred to a round bottom flask to be concentrated under reduced pressure and poured into EtOAc, which was washed with water and dried over MgSO₄, concentrated, and purified by silica gel chromatography (EtOAc/hexane=2:1) to afford the titled compound as yellow solid (69.8 mg, 90%).

Compound 1044 was characterized as follows: $^1$H NMR (400 MHz, acetone-d₆) δ 9.00 (bs, 1H, NH), 8.44 (s, 1H), 8.30 (s, 1H), 8.25 (d, J=8.4 Hz, 1H), 8.02 (d, J=8.4 Hz, 1H), 7.89 (dd, J=8.0, 2.4 Hz, 2H), 7.20 (d, J=8.8 Hz, 2H), 5.67 (s, 1H, OH), 4.92 (d, J=14.0 Hz, 1H), 4.72 (d, J=14.0 Hz, 1H), 1.60 (s, 3H); $^{19}$F NMR (acetone-d₆, decoupled) δ 114.68, 61.64; MS (ESI) m/z 432.11 [M−H]⁻ 434.08 [M+H]⁺. The structure of 1044 was distinguished from its isomer 1045 (see below) by the 2D NMR techniques of NOESY and COSY.

(S)—N-(4-Cyano-3-(trifluoromethyl)phenyl)-3-(4-(4-fluorophenyl)-1H-1,2,3-triazol-1-yl)-2-hydroxy-2-methylpropanamide (C₂₀H₁₅F₄N₅O₂) (1045)

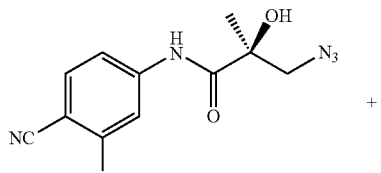

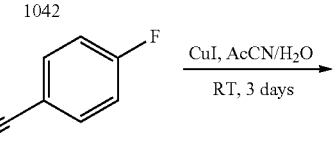

-continued

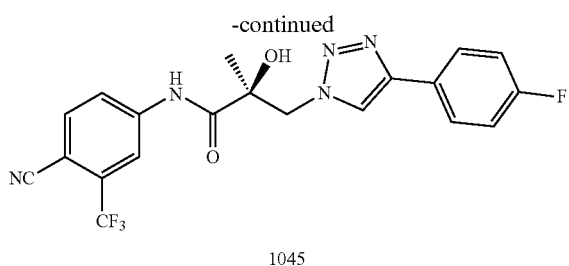

1045

To a suspension of copper(I)iodide (11 mg, 0.055 mmoL) in acetonitrile (7 mL)/water (3 mL) was added 1042 (57 mg, 0.182 mmol) at RT and then 1-ethynyl-4-fluorobenzene (0.015 mL, 0.182 mmol) was added. The resulting reaction mixture was stirred at RT for 3 days. The mixture was evaporated under reduced pressure, poured into water:brine (1:1, v/v) and then extracted with ethyl acetate. The combined organic extracts were then washed with brine, dried over sodium sulfate, filtered and evaporated. Purification was by chromatography (silica, 60% ethyl acetate in hexane) to afford a yellow solid (51.3 mg, 65%).

Compound 1045 was characterized as follows: $^1$H NMR (400 MHz, CDCl$_3$) δ 9.07 (bs, 1H, NH), 7.82-7.80 (m, 1H), 7.79 (s, 1H), 7.76-7.74 (m, 2H), 7.72 (dd, J=8.2, 2.8 Hz, 2H), 7.10 (t, J=8.8 Hz, 2H), 5.15 (bs, 1H, OH), 4.96 (d, J=14.0 Hz, 1H), 4.61 (d, J=14.0 Hz, 1H), 1.62 (s, 3H); $^{19}$F NMR (CDCl$_3$, decoupled) δ−62.24, −112.36; MS (ESI) m/z 432.17 [M−H]$^-$ −434.09 [M+H]$^+$. The structure of 1045 was distinguished from its isomer 1044 (see above) by the 2D NMR techniques of NOESY and COSY. E.g, 1045 showed an NOE cross-peak between the methylene proton and the triazole proton indicating that these protons are within ~4.5 Å of each other as would be the case for 1045 but not 1044. This cross-peak was not seen for 1044.

S)-3-(4-Fluoro-1H-pyrazol-1-yl)-2-hydroxy-2-methyl-N-(4-nitro-3-(trifluoromethyl)phenyl)-propanamide (C$_{14}$H$_{12}$F$_4$N$_4$O$_4$) (1046)

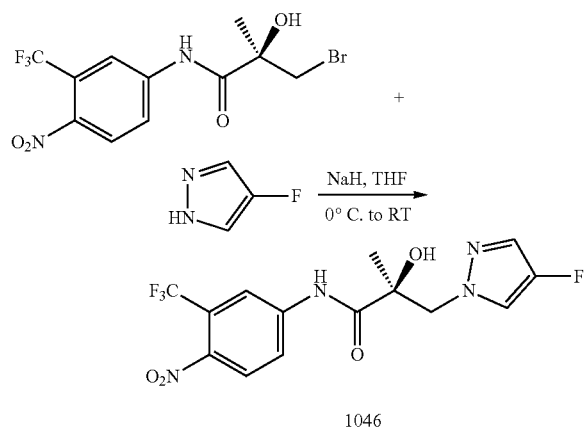

1046

To a dry, nitrogen-purged 100 mL round-bottom flask equipped with a dropping funnel under argon atmosphere containing 4-fluoro-1H-pyrazole (691 mg, 8.03 mmol), NaH of 60% dispersion in mineral oil (674 mg, 16.9 mmol) was added in 60 mL of anhydrous THF solvent at ice-water bath. The mixture was stirred 30 min at the ice-water bath. Into the flask through dropping funnel, a solution of (R)-3-bromo-2-hydroxy-2-methyl-N-(4-nitro-3-(trifluoromethyl)phenyl) propanamide (2.98 g, 8.03 mmol) in 10 mL of anhydrous THF was added under argon atmosphere at the ice-water bath, and stirred overnight at RT. After adding 1 mL of H$_2$O, the reaction mixture was condensed under reduced pressure, and then dispersed into 50 mL of EtOAc, washed with 50 mL (×2) water, evaporated, dried over anhydrous MgSO$_4$, and evaporated to dryness. The mixture was purified with flash column chromatography using as an eluent EtOAc/hexane in a 1:2 ratio to produce the titled compound (2.01 g, 67%) as yellow solid.

Compound 1046 was characterized as follows: $^1$H NMR (400 MHz, CDCl$_3$) δ 9.14 (bs, 1H, NH), 8.01 (s, 1H), 7.97-7.91 (m, 2H), 7.38 (d, J=3.6 Hz, 1H), 7.35 (d, J=4.4 Hz, 1H), 5.95 (s, 1H, OH), 4.56 (d, J=14.0 Hz, 1H), 4.17 (d, J=14.0 Hz, 1H), 1.48 (s, 3H); $^{19}$F NMR (CDCl$_3$, decoupled) δ −60.13, −176.47; MS (ESI) m/z 375.08 [M−H]$^-$; 377.22 [M+H]$^+$; 399.04 [M+Na]$^+$.

(S)—N-(4-Cyano-3-(trifluoromethyl)phenyl)-2-hydroxy-3-(4-iodo-1H-pyrazol-1-yl)-2-methylpropanamide (C$_{15}$H$_{12}$F$_3$IN$_4$O$_2$) (1047)

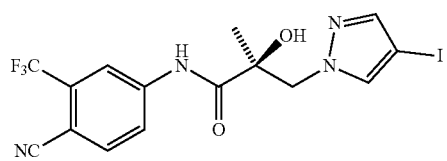

To a solution of 4-iodo-1H-pyrazole (0.20 g, 0.001031 mol) in anhydrous THF (5 mL), which was cooled in an ice water bath under an argon atmosphere, was added sodium hydride (60% dispersion in oil, 0.124 g, 0.003093 mol). After addition, the resulting mixture was stirred for 3 h. (R)-3-Bromo-N-(4-cyano-3-(trifluoromethyl)phenyl)-2-hydroxy-2-methylpropanamide (8, 0.36 g, 0.001031 mol) was added to the above solution, and the resulting reaction mixture was allowed to stir overnight at RT under argon. The reaction was quenched by water, and extracted with ethyl acetate. The organic layer was washed with brine, dried with MgSO$_4$, filtered, and concentrated under vacuum. The product was purified by a silica gel column using DCM and ethyl acetate (19:1) as eluent to afford 0.25 g (52%) of the titled compound as off-white solid.

Compound 1047 was characterized as follows: $^1$H NMR (400 MHz, DMSO-d$_6$) δ 10.36 (s, 1H, NH), 8.45 (s, 1H, ArH), 8.23 (d, J=8.8 Hz, J=1.2 Hz, 1H, ArH), 8.10 (d, J=8.8 Hz, 1H, ArH), 7.78 (s, 1H, Pyrazole-H), 7.46 (s, 1H, Pyrazole-H), 6.31 (s, 1H, OH), 4.48 (d, J=14.0 Hz, 1H, CH), 4.31 (d, J=14.0 Hz, 1H, CH), 1.35 (s, 3H, CH$_3$); mass (ESI, Negative): 463.18 [M−H]$^-$; (ESI, Positive): 486.96 [M+Na]$^+$.

(S)-3-(4-Cyano-1H-pyrazol-1-yl)-N-(4-cyano-3-(trifluoromethyl)phenyl)-2-hydroxy-2-methylpropanamide (C$_{16}$H$_{12}$F$_3$N$_5$O$_2$) (1048)

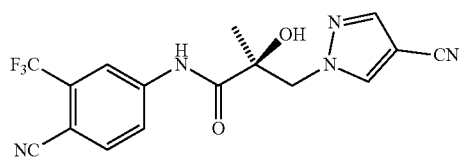 [SMILES: C[C@](O)(Cn1cc(C#N)cn1)C(=O)Nc1ccc(C#N)c(C(F)(F)F)c1]

To a solution of 1H-pyrazole-4-carbonitrile (0.10 g, 0.001074 mol) in anhydrous THF (5 mL), which was cooled in an ice water bath under an argon atmosphere, was added sodium hydride (60% dispersion in oil, 0.11 g, 0.003223 mol). After addition, the resulting mixture was stirred for 3 h. (R)-3-Bromo-N-(4-cyano-3-(trifluoromethyl)phenyl)-2-hydroxy-2-methylpropanamide (8, 0.377 g, 0.001074 mol) was added to the above solution, and the resulting reaction mixture was allowed to stir overnight at RT under argon. The reaction was quenched by water, and extracted with ethyl acetate. The organic layer was washed with brine, dried with $MgSO_4$, filtered, and concentrated under vacuum. The product was purified by a silica gel column using hexane and ethyl acetate (1:1 to 1:2) as eluent to afford 0.18 g (46%) of the titled compound as white solid.

Compound 1048 was characterized as follows: $^1$H NMR (400 MHz, DMSO-$d_6$) δ 10.35 (s, 1H, NH), 8.45 (d, J=1.2 Hz, 1H, ArH), 8.43 (s, 1H, Pyrazole-H), 8.22 (d, J=8.8 Hz, J=1.2 Hz, 1H, ArH), 8.10 (d, J=8.8 Hz, 1H, ArH), 7.98 (s, 1H, Pyrazole-H), 6.41 (s, 1H, OH), 4.45 (d, J=14.0 Hz, 1H, CH), 4.36 (d, J=14.0 Hz, 1H, CH), 1.38 (s, 3H, $CH_3$); mass (ESI, Negative): 362.11 [M−H]$^+$; (ESI, Positive): 386.07 [M+Na]$^+$.

(S)-3-(4-Chloro-1H-pyrazol-1-yl)-N-(4-cyano-3-(trifluoromethyl)phenyl)-2-hydroxy-2-methylpropanamide ($C_{15}H_{12}ClF_3N_4O_2$) (1049)

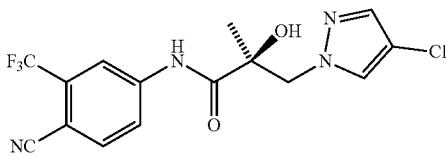 [SMILES: C[C@](O)(Cn1cc(Cl)cn1)C(=O)Nc1ccc(C#N)c(C(F)(F)F)c1]

To a solution of 4-chloro-1H-pyrazole (0.15 g, 0.001463 mol) in anhydrous THF (5 mL), which was cooled in an ice water bath under an argon atmosphere, was added sodium hydride (60% dispersion in oil, 0.18 g, 0.004389 mol). After addition, the resulting mixture was stirred for 3 h. (R)-3-Bromo-N-(4-cyano-3-(trifluoromethyl)phenyl)-2-hydroxy-2-methylpropanamide (8, 0.51 g, 0.001463 mol) was added to the above solution, and the resulting reaction mixture was allowed to stir overnight at RT under argon. The reaction was quenched by water, and extracted with ethyl acetate. The organic layer was washed with brine, dried with $MgSO_4$, filtered, and concentrated under vacuum. The product was purified by a silica gel column using dichloromethane and ethyl acetate (19:1) as eluent to afford 0.30 g (55%) of the titled compound as white solid.

Compound 1049 was characterized as follows: $^1$H NMR (400 MHz, DMSO-$d_6$) δ 10.38 (s, 1H, NH), 8.46 (s, 1H, ArH), 8.23 (d, J=8.6 Hz, J=1.2 Hz, 1H, ArH), 8.10 (d, J=8.6 Hz, 1H, ArH), 7.83 (s, 1H, Pyrazole-H), 7.47 (s, 1H, Pyrazole-H), 6.34 (s, 1H, OH), 4.45 (d, J=14.0 Hz, 1H, CH), 4.27 (d, J=14.0 Hz, 1H, CH), 1.36 (s, 3H, $CH_3$); mass (ESI, Negative): 371.68 [M−H]$^−$.

Example 2

Octanol-Water Partition Coefficient (Log P)

Log P is the log of the octanol-water partition coefficient, commonly used early in drug discovery efforts as a rough estimate of whether a particular molecule is likely to cross biological membranes. Log P was calculated using ChemDraw Ultra version is 12.0.2.1016 (Perkin-Elmer, Waltham, Mass. 02451). Calculated Log P values are reported in Table 1 in the column labeled 'Log P (−0.4 to +5.6)'. Lipinski's rule of five is a set of criteria intended to predict oral bioavailability. One of these criteria for oral bioavailability is that the Log P is between the values shown in the column heading (−0.4 (relatively hydrophilic) to +5.6 (relatively lipophilic) range), or more generally stated <5. One of the goals of SARD design was to improve water solubility. The monocyclic templates of this invention such as the pyrazoles, pyrroles, etc. were more water soluble than earlier analogs. For instance, one may compare the Log P values of SARDs from other templates, e.g., alkyl-amine 17, indoline 100 and indole 11, to the monocyclics of the invention (1001-1064).

TABLE 1

In vitro screening of LBD binding (Ki), AR antagonism (IC50), SARD activity, and metabolic stability

| Compound # | Structure | Log P (−0.4 to +5.6) | M.W. | wtAR Binding (K$_i$ (left)) & Transactivation (IC$_{50}$ (right)) (nM) | | SARD Activity (% inh): Full Length (left) and S.V. (right) | | DMPK (MLM) T$_{1/2}$ (min) & CL$_{int}$ (μL/min/mg) |
| --- | --- | --- | --- | --- | --- | --- | --- | --- |
| | | | | K$_i$ (nM) (DHT = 1 nM) | IC$_{50}$ (nM) | Full Length % inhibition at 1, 10 μM | S.V. % inhibition at 10 μM | |
| Enobosarm (agonist) | 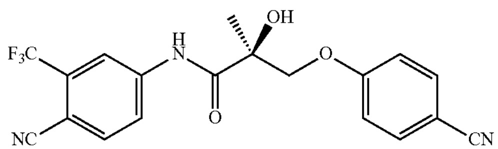 [SMILES: C[C@](O)(COc1ccc(C#N)cc1)C(=O)Nc1ccc(C#N)c(C(F)(F)F)c1] | 3.44 | 389.89 | 20.21 | ~20 (EC$_{50}$) | Not applicable | Not applicable | |
| R-Bicalutamide | 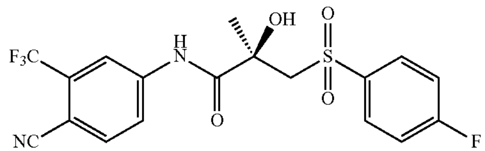 [SMILES: C[C@](O)(CS(=O)(=O)c1ccc(F)cc1)C(=O)Nc1ccc(C#N)c(C(F)(F)F)c1] | 2.57 | 430.37 | 508.84 | 248.2 | 0 | 0 | |
| Enzalutamide | 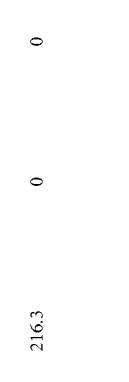 | 4.56 | 464.44 | 3641.29 | 216.3 | 0 | 0 | |
| ARN-509 | 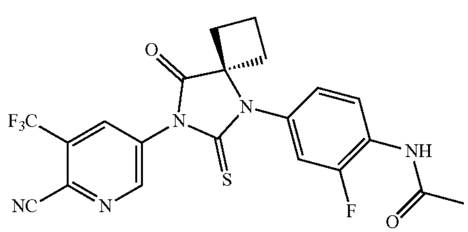 | 3.47 | 477.43 | 1452.29 | | 0 | 0 | |

TABLE 1-continued

In vitro screening of LBD binding (Ki), AR antagonism (IC50), SARD activity, and metabolic stability

| Compound # | Structure | Log P (−0.4 to +5.6) | M.W. | wtAR Binding (K$_i$ (left)) & Transactivation (IC$_{50}$ (right)) (nM) | | SARD Activity (% inh): Full Length (left) and S.V. (right) | | DMPK (MLM) T$_{1/2}$ (min) & CL$_{int}$ (µL/min/mg) |
|---|---|---|---|---|---|---|---|---|
| | | | | K$_i$ (nM) (DHT = 1 nM) | IC$_{50}$ (nM) | Full Length % inhibition at 1, 10 µM | S.V. % inhibition at 10 µM | |
| 17 | 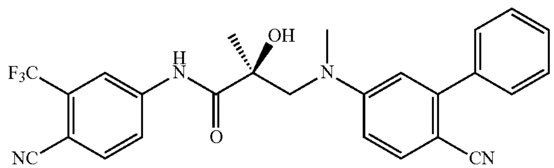 [SMILES: CN(C[C@](C)(O)C(=O)Nc1ccc(C#N)c(C(F)(F)F)c1)c1ccc(C#N)c(-c2ccccc2)c1] | 5.69 | 478.48 | 28.4 | 95 | | | |
| 100 | 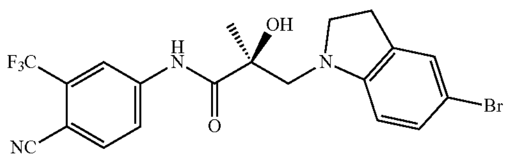 [SMILES: C[C@](O)(CN1CCc2cc(Br)ccc21)C(=O)Nc1ccc(C#N)c(C(F)(F)F)c1] | 4.62 | 468.27 | 197.67 | 530.95 | 60 | 41 | 66.87 10.38 |
| 11 | 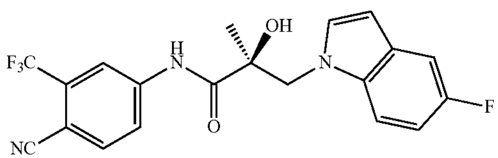 [SMILES: C[C@](O)(Cn1ccc2cc(F)ccc21)C(=O)Nc1ccc(C#N)c(C(F)(F)F)c1] | 3.47 | 405.35 | 267.39 | 85.10 | 65-83 | 60-100 | 12.35 56.14 |
| 1001 | 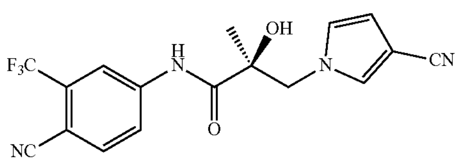 [SMILES: C[C@](O)(Cn1ccc(C#N)c1)C(=O)Nc1ccc(C#N)c(C(F)(F)F)c1] | 2.29 | 362.31 | 327.97 | partial agonist | 0 | 0 | 23.5 29.5 |
| 1002 | 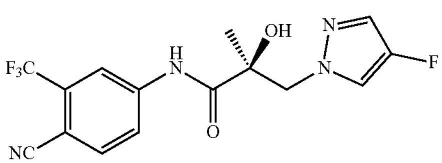 [SMILES: C[C@](O)(Cn1cc(F)cn1)C(=O)Nc1ccc(C#N)c(C(F)(F)F)c1] | 2.03 | 356.27 | No binding | 199.36 | 100 | 100 | 77.96 0.89 |

TABLE 1-continued

In vitro screening of LBD binding (Ki), AR antagonism (IC50), SARD activity, and metabolic stability

| Compound # | Structure | Log P (−0.4 to +5.6) | M.W. | wtAR Binding (K$_i$ (left)) & Transactivation (IC$_{50}$ (right)) (nM) | | SARD Activity (% inh): Full Length (left) and S.V. (right) | | DMPK (MLM) |
| --- | --- | --- | --- | --- | --- | --- | --- | --- |
| | | | | K$_i$ (nM) (DHT = 1 nM) | IC$_{50}$ (nM) | Full Length % inhibition at 1, 10 μM | S.V. % inhibition at 10 μM | T$_{1/2}$ (min) & CL$_{int}$ (μL/min/mg) |
| 1003 | 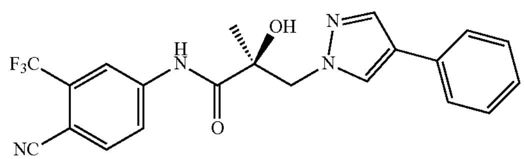 [SMILES: C[C@](O)(Cn1cc(-c2ccccc2)cn1)C(=O)Nc1ccc(C#N)c(C(F)(F)F)c1] | 3.54 | 414.38 | No binding | 1152.78 | 0 | 0 | 48.45 14.31 |
| 1004 | 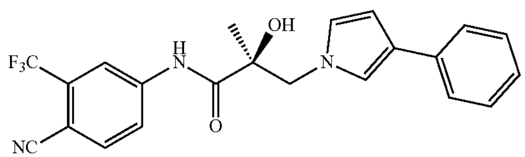 [SMILES: C[C@](O)(Cn1ccc(-c2ccccc2)c1)C(=O)Nc1ccc(C#N)c(C(F)(F)F)c1] | 3.93 | 413.39 | 322.11 | 178.77 (partial agonist) | 0%, 40% @ 10 μM | 0 | 3.96 175.2 |
| 1005 | 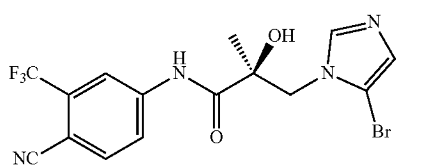 [SMILES: C[C@](O)(Cn1cncc1Br)C(=O)Nc1ccc(C#N)c(C(F)(F)F)c1] | 1.78 | 417.18 | No binding | 1019.38 | 50 | 70 | 16.51 41.58 |
| 1006 | 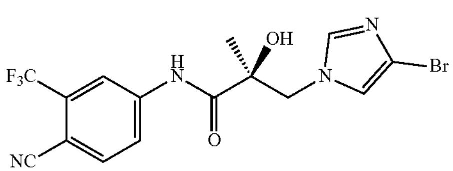 [SMILES: C[C@](O)(Cn1cnc(Br)c1)C(=O)Nc1ccc(C#N)c(C(F)(F)F)c1] | 2.3 | 417.18 | 905.71 | 148.94 (partial agonist) | 0 | 0 | |
| 1007 | 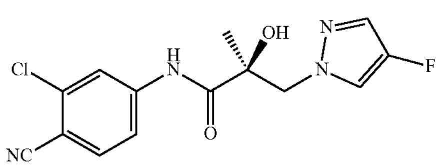 [SMILES: C[C@](O)(Cn1cc(F)cn1)C(=O)Nc1ccc(C#N)c(Cl)c1] | 1.66 | 322.72 | No binding | 958.77 | 0 | 0 | |

TABLE 1-continued

In vitro screening of LBD binding (Ki), AR antagonism (IC50), SARD activity, and metabolic stability

| Compound # | Structure | Log P (−0.4 to +5.6) | M.W. | wtAR Binding (K$_i$ (left)) & Transactivation (IC$_{50}$ (right)) (nM) | | SARD Activity (% inh): Full Length (left) and S.V. (right) | | DMPK (MLM) T$_{1/2}$ (min) & CL$_{int}$ (μL/min/mg) |
|---|---|---|---|---|---|---|---|---|
| | | | | K$_i$ (nM) (DHT = 1 nM) | IC$_{50}$ (nM) | Full Length % inhibition at 1, 10 μM | S.V. % inhibition at 10 μM | |
| 1008 | 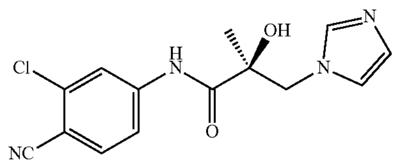 | 0.71 | 304.73 | No binding | 1856.8 | 0 | 30 | 24.61 / 28.16 |
| 1009 | 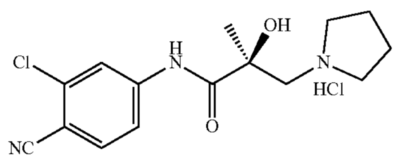 [SMILES: C[C@](O)(CN1CCCC1)C(=O)Nc1ccc(C#N)c(Cl)c1 ; Cl] | 1.69 (for free amine) | 307.78 (for free amine) | No binding | No inhibition | 0 | 0 | |
| 1010 | 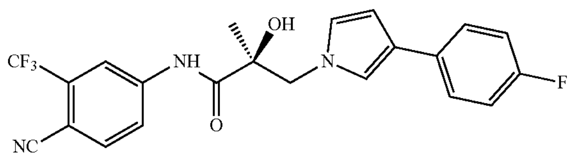 [SMILES: C[C@](O)(Cn1ccc(-c2ccc(F)cc2)c1)C(=O)Nc1ccc(C#N)c(C(F)(F)F)c1] | 4.09 | 431.38 | 259.29 | 225.91 | 100 | 60 | 17.93 / 38.66 |
| 1011 | 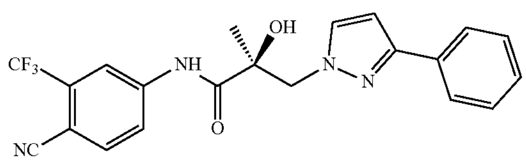 [SMILES: C[C@](O)(Cn1ccc(-c2ccccc2)n1)C(=O)Nc1ccc(C#N)c(C(F)(F)F)c1] | 3.97 | 414.38 | 3660 | 4770 | 0 | 0 | |
| 1012 | 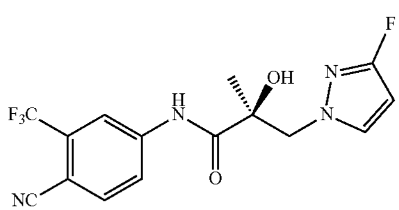 | 2.49 | 356.27 | 820.97 | 219.48 | 82 | 73 | 64.07 / 1.02 |

TABLE 1-continued

In vitro screening of LBD binding (Ki), AR antagonism (IC50), SARD activity, and metabolic stability

| Compound # | Structure | Log P (−0.4 to +5.6) | M.W. | wtAR Binding (K$_i$ (left)) & Transactivation (IC$_{50}$ (right)) (nM) | | SARD Activity (% inh): Full Length (left) and S.V. (right) | | DMPK (MLM) T$_{1/2}$ (min) & CL$_{int}$ (μL/min/mg) |
|---|---|---|---|---|---|---|---|---|
| | | | | K$_i$ (nM) (DHT = 1 nM) | IC$_{50}$ (nM) | Full Length % inhibition at 1, 10 μM | S.V. % inhibition at 10 μM | |
| 1013 | 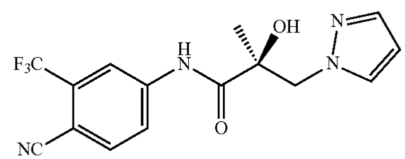 [SMILES: C[C@](O)(Cn1cccn1)C(=O)Nc1ccc(C#N)c(C(F)(F)F)c1] | 1.87 | 338.28 | 7398 | 1441.58 | 0 | | |
| 1014 | 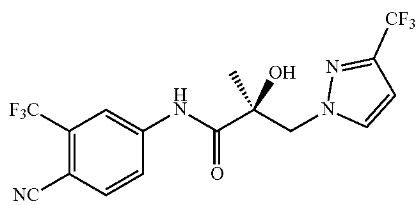 [SMILES: C[C@](O)(Cn1ccc(C(F)(F)F)n1)C(=O)Nc1ccc(C#N)c(C(F)(F)F)c1] | 3.21 | 406.28 | 512.3 | 204.59 | 67 (comparable to 11 in the same exp) | 54 (comparable to 11 in the same exp) | 330 0 |
| 1015 | 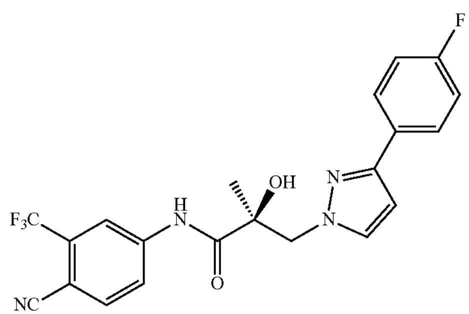 [SMILES: C[C@](O)(Cn1ccc(-c2ccc(F)cc2)n1)C(=O)Nc1ccc(C#N)c(C(F)(F)F)c1] | 4.13 | 432.37 | >10000 | 1742 | 72 | 0 | |
| 1016 | 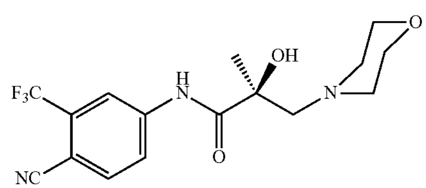 [SMILES: C[C@](O)(CN1CCOCC1)C(=O)Nc1ccc(C#N)c(C(F)(F)F)c1] | 1.34 | 357.33 | 1874.68 | 1018.68 | 52 | 80 | |

TABLE 1-continued

In vitro screening of LBD binding (Ki), AR antagonism (IC50), SARD activity, and metabolic stability

| Compound # | Structure | Log P (−0.4 to +5.6) | M.W. | wtAR Binding (K$_i$ (left)) & Transactivation (IC$_{50}$ (right)) (nM) | | SARD Activity (% inh): Full Length (left) and S.V. (right) | | DMPK (MLM) |
| --- | --- | --- | --- | --- | --- | --- | --- | --- |
| | | | | K$_i$ (nM) (DHT = 1 nM) | IC$_{50}$ (nM) | Full Length % inhibition at 1, 10 μM | S.V. % inhibition at 10 μM | T$_{1/2}$ (min) & CL$_{int}$ (μL/min/mg) |
| 1017 | 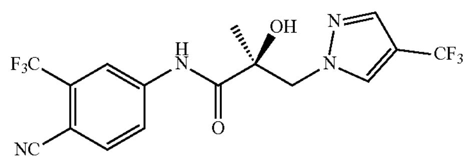 [SMILES: C[C@](O)(Cn1cc(C(F)(F)F)cn1)C(=O)Nc1ccc(C#N)c(C(F)(F)F)c1] | 2.79 | 406.28 | 898.23 | 404.39 | 80 | 100 | Infinity 0 |
| 1018 | 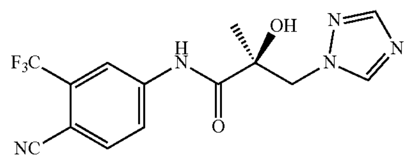 [SMILES: C[C@](O)(Cn1cncn1)C(=O)Nc1ccc(C#N)c(C(F)(F)F)c1] | 1.42 | 339.27 | No binding | 1091.56 | 0 | 0 | |
| 1019 | 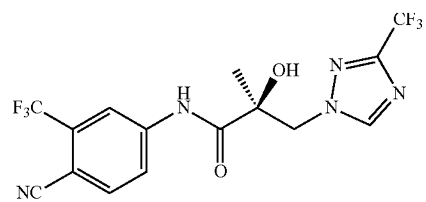 [SMILES: C[C@](O)(Cn1cnc(C(F)(F)F)n1)C(=O)Nc1ccc(C#N)c(C(F)(F)F)c1] | 3.23 | 407.23 | No binding | 1012.75 | 68 | 100 | |
| 1020 | 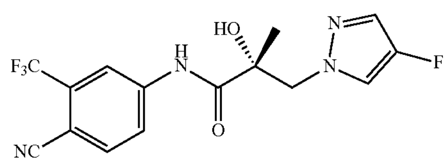 [SMILES: C[C@@](O)(Cn1cc(F)cn1)C(=O)Nc1ccc(C#N)c(C(F)(F)F)c1] | 2.03 | 356.27 | No binding | 192 | 84 | 0 | |
| 1021 | 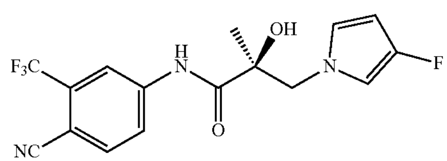 [SMILES: C[C@](O)(Cn1ccc(F)c1)C(=O)Nc1ccc(C#N)c(C(F)(F)F)c1] | 2.41 | 355.39 | 633.23 | partial | 0 | | |

TABLE 1-continued

In vitro screening of LBD binding (Ki), AR antagonism (IC50), SARD activity, and metabolic stability

| Compound # | Structure | Log P (−0.4 to +5.6) | M.W. | wtAR Binding (K_i (left)) & Transactivation (IC_{50} (right)) (nM) | | SARD Activity (% inh): Full Length (left) and S.V. (right) | | DMPK (MLM) |
| --- | --- | --- | --- | --- | --- | --- | --- | --- |
| | | | | K_i (nM) (DHT = 1 nM) | IC_{50} (nM) | Full Length % inhibition at 1, 10 μM | S.V. % inhibition at 10 μM | T_{1/2} (min) & CL_{int} (μL/min/mg) |
| 1022 | 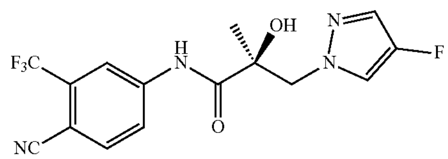 [SMILES: C[C@](O)(Cn1cc(F)cn1)C(=O)Nc1ccc(C#N)c(C(F)(F)F)c1] | 1.11 | 357.26 | No binding | 92.17 | 54 | 81 | |
| 1023 | 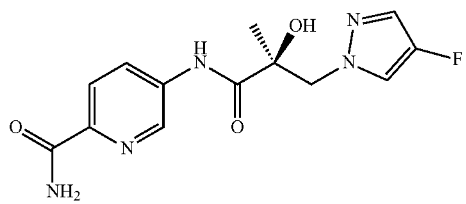 [SMILES: C[C@](O)(Cn1cc(F)cn1)C(=O)Nc1ccc(C(N)=O)nc1] | −0.93 | 307.28 | No binding | No effect | 0 | 0 | Infinity 0 |
| 1024 | 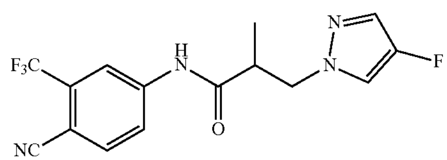 [SMILES: CC(Cn1cc(F)cn1)C(=O)Nc1ccc(C#N)c(C(F)(F)F)c1] | 2.86 | 340.28 | No binding | 463.9 | 60 | 70 | |
| 1025 | 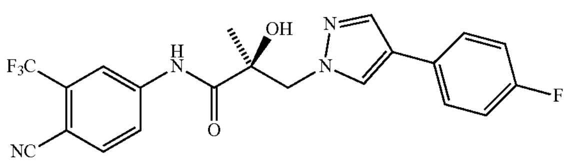 [SMILES: C[C@](O)(Cn1cc(-c2ccc(F)cc2)cn1)C(=O)Nc1ccc(C#N)c(C(F)(F)F)c1] | 3.7 | 432.37 | 612.4 | 969 | 60 | 0 | Infinity 0 |
| 1026 | 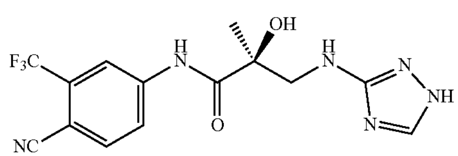 [SMILES: C[C@](O)(CNc1nc[nH]n1)C(=O)Nc1ccc(C#N)c(C(F)(F)F)c1] | 1.19 | 354.29 | — | — | 0 | | |

TABLE 1-continued

In vitro screening of LBD binding (Ki), AR antagonism (IC50), SARD activity, and metabolic stability

| Compound # | Structure | Log P (−0.4 to +5.6) | M.W. | wtAR Binding (K$_i$ (left)) & Transactivation (IC$_{50}$ (right)) (nM) | | SARD Activity (% inh): Full Length (left) and S.V. (right) | | DMPK (MLM) T$_{1/2}$ (min) & CL$_{int}$ (µL/min/mg) |
|---|---|---|---|---|---|---|---|---|
| | | | | K$_i$ (nM) (DHT = 1 nM) | IC$_{50}$ (nM) | Full Length % inhibition at 1, 10 µM | S.V. % inhibition at 10 µM | |
| 1027 | 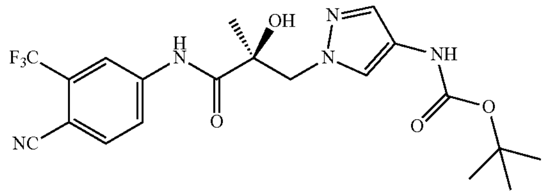 [SMILES: CC(C)(C)OC(=O)Nc1cnn(C[C@](C)(O)C(=O)Nc2ccc(C#N)c(C(F)(F)F)c2)c1] | 2.24 | 453.41 | 1382.06 | 1153 | 20 | | |
| 1028 | 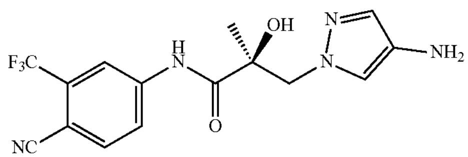 [SMILES: C[C@](O)(Cn1cc(N)cn1)C(=O)Nc1ccc(C#N)c(C(F)(F)F)c1] | 1.07 | 353.30 | 227.48 | Agonist | | | |
| 1029 | 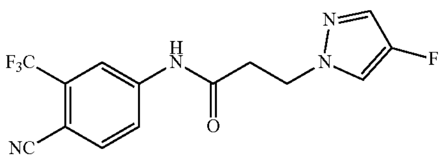 [SMILES: N#Cc1ccc(NC(=O)CCn2cc(F)cn2)cc1C(F)(F)F] | 2.29 | 326.25 | No binding | 2124 | 35 | 40 | |
| 1030 | 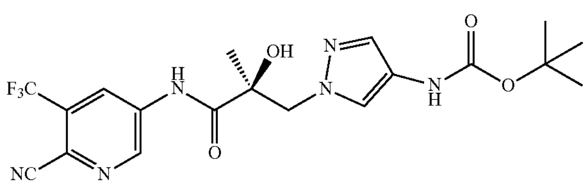 [SMILES: CC(C)(C)OC(=O)Nc1cnn(C[C@](C)(O)C(=O)Nc2cnc(C#N)c(C(F)(F)F)c2)c1] | 1.32 | 454.40 | No binding | 6108 | — | | |
| 1031 | 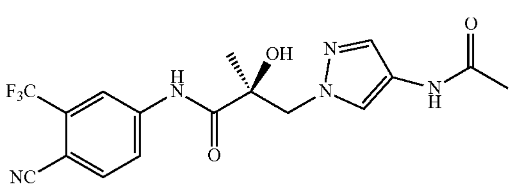 [SMILES: CC(=O)Nc1cnn(C[C@](C)(O)C(=O)Nc2ccc(C#N)c(C(F)(F)F)c2)c1] | 0.78 | 395.34 | No binding | No effect | — | | |

TABLE 1-continued

In vitro screening of LBD binding (Ki), AR antagonism (IC50), SARD activity, and metabolic stability

| Compound # | Structure | Log P (−0.4 to +5.6) | M.W. | wtAR Binding ($K_i$ (left)) & Transactivation ($IC_{50}$ (right)) (nM) | | SARD Activity (% inh): Full Length (left) and S.V. (right) | | DMPK (MLM) $T_{1/2}$ (min) & $CL_{int}$ (μL/min/mg) |
|---|---|---|---|---|---|---|---|---|
| | | | | $K_i$ (nM) (DHT = 1 nM) | $IC_{50}$ (nM) | Full Length % inhibition at 1, 10 μM | S.V. % inhibition at 10 μM | |
| 1032 | 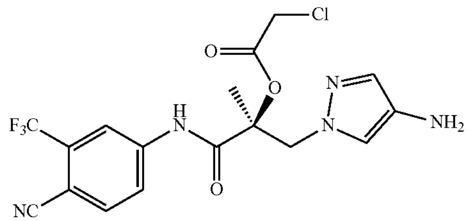 [SMILES: C[C@@](Cn1cc(N)cn1)(OC(=O)CCl)C(=O)Nc1ccc(C#N)c(C(F)(F)F)c1] | 1.82 | 429.78 | No binding | 900.86 | | | |
| 1033 | 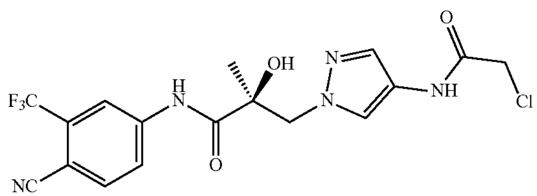 [SMILES: C[C@](O)(Cn1cc(NC(=O)CCl)cn1)C(=O)Nc1ccc(C#N)c(C(F)(F)F)c1] | 1.3 | 411.34 | No binding | No effect | | | |
| 1034 | 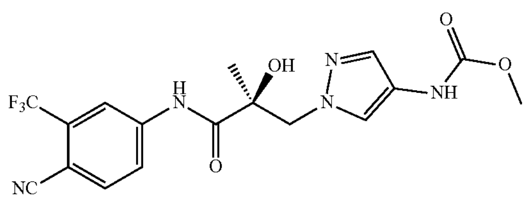 [SMILES: COC(=O)Nc1cnn(C[C@](C)(O)C(=O)Nc2ccc(C#N)c(C(F)(F)F)c2)c1] | 1.3 | 411.34 | | 827 | | | |
| 1035 | 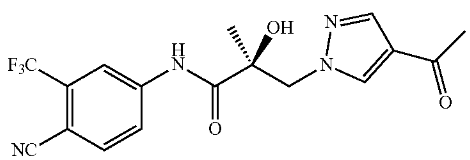 [SMILES: CC(=O)c1cnn(C[C@](C)(O)C(=O)Nc2ccc(C#N)c(C(F)(F)F)c2)c1] | 1.2 | 380.32 | | 757.7 | | | |

TABLE 1-continued

In vitro screening of LBD binding (Ki), AR antagonism (IC50), SARD activity, and metabolic stability

| | | | wtAR Binding (K$_i$ (left)) & Transactivation (IC$_{50}$ (right)) (nM) | | SARD Activity (% inh): Full Length (left) and S.V. (right) | | DMPK (MLM) |
|---|---|---|---|---|---|---|---|
| Compound # | Structure | Log P (−0.4 to +5.6) | M.W. | K$_i$ (nM) (DHT = 1 nM) | IC$_{50}$ (nM) | Full Length % inhibition at 1, 10 μM | S.V. % inhibition at 10 μM | T$_{1/2}$ (min) & CL$_{int}$ (μL/min/mg) |
| 1036 | | 1.9 | 383.28 | 2225 | 36.22 | 20 | | |
| 1037 | | 0.7 | 284.11 | 4547 | 350.5 | >50 | | |
| 1038 | | 1.6 | 352.11 | | 2490 | | | |
| 1039 | | 1.1 | 310.15 | | 1750 | | | |
| 1040 | | 2.8 | 321.09 | | — | | | |

TABLE 1-continued

In vitro screening of LBD binding (Ki), AR antagonism (IC50), SARD activity, and metabolic stability

| Compound # | Structure | Log P (−0.4 to +5.6) | M.W. | wtAR Binding (K$_i$ (left)) & Transactivation (IC$_{50}$ (right)) (nM) K$_i$ (nM) (DHT = 1 nM) | IC$_{50}$ (nM) | SARD Activity (% inh): Full Length (left) and S.V. (right) Full Length % inhibition at 1, 10 μM | S.V. % inhibition at 10 μM | DMPK (MLM) T$_{1/2}$ (min) & CL$_{int}$ (μL/min/mg) |
|---|---|---|---|---|---|---|---|---|
| 1041 | 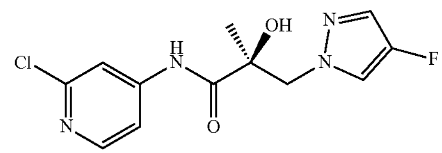 [SMILES: C[C@](O)(Cn1cc(F)cn1)C(=O)Nc1ccnc(Cl)c1] | 0.6 | 298.70 | | 2470 | >75 | | |
| 1042 | 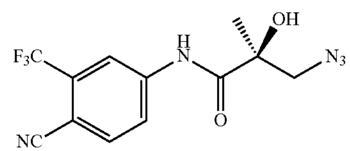 [SMILES: C[C@](O)(CN=[N+]=[N-])C(=O)Nc1ccc(C#N)c(C(F)(F)F)c1] | 0.8 | 313.24 | | — | | | |
| 1043 | 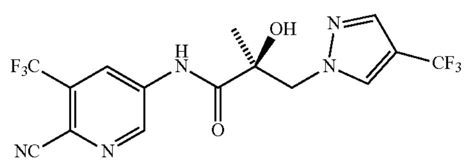 [SMILES: C[C@](O)(Cn1cc(C(F)(F)F)cn1)C(=O)Nc1cnc(C#N)c(C(F)(F)F)c1] | 1.8 | 407.27 | | 57.91 | 10 | | |
| 1044 | 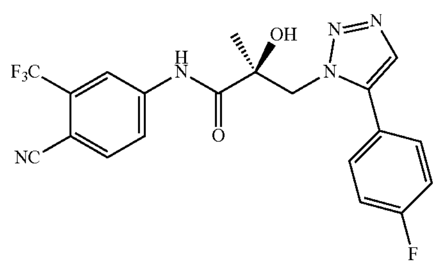 [SMILES: C[C@](O)(Cn1nncc1-c1ccc(F)cc1)C(=O)Nc1ccc(C#N)c(C(F)(F)F)c1] | 3.4 | 433.36 | | 316.7 | 73 | | |

TABLE 1-continued

In vitro screening of LBD binding (Ki), AR antagonism (IC50), SARD activity, and metabolic stability

| Compound # | Structure | Log P (−0.4 to +5.6) | M.W. | wtAR Binding (K$_i$ (left)) & Transactivation (IC$_{50}$ (right)) (nM) | | SARD Activity (% inh): Full Length (left) and S.V. (right) | | DMPK (MLM) |
|---|---|---|---|---|---|---|---|---|
| | | | | K$_i$ (nM) (DHT = 1 nM) | IC$_{50}$ (nM) | Full Length % inhibition at 1, 10 μM | S.V. % inhibition at 10 μM | T$_{1/2}$ (min) & CL$_{int}$ (μL/min/mg) |
| 1045 | 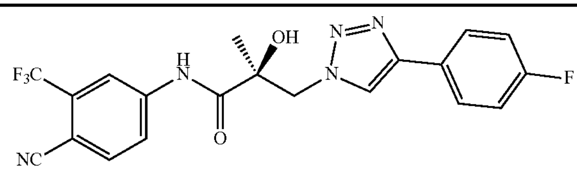 | 3.7 | 433.36 | | 250.9 | 84 | | |
| 1046 | 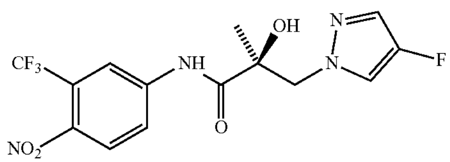 [SMILES: C[C@](O)(Cn1cc(F)cn1)C(=O)Nc1ccc([N+](=O)[O-])c(C(F)(F)F)c1] | 2.0 | 376.24 | | Partial | | | |
| 1047 | 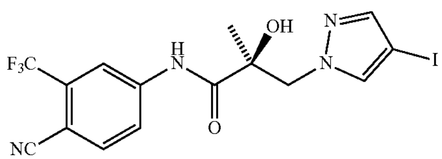 | 3.2 | 464.19 | | | | | |
| 1048 | 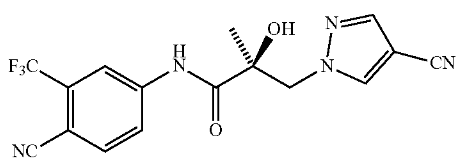 [SMILES: C[C@](O)(Cn1cc(C#N)cn1)C(=O)Nc1ccc(C#N)c(C(F)(F)F)c1] | 1.9 | 363.30 | | | | | |
| 1049 | 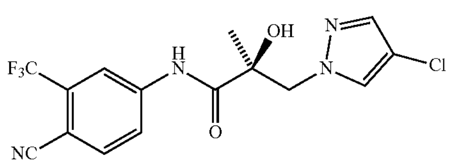 [SMILES: C[C@](O)(Cn1cc(Cl)cn1)C(=O)Nc1ccc(C#N)c(C(F)(F)F)c1] | 2.4 | 372.73 | | | | | |

TABLE 1-continued

In vitro screening of LBD binding (Ki), AR antagonism (IC50), SARD activity, and metabolic stability

| Compound # | Structure | Log P (−0.4 to +5.6) | M.W. | wtAR Binding (K$_i$ (left)) & Transactivation (IC$_{50}$ (right)) (nM) K$_i$ (nM) (DHT = 1 nM) | IC$_{50}$ (nM) | SARD Activity (% inh): Full Length (left) and S.V. (right) Full Length % inhibition at 1, 10 μM | S.V. % inhibition at 10 μM | DMPK (MLM) T$_{1/2}$ (min) & CL$_{int}$ (μL/min/mg) |
|---|---|---|---|---|---|---|---|---|
| 1002-oxalic acid salt | | | | | 57.99 | | | |
| 1002-succinic acid salt | | | | | 83.06 | | | |
| 1002-HBr | | | | | 77.2 | | | |
| 1002-tartaric acid salt | | | | | 259.1 (similar to 1002 in this experiment) | | | |
| 1002-HCl | | | | | 123.5 | | | |
| 1050 | 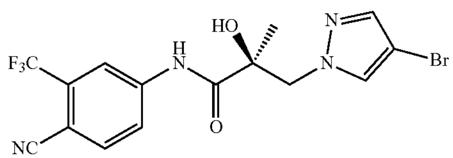 | 2.7 | 417.18 | >10000 | 427 | 42 | 0 | |
| 1051 | 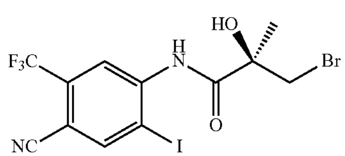 | 3.9 | 477.02 | | No effect | | | |
| 1052 | 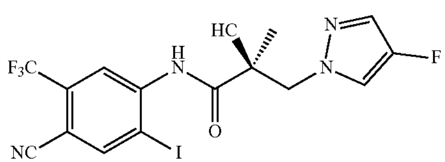 | 3.3 | 482.17 | | 5450 | | | |

TABLE 1-continued

In vitro screening of LBD binding (Ki), AR antagonism (IC50), SARD activity, and metabolic stability

| | | | wtAR Binding (K$_i$ (left)) & Transactivation (IC$_{50}$ (right)) (nM) | | SARD Activity (% inh): Full Length (left) and S.V. (right) | | |
|---|---|---|---|---|---|---|---|
| Compound # | Structure | Log P (−0.4 to +5.6) | M.W. | K$_i$ (nM) (DHT = 1 nM) | IC$_{50}$ (nM) | Full Length % inhibition at 1, 10 μM | S.V. % inhibition at 10 μM | DMPK (MLM) T$_{1/2}$ (min) & CL$_{int}$ (μL/min/mg) |
| 1053 | | 3.4 | 434.35 | | No effect | | | |
| 1054 | | 1.7 | 368.31 | | — | 0 | 0 | |
| 1055 | | 2.3 | 352.31 | 1552 | 8087 | | | |
| 1057 (Racemate) | | 2.03 | 356.27 | | | | | |

TABLE 1-continued

In vitro screening of LBD binding (Ki), AR antagonism (IC50), SARD activity, and metabolic stability

| Compound # | Structure | Log P (−0.4 to +5.6) | M.W. | wtAR Binding (K$_i$ (left)) & Transactivation (IC$_{50}$ (right)) (nM) | | SARD Activity (% inh): Full Length (left) and S.V. (right) | | DMPK (MLM) T$_{1/2}$ (min) & CL$_{int}$ (µL/min/mg) |
|---|---|---|---|---|---|---|---|---|
| | | | | K$_i$ (nM) (DHT = 1 nM) | IC$_{50}$ (nM) | Full Length % inhibition at 1, 10 µM | S.V. % inhibition at 10 µM | |
| 1058 | 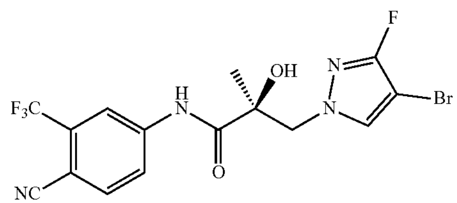 [SMILES: C[C@](O)(Cn1cc(Br)c(F)n1)C(=O)Nc1ccc(C#N)c(C(F)(F)F)c1] | 3.3 | 435.17 | 606.5 | 132.5 | 70 | 80 | |
| 1059 | 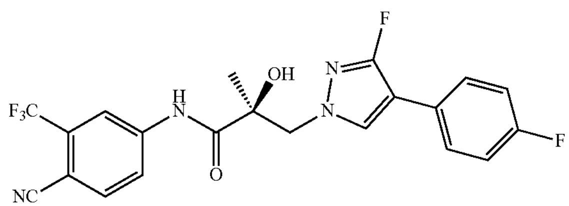 [SMILES: C[C@](O)(Cn1cc(-c2ccc(F)cc2)c(F)n1)C(=O)Nc1ccc(C#N)c(C(F)(F)F)c1] | 4.3 | 450.36 | 600.58 | 285.1 | 70 | toxic | |
| 1060 | 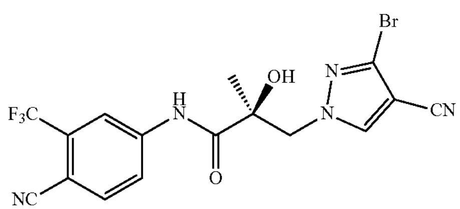 [SMILES: C[C@](O)(Cn1cc(C#N)c(Br)n1)C(=O)Nc1ccc(C#N)c(C(F)(F)F)c1] | | | | | | | No data for these two cpds |
| 1061 | 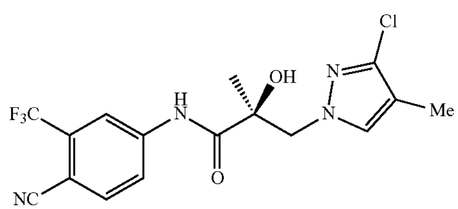 [SMILES: Cc1cn(C[C@](C)(O)C(=O)Nc2ccc(C#N)c(C(F)(F)F)c2)nc1Cl] | | | | | | | |

TABLE 1-continued

In vitro screening of LBD binding (Ki), AR antagonism (IC50), SARD activity, and metabolic stability

| Compound # | Structure | Log P (−0.4 to +5.6) | M.W. | wtAR Binding (K$_i$ (left)) & Transactivation (IC$_{50}$ (right)) (nM) | | SARD Activity (% inh): Full Length (left) and S.V. (right) | | DMPK (MLM) |
|---|---|---|---|---|---|---|---|---|
| | | | | K$_i$ (nM) (DHT = 1 nM) | IC$_{50}$ (nM) | Full Length % inhibition at 1, 10 μM | S.V. % inhibition at 10 μM | T$_{1/2}$ (min) & CL$_{int}$ (μL/min/mg) |
| 1062 | 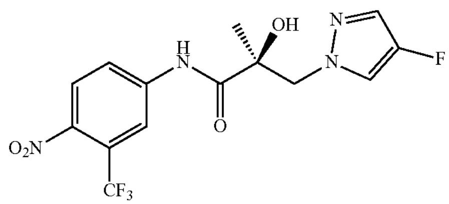 [SMILES: C[C@](O)(Cn1cc(F)cn1)C(=O)Nc1ccc([N+](=O)[O-])c(C(F)(F)F)c1] | 2.0 | 376.24 | | Partial | | | |
| 1062a | 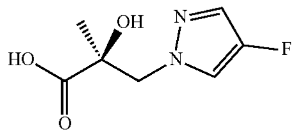 | — | 188.16 | | No effect | | | |
| 1063 | 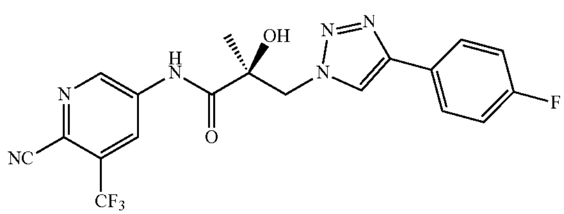 [SMILES: C[C@](O)(Cn1cc(-c2ccc(F)cc2)nn1)C(=O)Nc1cnc(C#N)c(C(F)(F)F)c1] | 2.8 | 434.35 | 1486 | 216.9 | | | |
| 1066 | 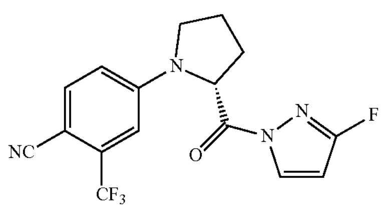 [SMILES: N#Cc1ccc(N2CCC[C@@H]2C(=O)n2ccc(F)n2)cc1C(F)(F)F] | | 352.29 | | No effect | | | |

TABLE 1-continued
In vitro screening of LBD binding (Ki), AR antagonism (IC50), SARD activity, and metabolic stability
| Compound # | Structure | Log P (−0.4 to +5.6) | M.W. | wtAR Binding (K_i (left)) & Transactivation (IC_50 (right)) (nM) | | SARD Activity (% inh): Full Length (left) and S.V. (right) | | DMPK (MLM) |
| --- | --- | --- | --- | --- | --- | --- | --- | --- |
| | | | | K_i (nM) (DHT = 1 nM) | IC_50 (nM) | Full Length % inhibition at 1, 10 µM | S.V. % inhibition at 10 µM | T_{1/2} (min) & CL_{int} (µL/min/mg) |
| 1067 | 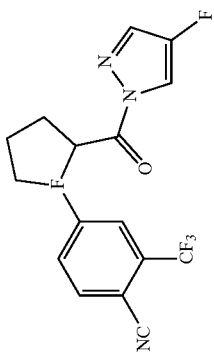 | | 352.29 | No effect | | | | |

TABLE 2

| Compd ID | Structure | MLM | | HLM | |
|---|---|---|---|---|---|
| | | $T_{1/2}$ (min) | $CL_{Int}$ (μL/min/mg) | $T_{1/2}$ (min) | $CL_{Int}$ (μL/min/mg) |
| 11 | 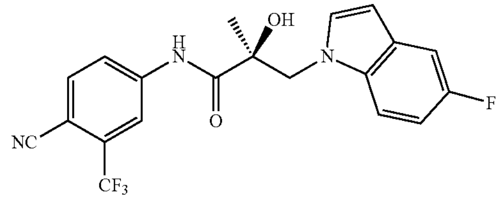 [SMILES: C[C@](O)(Cn1ccc2cc(F)ccc21)C(=O)Nc1ccc(C#N)c(C(F)(F)F)c1] | 14.35 | 48.30 | 14.62 | 47.40 |
| 1001 | 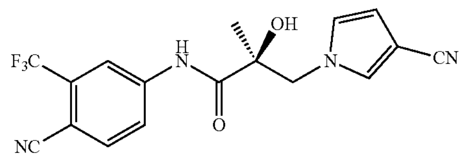 [SMILES: C[C@](O)(Cn1ccc(C#N)c1)C(=O)Nc1ccc(C#N)c(C(F)(F)F)c1] | 23.5 | 29.5 | | |
| 1002 | 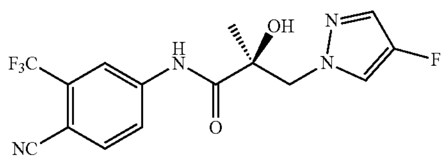 [SMILES: C[C@](O)(Cn1cc(F)cn1)C(=O)Nc1ccc(C#N)c(C(F)(F)F)c1] | 77.96 | 0.89 | 73.36 | 0.949 |
| 1004 | 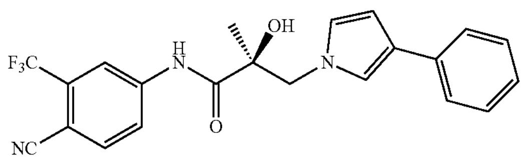 [SMILES: C[C@](O)(Cn1ccc(-c2ccccc2)c1)C(=O)Nc1ccc(C#N)c(C(F)(F)F)c1] | 3.96 | 175.2 | 2.261 | 306.5 |
| 1012 | 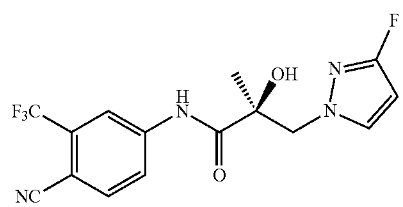 | 64.07 | 1.02 | | |

Example 3

Transactivation Assay

Methods: HEK-293 cells were transfected with the indicated receptors and GRE-LUC and CMV-renilla luc. Cells were treated 24 h after transfection and luciferase assay performed 48 h after transfection. The SARD compounds did not inhibit transactivation of receptors other than AR until 10 μM. The experimental method is described below.

Human AR was cloned into a CMV vector backbone and was used for the transactivation study. HEK-293 cells were plated at 120,000 cells per well of a 24 well plate in DME+5% csFBS. The cells were transfected using Lipofectamine (Invitrogen, Carlsbad, Calif.) with 0.25 μg GRE-LUC, 0.01 μg CMV-LUC (renilla luciferase) and 25 ng of the AR. The cells were treated 24 h after transfection and the luciferase assay performed 48 h after transfection. Transactivation results were based on measured luciferase light emissions and reported as relative light unit intensity (RLU). The assay was run in antagonist mode ($IC_{50}$) using known agonist R1881 at its $EC_{50}$ concentration of 0.1 nM and increasing concentrations of SARDs of this invention. Ago-nist mode data was reported qualitatively, e.g., partial agonist or an approximate $EC_{50}$ for enobosarm, for some compounds in Table 1. Antagonist data are represented as $IC_{50}$ (nM) obtained from four parameter logistics curve and are reported in Table 1 in the column labeled '$IC_{50}$'.

Figure 2A:
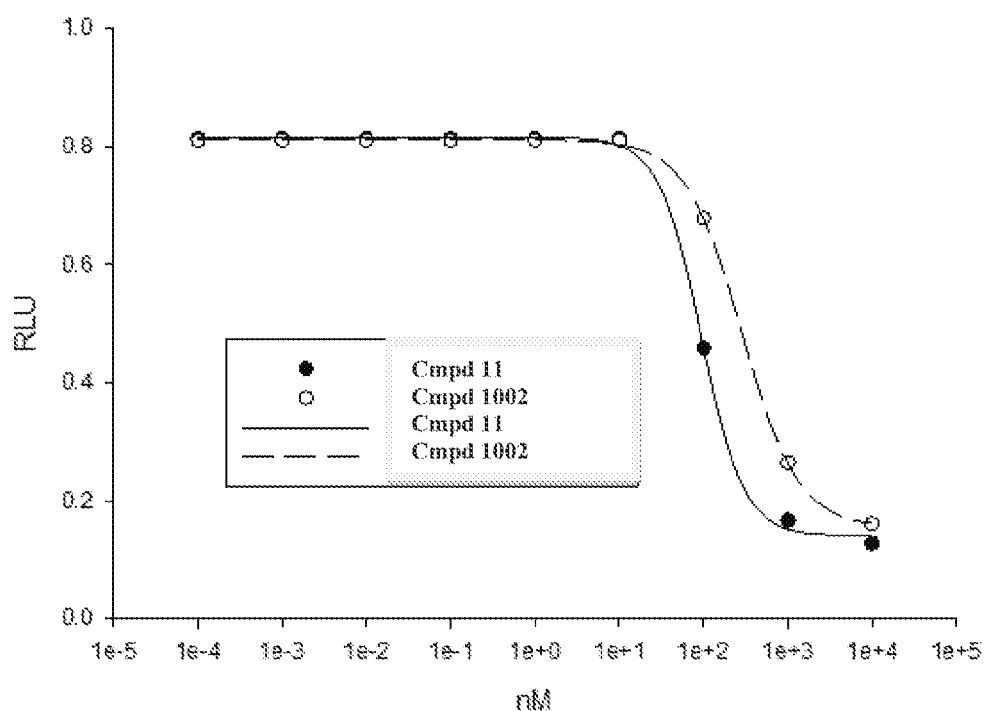
FIG. 2A and FIG. 2B: The transactivation results for 11 (an indole) and 1002 (a pyrazole of this invention) were reported based on measured luciferase light emissions and reported as relative light unit intensity (RLU).
Figure 2A:
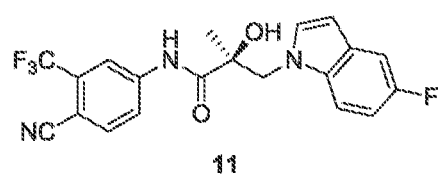
Figure 2B:
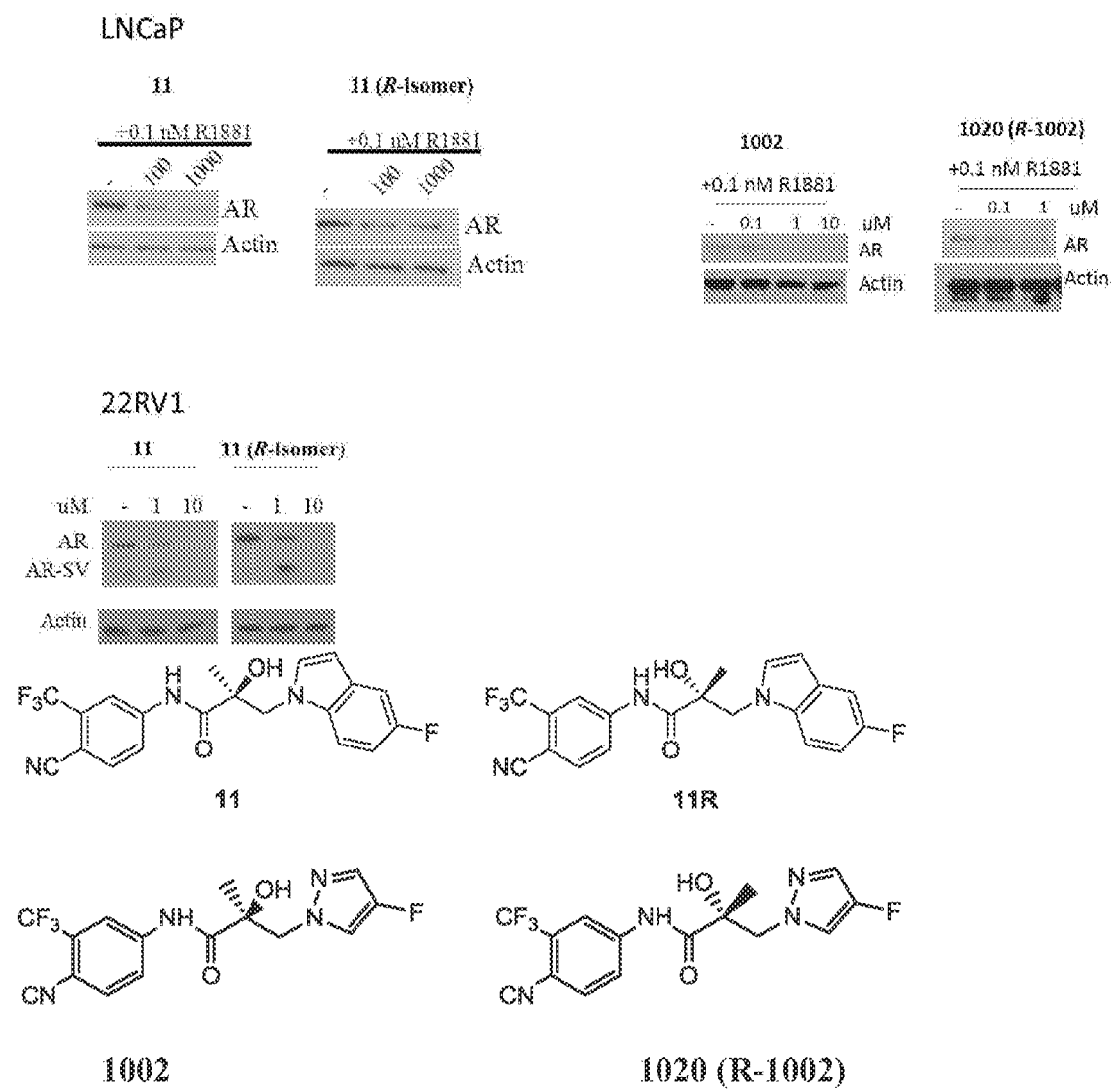
Figure 3A:
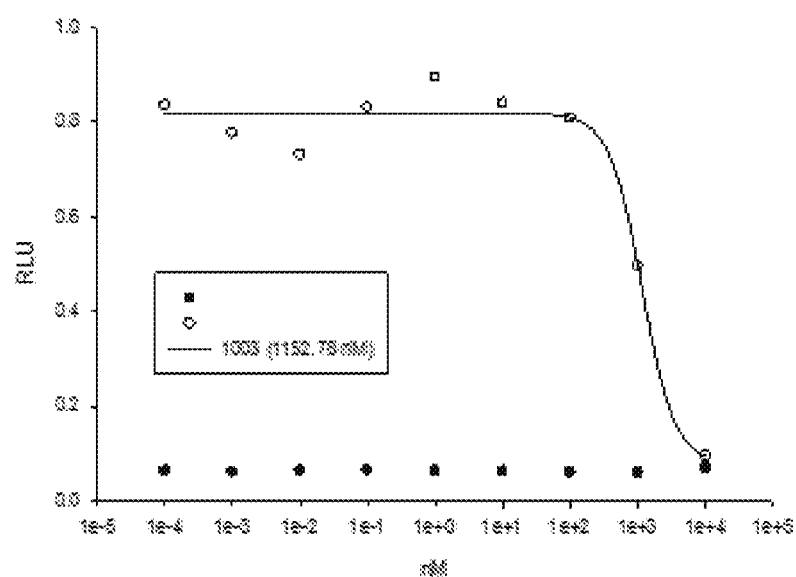
FIG. 3A and FIG. 3B: The transactivation result of 1003 was reported based on measured luciferase light emissions and reported as relative light unit intensity (RLU).
Figure 3B:
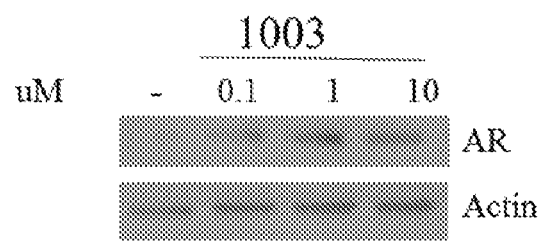

Results: Representative example graphs are shown in FIGS. 1A (1002), 2A (11 vs. 1002), 3A (1003), 4A (1004), 5A (1005), 6A (1006), 8-12 (1007-1011), and 13A (1001) with results plotted as RLU reported on the y-axis and SARD concentration on the x-axis (nM). In these Figures, antagonist mode data was shown as curve fitted data, whereas agonist mode data (if present) is reported without curve fitting. Only weak and partial agonism was seen. In vivo pharmacodynamics demonstrate potent and highly efficacious antagonism of androgen dependent tissues (see Examples 7 and 10 herein). FIG. 2 is a direct comparison of antagonism between 11 (closed dots) and 1002 (open dots). Other $IC_{50}$ values reported in Table 1 were calculated by the same method.

1002 was a potent antagonist (199.36 nM; Table 1 and FIG. 1A) with comparable inhibition as 11 (85.1 nM; FIG. 2) which is an extremely potent indole SARD lacking oral bioavailability. Despite the 2-fold increased $IC_{50}$ (Table 1)

and lack of AR-LBD binding (see Example 4 and Table 1), 1002 was a more potent AR degrader in vitro (see Example 5 and Table 1). Further and unlike 11, 1002 was very stable in vitro in mouse (Table 1) and human liver microsomes (Table 2) which translated into improved in vivo pharmacodynamics (see Example 7 herein) in mice and rats. Based on the structural differences alone, the increased SARD activity in vitro and metabolic stability were each unexpected results. Likewise, the greatly improved in vivo efficacy could not have been predicted (i.e., was unexpected) based on structural differences alone. 1012, 1014, and 1017 also demonstrated improved metabolic stability in vitro suggesting that the pyrazole moiety may be responsible for the unexpected stability of 1002.

As discussed below, 1002 and 1014 also demonstrated significant anti-tumor activity in in vivo xenograft studies (see Examples 8 and 10), suggesting that the bioavailability of these compounds is sufficient for their intended uses.

Figure 4A:
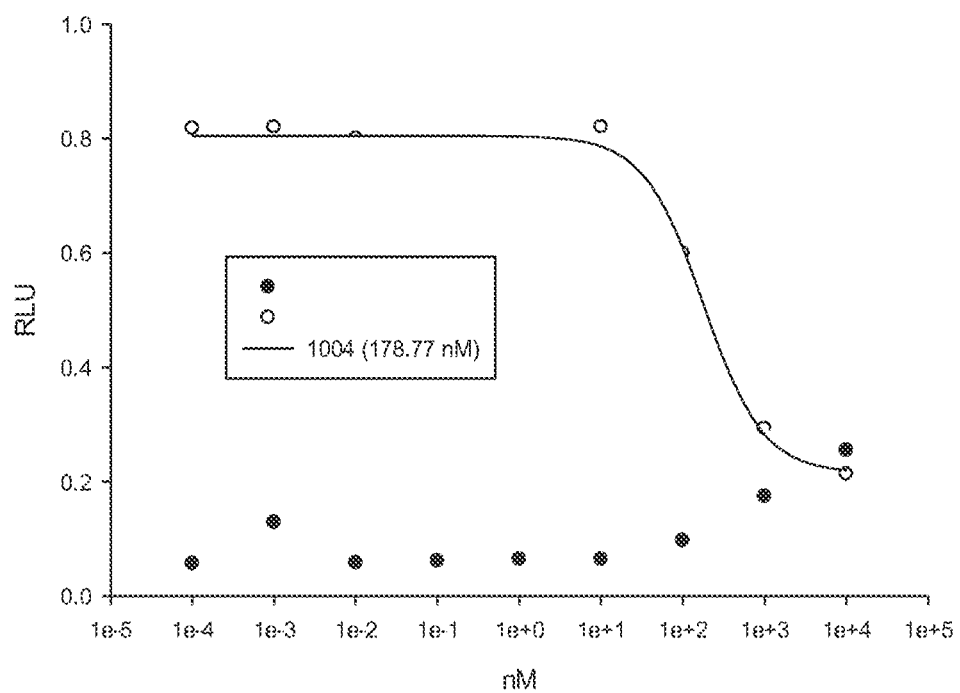
FIG. 4A and FIG. 4B: The transactivation result of 1004 was reported based on measured luciferase light emissions and reported as relative light unit intensity (RLU).
Figure 4B:
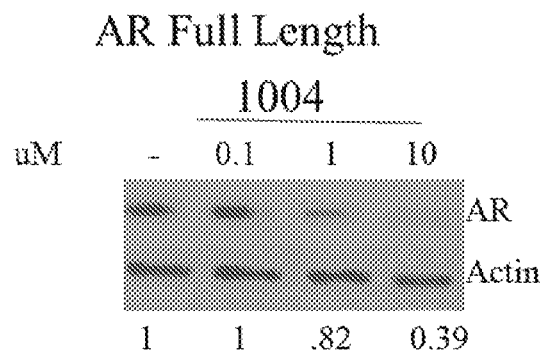
Figure 5A:
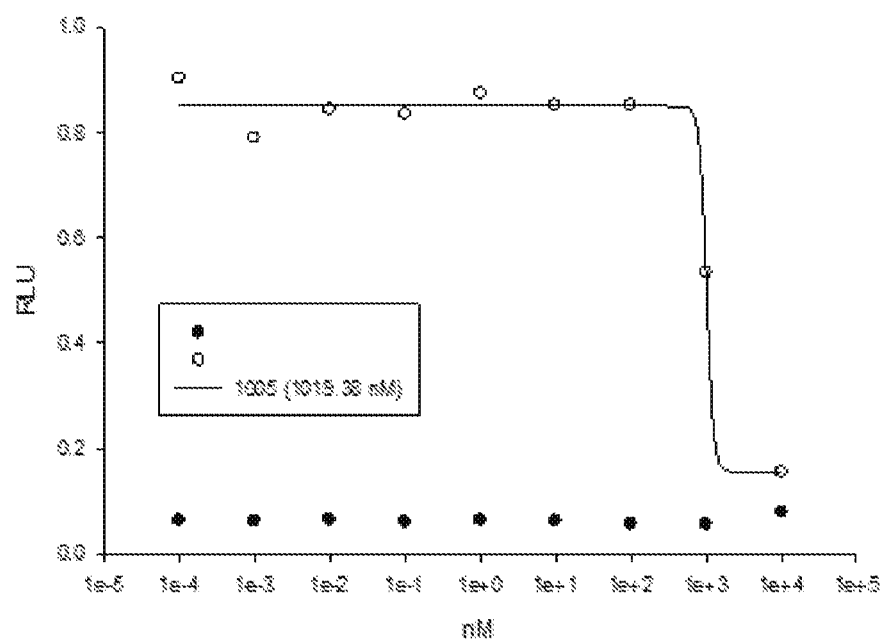
FIG. 5A and FIG. 5B: The transactivation results of 1005 were reported based on measured luciferase light emissions and reported as relative light unit intensity (RLU).
Figure 5B:
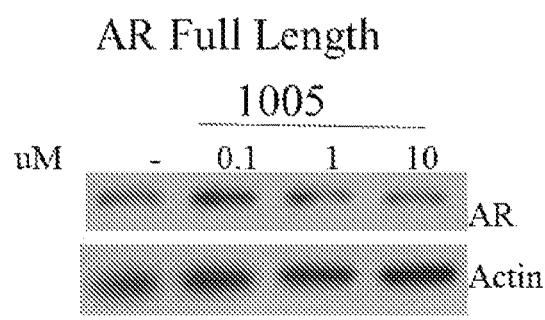
Figure 6A:
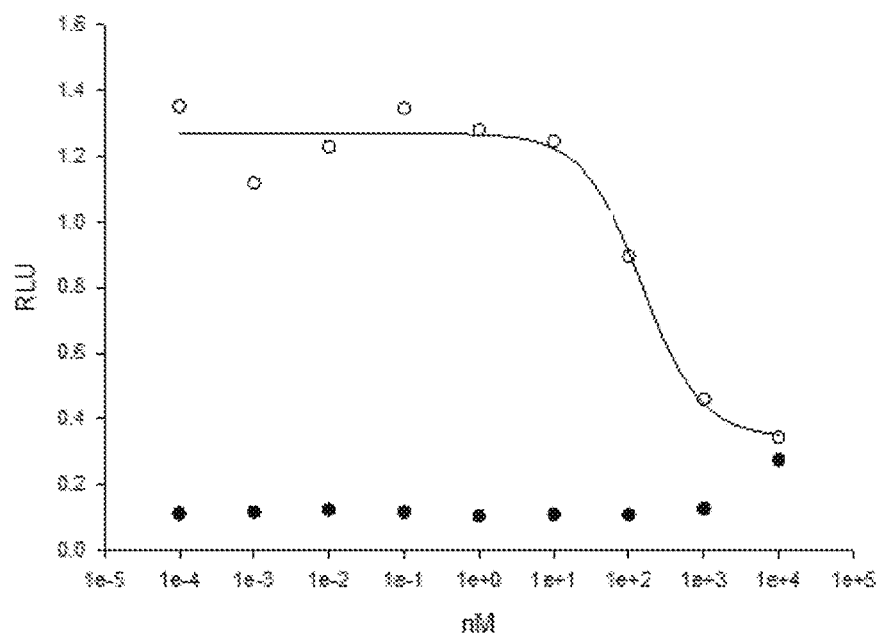
FIG. 6A and FIG. 6B: The transactivation result of 1006 was reported based on measured luciferase light emissions and reported as relative light unit intensity (RLU).
Figure 6B:
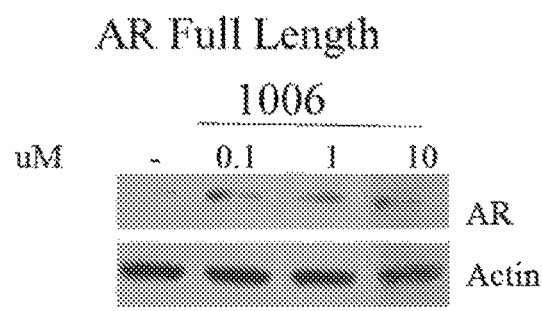
Figure 7:
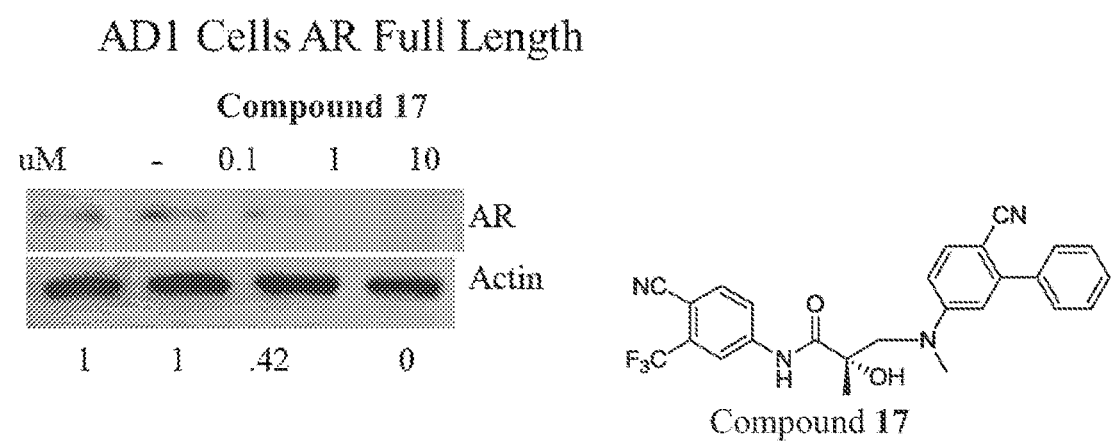
FIG. 7: The Western blot of the full length androgen receptor degradation assay is shown for compound 17 and the results are reported in Table 1, under SARD Activity: Full Length % Inhibition.
Figure 8:
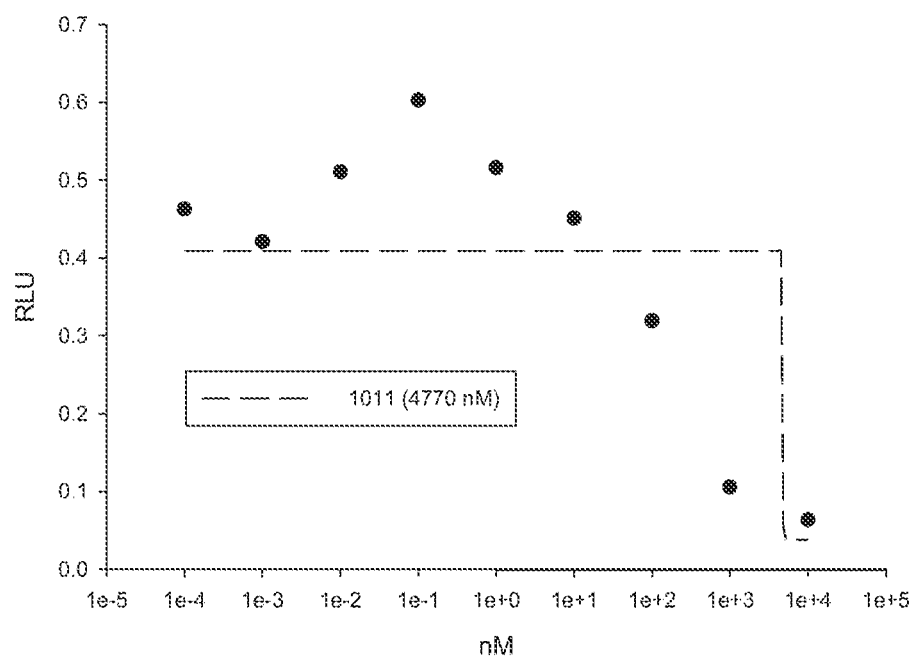
FIG. 8: The transactivation result of 1011 was reported based on measured luciferase light emissions and reported as relative light unit intensity (RLU).
Figure 9:
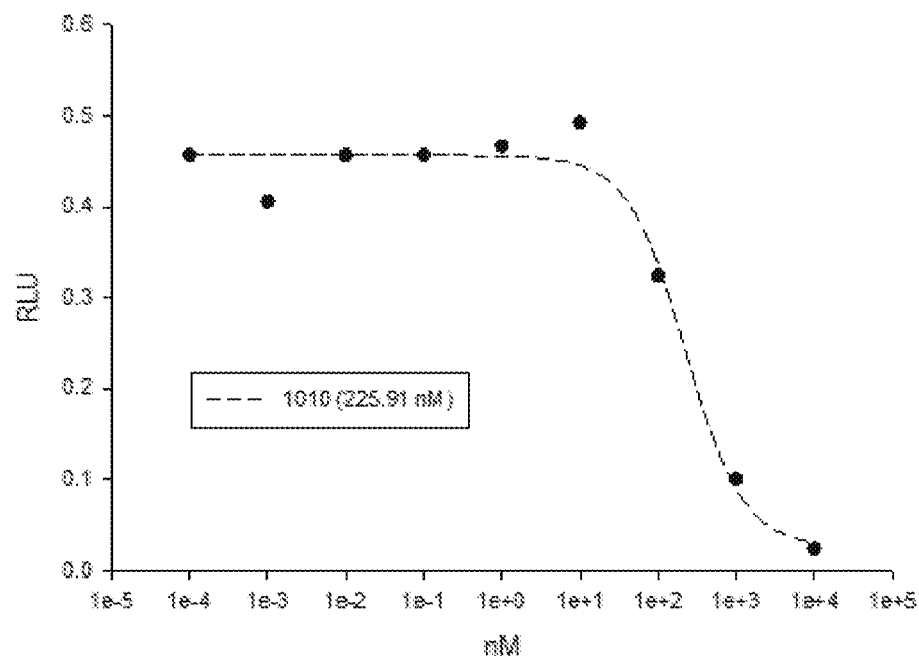
FIG. 9: The transactivation result of 1010 was reported based on measured luciferase light emissions and reported as relative light unit intensity (RLU).
Figure 10:
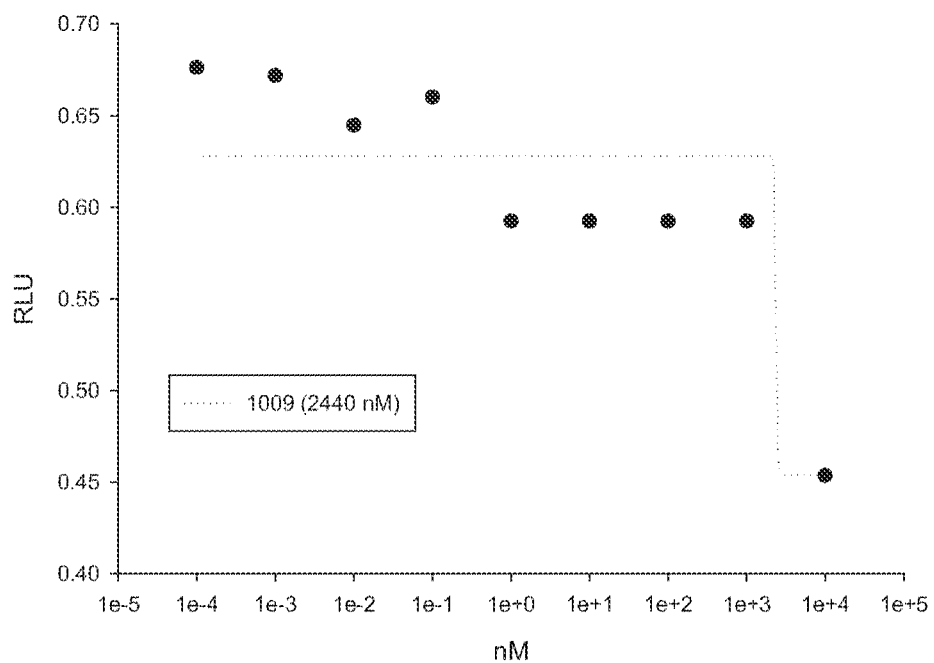
FIG. 10: The transactivation result of 1009 was reported based on measured luciferase light emissions and reported as relative light unit intensity (RLU).

1004 (pyrrole) and 1006 (imidazole) demonstrated potent inhibition (178.77 nM and 148.94 nM; Table 1; FIGS. 4A and 6A) but weak SARD activity, whereas 1005 and 1016 demonstrated weak inhibition but strong SARD activity, suggesting that in vitro inhibition is not well correlated with SARD activity. However, 1010 (pyrrole), 1012 (pyrazole), and 1014 (pyrazole) were potent inhibitors and degraders. In general, LBD binding or LBD-dependent inhibition and in vitro SARD activity seem to be separate but highly tolerant structure activity relationships. Values for other compounds of the invention are reported in Tables 1 and 2.

Figure 28A:
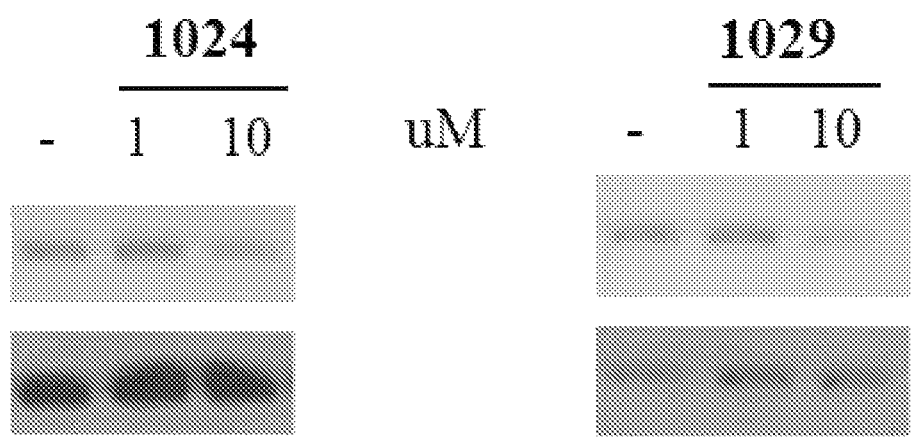
FIGS. 28A-28D: depicts degradation of full length and/or splice variant (22RV1) androgen receptors (in vitro) for 1024 (FIG. 28A), 1029 (FIG. 28B), 1037 and 1041 (FIG. 28C), and 1044-1045 (FIG. 28D).
Figure 28B:
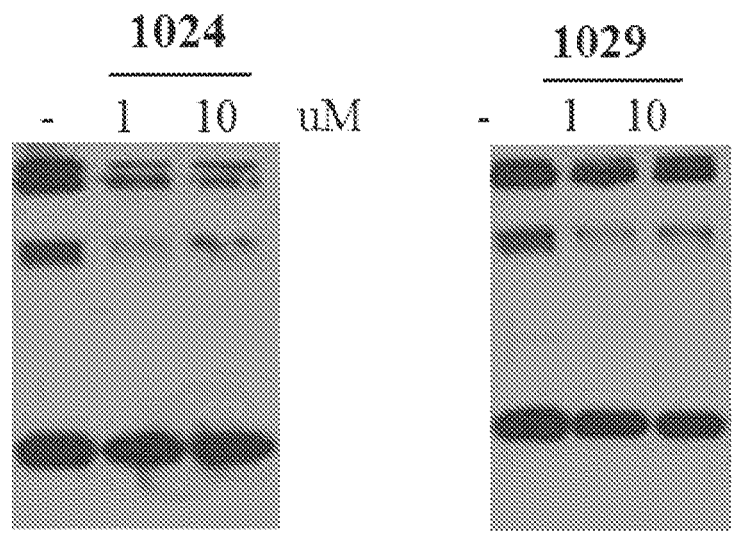
Figure 28C:
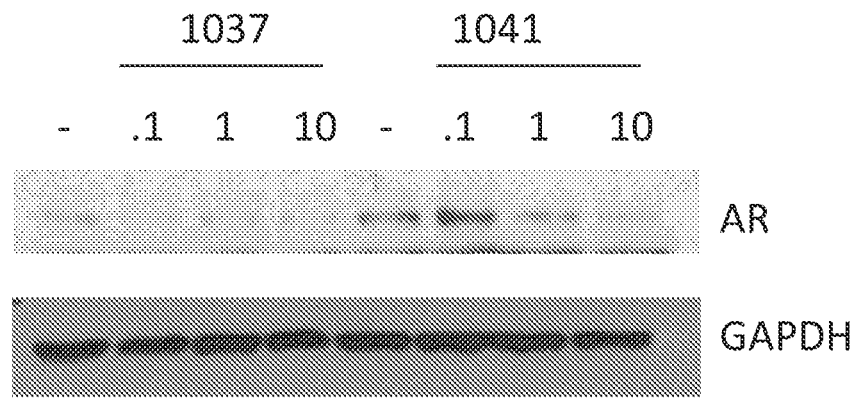
Figure 28C:
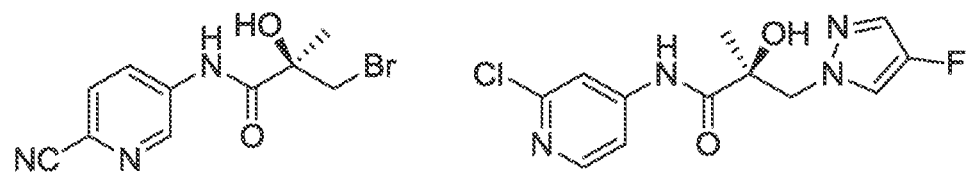
Figure 28D:
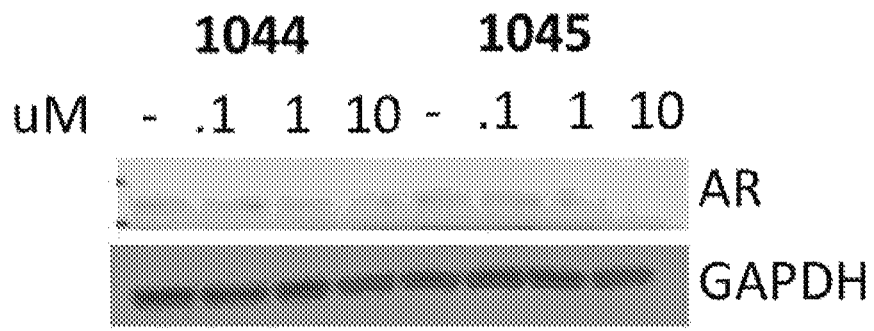
Figure 28D:
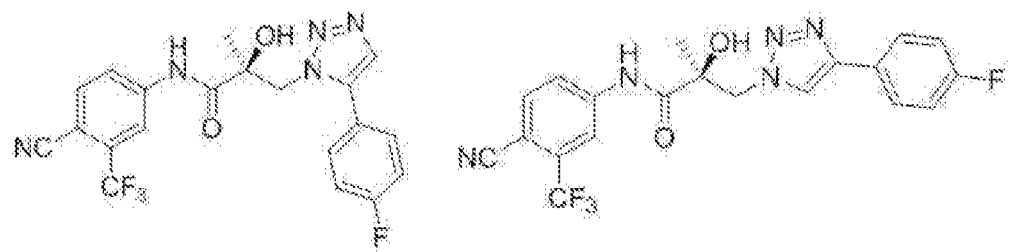

Potent inhibition of transactivation was also seen for 1020 (192 nM), 1022 (92 nM), and 1024 (464 nM). 1020 is an R-isomer of pyrazole 1002, and like 1002, does not bind to the LBD yet has strong SARD activity. Similarly, the indole SARD 11 and the R-isomer of 11 have comparable SARD activities (Table 1 and FIG. 2B) for AR-FL (LNCaP) and AR-SV (22RV1). This is in sharp contrast to propanamide SARMs such as enobosarm which typically have 100-fold lower LBD binding and agonist activity for R-isomers (data not shown). This is further evidence that SARD activity is not mediated through the LBD, as will be discussed in more detail in Example 9 below. Example 9 demonstrates a novel binding site in the N-terminal domain (NTD), providing a basis for the distinct structure activity relationships from traditional AR antagonists that bind to the LBD and SARD of this invention which act through the NTD. The retention of SARD activity in opposite isomers (unlike SARMs) suggests that the NTD binding site does not require stereospecificity in its ligands. Further, the NTD binding site does not seem to require the chiral hydroxyl group which is conserved for LBD-binding (agonists and) antagonists. E.g., 1024 is a non-chiral propanamide racemate which lacks the hydroxyl but retains SARD activity (Table 1: 60% degradation of AR-FL) and the ability to inhibit the AR (Table 1: $IC_{50}$=464 nM) despite not binding the LBD (Table 1: $K_i$: no binding). Also, 1029 replaces the chiral center with a methylene group and yet retains some SARD activity (Table 1: 35% degradation of AR-FL) and AR antagonism (Table 1: $IC_{50}$=2124 nM). 1032 has its hydroxyl group protected by acylation and does not bind the LBD yet is an antagonist of AR. Another possible divergence in SAR's is the A-ring which is conserved for LBD binders as 4-cyano or nitro and 3-trifluoromethyl or 3-chloro. However, changing the $CF_3$ of 1002 to the Cl of 1007 ablated SARD activity. Further, 1022 has a novel pyridine A-ring and does not bind to the LBD yet retains potent inhibition of transactivation (92 nM) and SARD activity (Table 1). Similarly, SARD activity is shown for 1037 and 1041 that contain pyridine A-rings (Table 1 and FIG. 28C), and 1043 is a highly potent pyridine antagonist but weak SARD activity (Table 1). Further, 1037 is a 3-bromopropanamide (i.e., lacks a heterocyclic B-ring) which binds weakly to the LBD (4547 nM) but is a potent antagonist (350.5 nM) and retains SARD activity, demonstrating that the B-ring may not be necessary (Table 1) for SARDs of this invention. Such observations confirm that SARD activity can be optimized in the absence of LBD binding data and provide a rationale for the degradation of AR splice variants lacking the LBD.

Example 4

Human Androgen Receptor (hAR) Ligand Binding Domain (LBD) Affinity Assay

Methods: hAR-LBD (633-919) was cloned into pGex4t.1. Large scale GST-tagged AR-LBD was prepared and purified using a GST column. Recombinant AR-LBD was combined with [$^3$H]mibolerone (PerkinElmer, Waltham, Mass.) in buffer A (10 mM Tris, pH 7.4, 1.5 mM disodium EDTA, 0.25 M sucrose, 10 mM sodium molybdate, 1 mM PMSF) to determine the equilibrium dissociation constant ($K_d$) of [$^3$H]mibolerone. Protein was incubated with increasing concentrations of [$^3$H]mibolerone with and without a high concentration of unlabeled mibolerone at 4° C. for 18 h in order to determine total and non-specific binding. Non-specific binding was then subtracted from total binding to determine specific binding and non-linear regression for the ligand binding curve with one site saturation was used to determine the $K_d$ of mibolerone.

Increasing concentrations of SARDs or DHT (range: $10^{-12}$ to $10^{-4}$ M) were incubated with [$^3$H]mibolerone and AR-LBD using the conditions described above. Following incubation, the ligand bound AR-LBD complex was isolated using BiogelHT hydroxyapatite, washed and counted in a scintillation counter after adding scintillation cocktail.

Results: The results of this assay are reported as $K_i$ values (nM) in Table 1 in the column labeled 'wt AR Binding ($K_i$ (left))'. As discussed above and is apparent from Table 1, there is a poor correlation between AR-LBD affinity and SARD activity. E.g., see in vitro SARD activity for 1002, 1005, 1015, 1019, 1020, and 1022 despite no binding affinity for the LBD (Table 1).

Example 5

In Vitro Assays to Determine SARD Activity

LNCaP or AD1 androgen receptor degradation (full length AR): The compounds of the invention were tested for their effect on full length AR protein expression. Methods: LNCaP or AD1 cells expressing full length AR were plated at 750,000-1,000,000 cells/well of a 6 well plate in growth medium (RPMI+10% FBS). Twenty four hours after plating, the medium was changed to RPMI+1% csFBS without phenol red and maintained in this medium for 2 days. The medium again was changed to RPMI+1% csFBS without phenol red and cells were treated with SARDs (1 nM to 10 mM) in combination with 0.1 nM R1881. After 24 h of treatment, cells were washed with cold PBS and harvested. Protein was extracted using salt-containing lysis buffer with three freeze-thaw cycles. The protein concentration was estimated and five microgram of total protein was loaded on a SDS-PAGE, fractionated, and transferred to a PVDF membrane. The membrane was probed with AR N-20 antibody (SantaCruz Biotechnology, Inc., Dallas, Tex. 75220) and actin antibody (Sigma-Aldrich, St. Louis, Mo.).

Figure 1B:
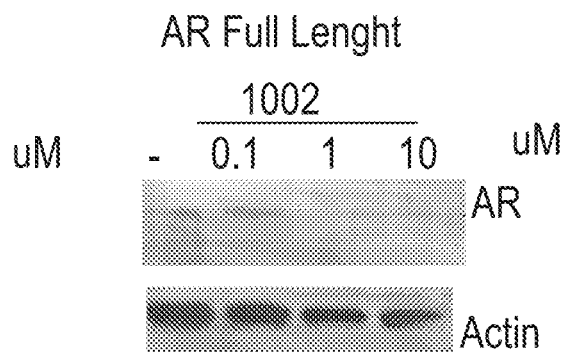

Results: Degradation in LNCaP or AD1 cells are reported in Table 1 in the column labeled 'Full Length % Inhibition at 1, 10 μM'. The results of this assay were reported in FIGS. 1B (1002), 2B (11, 11R, 1002, 1020), 3B-6B (1003-1006), 7 (17), 13B (1001), 20A (1010, 1012, 1014, 1015, 1017, 1019 and 1022), 28A (1024 and 1029), 28C (1037 and 1041), 28D (1044 and 1045) as images of Western blot films (chemiluminescence exposed films).

22RV1 or D567es androgen receptor degradation (splice variant (S.V.) AR): The effect of SARD treatment on the AR levels was measured in androgen-refractory 22RV-1 or D567es prostate cancer cells. Methods: 22RV1 or D567es cells expressing AR splice variants (AR-SV) were plated at 750,000-1,000,000 cells/well of a 6 well plate in growth medium (RPMI+10% FBS). Twenty four hours after plating, medium was changed and treated. After 24-30 h of treatment, cells were washed with cold PBS and harvested. Protein was extracted using salt-containing lysis buffer with three freeze-thaw cycles. Protein concentration was estimated and five microgram of total protein was loaded on a SDS-PAGE, fractionated, and transferred to a PVDF membrane. The membrane was probed with AR N-20 antibody (Santa Cruz Biotechnology, Inc., Dallas, Tex. 75220) and actin antibody (Sigma-Aldrich, St. Louis, Mo.).

Figure 1C:
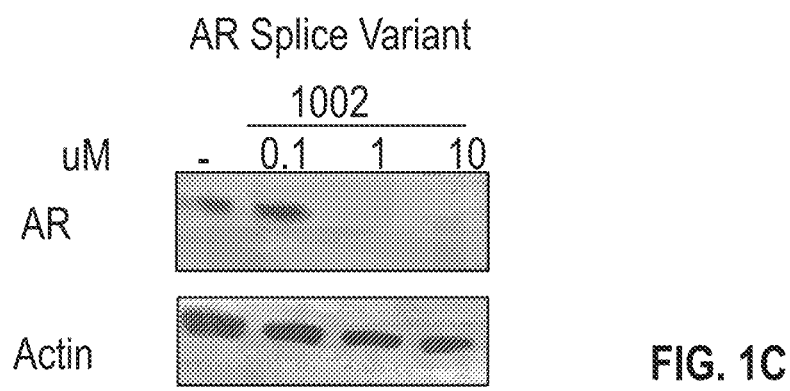

Results: Degradation in 22RV1 or D567es cells are reported in Table 1 in the column labeled "S.V. % inhibition at 10 μM." The results of this assay in D567es cells were reported in FIGS. 1C (1002) and 20B (1010, 1012, 1014-1017, 1019 and 1022), and in 22RV1 cells in FIGS. 2B (11, 11R), 13C (1001), and 28B (1024 and 1029) as images of Western blot films (chemiluminescence exposed films).

Example 6

Metabolism Studies with Mouse Liver Microsomes (DMPK (MLM))

Determination of metabolic stability (in vitro $CL_{int}$) of test compounds: Phase I metabolism: The assay was done in a final volume of 0.5 mL in duplicates (n=2). The test compound (1 mM) was pre-incubated for 10 minutes at 37° C. in 100 mM Tris-HCl, pH 7.5 containing 0.5 mg/mL liver microsomal protein. After pre-incubation, reaction was started by addition of 1 mM NADPH (pre-incubated at 37° C.). Incubations were carried out in triplicate and at various time-points (0, 5, 10, 15, 30 and 60 minutes). 100 mL aliquots were removed and quenched with 100 mL of acetonitrile containing internal standard. Samples were vortex mixed and centrifuged at 4000 rpm for 10 min. The supernatants were transferred to 96 well plates and submitted for LC-MS/MS analysis. As a control, sample incubations done in the absence of NADPH were included. From % PCR (% Parent Compound Remaining), rate of compound disappearance was determined (slope) and in vitro $CL_{int}$ (μl/min/mg protein) was calculated.

Figure 15A:
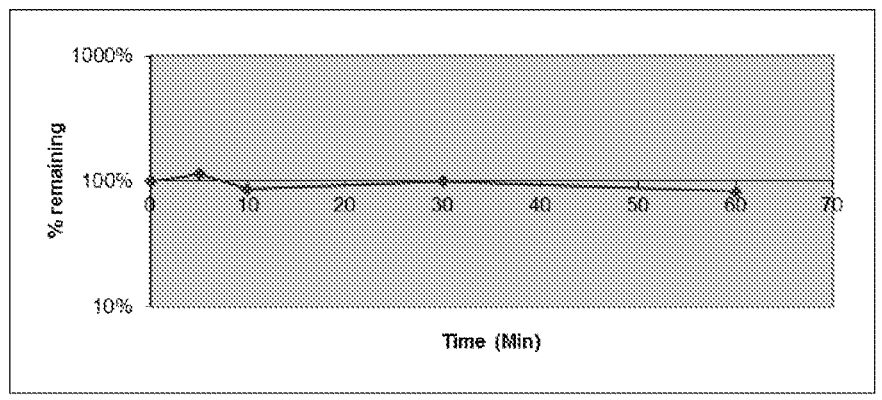
FIG. 15A and FIG. 15B.
Figure 16A:
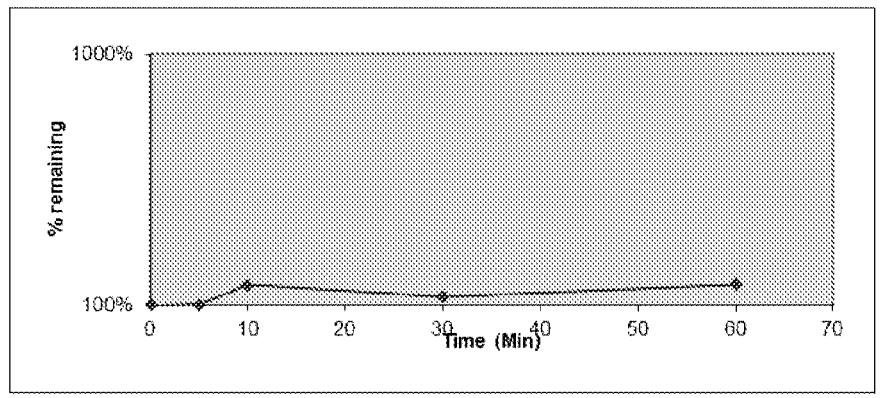
FIG. 16A and FIG. 16B.
Figure 16B:
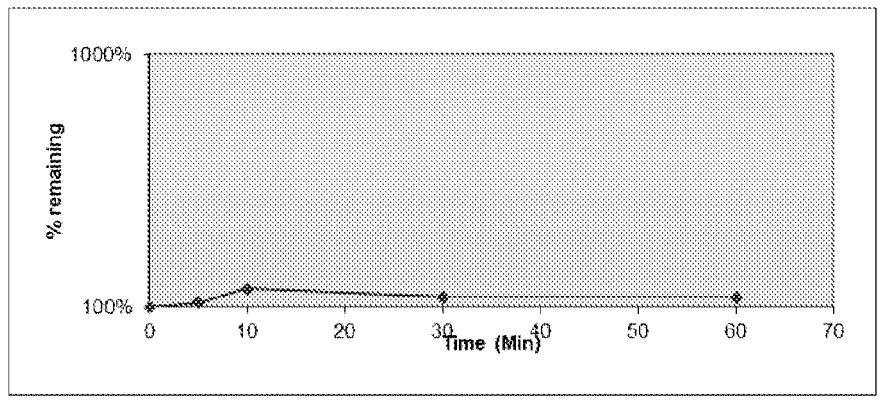
Figure 17:
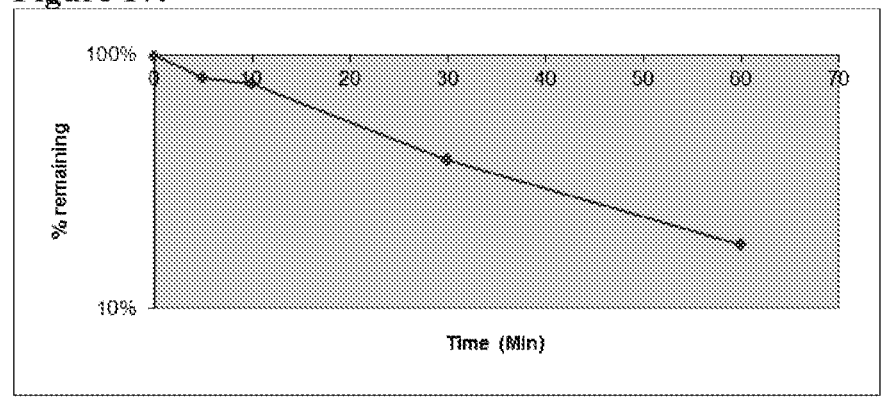
FIG. 17.

Results: FIG. 14 reported phase I data as a raw data table for one experiment in MLM for compound 1002 and the $T_{1/2}$ (half-life) and $CL_{int}$ (clearance) values calculated therefrom. FIGS. 15A and 16A report phase I data as a raw data table and graphed data for one experiment for 1002 in mouse liver microsomes (MLM) and human liver microsomes (HLM), respectively. Similarly, FIG. 17 reported MLM data for 1001 and the $T_{1/2}$ (half-life) and $CL_{int}$ (clearance) values in Tables 1 and 2 were calculated therefrom.

Metabolic Stability in Phase I & Phase II Pathways

In this assay, the test compound was incubated with liver microsomes and disappearance of drug was determined using discovery grade LC-MS/MS. To simulate Phase II metabolic pathway (glucuronidation), UDPGA and alamethicin were included in the assay. From % PCR (% Parent Compound Remaining), rate of compound disappearance is determined (slope of concentration vs. time plot) and in vitro $CL_{int}$ (μl/min/mg protein) was calculated. The results of this assay utilizing mouse liver microsomes (MLM) are reported in Table 1 in the column labeled "DMPK (MLM) $T_{1/2}$ (Min) & $CL_{int}$ (μL/min/mg)". The first value is the calculated half-life ($T_{1/2}$) of the test article in MLM expressed in minutes and the $2^{nd}$ value is the intrinsic CL ($CL_{int}$) of the test article in MLM expressed as mL/min/mg protein.

Figure 15B:
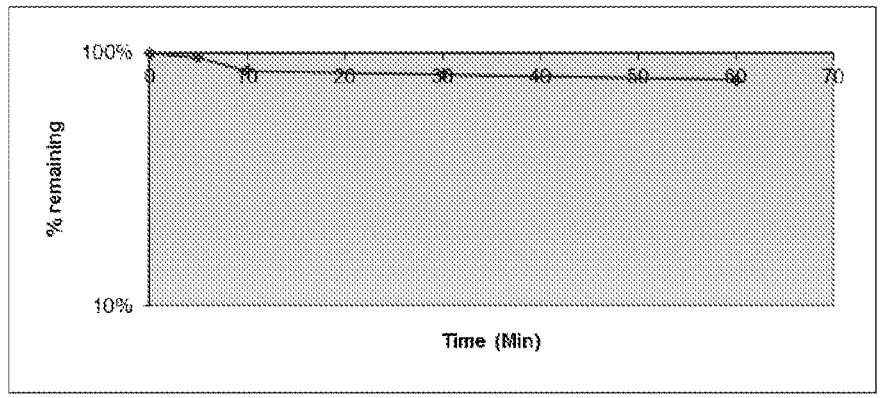

Results: FIG. 14 reported phase I & II data as a raw data table for one experiment and the $T_{1/2}$ (half-life) and $CL_{int}$ (clearance) values calculated therefrom. FIGS. 15B (using mouse liver microsomes (MLM)) and 16B (using human liver microsomes (HLM)) reported phase I & II data for 1002 as a raw data table for separate single experiments and graphed data. This data demonstrated that 1002 is stable in MLM and very stable in HLM. The LC-MS/MS analysis was performed as described below.

The metabolic stability of 1002 and other pyrazoles of this invention was unexpected in view of previous SARDs (100, 17, & 11; see Table 1). See also Examples 8 and 10 for comparisons of pyrazoles to previous SARD templates and their unexpected results in terms of metabolic stabilities, in vivo pharmacodynamics, in vivo serum and tumor concentrations, and in vivo anti-tumor efficacies in advanced prostate cancer (Example 10) and triple negative breast cancer (Example 8). Further, MLM data for 1024 (Table 1), a non-hydroxy variant, and 1023, a pyridine A-ring compound (non-carbonitrile), both revealed a lack of metabolism after incubation with MLM for 60 minutes. This demonstrates metabolic stability of SARDs of this invention including those with pyrazole B-rings, that lack the hydroxyl group, and/or include alternative A-rings.

LC-MS/MS Analysis:

The analysis of the compounds under investigation was performed using LC-MS/MS system consisting of Agilent 1100 HPLC with an MDS/Sciex 4000 Q-Trap™ mass spectrometer. The separation was achieved using a $C_{18}$ analytical column (Alltima™, 2.1×100 mm, 3 μm) protected by a $C_{18}$ guard cartridge system (SecurityGuard™ ULTRA Cartridges UHPLC for 4.6 mm ID columns, Phenomenex). Mobile phase was consisting of channel A (95% acetonitrile+5% water+0.1% formic acid) and channel C (95% water+5% acetonitrile+0.1% formic acid) and was delivered at a flow rate of 0.4 mL/min. The volume ratio of acetonitrile and water was optimized for each of the analytes. Multiple reaction monitoring scans were made with curtain gas, collision gas, nebulizer gas, and auxiliary gas optimized for each compound, and source temperature at 550° C. Molecular ions were formed using an ion spray voltage of −4200 V (negative mode). Declustering potential, entrance potential, collision energy, product ion mass, and cell exit potential were optimized for each compound.

Example 7

In Vivo Antagonism Demonstrated by SARD Compound 1002

Hershberger method: Male mice (20-25 grams body weight; n=5-7/group) were either left intact or castrated and treated as indicated in the figures for 13 days. Treatment of castrated mice was initiated 3 days after castration. Mice were sacrificed on day 14 of treatment and seminal vesicles were removed and weighed. Seminal vesicles weights were either represented as is or were normalized to body weight and represented.

Figure 18A:
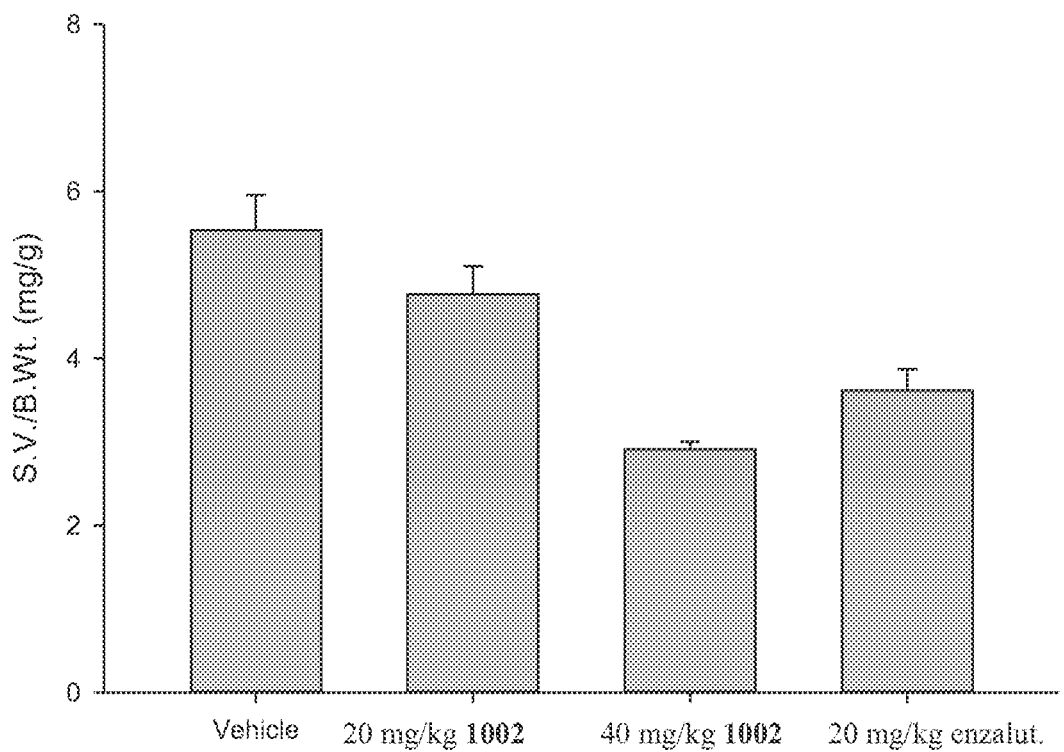
FIG. 18A and FIG. 18B: Hershberger method (mice): Male mice (20-25 grams body weight; n=5-7/group) were either left intact (FIG. 18A) or castrated (FIG. 18B) and treated as indicated in the figures for 13 days. Treatment of castrated mice was initiated 3 days after castration. Mice were sacrificed on day 14 after treatment initiation and seminal vesicles were removed and weighed. Seminal vesicles weights were either represented as is or were normalized to body weight and represented.
Figure 18B:
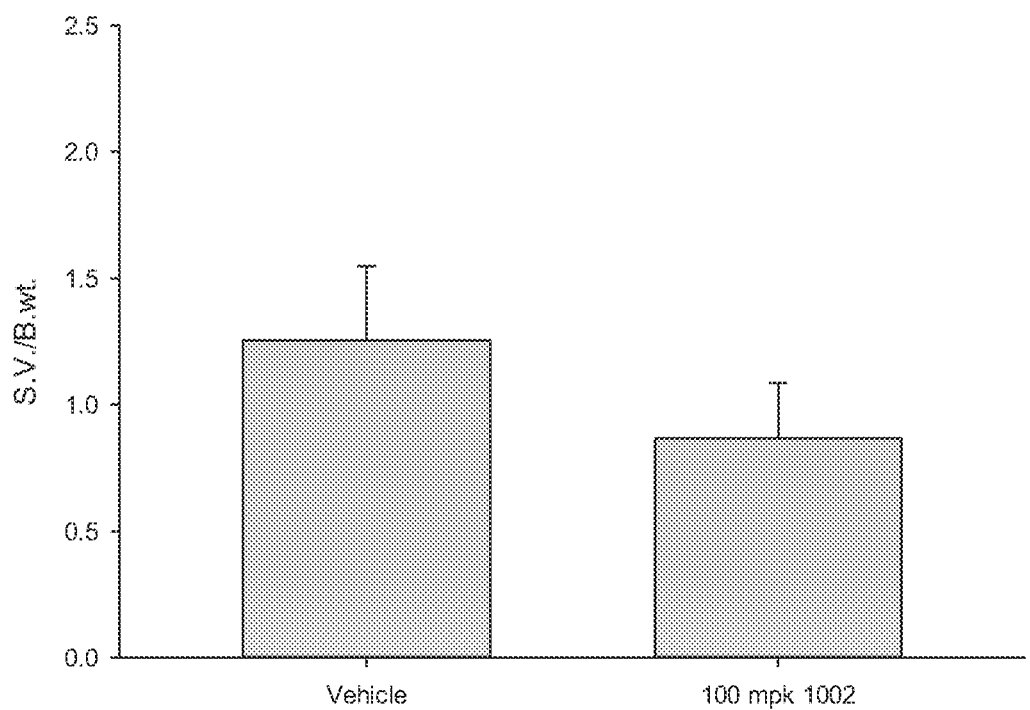

Results: 1002 significantly reduced the weight of seminal vesicles at 40 mg/kg oral daily dose in intact (FIG. 18A) and 100 mg/kg in castrated (FIG. 18B). The reduction in seminal vesicles weight, which is representative of androgen receptor (AR) antagonism, was more pronounced than that of the 20 mg/kg/day enzalutamide dose. 1002 was effective even in castrated mice, indicating that even any residual AR activity in castrated AR-target tissues was further inhibited by the potent activity of 1002 which bodes well for the abilities of SARDs of this invention to treat ADT-treated prostate cancer patients. This suggests that even though some weak partial AR agonism is observed in in vitro transactivation experiments, the predominant tone in vivo is AR antagonism. Further, in vivo activity at 40 mg/kg (40 mpk) for 1002 was a dramatic improvement over previously tested SARDs from our laboratory which typically only produced in vivo effects at 100 mg/kg or more despite comparable in vitro transcriptional inhibition potencies. This suggests the unexpected metabolic stability of 1002 translated into clinically significant oral bioavailability.

Figure 19A:
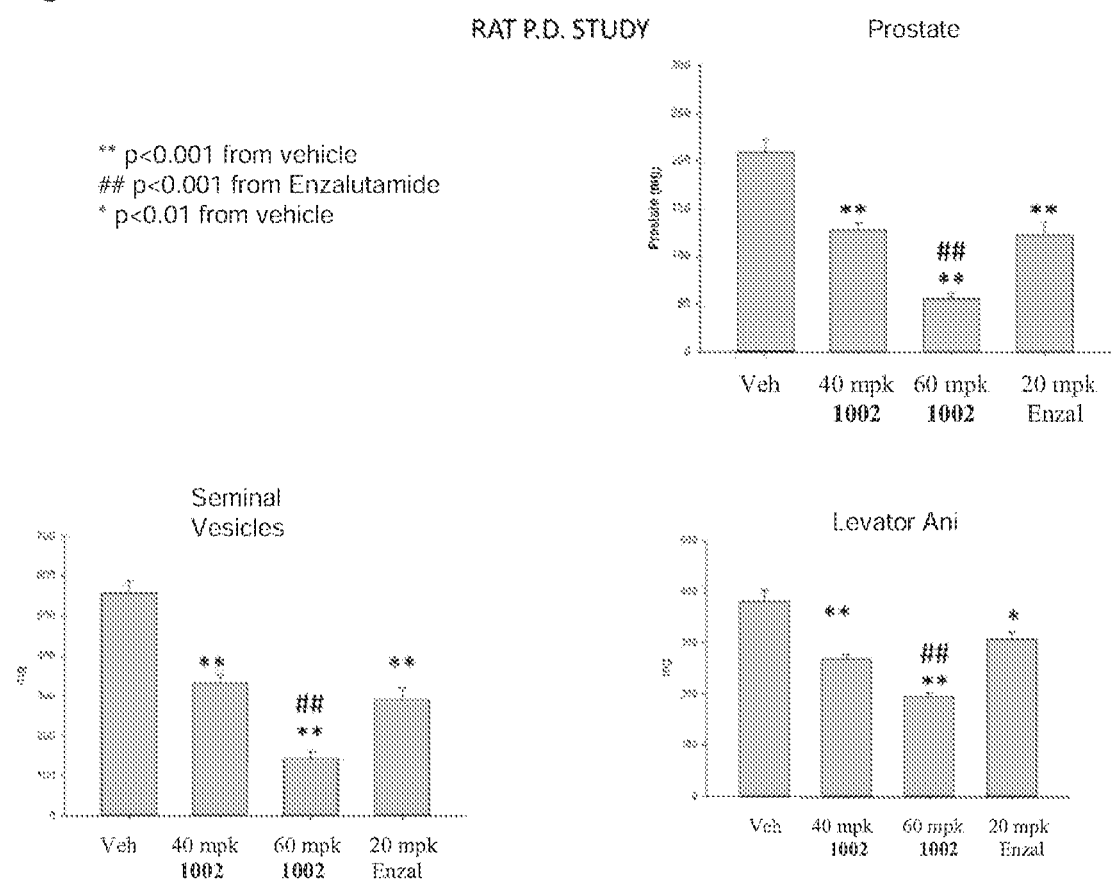
FIG. 19A and FIG. 19B: Hershberger method (rat)
Figure 19B:
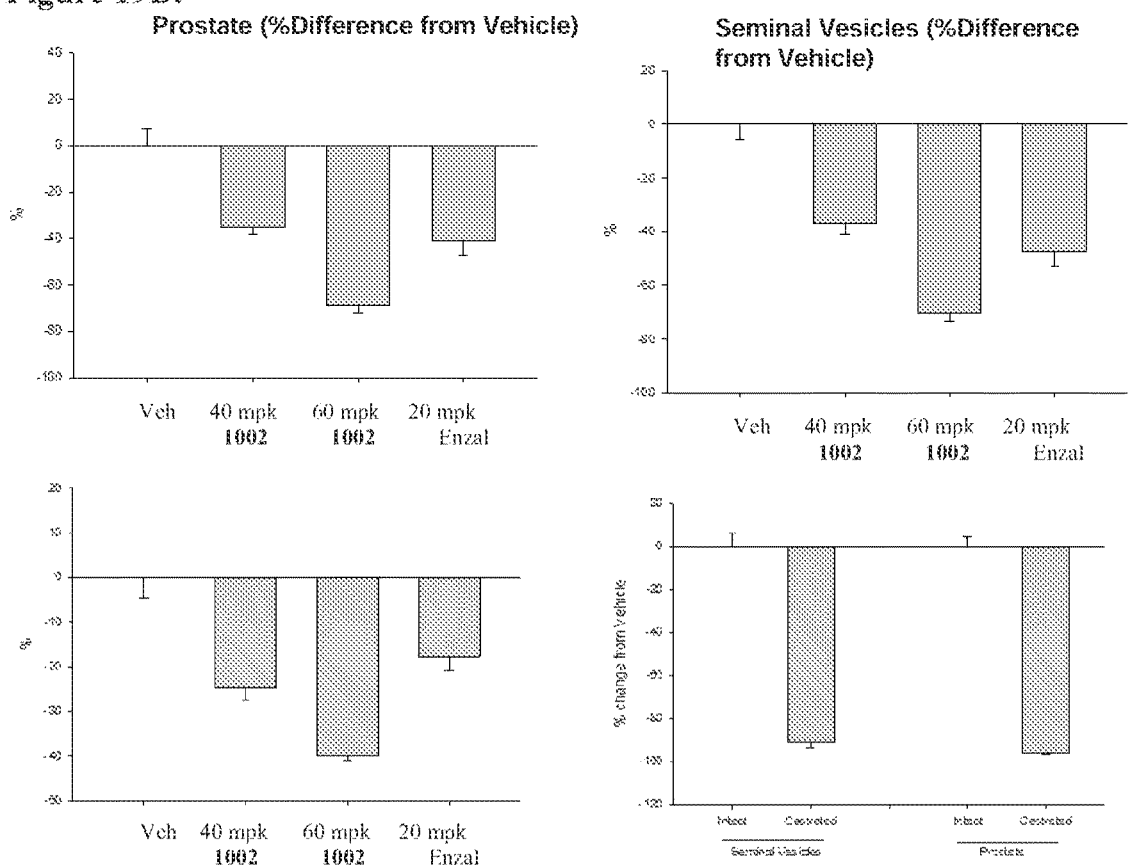
Figure 20A:
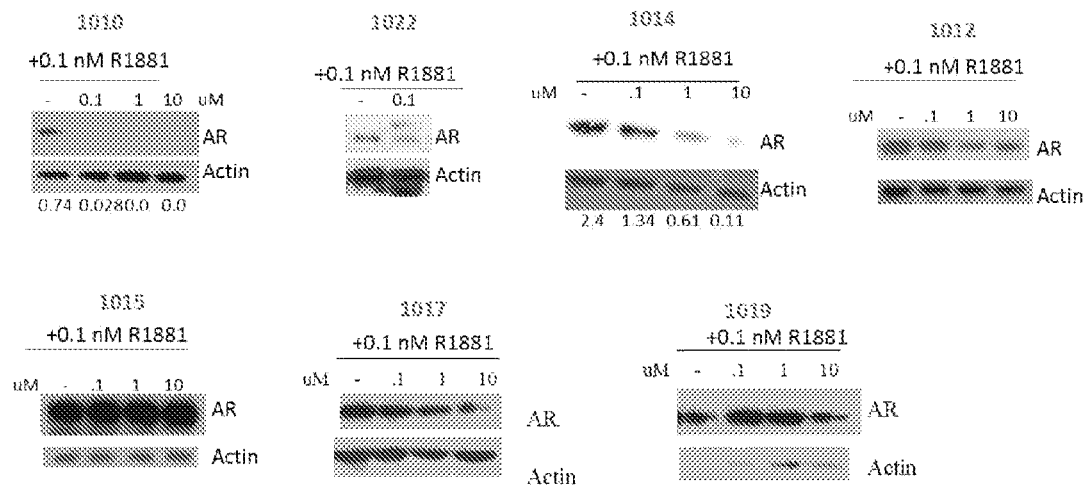
FIG. 20A and FIG. 20B: Degradation of full length and splice variant (AR-v567ES) androgen receptors (in vitro) for 1010, 1012, 1014, 1015, 1016, 1017, 1019 and 1022.
Figure 20B:
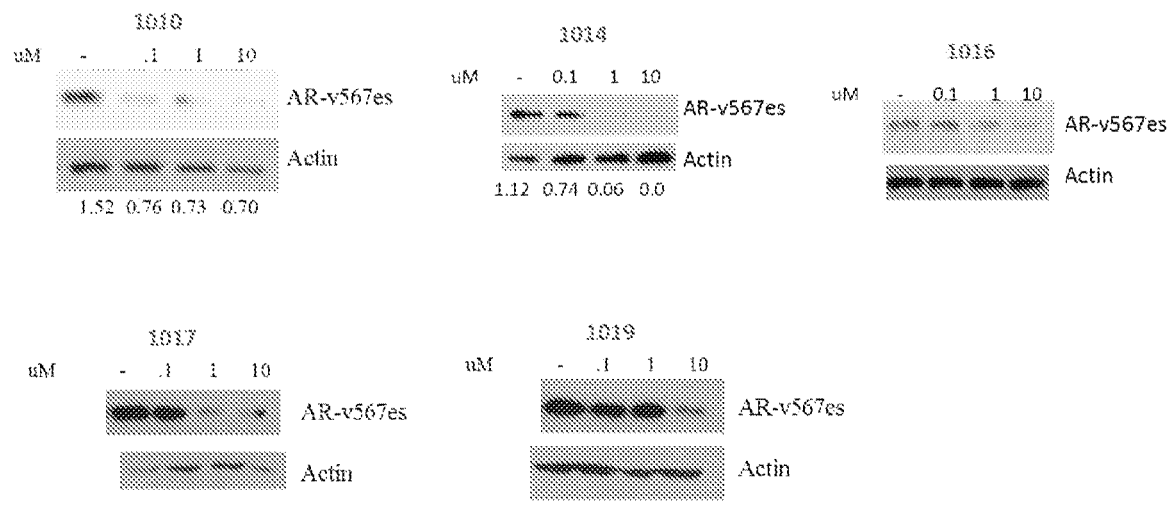

The Hershberger experiments were repeated in rats since rats are known to be more sensitive models of androgenic and anabolic activities of AR agonists and antagonists. Sprague Dawley rats (165-180 gms) body weight were treated with vehicle, 40 mpk 1002, 60 mpk 1002, or 20 mpk enzalutamide orally. After 13 days of treatment, the rats were sacrificed and the weights of prostate, seminal vesicles, and levator ani were measured. 1002 at 40 mg/kg antagonized the weights of seminal vesicles, prostate and levator ani muscle to approximately the same extent as 20 mg/kg enzalutamide and 60 mg/kg 1002 further suppressed the weights of each of these tissues to near castration levels (FIG. 19A). FIG. 19A shows the reductions in absolute organ weights in intact rats and FIG. 19B represents the same data of % inhibition relative to vehicle treated control. The bottom right panel of FIG. 19B presents the effect of castration on the weights of seminal vesicles and prostate. 1002 at 60 mg/kg reduced prostate and seminal vesicles weights by ~70% each compared to 90% and 85% reductions, respectively, produced by castration (not shown). 1002 is the first SARD with sufficient bioavailability to produce in vivo AR antagonism in excess of enzalutamide despite inferior in vitro potencies in transactivation ($IC_{50}$) and a lack of binding to LBD ($K_i$). 1002 possesses potent SARD degradation activities in vitro. Correspondingly, the unexpectedly superior in vivo antagonism of 1002 compared to enzalutamide (the IND of enzalutamide indicated that 100 mpk and 30 mpk had comparable in vivo efficacy, so the 20 mpk dose presumably was near $E_{max}$ and was barely soluble) is not explainable in terms of conventional inhibition of the AR through the LBD but rather suggests that the AR antagonism is attributable to the potent degradation of the AR which is a unique property to compounds of this invention.

See also Example 9 for multiple biophysical lines of evidence supporting NTD binding of 1002 and other SARDs of this invention. See also Example 10 for unexpected results for 1014 in a Hershberger assay, and other in vivo assays.

Example 8

In Vivo Anti-Tumor Activity Demonstrated by SARD Compound 1002 in Triple Negative Breast Cancer (TNBC) Patient Derived Xenografts (PDX)

Patient specimen collection and PDX creation: Specimens from breast cancer patients were collected with patient consent under a protocol approved by the University of Tennessee Health Science Center (UTHSC) Institutional Review Board (IRB). Briefly, specimens were collected immediately after surgery in RPMI medium containing penicillin:streptomycin and Fungizone (Thermo Fischer Scientific) and transported to the laboratory on ice. The tissues were minced finely and treated with collagenase for 2 h. The digested tissues were washed with serum-free medium and implanted as 1 $mm^3$ fragments subcutaneously in female Nod Scid Gamma (NSG) mice. Two such PDX from triple-negative patients (TNBC), HBrT-1071 and HBrT-1361, characterized as TNBC at the time of collection, were implanted in ovariectomized mice. All animal studies were conducted under the UTHSC Animal Care and Use Committee (ACUC) approved protocols. Female NSG mice (6-8 weeks old) purchased from JAX labs (Bar Harbor, Me.) were housed as five animals per cage and were allowed free access to water and commercial rodent chow (Harlan Teklad 22/5 rodent diet –8640). HBrT-1071 and HBrT-1361 were implanted (1 $mm^3$) under the mammary fat pad surgically under isofluorane anesthesia. Once tumor sizes reached 100-200 $mm^3$, the animals were randomized and treated with vehicle (polyethylene glycol-300: DMSO 85:15 ratio) or 1002 (60 mg/kg/day p.o.). Tumors were measured thrice weekly using caliper and the tumor volume was calculated using the formula length*width*width*0.5236. At the end of the experiments, animals were sacrificed, tumors were weighed and collected for further processing. Blood was collected, serum was separated, and stored in –80° C.

Figure 21A:
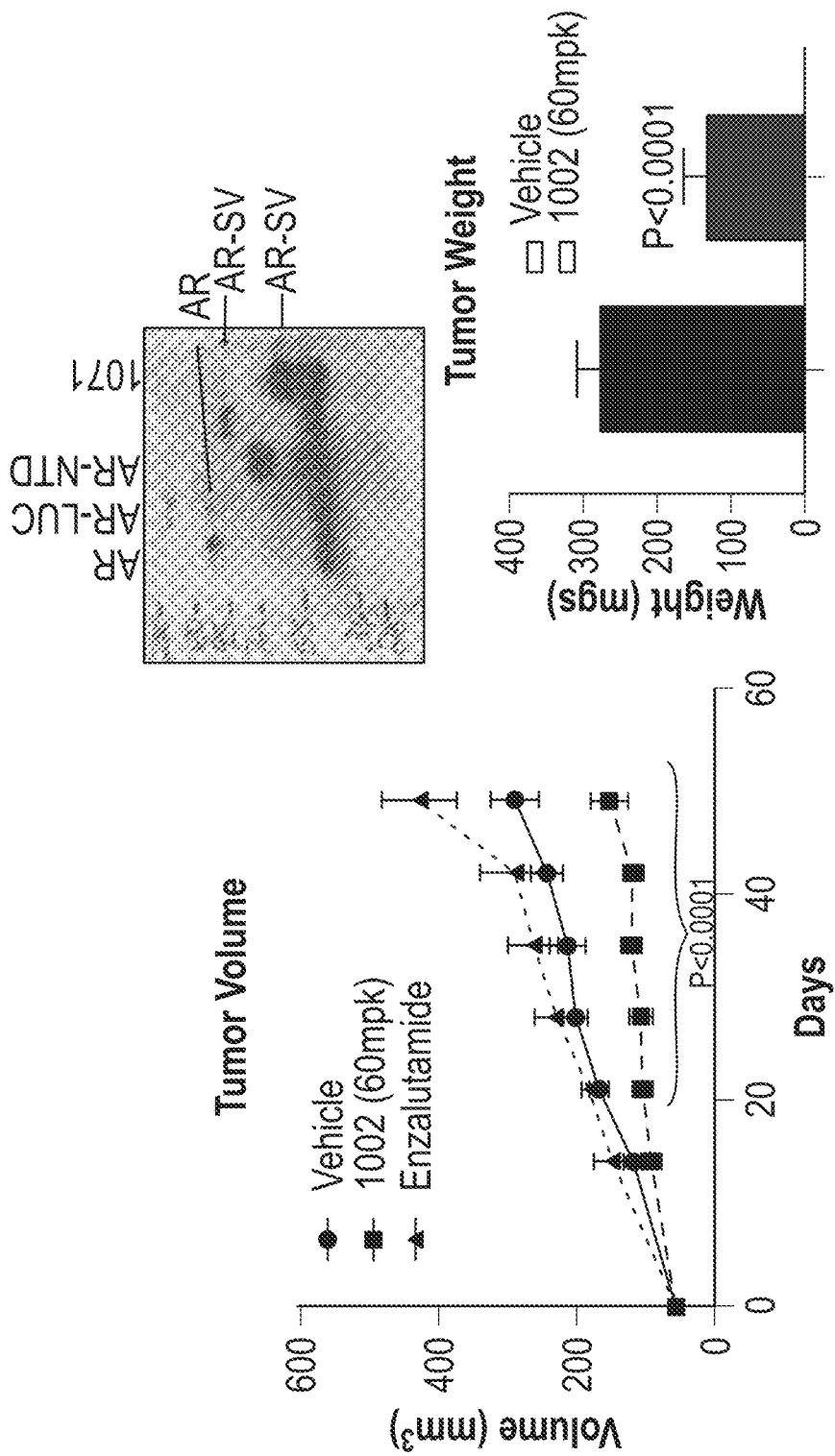
FIG. 21A and FIG. 21B: Anti-tumor efficacy for 1002 in triple negative breast cancer (TNBC) patient-derived xenograft (PDX) is presented in HBrt 1071 triple negative breast cancer (FIG. 21A) and in HBrt 1361 triple negative breast cancer (FIG. 21B).
Figure 21B:
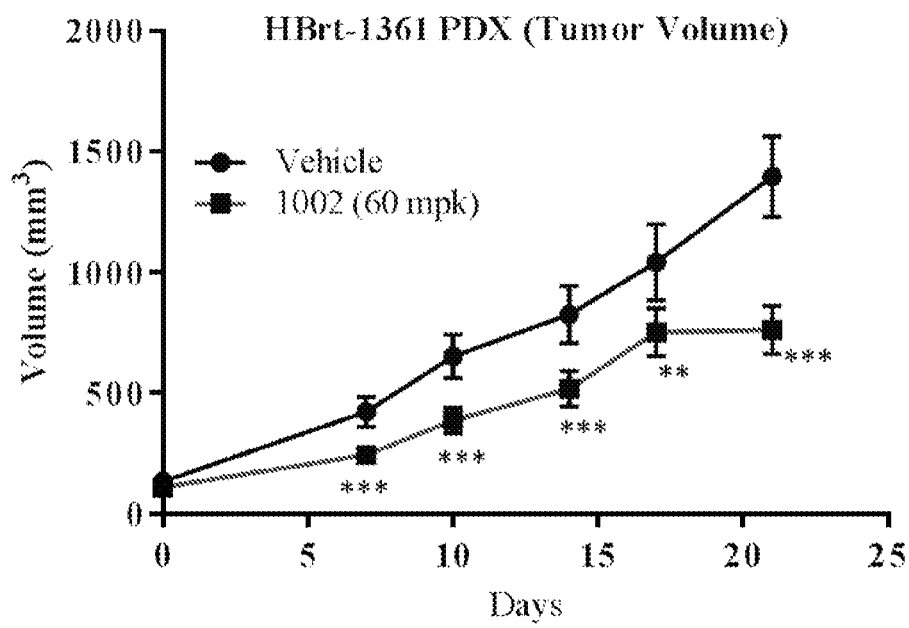
Figure 21B:
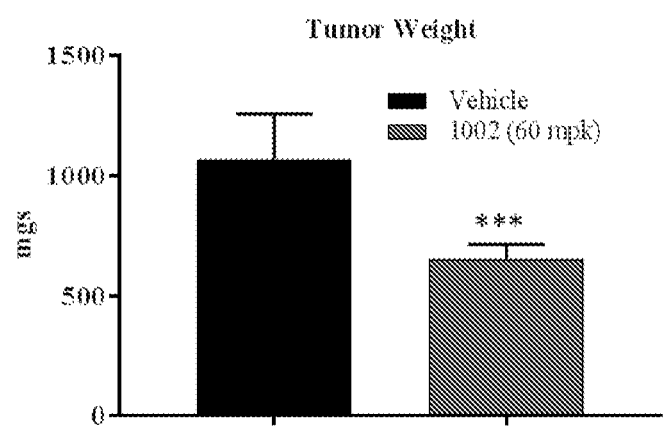

Results: The SARD compound 1002 was able to inhibit tumor growth in two different TNBC PDX models (FIGS. 21A and 21B) whereas enzalutamide failed to inhibit tumor growth (FIG. 21A). 1002 significantly inhibited the growth of HBrt 1071 TNBC PDX with a percent tumor growth inhibition of 65%. Similarly, 1002 inhibited the tumor weight by over 50% (FIG. 21A). In contrast, tumors from enzalutamide treated animals were indistinguishable in size from vehicle treated animals, or possible trended toward promoting tumor growth. 1002 significantly inhibited the growth of HBrt-1361 TNBC PDX with a percent tumor growth inhibition of ~50% and inhibited the tumor weight by over 40% (FIG. 21B). Further, analyses of the AR which was present in these tumors revealed high levels of AR splice variants (FIG. 21A, lane labeled 1071). This observation helps to rationalize why 1002, an NTD-binding SARD (see Example 9 below for biophysical evidence of NTD binding), was able to inhibit tumor growth whereas the LBD-dependent AR antagonist enzalutamide failed. This suggests that SARDs are able to inhibit AR splice variant dependent cancers such as TNBC and advanced prostate cancers (see Example 10), e.g. those expressing AR-V7 or other AR's lacking the LBD. Further, this is confirmation that the unexpected oral bioavailability of 1002 and other SARDs of this invention, e.g. 1014 and 1010, allowed serum and tumor (see also Example 10) levels following oral administration to be sufficient for treatment of advanced and refractory AR-dependent cancers.

Example 9

SARDs Bind to AF-1 Region of the N-Terminal Domain (NTD) of the Androgen Receptor Nuclear Magnetic Resonance (NMR): AF-1 and various fragments of AF-1 were cloned in pGex4t.1 and pGex6p.1 vectors. To purify proteins, large scale Luria broth cultures were induced with 1 Mm isopropyl β-D-1-thiogalactopyranoside (IPTG) when the O.D. reached 0.6 and incubated at 25° C. for 6 h. Cells were harvested and lysed in a lysis buffer (50 mM Tris pH 7.5, 25-250 mM NaCl, DNase, protease inhibitors, glycerol, EGTA, DTT, and sucrose). Protein lysates were purified using glutathione sepharose beads by incubating overnight at 4° C. with gentle rocking and the purified protein was eluted with elution buffer (lysis buffer without DNase) containing 50 mM reduced glutathione. Purified proteins were concentrated using Amicon or GE protein concentrators. In cases where GST needed to be cleaved, PreScission Protease (GE Life Sciences) was used to cleave the GST. The proteins were further purified using FPLC (GE AKTA FPLC) with gel filtration (Superdex75 10/300 GL) and ion exchange (HiPrep Q FF 16/10) columns. Compounds alone or in combination with purified protein were run in $^1$H NMR (Bruker 400) in a total volume of 500 µL with 5 mM protein and 200-500 mM small molecule (made in deuterated DMSO (DMSO-$d_6$)) in 20 mM phosphate buffer made in 100% deuterated water.

NMR data were collected using a Bruker AVANCEIII 400 MHz NMR spectrometer (Bruker BioSpin Co. Billerica, Mass. USA) equipped with a BBO 5 mm NMR probe, and TopSpin 3.0 software. $^1$H proton NMR and Saturation-Transfer Difference (STD) experiments were acquired using standard pulse sequences in the TopSpin library. Spectral width was set to 16 ppm with H$_2$O peak at center. 32K time domain (TD) complex data points and 256 scans were used for $^1$H proton NMR and 1024 scans for STD acquisition. For STD, on- and off-resonance [signals] were collected using interleaved method. Irradiation frequencies for on- and off-resonance were set at 0.8 ppm and −20 ppm, respectively. STD was acquired on a sample with ligand compound alone using identical settings to make sure the STD signals originated from protein in the protein-compound complex sample. Data were collected at room temperature. Chemical shift was referenced according to H$_2$O peak at 4.70 ppm.

Results: $^1$H NMR has been used in high-throughput screens to detect the binding of small molecules less than 500 Da to large proteins greater than 5 Kda. As opposed to other biophysical methods, it is easier to use one dimension NMR to observe changes in line-width or line broadening as a high-throughput method to identify the binding of the molecules to proteins and then use Water ligand-observed spectroscopy (WaterLOGSY) or Saturation-Transfer Difference (STD) NMR as confirmatory methodologies. These experiments are based on the fact that NMR observables such as linewidths and NOEs vary dramatically between small molecules and large molecules. The decreased rotational correlation times upon binding of a small molecule ligand to a heavy target molecule produces an atypical heavy molecule NMR result characterized by broadening and weakening of ligand peaks in $^1$H NMR and negative NOE peaks in the waterLOGSY as compared to the free state. In the absence of any affinity, the small molecule NMR result is obtained (sharp peaks in $^1$H NMR and positive NOEs) even in the presence of target protein. This distinction provides the basis for NMR screening experiments.

Figure 22:
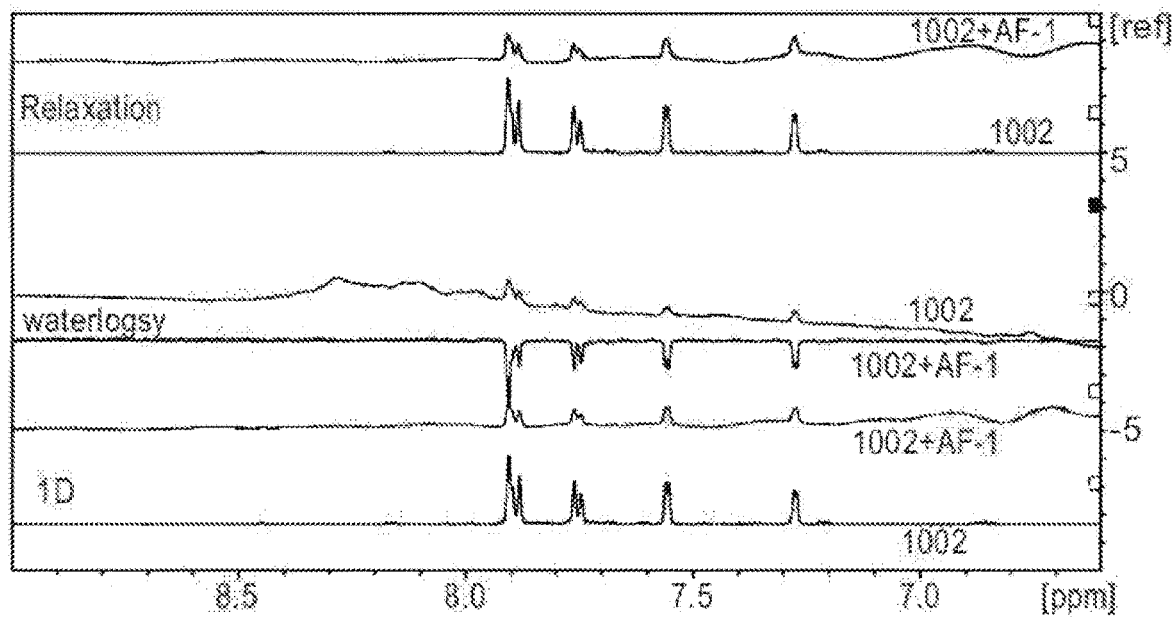
FIG. 22: depicts binding of 1002 to AF-1 region of the N-terminal domain (NTD) of the androgen receptor. 1D and waterLogsy NMR experiments demonstrate that 1002 bandwidth are broadened in the presence of a peptide derived from the AF-1 region of the NTD. Moreover, relaxation and waterLogsy demonstrate that the tumbling rate in solution for 1002 is slowed upon addition of AF-1, strongly suggestive of 1002 binding to AF-1 region as its targeted protein interaction.

Using these principles, $^1$H NMR was utilized to confirm the binding of 1002 to the AF-1 region. 1002 (500 mM) was dissolved in deuterated DMSO (DMSO-$d_6$) and was incubated alone or mixed with 5 mM AF-1 and the binding of the molecules to the protein was determined by NMR. While 1002 alone exhibited sharp peaks revealing the ligand present in the free state, 1002 in combination with AF-1 provided broad, diffused, and shorter ligand peaks revealing that 1002 has affinity for AF-1 (FIG. 22). To further confirm the 1D NMR results, we performed WaterLOGSY with 1002 alone or in combination with AF-1. While the 1002 alone gave a flattened positive signal, 1002 in combination with AF-1 provided a negative signal, characteristic of binding to the protein (FIG. 22). These results provide evidence that 1002 binds to AF-1 in the NTD of AR, explaining how a molecule that does not bind the LBD of AR (Table 1) can inhibit the AR in vitro and in vivo.

Steady State Fluorescence: Recombinant histidine tagged AR-NTD (amino acids 1-559) and AR-AF1 (amino acids 141-486) were purified as previously described. The steady-fluorescence spectrum for the proteins (1 µM) alone or after titration with increasing concentrations of 1002 (1 µM, 2 µM, 5 µM, 10 µM, 25 µM, & 50 µM) was measured after excitation at 278 nm on a Shimadzu Fluorescence spectrophotometer. Proteins were preincubated on ice for 30 minutes with 1002. The results represent three independent experiments (n-3) measured in duplicate.

Figure 27A:
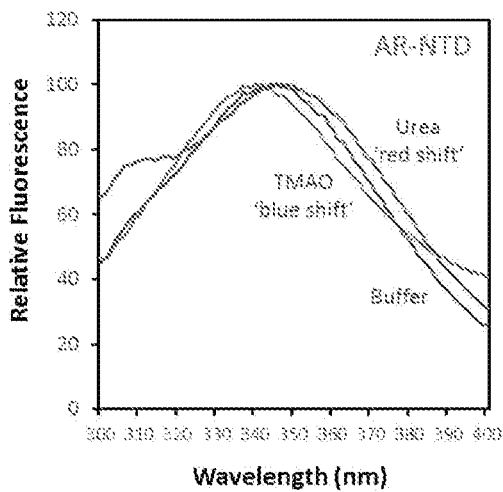
FIGS. 27A-27D: depict steady state fluorescence studies demonstrating interactions between SARDs 1002, 1010, and 36 (indole), and N-terminal fragments of the AR such AR-NTD (amino acids 1-559) and AR-AF1 (amino acids 141-486).
Figure 27A:
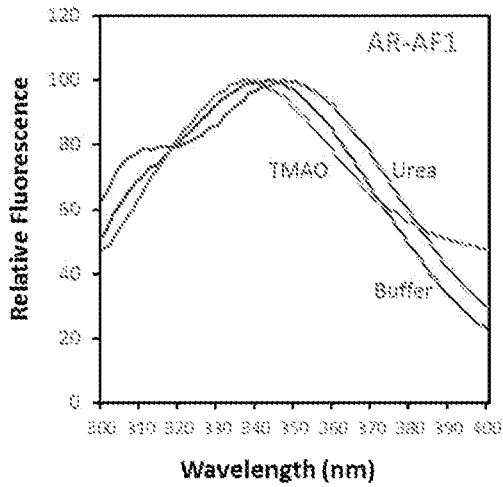
Figure 27B:
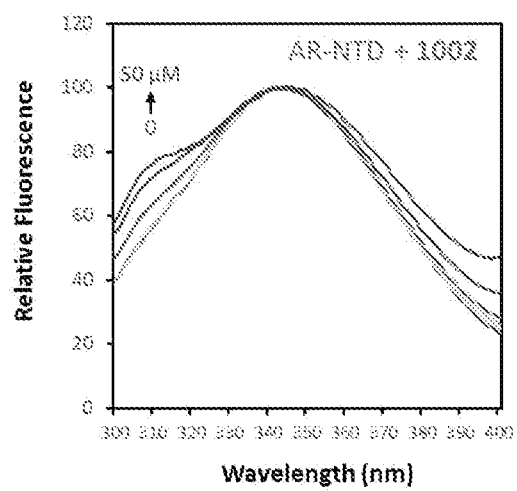
Figure 27B:
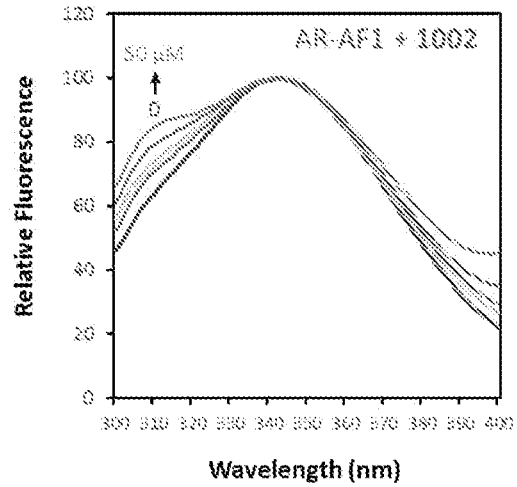

Results: The pyrazole SARD 1002 showed a dramatic increase in the fluorescence signal in the region seen for tyrosine emission (FIG. 27B, 307 nm). Normally, the tyrosine signal is not seen due to energy transfer to tryptophan residues in folded/partially folded polypeptides. The increase in the tyrosine signal is similar to what is seen in unfolded/denatured AR-NTD or AR-AF1, e.g., upon addition of urea (FIG. 27A). However, there is no corresponding 'red shift' (increase in wavelength) in the tryptophan signal (compare FIGS. 27A and 27B, in urea $\lambda_{max}$ 344 nm to 347 nm). 1002 may unfold the receptor polypeptides (resulting in tyrosine emission), but shield the tryptophan residues.

Figure 27C:
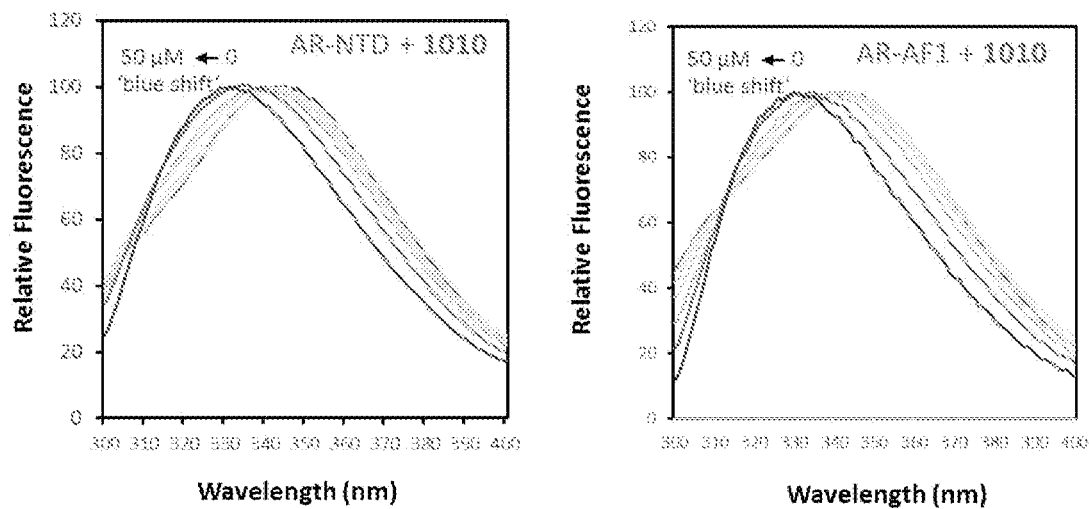
Figure 27D:
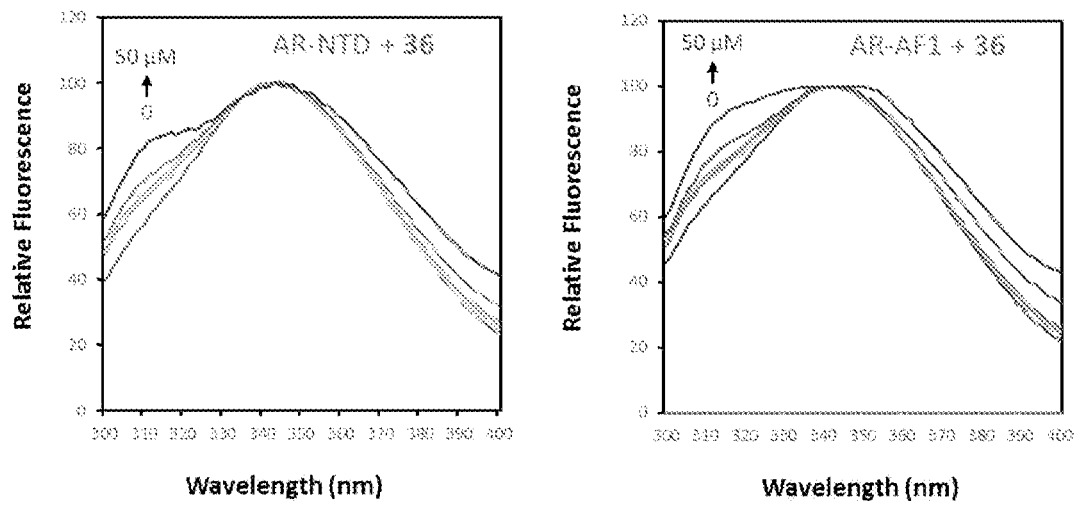
Figure 27D:
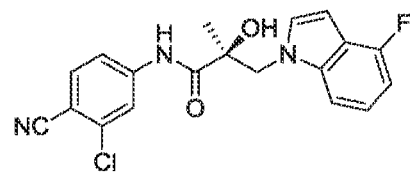

For the pyrrole SARD 1010, some evidence for quenching was observed, but the concentration dependence was poor. However, more strikingly there was a consistent and dramatic 'blue shift' (toward smaller wavelengths), which was consistent with the folded form of AR-NTD/AF (i.e. TMAO spectrum in FIG. 27C, $\lambda_{max}$ 344 nm to 340 nm). On the basis of data so far it seems 1010 may stabilize the structure of the AR polypeptides. The data with the indole SARD 36 (FIG. 27D) was similar to what was seen with 1002, but the changes in fluorescence were weaker. In each case, an interaction was observed between the SARD and the AR-1 or NTD. Though the perturbation of fluorescence polarization (FP) was not identical, these similar results across multiple templates of SARDs suggest that the interaction with the N-terminus of the androgen receptor is a conserved feature for the SARDs of this invention. Further, 1002 lacks an interaction with the LBD yet retains potent AR antagonism and SARD activity.

Example 10

Metabolic Stability of Pyrazoles Such as 1014 and 1002 Reveals the Therapeutic Potential of SARDs In Vivo In Vitro Characteristics:

Transactivation ($IC_{50}$): As reported in Table 1 using the method of Example 3, 1014 is a potent inhibitor of the AR with an $IC_{50}$ value of 205 nM which is similar to 1002 (199 nM).

LBD binding ($K_i$): As reported in Table 1 using the method of Example 4, 1014 binds to the LBD of the AR with a $K_i$ value of 512 nM, whereas 1002 does not bind to the LBD. SARD activity: As reported in Table 1 using the methods of Example 5, 1014 and 1002 are capable of potently degrading full length and splice variant androgen receptors.

LNCaP-Enzalutamide Resistant (LNCaP-EnzR) Cells MR49F Growth Assay: Cells were plated at 10,000 cells/well in RPMI+1% csFBS without phenol red medium in 96 well plates. Cells were treated in the indicated medium with a dose response of the SARDs. At the end of three days, medium was changed and the cells were re-treated. At the end of 6 days, the live cells were measured by Cell-Titer-Glo (Promega) assay.

Figure 23:
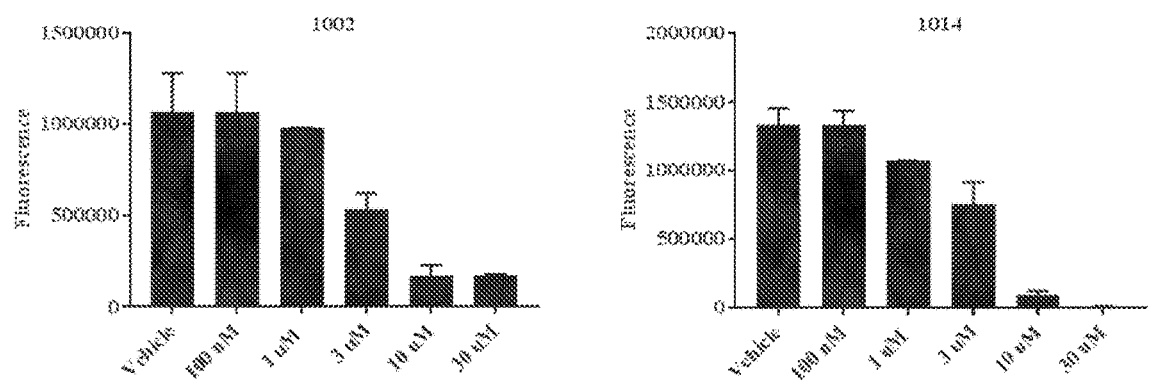
FIG. 23: depicts a LNCaP-enzalutamide resistant (LNCaP-EnzR) cells MR49F growth assay using 1002 and 1014. 1002 and 1014 inhibit the growth of LNCaP-EnzR cells in the low micromolar range.

Results: 1002 and 1014 demonstrated comparable growth inhibition of an enzalutamide resistant variation of the LNCaP (LNCaP-EnzR) cell line which bears the double mutant F876L/T877A, conferring resistance to enzalutamide. 1002 and 1014 both had $IC_{50}$ values of ~3 μM and almost complete inhibition at 10 μM (FIG. 23), suggesting that either SARD could be beneficial for enzalutamide resistant prostate cancer patients if these levels could be achieved in the tumor. (see Table 4 below)

Liver Microsome Metabolism Study:

Materials: Microsomes were purchased from Xenotech, LLC. Solution 'A' and 'B' (Cat #451220, and 451200, respectively) for NADPH regenerating system (NRS) solution were obtained from Corning Life Sciences. Verapamil, genistein, UDPGA, alamethicin and magnesium chloride were purchased from Sigma-Aldrich. Saccharolactone was obtained from Santa Cruz Biotechnology.

Method: Phase I

Test compound stock solutions were prepared at 10 mM in DMSO. They were diluted to a concentration of 50 μM in 50% acetonitrile (ACN)/$H_2O$ resulting in a working stock solution of 100×. Liver microsomes were utilized at a final concentration of 1.0 mg/mL of protein. Duplicate wells were used for each time point (0, 5, 10, 30, and 60 minutes). Reactions were carried out at 37° C. in a shaking water bath, and the final concentration of solvent was kept constant at 0.5%. At each time point, 100 μL of reaction was removed and added to a sample well containing 100 μL, of ice-cold, 100% ACN (plus internal standard), to stop the reaction. The final volume for each reaction was 200 μL, composed of: 66 μL of 0.2 M $KPO_4$ buffer, (pH 7.4); 50 μL of NRS solution; and 10 μL of microsomes (20 mg/mL stock).

The NRS is a solution of glucose-6-phosphate dehydrogenase, $NADP^+$, $MgCl_2$, and glucose-6-phosphate, prepared per manufacturer's instructions. Each 5.0 mL stock of NRS solution contains 3.8 mL $H_2O$, 1.0 mL solution "A", and 0.2 mL solution "B". The reaction from the positive control wells (verapamil, 0.5 μM) were stopped with ice cold acetonitrile containing internal standard.

Phase I and II

Reaction conditions were followed similarly as described above. Additional cofactors were also included in each reaction. UDPGA was added at a final concentration of 5.0 mM. Saccharolactone (β-glucuronidase inhibitor) and alamethicin (pore forming peptide) were added to each reaction at a final concentration of 5.0 mM and 50 μg/mL, respectively. Each 200 μL of microsomal reaction was comprised of 65 μL of 0.2 M $KPO_4$ (pH 7.4), 50 μL of NRS mixture, 66 μL of UDPGA (15 Mm stock); 5.0 μL of saccharolactone (200 mM stock); 0.5 μL of alamethicin (20 mg/mL); 0.6 μL of $MgCl_2$ (1 M stock), and 10 μL of microsomes (20 mg/mL stock). The reaction from the positive control wells (genistein, 2.0 μM) was stopped with ice cold acetonitrile containing internal standard.

Samples were centrifuged at 3,000 rpm for 10 minutes to remove debris and precipitated protein. Approximately 150 μL of supernatant was subsequently transferred to a new sample block for analysis.

Data Analysis

For half-life determination and clearance, data was fitted using GraphPad Prism with a non-linear regression equation, and one phase exponential decay.

Results: 1014 was compared to other compounds, including 1002 in liver microsome metabolism studies. Interestingly, while 1002 showed a half-life around 1 h in vitro, 1014 had a half-life of infinity in the same test, i.e., after 120 min of incubation over 50% of the compound still remained in the reaction (Table 3). As seen in Table 3, the pyrazoles 1002, 1014, and 1022 (see also Table 1 for 1023 and 1024) demonstrated much improved in vitro metabolic stabilities compared to indole (11, 34, 36) and indoline (103) based compounds (and the pyrrole 1010) (Table 3) while retaining SARD activity (Table 1). This suggested that significant in vivo bioavailabilities may be possible for 1002 and 1014.

TABLE 3

| | Liver microsomes MLM/RLM | |
|---|---|---|
| | $t_{1/2}$ (min) | $CL_{int}$ (μL/min/mg) |
| 1002 | 77.96 | 0.89 |
| 1014 | infinity | ~0 |
| 96 (S)-N-(4-Cyano-3-(trifluoromethyl)phenyl)-2-hydroxy-2-methyl-3-(4-(trifluoromethyl)-1H-indazol-1-yl)propanamide | 54.44 | 12.73 |
| 1010 | 17.93 | 38.66 |
| 36 (S)-N-(3-Chloro-4-cyanophenyl)-3-(4-fluoro-1H-indol-1-yl)-2-hydroxy-2-methylpropanamide | 11.77 | 58.8 |
| 34 (S)-N-(3-Chloro-4-cyanophenyl)-3-(5-fluoro-6-phenyl-1H-indol-1-yl)-2-hydroxy-2-methylpropanamide | 15.50 | 58.87 |
| 11 (S)-N-(4-Cyano-3-(trifluoromethyl)phenyl)-3-(5-fluoro-1H-indol-1-yl)-2-hydroxy-2-methylpropanamide | 14.35 | 48.30 |
| 103 | 15 | 46.22 |

TABLE 3-continued

| | Liver microsomes MLM/RLM | |
|---|---|---|
| | $t_{1/2}$ (min) | $CL_{int}$ (µL/min/mg) |
| (S)-N-(3-Chloro-4-cyanophenyl)-3-(4-fluoroindolin-1-yl)-2-hydroxy-2-methylpropanamide 1022 | 58.06 | 11.94 |

Figure 24:
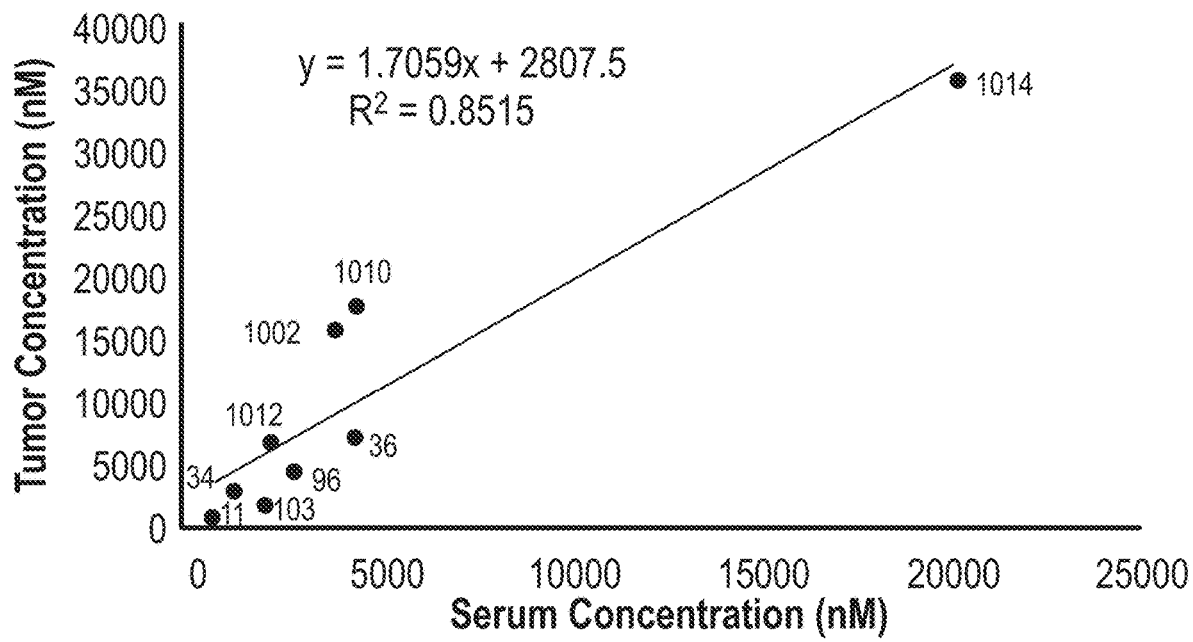
FIG. 24: depicts the serum and tumor levels of 11, 34, 36, 96, 103, 1002, 1010, 1012, and 1014 achieved in a 22RV1 xenograft experiment.
Figure 24:
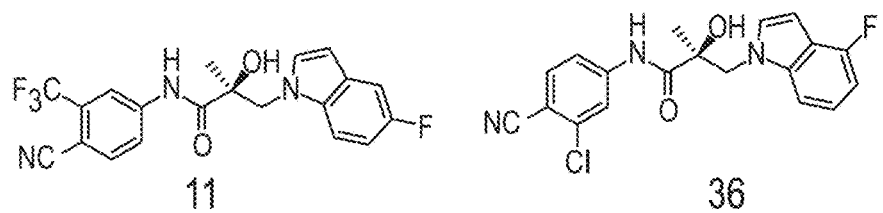
Figure 24:
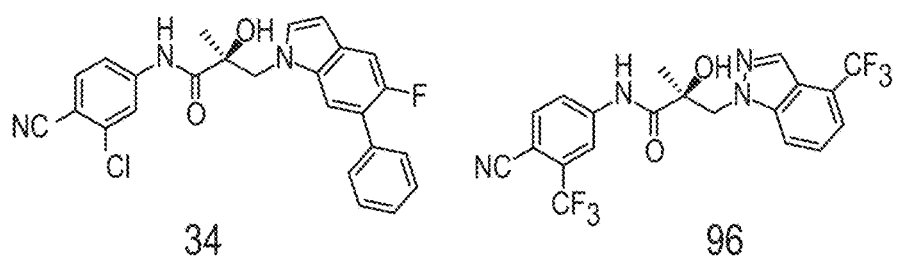
Figure 24:
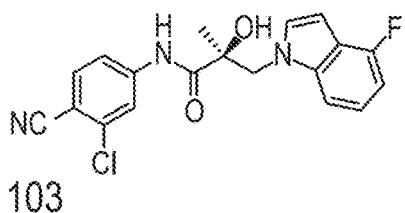

In Vivo Characteristics:

1014 drug concentrations in serum and tumor in a xenograft experiment: Nude mice implanted with 22RV1 cells subcutaneously were randomized when the tumors reached between 100 and 200 mm³. The mice were treated with vehicle (20:80 water:PEG-400) or 60 mg/kg/day 1014 (or indicated doses of other SARDs) in vehicle for 21 days. At the end of 21 days, the mice were sacrificed and blood and tumors were collected for further analysis. Measurement of drug concentration in animals treated with 1014 demonstrated a significant accumulation of the drug in serum (20.1 µM) and tumor (35.6 µM) (Table 4 and FIG. 24) compared to other molecules tested in parallel in the same experiment. These in vivo levels for 1014, even in view of structurally similar pyrazoles 1002 and 1012, was unexpected. Further, these levels help to explain the efficacy in LNCaP-EnzR xenografts (see FIG. 26 and its description below). Although 22RV1 tumors were not susceptible to SARDs in this particular experiment, likely due to androgen independent growth, this result suggests that androgen-dependent tumors, e.g., LNCaP-EnzR, would be susceptible. Another observation from these data is that tumor concentrations were in excess of serum concentrations, suggesting accumulation of drug in the tumor. The results are shown in Table 4 and FIG. 24.

TABLE 4

| | Xenograft dose | Tumor concentration (nM) | Xenograft PK Serum concentration (nM) | |
|---|---|---|---|---|
| | (mg/kg) | At sacrifice (8 hrs) | 2 hrs | 8 hrs |
| 1002 | 60 | 15,725 | 3,560 | 3,620 |
| 11 | 100 | 854 | 365 | 338 |
| 1012 | 60 | 6,655 | 2,114 | 1,914 |
| 1014 | 60 | 35,638 | 4,469 | 20,119 |
| 96 | 100 | 4,458 | 1,207 | 2,563 |
| 1010 | 100 | 17,683 | 862 | 4,173 |
| 103 | 100 | 1,748 | 380 | 1,776 |
| 36 | 100 | 7,128 | 570 | 4,142 |
| 34 | 100 | 2,948 | 261 | 965 |

Figure 25:
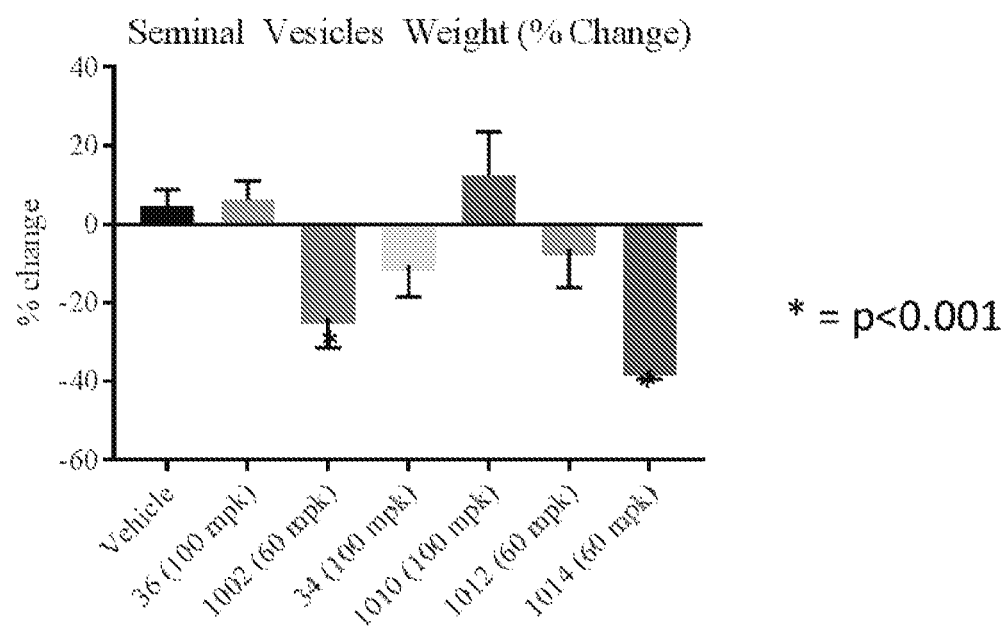
FIG. 25: depicts reductions in seminal vesicles weights (% change) for animals treated with 34, 36, 1002, 1010, 1012, and 1014 in a Hershberger assay.
Figure 25:
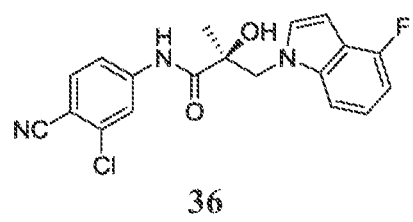
Figure 25:
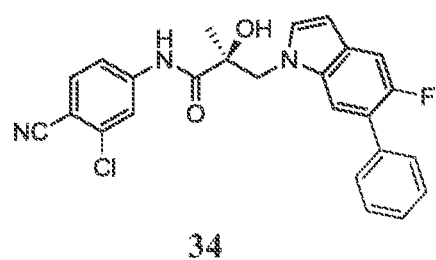

Hershberger assay: Intact C57BL/6 male mice (6-8 weeks old) were randomized based on body weight and treated with various compounds indicated in FIG. 25 for 14 days. At the end of 14 days, the mice were sacrificed and seminal vesicles were weighed. 1014 demonstrated the best inhibition of seminal vesicles weight compared to other compounds, following by 1002, suggesting that these orally administered SARDs were present in levels sufficient to antagonize the AR in androgen-dependent tissues of intact animals. The indoles 34 and 36, pyrrole 1010, and the pyrazole 1012 did not exhibit strong AR antagonism in vivo in this assay.

Figure 26:
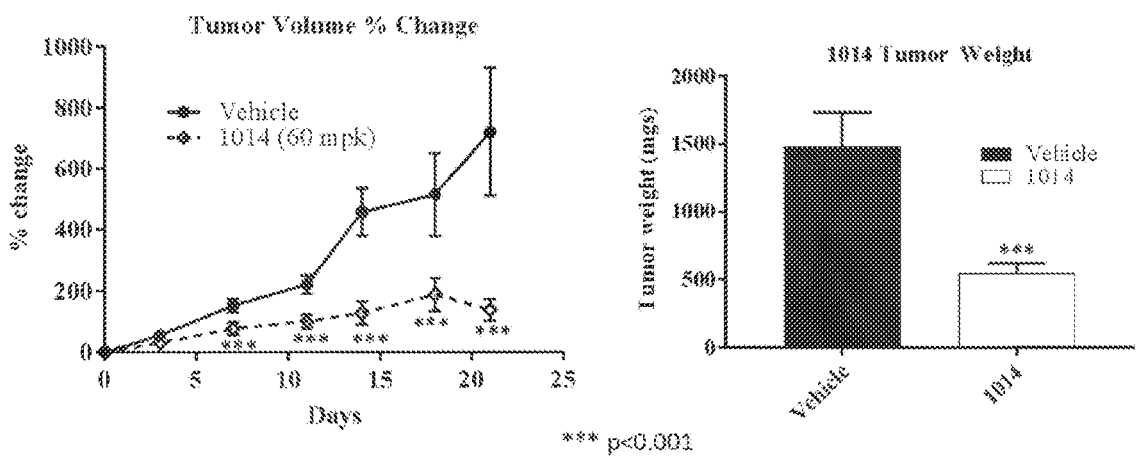
FIG. 26: depicts tumor growth inhibition of LNCaP-enzalutamide-resistant (LNCaP-EnzR) xenografts treated with 1014 at 60 mg/kg administered orally. Two different experiments (Experiment 1 and Experiment 2) are shown.
Figure 26:
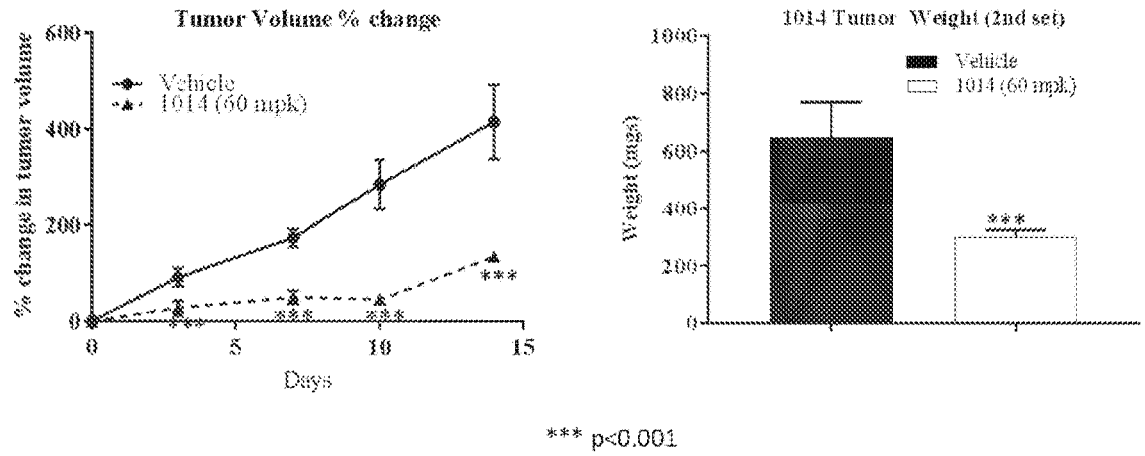

LNCaP-Enzalutamide-Resistant (LNCaP-EnzR) Xenograft: LNCaP-EnzR cells MR49F in RPMI+10% FBS were mixed with Matrigel (BD Biosciences) (1:1) and injected subcutaneously in NOD SCID Gamma (NSG) mice (100 µL). Once the tumors reached 100-200 mm³, the animals were randomized and were treated with vehicle (20:80 water:PEG-300) or 1014 (60 mg/kg/day) in vehicle. Tumor volume was measured twice weekly. At the end of the study, animals were sacrificed, tumors isolated, weighed, and stored for further analysis. The experiment was performed twice with two different batches of cells and the results are shown in FIG. 26. Results: In two separate experiments, 1014 was able attain high efficacy tumor growth inhibition, reducing tumor volumes by approximately 60-70% compared to vehicle treated animals. These results suggest that 1014 and other SARDs of this invention administered orally were capable of therapeutic efficacy in enzalutamide resistant (i.e., advanced and refractory) prostate cancers.

Conclusion: All these results indicate that 1014 has unexpected properties due to its slow metabolism and tumor accumulation. Although, 1014 structurally is comparable to 1002, only differing slightly in the substitution with a $CF_3$ in the third position of the pyrazole ring (vs. 4-fluoro for 1002), it is extremely resistant to metabolism by liver microsomes and thereby has significant accumulation in serum, androgen dependent organs, and in tumors which is unexpected in view of other SARDs tested and in the prior art. This allowed for unexpected in vivo efficacies following oral administration, such as pharmacodynamics (Hershberger assay demonstrated most efficacious seminal vesicles weight effect seen with a SARD) and xenograft tumor growth inhibition (LNCaP-EnzR xenograft), that would not have been possible with our earlier reported SARD templates such as 11, 100, and 17, or other SARDs known in the prior art.

Example 11

SARDs Antagonize F876L

Figure 29A:
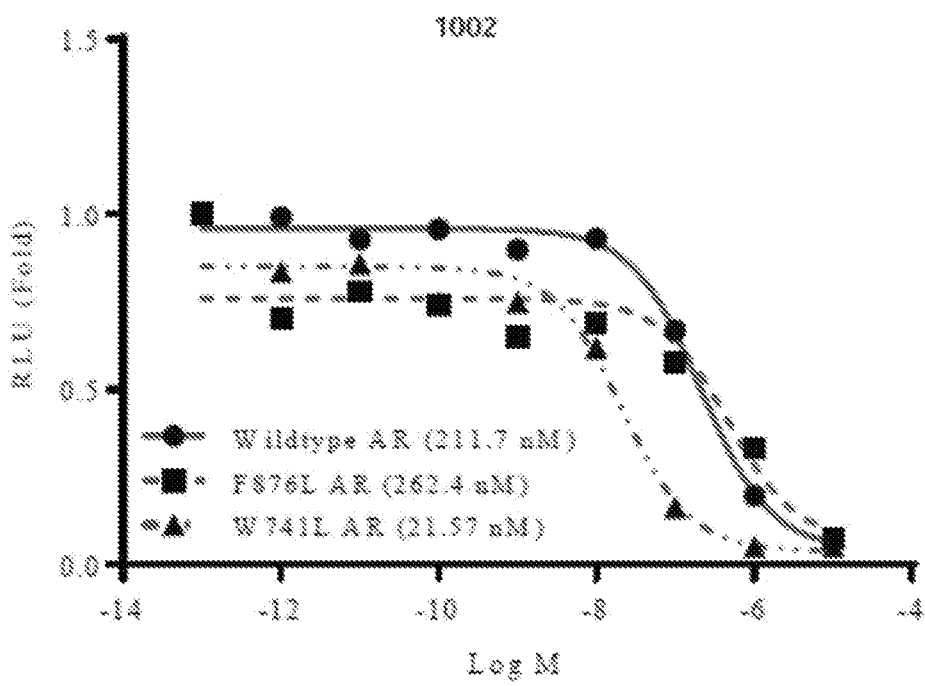
FIGS. 29A-29C: depict that SARDs such as 1002 can antagonize F876L AR at doses comparable to the wildtype AR and W741L AR at more potent doses than wildtype AR.
Figure 29B:
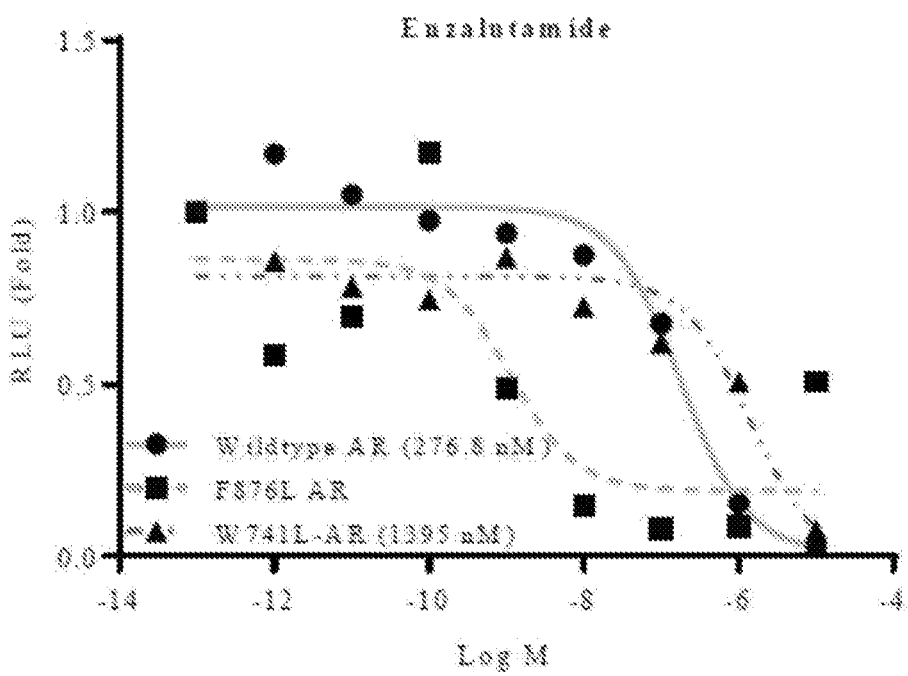
Figure 29C:
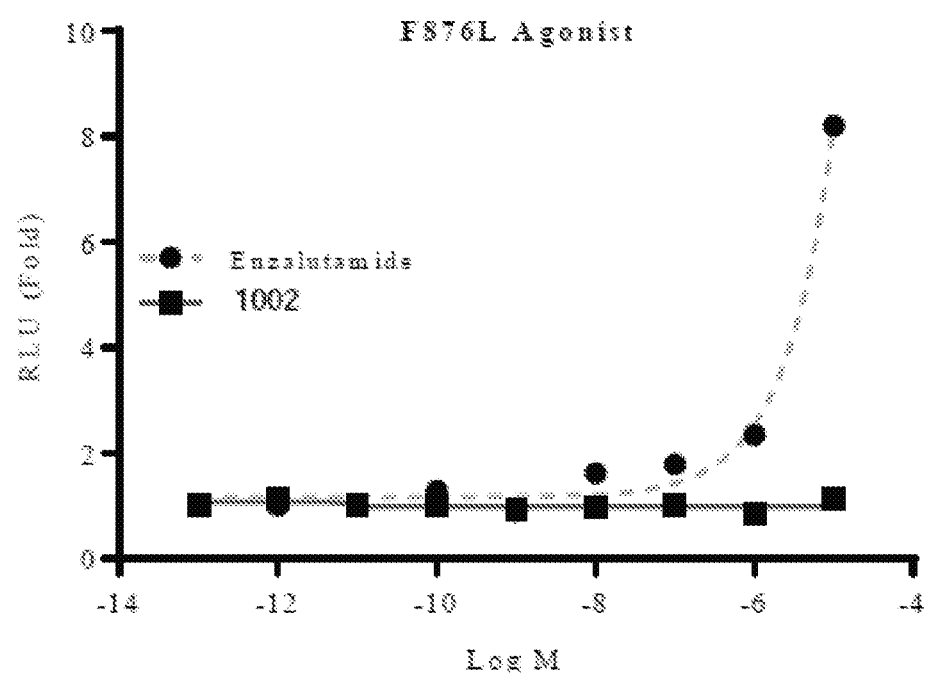
Figure 30A:
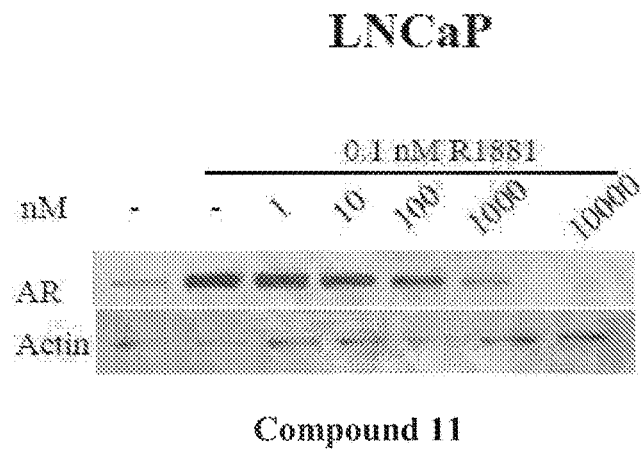
Figure 30B:
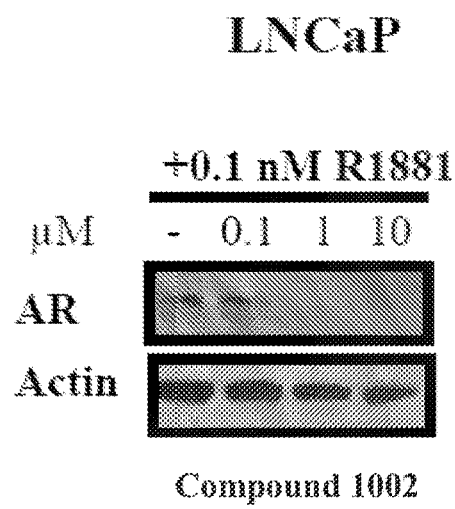
Figure 30C:
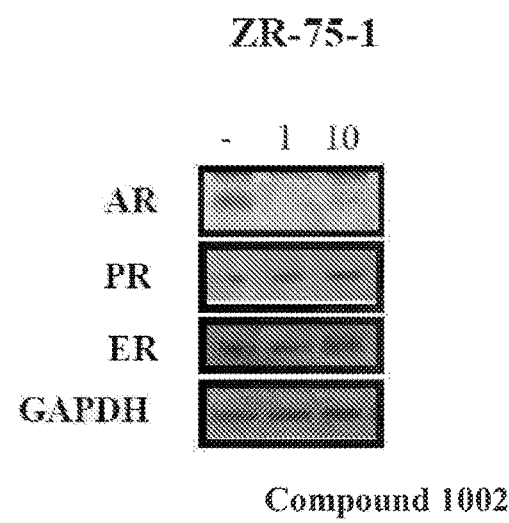
Figure 30D:
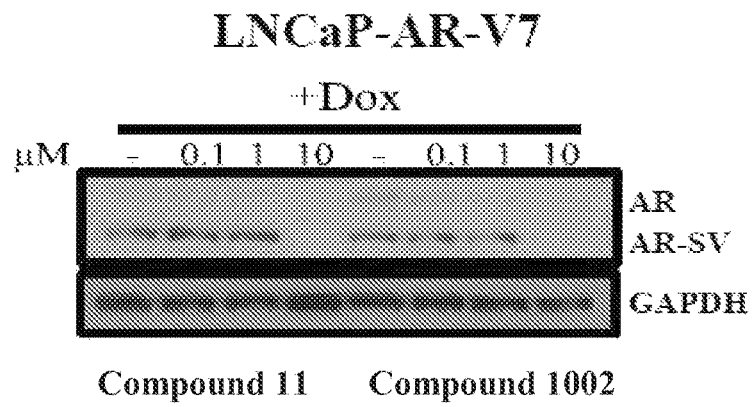
Figure 30E:
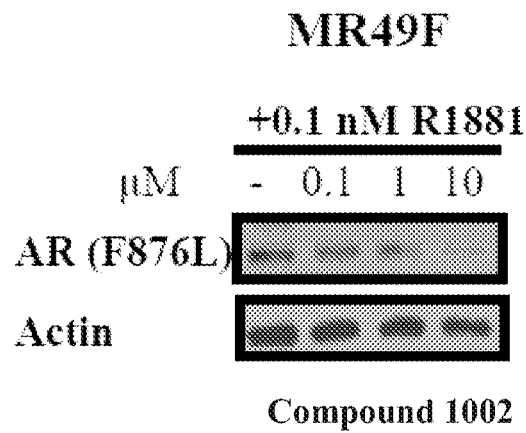
FIG. 30E demonstrates that SARDs of this invention can degrade F876L AR.
Figure 31A:
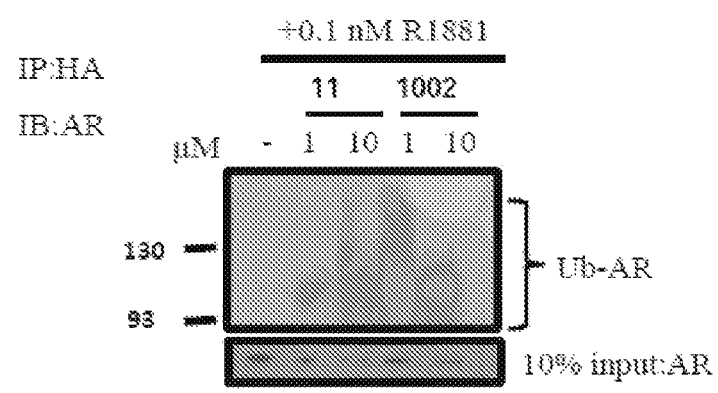
FIGS. 31A and 31B: SARDs promote ubiquitination and require the proteasome to degrade the AR.
Figure 31B:
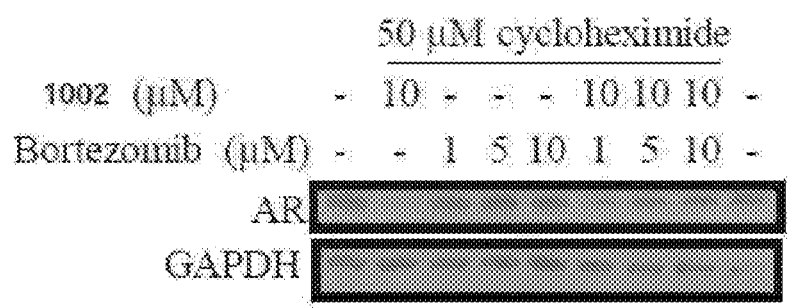

FIGS. 29A-29C illustrate that SARDs antagonized F876L AR at doses comparable to the wildtype AR and do not have any intrinsic agonist activity in F876L, showing their ability to overcome enzalutamide resistance. In FIGS. 29A-29C, compound 1002 was able to inhibit the transcriptional activation of wtAR and F876L (enzalutamide resistance) and W741L (bicalutamide resistance). Enzalutamide behaved similarly, however enzalutamide acted as an agonist at higher levels of treatment of F876L. This demonstrated the ability of SARDs to overcome antagonist switch mechanisms of resistance which are prevalent in CPRC. Further, Example 10 shows the ability of SARDs to overcome enzalutamide resistance with regard to cellular growth and with regard to xenograft growth.

Example 12

Binding to AR-NTD to Degrade

Figure 32:
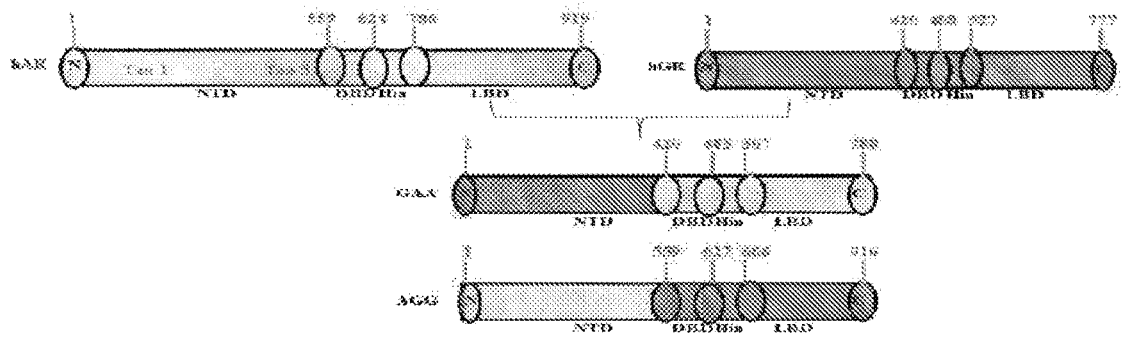
FIG. 32: SARDs require AR-NTD containing constructs (e.g. AR or AGG chimera) to degrade the AR whereas SARDs were unable to degrade GR-NTD containing constructs (GR and GAA chimera).
Figure 32:
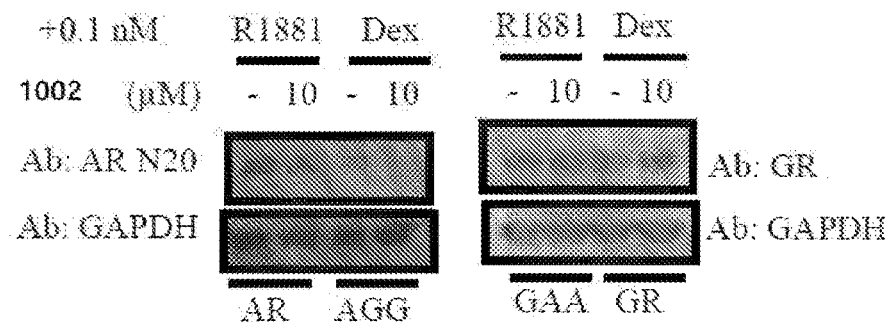
Figure 33:
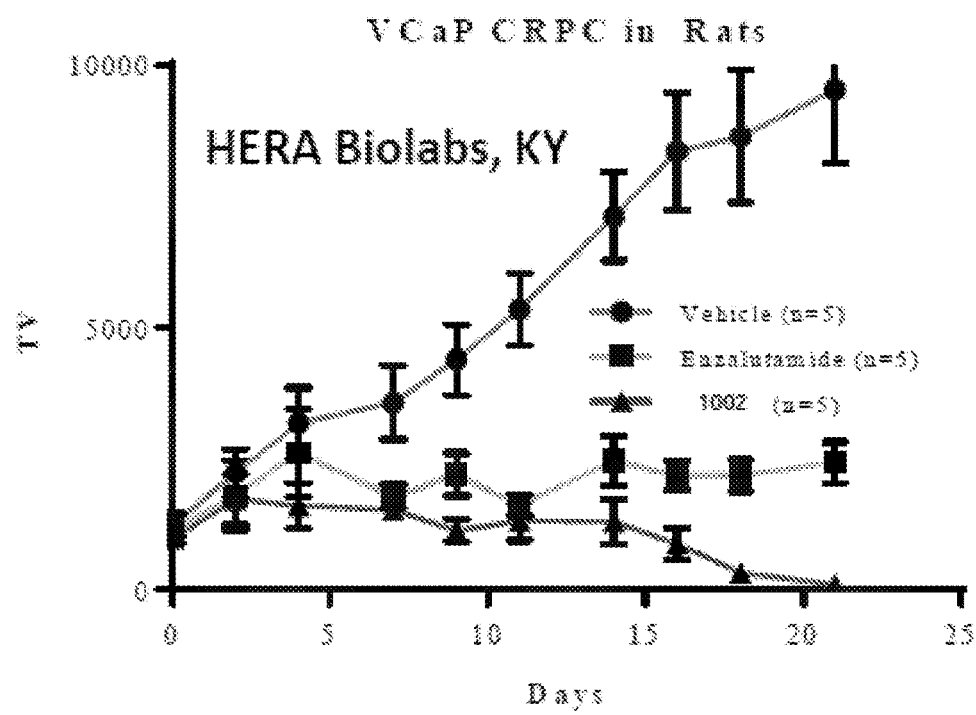
FIG. 33: SARDs inhibit the growth of enzalutamide-resistant VCaP CPRC xenografts in rats. The graph of tumor volume (TV) over timeof VCaP CRPC in rats showed the ability of compound 1002 in rats (there is less metabolism of compound 1002 in rats than mice) to completely resolve VCaP xenografts (tumor volumes plotted as triangles) within 21 days, whereas enzalutamide only caused partial regression (tumor volumes plotted as squares). VCaP is an androgen-dependent CRPC cell line that is partially sensitive to enzalutamide, but fully sensitive to SARDs of this invention. This model demonstrated that in the absence of pharmacokinetic barriers (i.e., high levels of metabolism and/or poor absorption and distribution in mice tumor xenograft models), that SARDs can lead to the complete resolution of castration resistant prostate cancers.
Figure 34A:
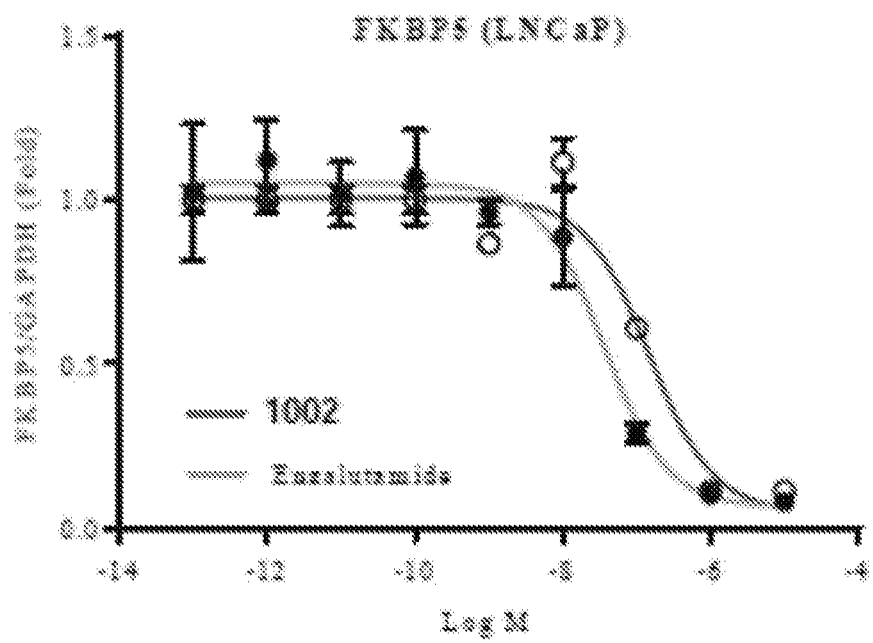
FIGS. 34A-34D: SARDs inhibit AR and Enz-R-AR function and cell growth.
Figure 34B:
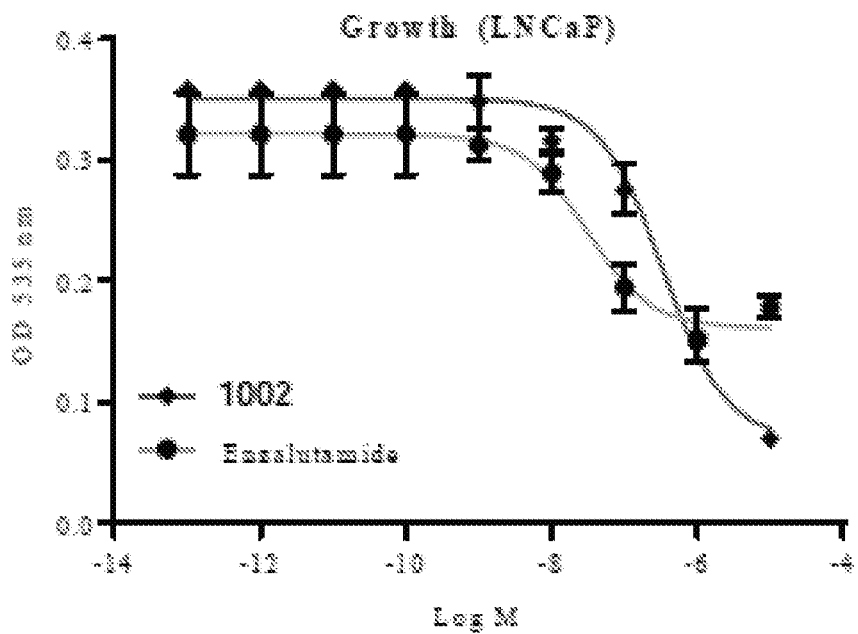
Figure 34C:
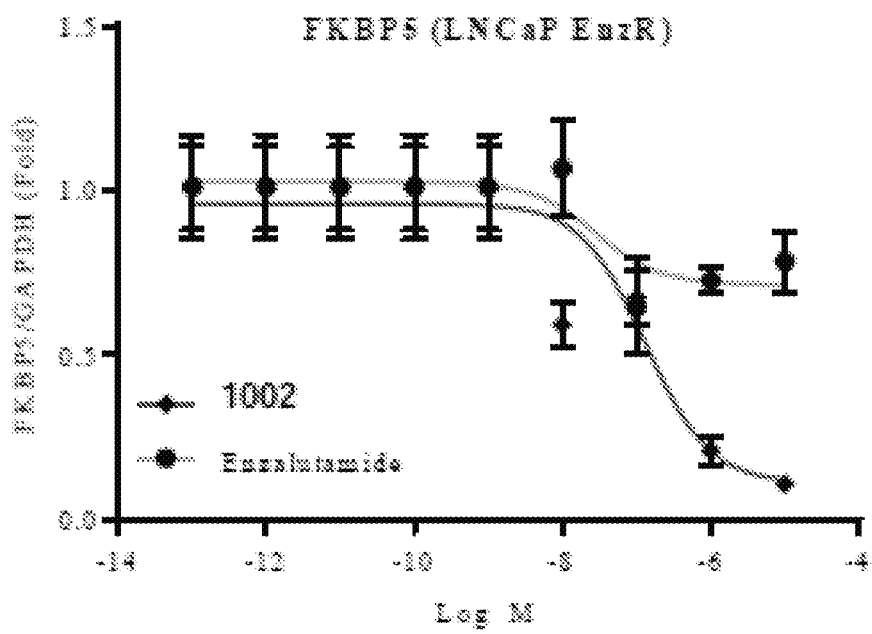
Figure 34D:
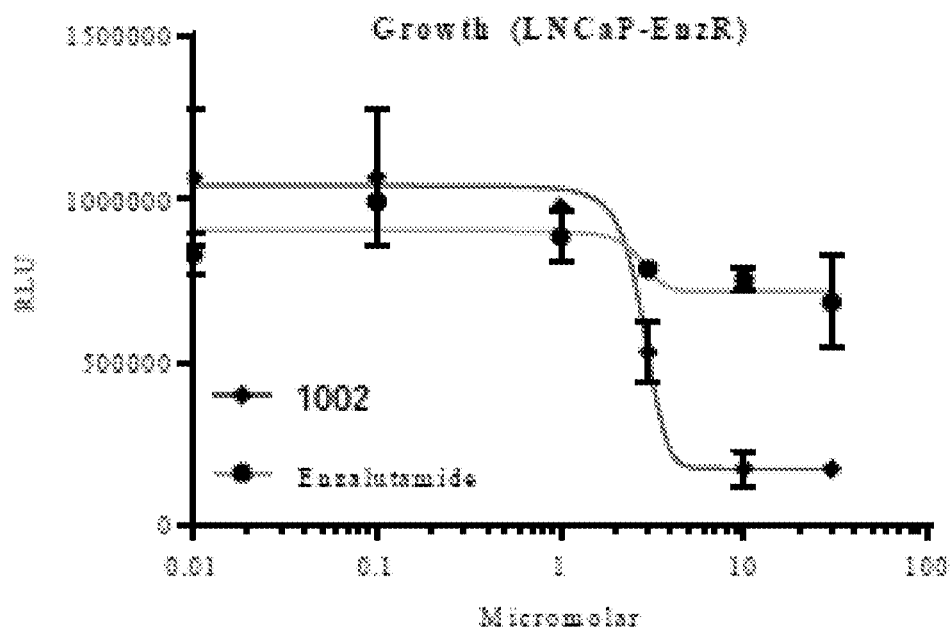

FIG. 32 shows that AR NTD binding of 1002 for required for degradation. Chimeric constructs were created in which the AR and GR were cloned such that the entire sequence was AR or GR, or the N-terminal domain was derived from AR but the DNA binding and ligand binding domains were derived from GR (AGG) or vice versa (GAA). Several lines of evidence summarized below suggested either NTD binding and/or dependence upon NTD for SARD activity. Further to that line of reasoning, the SARD 1002 was tested for its ability to degrade the AR, GR, AGG or GAA constructs as a way to demonstrate that AR NTD was required in order for the SARD to degrade the protein (i.e., demonstrate NTD-dependence). Other lines of evidence suggesting NTD-dependent SARD activity included: FIGS. 22 (NMR) and 27 (fluorescent polarization) demonstrated 1002 binding to NTD and their ability to degrade SV's which lack any LBD further suggested NTD binding. Example 3 discusses potent transcriptional activity in the absence of demonstrable LBD binding and structure-activity relationships of NTD binding that differ from known LBD SAR patterns. Example 8 discusses the ability of 1002 to inhibit SV-driven growth (i.e., FL AR is not expressed) of TNBC xenografts with SARD 1002, suggesting NTD binding. Consistent with this interpretation, the LBD-dependent AR antagonist enzalutamide failed to inhibit TNBC xenograft growth in these same TNBC xenografts.

The chimeric receptor data as provided in FIG. 32 is a strong evidence for NTD-dependence of SARD activity. From the Western blots of FIG. 32, it is apparent that SARDs degraded AR and/or AGG (NTD is AR and rest is GR) but not GR or GAA (NTD is GR and rest is AR). This suggests that AR NTD is required for SARD activity.

(S)-3-(4-Bromo-1H-pyrazol-1-yl)-N-(4-cyano-3-(trifluoromethyl)phenyl)-2-hydroxy-2-methylpropanamide ($C_{15}H_{12}BrF_3N_4O_2$) (1050)

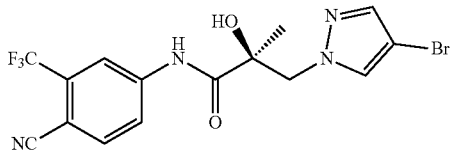

To a solution of 4-bromo-1H-pyrazole (0.20 g, 0.0013608 mol) in anhydrous THF (5 mL), which was cooled in an ice water bath under an argon atmosphere, was added sodium hydride (60% dispersion in oil, 0.16 g, 0.0040827 mol). After addition, the resulting mixture was stirred for three hours. (R)-3-Bromo-N-(4-cyano-3-(trifluoromethyl)phenyl)-2-hydroxy-2-methylpropanamide (0.478 g, 0.001608 mol) was added to the above solution, and the resulting reaction mixture was allowed to stir overnight at room temperature under argon. The reaction was quenched by water and extracted with ethyl acetate. The organic layer was washed with brine, dried with MgSO$_4$, filtered, and concentrated under vacuum. The product was purified by a silica gel column using DCM and ethyl acetate (19:1) as eluent to afford 0.47 g (79.6%) of the titled compound as white foam.

$^1$H NMR (400 MHz, CDCl$_3$) δ 9.08 (s, 1H, NH), 8.00 (d, J=2.0 Hz, 1H, ArH), 7.87 (dd, J=8.4 Hz, J=2.0 Hz, 1H, ArH), 7.79 (d, J=8.4 Hz, 1H, ArH), 7.49 (s, 1H, Pyrazole-H), 7.47 (s, 1H, Pyrazole-H), 5.92 (s, 1H, OH), 4.64 (d, J=14.0 Hz, 1H, CH), 4.24 (d, J=14.0 Hz, 1H, CH), 1.47 (s, 3H, CH$_3$).

Mass (ESI, Negative): 371.68 [M−H]$^-$; (ESI, Positive): 440.94 [M+Na]$^+$.

(R)-3-Bromo-N-(4-cyano-2-iodo-5-(trifluoromethyl)phenyl)-2-hydroxy-2-methylpropanamide ($C_{12}H_9BrF_3IN_2O_2$) (1051)

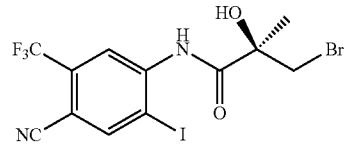 [SMILES: C[C@](O)(CBr)C(=O)Nc1cc(C(F)(F)F)c(C#N)cc1I]

3-Bromo-2-methyl-2-hydroxypropanoic acid (0.50 g, 0.00273224 mol) was reacted with thionyl chloride (0.39 g, 0.0032787 mol), trimethylamine (0.36 g, 0.0035519 mol), and 4-amino-5-iodo-2-(trifluoromethyl)benzonitrile (0.81 g, 0.0025956 mol) to afford the titled compound. The product was purified by a silica gel column using DCM and ethyl acetate (9:1) as eluent to afford 0.80 g (64.6%) of the titled compound as a light brown solid.

$^1$H NMR (400 MHz, CDCl$_3$) δ 9.53 (s, 1H, NH), 8.92 (s, 1H, ArH), 8.24 (s, 1H, ArH), 7.26 (s, 1H, OH), 4.04 (d, J=10.4 Hz, 1H, CH), 3.62 (d, J=10.4 Hz, 1H, CH), 1.67 (s, 3H, CH$_3$).

Mass (ESI, Positive): 479.25 [M+H]$^+$.

(S)—N-(4-Cyano-2-iodo-5-(trifluoromethyl)phenyl)-3-(4-fluoro-1H-pyrazol-1-yl)-2-hydroxy-2-methylpropanamide ($C_{15}H_{11}F_4IN_4O_2$) (1052)

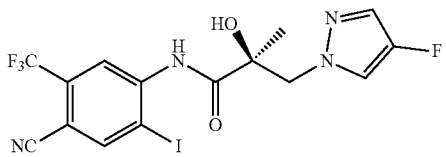 [SMILES: C[C@](O)(Cn1cc(F)cn1)C(=O)Nc1cc(C(F)(F)F)c(C#N)cc1I]

To a solution of 4-fluoro-1H-pyrazole (0.09 g, 0.001048 mol) in anhydrous THF (5 mL), which was cooled in an ice water bath under an argon atmosphere, was added sodium hydride (60% dispersion in oil, 0.15 g, 0.003669 mol). After addition, the resulting mixture was stirred for three hours. (R)-3-Bromo-N-(4-cyano-2-iodo-5-(trifluoromethyl)phenyl)-2-hydroxy-2-methylpropanamide (0.50 g, 0.001048 mol) was added to above solution, and the resulting reaction mixture was allowed to stir overnight at room temperature under argon. The reaction was quenched by water and extracted with ethyl acetate. The organic layer was washed with brine, dried with MgSO$_4$, filtered, and concentrated under vacuum. The product was purified by a silica gel column using hexanes and ethyl acetate (2:1 to 1:1) as eluent to afford 0.32 g (64%) of the titled compound as a white solid.

$^1$H NMR (400 MHz, CDCl$_3$) δ 9.60 (s, 1H, NH), 8.76 (s, 1H, ArH), 8.69 (s, 1H, ArH), 7.76 (d, J=4.8 Hz, 1H, Pyrazole-H), 7.36 (d, J=4.4 Hz, 1H, Pyrazole-H), 6.85 (s, 1H, OH), 4.39 (d, J=14.0 Hz, 1H, CH), 4.20 (d, J=14.0 Hz, 1H, CH), 1.41 (s, 3H, CH$_3$).

Mass (ESI, Negative): 481.00 [M−H]$^-$;

(S)—N-(4-Cyano-3-(trifluoromethyl)phenyl)-3-(5-(4-fluorophenyl)-1H-tetrazol-1-yl)-2-hydroxy-2-methylpropanamide ($C_{19}H_{14}F_4N_6O_2$) (1053)

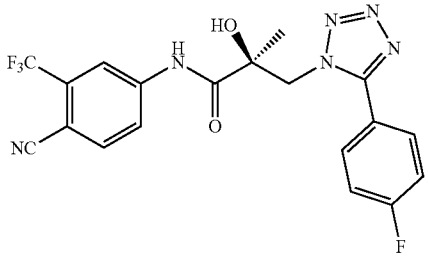 [SMILES: C[C@](O)(Cn1nnnc1-c1ccc(F)cc1)C(=O)Nc1ccc(C#N)c(C(F)(F)F)c1]

To a solution of 5-(4-fluorophenyl)-1H-tetrazole (0.20 g, 0.001219 mol) in anhydrous THF (5 mL), which was cooled in an ice water bath under an argon atmosphere, was added sodium hydride (60% dispersion in oil, 0.17 g, 0.004265 mol). After addition, the resulting mixture was stirred for three hours. (R)-3-Bromo-N-(4-cyano-3-(trifluoromethyl)phenyl)-2-hydroxy-2-methylpropanamide (0.43 g, 0.001219 mol) was added to above solution, and the resulting reaction mixture was allowed to stir 2 days at room temperature under argon. The reaction was quenched by water and extracted with ethyl acetate. The organic layer was washed with brine, dried with $MgSO_4$, filtered, and concentrated under vacuum. The product was purified by a silica gel column using DCM and ethyl acetate (9:1) as eluent to afford 0.053 g (10%) of the titled compound as a yellowish solid.

$^1$H NMR (400 MHz, $CDCl_3$) δ 10.39 (s, 1H, NH), 8.44 (s, 1H, ArH), 8.26 (d, J=8.2 Hz, 1H, ArH), 8.10 (d, J=8.2 Hz, 1H, ArH), 7.93-7.89 (m, 2H, ArH), 7.30 (t, J=8.2 Hz, 2H, ArH), 6.64 (s, 1H, OH), 5.09 (d, J=14.0 Hz, 1H, CH), 4.92 (d, J=14.0 Hz, 1H, CH), 1.55 (s, 3H, $CH_3$).

Mass (ESI, Negative): 433.17 [M−H]$^-$.

(S)—N-(4-Cyano-3-(trifluoromethyl)phenyl)-2-hydroxy-3-(4-methoxy-1H-pyrazol-1-yl)-2-methylpropanamide ($C_{16}H_{15}F_3N_4O_3$) (1054)

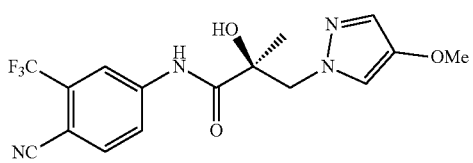 [SMILES: COc1cnn(C[C@](C)(O)C(=O)Nc2ccc(C#N)c(C(F)(F)F)c2)c1]

To a solution of 4-methoxy-1H-pyrazole (0.12 g, 0.001233 mol) in anhydrous THF (5 mL), which was cooled in an ice water bath under an argon atmosphere, was added sodium hydride (60% dispersion in oil, 0.17 g, 0.004281 mol). After addition, the resulting mixture was stirred for three hours. (R)-3-Bromo-N-(4-cyano-3-(trifluoromethyl)phenyl)-2-hydroxy-2-methylpropanamide (0.43 g, 0.001233 mol) was added to above solution, and the resulting reaction mixture was allowed to stir overnight at room temperature under argon. The reaction was quenched by water and extracted with ethyl acetate. The organic layer was washed with brine, dried with $MgSO_4$, filtered, and concentrated under vacuum. The product was purified by a silica gel column using DCM and ethyl acetate (9:1) as eluent to afford 0.30 g (60%) of the titled compound as a white solid.

$^1$H NMR (400 MHz, DMSO-$d_6$) δ 10.38 (s, 1H, NH), 8.46 (d, J=2.0 Hz, 1H, ArH), 8.24 (dd, J=8.2 Hz, J=2.0 Hz, 1H, ArH), 8.10 (d, J=8.2 Hz, 1H, ArH), 7.35 (d, J=0.8 Hz, 1H, Pyrazole-H), 7.15 (d, J=0.8 Hz, 1H, Pyrazole-H), 6.25 (s, 1H, OH), 4.35 (d, J=14.0 Hz, 1H, CH), 4.18 (d, J=14.0 Hz, 1H, CH), 3.61 (s, 3H, $CH_3$), 1.36 (s, 3H, $CH_3$).

HRMS $C_{16}H_{16}F_3N_4O_3^+$: calcd 369.1175, found 369.1182 [M+H]$^+$. Purity: 99.28% (HPLC).

(S)—N-(4-Cyano-3-(trifluoromethyl)phenyl)-2-hydroxy-2-methyl-3-(4-methyl-1H-pyrazol-1-yl)propanamide ($C_{16}H_{15}F_3N_4O_2$) (1055)

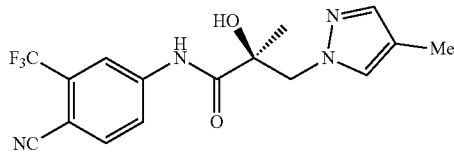

To a solution of 4-methyl-1H-pyrazole (0.10 g, 0.001218 mol) in anhydrous THF (5 mL), which was cooled in an ice water bath under an argon atmosphere, was added sodium hydride (60% dispersion in oil, 0.17 g, 0.004263 mol). After addition, the resulting mixture was stirred for three hours. (R)-3-Bromo-N-(4-cyano-3-(trifluoromethyl)phenyl)-2-hydroxy-2-methylpropanamide (0.428 g, 0.001218 mol) was added to above solution, and the resulting reaction mixture was allowed to stir overnight at room temperature under argon. The reaction was quenched by water and extracted with ethyl acetate. The organic layer was washed with brine, dried with $MgSO_4$, filtered, and concentrated under vacuum. The product was purified by a silica gel column using DCM and ethyl acetate (19:1) as eluent to afford 0.28 g (66%) of the titled compound as a white solid.

$^1$H NMR (400 MHz, DMSO-$d_6$) δ 10.38 (s, 1H, NH), 8.46 (d, J=2.0 Hz, 1H, ArH), 8.23 (dd, J=8.8 Hz, J=2.0 Hz, 1H, ArH), 8.10 (d, J=8.8 Hz, 1H, ArH), 7.41 (s, 1H, Pyrazole-H), 7.17 (s, 1H, Pyrazole-H), 6.24 (s, 1H, OH), 4.40 (d, J=14.0 Hz, 1H, CH), 4.22 (d, J=14.0 Hz, 1H, CH), 1.97 (s, 3H, $CH_3$), 1.36 (s, 3H, $CH_3$).

HRMS [$C_{16}H_{16}F_3N_4O_2^{30}$]: calcd 353.1225, found 353.1232 [M+H]$^+$. Purity: 99.75% (HPLC).

N-(4-Cyano-3-(trifluoromethyl)phenyl)-2-methyl-oxirane-2-carboxamide ($C_{12}H_9F_3N_2O_2$) (1056)

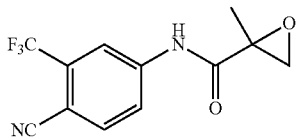 [SMILES: CC1(C(=O)Nc2ccc(C#N)c(C(F)(F)F)c2)CO1]

2-Methyloxirane-2-carboxylic acid (1.00 g, 0.009892 mol) was reacted with thionyl chloride (1.41 g, 0.011871 mol), trimethylamine (1.30 g, 0.01286 mol), and 4-amino-2-(trifluoromethyl)benzonitrile (1.84 g, 0.009892 mol) to afford the titled compound. The product was purified by a silica gel column using DCM and ethyl acetate (19:1) as eluent to afford 1.52 g (57%) of the titled compound as a yellowish solid.

$^1$H NMR (400 MHz, DMSO-d$_6$) δ 10.54 (s, 1H, NH), 8.55 (d, J=1.6-2.0 Hz, 1H, ArH), 8.32 (dd, J=8.8 Hz, J=2.0 Hz, 1H, ArH), 8.12 (d, J=8.8 Hz, 1H, ArH), 6.39 (s, 1H, OH), 3.94 (d, J=11.2 Hz, 1H, CH), 3.70 (d, J=11.2 Hz, 1H, CH), 1.44 (s, 3H, CH$_3$).

Mass (ESI, Negative): [M−H]$^-$; (ESI, Positive): [M+H]$^+$.

N-(4-Cyano-3-(trifluoromethyl)phenyl)-3-(4-fluoro-1H-pyrazol-1-yl)-2-hydroxy-2-methylpropanamide (C$_{15}$H$_{12}$F$_4$N$_4$O$_2$) (1057)

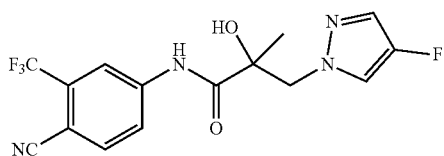 [SMILES: CC(O)(Cn1cc(F)cn1)C(=O)Nc1ccc(C#N)c(C(F)(F)F)c1]

To a solution of 4-fluoro-pyrazole (0.10 g, 0.001162 mol) in anhydrous THF (10 mL), which was cooled in an ice water bath under an argon atmosphere, was added sodium hydride (60% dispersion in oil, 0.14 g, 0.003486 mol). After addition, the resulting mixture was stirred for three hours. N-(4-Cyano-3-(trifluoromethyl)phenyl)-2-methyloxirane-2-carboxamide (0.31 g, 0.001162 mol) was added to above solution, and the resulting reaction mixture was allowed to stir overnight at room temperature under argon. The reaction was quenched by water, extracted with ethyl acetate. The organic layer was washed with brine, dried with MgSO$_4$, filtered, and concentrated under vacuum. The product was purified by a silica gel column using hexanes and ethyl acetate (2:1 to 1:1) as eluent to afford 0.37 g (90%) of the titled compound as a yellowish solid.

$^1$H NMR (400 MHz, DMSO-d$_6$) δ 10.38 (s, 1H, NH), 8.47 (d, J=2.0 Hz, 1H, ArH), 8.24 (dd, J=8.8 Hz, J=2.0 Hz, 1H, ArH), 8.10 (d, J=8.8 Hz, 1H, ArH), 7.74 (d, J=4.4 Hz, 1H, Pyrazole-H), 7.41 (d, J=4.0 Hz, 1H, Pyrazole-H), 6.31 (s, 1H, OH), 4.39 (d, J=14.0 Hz, 1H, CH), 4.21 (d, J=14.4 Hz, 1H, CH), 1.34 (s, 3H, CH$_3$).

Mass (ESI, Negative): [M−H]$^-$; (ESI, Positive): [M+Na]$^+$.

(S)-3-Bromo-N-(4-cyano-3-(trifluoromethyl)phenyl)-2-hydroxy-2-methylpropanamide (C$_{12}$H$_9$F$_3$N$_2$O$_2$)

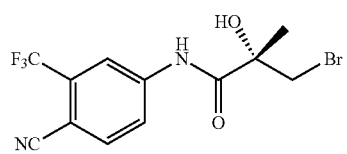 [SMILES: C[C@@](O)(CBr)C(=O)Nc1ccc(C#N)c(C(F)(F)F)c1]

(S)-3-Bromo-2-hydroxy-2-methylpropanoic acid (1.00 g, 0.0054645 mol) reacted with thionyl chloride (0.78 g, 0.0065574 mol), trimethylamine (0.72 g, 0.0071038 mol), and 4-amino-2-(trifluoromethyl)benzonitrile (1.02 g, 0.0054645 mol) to afford the titled compound. The product was purified by a silica gel column using DCM and ethyl acetate (19:1) as eluent to afford 1.75 g (90%) of the titled compound as a yellowish solid.

Mass (ESI, Positive): 351.08 [M+Na]$^+$.

(R)—N-(4-Cyano-3-(trifluoromethyl)phenyl)-3-(4-fluoro-1H-pyrazol-1-yl)-2-hydroxy-2-methylpropanamide (C$_{15}$H$_{12}$F$_4$N$_4$O$_2$)

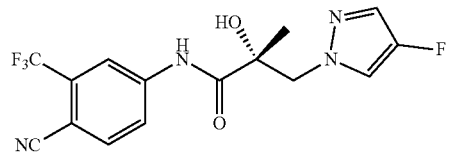 [SMILES: C[C@@](O)(Cn1cc(F)cn1)C(=O)Nc1ccc(C#N)c(C(F)(F)F)c1]

To a solution of 4-fluoro-pyrazole (0.10 g, 0.001162 mol) in anhydrous THF (10 mL), which was cooled in an ice water bath under an argon atmosphere, was added sodium hydride (60% dispersion in oil, 0.16 g, 0.0040665 mol). After addition, the resulting mixture was stirred for three hours. (S)-3-Bromo-N-(4-cyano-3-(trifluoromethyl)phenyl)-2-hydroxy-2-methylpropanamide (0.41 g, 0.001162 mol) was added to above solution, and the resulting reaction mixture was allowed to stir overnight at room temperature under argon. The reaction was quenched by water, extracted with ethyl acetate. The organic layer was washed with brine, dried with MgSO$_4$, filtered, and concentrated under vacuum. The product was purified by a silica gel column using hexanes and ethyl acetate (2:1 to 1:1) as eluent to afford 0.27 g (64%) of the titled compound as yellowish solid.

$^1$H NMR (400 MHz, DMSO-d$_6$) δ 10.38 (s, 1H, NH), 8.47 (d, J=1.6-2.0 Hz, 1H, ArH), 8.24 (dd, J=8.4 Hz, J=2.0 Hz, 1H, ArH), 8.10 (d, J=8.4 Hz, 1H, ArH), 7.74 (d, J=4.4 Hz, 1H, Pyrazole-H), 7.41 (d, J=4.4 Hz, 1H, Pyrazole-H), 6.31 (s, 1H, OH), 4.39 (d, J=14.0 Hz, 1H, CH), 4.21 (d, J=14.4 Hz, 1H, CH), 1.34 (s, 3H, CH$_3$).

Mass (ESI, Positive): 357.11 [M+Na]$^+$.

(S)-3-(4-Bromo-3-fluoro-1H-pyrazol-1-yl)-N-(4-cyano-3-(trifluoromethyl)phenyl)-2-hydroxy-2-methylpropanamide (C$_{15}$H$_{11}$BrF$_4$N$_4$O$_2$) (1058)

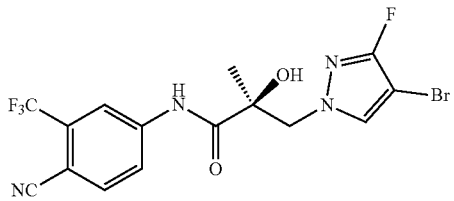

To a solution of 4-bromo-3-fluoro-1H-pyrazole (0.30 g, 0.001819 mol) in anhydrous THF (10 mL), which was cooled in an ice water bath under an argon atmosphere, was added sodium hydride (60% dispersion in oil, 0.26 g, 0.006365 mol). After addition, the resulting mixture was stirred for three hours. (R)-3-Bromo-N-(4-cyano-3-(trifluoromethyl)phenyl)-2-hydroxy-2-methylpropanamide (0.64 g, 0.001819 mol) was added to above solution, and the resulting reaction mixture was allowed to stir overnight at room temperature under argon. The reaction was quenched by water and extracted with ethyl acetate. The organic layer was washed with brine, dried with MgSO$_4$, filtered, and concentrated under vacuum. The product was purified by a silica gel column using ethyl acetate and hexanes (2:1) as eluent to afford 0.34 g (34%) of the titled compound as a pinkish solid.

¹H NMR (400 MHz, DMSO-d₆) δ 10.38 (s, 1H, NH), 8.45 (d, J=2.0-1.6 Hz, 1H, ArH), 8.23 (dd, J=8.2 Hz, J=2.0 Hz, 1H, ArH), 8.11 (d, J=8.2 Hz, 1H, ArH), 7.82 (d, J=2.0 Hz, 1H, Pyrazole-H), 6.35 (s, 1H, OH), 4.35 (d, J=14.0 Hz, 1H, CH), 4.04 (d, J=14.0 Hz, 1H, CH), 1.37 (s, 3H, CH₃).

HRMS [C₁₅H₁₂BrF₄NO₄O₂⁺]: calcd 435.0080, found 435.0080 [M+H]⁺. Purity: 96.98% (HPLC).

(S)—N-(4-Cyano-3-(trifluoromethyl)phenyl)-3-(3-fluoro-4-(4-fluorophenyl)-1H-pyrazol-1-yl)-2-hydroxy-2-methylpropanamide (C₂₁H₁₅F₅N₄O₂) (1059)

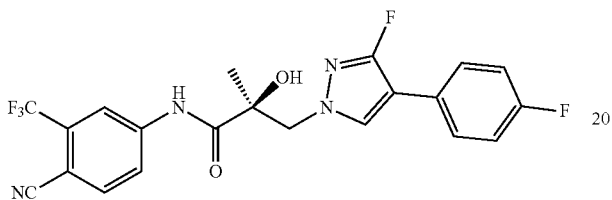

The mixture of (S)-3-(4-bromo-3-fluoro-1H-pyrazol-1-yl)-N-(4-cyano-3-(trifluoromethyl)phenyl)-2-hydroxy-2-methylpropanamide (0.20 g, 0.4596 mmol), 4-fluoro boronic acid (77 mg, 0.5515 mmol), Pd(II)(OAc)₂ (2-3 mg, 0.009192 mmol), PPh₃ (7-8 mg, 0.02758 mmol), and K₂CO₃ (0.13 g, 0.965 mmol) in the mixture of ACN (4-5 mL) and H₂O (2-3 mL) was degassed and refilled with argon three times. The resulting reacting mixture was heated at reflux for 3 hours under argon. The product was purified by a silica gel column using hexanes and ethyl acetate (2:1 to 1:1) as eluent to afford 51 mg (25%) of the titled compound as a off-white solid.

¹H NMR (400 MHz, CDCl₃) δ 9.12 (s, 1H, NH), 8.06 (d, J=1.6 Hz, 1H, ArH), 7.85 (dd, J=8.2 Hz, J=1.6 Hz, 1H, ArH), 7.77 (d, J=8.2 Hz, 1H, ArH), 7.51 (d, J=3.0 Hz, 1H, Pyrazole-H), 7.43-7.40 (m, 2H, ArH), 7.08-7.04 (m, 2H, ArH), 4.57 (d, J=10.5 Hz, 1H, CH), 4.7 (d, J=10.5 Hz, 1H, CH), 1.26 (s, 3H, CH₃).

HRMS [C₂₁H₁₆F₅N₄O₂⁺]: calcd 451.1193, found 451.1196 [M+H]⁺. Purity: % (HPLC).

(S)-3-(3-Bromo-4-cyano-1H-pyrazol-1-yl)-N-(4-cyano-3-(trifluoromethyl)phenyl)-2-hydroxy-2-methylpropanamide (C₁₆H₁₁BrF₃N₅O₂) (1060)

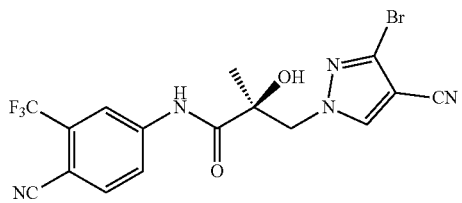 [SMILES: C[C@](O)(Cn1cc(C#N)c(Br)n1)C(=O)Nc1ccc(C#N)c(C(F)(F)F)c1]

To a solution of 3-bromo-4-cyano-1H-pyrazole (0.20 g, 0.0011629 mol) in anhydrous THF (10 mL), which was cooled in an ice water bath under an argon atmosphere, was added sodium hydride (60% dispersion in oil, 0.163 g, 0.00407 mol). After addition, the resulting mixture was stirred for three hours. (R)-3-Bromo-N-(4-cyano-3-(trifluoromethyl)phenyl)-2-hydroxy-2-methylpropanamide (0.41 g, 0.0011629 mol) was added to above solution, and the resulting reaction mixture was allowed to stir overnight at room temperature under argon. The reaction was quenched by water and extracted with ethyl acetate. The organic layer was washed with brine, dried with MgSO₄, filtered, and concentrated under vacuum. The product was purified by a silica gel column using ethyl acetate and hexanes (2:1) as eluent to afford 0.10 g (20%) of the titled compound as an off-white solid.

¹H NMR (400 MHz, DMSO-d₆) δ 10.32 (s, 1H, NH), 8.40 (s 1H, Pyrazole-H), 8.41 (s, 1H, ArH), 8.20 (d, J=8.4 Hz, 1H, ArH), 8.11 (d, J=8.4 Hz, 1H, ArH), 6.47 (s, 1H, OH), 4.52 (d, J=13.6 Hz, 1H, CH), 4.33 (d, J=13.6 Hz, 1H, CH), 1.41 (s, 3H, CH₃).

HRMS [C₁₆H₁₂BrF₃N₅O₂⁺]: calcd 442.0126, found 442.0109 [M+H]⁺. Purity: 98.84% (HPLC).

(S)-3-(3-Chloro-4-methyl-1H-pyrazol-1-yl)-N-(4-cyano-3-(trifluoromethyl)phenyl)-2-hydroxy-2-methylpropanamide (C₁₆H₁₄ClF₃N₄O₂) (1061)

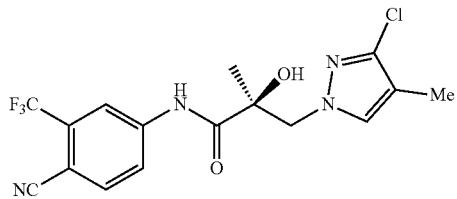

To a solution of 3-chloro-4-methyl-1H-pyrazole (0.15 g, 0.001287 mol) in anhydrous THF (10 mL), which was cooled in an ice water bath under an argon atmosphere, was added sodium hydride (60% dispersion in oil, 0.18 g, 0.0045045 mol). After addition, the resulting mixture was stirred for three hours. (R)-3-Bromo-N-(4-cyano-3-(trifluoromethyl)phenyl)-2-hydroxy-2-methylpropanamide (0.45 g, 0.001287 mol) was added to above solution, and the resulting reaction mixture was allowed to stir overnight at room temperature under argon. The reaction was quenched by water and extracted with ethyl acetate. The organic layer was washed with brine, dried with MgSO₄, filtered, and concentrated under vacuum. The product was purified by a silica gel column using DCM and ethyl acetate (98:2 to 95:5) as eluent to afford 0.27 g (54%) of the titled compound as a white solid.

¹H NMR (400 MHz, DMSO-d₆) δ 10.33 (s, 1H, NH), 8.42 (d, J=0.8 Hz, 1H, ArH), 8.21 (dd, J=8.4 Hz, J=0.8 Hz, 1H, ArH), 8.10 (d, J=8.2 Hz, 1H, ArH), 7.50 (s 1H, Pyrazole-H), 6.29 (s, 1H, OH), 4.36 (d, J=14.4 Hz, 1H, CH), 4.18 (d, J=14.4 Hz, 1H, CH), 1.91 (s, 3H, CH₃), 1.35 (s, 3H, CH₃).

HRMS [C₁₆H₁₅ClF₃N₄O₂⁺]: calcd 387.0836, found 387.0839 [M+H]⁺. Purity: 97.07% (HPLC).

(S)-3-(4-Fluoro-1H-pyrazol-1-yl)-2-hydroxy-2-methyl-N-(4-nitro-3-(trifluoromethyl)phenyl)propanamide (1062)

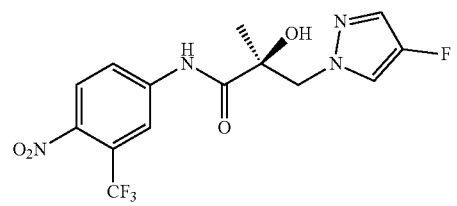

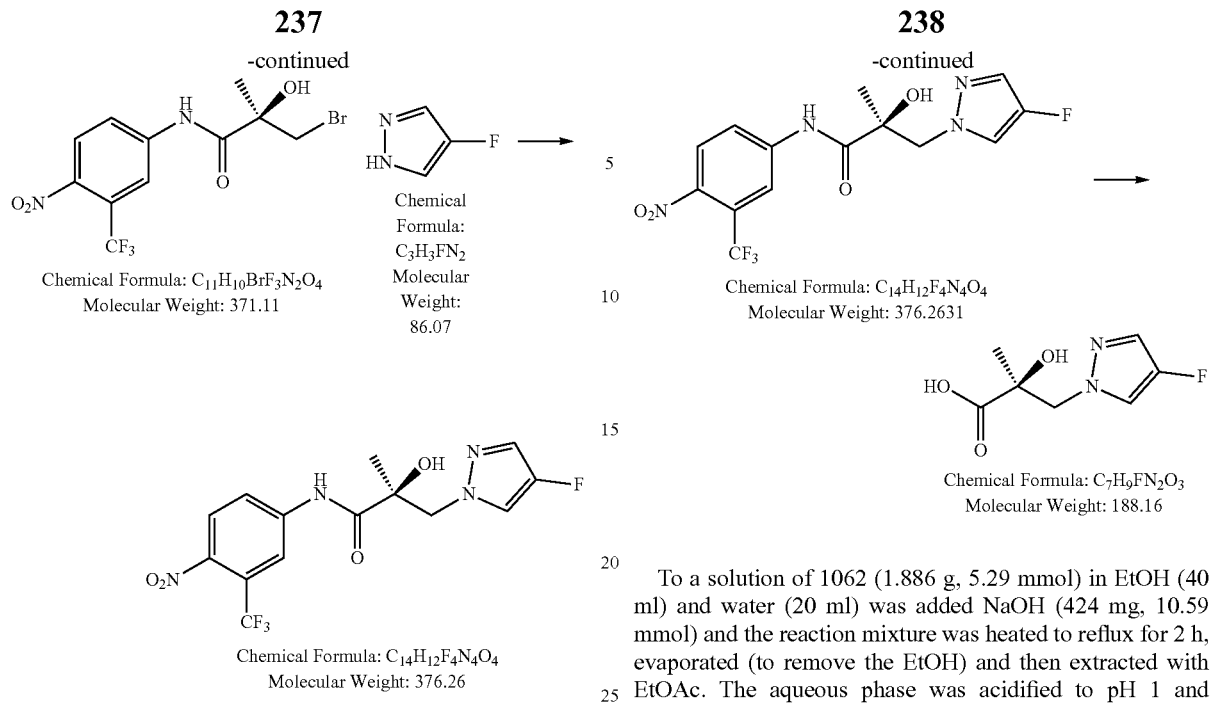

To a dry, nitrogen-purged 100 mL round-bottom flask equipped with a dropping funnel under argon atmosphere, NaH of 60% dispersion in mineral oil (674 mg, 16.9 mmol) was added in 60 mL of anhydrous THF solvent in the flask at ice-water bath, and 4-fluoro-1H-pyrazole (691 mg, 8.03 mmol) was stirred in over 30 min at the ice-water bath. Into the flask, the solution of (R)-3-bromo-2-hydroxy-2-methyl-N-(4-nitro-3-(trifluoromethyl)phenyl)propanamide (2.98 g, 8.03 mmol) in 10 mL of anhydrous THF was added through dropping funnel under argon atmosphere at the ice-water bath and stirred overnight at room temperature. After adding 1 mL of H$_2$O, the reaction mixture was condensed under reduced pressure, and then dispersed into 50 mL of EtOAc, washed with 50 mL (×2) water, evaporated, dried over anhydrous MgSO$_4$, and evaporated to dryness. The mixture was purified with flash column chromatography as an eluent EtOAc/hexane=1/2 to produce designed compound (2.01 g, 67%) as yellowish solid.

MS (ESI) m/z 375.08 [M−H]$^−$; 377.22 [M+H]$^+$; 399.04 [M+Na]$^+$;

$^{19}$F NMR (CDCl$_3$, decoupled) δ−60.13, −176.47; assigned by NOE and COSY; $^1$H NMR (400 MHz, CDCl$_3$) δ 9.14 (bs, 1H, NH), 8.01 (s, 1H), 7.97-7.91 (m, 2H), 7.38 (d, J=3.6 Hz, 1H), 7.35 (d, J=4.4 Hz, 1H), 5.95 (s, 1H, OH), 4.56 (d, J=14.0 Hz, 1H), 4.17 (d, J=14.0 Hz, 1H), 1.48 (s, 3H).

(S)-3-(4-Fluoro-1H-pyrazol-1-yl)-2-hydroxy-2-methylpropanoic acid (1062a)

To a solution of 1062 (1.886 g, 5.29 mmol) in EtOH (40 ml) and water (20 ml) was added NaOH (424 mg, 10.59 mmol) and the reaction mixture was heated to reflux for 2 h, evaporated (to remove the EtOH) and then extracted with EtOAc. The aqueous phase was acidified to pH 1 and extracted with EtOAc. The extract was dried over Na$_2$SO$_4$, filtered and evaporated to afford the title compound (845 mg, 85%) as a brown oil. MS (ESI) m/z 187.06 [M−H]$^−$; 188.91 [M+H]$^+$;

$^{19}$F NMR (acetone-d$_6$, decoupled) δ−0.24; assigned by NOE and COSY.

$^1$H NMR (400 MHz, acetone-d$_6$) δ 7.66 (d, J=4.4 Hz, 1H), 7.36 (d, J=4.0 Hz, 1H), 4.45 (d, J=14.0 Hz, 1H), 4.27 (d, J=14.0 Hz, 1H), 1.38 (s, 3H). $^{13}$C NMR (100 MHz, acetone-d$_6$) δ 175.70, 150.36 (d, J=24.12 Hz), 126.53 (d, J=13.6 Hz), 118.21 (d, J=28.0 Hz), 74.86, 60.59, 23.77.

Preparation of (S)—N-(6-Cyano-5-(trifluoromethyl)pyridin-3-yl)-3-(4-(4-fluorophenyl)-1H-1,2,3-triazol-1-yl)-2-hydroxy-2-methylpropanamide (1063)

(S)-3-Azido-N-(6-cyano-5-(trifluoromethyl)pyridin-3-yl)-2-hydroxy-2-methylpropanamide (1064)

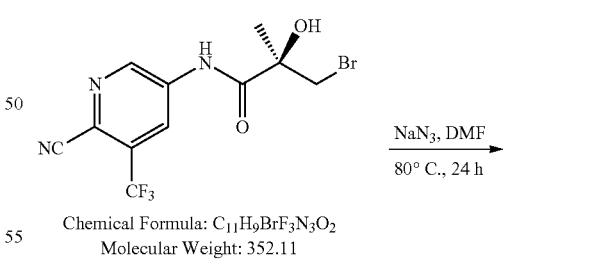

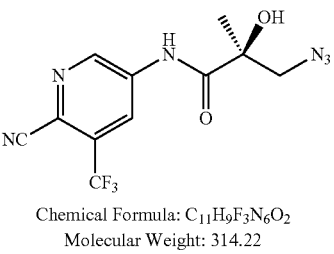

A solution of (R)-3-bromo-N-(6-cyano-5-(trifluoromethyl)pyridin-3-yl)-2-hydroxy-2-methylpropanamide (352 mg, 1 mmol) in 10 mL of DMF was treated with NaN₃ (325 mg, 5 mmol) under Ar at 80° C. for 24 h. The reaction mixture was then cooled and extracted with CH₂Cl₂ (3×20 mL). The combined organic layers were washed with H₂O (3×20 mL) and brine, dried and evaporated to give a crude oil, which purified by silica gel chromatography (EtOAc/n-hexane=1:2, v/v) to afford product. Yield=87%;

MS (ESI) m/z 313.03 [M–H]⁻; ¹⁹F NMR (CDCl₃, decoupled) δ–62.11;

¹H NMR (400 MHz, CDCl₃) δ 9.16 (bs, 1H, NH), 8.89 (s, 1H), 8.77 (s, 1H), 3.90 (d, J=12.0 Hz, 1H), 3.52 (d, J=12.0 Hz, 1H), 3.20 (bs, 1H, OH), 1.55 (s, 3H).

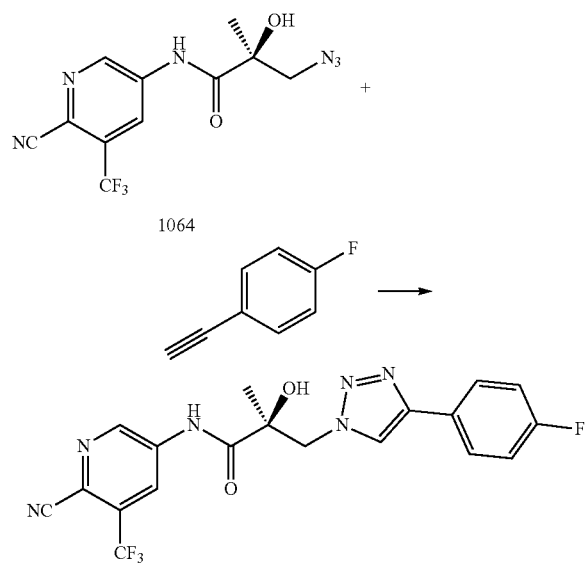

(S)—N-(6-Cyano-5-(trifluoromethyl)pyridin-3-yl)-3-(4-(4-fluorophenyl)-1H-1,2,3-triazol-1-yl)-2-hydroxy-2-methylpropanamide (1063)

To a suspension of copper(I)iodide (11 mg, 0.055 mmoL) in acetonitrile (7 mL)/water (3 mL) mixture was added 1064 (57 mg, 0.182 mmol) at room temperature and then 1-ethynyl-4-fluorobenzene (0.015 mL, 0.182 mmol) was added. The resulting reaction mixture was stirred at room temperature for 3 days. The mixture was evaporated under reduced pressure, poured into water:brine (1:1) and then extracted with ethyl acetate. The combined organic extracts were then washed with brine, dried over sodium sulphate, filtered and evaporated. Purification by chromatography (silica, 60% ethyl acetate in hexane) to afford the product as a yellow solid (51.3 mg, 65%).

MS (ESI) m/z 433.09 [M–H]⁻ –435.06 [M+H]⁺;

¹⁹F NMR (acetone-d₆, decoupled) δ 114.58, 61.66; assigned by NOE and COSY;

¹H NMR (400 MHz, acetone-d₆) δ 10.16 (bs, 1H, NH), 9.28 (s, 1H), 8.88 (s, 1H), 8.31 (s, 1H), 7.90 (t, J=7.8 Hz, 2H), 7.20 (t, J=8.8 Hz, 2H), 5.73 (bs, 1H, OH), 4.94 (d, J=14.2 Hz, 1H), 4.73 (d, J=14.2 Hz, 1H), 1.62 (s, 3H).

Example 14

SARDs Regressed CPRC VCaP Tumors

VCaP prostate cancer cells were implanted (in combination with matrigel (1:1 mix)) on the flanks subcutaneously in SRG rats (10 million cells/rat). When the tumors reach 300-500 mm³, the animals were castrated and the tumors were allowed to regrow as castration-resistant prostate cancer. When the tumors regrew, the animals were randomized into three groups, vehicle (15% DMSO+85% PEG-300), enzalutamide (30 mg/kg/day), or compound 1002 (60 mg/kg/day). The animals were orally treated and tumor volume and body weight were recorded thrice weekly. Tumor volume or percent change in tumor volume was calculated.

Figure 35:
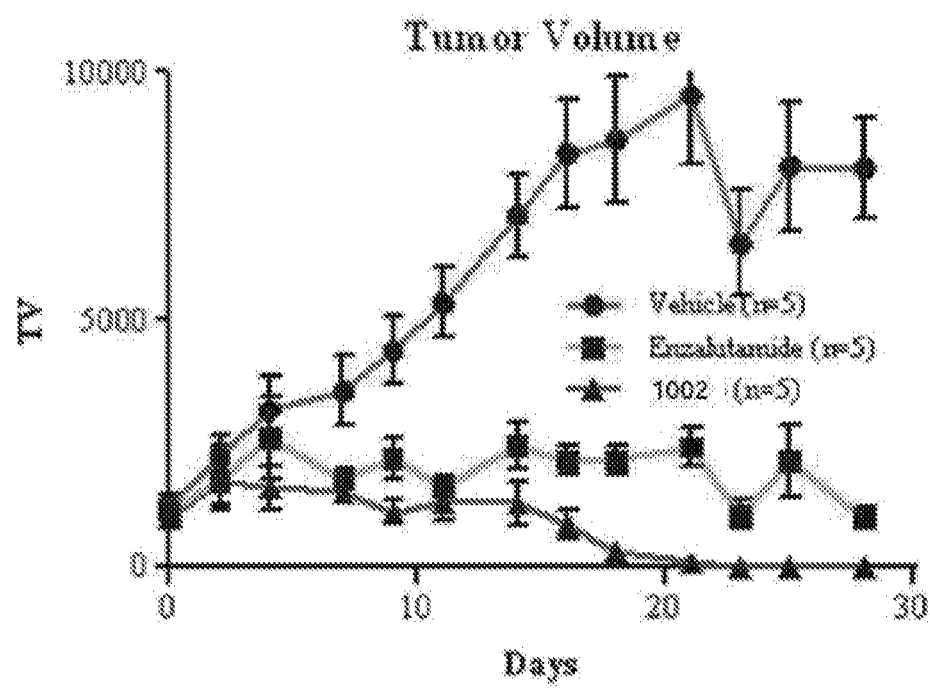
FIG. 35: SARDs regressed the tumors to undetectable levels.

Vehicle-treated tumors grew robustly in castrated environment indicating that the tumors were castration-resistant, i.e., tumor were CRPC. Enzalutamide inhibited the growth of the tumors, while compound 1002 regressed the tumors to undetectable levels (FIG. 35). All individual animals treated with 1002 had tumor volume reduced to unmeasurable by 22 days (FIG. 35), whereas enzalutamide response was more variable and incomplete even at 30 days.

Example 15

SARDs Inhibited Growth of Tumor and Caused Rapid Tumor Regression in Anti-Androgen Resistant (MDVR) VCaP Cells in Intact and Castrated Animals VCaP cells that have been rendered enzalutamide resistant were implanted (in combination with matrigel (1:1 mix)) on the flanks subcutaneously in SRG rats (10 million cells/rat). When the tumor reached 10,800 mm³, the animal was treated orally with compound 1002 (60 mg/kg/day) to determine if the tumor growth is slowed. Tumor volume and body weight was recorded thrice weekly.

Figure 36:
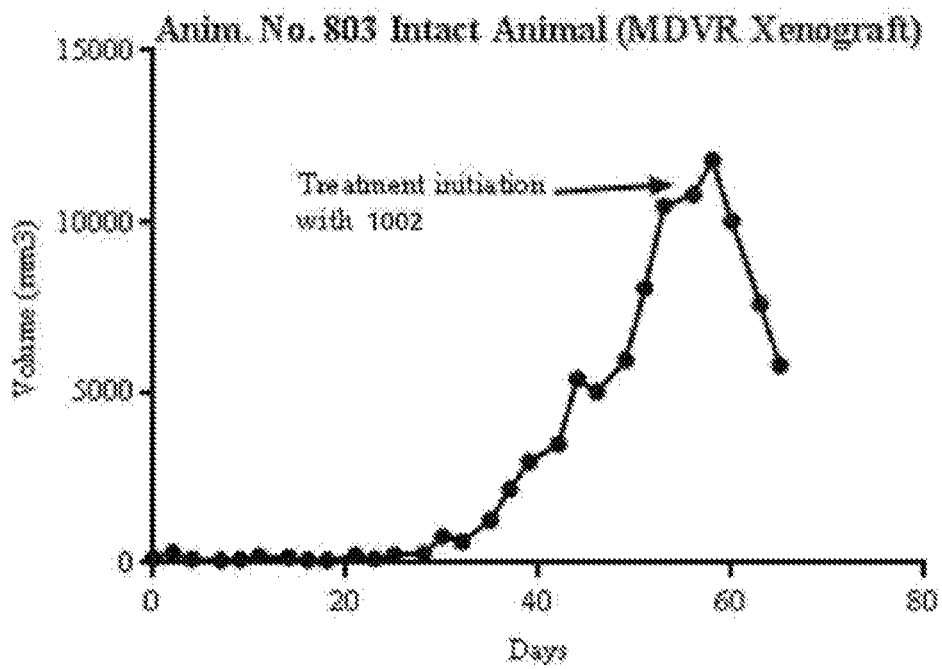
FIG. 36: SARDs inhibited growth of tumor and caused rapid tumor regression.

Animal No. 803 was cryptorchid and there were complications upon trying to remove testes, so the animal was left intact. Before initiation of 1002 treatments the MDV3100 (enzalutamide) resistant (MDVR) VCaP cells grew robustly, presumably supported by the endogenous androgens. 1002 quickly inhibited growth and caused rapid tumor regression, however, the animal was sacrificed due to loose stools (FIG. 36). Interestingly, the response to treatment in this animal was rapid despite the androgen replete milieu of an intact rat. E.g., FIG. 36A demonstrates that as the tumor began to grow, the serum PSA levels began to rise as shown by the numbers above each time point in the tumor volume graph (left panel in FIG. 36A), however, immediately after initiation of 1002 treatments the PSA levels fell to zero.

Serum PSA levels are graphed (number provided on the graph are serum PSA values (ng/mL); blood was obtained weekly and serum separated and stored for PSA analysis; tumor volume was measured thrice weekly) for this animal allowing visualization of the dramatic rise in PSA with tumor growth and rapid PSA response upon initiation around day 58. Vehicle treated and enzalutamide treated animal experienced rapid tumor volume increases. This is preliminary evidence that SARDs of this invention can overcome enzalutamide resistance in the presence of androgens and that the rapid tumor response is based on blocking the AR-axis. This provided the inspiration to test MDVR xenografts in intact animals. The experiment was repeated with three rats per group and the same result was observed. Rapid and robust tumor response in MDVR VCaP tumors in intact rats treated with 1002 and rapid progression in enzalutamide and vehicle treated intact rats. This is the first evidence that an AR antagonist can inhibit CRPC tumor growth in an intact animal species (rat). This result provide evidence that SARDs of this invention can be used to treat prostate cancer even in the presence of endogenous agonist (i.e., intact animals) which is an unexpected result and differs from the standard of care in which the first pharmacotherapy is typically androgen-deprivation therapy. Although this result is in an enzalutamide resistant CPRC, it provides a basis for testing in early prostate cancers and suggests the possibility of adjuvant or neoadjuvant use of SARDs of this invention in intact men.

MDVR VCaP Xenograft Growth in Castrated Rats: MDVR VCaP prostate cancer cells were implanted (in combination with matrigel (1:1 mix)) on the flanks subcutaneously in SRG rats (10 million cells/rat). When the tumors reach 300-500 mm³, the animals were castrated and the tumors were allowed to regrow as castration-resistant prostate cancer. When the tumors regrew, the animals were randomized into three groups, vehicle (15% DMSO+85% PEG-300), enzalutamide (30 mg/kg/day), or compound 1002 (60 mg/kg/day). The animals were orally treated and tumor volume and body weight were recorded thrice weekly. Tumor volume or percent change in tumor volume was calculated.

Vehicle-treated tumors grew robustly in castrated environment indicating that the tumors were castration-resistant, i.e., tumor were CRPC. Enzalutamide treated tumors also continued to grow almost comparably to vehicle, while compound 1002 regressed the tumors to inhibited tumor growth significantly (FIG. 109) with tumor at sacrifice (approximately day 26) slightly smaller than at initiation of treatment or ~2000 mm³. By comparison, vehicle and enzalutamide tumor grew by from ~2000 mm³ to ~6000 mm³ or ~200% increased tumor volume. This demonstrated that SARDs of this invention are able to treat antiandrogen resistant castration resistant prostate cancer (MDVR VCaP) which over expresses CYP17A1 such that there is intratumoral androgen synthesis as well. Correspondingly, SARDs of this invention are expected to be able to treat CRPC (and possibly CSPC) including patients that have failed enzalutamide or apalutamide and possibly abiraterone treatments, or patients overexpressing CYP17A1 or AKR1C3.

Example 16

X-Linked Spinal-Bulbar Muscular Atrophy (SBMA) Method

Transgenic mice that express AR121Q (121 polyglutamine repeats instead of the usual 15-24 repeats) will be treated with vehicle or SARD orally. One group of mice will be castrated to serve as positive control as circulating androgens will worsen the SBMA condition. Body weight, composition, and grip strength will be measured before the initiation of the experiment. Animals will be treated and weekly measurements will be performed. Animals will be treated and monitored until they die. AR121Q mice lives only up to 60-80 days and hence evaluating the survival in the presence of SARD treatment is possible.

Example 17

Synthesis of Indole/Pyrrolo-Pyridine SARD Compounds of this Invention

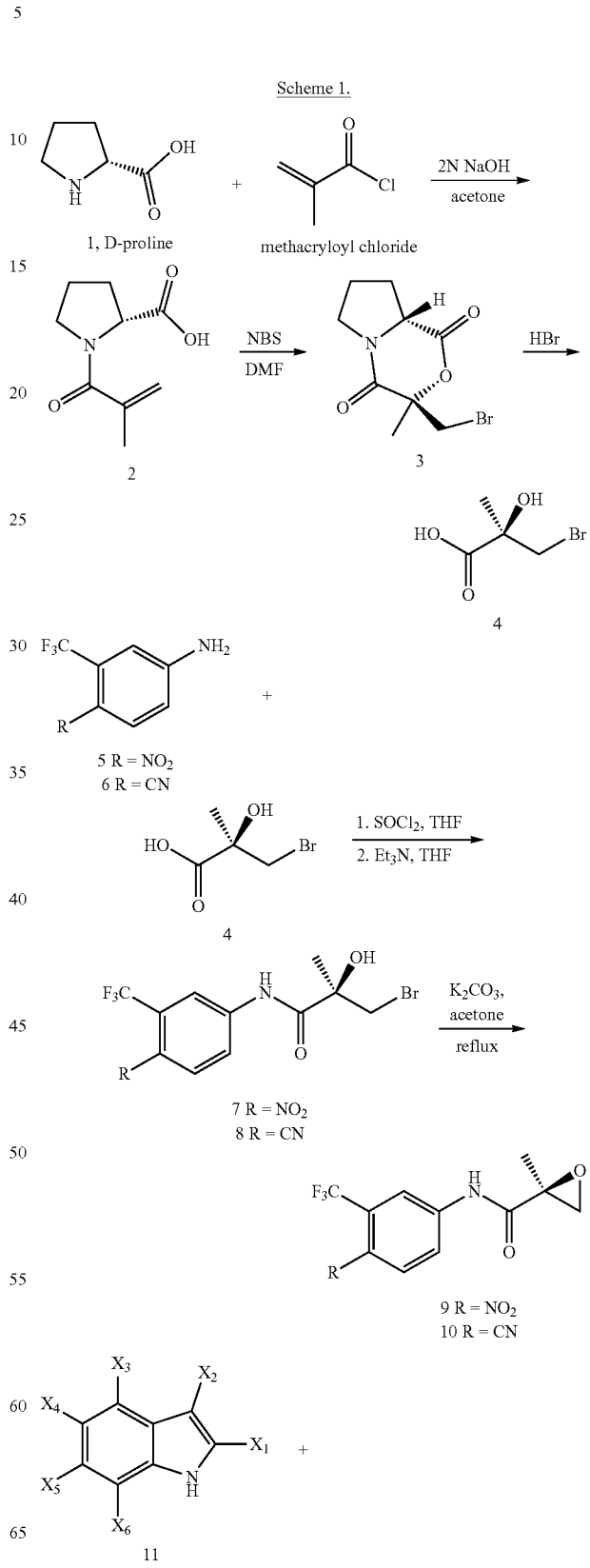

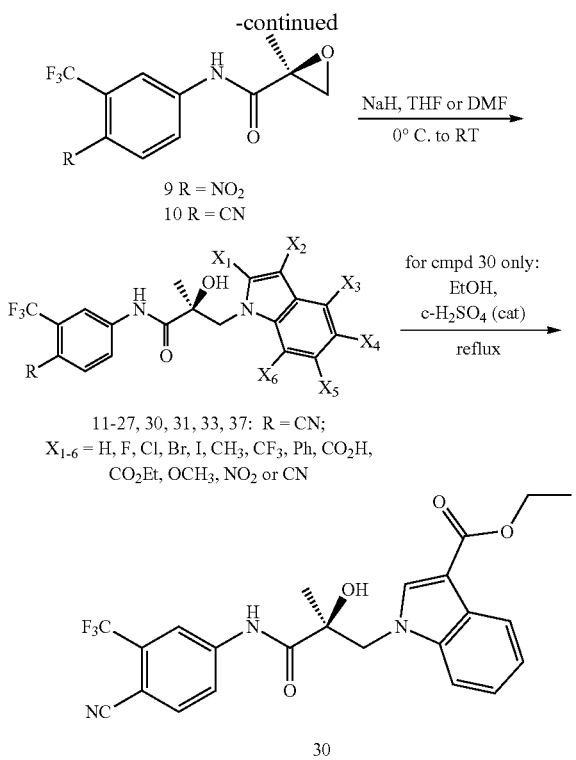

11-27, 30, 31, 33, 37: R = CN;
$X_{1-6}$ = H, F, Cl, Br, I, $CH_3$, $CF_3$, Ph, $CO_2H$, $CO_2Et$, $OCH_3$, $NO_2$ or CN (2R)-1-Methacryloylpyrrolidin-2-carboxylic acid (2)

D-Proline (14.93 g, 0.13 mol) was dissolved in 71 mL of 2 N NaOH and cooled in an ice bath. The resulting alkaline solution was diluted with acetone (71 mL). An acetone solution (71 mL) of methacryloyl chloride (13.56 g, 0.13 mol) and 2 N NaOH solution (71 mL) were simultaneously added over 40 min to the aqueous solution of D-proline in an ice bath. The temperature of the mixture was kept at 10-11° C. during the addition of the methacryloyl chloride. After stirring (3 h, room temperature (RT)), the mixture was evaporated in vacuo at a temperature at 35-45° C. to remove acetone. The resulting solution was washed with ethyl ether and was acidified to pH 2 with concentrated HCl. The acidic mixture was saturated with NaCl and was extracted with EtOAc (100 mL×3). The combined extracts were dried over $Na_2SO_4$, filtered through Celite®, and evaporated in vacuo to give the crude product as a colorless oil. Recrystallization of the oil from ethyl ether and hexanes afforded 16.2 g (68%) of the desired compound as colorless crystals: mp 102.1-103.4° C. (Marhefka, C. A.; Moore, B. M., 2nd; Bishop, T. C.; Kirkovsky, L.; Mukherjee, A.; Dalton, J. T.; Miller, D. D. Homology modeling using multiple molecular dynamics simulations and docking studies of the human androgen receptor ligand binding domain bound to testosterone and nonsteroidal ligands. *J Med Chem* 2001, 44, 1729-40: mp 102.5-103.5° C.); the NMR spectrum of this compound demonstrated the existence of two rotamers of the title compound. $^1$H NMR (300 MHz, DMSO-$d_6$) δ 5.28 (s) and 5.15 (s) for the first rotamer, 5.15 (s) and 5.03 (s) for the second rotamer (totally 2H for both rotamers, vinyl $CH_2$), 4.48-4.44 for the first rotamer, 4.24-4.20 (m) for the second rotamer (totally 1H for both rotamers, CH at the chiral center), 3.57-3.38 (m, 2H, $CH_2$), 2.27-2.12 (1H, CH), 1.97-1.72 (m, 6H, $CH_2$, CH, Me); $^{13}$C NMR (75 MHz, DMSO-$d_6$) δ for major rotamer 173.3, 169.1, 140.9, 116.4, 58.3, 48.7, 28.9, 24.7, 19.5: for minor rotamer 174.0, 170.0, 141.6, 115.2, 60.3, 45.9, 31.0, 22.3, 19.7; IR (KBr) 3437 (OH), 1737 (C=O), 1647 (CO, COOH), 1584, 1508, 1459, 1369, 1348, 1178 cm$^{-1}$; $[α]_D^{26}$+80.8° (c=1, MeOH); Anal. Calcd. for $C_9H_{13}NO_3$: C, 59.00, H, 7.15, N, 7.65. Found: C, 59.13, H, 7.19, N, 7.61.

(3R,8aR)-3-Bromomethyl-3-methyl-tetrahydro-pyrrolo[2,1-c][1,4]oxazine-1,4-dione (3)

A solution of NBS (23.5 g, 0.132 mol) in 100 mL of DMF was added dropwise to a stirred solution of the (2R)-1-methacryloylpyrrolidin-2-carboxylic acid (2) (16.1 g, 88 mmol) in 70 mL of DMF under argon at RT, and the resulting mixture was stirred 3 days. The solvent was removed in vacuo, and a yellow solid was precipitated. The solid was suspended in water, stirred overnight at RT, filtered, and dried to give 18.6 g (81%) (smaller weight when dried −34%) of the titled bromolactone (3) as a yellow solid: mp 158.1-160.3° C.; $^1$H NMR (300 MHz, DMSO-$d_6$) δ 4.69 (dd, J=9.6 Hz, J=6.7 Hz, 1H, CH at the chiral center), 4.02 (d, J=11.4 Hz, 1H, CHH$_a$), 3.86 (d, J=11.4 Hz, 1H, CHH$_b$), 3.53-3.24 (m, 4H, $CH_2$), 2.30-2.20 (m, 1H, CH), 2.04-1.72 (m, 3H, $CH_2$ and CH), 1.56 (s, 2H, Me); $^{13}$C NMR (75 MHz, DMSO-$d_6$) δ 167.3, 163.1, 83.9, 57.2, 45.4, 37.8, 29.0, 22.9, 21.6; IR (KBr) 3474, 1745 (C=O), 1687 (C=O), 1448, 1377, 1360, 1308, 1227, 1159, 1062 cm$^{-1}$; $[α]_D^{26}$+124.5° (c=1.3, chloroform); Anal. Calcd. for $C_9H_{12}BrNO_3$: C, 41.24, H, 4.61, N, 5.34. Found: C, 41.46, H, 4.64, N, 5.32.

(2R)-3-Bromo-2-hydroxy-2-methylpropanoic acid (4)

A mixture of bromolactone (3) (18.5 g, 71 mmol) in 300 mL of 24% HBr was heated at reflux for 1 h. The resulting solution was diluted with brine (200 mL), and was extracted with ethyl acetate (100 mL×4). The combined extracts were washed with saturated NaHCO$_3$ (100 mL×4). The aqueous solution was acidified with concentrated HCl to pH=1, which, in turn, was extracted with ethyl acetate (100 mL×4). The combined organic solution was dried over Na$_2$SO$_4$, filtered through Celite®, and evaporated in vacuo to dryness. Recrystallization from toluene afforded 10.2 g (86%) of the desired compound as colorless crystals: mp 110.3-113.8° C.; $^1$H NMR (300 MHz, DMSO-$d_6$) δ 3.63 (d, J=10.1 Hz, 1H, CHH$_a$), 3.52 (d, J=10.1 Hz, 1H, CHH$_b$), 1.35 (s, 3H, Me); IR (KBr) 3434 (OH), 3300-2500 (COOH), 1730 (C=O), 1449, 1421, 1380, 1292, 1193, 1085 cm$^{-1}$; $[α]_D^{26}$+10.5° (c=2.6, MeOH); Anal. Calcd. for $C_4H_7BrO_3$: C, 26.25, H, 3.86. Found: C, 26.28, H, 3.75.

(2R)-3-Bromo-N-[4-cyano-3-(trifluoromethyl)phenyl]-2-hydroxy-2-methylpropanamide (8)

Thionyl chloride (46.02 g, 0.39 mol) was added dropwise to a cooled solution (less than 4° C.) of (R)-3-bromo-2-hydroxy-2-methylpropanoic acid (4) (51.13 g, 0.28 mol) in 300 mL of THF under an argon atmosphere. The resulting mixture was stirred for 3 h under the same condition. To this was added Et$_3$N (39.14 g, 0.39 mol) and stirred for 20 min under the same condition. After 20 min, 5-amino-2-cyano-benzotrifluoride (40.0 g, 0.21 mol), 400 mL of THF were added and then the mixture was allowed to stir overnight at RT. The solvent was removed under reduced pressure to give a solid which was treated with 300 mL of H$_2$O, extracted with EtOAc (2×400 mL). The combined organic extracts were washed with saturated NaHCO$_3$ solution (2×300 mL)

and brine (300 mL). The organic layer was dried over MgSO₄ and concentrated under reduced pressure to give a solid which was purified from column chromatography using CH₂Cl₂/EtOAc (80:20) to give a solid. This solid was recrystallized from CH₂Cl₂/hexane to give 55.8 g (73.9%) of (2R)-3-bromo-N-[4-cyano-3-(trifluoromethyl)phenyl]-2-hydroxy-2-methylpropanamide (8) as a light-yellow solid. M.p. 134.0-136.5° C.; ¹H NMR (CDCl₃/TMS) δ 1.66 (s, 3H, CH₃), 3.11 (s, 1H, OH), 3.63 (d, J=10.8 Hz, 1H, CH₂), 4.05 (d, J=10.8 Hz, 1H, CH₂), 7.85 (d, J=8.4 Hz, 1H, ArH), 7.99 (dd, J=2.1, 8.4 Hz, 1H, ArH), 8.12 (d, J=2.1 Hz, 1H, ArH), 9.04 (bs, 1H, NH). Calculated Mass: 349.99, [M−H]⁻ −349.0.

Structures of Compounds Synthesized with Different Substituents: (R)- or (S)—N-(4-cyano-3-(trifluoromethyl)-phenyl)-3-(Substituted-1H-indol-1-yl)-2-hydroxy-2-methylpropanamides (11-27, 11R, 30-32, and 80)

Compounds 11-27, 11R, 30-32, and 80 were prepared by the general procedures as shown in Scheme 1 or Scheme 2, or Example 18. 11R was synthesized by same procedures as the other compounds but using L-proline instead of D-proline as a starting material. And also, 19 was isolated from the synthetic product of 11 as a by-product.

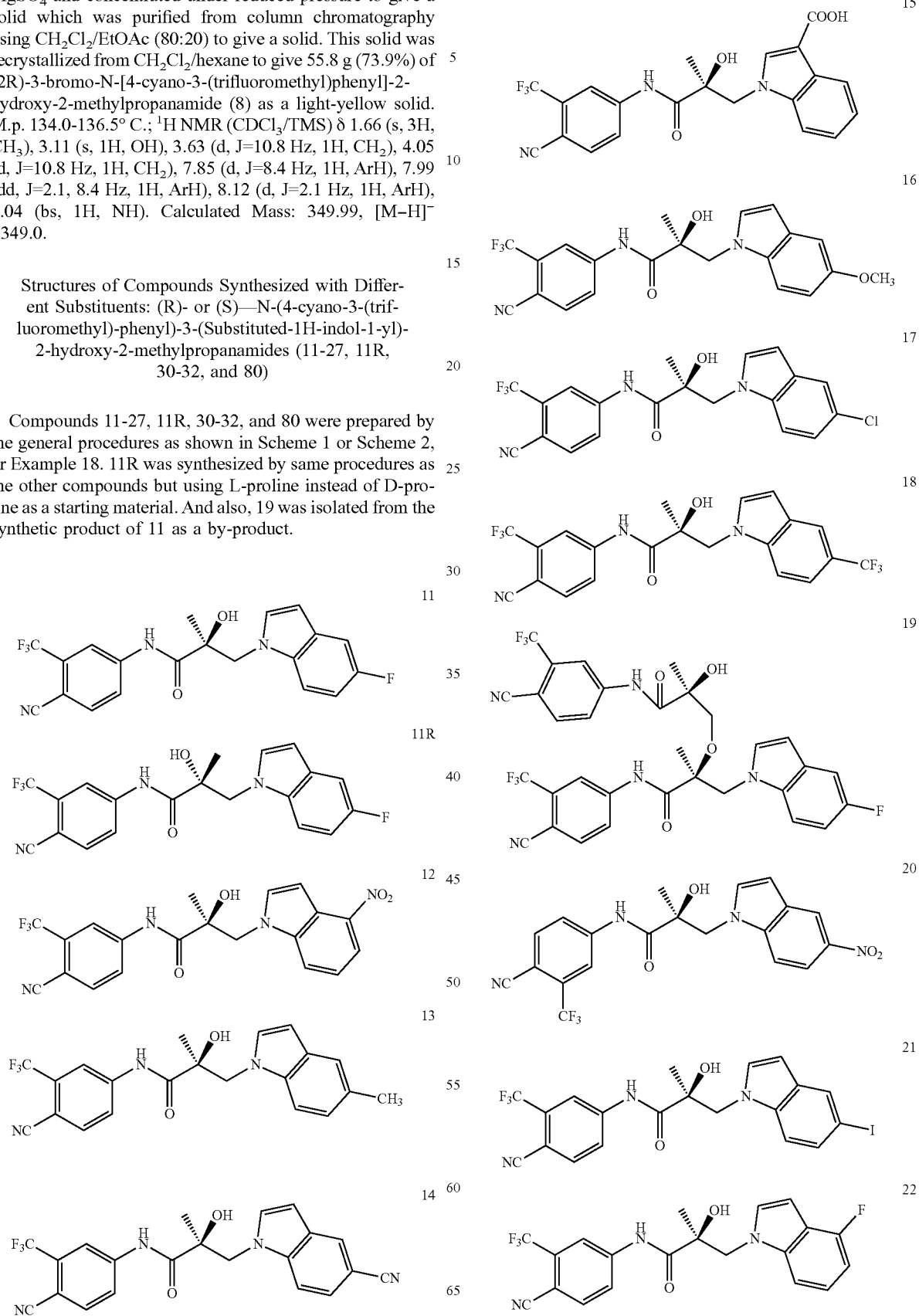

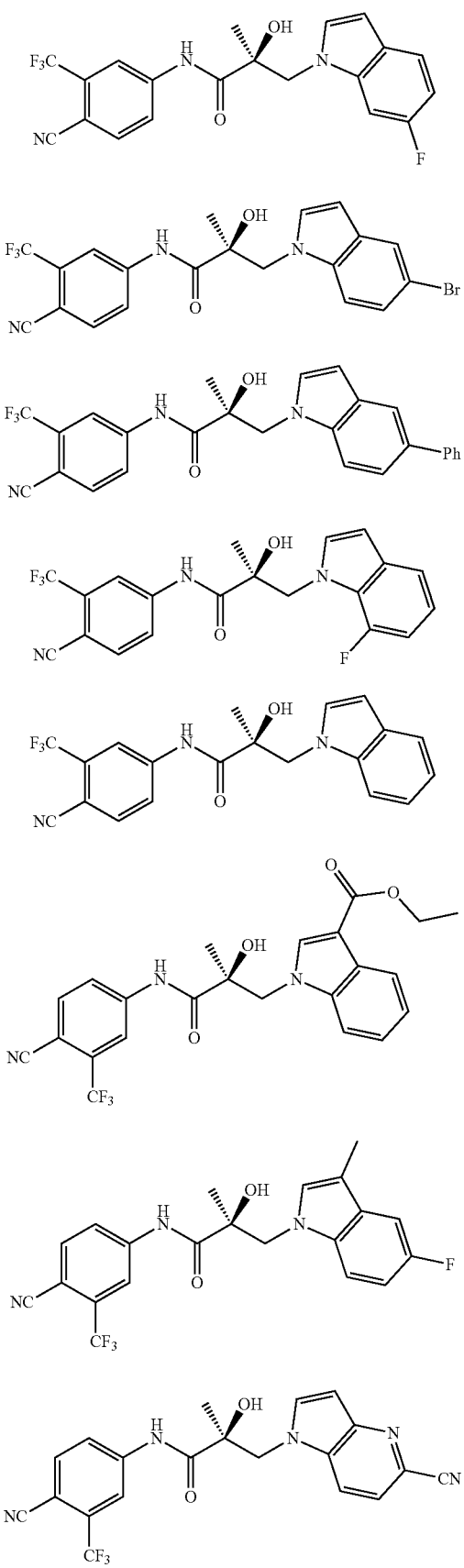

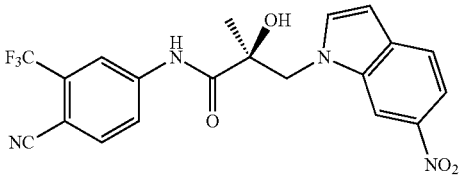

General Synthetic Procedure of Compounds 11-27, 11R, 30-32, and 80.

Step 1. Preparation of (S)—N-(4-cyano-3-(trifluoromethyl)phenyl)-2-methyloxirane-2-carboxamide (10) in THF: A mixture of hydroxylbromide 8 (1.0 g, 2.84 mmol) and potassium carbonate (790 mg, 5.70 mmol) in 60 mL acetone was heated to reflux for 30 min. After complete conversion of starting bromide 8 to desired epoxide 10 as monitored by TLC, the solvent was evaporated under reduced pressure to give yellowish residue, which was poured into 20 mL of anhydrous EtOAc. The solution was filtered through Celite® pad to remove $K_2CO_3$ residue and condensed under reduced pressure to give a yellowish solid of epoxide 10, which was dissolved in 5 mL of anhydrous THF to prepare a solution of epoxide 10 in THF. The resulting solution was directly used as next reactant without analysis.

Step 2. NaH of 60% dispersion in mineral oil (228 mg, 5.7 mmol) was added in 30 mL of anhydrous THF solvent into a 100 mL dried two necked round bottom flask equipped with a dropping funnel and substituted indole/pyrrolo-pyridine (2.84 mmol) was added to the solution under argon atmosphere in ice-water bath, and the resulting solution was stirred for 30 min in an ice-water bath. Into the flask, the prepared solution of epoxide 10 (2.84 mmol in THF) was added through dropping funnel under argon atmosphere at the ice-water bath and stirred overnight at RT. After adding 1 mL of $H_2O$ (1N HCl in case for compound 15), the reaction mixture was condensed under reduced pressure, and then dispersed into 50 mL of EtOAc, washed with 50 mL (×2) water, brine, dried over anhydrous $MgSO_4$, and evaporated to dryness. The mixture was purified with flash column chromatography as an eluent EtOAc/hexane, and then the condensed compounds were then recrystallized in EtOAc/hexane to give any one of the target products 11-27, 11R, 30-32, and 80.

(S)—N-(4-Cyano-3-(trifluoromethyl)phenyl)-3-(5-fluoro-1H-indol-1-yl)-2-hydroxy-2-methylpropanamide (11): Yield 68%; White solid. MS (ESI): 404.0 [M−H]$^-$; 428.2 [M+Na]$^+$; mp 147.5-148.9° C.; $^1$H NMR (CDCl$_3$, 400 MHz) δ 8.77 (bs, 1H, NH), 7.90 (d, J=1.7 Hz, 1H), 7.78-7.76 (m, 2H), 7.38 (dd, J=9.0, 4.2 Hz, 1H), 7.23 (dd, J=9.3, 2.5 Hz, 1H), 7.19 (d, J=3.2 Hz, 1H), 6.98 (dt, J=9.0, 2.5 Hz, 1H), 6.50 (d, J=3.2 Hz, 1H), 4.62 (d, J=14.8 Hz, 1H), 4.38 (d, J=14.8 Hz, 1H), 2.49 (bs, 1H, OH), 1.61 (s, 3H).

(S)—N-(4-Cyano-3-(trifluoromethyl)phenyl)-2-hydroxy-2-methyl-3-(4-nitro-1H-indol-1-yl)propanamide (12): Yield 41%; Yellowish solid; mp 152.9-154.8° C.; MS (ESI): 430.9 [M−H]$^-$; $^1$H NMR (CDCl$_3$, 400 MHz) δ 8.88 (bs, 1H), 8.04 (d, J=1.6 Hz, 1H), 7.89 (s, 1H), 7.79-7.75 (m, 3H), 7.31 (m, 1H), 7.26 (m, 2H), 4.69 (d, J=14.8 Hz, 1H), 4.42 (d, J=14.8 Hz, 1H), 2.43 (bs, 1H, OH), 1.63 (s, 3H).

(S)—N-(4-Cyano-3-(trifluoromethyl)phenyl)-2-hydroxy-2-methyl-3-(5-methyl-1H-indol-1-yl)propanamide (13): Yield 59%; Yellowish solid: mp 148.6-150.2° C.; MS (ESI): 400.0 [M−H]$^-$; 424.2 [M+Na]$^+$; $^1$H NMR (CDCl$_3$, 400 MHz) δ 8.72 (bs, 1H), 7.86 (d, J=2.0 Hz, 1H), 7.78 (m, 2H), 7.31 (d, J=8.8 Hz, 1H), 6.84 (dd, J=21.2, 3.2 Hz, 1H), 6.84

(dd, J=8.8, 2.4 Hz, 1H), 6.43 (d, J=2.4 Hz, 1H), 6.63 (d, J=14.8 Hz, 1H), 4.31 (d, J=14.8 Hz, 1H), 3.82 (s, 3H), 2.51 (s, 1H, OH), 1.60 (s, 3H).

(S)-3-(5-Cyano-1H-indol-1-yl)-N-(4-cyano-3-(trifluoromethyl)phenyl)-2-hydroxy-2-methylpropanamide (14): Yield 54%; White solid: MS (ESI): 411.0 [M–H]⁻; ¹H NMR (CDCl₃, 400 MHz) δ 8.85 (bs, 1H), 7.91 (d, J=1.6 Hz, 1H), 7.85 (s, 1H), 7.80-7.73 (m, 2H), 7.53 (d, J=8.6 Hz, 1H), 7.34 (d, J=8.6 Hz, 1H), 7.26 (m, 1H), 6.59 (d, J=3.2 Hz, 1H), 4.68 (d, J=14.8 Hz, 1H), 4.40 (d, J=14.8 Hz, 1H), 2.94 (bs, 1H, OH), 1.64 (s, 3H).

(S)-1-(3-((4-Cyano-3-(trifluoromethyl)phenyl)amino)-2-hydroxy-2-methyl-3-oxopropyl)-1H-indole-3-carboxylic acid (15): Yield 31%; Light yellowish solid: MS (ESI): 429.9 [M–H]⁻; ¹H NMR (CDCl₃, 400 MHz) δ 9.10 (bs, 1H), 8.11 (m, 1H), 8.01 (s, 1H), 7.91 (m, 2H), 7.84 (d, J=1.6 Hz, 1H), 7.74-7.67 (m, 2H), 7.51-7.49 (m, 1H), 7.22-7.20 (m, 1H), 4.62 (d, J=14.8 Hz, 1H), 4.43 (d, J=14.8 Hz, 1H), 2.94 (s, 1H, OH), 1.61 (s, 3H).

(S)—N-(4-Cyano-3-(trifluoromethyl)phenyl)-2-hydroxy-3-(5-methoxy-1H-indol-1-yl)-2-methylpropanamide (16): Yield 53%; Brown solid: MS (ESI): 416.0 [M–H]⁻; 418.2 [M+H]⁺; 440.2 [M+Na]⁺; ¹H NMR (CDCl₃, 400 MHz) δ 8.74 (bs, 1H), 7.87 (d, J=2.2 Hz, 1H), 7.81-7.75 (m, 2H), 7.30 (d, J=3.2 Hz, 1H), 7.09 (d, J=3.2 Hz, 1H), 7.03 (d, J=2.2 Hz, 1H), 6.43 (d, J=2.8 Hz, 1H), 4.63 (d, J=14.8 Hz, 1H), 4.30 (d, J=14.8 Hz, 1H), 3.82 (s, 3H), 2.60 (bs, 1H, OH), 1.62 (s, 3H).

(S)-3-(5-Chloro-1H-indol-1-yl)-N-(4-cyano-3-(trifluoromethyl)phenyl)-2-hydroxy-2-methylpropanamide (17): Yield 62%; White solid: MS (ESI): 420.0 [M–H]⁻; ¹H NMR (CDCl₃, 400 MHz) δ 8.85 (bs, 1H), 7.88 (d, J=1.6 Hz, 1H), 7.78 (m, 2H), 7.62 (s, 1H), 7.32 (d, J=3.2 Hz, 1H), 7.12 (m, 2H), 6.65 (d, J=3.2 Hz, 1H), 4.65 (d, J=14.8 Hz, 1H), 4.31 (d, J=14.8 Hz, 1H), 2.52 (bs, 1H, OH), 1.61 (s, 3H).

(S)—N-(4-Cyano-3-(trifluoromethyl)phenyl)-2-hydroxy-2-methyl-3-(5-(trifluoromethyl)-1H-indol-1-yl)propanamide (18): Yield 57%; White solid: MS (ESI): 453.9 [M–H]⁻; ¹H NMR (CDCl₃, 400 MHz) δ 8.80 (bs, 1H), 7.83 (d, J=1.6 Hz, 1H), 7.75 (m, 2H), 7.51 (d, J=3.2 Hz, 1H), 7.41 (m, 1H), 7.21 (m, 1H), 6.62 (d, J=3.2 Hz, 1H), 4.68 (d, J=14.8 Hz, 1H), 4.38 (d, J=14.8 Hz, 1H), 2.49 (s, 1H, OH), 1.61 (s, 3H).

(S)—N-(4-Cyano-3-(trifluoromethyl)phenyl)-2-((S)-3-((4-cyano-3-(trifluoromethyl)phenyl)amino)-2-hydroxy-2-methyl-3-oxopropoxy)-3-(5-fluoro-1H-indol-1-yl)-2-methylpropanamide (19): White solid: MS (ESI): 673.9 [M–H]⁻; 698.2 [M+Na]⁺; ¹H NMR (CDCl₃, 400 MHz) δ 9.14 (bs, 1H), 8.62 (bs, 1H), 8.16 (d, J=1.8 Hz, 1H), 8.06 (dd, J=8.8, 1.8 Hz, 1H), 7.94 (d, J=1.8 Hz, 1H), 7.84 (d, J=8.8 Hz, 1H), 7.75 (d, J=8.8 Hz, 1H), 7.55 (dd, J=8.4, 2.0 Hz, 1H), 7.45 (s, 1H), 7.35 (m, 1H), 7.24 (m, 1H), 6.98 (d, J=3.2 Hz, 1H), 6.24 (d, J=3.2 Hz, 1H), 4.54 (d, J=14.8 Hz, 1H), 4.36 (d, J=14.8 Hz, 1H), 3.96 (d, J=8.8 Hz, 1H), 3.55 (d, J=8.8 Hz, 1H), 2.76 (s, 1H, OH), 1.69 (s, 3H), 1.38 (s, 3H).

(S)—N-(4-Cyano-3-(trifluoromethyl)phenyl)-2-hydroxy-2-methyl-3-(5-nitro-1H-indol-1-yl)propanamide (20): Yield 47%; Yellowish solid: MS (ESI): 431.0 [M–H]⁻; ¹H NMR (Acetone-d₆, 400 MHz) δ 9.68 (bs, 1H, NH), 8.35 (d, J=2.0 Hz, 1H), 8.16 (s, 1H), 8.01 (m, 1H), 7.88-7.81 (m, 2H), 7.58 (d, J=8.8 Hz, 1H), 7.38 (d, J=3.4 Hz, 1H), 6.58 (d, J=3.4 Hz, 1H), 5.49 (s, 1H, OH), 4.66 (d, J=14.8 Hz, 1H), 4.38 (d, J=14.8 Hz, 1H), 1.50 (s, 3H).

(S)—N-(4-Cyano-3-(trifluoromethyl)phenyl)-2-hydroxy-3-(5-iodo-1H-indol-1-yl)-2-methylpropanamide (21): Yield 48%; MS (ESI): 511.9 [M–H]⁻; ¹H NMR (CDCl₃, 400 MHz) δ 8.71 (bs, 1H, NH), 7.91 (d, J=1.6 Hz, 1H), 7.74 (m, 2H), 7.43 (dd, J=8.8, 1.6 Hz, 1H), 7.21 (d, J=8.8 Hz, 1H), 7.08 (d, J=3.2 Hz, 1H), 6.44 (d, J=3.2 Hz, 1H), 4.62 (d, J=15.0 Hz, 1H), 4.32 (d, J=15.0 Hz, 1H), 2.44 (bs, 1H, OH), 1.61 (s, 3H).

(S)—N-(4-Cyano-3-(trifluoromethyl)phenyl)-3-(4-fluoro-1H-indol-1-yl)-2-hydroxy-2-methylpropanamide (22): Yield 48%; MS (ESI) 511.9 [M–H]⁻; ¹H NMR (CDCl₃, 400 MHz) δ 8.71 (bs, 1H, NH), 7.91 (d, J=1.6 Hz, 1H), 7.74 (m, 2H), 7.43 (dd, J=8.8, 1.6 Hz, 1H), 7.21 (d, J=8.8 Hz, 1H), 7.08 (d, J=3.2 Hz, 1H), 6.44 (d, J=3.2 Hz, 1H), 4.62 (d, J=15.0 Hz, 1H), 4.32 (d, J=15.0 Hz, 1H), 2.44 (bs, 1H, OH), 1.61 (s, 3H).

(S)—N-(4-Cyano-3-(trifluoromethyl)phenyl)-3-(6-fluoro-1H-indol-1-yl)-2-hydroxy-2-methylpropanamide (23): Yield 48%; White solid; MS (ESI) 404.0 [M–H]⁻; ¹H NMR (CDCl₃, 400 MHz) δ 8.79 (bs, 1H, NH), 7.89 (d, J=1.6 Hz, 1H), 7.83 (d, J=8.4 Hz, 1H), 7.77 (d, J=8.0 Hz, 1H), 7.51 (dd, J=8.4, 5.2 Hz, 1H), 7.14 (dd, J=10.0, 2.0 Hz, 1H), 7.11 (d, J=3.2 Hz, 1H), 6.87 (dt, J=8.8, 2.0 Hz, 1H), 6.51 (d, J=3.2 Hz, 1H), 4.62 (d, J=14.8 Hz, 1H), 4.32 (d, J=14.8 Hz, 1H), 2.56 (bs, 1H, OH), 1.65 (s, 3H).

(S)-3-(5-Bromo-1H-indol-1-yl)-N-(4-cyano-3-(trifluoromethyl)phenyl)-2-hydroxy-2-methylpropanamide (24): Yield; 71%; MS (ESI) 465.1 [M–H]⁻; ¹H NMR (CDCl₃, 400 MHz) d 8.73 (bs, 1H, NH), 7.88 (s, 1H), 7.74 (d, J=1.8 Hz, 1H), 7.69 (d, J=1.8 Hz, 1H), 7.30 (d, J=8.8 Hz, 1H), 7.24 (m, 1H), 7.24 (dd, J=8.8, 2.0 Hz, 1H), 7.13 (d, J=3.2 Hz, 1H), 6.45 (d, J=3.2 Hz, 1H), 4.39 (d, J=14.8 Hz, 1H), 2.60 (bs, 1H, OH), 1.65 (s, 3H).

(S)—N-(4-Cyano-3-(trifluoromethyl)phenyl)-2-hydroxy-3-(1H-indol-1-yl)-2-methylpropanamide (27)

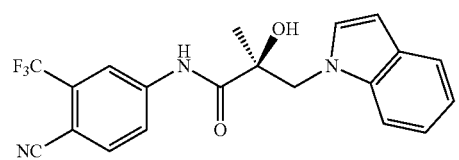

Yield 55%; Light brown solid; MS (ESI) 358.9 [M–H]⁻; ¹H NMR (CDCl₃, 400 MHz) δ 8.67 (bs, 1H, NH), 7.96 (dd, J=8.4, 2.0 Hz, 1H), 7.80 (s, 1H), 7.71-7.65 (m, 2H), 7.51 (d, J=8.0 Hz, 1H), 7.35 (d, J=8.0 Hz, 1H), 7.12 (t, J=8.0 Hz, 1H), 7.02 (m, 1H), 6.45 (d, J=3.2 Hz, 1H), 4.58 (d, J=14.8 Hz, 1H), 4.30 (d, J=14.8 Hz, 1H), 2.50 (bs, 1H, OH), 1.54 (s, 3H).

Preparation of 30 from 15

(S)-Ethyl 1-(3-((4-cyano-3-(trifluoromethyl)phenyl)amino)-2-hydroxy-2-methyl-3-oxopropyl)-1H-indole-3-carboxylate (30)

To a solution of carboxylic acid 15 (200 mg, 0.46 mmol) in absolute ethanol of 10 mL was added dropwise a catalytic amount of c-H2SO4 under argon atmosphere. The solution was heated to reflux for 30 min and cooled down to RT. The solution was concentrated under reduced pressure and dispersed in EtOAc and then washed with water. The resulting solution was dried over anhydrous Na₂SO₄ and purified with flash column chromatography as an eluent EtOAc/hexane (1/2, v/v) to give the title compound.

Yield; 92%; MS (ESI) m/z 458.1 [M–H]⁻; 482.4 [M+Na]⁺; ¹H NMR (400 MHz, CDCl₃) δ 8.86 (bs, 1H, NH), 8.00 (m, 2H), 7.81 (s, 1H), 7.65 (s, 2H), 7.46 (d, J=8.0 Hz, 1H), 7.24-7.18 (m, 2H), 4.65 (d, J=14.4 Hz, 1H), 4.39 (d, J=14.4 Hz, 1H), 4.36 (bs, 1H, OH), 4.23-4.11 (m, 2H), 1.66 (s, 3H), 1.35 (t, J=7.2 Hz, 3H).

(S)—N-(4-Cyano-3-(trifluoromethyl)phenyl)-3-(5-fluoro-3-methyl-1H-indol-1-yl)-2-hydroxy-2-methylpropanamide (31)

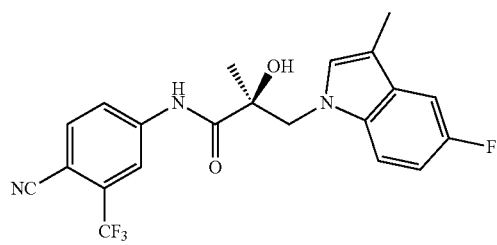 [SMILES: Cc1cn(C[C@](C)(O)C(=O)Nc2ccc(C#N)c(C(F)(F)F)c2)c2ccc(F)cc12]

Yield; 64%; MS (ESI) m/z 418.1 [M–H]⁻; ¹H NMR (400 MHz, CDCl₃) δ 8.85 (bs, 1H, NH), 7.86 (m, 1H), 7.81-7.74 (m, 2H), 7.29 (dd, J=9.0, 4.0 Hz, 1H), 7.14 (dd, J=9.0, 2.4 Hz, 1H), 6.92 (m, 2H), 4.60 (d, J=15.2 Hz, 1H), 4.27 (d, J=15.2 Hz, 1H), 2.22 (s, 3H), 1.57 (s, 3H).

(S)-3-(5-Cyano-1H-pyrrolo[3,2-b]pyridin-1-yl)-N-(4-cyano-3-(trifluoromethyl)phenyl)-2-hydroxy-2-methylpropanamide (80)

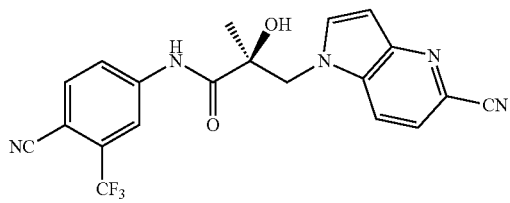

Yield; 67%; MS (ESI) m/z 412.1 [M–H]⁻; 436.1 [M+Na]⁺; ¹H NMR (400 MHz, acetone-d₆) δ 9.84 (bs, 1H, NH), 8.31 (s, 1H), 8.14 (m, 2H), 8.01 (m, 1H), 7.81 (d, J=2.8 Hz, 1H), 7.60 (d, J=8.4 Hz, 1H), 6.67 (d, J=2.8 Hz, 1H), 5.64 (bs, 1H), 4.84 (d, J=14.8 Hz, 1H), 4.52 (d, J=14.8 Hz, 1H), 1.66 (s, 3H).

(S)—N-(4-Cyano-3-(trifluoromethyl)phenyl)-2-hydroxy-2-methyl-3-(6-nitro-1H-indol-1-yl)propanamide (32)

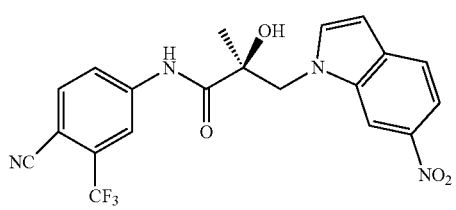 [SMILES: C[C@](O)(Cn1ccc2ccc([N+](=O)[O-])cc21)C(=O)Nc1ccc(C#N)c(C(F)(F)F)c1]

Yield; 31%; MS (ESI) m/z 431.1 [M–H]⁻; ¹H NMR (400 MHz, CDCl₃) δ 8.87 (bs, 1H, NH), 8.53 (m, 1H), 8.01 (dd, J=8.8, 2.0 Hz, 1H), 7.92 (d, J=2.0 Hz, 1H), 7.86 (dd, J=8.4, 2.0 Hz, 1H), 7.78 (d, J=8.4 Hz, 1H), 7.64 (d, J=8.8 Hz, 1H), 7.43 (d, J=3.0 Hz, 1H), 6.61 (d, J=3.0 Hz, 1H), 4.76 (d, J=14.8 Hz, 1H), 4.48 (d, J=14.8 Hz, 1H), 3.14 (s, 1H, OH), 1.74 (s, 3H).

(R)—N-(4-Cyano-3-(trifluoromethyl)phenyl)-3-(5-fluoro-1H-indol-1-yl)-2-hydroxy-2-methylpropanamide (11R): 11R was synthesized by the same procedures as the other compounds but using L-proline instead of D-proline as a starting material.

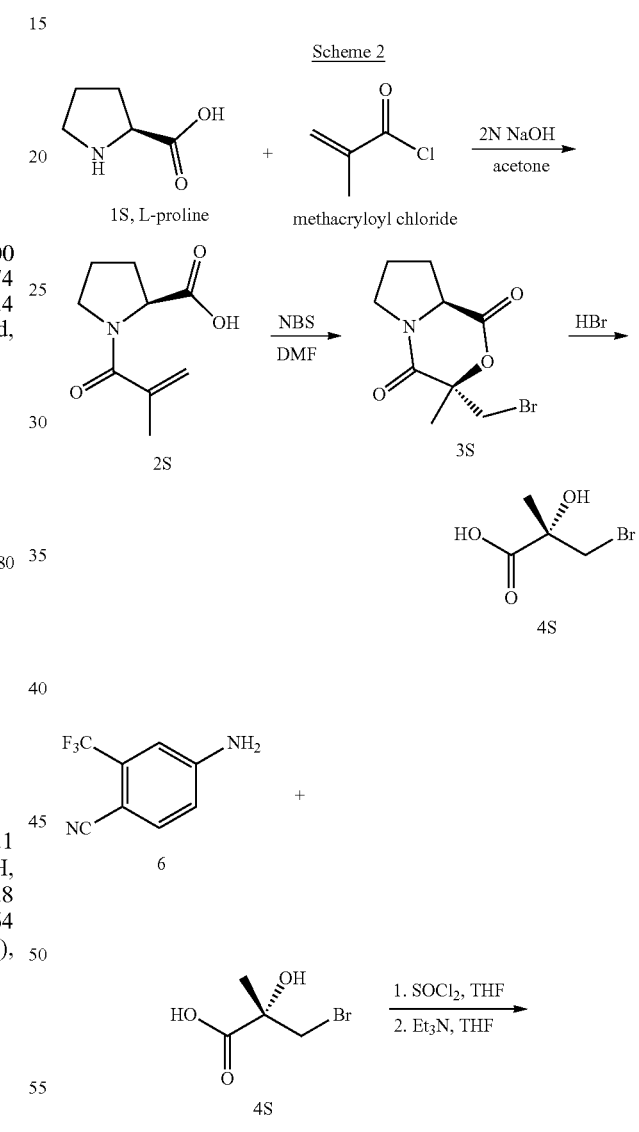

Example 18

Synthesis of Benzimidazole and Indazole SARD Compounds of this Invention

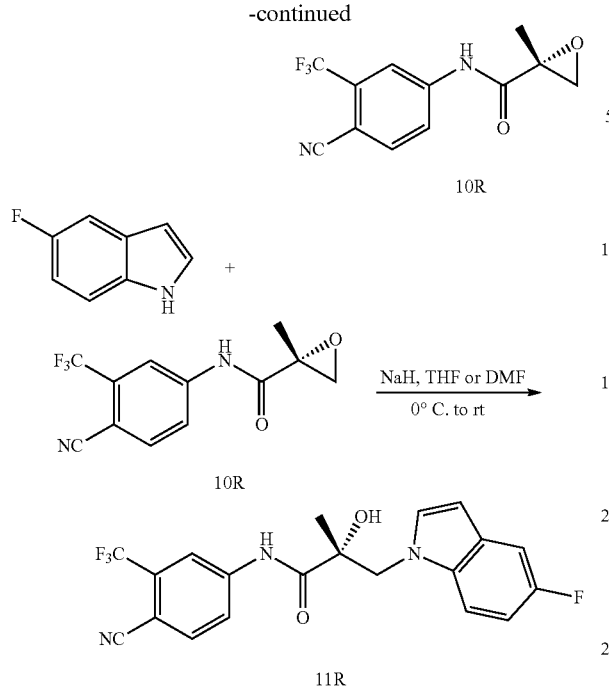

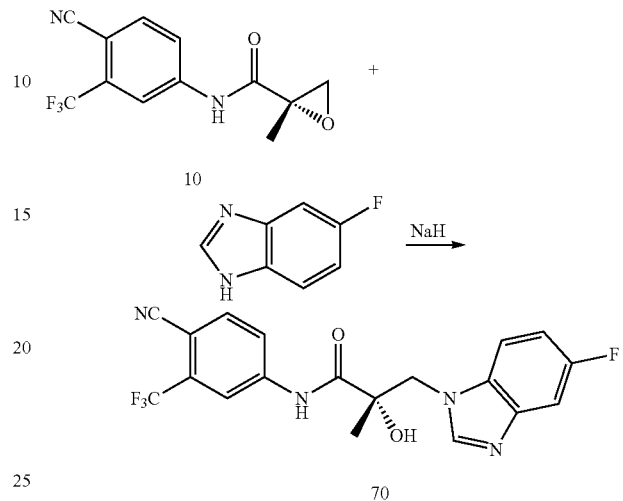

NaH of 60% dispersion in mineral oil (228 mg, 5.7 mmol) was added in 20 mL of anhydrous THF solvent into a 100 mL dried two necked round bottom flask equipped with a dropping funnel. 5-Fluoroindole (390 mg, 2.84 mmol) was added to the solution under argon atmosphere in ice-water bath, and the resulting solution was stirred for 30 min in an ice-water bath. Into the flask, epoxide 10R (2.84 mmol in THF) was added through a dropping funnel under argon atmosphere in an ice-water bath and stirred overnight at RT. After adding 1 mL of H$_2$O, the reaction mixture was condensed under reduced pressure, and then dispersed into 50 mL of EtOAc, washed with 50 mL (×2) water, brine, dried over anhydrous MgSO$_4$, and evaporated to dryness. The mixture was purified with flash column chromatography as an eluent EtOAc/hexane, and then the condensed compounds were then recrystallized in EtOAc/hexane to give a target product 11R.

Yield 69%; White solid. MS (ESI): 404.1 [M−H]$^-$; 428.1 [M+Na]$^+$; $^1$H NMR (CDCl$_3$, 400 MHz) δ 8.69 (bs, 1H, NH), 7.80 (d, J=1.2 Hz, 1H), 7.71-7.66 (m, 2H), 7.29-7.26 (m, 2H), 7.14 (dd, J=9.2, 2.4 Hz, 1H), 7.09 (d, J=3.2 Hz, 1H), 6.86 (dt, J=9.0, 2.5 Hz, 1H), 6.39 (d, J=3.2 Hz, 1H), 4.56 (d, J=14.8 Hz, 1H), 4.26 (d, J=14.8 Hz, 1H), 2.51 (bs, 1H, OH), 1.54 (s, 3H).

(S)—N-(4-Cyano-3-trifluoromethyl-phenyl)-3-(5-fluoro-benzoimidazol-1-yl)-2-hydroxy-2-methyl-propionamide (C$_{19}$H$_{14}$F$_4$N$_4$O$_2$) (70)

To a solution of 5-fluoro-1H-benzoimidazole (0.50 g, 0.00367 mol) in anhydrous THF (10 mL), which was cooled in an ice water bath under an argon atmosphere, was added sodium hydride (60% dispersion in oil, 0.44 g, 0.011 mol). After addition, the resulting mixture was stirred for 2 h. (S)—N-(4-Cyano-3-(trifluoromethyl)phenyl)-2-methyloxirane-2-carboxamide (1.29 g, 0.00367 mol) was added to above solution, and the resulting reaction mixture was allowed to stir overnight at RT under argon. The reaction was quenched by water, extracted with ethyl acetate. The organic layer was dried with MgSO$_4$, filtered, and concentrated under vacuum. The product was purified by a silicon gel column using methylene chloride and methanol (19:1) as eluent to afford 0.17 g of the desired compound as white solid.

$^1$H NMR (400 MHz, DMSO-d$_6$) δ 10.37 (s, 1H, NH), 8.31 (d, J=17.2 Hz, 1H, ArH), 8.16-8.05 (m, 3H, ArH), 7.62-7.56 (m, 1H, ArH), 7.44 (dd, J=9.60 Hz, J=2.4 Hz, 1H, ArH), 7.04 (dd, J=9.60 Hz, J=2.4 Hz, 1H, ArH), 6.49 (s, 1H, OH), 4.65 (d, J=5.6 Hz, 1H, CH), 4.62 (d, J=5.6 Hz, 1H, CH), 1.47 (s, 3H, CH$_3$). Mass (ESI, Negative): 404.8 [M−H]$^-$; (ESI, Positive): 429.0 [M+Na]$^+$.

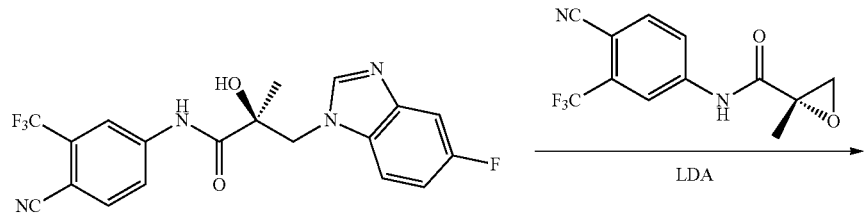

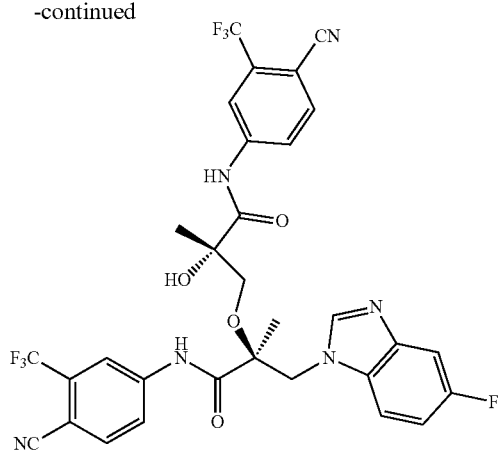

72

(S)—N-(4-Cyano-3-(trifluoromethyl)phenyl)-2-((4S)-3-((4-cyano-3-(trifluoromethyl)phenyl)amino)-2-hydroxy-2-methyl-3-oxopropoxy)-3-(5-fluoro-1H-benzo[d]imidazol-1-yl)-2-methylpropanamide ($C_{31}H_{23}F_7N_6O_4$) (72)

This byproduct was purified by a silicon gel column using methylene chloride and methanol (19:1) as eluent to afford 50 mg of the titled compound as yellowish solid.

$^1$H NMR (400 MHz, DMSO-d$_6$) δ 10.75 (s, 1H, NH), 9.64 (s, 1H, NH), 8.31 (d, J=17.2 Hz, 1H, ArH), 8.33-8.30 (m, 1H, ArH), 8.11-7.86 (m, 6H, ArH), 7.54-7.52 (m, 1H, ArH), 7.35-7.33 (m, 1H, ArH), 6.77-6.73 (m, 1H, ArH), 6.31 (s, 1H, OH), 4.66-4.63 (m, 1H, CH), 4.50-4.44 (m, 1H, CH), 3.83-3.82 (m, 1H, CH), 3.66-3.64 (m, 1H, CH), 1.54 (s, 3H, CH$_3$), 1.34 (s, 3H, CH$_3$). Mass (ESI, Negative): 675.0 [M−H]$^-$; (ESI, Positive): 699.3 [M+Na]$^+$.

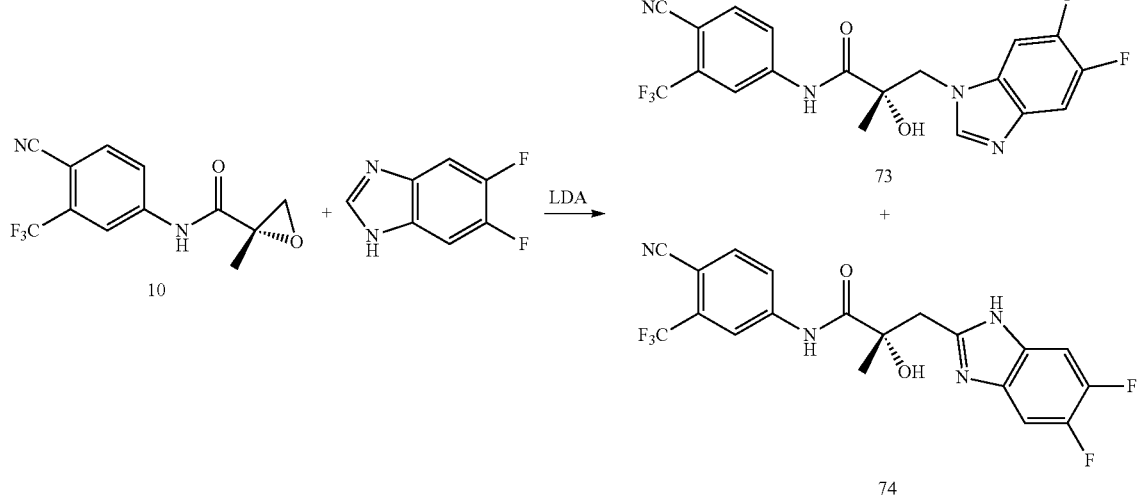

To a solution of 5,6-difluoro-1H-benzoimidazole (0.23 g, 0.00148 mol) in anhydrous THF (10 mL), which was cooled in an dry-ice acetone bath under an argon atmosphere, was added LDA (2.0 M in THF, 1.11 mL, 0.0022 mol). After addition, the resulting mixture was stirred for 2 h. (S)—N-(4-Cyano-3-(trifluoromethyl)phenyl)-2-methyloxirane-2-carboxamide (0.40 g, 0.00148 mol) was added to above solution, and the resulting reaction mixture was allowed to stir overnight at RT under argon. The reaction was quenched by water, extracted with ethyl acetate. The organic layer was dried with MgSO$_4$, filtered, and concentrated under vacuum. The product was purified by a silicon gel column using methylene chloride and methanol (19:1) as eluent to afford the desired compound as white solid.

(S)—N-(4-Cyano-3-trifluoromethyl-phenyl)-3-(5,6-difluoro-benzoimidazol-1-yl)-2-hydroxy-2-methyl-propionamide ($C_{19}H_{13}F_5N_4O_2$) (73)

$^1$H NMR (400 MHz, DMSO-$d_6$) δ 10.36 (s, 1H, NH), 8.25 (d, J=2.0 Hz, 1H, ArH), 8.21 (s, 1H, ArH), 8.14 (dd, J=8.8 Hz, J=2.0 Hz, 1H, ArH), 8.06 (d, J=8.8 Hz, 1H, ArH), 7.43-7.40 (m, 1H, ArH), 7.26-7.19 (m, 1H, ArH), 6.51 (s, 1H, OH), 4.65 (d, J=14.8 Hz, 1H, CH), 4.41 (d, J=14.8 Hz, 1H, CH), 1.42 (s, 3H, $CH_3$). Mass (ESI, Negative): 422.7 [M−H]$^−$; (ESI, Positive): 447.0 [M+Na]$^+$.

(S)—N-(4-Cyano-3-(trifluoromethyl)phenyl)-3-(5,6-difluoro-1H-benzo[d]imidazol-2-yl)-2-hydroxy-2-methylpropanamide ($C_{19}H_{13}F_5N_4O_2$) (74)

$^1$H NMR (400 MHz, DMSO-$d_6$) δ 10.44 (s, 1H, NH), 8.36 (d, J=2.0 Hz, 1H, ArH), 8.17 (dd, J=8.4 Hz, J=2.0 Hz, 1H, ArH), 8.11 (s, 1H, ArH), 8.07 (d, J=8.4 Hz, 1H, ArH), 7.44-7.41 (m, 1H, ArH), 7.21-7.14 (m, 1H, ArH), 6.54 (s, 1H, OH), 4.62 (d, J=14.4 Hz, 1H, CH), 4.52 (d, J=14.4 Hz, 1H, CH), 1.41 (s, 3H, $CH_3$). Mass (ESI, Negative): 422.7 [M−H]$^−$; (ESI, Positive): 447.0 [M+Na]$^+$.

(S)—N-(4-Cyano-3-(trifluoromethyl)phenyl)-3-(7-fluoro-1H-benzo[d]imidazol-1-yl)-2-hydroxy-2-methylpropanamide ($C_{19}H_{14}F_4N_4O_2$) (75)

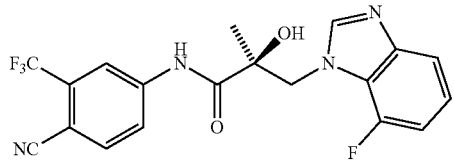

75

To a solution of 7-fluoro-benzimidazole (0.30 g, 0.0022 mol) in anhydrous THF (10 mL), which was cooled in an ice water bath under an argon atmosphere, was added sodium hydride (60% dispersion in oil, 0.132 g, 0.00331 mol). After addition, the resulting mixture was stirred for two hours. (R)-3-Bromo-N-(4-cyano-3-trifluoromethyl-phenyl)-2-hydroxy-2-methylpropanamide (0.77 g, 0.0022 mol) was added to above solution, and the resulting reaction mixture was allowed to stir overnight at RT under argon. The reaction was quenched by water, and extracted with ethyl acetate. The organic layer was dried with $MgSO_4$, filtered, and concentrated under vacuum. The product was purified by a silica gel column using methylene chloride and methanol (19:1) as eluent to afford 0.18 g of the titled compound as yellowish solid.

$^1$H NMR (400 MHz, DMSO-$d_6$) δ 10.49 (s, 1H, NH), 8.39 (d, J=2.0 Hz, 1H, ArH), 8.21 (dd, J=8.8 Hz, J=2.0 Hz, 1H, ArH), 8.11 (s, 1H, ArH), 8.08 (d, J=8.8 Hz, 1H, ArH), 7.46 (d, J=8.0 Hz, 1H, ArH), 7.16-7.10 (m, 1H, ArH), 7.05-7.00 (m, 1H, ArH), 6.52 (s, 1H, OH), 4.64-4.56 (m, 2H, CH), 1.35 (s, 3H, $CH_3$). Mass (ESI, Negative): 404.8 [M−H]$^−$.

Synthesis of (S)—N-(4-cyano-3-(trifluoromethyl)phenyl)-3-(4-fluoro-1H-benzo[d]imidazol-1-yl)-2-hydroxy-2-methylpropanamide (76) & (S)—N-(4-cyano-3-(trifluoromethyl)phenyl)-3-(7-fluoro-1H-benzo[d]imidazol-1-yl)-2-hydroxy-2-methylpropanamide (75)

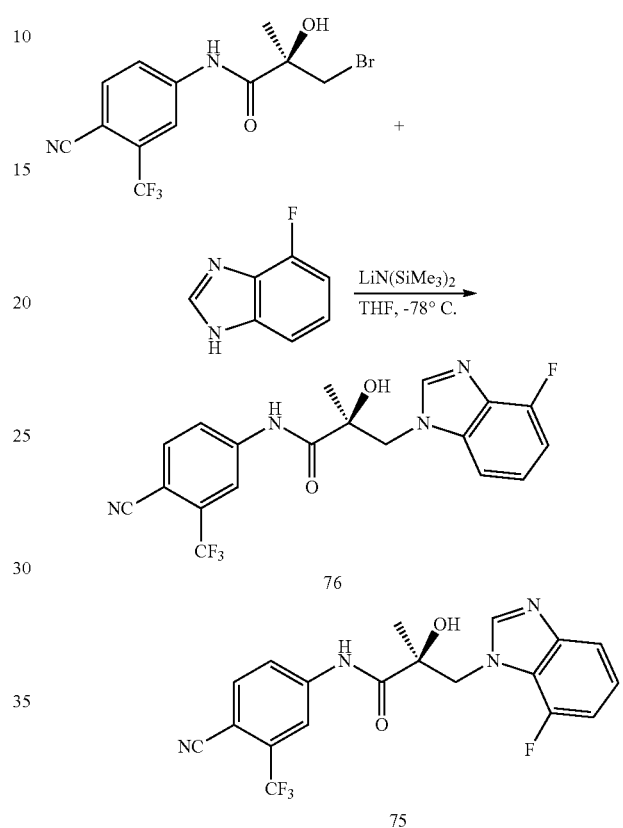

Under an argon atmosphere, 1.5 mL of lithium bis(trimethylsilyl)amide in THF (1.5 mmol, Aldrich, 1 M solution in THF) was slowly added to a solution of 4-fluoro-1H-benzo[d]imidazole (136 mg, 1 mmol) in THF (10 mL) at −78° C. and stirred for 30 min at the same temperature. A solution of 8R (318 mg, 1 mmol) in 5 mL of THF was added dropwise to the solution. The reaction mixture was stirred at the same temperature for 30 min and stirred overnight at RT, quenched by an addition of sat. $NH_4Cl$ solution. The mixture was concentrated under reduced pressure and dispersed into excess EtOAc and dried over $Na_2SO_4$, concentrated and purified by flash column chromatography (EtOAc/hexane) to give the target compound give total 70% yield of 76 (30%, 120.3 mg) and 75 (40%, 163.1 mg) as white solid.

(S)—N-(4-Cyano-3-(trifluoromethyl)phenyl)-3-(4-fluoro-1H-benzo[d]imidazol-1-yl)-2-hydroxy-2-methylpropanamide (76)

HRMS (ESI) m/z calcd for $C_{19}H_{15}F_4N_4O_2$: 407.1131 [M+H]$^+$. Found: 407.1137 [M+H]$^+$.

$^1$H NMR (CDCl$_3$, 400 MHz) δ 9.10 (bs, 1H, NH), 8.11 (s, 1H), 7.79 (s, 1H), 7.75-7.71 (m, 2H), 7.38 (m, 1H), 7.31-7.26 (m, 1H), 6.81 (t, J=8.0 Hz, 1H), 6.01 (bs, 1H, OH), 4.93 (d, J=14.0 Hz, 1H), 4.44 (d, J=14.0 Hz, 1H), 1.53 (s, 3H).

$^{19}$F NMR (CDCl$_3$, 400 MHz) δ−62.22, −117.60.

(S)—N-(4-Cyano-3-(trifluoromethyl)phenyl)-3-(7-fluoro-1H-benzo[d]imidazol-1-yl)-2-hydroxy-2-methylpropanamide (75)

HRMS (ESI) m/z calcd for $C_{19}H_{15}F_4N_4O_2$: 407.1131. Found: 407.1126 [M+H]$^+$.

$^1$H NMR (CDCl$_3$, 400 MHz) δ 9.14 (bs, 1H, NH), 8.08 (s, 1H), 7.96 (s, 1H), 7.82 (d, J=8.2 Hz, 1H), 7.73 (d, J=8.4 Hz, 1H), 7.72 (d, J=8.4 Hz, 1H), 7.42 (d, J=8.8 Hz, 1H), 7.23 (m, 1H), 7.67 (dd, J=10.0, 7.6 Hz, 1H), 6.67 (bs, 1H, OH), 4.96 (d, J=13.6 Hz, 1H), 4.54 (d, J=13.6 Hz, 1H), 1.54 (s, 3H).

$^{19}$F NMR (CDCl$_3$, 400 MHz) δ −62.22, −116.56.

2-Dimensional nuclear Overhauser effect (NOE) spectroscopy (NOESY): NOESY was used to assign the correct chemical structures to these two isomers. 76 demonstrated an NOEs between the aromatic proton located at the 7-position of the benzo[d]imidazole ring (annotated as H) and the methylene protons (annotated as H$_1$ and H$_2$),

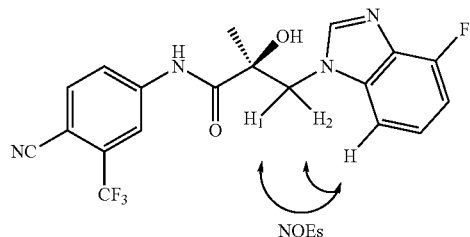

76 indicating that the point of attachment to the benzo[d]imidazole ring must be the 1-position. Whereas for 75, an NOE was observed between 2-position aromatic proton of the benzo[d]imidazole ring (annotated as H) and the methylene protons (annotated as H$_1$ and H$_2$),

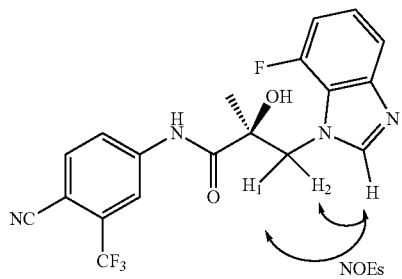

75 indicating that the point of attachment to the benzo[d]imidazole ring must be the 1-position (opposite nitrogen as for 76) hence fluorine is substituted at the 7-position of the benzo[d]imidazole ring and this product is identical to the other 75 reported above. The variable NMR values are due to the different NMR solvents used.

Synthesis of (S)—N-(4-cyano-3-(trifluoromethyl)phenyl)-2-hydroxy-2-methyl-3-(4-(trifluoromethyl)-1H-benzo[d]imidazol-1-yl)propanamide (77) and (S)—N-(4-cyano-3-(trifluoromethyl)phenyl)-2-hydroxy-2-methyl-3-(7-(trifluoromethyl)-1H-benzo[d]imidazol-1-yl)propanamide (78)

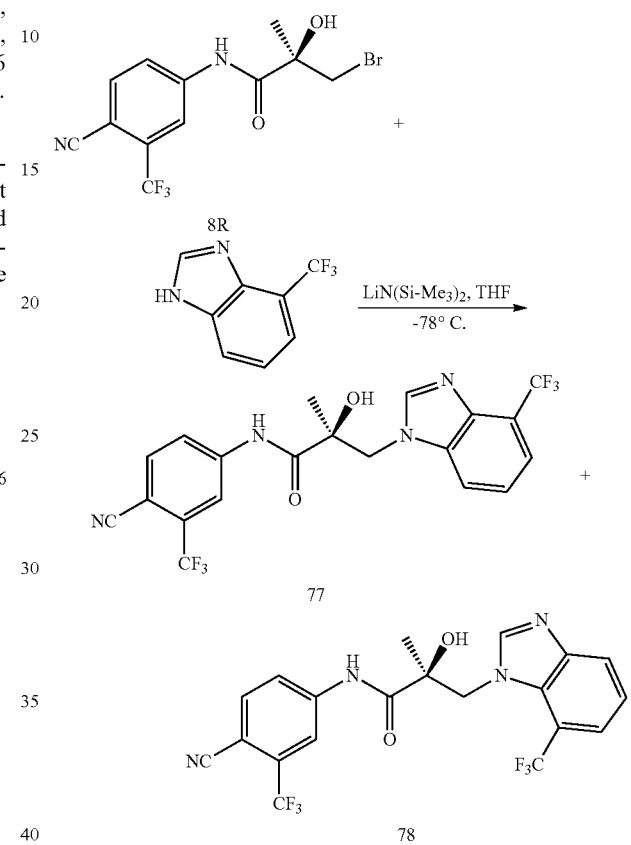

Under an argon atmosphere, 2.0 mL of lithium bis(trimethylsilyl)amide in THF (2 mmol, Aldrich, 1 M solution in THF) was slowly added to a solution of 4-(trifluoromethyl)-1H-benzo[d]imidazole (186 mg, 1 mmol) in THF (10 mL) at −78° C. and stirred for 30 min at that temperature. A solution of R-bromo amide 8R (351 mg, 1 mmol) in 5 mL of THF was added dropwise to the solution. The reaction mixture was stirred at the same temperature for 30 min and stirred overnight at RT, quenched by an addition of sat. NH$_4$Cl solution. The mixture was concentrated under reduced pressure and dispersed into excess EtOAc and dried over Na$_2$SO$_4$, concentrated and purified by flash column chromatography (EtOAc/hexane; 1/1 and then EtOAc only) to give 77 and 78 as a white solid.

(S)—N-(4-Cyano-3-(trifluoromethyl)phenyl)-2-hydroxy-2-methyl-3-(4-(trifluoromethyl)-1H-benzo[d]imidazol-1-yl)propanamide (77)

HRMS (ESI) m/z calcd for $C_{20}H_{15}F_6N_4O_2$: 457.1099 [M+H]$^+$. Found: 457.1094 [M+H]$^+$.

$^1$H NMR (CDCl$_3$, 400 MHz) δ 9.16 (bs, 1H, NH), 8.07 (s, 1H), 9.95 (s, 1H), 7.76 (m, 2H), 7.73 (d, J=8.0 Hz, 1H), 7.54 (d, J=7.6 Hz, 1H), 7.34 (t, J=7.8 Hz, 1H), 6.37 (bs, 1H, OH), 4.70 (d, J=14.4 Hz, 1H), 4.47 (d, J=14.4 Hz, 1H), 1.58 (s, 3H).

$^{19}$F NMR (CDCl$_3$, 400 MHz) δ −60.52, −62.29.

(S)—N-(4-Cyano-3-(trifluoromethyl)phenyl)-2-hydroxy-2-methyl-3-(7-(trifluoromethyl)-1H-benzo[d]imidazol-1-yl)propanamide (78)

HRMS (ESI) m/z calcd for $C_{20}H_{15}F_6N_4O_2$: 457.1099 [M+H]$^+$. Found: 457.1090 [M+H]$^+$.

$^1$H NMR (CDCl$_3$, 400 MHz) δ 9.32 (bs, 1H, NH), 8.26 (s, 1H), 8.12 (d, J=2.0 Hz, 1H), 7.99 (dd, J=8.6, 2.0 Hz, 1H), 7.83 (d, J=8.6 Hz, 1H), 7.77 (d, J=8.0 Hz, 1H), 7.65 (d, J=7.6 Hz, 1H), 7.29 (t, J=7.6 Hz, 1H), 5.91 (bs, 1H, OH), 4.94 (d, J=15.2 Hz, 1H), 4.67 (d, J=15.2 Hz, 1H), 1.48 (s, 3H).

$^{19}$F NMR (CDCl$_3$, 400 MHz) δ −55.42, 62.14.

Synthesis of (S)—N-(3-chloro-4-cyanophenyl)-3-(4-fluoro-1H-benzo[d]imidazol-1-yl)-2-hydroxy-2-methylpropanamide (79)

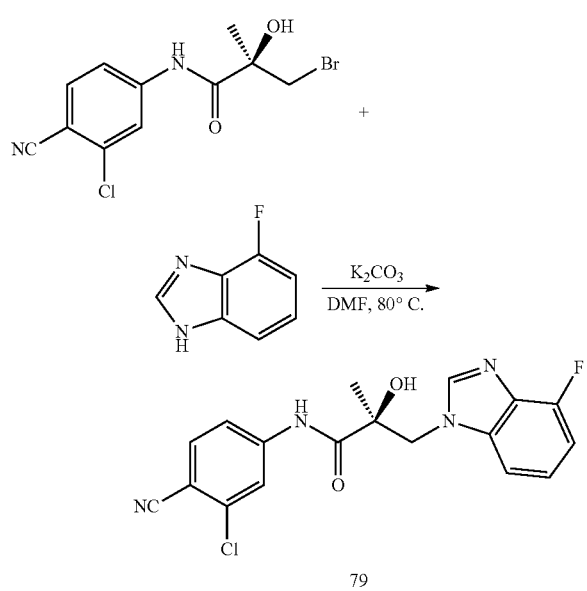

79

To a dry, nitrogen-purged 50 mL round-bottom flask, (R)-3-bromo-N-(3-chloro-4-cyanophenyl)-2-hydroxy-2-methylpropanamide (318 mg, 1 mmol), 4-fluoro-1H-benzo[d]imidazole (136 mg, 1 mmol) and K$_2$CO$_3$ (415 mg, 3 mmol) were dissolved into 10 mL of DMF. The mixture was heated up to 80° C. for 3 h. The resulting mixture was cooled down to RT. The volume of the mixture was reduced under reduced pressure and poured into water, and extracted with ethyl acetate (3 times). The organic layer was dried over anhydrous MgSO$_4$, concentrated and purified by flash column chromatography (ethyl acetate only, rf=0.31) on silica gel to produce 79 (38%).

(S)—N-(3-Chloro-4-cyanophenyl)-3-(4-fluoro-1H-benzo[d]imidazol-1-yl)-2-hydroxy-2-methylpropanamide (79)

HRMS (ESI) m/z calcd for $C_{18}H_{15}ClF_4N_4O_2$: 373.0868 [M+H]$^+$. Found: 373.0878 [M+H]$^+$.

$^1$H NMR (Acetone-d$_6$, 400 MHz) δ 9.77 (bs, 1H, NH), 8.16 (d, J=1.6 Hz, 1H), 8.04 (s, 1H), 7.83 (dd, J=8.4, 1.6 Hz, 1H), 7.75 (d, J=1.6 Hz, 1H), 7.44 (d, J=4.8 Hz, 1H), 7.18 (m, 1H), 6.99 (dd, J=11.6, 8.0 Hz, 1H), 5.83 (bs, 1H, OH), 4.78 (d, J=14.4 Hz, 1H), 4.69 (d, J=14.4 Hz, 1H), 1.56 (s, 3H).

Synthesis of Indazole SARDs:

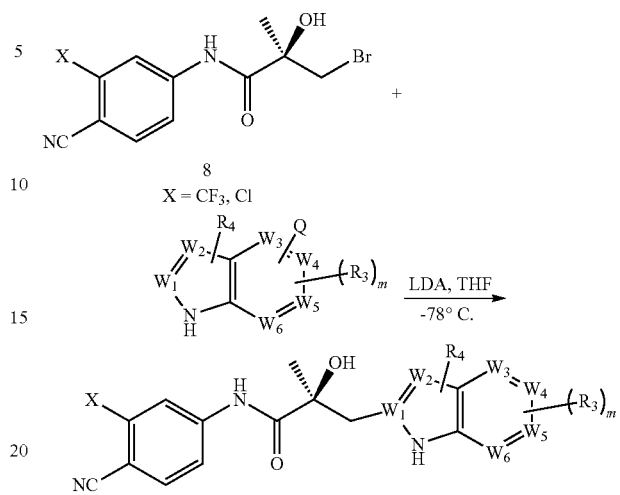

X = CF$_3$, Cl

To a solution of substituted-1H-indazole (0.00148 mol; e.g., 5-fluoro-1H-indazole for 90) in anhydrous THF (10 mL), which was cooled in an dry-ice acetone bath under an argon atmosphere, was added LDA (2.0 M in THF, 1.11 mL, 0.0022 mol). After addition, the resulting mixture was stirred for 2 h. (S)—N-(4-Cyano-3-(trifluoromethyl)phenyl)-2-methyloxirane-2-carboxamide (0.40 g, 0.00148 mol) was added to above solution, and the resulting reaction mixture was allowed to stir overnight at RT under argon. The reaction was quenched by water, extracted with ethyl acetate. The organic layer was dried with MgSO$_4$, filtered, and concentrated under vacuum. The product was purified by a silicon gel column using methylene chloride and methanol (19:1) as eluent to afford the desired compound as white solid.

Example 19

Synthesis of Quinoline, Isoquinoline, and Indoline SARD Compounds of this Invention Quinoline compounds

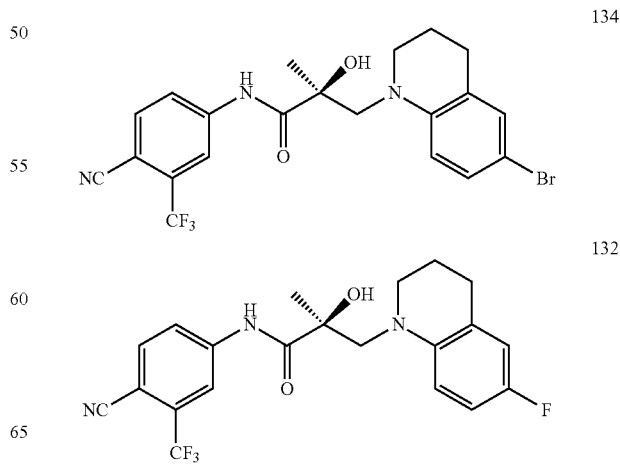

134

132

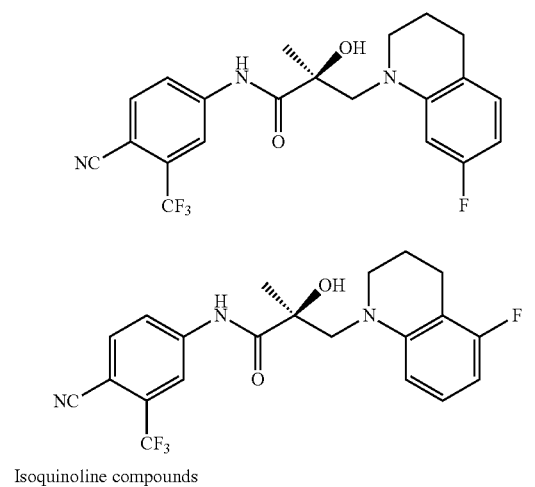
Isoquinoline compounds
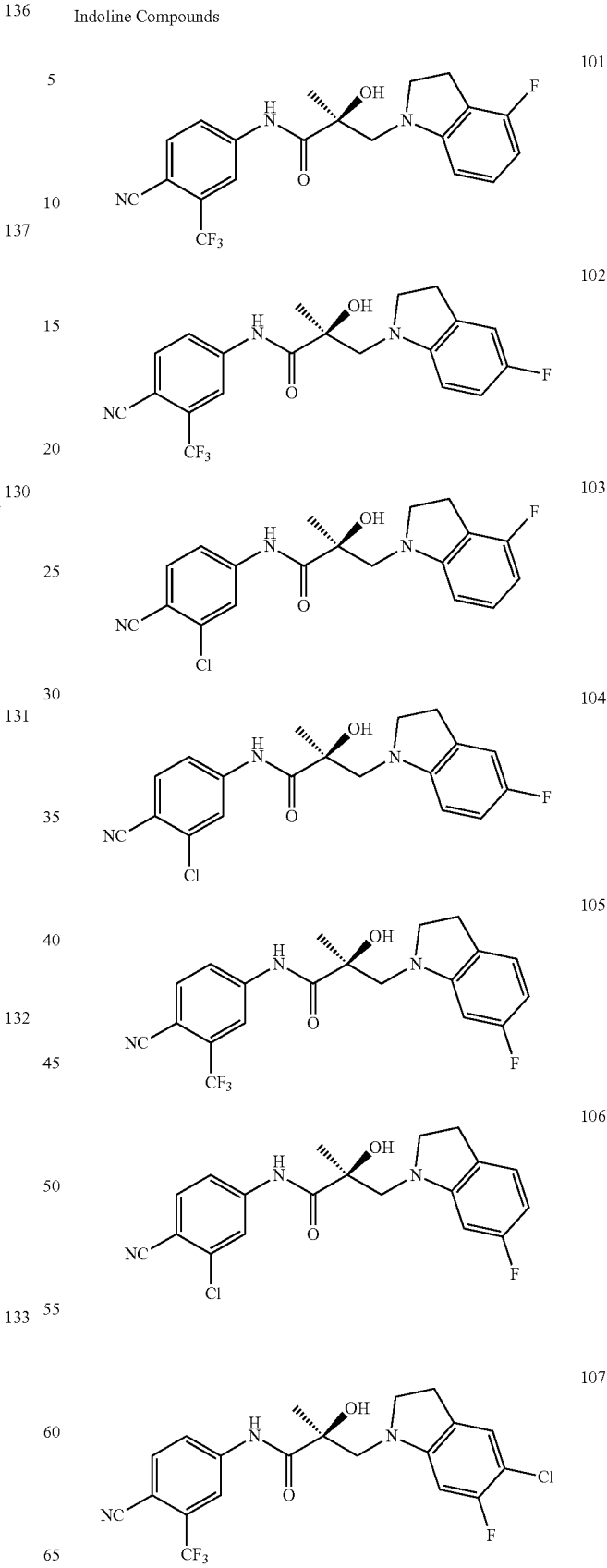
Indoline Compounds

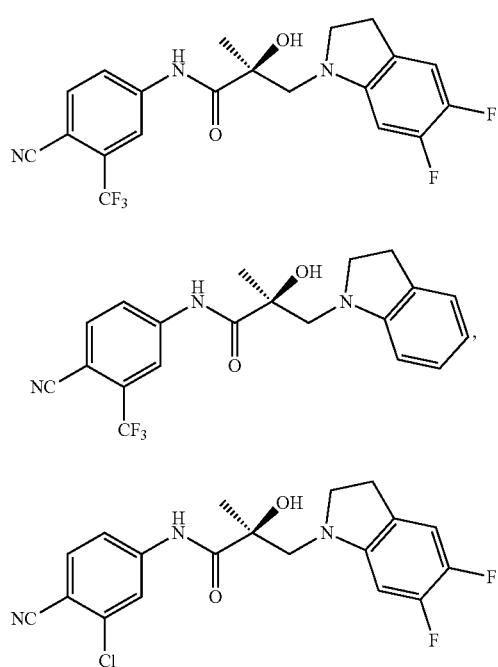

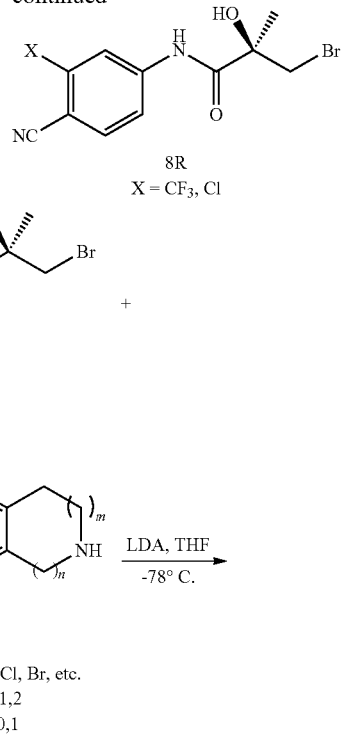

General Procedure: Method A: General Scheme for the Synthesis of Indoline, Quinoline and Isoquinoline Derivatives

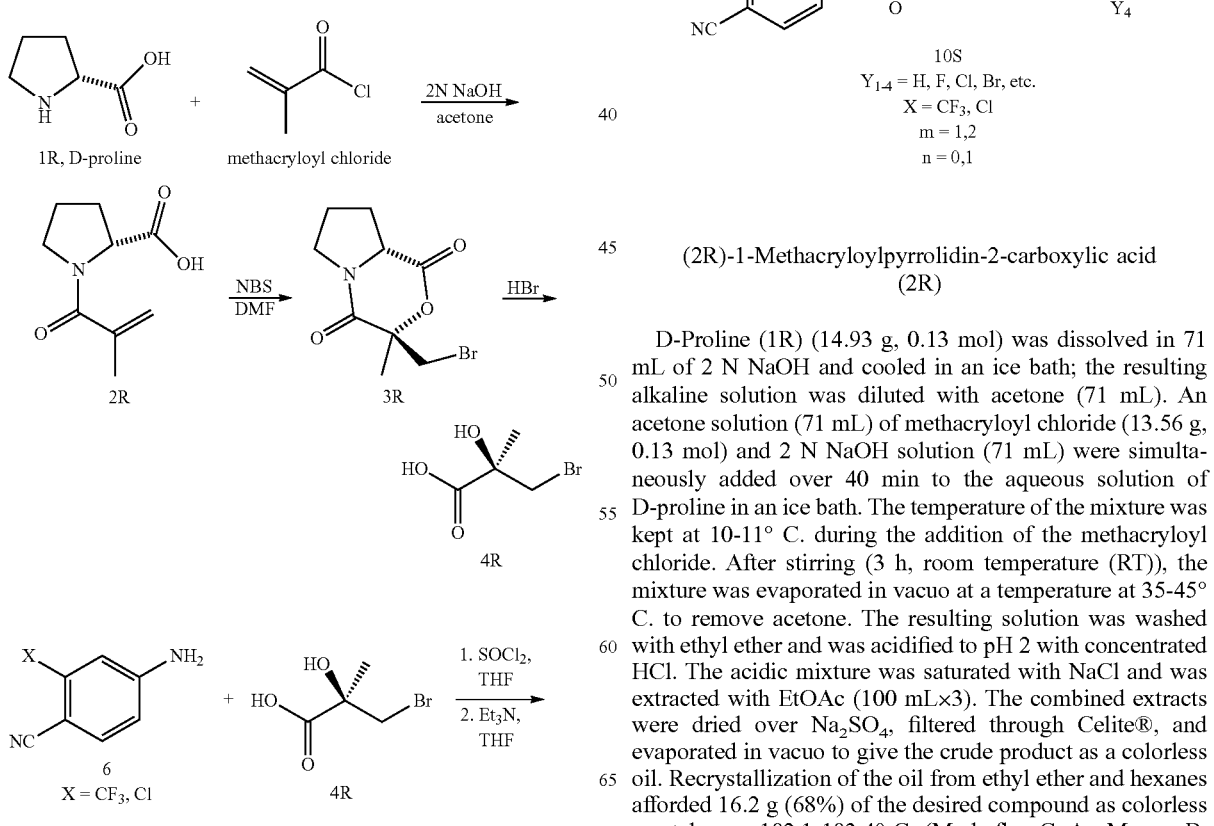

(2R)-1-Methacryloylpyrrolidin-2-carboxylic acid (2R)

D-Proline (1R) (14.93 g, 0.13 mol) was dissolved in 71 mL of 2 N NaOH and cooled in an ice bath; the resulting alkaline solution was diluted with acetone (71 mL). An acetone solution (71 mL) of methacryloyl chloride (13.56 g, 0.13 mol) and 2 N NaOH solution (71 mL) were simultaneously added over 40 min to the aqueous solution of D-proline in an ice bath. The temperature of the mixture was kept at 10-11° C. during the addition of the methacryloyl chloride. After stirring (3 h, room temperature (RT)), the mixture was evaporated in vacuo at a temperature at 35-45° C. to remove acetone. The resulting solution was washed with ethyl ether and was acidified to pH 2 with concentrated HCl. The acidic mixture was saturated with NaCl and was extracted with EtOAc (100 mL×3). The combined extracts were dried over $Na_2SO_4$, filtered through Celite®, and evaporated in vacuo to give the crude product as a colorless oil. Recrystallization of the oil from ethyl ether and hexanes afforded 16.2 g (68%) of the desired compound as colorless crystals: mp 102.1-103.4° C. (Marhefka, C. A.; Moore, B.

M., 2nd; Bishop, T. C.; Kirkovsky, L.; Mukherjee, A.; Dalton, J. T.; Miller, D. D. Homology modeling using multiple molecular dynamics simulations and docking studies of the human androgen receptor ligand binding domain bound to testosterone and nonsteroidal ligands. *J Med Chem* 2001, 44, 1729-40) mp 102.5-103.5° C.; the NMR spectrum of this compound demonstrated the existence of two rotamers of the title compound.

$^1$H NMR (300 MHz, DMSO-$d_6$) δ 5.28 (s) and 5.15 (s) for the first rotamer, 5.15 (s) and 5.03 (s) for the second rotamer (totally 2H for both rotamers, vinyl $CH_2$), 4.48-4.44 for the first rotamer, 4.24-4.20 (m) for the second rotamer (totally 1H for both rotamers, CH at the chiral center), 3.57-3.38 (m, 2H, $CH_2$), 2.27-2.12 (1H, CH), 1.97-1.72 (m, 6H, $CH_2$, CH, Me); $^{13}$C NMR (75 MHz, DMSO-$d_6$) δ for major rotamer 173.3, 169.1, 140.9, 116.4, 58.3, 48.7, 28.9, 24.7, 19.5: for minor rotamer 174.0, 170.0, 141.6, 115.2, 60.3, 45.9, 31.0, 22.3, 19.7; IR (KBr) 3437 (OH), 1737 (C=O), 1647 (CO, COOH), 1584, 1508, 1459, 1369, 1348, 1178 cm$^{-1}$; $[\alpha]_D^{26}$+80.8° (c=1, MeOH); Anal. Calcd. for $C_9H_{13}NO_3$: C, 59.00, H, 7.15, N, 7.65. Found: C, 59.13, H, 7.19, N, 7.61.

(3R,8aR)-3-Bromomethyl-3-methyl-tetrahydro-pyrrolo[2,1-c][1,4]oxazine-1,4-dione (3R)

A solution of NBS (23.5 g, 0.132 mol) in 100 mL of DMF was added dropwise to a stirred solution of the (2R)-1-methacryloylpyrrolidin-2-carboxylic acid (2R) (16.1 g, 88 mmol) in 70 mL of DMF under argon at RT, and the resulting mixture was stirred 3 days. The solvent was removed in vacuo, and a yellow solid was precipitated. The solid was suspended in water, stirred overnight at RT, filtered, and dried to give 18.6 g (81%) (smaller weight when dried ~34%) of the titled bromolactone (3R) as a yellow solid: mp 158.1-160.3° C.;

$^1$H NMR (300 MHz, DMSO-$d_6$) δ 4.69 (dd, J=9.6 Hz, J=6.7 Hz, 1H, CH at the chiral center), 4.02 (d, J=11.4 Hz, 1H, CHH$_a$), 3.86 (d, J=11.4 Hz, 1H, CHH$_b$), 3.53-3.24 (m, 4H, $CH_2$), 2.30-2.20 (m, 1H, CH), 2.04-1.72 (m, 3H, $CH_2$ and CH), 1.56 (s, 2H, Me); $^{13}$C NMR (75 MHz, DMSO-$d_6$) δ 167.3, 163.1, 83.9, 57.2, 45.4, 37.8, 29.0, 22.9, 21.6; IR (KBr) 3474, 1745 (C=O), 1687 (=O), 1448, 1377, 1360, 1308, 1227, 1159, 1062 cm$^{-1}$; $[\alpha]_D^{26}$+124.5° (c=1.3, chloroform); Anal. Calcd. for $C_9H_{12}BrNO_3$: C, 41.24, H, 4.61, N, 5.34. Found: C, 41.46, H, 4.64, N, 5.32.

(2R)-3-Bromo-2-hydroxy-2-methylpropanoic acid (4R)

A mixture of bromolactone (3R) (18.5 g, 71 mmol) in 300 mL of 24% HBr was heated at reflux for 1 h. The resulting solution was diluted with brine (200 mL), and was extracted with ethyl acetate (100 mL×4). The combined extracts were washed with saturated NaHCO$_3$ (100 mL×4). The aqueous solution was acidified with concentrated HCl to pH=1, which, in turn, was extracted with ethyl acetate (100 mL×4). The combined organic solution was dried over Na$_2$SO$_4$, filtered through Celite®, and evaporated in vacuo to dryness. Recrystallization from toluene afforded 10.2 g (86%) of the desired compound as colorless crystals: mp 110.3-113.8° C.

$^1$H NMR (300 MHz, DMSO-$d_6$) δ 3.63 (d, J=10.1 Hz, 1H, CHH$_a$), 3.52 (d, J=10.1 Hz, 1H, CHH$_b$), 1.35 (s, 3H, Me).

IR (KBr) 3434 (OH), 3300-2500 (COOH), 1730 (C=O), 1449, 1421, 1380, 1292, 1193, 1085 cm$^{-1}$.

$[\alpha]_D^{26}$+10.5 (c=2.6, MeOH).

Anal. Calcd. for $C_4H_7BrO_3$: C, 26.25, H, 3.86. Found: C, 26.28, H, 3.75.

(2R)-3-Bromo-N-[4-cyano-3-(trifluoromethyl)phenyl]-2-hydroxy-2-methylpropanamide (8R, X=CF$_3$)

Thionyl chloride (46.02 g, 0.39 mol) was added dropwise to a cooled solution (less than 4° C.) of (R)-3-bromo-2-hydroxy-2-methylpropanoic acid (4R) (51.13 g, 0.28 mol) in 300 mL of THF under an argon atmosphere. The resulting mixture was stirred for 3 h under the same condition. To this was added Et$_3$N (39.14 g, 0.39 mol) and stirred for 20 min under the same condition. After 20 min, 5-amino-2-cyano-benzotrifluoride (40.0 g, 0.21 mol), 400 mL of THF were added and then the mixture was allowed to stir overnight at RT. The solvent was removed under reduced pressure to give a solid which was treated with 300 mL of H$_2$O, extracted with EtOAc (2×400 mL). The combined organic extracts were washed with saturated NaHCO$_3$ solution (2×300 mL) and brine (300 mL). The organic layer was dried over MgSO$_4$ and concentrated under reduced pressure to give a solid which was purified from column chromatography using CH$_2$Cl$_2$/EtOAc (80:20) to give a solid. This solid was recrystallized from CH$_2$Cl$_2$/hexane to give 55.8 g (73.9%) of (2R)-3-bromo-N-[4-cyano-3-(trifluoromethyl)phenyl]-2-hydroxy-2-methylpropanamide (8R, X=CF$_3$) as a light-yellow solid. M.p. 134.0-136.5° C.

$^1$H NMR (CDCl$_3$/TMS) δ 1.66 (s, 3H, CH$_3$), 3.11 (s, 1H, OH), 3.63 (d, J=10.8 Hz, 1H, CH$_2$), 4.05 (d, J=10.8 Hz, 1H, CH$_2$), 7.85 (d, J=8.4 Hz, 1H, ArH), 7.99 (dd, J=2.1, 8.4 Hz, 1H, ArH), 8.12 (d, J=2.1 Hz, 1H, ArH), 9.04 (bs, 1H, NH). Calculated Mass: 349.99, [M−H]$^-$ −349.0.

General Procedure for Preparation of Indoline, Quinoline and Isoquinoline Derivatives (Last Step):

Preparation of LDA solution in THF. To a stirred solution of freshly distilled diisopropylamine (0.14 mL, 1.2 mmol) in anhydrous 5 mL of THF was added a solution of n-butyl-lithium (0.53 mL, 1.32 mmol, 2.5 M solution in hexane) at −78° C. under argon atmosphere. The prepared solution of LDA or 2.0 M LDA was slowly warmed to 0° C. and stirred for 10 min and cooled again to −78° C.

To the LDA solution was added dropwise a solution of 9 (1.0 mmol) in 5 mL of THF for 20 min. The reaction mixture was stirred at the same temperature for 30 min and quenched by addition of sat. NH$_4$Cl. The solution was concentrated under reduced pressure and dispersed into excess EtOAc and dried over Na$_2$SO$_4$. The solution was concentrated and the resulting solid was recrystallized from EtOAc/hexane or DCM/hexane to give desired compound 10S. The mother liquor was concentrated and purified by flash column chromatography (EtOAc/hexane) to give additional 10S.

Alternative Procedure for Preparation of Indoline Compounds (Last Step):

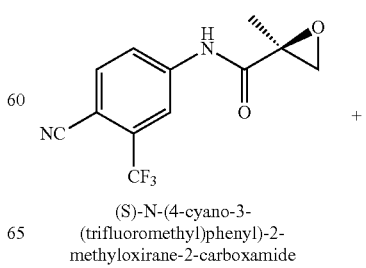

(S)-N-(4-cyano-3-(trifluoromethyl)phenyl)-2-methyloxirane-2-carboxamide

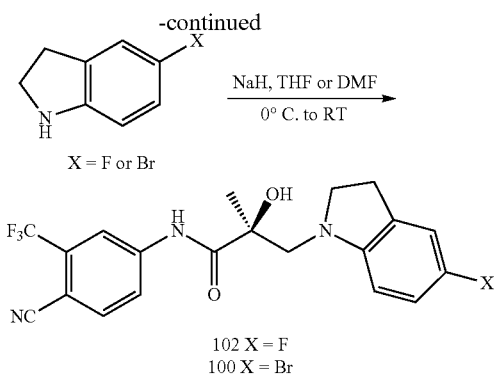

X = F or Br

102 X = F
100 X = Br

NaH of 60% dispersion in mineral oil (61 mg, 1.5 mmol) was added in 5 mL of anhydrous THF solvent into a 50 mL dried two necked round bottom flask equipped with a dropping funnel. 5-Fluoroindoline or 5-bromoindoline (1.48 mmol) was added to the solution under argon atmosphere in an ice-water bath, and the resulting solution was stirred for 30 min in an ice-water bath. Into the flask, the prepared solution of the oxirane: (S)—N-(4-cyano-3-(trifluoromethyl)phenyl)-2-methyloxirane-2-carboxamide, (1.48 mmol in THF) was added through dropping funnel under argon atmosphere in an ice-water bath and stirred overnight at RT. After adding 1 mL of $H_2O$, the reaction mixture was condensed under reduced pressure, and then dispersed into 20 mL of EtOAc, washed with 20 mL (×2) water, brine, dried over anhydrous $Na_2SO_4$, and evaporated to dryness. The mixture was purified with flash chromatography (EtOAc/hexane 40% solvent, $SiO_2$) and afforded the desired products 100 or 102.

(S)-3-(5-Bromoindolin-1-yl)-N-(4-cyano-3-(trifluoromethyl)phenyl)-2-hydroxy-2-methylpropanamide (100)

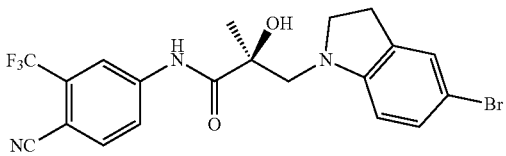 [SMILES: C[C@](O)(CN1CCc2cc(Br)ccc21)C(=O)Nc1ccc(C#N)c(C(F)(F)F)c1]

Yield 45%; Light brown solid; MS (ESI) 466.3 [M−H]$^−$; $^1$H NMR (CDCl$_3$, 400 MHz) δ 9.17 (bs, 1H, NH), 8.09 (d, J=2.0 Hz, 1H), 7.96 (dd, J=8.4, 2.0 Hz, 1H), 7.80 (d, J=8.4 Hz, 1H), 7.19-7.16 (m, 2H), 6.49 (d, J=8.4 Hz, 1H), 3.66 (d, J=14.4 Hz, 1H), 3.48 (bs, 1H, OH), 3.47-3.41 (m, 1H), 3.34 (q, J=9.2 Hz, 1H), 3.25 (d, J=14.4 Hz, 1H), 3.00-2.91 (m, 2H), 1.56 (s, 3H).

(S)-3-(6-Bromo-3,4-dihydroquinolin-1(2H)-yl)-N-(4-cyano-3-(trifluoromethyl) phenyl)-2-hydroxy-2-methylpropanamide (134). Yield; 62%; MS (ESI) m/z 481.6 [M−H]$^−$; $^1$H NMR (400 MHz, CDCl$_3$) δ 9.19 (bs, 1H, NH), 8.00 (s, 1H), 7.97-7.92 (m, 1H), 7.78 (d, J=8.4 Hz, 1H), 7.12 (dd, J=8.8, 2.4 Hz, 1H), 7.08 (d, J=2.4 Hz, 1H), 6.67 (d, J=8.8 Hz, 1H), 3.86 (d, J=15.2 Hz, 1H), 3.45 (d, J=15.2 Hz, 1H), 3.21 (t, J=5.4 Hz, 2H), 2.74 (m, 2H), 1.87 (m, 2H), 1.60 (s, 3H).

(S)—N-(4-Cyano-3-(trifluoromethyl)phenyl)-3-(4-fluoroindolin-1-yl)-2-hydroxy-2-methylpropanamide (101). Yield; 68%; MS (ESI) m/z 406.0 [M−H]$^−$; $^1$H NMR (400 MHz, CDCl$_3$) δ 9.21 (bs, 1H, NH), 8.10 (d, J=2.4 Hz, 1H), 7.96 (dd, J=8.8, 2.4 Hz, 1H), 7.89 (d, J=8.8 Hz, 1H), 7.07-7.02 (m, 1H), 6.47 (t, J=8.4 Hz, 1H), 6.39 (d, J=8.0 Hz, 1H), 3.69 (d, J=14.4 Hz, 1H), 3.53 (bs, 1H, OH), 3.50 (m, 1H), 3.40 (q, J=8.0 Hz, 1H), 3.29 (d, J=14.4 Hz, 1H), 3.09 (m, 1H), 2.99 (m, 1H), 1.57 (s, 3H).

(S)—N-(4-Cyano-3-(trifluoromethyl)phenyl)-3-(5-fluoroindolin-1-yl)-2-hydroxy-2-methylpropanamide (102). Yield; 75%; MS (ESI) m/z 406.0 [M−H]$^−$; $^1$H NMR (400 MHz, CDCl$_3$) δ 9.24 (bs, 1H, NH), 8.10 (d, J=2.2 Hz, 1H), 7.95 (dd, J=8.8, 2.2 Hz, 1H), 7.79 (d, J=8.8 Hz, 1H), 6.83 (dd, J=8.4, 2.4 Hz, 1H), 6.77 (m, 1H), 6.52 (dd, J=8.4, 4.0 Hz, 1H), 3.75 (bs, 1H, OH), 3.64 (d, J=14.0 Hz, 1H), 3.44 (m, 1H), 3.30 (q, J=9.2 Hz, 1H), 3.22 (d, J=14.0 Hz, 1H), 2.94 (m, 2H), 1.56 (s, 3H).

(S)—N-(4-Cyano-3-(trifluoromethyl)phenyl)-3-(6-fluoro-3,4-dihydroquinolin-1(2H)-yl)-2-hydroxy-2-methylpropanamide (135). Yield; 42%; MS (ESI) m/z 420.0 [M−H]$^1$; $^1$H NMR (400 MHz, CDCl$_3$) δ 9.25 (bs, 1H, NH), 8.09 (d, J=2.0 Hz, 1H), 7.95 (dd, J=8.4, 2.0 Hz, 1H), 7.80 (d, J=8.4 Hz, 1H), 6.78-6.69 (m, 1H), 6.77 (m, 3H), 3.88 (d, J=15.2 Hz, 1H), 3.82 (bs, 1H, OH), 3.36 (d, J=15.2 Hz, 1H), 3.16 (m, 2H), 3.16-2.70 (m, 2H), 1.94-1.83 (m, 2H), 1.56 (s, 3H).

(S)—N-(4-Cyano-3-(trifluoromethyl)phenyl)-3-(6-fluoro-3,4-dihydroisoquinolin-2(1H)-yl)-2-hydroxy-2-methylpropanamide (131). Yield; 43%; MS (ESI) m/z 419.9 [M−H]$^−$; $^1$H NMR (400 MHz, CDCl$_3$) δ 9.51 (bs, 1H, NH), 8.10 (d, J=1.8 Hz, 1H), 7.95 (dd, J=8.6, 1.8 Hz, 1H), 7.79 (d, J=8.6 Hz, 1H), 6.88 (m, 1H), 6.81 (m. 2H), 3.69 (s, 2H), 3.42 (d, J=13.2 Hz, 1H), 2.91 (m, 4H), 2.60 (d, J=13.2 Hz, 1H), 2.17 (s, 1H, OH), 1.46 (s, 3H).

(S)—N-(4-Cyano-3-(trifluoromethyl)phenyl)-3-(6-fluoroindolin-1-yl)-2-hydroxy-2-methylpropanamide (105). Yield; 70%; MS (ESI) m/z 405.9 [M−H]$^−$; $^1$H NMR (400 MHz, CDCl$_3$) δ 9.21 (bs, 1H, NH), 8.10 (s, 1H), 7.97 (d, J=8.4 Hz, 1H), 7.79 (d, J=8.4 Hz, 1H), 6.98 (t, J=6.8 Hz, 1H), 6.41 (t, J=7.6 Hz, 1H), 3.35 (m, 1H), 3.66 (d, J=14.0 Hz, 1H), 3.52 (bs, 1H, OH), 3.47 (m, 1H), 3.41 (q, J=9.2 Hz, 1H), 3.24 (d, J=14.0 Hz, 1H), 3.00-2.87 (m, 2H), 1.57 (s, 3H).

(S)—N-(4-Cyano-3-(trifluoromethyl)phenyl)-3-(7-fluoro-3,4-dihydroisoquinolin-2(1H)-yl)-2-hydroxy-2-methylpropanamide (132). Yield; 69%; MS (ESI) 420.0 [M−H]$^−$; $^1$H NMR (400 MHz, CDCl$_3$) δ 9.09 (bs, 1H, NH), 7.93 (d, J=8.4 Hz, 1H), 7.80 (d, J=8.4 Hz, 1H), 7.05 (t, J=8.0 Hz, 1H), 6.86 (m, 1H), 6.63 (d, J=8.0 Hz, 1H), 3.71 (s, 2H), 3.42 (d, J=13.2 Hz, 1H), 2.91-2.82 (m, 5H), 2.60 (d, J=13.2 Hz, 1H), 1.46 (s, 3H).

Example 20

Synthesis of SARD Compounds of this Invention

Method A. General Scheme for Preparation of Indoline, Quinolone and Isoquinoline Derivatives

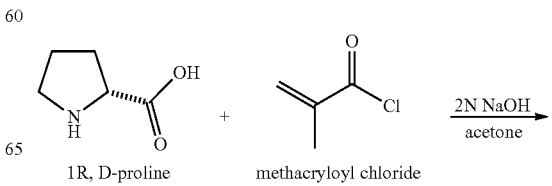

1R, D-proline    methacryloyl chloride

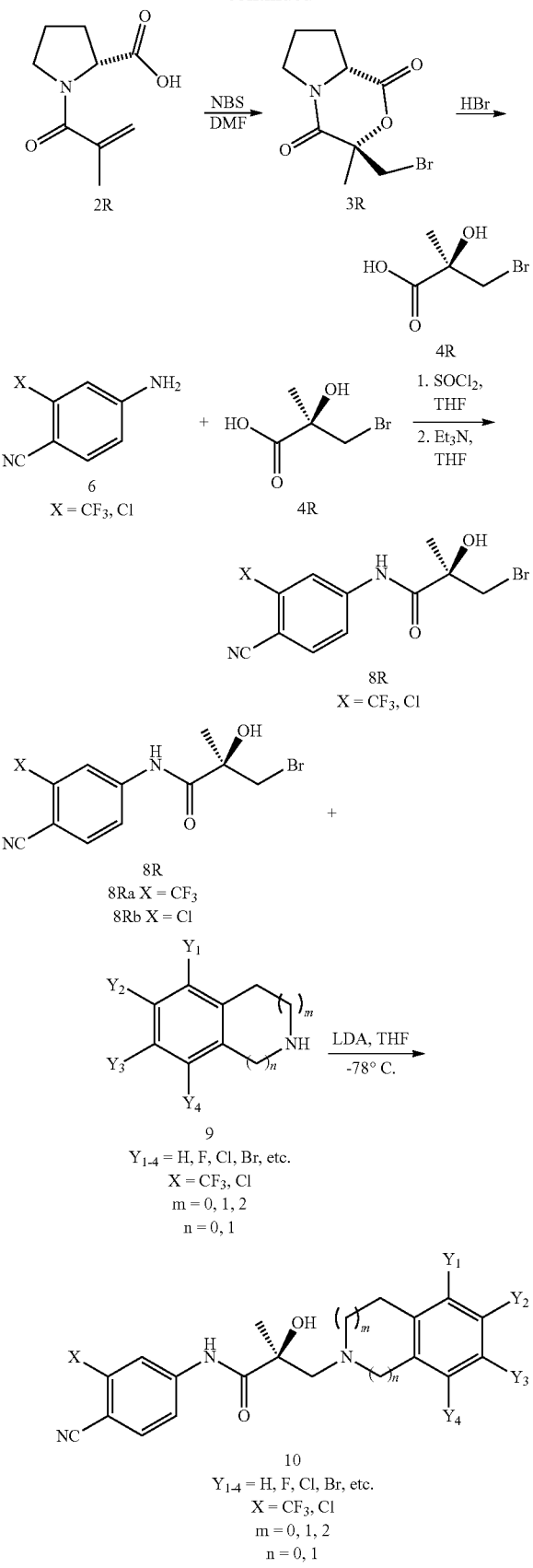

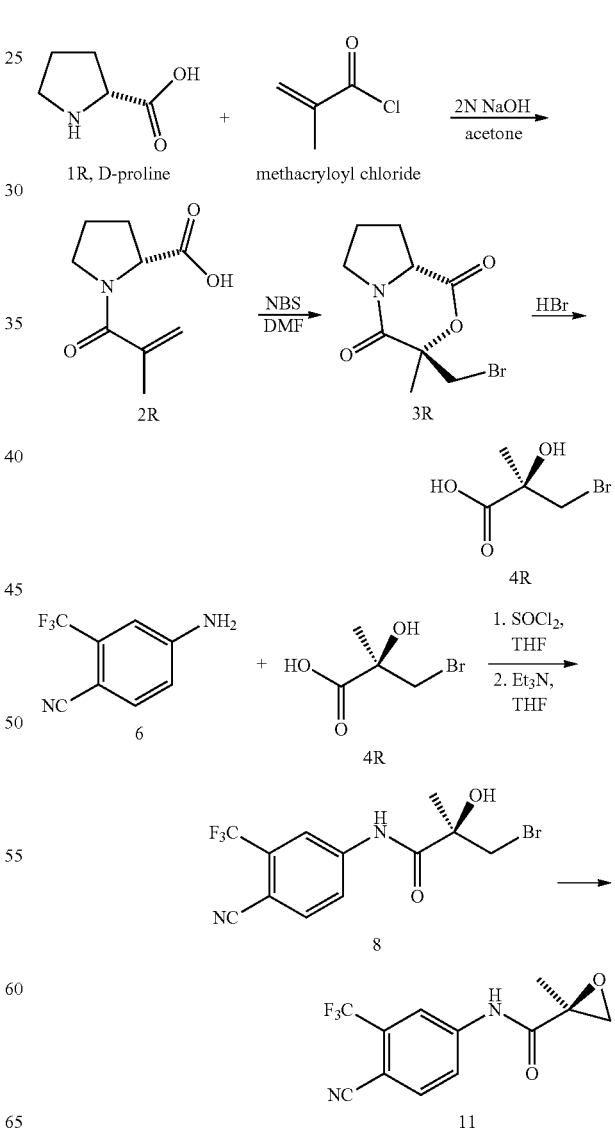

Preparation of LDA solution in THF: To a stirred solution of freshly distilled diisopropylamine (0.14 mL, 1.2 mmol) in anhydrous 5 mL of THF was added a solution of n-butyllithium (0.53 mL, 1.32 mmol, 2.5 M solution in hexane) at −78° C. under argon atmosphere. The prepared solution of LDA or commercial 2.0 M LDA was slowly warmed to 0° C. and stirred for 10 min and cooled again to −78° C. To the LDA solution was added dropwise a solution of 9 (1.0 mmol) in 5 mL of THF for 20 min. 8R in THF was added dropwise through dropping funnel under argon atmosphere at −78° C. The reaction mixture was stirred at the same temperature for 30 min and quenched by addition of sat. $NH_4Cl$. The solution was concentrated under reduced pressure and dispersed into excess EtOAc and dried over $Na_2SO_4$. The solution was concentrated and the resulting solid was recrystallized from EtOAc/hexane or DCM/hexane to give designed compound 10. The mother liquor was concentrated and purified by flash column chromatography (EtOAc/hexane) to give the 10 additionally.

Method B. Preparation of Indoles and Carbazoles

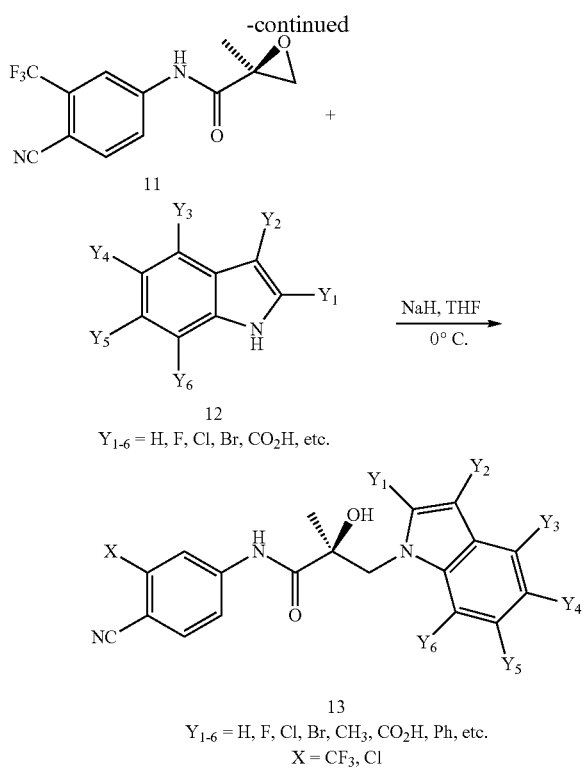

$Y_{1-6}$ = H, F, Cl, Br, CO$_2$H, etc.

$Y_{1-6}$ = H, F, Cl, Br, CH$_3$, CO$_2$H, Ph, etc.
X = CF$_3$, Cl

NaH of 60% dispersion in mineral oil (228 mg, 5.7 mmol) was added in 20 mL of anhydrous THF solvent into a 100 mL dried two necked round bottom flask equipped with a dropping funnel. Indole (general structure 12, 2.84 mmol) was added to the solution under argon atmosphere in ice-water bath, and the resulting solution was stirred for 30 min at the ice-water bath. Into the flask, epoxide 11 (2.84 mmol in THF) was added through dropping funnel under argon atmosphere at the ice-water bath and stirred overnight at RT. After adding 1 mL of H$_2$O, the reaction mixture was condensed under reduced pressure, and then dispersed into 50 mL of EtOAc, washed with 50 mL (×2) water, brine, dried over anhydrous MgSO$_4$, and evaporated to dryness. The mixture was purified with flash column chromatography with an eluent of EtOAc/hexane, and then the condensed compounds were then recrystallized in EtOAc/hexane to give a target product of general structure 13.

(S)—N-(3-Chloro-4-cyanophenyl)-2-methyloxirane-2-carboxamide (epoxide intermediate)

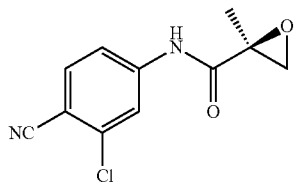 [SMILES: C[C@@]1(C(=O)Nc2ccc(C#N)c(Cl)c2)CO1]

Yield 98%;
Light brown solid.
MS (ESI) m/z 235.4 [M−H]⁻.
$^1$H NMR (CDCl$_3$, 400 MHz) δ 7.90 (d, J=2.0 Hz, 1H), 7.61 (d, J=8.4 Hz, 1H), 7.50 (dd, J=8.4, 2.0 Hz, 1H), 2.99 (s, 2H), 1.67 (s, 3H).

Indole Derivatives (S)—N-(4-Cyano-3-(trifluoromethyl)phenyl)-3-(5-fluoro-6-phenyl-1H-indol-1-yl)-2-hydroxy-2-methyl-propanamide (33)

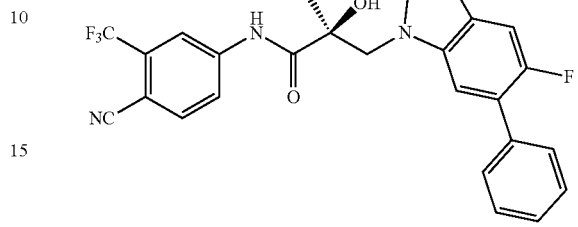

To a solution of 5-fluoro-6-phenyl-1H-indole (0.37 g, 0.00175 mol) in anhydrous THF (10 mL), which was cooled in an ice water bath under an argon atmosphere, was added sodium hydride (60% dispersion in oil, 0.11 g, 0.00263 mol). After addition, the resulting mixture was stirred for three hours. (S)—N-(4-Cyano-3-(trifluoromethyl)phenyl)-2-methyloxirane-2-carboxamide (0.47 g, 0.002175 mol) was added to above solution, and the resulting reaction mixture was allowed to stir overnight at RT under argon. The reaction was quenched by water, extracted with ethyl acetate. The organic layer was washed with brine, dried with MgSO$_4$, filtered, and concentrated under vacuum. The product was purified by a silica gel column using ethyl acetate and hexane (1:2) as eluent to afford 0.83 g (98%) of the titled compound as off-white foam.

$^1$H NMR (400 MHz, DMSO-d$_6$) δ 10.29 (s, 1H, NH), 8.28 (s, 1H, ArH), 8.08 (d, J=8.8 Hz, 1H, ArH), 7.96 (d, J=8.8 Hz, 1H, ArH), 7.58 (d, J=6.8 Hz, 1H, ArH), 7.49-7.31 (m, 7H, ArH), 6.42 (d, J=3.2 Hz, 1H, ArH), 6.35 (s, 1H, OH), 4.61 (d, J=14.4 Hz, 1H, CH), 4.35 (d, J=14.4 Hz, 1H, CH), 1.46 (s, 3H, CH$_3$).

Mass (ESI, Negative): 479.9 [M−H]⁻; (ESI, Positive): 504.1 [M+Na]+.

(S)—N-(3-Chloro-4-cyanophenyl)-3-(5-fluoro-6-phenyl-1H-indol-1-yl)-2-hydroxy-2-methylpropanamide (34)

5-Fluoro-6-phenyl-1H-indole (C$_{14}$H$_{10}$FN)

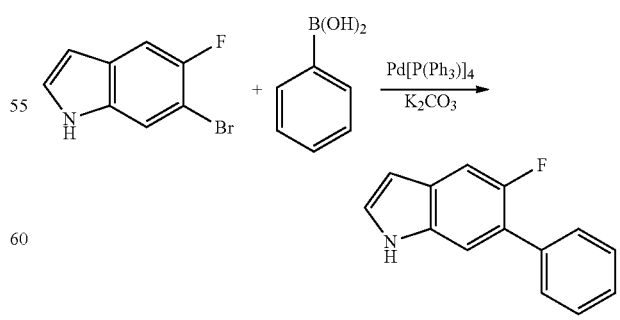

To a suspension of tetrakis(triphenylphosphine)palladium (0) [Pd(PPh$_3$)$_4$, 0.54 g, 0.467 mmol] in 20 mL of ethylene glycol dimethyl ether (DME) was added 6-bromo-5-fluoroindole (1.00 g, 4.67 mmol), and the mixture was stirred for 15 minutes under argon at RT. A solution of phenylboronic acid (0.57 g, 4.67 mmol) in 2-3 mL of ethanol was added and the mixture was stirred for 10 minutes under the same conditions. A solution of potassium carbonate (0.97 g, 7.01 mmol) in 2 mL of water was added to above mixture and the resulting reaction mixture was heated at reflux for 3-4 hours under the argon atmosphere. After the end of the reaction was established by TLC, the reaction was diluted by brine, and extracted with ethyl acetate. The organic layer was washed with brine, dried with MgSO$_4$, filtered, and concentrated under vacuum. The product was purified by a silica gel column using ethyl acetate and hexane (1:3) as eluent to afford 0.90 g (92% yield) of the titled compound as light brown solid.

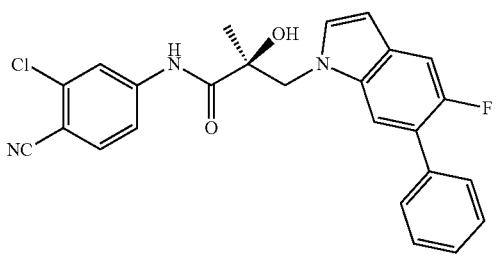 [SMILES: C[C@](O)(Cn1ccc2cc(F)c(-c3ccccc3)cc21)C(=O)Nc1ccc(C#N)c(Cl)c1]

To a solution of 5-fluoro-6-phenyl-1H-indole (0.20 g, 0.000947 mol) in anhydrous THF (10 mL), which was cooled in an ice water bath under an argon atmosphere, was added sodium hydride (60% dispersion in oil, 0.076 g, 0.00189 mol). After addition, the resulting mixture was stirred for three hours. (R)-3-Bromo-N-(4-cyano-3-chlorophenyl)-2-hydroxy-2-methylpropanamide (0.30 g, 0.000947 mol) was added to the above solution, and the resulting reaction mixture was allowed to stir overnight at RT under argon. The reaction was quenched by water, and extracted with ethyl acetate. The organic layer was washed with brine, dried with MgSO$_4$, filtered, and concentrated under vacuum. The product was purified by a silica gel column using ethyl acetate and hexane (1:2) as eluent to afford 0.26 g of the titled compound as yellowish solid.

$^1$H NMR (400 MHz, DMSO-d$_6$) δ 10.11 (s, 1H, NH), 8.04 (d, J=1.6 Hz, 1H, ArH), 7.80 (d, J=8.8 Hz, 1H, ArH), 7.74 (dd, J=8.2 Hz, J=2.0 Hz, 1H, ArH), 7.62 (d, J=6.4 Hz, 1H, ArH), 7.51-7.44 (m, 4H, ArH), 7.39-7.32 (m, 3H, ArH), 6.42 (d, J=3.2 Hz, 1H, ArH), 6.33 (s, 1H, OH), 4.60 (d, J=15.2 Hz, 1H, CH), 4.35 (d, J=15.2 Hz, 1H, CH), 1.45 (s, 3H, CH$_3$).

Mass (ESI, Negative): 445.8 [M−H]$^-$; (ESI, Positive): 470.0 [M+Na]$^+$.

(S)—N-(3-Chloro-4-cyanophenyl)-3-(6-fluoro-1H-indol-1-yl)-2-hydroxy-2-methylpropanamide (35)

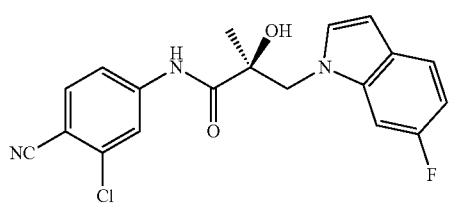 [SMILES: C[C@](O)(Cn1ccc2ccc(F)cc21)C(=O)Nc1ccc(C#N)c(Cl)c1]

Method B

Yield 67%;

White solid;

MS (ESI) m/z 376.9 [M−H]$^-$;

$^1$H NMR (CDCl$_3$, 400 MHz) δ 8.67 (bs, 1H, NH), 7.79 (d, J=2.0 Hz, 1H), 7.56 (d, J=8.4 Hz, 1H), 7.49 (dd, J=8.4, 5.4 Hz, 1H), 7.38 (dd, J=8.4, 2.0 Hz, 1H), 7.13 (dd, J=10.0, 2.0 Hz, 1H), 7.09 (d, J=3.2 Hz, 1H), 6.86 (m, 2H), 6.48 (d, J=3.2 Hz, 1H), 4.58 (d, J=14.8 Hz, 1H), 4.28 (d, J=14.8 Hz, 1H), 2.61 (bs, 1H, OH), 1.60 (s, 3H);

$^{19}$F NMR (CDCl$_3$) δ −120.03.

(S)—N-(3-Chloro-4-cyanophenyl)-3-(4-fluoro-1H-indol-1-yl)-2-hydroxy-2-methylpropanamide (36)

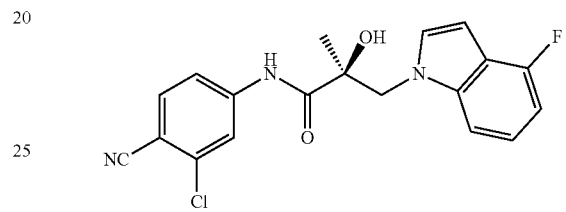

Method B

Under argon atmosphere into a 100 mL, dried, two-necked round bottom flask equipped with a dropping funnel in ice-water bath, NaH of 60% dispersion in mineral oil (228 mg, 5.70 mmol) was added in 20 mL of anhydrous THF solvent into the flask and 4-fluoroindole (390 mg, 2.84 mmol) solution in 10 mL of anhydrous THF was added to the solution under the argon atmosphere in the ice-water bath, and then the resulting solution was stirred at the ice-water bath. After 30 min, into the flask, a solution of (S)—N-(3-chloro-4-cyanophenyl)-2-methyloxirane-2-carboxamide (2.84 mmol in THF) was added through dropping funnel under argon atmosphere at the ice-water bath and stirred overnight at RT. After adding 1 mL of H$_2$O, the reaction mixture was condensed under reduced pressure, and then dispersed into 50 mL of EtOAc, washed with 50 mL (×2) water, brine, dried over anhydrous MgSO$_4$, and evaporated to dryness. The mixture was purified with flash column chromatography as an eluent EtOAc/hexane, and then the condensed compounds were then recrystallized in EtOAc/hexane to give a target product, 36.

Yield 73%.

White solid.

MS (ESI) m/z 369.9 [M−H]$^-$; HRMS (ESI) m/z calcd for C$_{19}$H$_{16}$ClFN$_3$O$_2$: 372.0915. Found: 372.0915 [M+H]$^+$.

$^1$H NMR (CDCl$_3$, 400 MHz) δ 8.64 (bs, 1H, NH), 7.81 (s, 1H), 7.57 (d, J=8.4 Hz, 1H), 7.35 (d, J=7.2 Hz, 1H), 7.21 (d, J=8.4 Hz, 1H), 7.14-7.10 (m, 2H), 6.77 (t, J=8.4 Hz, 1H), 6.63 (d, J=2.8 Hz, 1H), 6.60 (s, 1H), 4.64 (d, J=14.8 Hz, 1H), 4.35 (d, J=14.8 Hz, 1H), 2.48 (bs, 1H, OH), 1.60 (s, 3H).

$^{13}$C NMR (acetone-d$_6$, 100 MHz) δ 174.8, 158.1, 155.7, 144.3, 141.5 (d, J=11.0 Hz), 137.2, 135.5, 130.7, 122.4 (d, J=7.0 Hz), 121.0, 119.3, 118.0 (d, J=22.0 Hz), 116.6, 107.9 (t, J=5.0 Hz), 104.4 (d, J=19.0 Hz), 97.7, 77.6, 55.0, 24.2.

$^{19}$F NMR (CDCl$_3$, decoupled) δ −121.78.

(S)—N-(3-Chloro-4-cyanophenyl)-3-(5-fluoro-1H-indol-1-yl)-2-hydroxy-2-methylpropanamide (37)

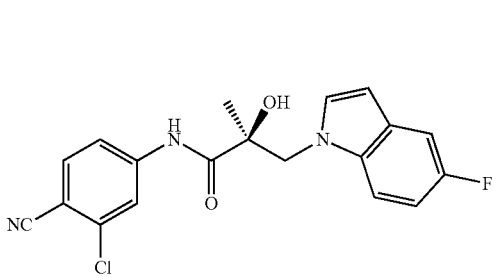 [SMILES: C[C@](O)(Cn1ccc2cc(F)ccc21)C(=O)Nc1ccc(C#N)c(Cl)c1]

Method B

Yield 79%.

White solid.

MS (ESI) m/z 371.0 [M−H]⁻; HRMS (ESI) m/z calcd for C₁₉H₁₆ClFN₃O₂: 372.0915.

Found: 372.0922 [M+H]⁺.

¹H NMR (CDCl₃, 400 MHz) δ 8.62 (bs, 1H, NH), 7.80 (d, J=2.0 Hz, 1H), 7.56 (d, J=8.4 Hz, 1H), 7.38-7.34 (m, 2H), 7.23 (dd, J=9.2, 2.4 Hz, 1H), 7.15 (d, J=3.2 Hz, 1H), 7.22 (dt, J=9.2, 2.8 Hz, 1H), 6.47 (d, J=3.2 Hz, 1H), 4.63 (d, J=14.8 Hz, 1H), 4.32 (d, J=14.8 Hz, 1H), 2.49 (bs, 1H, OH), 1.60 (s, 3H).

¹⁹F NMR (CDCl₃) δ −124.52.

(S)—N-(3-Chloro-4-cyanophenyl)-3-(3-fluoro-1H-indol-1-yl)-2-hydroxy-2-methylpropanamide (38)

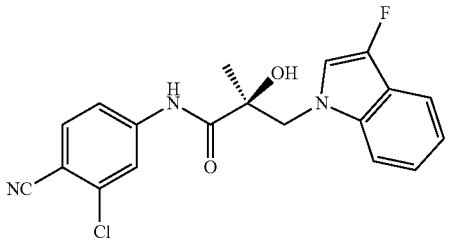 [SMILES: C[C@](O)(Cn1cc(F)c2ccccc21)C(=O)Nc1ccc(C#N)c(Cl)c1]

Method B

Yield 68%;

Mp 168.9-170.1° C.

Light Brown solid.

MS (ESI) m/z 369.8 [M−H]⁻; LCMS (ESI) m/z calcd for C₁₉H₁₆ClFN₃O₂: 372.0915. Found: 372.0910 [M+H]⁺.

¹H NMR (CDCl₃, 400 MHz) δ 8.66 (bs, 1H, NH), 7.81 (d, J=2.0 Hz, 1H), 7.60-7.56 (m, 2H), 7.37 (dd, J=8.4, 2.0 Hz, 2H), 7.23 (m, 1H), 7.12 (t, J=7.4 Hz, 1H), 6.93 (d, J=2.8 Hz, 1H), 4.56 (d, J=15.2 Hz, 1H), 4.27 (d, J=15.2 Hz, 1H), 2.44 (s, 1H, OH), 1.59 (s, 3H).

¹⁹F NMR (CDCl₃) δ −173.91.

(S)—N-(3-Chloro-4-cyanophenyl)-3-(7-fluoro-1H-indol-1-yl)-2-hydroxy-2-methylpropanamide (39)

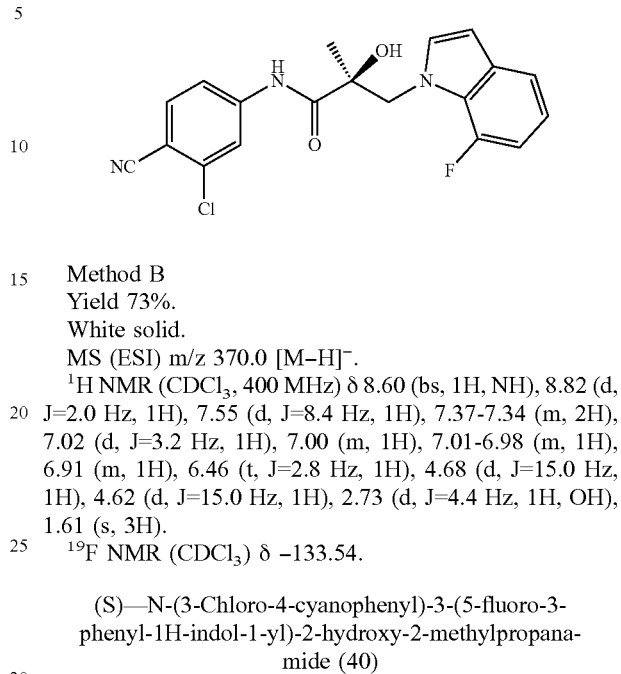

Method B

Yield 73%.

White solid.

MS (ESI) m/z 370.0 [M−H]⁻.

¹H NMR (CDCl₃, 400 MHz) δ 8.60 (bs, 1H, NH), 8.82 (d, J=2.0 Hz, 1H), 7.55 (d, J=8.4 Hz, 1H), 7.37-7.34 (m, 2H), 7.02 (d, J=3.2 Hz, 1H), 7.00 (m, 1H), 7.01-6.98 (m, 1H), 6.91 (m, 1H), 6.46 (t, J=2.8 Hz, 1H), 4.68 (d, J=15.0 Hz, 1H), 4.62 (d, J=15.0 Hz, 1H), 2.73 (d, J=4.4 Hz, 1H, OH), 1.61 (s, 3H).

¹⁹F NMR (CDCl₃) δ −133.54.

(S)—N-(3-Chloro-4-cyanophenyl)-3-(5-fluoro-3-phenyl-1H-indol-1-yl)-2-hydroxy-2-methylpropanamide (40)

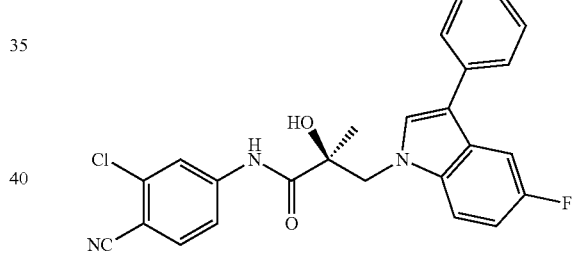

To a solution of 5-fluoro-3-phenyl-1H-indole (0.50 g, 0.002267 mol) in anhydrous THF (10 mL), which was cooled in an ice water bath under an argon atmosphere, was added sodium hydride (60% dispersion in oil, 0.24 g, 0.005918 mol). After addition, the resulting mixture was stirred for three hours. (R)-3-Bromo-N-(4-cyano-3-chlorophenyl)-2-hydroxy-2-methylpropanamide (0.75 g, 0.002267 mol) was added to above solution, and the resulting reaction mixture was allowed to stir overnight at RT under argon. The reaction was quenched by water, and extracted with ethyl acetate. The organic layer was washed with brine, dried with MgSO₄, filtered, and concentrated under vacuum. The product was purified by a silica gel column using ethyl acetate and hexanes (1:2 to 1:1) as eluent to afford 0.43 g of the titled compound as yellowish solid.

¹H NMR (400 MHz, DMSO-d₆) δ 10.17 (s, 1H, NH), 8.06 (d, J=2.0 Hz, 1H, ArH), 7.86-7.79 (m, 2H, ArH), 7.64 (s, 1H, ArH), 7.62-7.58 (m, 1H, ArH), 7.55-7.52 (m, 2H, ArH), 7.50 (dd, J=10.4 Hz, J=2.4 Hz, 1H, ArH), 7.43-7.40 (m, 2H, ArH), 7.26-7.22 (m, 1H, ArH), 7.03-6.98 (m, 1H, ArH), 6.37 (s, 1H, OH), 4.60 (d, J=14.8 Hz, 1H, CH), 4.38 (d, J=14.8 Hz, 1H, CH), 1.46 (s, 3H, CH₃).

Mass (ESI, Negative): 446.8 [M−H]⁻; (ESI, Positive): 448.1248 [M+H]+.

(S)—N-(4-Cyano-3-(trifluoromethyl)phenyl)-2-hydroxy-2-methyl-3-(4-phenyl-1H-indol-1-yl)propanamide (41)

Phenyl-1H-indole (C₁₄H₁₁N)

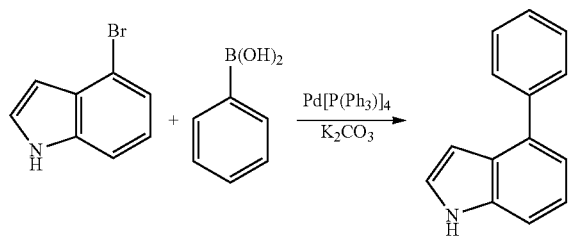

To a suspension of tetrakis(triphenylphosphine)palladium (0) [Pd(PPh₃)₄, 1.179 g, 1.0212 mmol] in 40 mL of ethylene glycol dimethyl ether (DME) was added 4-bromo-indole (2.00 g, 10.202 mmol), and the mixture was stirred for 15 minutes under argon at RT. A solution of phenylboronic acid (1.24 g, 10.202 mmol) in 4.5 mL of ethanol was added and the mixture was stirred for 10 minutes under the same conditions. A solution of potassium carbonate (2.16 g, 15.306 mmol) in 3.5 mL of water was added to above mixture and the resulting reaction mixture was heated at reflux for 3-4 hours under the argon atmosphere. After the end of the reaction was established by TLC, the reaction was diluted by brine, and extracted with ethyl acetate. The organic layer was washed with brine, dried with MgSO₄, filtered, and concentrated under vacuum. The product was purified by a silica gel column using ethyl acetate and hexane (1:3 to 2:1) as eluent to afford 1.67 g (84.8% yield) of the titled compound as yellowish oil.

41

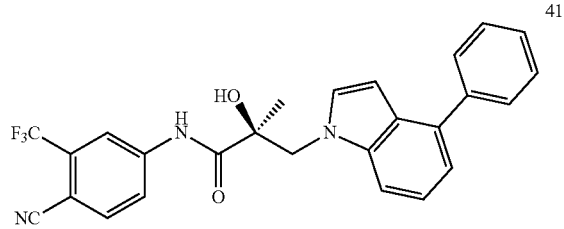 [SMILES: C[C@](O)(Cn1ccc2c(-c3ccccc3)cccc21)C(=O)Nc1ccc(C#N)c(C(F)(F)F)c1]

To a solution of 4-phenyl-1H-indole (0.42 g, 0.002173 mol) in anhydrous THF (10 mL), which was cooled in an ice water bath under an argon atmosphere, was added sodium hydride (60% dispersion in oil, 0.22 g, 0.005434 mol). After addition, the resulting mixture was stirred for three hours. (S)—N-(4-Cyano-3-(trifluoromethyl)phenyl)-2-methyloxirane-2-carboxamide (0.76 g, 0.002173 mol) was added to above solution, and the resulting reaction mixture was allowed to stir overnight at RT under argon. The reaction was quenched by water, and extracted with ethyl acetate. The organic layer was washed with brine, dried with MgSO₄, filtered, and concentrated under vacuum. The product was purified by a silica gel column using ethyl acetate and hexane (1:2) as eluent to afford 0.69 g (69%) of the titled compound as off-white solid.

¹H NMR (400 MHz, DMSO-d₆) δ 10.37 (s, 1H, NH), 8.37 (d, J=2.0 Hz, 1H, ArH), 8.18 (dd, J=8.4 Hz, J=2.0 Hz, 1H, ArH), 8.05 (d, J=8.4 Hz, 1H, ArH), 7.60-7.54 (m, 3H, ArH), 7.49-7.45 (m, 2H, ArH), 7.38-7.34 (m, 2H, ArH), 7.18-7.14 (m, 1H, ArH), 7.04 (d, J=7.2 Hz, 1H, ArH), 6.51 (d, J=3.2 Hz, 1H, ArH), 6.35 (s, 1H, OH), 4.58 (d, J=14.4 Hz, 1H, CH), 4.38 (d, J=14.4 Hz, 1H, CH), 1.45 (s, 3H, CH₃).

Mass (ESI, Positive): 464.1536 [M+H]⁺; 486.1351 [M+Na]⁺.

(S)—N-(4-Cyano-3-(trifluoromethyl)phenyl)-3-(4-fluoro-5-phenyl-1H-indol-1-yl)-2-hydroxy-2-methylpropanamide (42)

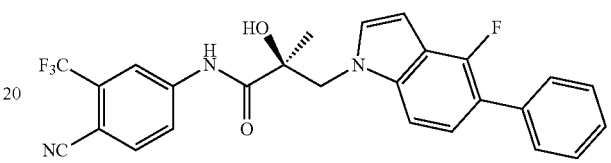

To a solution of 4-fluoro-5-phenyl-1H-indole (0.33 g, 0.00156 mol) in anhydrous THF (10 mL), which was cooled in an ice water bath under an argon atmosphere, was added sodium hydride (60% dispersion in oil, 0.16 g, 0.00391 mol). After addition, the resulting mixture was stirred for three hours. (S)—N-(4-Cyano-3-(trifluoromethyl)phenyl)-2-methyloxirane-2-carboxamide (0.55 g, 0.00156 mol) was added to above solution, and the resulting reaction mixture was allowed to stir overnight at RT under argon. The reaction was quenched by water, and extracted with ethyl acetate. The organic layer was washed with brine, dried with MgSO₄, filtered, and concentrated under vacuum. The product was purified by a silica gel column using ethyl acetate and hexane (1:2) as eluent to afford 0.47 g (63%) of the titled compound as off-white solid.

¹H NMR (400 MHz, DMSO-d₆) δ 10.33 (s, 1H, NH), 8.35 (d, J=2.0 Hz, 1H, ArH), 8.17 (dd, J=8.4 Hz, J=2.0 Hz, 1H, ArH), 8.05 (d, J=8.4 Hz, 1H, ArH), 7.51-7.40 (m, 5H, ArH), 7.36-7.32 (m, 2H, ArH and indole-H), 7.17-7.13 (m, 1H, ArH), 6.53 (d, J=3.2 Hz, 1H, ArH), 6.38 (s, 1H, OH), 4.60 (d, J=14.8 Hz, 1H, CH), 4.38 (d, J=14.8 Hz, 1H, CH), 1.45 (s, 3H, CH₃).

Mass (ESI, Negative): [M−H]⁻; (ESI, Positive): 482.1490 [M+H]⁺; 504.1310 [M+Na]⁺.

(S)—N-(4-Cyano-3-(trifluoromethyl)phenyl)-3-(4-fluoro-6-(4-fluorophenyl)-1H-indol-1-yl)-2-hydroxy-2-methylpropanamide (43)

4-Fluoro-6-(4-fluorophenyl)-1H-indole

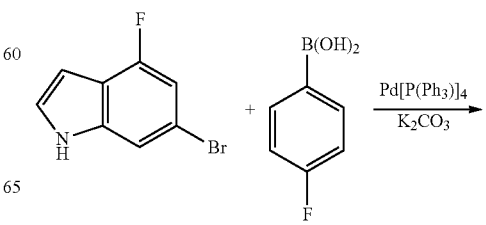

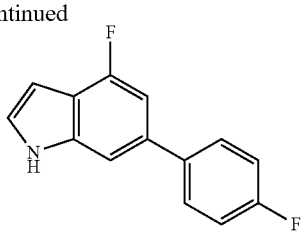

To a suspension of tetrakis(triphenylphosphine)palladium (0) [Pd(PPh₃)₄, 0.27 g, 0.2336 mmol] in 10 mL of ethylene glycol dimethyl ether (DME) was added 6-bromo-4-fluoro-indole (0.50 g, 2.336 mmol), and the mixture was stirred for 15 minutes under argon at RT. A solution of 4-fluoro-phenylboronic acid (0.33 g, 2.336 mmol) in 1.2 mL of ethanol was added and the mixture was stirred for 10 minutes under the same conditions. A solution of potassium carbonate (0.48 g, 3.504 mmol) in 1.0 mL of water was added to above mixture and the resulting reaction mixture was heated at reflux for 3-4 h under the argon atmosphere. After the end of the reaction was established by TLC, the reaction was diluted by brine, and extracted with ethyl acetate. The organic layer was washed with brine, dried with MgSO₄, filtered, and concentrated under vacuum. The product was purified by a silica gel column using ethyl acetate and hexane (1:3) as eluent to afford 0.33 g (61.6% yield) of the titled compound as brown solid.

(S)—N-(4-Cyano-3-(trifluoromethyl)phenyl)-3-(4-fluoro-6-(4-fluorophenyl)-1H-indol-1-yl)-2-hydroxy-2-methylpropanamide (43)

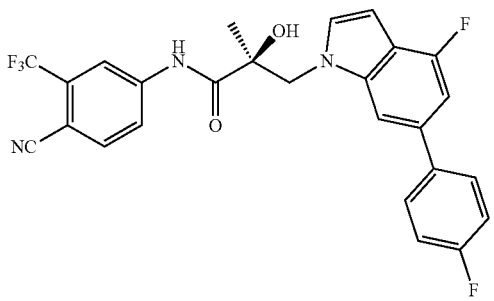 [SMILES: C[C@](O)(Cn1ccc2c(F)cc(-c3ccc(F)cc3)cc21)C(=O)Nc1ccc(C#N)c(C(F)(F)F)c1]

To a solution of 4-fluoro-6-(4-fluorophenyl)-1H-indole (0.32 g, 0.0014 mol) in anhydrous THF (10 mL), which was cooled in an ice water bath under an argon atmosphere, was added sodium hydride (60% dispersion in oil, 0.17 g, 0.00419 mol). After addition, the resulting mixture was stirred for three hours. (S)—N-(4-Cyano-3-(trifluoromethyl) phenyl)-2-methyloxirane-2-carboxamide (0.49 g, 0.00140 mol) was added to the above solution, and the resulting reaction mixture was allowed to stir overnight at RT under argon. The reaction was quenched by water, and extracted with ethyl acetate. The organic layer was washed with brine, dried with MgSO₄, filtered, and concentrated under vacuum. The product was purified by a silica gel column using ethyl acetate and hexane (1:2) as eluent to afford 0.35 g (50.5%) of the titled compound as off-white solid.

¹HNMR (400 MHz, DMSO-d₆) δ 10.30 (s, 1H, NH), 8.26 (d, J=2.0 Hz, 1H, ArH), 8.07 (dd, J=8.8 Hz, J=2.0 Hz, 1H, ArH), 7.97 (d, J=8.8 Hz, 1H, ArH), 7.68-7.64 (m, 2H, ArH), 7.60 (s, 1H, ArH), 7.35 (d, J=3.0 Hz, 1H, ArH), 7.28-7.24 (m, 2H, ArH)), 7.04 (dd, J=12.0 Hz, J=1.2 Hz, 1H, ArH), 6.48 (d, J=1.0 Hz, 1H, ArH), 6.39 (s, 1H, OH), 4.67 (d, J=14.8 Hz, 1H, CH), 4.42 (d, J=14.8 Hz, 1H, CH), 1.49 (s, 3H, CH₃).

Mass (ESI, Negative): [M−H]⁻; (ESI, Positive): 499.2056 [M+H]⁺.

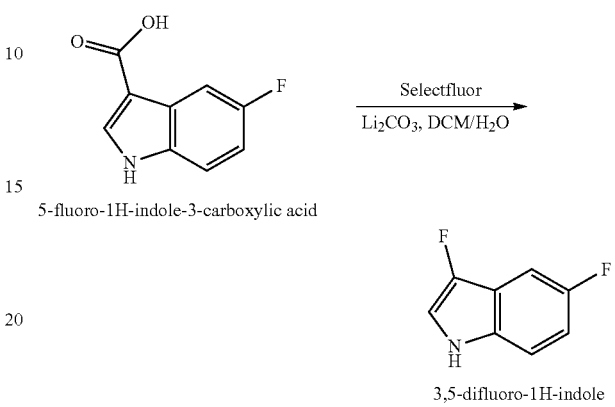

5-fluoro-1H-indole-3-carboxylic acid 3,5-difluoro-1H-indole

Synthesis of 3,5-difluoro-1H-indole

To a 50 mL round-bottle flask with a magnetic stirring bar were added Selectfluor® (872 mg, 2.0 mmol, 2.0 equiv), Li₂CO₃ (296 mg, 4.0 mmol, 4.0 equiv), dichloromethane (3.3 mL) and water (1.7 mL). Then carboxylic acid (1.0 mmol, 1.0 equiv) were added. The reaction mixture was stirred for 2 hours in ice bath. The reaction mixture was diluted with water (40 mL), followed by extracting with DCM (20 mL×2). The combined organic extracts were washed with brine, dried over anhydrous sodium sulfate and concentrated in vacuo. The crude product was purified by flash column chromatography (n-hexane:DCM=2:1) to afford 3,5-difluoro-1H-indole as deep brown oil. Yield=68%;

MS (ESI) m/z 154.83 [M+H]⁺; 152.03 [M−H]⁻;

¹H NMR (CDCl₃, 400 MHz) δ 7.86 (bs, 1H, NH), 7.25 (dd, J=9.2, 2.4 Hz, 1H), 7.20-7.16 (m, 1H), 6.97 (t, J=2.6 Hz, 1H), 6.93 (dd, J=9.2, 2.4 Hz, 1H);

¹⁹F NMR (CDCl₃) δ−123.99 (d, J_{F-F}=2.8 Hz), −174.74 (d, J_{F-F}=4.0 Hz).

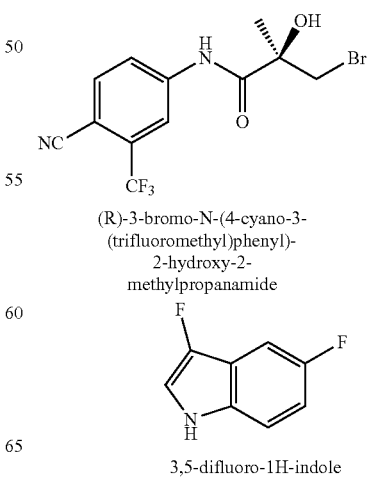

(R)-3-bromo-N-(4-cyano-3-(trifluoromethyl)phenyl)-2-hydroxy-2-methylpropanamide 3,5-difluoro-1H-indole NaH, THF →

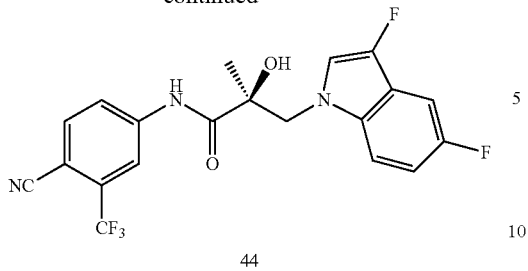

(S)—N-(4-Cyano-3-(trifluoromethyl)phenyl)-3-(3,5-difluoro-1H-indol-1-yl)-2-hydroxy-2-methylpropanamide (44)

To a dry, nitrogen-purged 50 mL round-bottom flask equipped with a dropping funnel under argon atmosphere, NaH of 60% dispersion in mineral oil (63 mg, 1.56 mmol) was added in 10 mL of anhydrous THF solvent in the flask at ice-water bath, and 3,5-difluoro-1H-indole (120 mg, 0.78 mmol) was stirred 30 min at the ice-water bath. Into the flask, (R)-3-bromo-N-(4-cyano-3-(trifluoromethyl)phenyl)-2-hydroxy-2-methylpropanamide (275 mg, 0.78 mmol) in 10 mL of anhydrous THF was added through dropping funnel under argon atmosphere at the ice-water bath and stirred overnight at room temperature. After adding 1 mL of H$_2$O, the reaction mixture was condensed under reduced pressure, and then dispersed into 50 mL of EtOAc, washed with 50 mL (×2) water, evaporated, dried over anhydrous MgSO$_4$, and evaporated to dryness. The mixture was purified with flash column chromatography as an eluent EtOAc/hexane=1/2 to produce 44 as white solid as white powder.

Yield 53%;

MS (ESI) m/z 424.11 [M+H]$^+$; 423.11 [M−H]$^−$;

HRMS (ESI) m/z calcd for C$_{20}$H$_{15}$F$_5$N$_3$O$_2$ [M+H]$^+$; Exact Mass: 424.1084 [M+H]$^+$. Found: 424.1065 [M+H]$^+$.

HPLC: t$_R$ 2.77 min, purity 99.06%, UV ($\lambda_{abs}$) 196.45, 270.45 nm $^1$H NMR (CDCl$_3$, 400 MHz) δ 8.80 (bs, 1H, NH), 7.89 (d, J=1.6 Hz, 1H), 7.77 (dd, J=8.4, 1.6 Hz, 1H), 7.74 (d, J=8.4 Hz, 1H), 7.33-7.29 (m, 1H), 7.20 (dd, J=9.0, 2.4 Hz, 1H), 6.99 (t, J=2.8 Hz, 1H), 6.97 (td, J=9.0, 2.4 Hz, 1H), 4.56 (d, J=14.8 Hz, 1H), 4.24 (d, J=14.8 Hz, 1H), 2.57 (s, OH), 1.61 (s, 3H);

$^{13}$C NMR (CDCl$_3$, 100 MHz) δ 172.3, 157.5 (d, J$_{F-F}$=235 Hz), 140.9, 135.8, 134.1 (d, J$_{F-F}$=32.8 Hz), 130.4 (d, J$_{F-F}$=4.5 Hz), 123.4, 121.9, 120.6, 117.4 (q, J$_{F-F}$=4.9 Hz), 115.3, 113.1 (d, J$_{F-F}$=2.59 Hz), 111.1 (d, J$_{F-F}$=9.3 Hz), 105.0, 102.3, 102.2, 102.0 (d, J$_{F-F}$=25 Hz), 77.6, 53.9, 24.2;

$^{19}$F NMR (CDCl$_3$) δ −62.25, −123.48 (d, J$_{F-F}$=3.2 Hz), −173.54 (d, J$_{F-F}$=2.8 Hz); assigned by 2D NMR as NOE and COSY.

(S)-3-(3-Chloro-5-fluoro-1H-indol-1-yl)-N-(4-cyano-3-(trifluoromethyl)phenyl)-2-hydroxy-2-methylpropanamide (45)

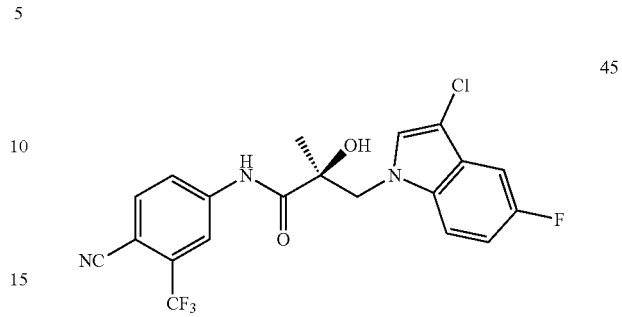

To a dry, nitrogen-purged 50 mL round-bottom flask equipped with a dropping funnel under argon atmosphere, NaH of 60% dispersion in mineral oil (167 mg, 2.5 mmol) was added in 10 mL of anhydrous THF solvent in the flask at ice-water bath, and 3-chloro-5-fluoro-1H-indole (170 mg, 1 mmol) was stirred 30 min at the ice-water bath. Into the flask, (R)-3-Bromo-N-(4-cyano-3-(trifluoromethyl)phenyl)-2-hydroxy-2-methylpropanamide (351 mg, 1 mmol) in 10 mL of anhydrous THF was added through dropping funnel under argon atmosphere at the ice-water bath and stirred overnight at room temperature. After adding 1 mL of H$_2$O, the reaction mixture was condensed under reduced pressure, and then dispersed into 50 mL of EtOAc, washed with 50 mL (×2) water, evaporated, dried over anhydrous MgSO$_4$, and evaporated to dryness. The mixture was purified with flash column chromatography as an eluent EtOAc/hexane=1/2 to produce 45 as white solid as white powder.

Yield 58%;

MS (ESI) m/z 440.08 [M+H]$^+$; 439.01 [M−H]$^−$;

HRMS (ESI) m/z calcd for C$_{20}$H$_{15}$ClF$_4$N$_3$O$_2$ Exact Mass: m/z C$_{20}$H$_{15}$ClF$_4$N$_3$O$_2$: 440.0789 [M+H]$^+$; 440.0797 [M+H]$^+$;

HPLC: t$_R$ 2.89 min, purity 99.06%;

UV ($\lambda_{abs}$) 196.45, 270.45 nm;

$^1$H NMR (CDCl$_3$, 400 MHz) δ 8.76 (bs, 1H, NH), 7.86 (s, 1H), 7.78-7.73 (m, 2H), 7.34 (dd, J=9.2, 4.0 Hz, 1H), 7.29 (dd, J=8.8, 2.4 Hz, 1H), 7.17 (s, 1H), 6.97 (td, J=9.2, 2.4 Hz, 1H), 4.58 (d, J=14.8 Hz, 1H), 4.28 (d, J=14.8 Hz, 1H), 2.64 (s, OH), 1.61 (s, 3H);

$^{13}$C NMR (CDCl$_3$, 100 MHz) δ 172.3, 157.5 (d, J$_{F-F}$=235 Hz), 140.8, 135.8, 134.0 (d, J$_{F-F}$=32 Hz), 132.6, 126.9, 126.2 (d, J$_{F-F}$=10 Hz), 123.4, 117.4 (q, J$_{F-F}$=4.9 Hz), 115.3, 112.0 (d, J$_{F-F}$=26.4 Hz), 111.1 (d, J$_{F-F}$=9.5 Hz), 106.1, 106.0, 105.0, 103.5 (d, J$_{F-F}$=25 Hz), 77.5, 53.8, 24.2.

$^{19}$F NMR (CDCl$_3$) δ −62.25, −12.76; assigned by 2D NMR as NOE and COSY.

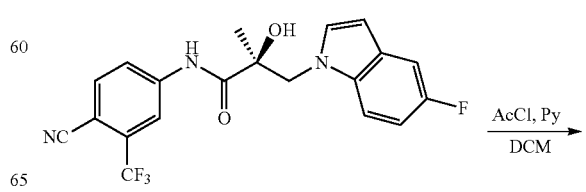

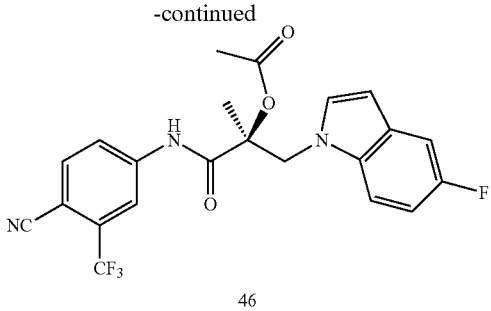

46

(S)-1-((4-Cyano-3-(trifluoromethyl)phenyl)amino)-3-(5-fluoro-1H-indol-1-yl)-2-methyl-1-oxopropan-2-yl acetate (46)

Under argon atmosphere, to a solution of 11 (100 mg, 0.247 mmol) and triethyl amine (0.07 mL, 0.5 mmol) in 10 mL of anhydrous DCM was added acetyl chloride (0.02 mL, 0.3 mmol) at ice-water bath. After stirring for 30 min, the temperature was raised to room temperature and the mixture stirred for 2 hours. The reaction mixture was washed with water, evaporated, dried over anhydrous MgSO$_4$, and evaporated to dryness. The mixture was purified with flash column chromatography as an eluent EtOAc/Hexane (1/1, v/v) to produce target product as white solid.

Yield=86%;
MS (ESI) m/z 446.0 [M–H]$^-$;
$^1$H NMR (CDCl$_3$, 400 MHz) δ 8.75 (bs, 1H,C(O)NH), 7.88 (s, 1H, ArH), 7.79-7.73 (m, 2H, ArH), 7.35 (dd, J=8.8, 4.2 Hz, 1H, ArH), 7.22 (dd, J=9.6, 2.6 Hz, 1H, ArH), 7.16 (d, J=2.6 Hz, 1H, ArH), 6.94 (m, 1H, ArH), 6.46 (d, J=3.2 Hz, 1H, ArH), 4.65 (d, J=14.8 Hz, 1H, CH$_2$), 4.33 (d, J=14.8 Hz, 1H, CH$_2$), 2.59 (s, 3H, OC(O)CH$_3$), 1.57 (s, 3H, CH$_3$);
$^{19}$F NMR (CDCl$_3$, 400 MHz) δ –62.24, –124.54; assigned by 2D NMR as NOE and COSY.

Carbazole
Methods A and B: Preparation of Carbazoles

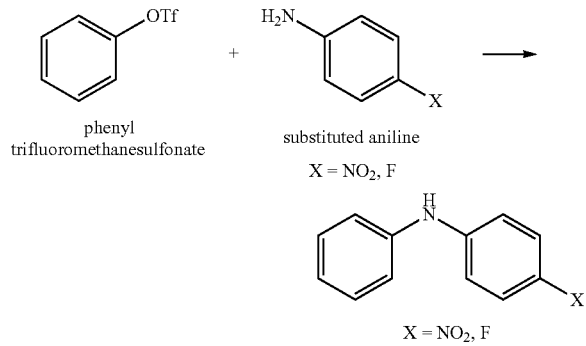

Method A (non microwave): A mixture of phenyl trifluoromethanesulfonate (500 mg, 2.21 mmol), palladium acetate (II) (50 mg, 0.22 mmol), (±) 2,2'-bis(diphenylphosphino)-1,1'-binaphthyl (317 mg, 0.66 mmol) and cesium carbonate (1.09 g, 3.31 mmol) in 50 mL of toluene were inertized with argon. Then, substituted aniline (2.43 mmol) was added and the mixture was heated at 110° C. overnight. The reaction mixture was allowed to cool to RT and filtered through a pad of Celite®. The filtrate was diluted with CH$_2$Cl$_2$ and water. The phases were separated and the aqueous phase was re-extracted 2 times with CH$_2$Cl$_2$. The combined organic phases were dried over Na$_2$SO$_4$ and the solvent was evaporated.

Method B (microwave): A mixture of phenyl trifluoromethanesulfonate (200 mg, 0.88 mmol), palladium acetate (II) (20 mg, 0.09 mmol), (±) 2,2'-bis(diphenylphosphino)-1,1'-binaphthyl (64 mg, 0.13 mmol) and cesium carbonate (430 mg, 1.32 mmol), and substituted aniline (0.97 mmol) in 5 mL of toluene were loaded into a vessel with a cap. Reaction vessels were placed in a reactor block in the microwave. A programmable microwave irradiation cycle of 30 min at 300 W at 110° C. and 25 min of fan-cooling was executed (irradiation time, 30 min). The mixture was transferred to a round bottom flask to be concentrated under reduced pressure and poured into EtOAc, which was washed with water and dried over anhydrous MgSO$_4$, concentrated. The crude product obtained was purified by chromatography on silica gel using EtOAc/hexane (6/1, v/v) as an eluent to produce the target product (~89%) as deep brown oil.

4-Fluoro-N-phenyl aniline: $^1$H NMR (400 MHz, CDCl$_3$) δ 7.27-7.24 (m, 2H), 7.07-7.02 (m, 2H), 7.01-6.95 (m, 4H), 6.89 (t, J=7.2 Hz, 1H), 5.57 (bs, 1H, NH).

3-Nitro-9H-carbazole

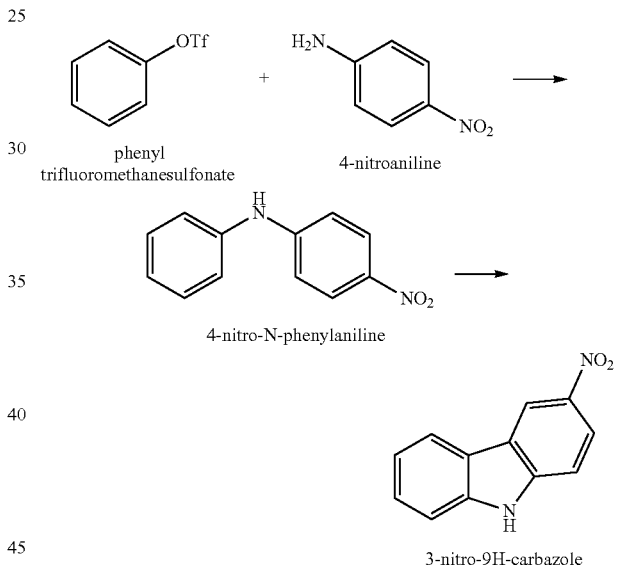

A mixture of phenyl trifluoromethanesulfonate (500 mg, 2.21 mmol), palladium acetate (II) (50 mg, 0.22 mmol), (±) 2,2'-bis(diphenylphosphino)-1,1'-binaphthyl (317 mg, 0.66 mmol) and cesium carbonate (1.09 g, 3.31 mmol) in 50 mL of toluene were inertized with argon. Then, 4-nitroaniline (331 mg, 2.43 mmol) was added and the mixture was heated at 110° C. overnight. The reaction mixture was allowed to cool to RT and filtered through a pad of Celite®. The filtrate was diluted with CH$_2$Cl$_2$ and water. The phases were separated and the aqueous phase was re-extracted 2 times with CH$_2$Cl$_2$. The combined organic phases were dried over Na$_2$SO$_4$ and the resulting solution was dried over anhydrous Na$_2$SO$_4$ and purified with flash column chromatography as an eluent EtOAc/hexane (1/6, v/v) to give 4-nitro-N-phenylaniline. The aniline (450 mg, 2 mmol), Pd(OAc)$_2$ (23 mg, 0.1 mmol), K$_2$CO$_3$ (30 mg, 0.2 mmol), and pivalic acid (408 mg, 4 mmol) was placed into a glass test tube. The uncapped test tube was placed in an oil bath and the mixture was stirred under air at the indicated temperature. The solution was then cooled to RT, diluted with EtOAc, washed with a saturated Na₂CO₃, dried over Na₂SO₄, concentrated, and purified by flash column chromatography as an eluent of EtOAc/hexane to give 3-nitro-9H-carbazole.

(S)-3-(9H-Carbazol-9-yl)-N-(4-cyano-3-(trifluoromethyl)phenyl)-2-hydroxy-2-methylpropanamide (200)

Method B: Yield 88%; MS (ESI) m/z 436.1 [M−H]⁻;
¹H NMR (CDCl₃, 400 MHz) δ 8.82 (bs, 1H, NH), 8.09-8.06 (m, 3H), 7.84 (d, J=1.6 Hz, 1H), 7.77-7.71 (m, 2H), 7.54 (d, J=8.4 Hz, 2H), 7.45-7.39 (m, 3H), 7.24-7.23 (m, 2H), 4.80 (d, J=15.2 Hz, 1H), 4.63 (d, J=15.2 Hz, 1H) 2.57 (s, 1H, OH), 1.69 (s, 3H).

(S)—N-(4-Cyano-3-(trifluoromethyl)phenyl)-2-hydroxy-2-methyl-3-(3-nitro-9H-carbazol-9-yl)propanamide (201)

Method B: MS (ESI) m/z 481.1 [M−H]⁻.
¹H NMR (CDCl₃, 400 MHz) δ 9.01 (s, 1H), 8.92 (bs, 1H, NH), 8.39 (m, 1H), 8.08 (m, 1H), 7.92 (d, J=1.6 Hz, 1H), 7.78 (d, J=8.4 Hz, 1H), 7.62 (dd, J=8.4, 1.6 Hz, 1H), 7.45 (m, 1H), 7.48-7.22 (m, 3H), 4.91 (d, J=15.0 Hz, 1H), 4.85 (d, J=15.0 Hz, 1H) 2.62 (s, 1H, OH), 1.70 (s, 3H).

(S)—N-(4-Cyano-3-(trifluoromethyl)phenyl)-3-(3-fluoro-9H-carbazol-9-yl)-2-hydroxy-2-methylpropanamide (202)

To a solution of 4-fluoro-carbazole (0.20 g, 0.00108 mol) in anhydrous THF (10 mL), which was cooled in an ice water bath under an argon atmosphere, was added sodium hydride (60% dispersion in oil, 0.09 g, 0.00216 mol). After addition, the resulting mixture was stirred for two hours. (R)-3-Bromo-N-(4-cyano-3-trifluoromethyl-phenyl)-2-hydroxy-2-methylpropanamide (0.38 g, 0.00108 mol) was added to the above solution, and the resulting reaction mixture was allowed to stir overnight at RT under argon. The reaction was quenched by water, and extracted with ethyl acetate. The organic layer was dried with MgSO₄, filtered, and concentrated under vacuum. The product was purified by a silica gel column using methylene chloride as eluent to afford 0.36 g (73.5%) of the titled compound as white solid.
¹H NMR (400 MHz, DMSO-d₆) δ 10.36 (s, 1H, NH), 8.25 (d, J=1.6 Hz, 1H, ArH), 8.12-8.09 (m, 2H, ArH), 8.04 (d, J=8.8 Hz, 1H, ArH), 7.95 (dd, J=9.2 Hz, J=2.1 Hz, 1H, ArH), 7.66 (t, J=4.8 Hz, 1H, ArH), 7.64 (s, 1H, ArH), 7.37 (dt, J=9.2 Hz, J=1.2 Hz, 1H, ArH), 7.20 (td, J=9.2 Hz, J=2.0 Hz, 1H, ArH), 7.13 (t, J=8.0 Hz, 1H, ArH), 6.34 (s, 1H, OH), 4.70 (d, J=14.8 Hz, 1H, CH), 4.55 (d, J=14.8 Hz, 1H, CH), 1.52 (s, 3H, CH₃).
Mass (ESI, Negative): 453.9 [M−H]−; (ESI, Positive): 478.1 [M+Na]+.

(S)—N-(3-Chloro-4-cyanophenyl)-3-(3-fluoro-9H-carbazol-9-yl)-2-hydroxy-2-methylpropanamide (203)

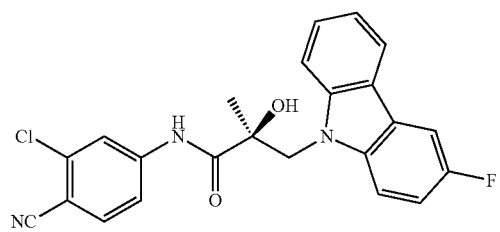 [SMILES: C[C@](O)(Cn1c2ccccc2c2cc(F)ccc21)C(=O)Nc1ccc(C#N)c(Cl)c1]

To a solution of 3-fluoro-carbazole (0.10 g, 0.00054 mol) in anhydrous THF (5 mL), which was cooled in an ice water bath under an argon atmosphere, was added sodium hydride (60% dispersion in oil, 0.033 g, 0.00081 mol). After addition, the resulting mixture was stirred for two hours. (R)-3-Bromo-N-(4-cyano-3-chloro-phenyl)-2-hydroxy-2-methylpropanamide (0.17 g, 0.00054 mol) was added to above solution, and the resulting reaction mixture was allowed to stir overnight at RT under argon. The reaction was quenched by water, and extracted with ethyl acetate. The organic layer was dried with MgSO₄, filtered, and concentrated under vacuum. The product was purified by a silica gel column using hexane and ethyl acetate (2:1) as eluent to afford 0.22 g (98%) of the titled compound as white solid/needles.
¹H NMR (400 MHz, DMSO-d₆) δ 10.20 (s, 1H, NH), 8.12 (d, J=7.6 Hz, 1H, ArH), 8.05 (d, J=2.0 Hz, 1H, ArH), 7.96 (dd, J=9.2 Hz, J=2.0 Hz, 1H, ArH), 7.86 (d, J=8.8 Hz, 1H, ArH), 7.80 (dd, J=8.4 Hz, J=2.0 Hz, 1H, ArH), 7.69-7.66 (m, 2H, ArH), 7.41 (t, J=8.0 Hz, 1H, ArH), 7.24 (dt, J=9.6 Hz, J=2.4 Hz, 1H, ArH), 7.16 (t, J=7.2 Hz, 1H, ArH), 6.34 (s, 1H, OH), 4.70 (d, J=15.2 Hz, 1H, CH), 4.54 (d, J=15.2 Hz, 1H, CH), 1.52 (s, 3H, CH₃).
Mass (ESI, Negative): 420.1 [M−H]−; (ESI, Positive): 444.1 [M+Na]+.

(S)—N-(4-Cyano-3-(trifluoromethyl)phenyl)-3-(3,6-difluoro-9H-carbazol-9-yl)-2-hydroxy-2-methylpropanamide (204)

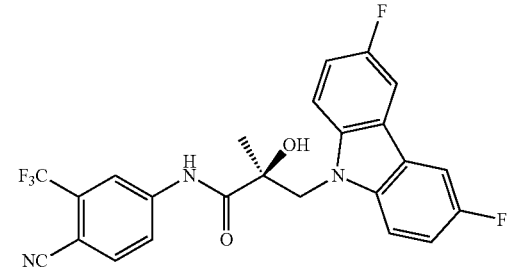 [SMILES: C[C@](O)(Cn1c2ccc(F)cc2c2cc(F)ccc21)C(=O)Nc1ccc(C#N)c(C(F)(F)F)c1]

To a solution of 3,6-difluorocarbazole (0.20 g, 0.00098 mol) in anhydrous THF (10 mL), which was cooled in an ice water bath under an argon atmosphere, was added sodium hydride (60% dispersion in oil, 0.06 g, 0.001476 mol). After addition, the resulting mixture was stirred for three hours. (S)—N-(4-Cyano-3-(trifluoromethyl)phenyl)-2-methyloxirane-2-carboxamide (0.266 g, 0.00098 mol) was added to above solution, and the resulting reaction mixture was allowed to stir overnight at RT under argon. The reaction was quenched by water, and extracted with ethyl acetate. The organic layer was washed with brine, dried with MgSO₄, filtered, and concentrated under vacuum. The product was purified by a silica gel column using ethyl acetate and hexane (1:2) as eluent to afford 0.40 g of the titled compound as white solid.
¹H NMR (400 MHz, DMSO-d₆) δ 10.33 (s, 1H, NH), 8.22 (d, J=1.6 Hz, 1H, ArH), 8.11 (dd, J=8.8 Hz, J=2.0 Hz, 1H, ArH), 8.05 (d, J=8.8 Hz, 1H, ArH), 7.98 (d, J=2.4 Hz, 1H, ArH), 7.96 (d, J=2.4 Hz, 1H, ArH), 7.68-7.65 (m, 2H, ArH), 7.27-7.22 (m, 2H, ArH), 6.36 (s, 1H, OH), 4.72 (d, J=15.2 Hz, 1H, CH), 4.54 (d, J=15.2 Hz, 1H, CH), 1.53 (s, 3H, CH₃).
Mass (ESI, Negative): 471.9 [M−H]−; (ESI, Positive): 496.1 [M+Na]+.

(S)-3-(9H-Carbazol-9-yl)-N-(3-chloro-4-cyanophenyl)-2-hydroxy-2-methylpropanamide (205)

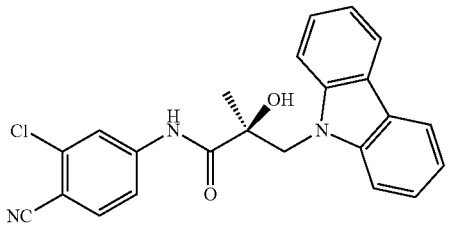 [SMILES: C[C@](O)(Cn1c2ccccc2c2ccccc21)C(=O)Nc1ccc(C#N)c(Cl)c1]

Method B
Yield 77%;
MS (ESI) m/z 402.3 [M−H]$^-$;
$^1$H NMR (400 MHz, CDCl$_3$) δ 8.75 (bs, 1H, NH), 8.08 (d, J=7.6 Hz, 2H), 7.78 (d, J=1.6 Hz, 1H), 7.56-7.54 (m, 3H), 7.44 (t, J=7.6 Hz, 2H), 7.37 (dd, J=8.8, 1.8 Hz, 1H), 7.27-7.25 (m, 2H), 4.78 (d, J=15.6 Hz, 1H), 4.63 (d, J=15.6 Hz, 1H), 2.65 (bs, 1H, OH), 1.66 (s, 3H).

Isoquinoline Derivative

(S)—N-(4-Cyano-3-(trifluoromethyl)phenyl)-3-(7-fluoro-3,4-dihydroisoquinolin-2(1H)-yl)-2-hydroxy-2-methylpropanamide (132)

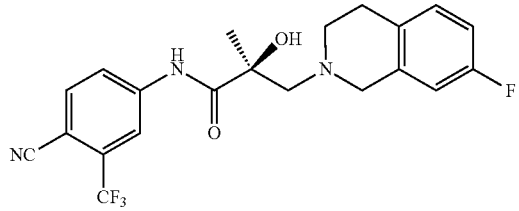

132

Method A
Yield 69%;
MS (ESI) m/z 420.0 [M−H]$^-$;
$^1$H NMR (400 MHz, CDCl$_3$) δ 9.09 (bs, 1H, NH), 7.93 (d, J=8.4 Hz, 1H), 7.80 (d, J=8.4 Hz, 1H), 7.05 (t, J=8.0 Hz, 1H), 6.86 (m, 1H), 6.63 (d, J=8.0 Hz, 1H), 3.71 (s, 2H), 3.42 (d, J=13.2 Hz, 1H), 2.91-2.82 (m, 5H), 2.60 (d, J=13.2 Hz, 1H), 1.46 (s, 3H).

Indoline Derivatives

(S)—N-(3-Chloro-4-cyanophenyl)-3-(4-fluoroindolin-1-yl)-2-hydroxy-2-methylpropanamide (103)

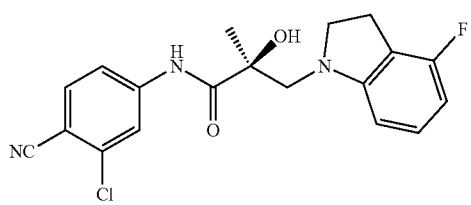 [SMILES: C[C@](O)(CN1CCc2c(F)cccc21)C(=O)Nc1ccc(C#N)c(Cl)c1]

Preparation of LDA solution in THF: To a stirred solution of freshly distilled diisopropylamine (0.14 mL, 1.2 mmol) in anhydrous 5 mL of THF was added a solution of n-butyllithium (0.53 mL, 1.32 mmol, 2.5 M solution in hexane) at −78° C. under argon atmosphere. Under the argon atmosphere into a 100 mL dried two necked round bottom flask equipped with a dropping funnel, the prepared solution of LDA or commercial 2.0 M LDA solution (1.2 mmol, Aldrich) in THF was placed in the flask, and then 4-fluoroindoline (1.0 mmol) in 10 mL of anhydrous THF was dropwise added to the LDA solution at the −78° C. under argon atmosphere. The solution was stirred for 10 min and warmed to 0° C. and cooled down again to −78° C. To the solution, a solution of (R)-3-bromo-N-(3-chloro-4-cyanophenyl)-2-hydroxy-2-methylpropanamide (1.0 mmol in THF) was added through dropping funnel under argon atmosphere at −78° C. and allowed to warm gradually to RT and stirred overnight. And then quenched by an addition of 0.5 mL of sat. NH$_4$Cl. The solution was reduced in volume under reduced pressure and dispersed into excess EtOAc, and then dried over anhydrous MgSO$_4$. The solution was concentrated on and purified by flash column chromatography (EtOAc/hexane) or recrystallized from EtOAc/hexane (or DCM/hexane) to give the designed compound, 103.

Yield 71%.
White solid.
MS (ESI) m/z 372.0 [M−H]$^-$.
HRMS (ESI) m/z calcd for $C_{19}H_{18}ClFN_3O_2$: 374.1072. Found: 374.1072 [M+H]$^+$.
$[α]_D^{20}$ −173° (c 1.0, CH$_3$OH).
$^1$H NMR (acetone-d$_6$, 400 MHz) δ 9.84 (bs, 1H, NH), 8.26 (d, J=2.0 Hz, 1H), 7.90 (dd, J=8.4, 2.0 Hz, 1H), 7.80 (d, J=8.4 Hz, 1H), 6.99 (m, 1H), 6.43 (d, J=8.0 Hz, 1H), 6.31 (t, J=8.4 Hz, 1H), 5.21 (bs, 1H, OH), 3.66 (m, 1H), 3.63 (d, J=14.4 Hz, 1H), 3.53 (q, J=8.0 Hz, 1H), 3.26 (d, J=14.4 Hz, 1H), 2.89 (m, 2H), 1.53 (s, 3H).
$^{13}$C NMR (acetone-d$_6$, 100 MHz) δ 175.9, 160.6 (d, J=239.7 Hz), 160.6 (d, J=9.3 Hz), 144.6, 137.3, 135.6, 129.9 (d, J=8.7 Hz), 120.8, 119.2, 116.7, 114.8 (d, J=21.7 Hz), 107.8, 105.1 (d, J=21.0 Hz), 104.1 (d, J=8.0 Hz), 77.8, 60.4, 56.7, 25.4, 24.3.
$^{19}$F NMR (CDCl$_3$, decoupled) δ 118.95.

(S)—N-(3-Chloro-4-cyanophenyl)-3-(5-fluoroindolin-1-yl)-2-hydroxy-2-methylpropanamide (104)

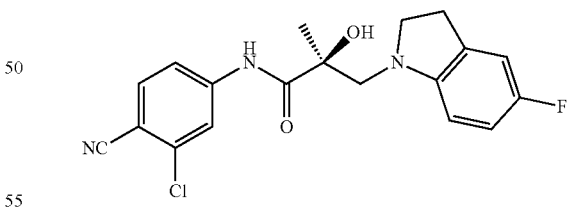

Method A
Yield; 68%.
$^1$H NMR (400 MHz, CDCl$_3$) δ 9.09 (bs, 1H, NH), 7.98 (d, J=2.0 Hz, 1H), 7.61 (d, J=8.4 Hz, 1H), 7.52 (dd, J=8.4, 2.0 Hz, 1H), 6.83 (m, 1H), 6.77 (m, 1H), 6.51 (m, 1H), 3.62 (d, J=14.4 Hz, 1H), 3.56 (bs, 1H, OH), 3.42 (m, 1H), 3.30 (q, J=9.2 Hz, 1H), 3.21 (d, J=14.4 Hz, 1H), 3.01 (t, J=8.4 Hz, 2H), 1.54 (s, 3H).
MS (ESI) m/z 372.0 [M−H]$^-$;
$[α]_D^{20}$ −202° (c 1.0, CH$_3$OH)
$^{19}$F NMR (CDCl$_3$, decoupled) δ 125.35.

(S)—N-(3-Chloro-4-cyanophenyl)-3-(6-fluoroindolin-1-yl)-2-hydroxy-2-methylpropanamide (106)

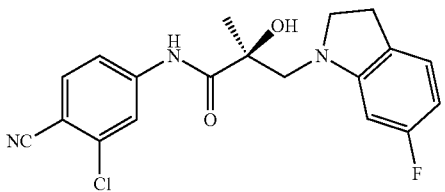 [SMILES: C[C@](O)(CN1CCc2ccc(F)cc21)C(=O)Nc1ccc(C#N)c(Cl)c1]

Method A
Yield 76%.
MS (ESI) m/z 372.1 [M–H]⁻.
¹H NMR (400 MHz, CDCl₃) δ 9.08 (bs, 1H, NH), 7.97 (d, J=1.6 Hz, 1H), 7.60 (d, J=8.4 Hz, 1H), 7.53 (dd, J=8.4, 1.6 Hz, 1H), 6.77 (t, J=6.4 Hz, 1H), 6.39 (m, 1H), 6.33 (d, J=10.0 Hz, 1H), 3.64 (d, J=14.2 Hz, 1H), 3.49 (bs, 1H, OH), 3.47 (m, 1H), 3.38 (q, J=9.2 Hz, 1H), 3.23 (d, J=14.2 Hz, 1H), 2.95 (m, 2H), 1.56 (s, 3H).

(S)-3-(5-Chloro-6-fluoroindolin-1-yl)-N-(4-cyano-3-(trifluoromethyl)phenyl)-2-hydroxy-2-methylpropanamide (107)

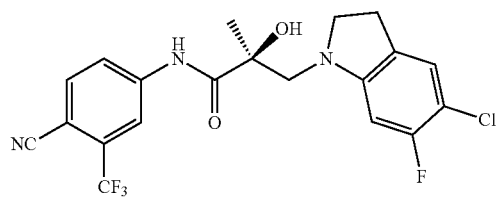 [SMILES: C[C@](O)(CN1CCc2cc(Cl)c(F)cc21)C(=O)Nc1ccc(C#N)c(C(F)(F)F)c1]

Method A
Yield; 47%.
MS (ESI) m/z 440.3 [M–H]⁻.
¹H NMR (400 MHz, CDCl₃) δ 9.15 (bs, 1H, NH), 8.08 (s, 1H), 7.97 (d, J=8.4 Hz, 1H), 7.80 (d, J=8.4 Hz, 1H), 7.03 (d, J=7.2 Hz, 1H), 6.42 (d, J=10.0 Hz, 1H), 3.66 (d, J=14.4 Hz, 1H), 3.52-3.42 (m, 2H), 3.38 (s, 1H, OH), 3.21 (d, J=14.4 Hz, 1H), 2.96-2.80 (m, 2H), 1.52 (s, 3H).

(S)—N-(4-Cyano-3-(trifluoromethyl)phenyl)-3-(5,6-difluoroindolin-1-yl)-2-hydroxy-2-methylpropanamide (108)

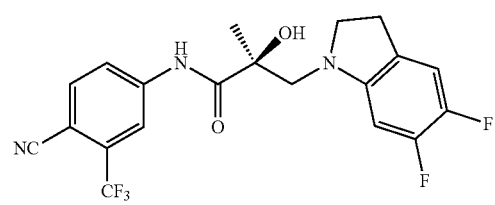 [SMILES: C[C@](O)(CN1CCc2cc(F)c(F)cc21)C(=O)Nc1ccc(C#N)c(C(F)(F)F)c1]

Method A
Yield; 59%.
MS (ESI) m/z 423.9 [M–H]⁻.
¹H NMR (400 MHz, CDCl₃) δ 9.18 (bs, 1H, NH), 8.09 (d, J=2.0 Hz, 1H), 7.97 (dd, J=8.4, 2.0 Hz, 1H), 7.80 (d, J=8.4 Hz, 1H), 6.89 (t, J=8.8 Hz, 1H), 6.43 (m, 1H), 3.64 (d, J=14.4 Hz, 1H), 3.46 (s, 1H, OH), 3.40-3.35 (m, 2H), 3.17 (d, J=14.4 Hz, 1H), 2.99-2.91 (m, 2H), 1.57 (s, 3H).

(S)—N-(4-Cyano-3-(trifluoromethyl)phenyl)-2-hydroxy-3-(indolin-1-yl)-2-methylpropanamide (109)

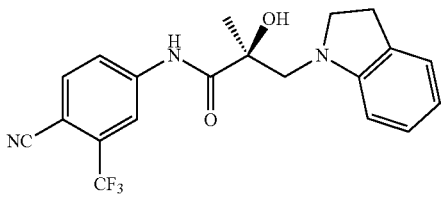 [SMILES: C[C@](O)(CN1CCc2ccccc21)C(=O)Nc1ccc(C#N)c(C(F)(F)F)c1]

Method A
Yield 69%.
MS (ESI) m/z 387.8 [M–H]⁻.
¹H NMR (400 MHz, CDCl₃) δ 9.24 (bs, 1H, NH), 8.09 (d, J=2.0 Hz, 1H), 7.94 (dd, J=8.8, 2.0 Hz, 1H), 7.79 (d, J=2.0 Hz, 1H), 7.13-7.10 (m, 2H), 6.78 (dt, J=8.0, 0.8 Hz, 1H), 6.62 (d, J=8.0, 1H), 3.77 (bs, 1H, OH), 3.66 (d, J=14.4 Hz, 1H), 3.54 (t, J=8.4 Hz, 1H), 3.46-3.40 (m, 1H), 3.30 (d, J=14.4 Hz, 1H), 3.04-2.92 (m, 2H), 1.57 (s, 3H).

(S)—N-(3-Chloro-4-cyanophenyl)-3-(5,6-difluoroindolin-1-yl)-2-hydroxy-2-methylpropanamide (110)

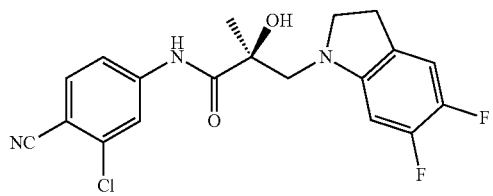 [SMILES: C[C@](O)(CN1CCc2cc(F)c(F)cc21)C(=O)Nc1ccc(C#N)c(Cl)c1]

Method A
Yield 64%.
MS (ESI) m/z 390.0 [M–H]⁻. ¹H NMR (400 MHz, CDCl₃) δ 9.05 (bs, 1H, NH), 7.98 (s, 1H), 7.62 (d, J=8.2 Hz, 1H), 7.53 (d, J=8.2 Hz, 1H), 6.88 (t, J=8.8 Hz, 1H), 6.43 (m, 1H), 3.64 (d, J=14.4 Hz, 1H), 3.46 (s, 1H, OH), 3.44 (m, 1H), 3.42-3.34 (m, 1H), 3.16 (d, J=14.4 Hz, 1H), 3.95-3.88 (m, 2H), 1.55 (s, 3H).

(S)-3-(5-Bromoindolin-1-yl)-N-(3-chloro-4-cyanophenyl)-2-hydroxy-2-methylpropanamide (114)

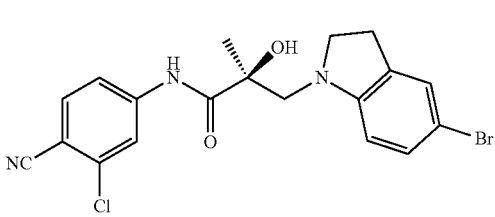 [SMILES: C[C@](O)(CN1CCc2cc(Br)ccc21)C(=O)Nc1ccc(C#N)c(Cl)c1]

Method A
Yield 54%.
MS (ESI) m/z 433.6 [M−H]⁻.

¹H NMR (400 MHz, CDCl₃) δ 9.04 (bs, 1H, NH), 7.98 (d, J=2.0 Hz, 1H), 7.60 (d, J=6.0 Hz, 1H), 7.52 (dd, J=6.0, 2.0 Hz, 1H), 7.19-7.17 (m, 2H), 6.49 (d, J=8.4 Hz, 1H), 3.65 (d, J=14.4, 1H), 3.47 (bs, 1H, OH), 3.36-3.41 (m, 1H), 3.32 (q, J=9.2 Hz, 1H), 3.23 (d, J=14.4, 1H), 2.99-2.91 (m, 2H), 1.56 (s, 3H).

(S)—N-(3-Chloro-4-cyanophenyl)-3-(5-fluoro-6-phenylindolin-1-yl)-2-hydroxy-2-methylpropanamide (115)

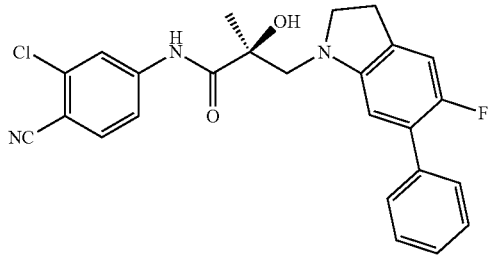 [SMILES: C[C@](O)(CN1CCc2cc(F)c(-c3ccccc3)cc21)C(=O)Nc1ccc(C#N)c(Cl)c1]

To a solution of (S)—N-(3-chloro-4-cyanophenyl)-3-(5-fluoro-6-phenyl-1H-indol-1-yl)-2-hydroxy-2-methylpropanamide (34, 0.185 g, 0.000413 mol) in 5 mL of glacial acetic acid, which was cooled in an ice-water bath, was added drop-wise sodium cyanoborohydride (1.0 M in THF, 0.62 mL, 0.00124 mol) under as argon atmosphere. After addition, the resulting reaction mixture was allowed to stir for overnight at RT under argon. The reaction was quenched by aqueous NH₄Cl solution, and extracted with ethyl acetate. The organic layer was washed with brine twice, dried with MgSO₄, filtered, and concentrated under vacuum. The product was purified by a silica gel column using ethyl acetate and hexane (1:2) as eluent to afford 0.17 g of the titled compound as yellowish foam.

¹H NMR (400 MHz, DMSO-d₆) δ 10.29 (s, 1H, NH), 8.21 (d, J=2.0 Hz, 1H, ArH), 7.92-7.84 (m, 2H, ArH), 7.45-7.34 (m, 5H, ArH), 6.95 (d, J=10.4 Hz, 1H, ArH), 6.55 (d, J=6.4 Hz, 1H, ArH), 6.02 (s, 1H, OH), 3.61 (q, J=8.8 Hz, 1H, CH), 4.50 (d, J=14.4 Hz, 1H, CH), 3.40 (d, J=14.4 Hz, 1H, CH), 4.19 (d, J=14.4 Hz, 1H, CH), 2.91 (t, J=8.4 Hz, 2H, CH₂), 1.42 (s, 3H, CH₃).

Mass (ESI, Negative): [M−H]⁻; (ESI, Positive): 450.1394 [M+H]⁺.

Indazole Derivatives (S)—N-(4-Cyano-3-(trifluoromethyl)phenyl)-3-(5-fluoro-1H-indazol-1-yl)-2-hydroxy-2-methylpropanamide (90) and (S)—N-(4-cyano-3-(trifluoromethyl)phenyl)-3-(5-fluoro-1H-indazol-2-yl)-2-hydroxy-2-methylpropanamide (91)

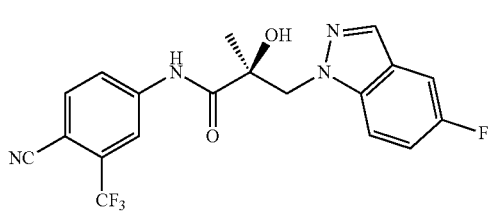

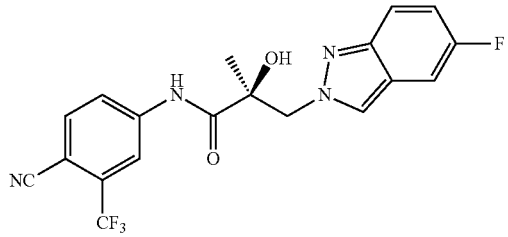

Method B
Yield; 67%.
MS (ESI) 405.1 [M−H]⁻.

¹H NMR (400 MHz, CDCl₃) δ 9.16 (bs, 1H, NH), 8.05-7.88 (m, 2H), 7.81-7.72 (m, 2H), 7.62-7.13 (m, 4H), 6.72 (bs, OH, 0.56H), 6.15 (s, OH, 0.44H), 4.94 (d, J=13.6 Hz, 0.56H), 4.95 (d, J=14.2 Hz, 0.46H), 4.52 (d, J=13.6 Hz, 0.56H), 4.43 (d, J=14.2 Hz, 0.46H), 1.53 (s, 3H).

(S)—N-(3-Chloro-4-cyanophenyl)-3-(5-fluoro-1H-indazol-1-yl)-2-hydroxy-2-methylpropanamide (92) and (S)—N-(3-chloro-4-cyanophenyl)-3-(5-fluoro-1H-indazol-2-yl)-2-hydroxy-2-methylpropanamide (93)

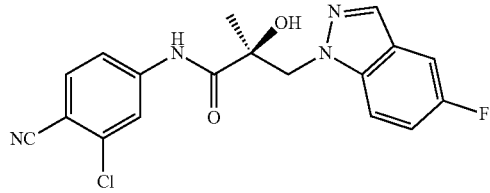

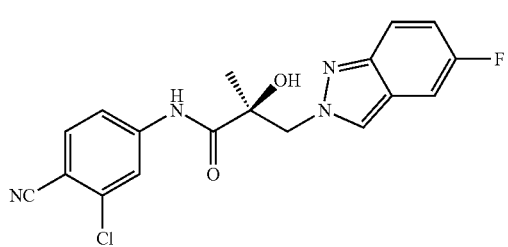

Method B
Yield; 74%.
MS (ESI) 370.8 [M−H]⁻.

¹H NMR (400 MHz, CDCl₃) δ 8.97 (bs, 1H, NH), 7.99 (s, 0.56H), 7.95 (s, 0.46H), 7.83 (d, J=2.4 Hz, 0.46H), 7.83 (d, J=2.0 Hz, 0.54H), 7.64-7.45 (m, 2H), 7.39-7.31 (m, 1H), 7.24-7.22 (m, 1H), 7.16-7.11 (m, 1H), 6.63 (s, OH, 0.46H), 6.04 (s, OH, 0.54H), 4.92 (d, J=13.6 Hz, 0.46H), 4.92 (d, J=14.0 Hz, 0.54H), 4.50 (d, J=13.6 Hz, 0.46H), 4.40 (d, J=14.0 Hz, 0.54H), 1.58 (s, 3H).

Synthesis of (S)—N-(4-cyano-3-(trifluoromethyl)phenyl)-3-(4-fluoro-1H-indazol-1-yl)-2-hydroxy-2-methylpropanamide (94) and (S)—N-(4-cyano-3-(trifluoromethyl)phenyl)-3-(4-fluoro-2H-indazol-2-yl)-2-hydroxy-2-methylpropanamide (95)

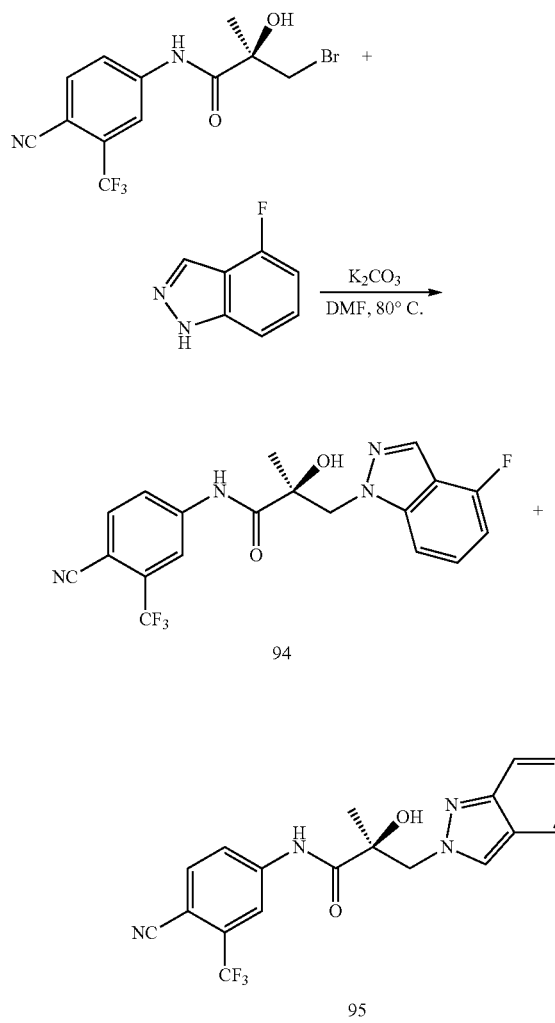

To a dry, nitrogen-purged 50 mL round-bottom flask, R-bromo amide of 8R (351 mg, 1 mmol), 4-fluoro-1H-indazole (136 mg, 1 mmol) and K$_2$CO$_3$ (415 mg, 3 mmol) were dissolved into 10 mL of DMF. The mixture was heated up to 80° C. and stirred overnight at that temperature. The resulting mixture was cooled down to RT. The volume of mixture was reduced under reduced pressure and poured into water, and extracted with ethyl acetate (3 times). The organic layer was dried over MgSO$_4$, concentrated and purified by flash column chromatography (ethyl acetate/hexane 1:2 v/v) on silica gel to produce two products (total 65% yield; 94 (36% yield at R$_f$=0.14) and 95 (29% yield at R$_f$=0.12).

(S)—N-(4-Cyano-3-(trifluoromethyl)phenyl)-3-(4-fluoro-1H-indazol-1-yl)-2-hydroxy-2-methylpropanamide (94)

HRMS (ESI) m/z calcd for C$_{19}$H$_{15}$F$_4$N$_4$O$_2$: 407.1131 [M+H]$^+$. Found: 407.1150 [M+H]$^+$.

$^1$H NMR (CDCl$_3$, 400 MHz) δ 9.10 (bs, 1H, NH), 8.11 (d, J=0.8 Hz, 1H), 7.91 (d, J=2.0 Hz, 1H), 7.76 (dd, J=8.4, 2.0 Hz, 1H), 7.71 (d, J=8.4 Hz, 1H), 7.41-7.36 (m, 1H), 7.30 (d, J=8.4 Hz, 1H), 6.80 (dd, J=9.6, 7.2 Hz, 1H), 6.02 (s, 1H, OH), 4.93 (d, J=14.0 Hz, 1H), 4.43 (d, J=14.0 Hz, 1H), 1.53 (s, 3H).

$^{19}$F NMR (CDCl$_3$, 400 MHz) δ −62.25, −117.48.

(S)—N-(4-Cyano-3-(trifluoromethyl)phenyl)-3-(4-fluoro-2H-indazol-2-yl)-2-hydroxy-2-methylpropanamide (95)

HRMS (ESI) m/z calcd for C$_{19}$H$_{15}$F$_4$N$_4$O$_2$: 407.1131 [M+H]$^+$. Found: 407.1168 [M+H]$^+$.

$^1$H NMR (CDCl$_3$, 400 MHz) δ 9.15 (bs, 1H, NH), 8.08 (s, 1H), 7.96 (d, J=1.6 Hz, 1H), 7.84 (dd, J=8.8, 1.6 Hz, 1H), 7.74 (d, J=8.8 Hz, 1H), 7.42 (d, J=8.8 Hz, 1H), 7.26 (m, 1H), 6.72 (dd, J=10.0, 7.2 Hz, 1H), 6.67 (bs, 1H, OH), 4.96 (d, J=13.6 Hz, 1H), 4.54 (d, J=13.6 Hz, 1H), 1.54 (s, 3H).

$^{19}$F NMR (CDCl$_3$, 400 MHz) δ −62.41, −116.55.

2-Dimensional nuclear Overhauser effect (NOE) spectroscopy (NOESY): NOESY was used to assign the correct chemical structures to these two isomers. 94 demonstrated NOEs between the aromatic proton located at the 7-position of the indazole ring (annotated as H) and the methylene protons (annotated as H$_1$ and H$_2$),

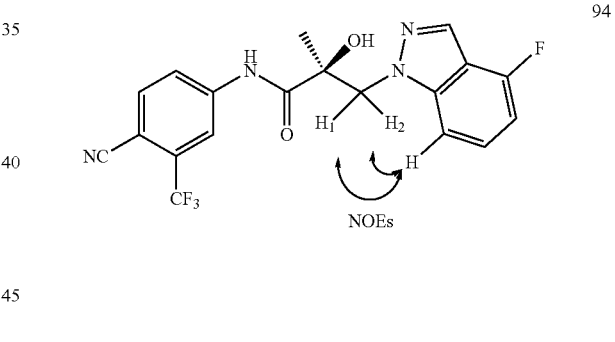

indicating that the point of attachment to the indazole ring must be the 1-position. Whereas for 95, an NOE was observed between 3-position aromatic proton of the indazole ring (annotated as H) and the methylene protons (annotated as H$_1$ and H$_2$),

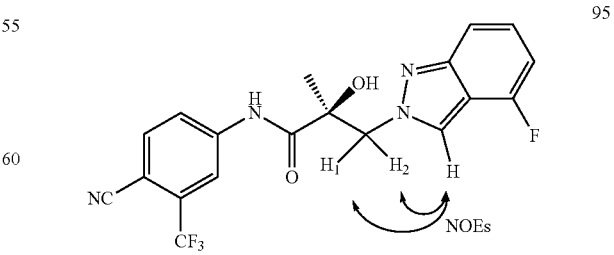

indicating that the point of attachment to the indazole ring must be the 2-position.

Synthesis of (S)—N-(4-cyano-3-(trifluoromethyl) phenyl)-2-hydroxy-2-methyl-3-(4-(trifluoromethyl)-1H-indazol-1-yl)propanamide (96) and (S)—N-(4-cyano-3-(trifluoromethyl)phenyl)-2-hydroxy-2-methyl-3-(4-(trifluoromethyl)-2H-indazol-2-yl) propanamide (97)

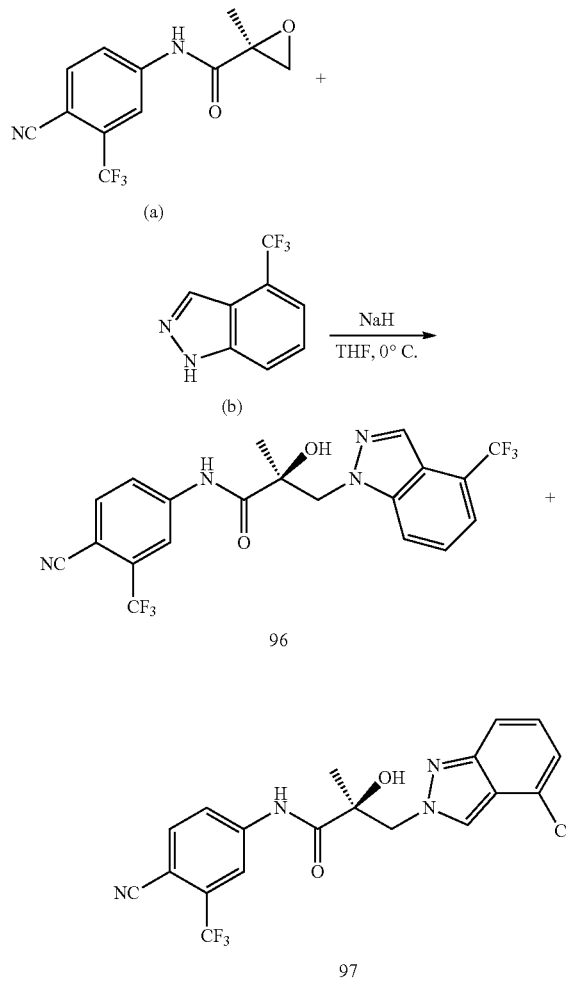

To a dry, nitrogen-purged 100 mL round-bottom flask equipped a dropping funnel under argon atmosphere, NaH of 60% dispersion in mineral oil (160 mg, 4.0 mmol) was added in 30 mL of anhydrous THF solvent to the flask at ice-water bath, and then 4-trifluoromethyl-indazole (b) (372 mg, 2.0 mmol) was stirred in over 30 min at the ice-water bath. Into the flask, a prepared solution of epoxide (a), (541 mg, 2.0 mmol) in 10 mL of anhydrous THF was added through dropping funnel under argon atmosphere at the ice-water bath and stirred overnight at RT. After adding 1 mL of H$_2$O, the reaction mixture was condensed under reduced pressure, and then dispersed into 50 mL of EtOAc, washed with 50 mL (×2) water, evaporated, dried over anhydrous MgSO$_4$, and evaporated to dryness. The mixture was purified with flash column chromatography as an eluent EtOAc/hexane at a 1:2 ratio to produce compounds 97 (22.9%, @ rf=0.29) and 96 (30.1%, @ rf=0.37) as white solids (total 53% yield).

(S)—N-(4-Cyano-3-(trifluoromethyl)phenyl)-2-hydroxy-2-methyl-3-(4-(trifluoromethyl)-1H-indazol-1-yl)propanamide (96)

HRMS (ESI) m/z calcd for C$_{20}$H$_{14}$F$_6$N$_4$O$_2$ Exact Mass: 457.1099 [M+H]$^+$. Found: 457.1117 [M+H]$^+$.

$^1$H NMR (CDCl$_3$, 400 MHz) δ 9.08 (bs, 1H, NH), 8.19 (t, J=1.2 Hz, 1H), 7.90 (d, J=1.6 Hz, 1H), 7.61-7.70 (m, 3H), 7.55-7.47 (m, 2H), 5.93 (bs, 1H, OH), 5.01 (d, J=14.0 Hz, 1H), 4.47 (d, J=14.0 Hz, 1H), 1.55 (s, 3H).

$^{19}$F NMR (CDCl$_3$, 400 MHz) δ −61.54, 62.27.

(S)—N-(4-Cyano-3-(trifluoromethyl)phenyl)-2-hydroxy-2-methyl-3-(4-(trifluoromethyl)-2H-indazol-2-yl)propanamide (97)

HRMS (ESI) m/z calcd for C$_{20}$H$_{14}$F$_6$N$_4$O$_2$ Exact Mass: 457.1099 [M+H]$^+$. Found: 457.1110 [M+H]$^+$.

$^1$H NMR (CDCl$_3$, 400 MHz) δ 9.09 (bs, 1H, NH), 8.14 (s, 1H), 7.92 (d, J=2.0 Hz, 1H), 7.85-7.82 (m, 1H), 7.73 (d, J=8.4 Hz, 1H), 7.44 (dt, J=6.8, 0.8 Hz, 1H), 7.41 (q, J=8.4 Hz, 1H), 6.56 (bs, 1H, OH), 4.98 (d, J=14.0 Hz, 1H), 4.57 (d, J=14.0 Hz, 1H), 1.54 (s, 3H).

$^{19}$F NMR (CDCl$_3$, 400 MHz) δ −61.28, 62.55.

2-Dimensional nuclear Overhauser effect (NOE) spectroscopy (NOESY): NOESY was used to assign the correct chemical structures to these two isomers. 96 demonstrated an NOE between the aromatic proton located at the 7-position of the indazole ring (annotated as H$_2$) and the methylene protons (each annotated as H),

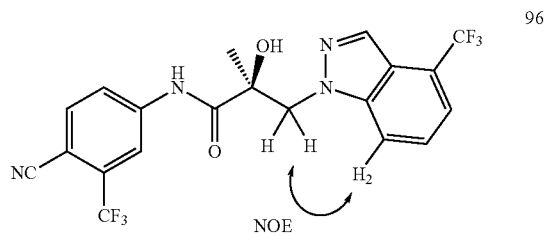

indicating that the point of attachment to the indazole ring must be the 1-position. Whereas for 97, an NOE was observed between 3-position aromatic proton of the indazole ring (annotated as H$_1$) and the methylene protons (each annotated as H),

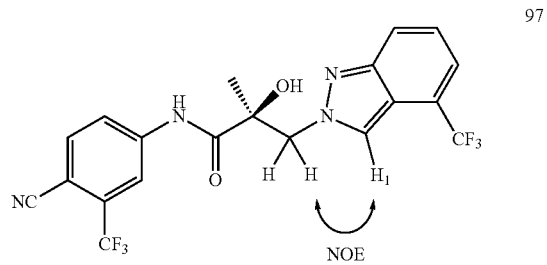

indicating that the point of attachment to the indazole ring must be the 2-position.

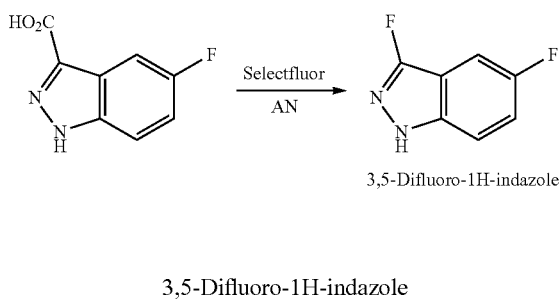

3,5-Difluoro-1H-indazole 3,5-Difluoro-1H-indazole

To a 50 mL round-bottle flask with a magnetic stirring bar were added Selectfluor® (872 mg, 2.0 mmol, 2.0 equiv), Li$_2$CO$_3$ (296 mg, 4.0 mmol, 4.0 equiv), dichloromethane (3.3 mL) and water (1.7 mL). Then carboxylic acid (1.0 mmol, 1.0 equiv) was added. The reaction mixture was stirred for 2 hours in ice bath. The reaction mixture was diluted with water (40 mL), followed by extracting with DCM (20 mL×2). The combined organic extracts were washed with brine, dried over anhydrous sodium sulfate and concentrated in vacuo. The crude product was purified by flash column chromatography (n-hexane:DCM=2:1) to afford the desired product.

Yield 48%;

MS (ESI) m/z 152.0 [M−H]$^-$;

$^1$H NMR (CDCl$_3$, 400 MHz) δ 9.80 (bs, 1H, NH), 7.37 (dt, J=8.8, 2.4 Hz, 1H), 7.31 (dd, J=8.0, 1.6 Hz, 1H), 7.23 (td, J=8.8, 2.0 Hz, 1H);

$^{19}$F NMR (CDCl$_3$) δ −121.46 (d, J$_{F-F}$=4.4 Hz), −133.92 (d, J$_{F-F}$=4.4 Hz).

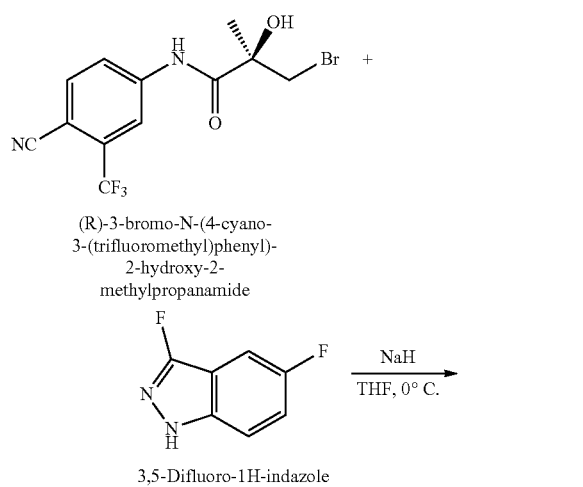

(R)-3-bromo-N-(4-cyano-3-(trifluoromethyl)phenyl)-2-hydroxy-2-methylpropanamide 3,5-Difluoro-1H-indazole

98

S)—N-(4-Cyano-3-(trifluoromethyl)phenyl)-3-(3,5-difluoro-1H-indazol-1-yl)-2-hydroxy-2-methylpropanamide (98)

To a dry, nitrogen-purged 50 mL round-bottom flask equipped with a dropping funnel under argon atmosphere, NaH of 60% dispersion in mineral oil (32 mg, 0.8 mmol) was added in 5 mL of anhydrous THF solvent in the flask at ice-water bath, and 3,5-difluoro-1H-indazole (60 mg, 0.41 mmol) was stirred 30 min at the ice-water bath. Into the flask, (R)-3-bromo-N-(4-cyano-3-(trifluoromethyl)phenyl)-2-hydroxy-2-methylpropanamide (148 mg, 0.41 mmol) in 5 mL of anhydrous THF was added through dropping funnel under argon atmosphere at the ice-water bath and stirred overnight at room temperature. After adding 1 mL of H$_2$O, the reaction mixture was condensed under reduced pressure, and then dispersed into 50 mL of EtOAc, washed with 50 mL (×2) water, evaporated, dried over anhydrous MgSO$_4$, and evaporated to dryness. The mixture was purified with flash column chromatography as an eluent EtOAc/hexane=2/3 to produce 98 as white solid.

Yield=57%;

MS (ESI) m/z 423.17 [M−H]$^-$; 447.21 [M+Na]$^+$;

$^1$H NMR (CDCl$_3$, 400 MHz) δ 9.07 (bs, 1H, NH), 7.92 (s, 1H), 7.78 (d, J=8.6 Hz, 1H), 7.73 (d, J=8.6 Hz, 1H), 7.42 (d, J=8.4 Hz, 1H), 7.28 (m, 1H), 7.25 (m, 1H), 5.28 (bs, 1H, OH), 4.82 (d, J=14.0 Hz, 1H), 4.27 (d, J=14.0 Hz, 1H), 1.52 (s, 3H);

$^{19}$F NMR (CDCl$_3$, 400 MHz) δ −61.27, −120.39, −131.15; assigned by 2D NMR as NOE and COSY.

Example 21

Androgen Receptor Binding, Transactivation, and Metabolism of Indole, Benzimidazole, and Indazole SARDs Ligand Binding Assay Objective: To determine SARD binding affinity to the AR-LBD.

Method: hAR-LBD (633-919) was cloned into pGex4t.1. Large scale GST-tagged AR-LBD was prepared and purified using a GST column. Recombinant AR-LBD was combined with [$^3$H]mibolerone (PerkinElmer, Waltham, Mass.) in buffer A (10 mM Tris, pH 7.4, 1.5 mM disodium EDTA, 0.25 M sucrose, 10 mM sodium molybdate, 1 mM PMSF) to determine the equilibrium dissociation constant (K$_d$) of [$^3$H]mibolerone. Protein was incubated with increasing concentrations of [$^3$H]mibolerone with and without a high concentration of unlabeled mibolerone at 4° C. for 18 h in order to determine total and non-specific binding. Non-specific binding was then subtracted from total binding to determine specific binding and non-linear regression for ligand binding curve with one site saturation to determine the K$_d$ of mibolerone.

Increasing concentrations of SARDs or DHT (range: 10$^{-12}$ to 10$^{-2}$ M) were incubated with [$^3$H]mibolerone and AR LBD using the conditions described above. Following incubation, the ligand bound AR-LBD complex was isolated using BioGel® HT hydroxyapatite, washed and counted in a scintillation counter after adding scintillation cocktail. Values are expressed as K.

Transactivation Assay for Wt and Mutant AR

Objective: To determine the effect of SARDs on androgen-induced transactivation of AR wildtype (wt) or AR carrying known AR-LBD mutants (i.e., W741L or T877A).

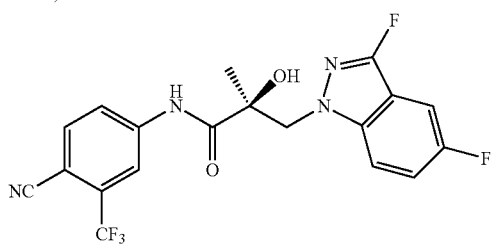

98

Figure 37A:
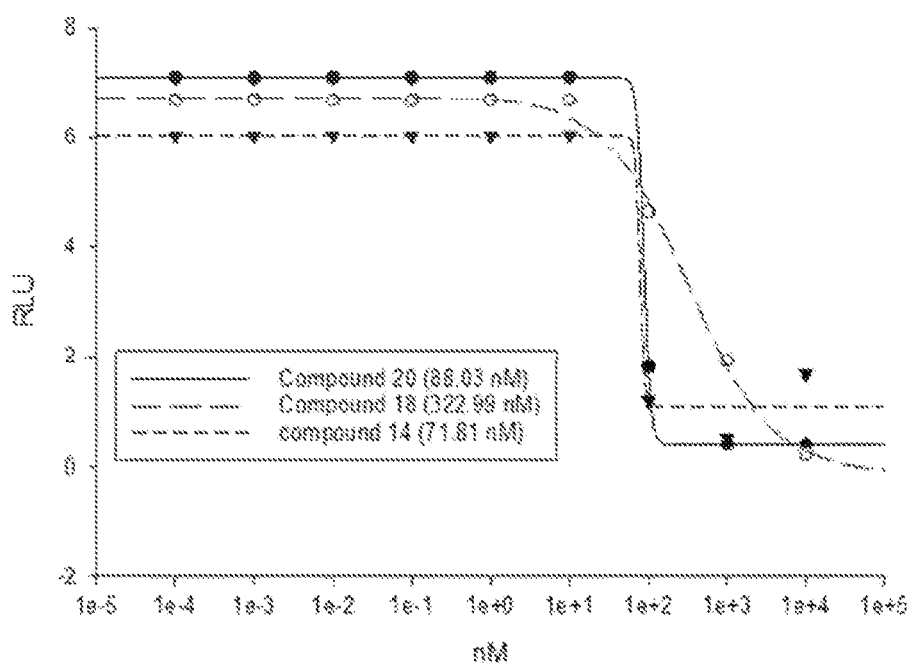
FIGS. 37A-37C present inhibition of AR transactivation for the SARD compounds.
Figure 37A:
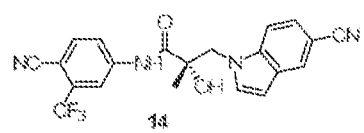
Figure 37A:
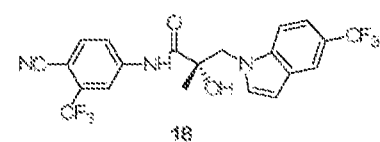
Figure 37A:
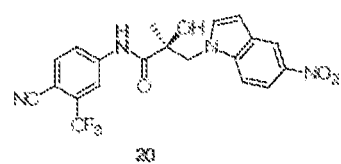
Figure 37B:
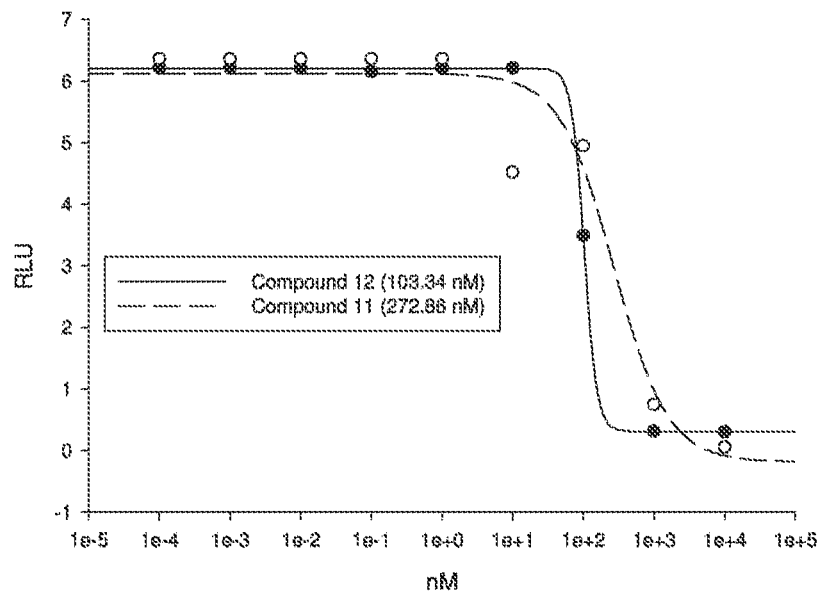
Figure 37B:
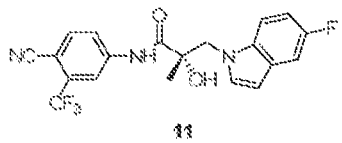
Figure 37B:
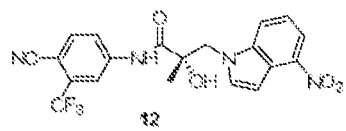
Figure 37C:
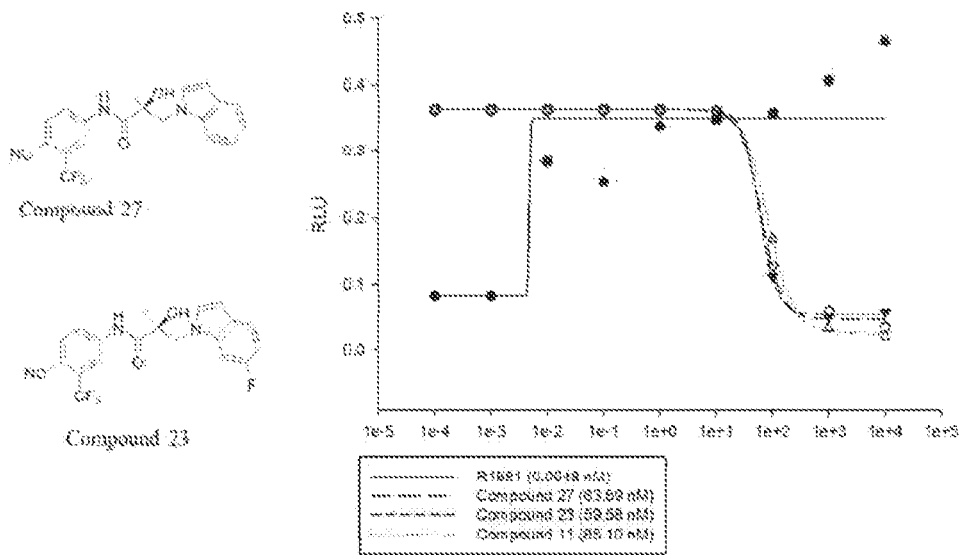

Method: HEK-293 cells were plated at 125,000 cells/well of a 24 well plate in DME+5% csFBS without phenol red. Cells were transfected with 0.25 ug GRE-LUC, 10 ng CMV-renilla LUC, and 50 ng CMV-hAR(wt) or CMV-hAR (W741L) or CMV-hAR(T877A) using lipofectamine transfection reagent in optiMEM medium. Medium was changed 24 h after transfection to DME+5% csFBS without phenol red and treated with a dose response of various drugs (Table 5: 11-18, 20-27, 30, 31, 33, 70-74) (1 µM to 10 µM). SARDs and antagonists were treated in combination with known agonist 0.1 nM R1881 in order to produce an antagonism curve. Luciferase assay was performed 24 h after treatment on a Biotek synergy 4 plate reader. Firefly luciferase values were normalized to renilla luciferase values. For FIG. 37A-37C, the following variation of the method was used:

HEK cells were plated in 24 well plates at 60,000 cells per well in DMEM +5% csFBS without phenol red. After overnight incubation, changed medium to OptiMEM (0.25 ml). All the wells were transfected with 0.25 ug GRE-LUC, 5 ng CMV-renilla LUC, and 25 ng CMV-hAR. Twenty four hours after transfection, medium was replaced with 1 ml of DME +5% csFBS without phenol red. Twenty-four hrs after transfection, the cells were treated with 20, 18, and 14 (FIG. 37A), 12 and 11 (FIG. 37B), 11, 27, and 23 (FIG. 37C), or 34-42 (FIGS. 65A, 65B, 65D-65I, 65K, & 65O) and were harvested 48 hrs after transfection and firefly and renilla luciferase assay performed. Transactivation. HEK-293 cells were plated at 120,000 cells per well of a 24 well plate in DME+5% csFBS. The cells were transfected using Lipofectamine (Invitrogen, Carlsbad, Calif.) with 0.25 µg GRE-LUC, 0.01 µg CMV-LUC (renilla luciferase) and 25 ng of the AR, PR, GR, or MR. The cells were treated 24 hrs after transfection as indicated in the figures and the luciferase assay performed 48 hrs after transfection. Data are represented as $IC_{50}$ values obtained from four parameter logistics curve.

AR Degradation Using Compounds of this Invention

Objective: To determine the efficacy and potency of AR degradation by SARD compounds in AD1 cells (full-length), LNCaP (T877A AR), D567es (splice variant lacking exons 5,6,&7) or 22RV-1 (full length AR and truncated splice variant AR (AR-V7)) cell lines.

Method: See Example 22 below.

Determination of Metabolic Stability (In Vitro $CL_{int}$) of Test Compounds:

Phase I Metabolism

The assay was done in a final volume of 0.5 ml in duplicates (n=2). Test compound (1 µM) was pre-incubated for 10 minutes at 37° C. in 100 mM Tris-HCl, pH 7.5 containing 0.5 mg/ml liver microsomal protein. After pre-incubation, reaction was started by addition of 1 mM NADPH (pre-incubated at 37° C.). Incubations were carried out in triplicate and at various time-points (0, 5, 10, 15, 30 and 60 minutes) 100 µl aliquots were removed and quenched with 100 µl of acetonitrile containing internal standard. Samples were vortex mixed and centrifuged at 4000 rpm for 10 minutes. The supernatants were transferred to 96 well plates and submitted for LC-MS/MS analysis. As control, sample incubations done in absence of NADPH were included. From % PCR (% Parent Compound Remaining), rate of compound disappearance is determined (slope) and in vitro $CL_{int}$ (µl/min/mg protein) was calculated.

Metabolic Stability in Phase I & Phase II Pathways

In this assay, test compound was incubated with liver microsomes and disappearance of drug was determined using discovery grade LC-MS/MS. To stimulate Phase II metabolic pathway (glucuronidation), UDPGA and alamethicin was included in the assay.

LC-MS/MS analysis: The analysis of the compounds under investigation was performed using LC-MS/MS system consisting of Agilent 1100 HPLC with an MDS/Sciex 4000 Q-Trap™ mass spectrometer. The separation was achieved using a C18 analytical column (Alltima, 2.1×100 mm, 3 µm) protected by a C18 guard cartridge system (SecurityGuard™ ULTRA Cartridges UHPLC for 4.6 mm ID columns, Phenomenex). Mobile phase was consisting of channel A (95% acetonitrile+5% water+0.1% formic acid) and channel C (95% water+5% acetonitrile+0.1% formic acid) and was delivered at a flow rate of 0.4 mL/min. The volume ratio of acetonitrile and water was optimized for each of the analytes. Multiple reaction monitoring (MRM) scans were made with curtain gas, collision gas, nebulizer gas, and auxiliary gas optimized for each compound, and source temperature at 550° C. Molecular ions were formed using an ion spray voltage (IS) of −4200 V (negative mode). Declustering potential, entrance potential, collision energy, product ion mass, and cell exit potential were optimized for each compound.

Log P: Octanol-Water Partition Coefficient (Log P)

Log P is the log of the octanol-water partition coefficient, commonly used early in drug discovery efforts as a rough estimate of whether a particular molecule is likely to cross biological membranes. Log P was calculated using ChemDraw Ultra version is 12.0.2.1016 (Perkin-Elmer, Waltham, Mass. 02451). Calculated Log P values are reported in Tables 7 & 10 in the column labeled Log P (−0.4 to +5.6). Lipinski's rule of five is a set of criteria intended to predict oral bioavailability. One of these criteria for oral bioavailability is that the Log P is between the values shown in the column heading (−0.4 (relatively hydrophilic) to +5.6 (relatively lipophilic) range), or more generally stated <5. One of the goals of SARD design was to improve water solubility.

TABLE 5

AR Binding, Inhibition of AR (wt and Mutant) Transactivation, AR Degradation and in vitro Metabolic Stability of Indole and Benzimidazole SARDs.

| Compound | Binding $K_i$ (nM) | Transactivation (+0.1 nM R1881; R1881 $EC_{50}$ = 0.11 nM) | | | SARD activity (FIG. numbers herein) | $T_{1/2}$ (min) $CL_{int}$ (µl/min/mg) |
|---|---|---|---|---|---|---|
| | | Wt $IC_{50}$ (nM) | W741L $IC_{50}$ (nM) | T877A $IC_{50}$ (nM) | | |
| DHT | 1 | — | — | — | | |
| R-Bicalutamide | 545.5 | 248.2 | — | 557 | | |
| Enzalutamide | 205.2 | 216.3 | 939 | 331.94 | 39, 45C | |
| ARN-509 (apalutamide) | — | 297.0 | 1939.41 | 390.50 | 39, 41, 42B, 50 | |

TABLE 5-continued

AR Binding, Inhibition of AR (wt and Mutant) Transactivation, AR Degradation and in vitro Metabolic Stability of Indole and Benzimidazole SARDs.

| Compound | Binding $K_i$ (nM) | Transcriptional Activation (+0.1 nM R1881; R1881 $EC_{50}$ = 0.11 nM) | | | SARD activity (FIG. numbers herein) | $T_{1/2}$ (min) $CL_{int}$ (µl/min/mg) |
|---|---|---|---|---|---|---|
| | | Wt $IC_{50}$ (nM) | W741L $IC_{50}$ (nM) | T877A $IC_{50}$ (nM) | | |
| ASC-J9 | — | 1008.0 | 3487.68 | 2288.16 | 41, 42A | |
| 11 | 57.8 | 33.4-272 | 13.68 | 48.47 | 38A, 39, 41, 42C, 45C | 12.35 min 56.14 µl/min/mg |
| 11R | — | 351.21 | — | — | | |
| 12 | 314.22 | 103.34 | | | 39, 47, 50 | 37.27 18.6 |
| 13 | 625.01 | — | | | 39 | |
| 14 | 223.74 | 71.81 (partial) | | | | 15.97 43.4 |
| 15 | >10,000 | — | | | | 29.79 23.28 |
| 16 | 489.88 | 2285.14 | | | | |
| 17 | 80.43 | | | | | |
| 18 | 416.03 | 322.99 | | | | 21.07 32.9 |
| 20 | 432.69 | 88.03 | | | 38A, 39, 40, 47, 48 | 19.27 35.97 |
| 21 | 293.84 | 984.52 | | | | 20.37 34.02 |
| 22 | 419.35 | 126.73 | | | | 36.32 19.08 |
| 23 | 212.49 | 85.10 | | | 47 | 22.39 30.96 |
| 24 | 315.84 | 917.68 | | | 48 | 17.02 40.73 |
| 27 | 2079.94 | 63.69 | | | 47 | 13.66 50.75 |
| 30 | 995.23 | 971.78 (11 38 nM in the same exp) | | | 48 | 25.78 26.89 |
| 31 | 547.27 | 157.41 | | | 49, 51 | 21.77 31.84 |
| 33 | >10,000 | 684.64 | | | | |
| 70 | 530.72 | 299.78 | | | 52 | |
| 72 | — | 1016 | | | | |
| 32 | 46.58 | 57.76 | | | 47 | 13.48 51.43 |
| 73 | 724.07 | 998.56 | | | 52 | |
| 74 | 1399.69 | 720.61 | | | | |

The short half-lives ($t_{1/2}$) and high metabolic clearance ($CL_{int}$) values in vitro of many of the compounds of this invention suggest rapid plasma clearance which could be favorable for topical treatment of androgenic dermatologic disorders as it would limit the risk of systemic side effects, even if the skin is penetrated.

Figure 73A:
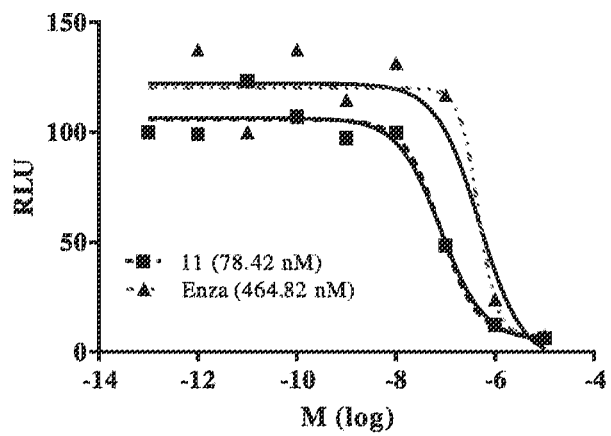
FIGS. 73A-73E depict inhibition of AR function by 11. AR ligand binding assay was performed with GST-tagged purified human AR-LBD protein producing a Ki of 78.06 nM (data not shown). 11 potently inhibits AR transactivation. AR transactivation was performed by transfecting human AR cDNA, GRE-LUC, and CMV-renilla LUC into HEK-293 cells. Cells were treated 24 hrs after transfection with a dose response of antagonists in combination with 0.1 nM R1881 and luciferase assay was performed 48 hrs after transfection. Values provided are $IC_{50}$ (FIG. 73A). 11, but not enzalutamide, comparably inhibits transactivation of wildtype and LBD-mutant AR. Transactivation assay with 11 or enzalutamide was performed with wildtype AR or AR carrying commonly known LBD mutants (FIG. 73B). 11 cross-reacts with progesterone receptor (PR), but minimally with mineralocorticoid receptor (MR) or glucocorticoid receptor (GR). Transactivation was performed by transfecting human AR, PR, GR, or MR cDNA, GRE-LUC, and CMV-renilla LUC into HEK-293 cells. Cells were treated 24 hrs after transfection with indicated doses of 11 in combination with 0.1 nM progesterone (PR), dexamethasone (GR), and aldosterone (MR) and luciferase assay was performed 48 hrs after transfection (FIG. 73C). 11 inhibits AR-65Q transactivation. Transactivation assay with an AR cDNA that has extended poly-glutamide repeat (65Q) was performed (FIG. 73D). 11 inhibits AR N-C interaction. Mammalian two hybrid assay was performed by transfecting HEK-293 cells with VP16-ARNTD, Gal-4-DBD-ARLBD, Gal-4-RE-LUC, and CMV-renilla-luciferase. Cells were treated 24 hours after transfection with a dose response of 11 in combination with 0.1 nM R1881, and luciferase assay was performed 48 hours after transfection. All experiments were performed at least twice with a dose range of 1 pM to 10 µM. Enza-Enzalutamide.
Figure 73B:
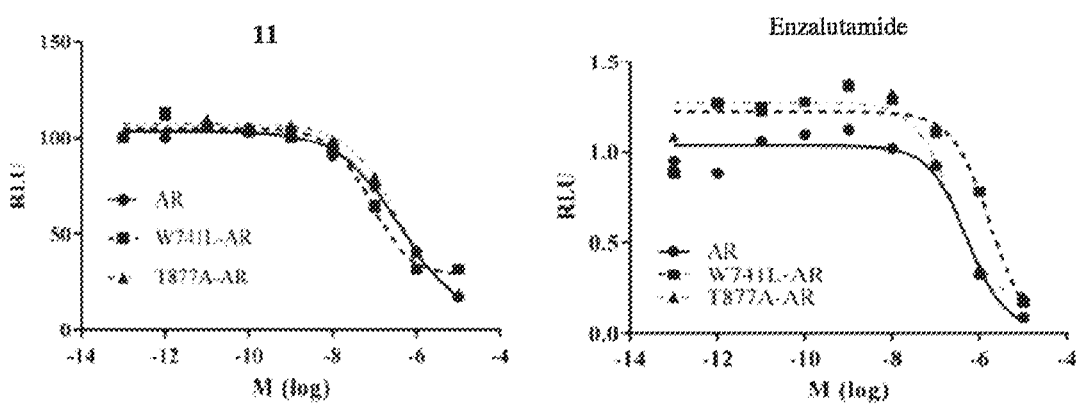
Figure 73C:
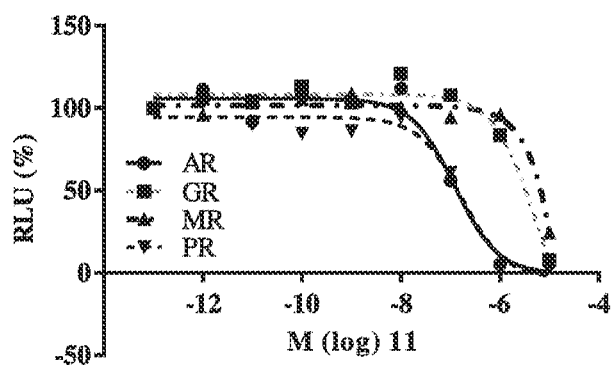

AR transactivation assay was performed with wildtype, W741L, and T877A AR constructs. W741 mutation to leucine or cysteine (L/C) confers resistance to bicalutamide (Hara, T., Miyazaki, J., Araki, H., Yamaoka, M., Kanzaki, N., Kusaka, M., and Miyamoto, M. (2003). Novel mutations of androgen receptor: a possible mechanism of bicalutamide withdrawal syndrome. Cancer research 63, 149-153), while T877 mutation results in resistance to hydroxyflutamide (Tan, J., Sharief, Y., Hamil, K. G., Gregory, C. W., Zang, D. Y., Sar, M., Gumerlock, P. H., deVere White, R. W., Pretlow, T. G., Harris, S. E., et al. (1997). Dehydroepiandrosterone activates mutant androgen receptors expressed in the androgen-dependent human prostate cancer xenograft CWR22 and LNCaP cells. Mol Endocrinol 11, 450-459). 11 potently inhibited the R1881-induced wildtype AR transactivation with much higher potency than enzalutamide (FIG. 73A). While 11 effectively antagonized both wildtype and mutant ARs comparably, similar to enzalutamide, was weaker in W741L mutant AR (FIG. 73B). Although 11 inhibited glucocorticoid receptor (GR) and mineralocorticoid receptor (MR) transactivation only at ~10 µM, it cross-reacted with the progesterone receptor (PR) robustly (FIG. 73C).

Kennedy's disease is a neuromuscular disease caused by AR with an extended polyglutamine tract (La Spada, A. R., Wilson, E. M., Lubahn, D. B., Harding, A. E., and Fischbeck, K. H. (1991). Androgen receptor gene mutations in X-linked spinal and bulbar muscular atrophy. Nature 352, 77-79). While in normal healthy humans, the AR contains 15-24 polyglutamines, in patients suffering from Kennedy's disease, the polyglutamine tracts are extended to over 40 or even 100 repeats (La Spada et al., 1991). This extended polyglutamine tract results in AR mis-folding causing neuromuscular toxicity (La Spada et al., 1991).

Figure 73D:
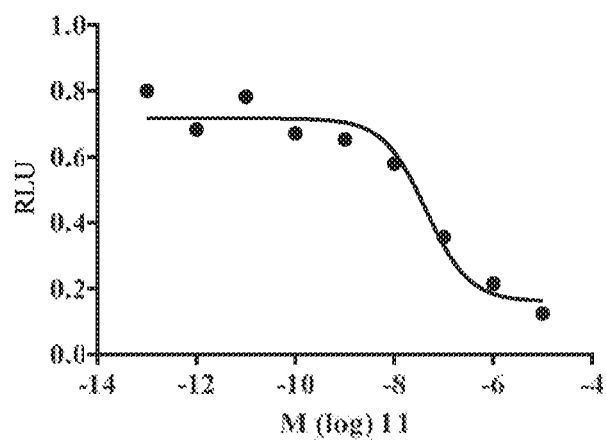

11 was tested in a transactivation assay with the AR containing an extended polyglutamine tract. 11 inhibited the R1881-stimulated transactivation of the AR that contains 65 polyglutamine repeats (FIG. 73D) with an $IC_{50}$ value comparable to that observed with the wildtype AR.

Figure 73E:
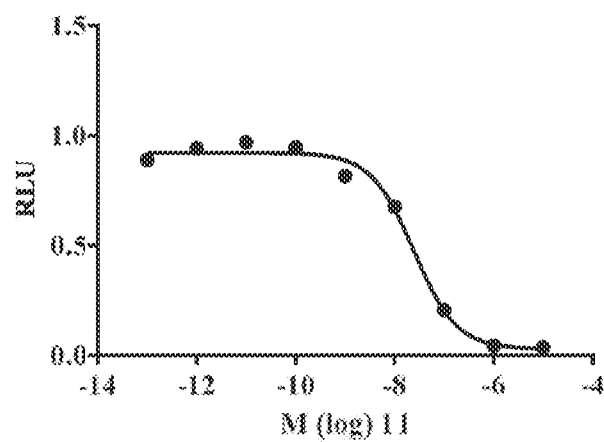

AR N-C interaction is a measure of the AR activity (He et al., 2002) and inhibiting the AR N-C interaction is another measure of antagonistic activity. A mammalian two hybrid assay was performed with a Gal-4-DBD-fused AR-LBD, VP16 activation domain fused AR-NTD, and a dose response of 11. 11 inhibited the R1881-induced AR N-C interaction at concentrations comparable to that observed in AR transactivation (FIG. 73E).

TABLE 6

Binding Affinity of Indole SARDs of this Invention.

| Compound | $K_i$ (nM) | Relative binding affinity (RBA) |
|---|---|---|
| DHT | 8.88 | 1.00 |
|  | 6.62 |  |
| 12 | 817.3 | 0.011 |
| 11 | 57.8 | 0.152 |
| 11R | 333.07 | 0.027 |

TABLE 6-continued

Binding Affinity of Indole SARDs of this Invention.

| Compound | $K_i$ (nM) | Relative binding affinity (RBA) |
|---|---|---|
| 14 | 179.77 | 0.049 |
| 15 | 663.05 | 0.010 |

FIG. 37A-37C and FIGS. 65A-65C and Tables 5-7 show that many of the SARDs of this invention had higher AR binding affinity (see tables) and more potent AR antagonism in vitro (see Tables 5-8 and figures referenced above and in the tables) than all the other AR antagonists tested (bicalutamide, enzalutamide, ARN-509, and ASC-J9). Further compounds 11 (Table 5 above) and 96 (Table 14 of Example 26) retained highly potent antagonist activity in the two resistance mutants tested unlike the known antiandrogens tested.

TABLE 7

AR Binding ($K_i$), Inhibition of AR Transactivation ($IC_{50}$), AR Degradation and Metabolic Stability of Indole Based SARDs.

| Compd ID | Structure | Log P (−0.4 to +5.6) | Binding/Transactivation (wt AR) $K_i$ (nM) (DHT = 1 nM) | $IC_{50}$ (nM) | SARD Activity Full Length % inhibition at 1, 10 μM | S.V. (22RV1) % inhibition at 10 μM | DMPK (MLM) $T_{1/2}$ (min) $CL_{int}$ (μl/min/mg) |
|---|---|---|---|---|---|---|---|
| Enobosarm | 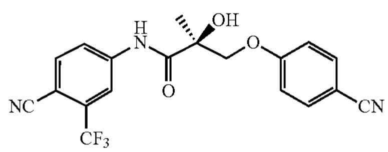 [SMILES: C[C@](O)(COc1ccc(C#N)cc1)C(=O)Nc1ccc(C#N)c(C(F)(F)F)c1] | 3.44 | 20.21 | ~20 |  |  |  |
| R-Bicalutamide | 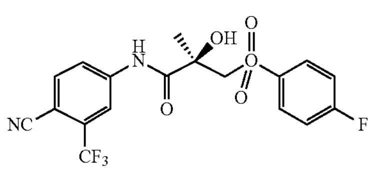 | 2.57 | 508.84 | 248.2 |  |  |  |
| Enzalutamide | 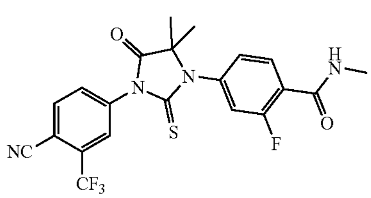 [SMILES: CNC(=O)c1ccc(N2C(=S)N(c3ccc(C#N)c(C(F)(F)F)c3)C(=O)C2(C)C)cc1F] | 4.56 | 3641.29 | 216.3 |  |  |  |
| ARN-509 (apalutamide) | 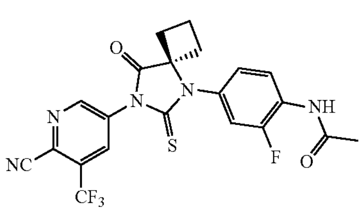 | 3.47 | 1452.29 |  | 0 | 0 |  |
|  |  | 2.57 | 87.67 | — |  |  |  |

TABLE 7-continued

AR Binding (K$_i$), Inhibition of AR Transactivation (IC$_{50}$), AR Degradation and Metabolic Stability of Indole Based SARDs.

| | | | Binding/Transactivation (wt AR) | | SARD Activity | | DMPK (MLM) |
| | | | | | Full | S.V. (22RV1) | |
| Compd ID | Structure | Log P (−0.4 to +5.6) | K$_i$ (nM) (DHT = 1 nM) | IC$_{50}$ (nM) | Length % inhibition at 1, 10 μM | % inhibition at 10 μM | T$_{1/2}$ (min) CL$_{int}$ (μl/ min/mg) |
|---|---|---|---|---|---|---|---|
| | (structure) | 1.86 | 407.08 | | | | |
| 27 | (structure) | 3.31 | 2079.94 | 63.69 | 13, 89 | | 13.66 / 50.75 |
| 22 | (structure) | 3.47 | 419.35 | 126.73 | 54, 81 | | 36.32 / 19.08 |
| 11 | (structure) | 3.47 | 267.39 | 85.10 | 65-83 | 60-100 | 12.35 / 56.14 |
| 11R | (structure) | 3.47 | >10000 | 589.84 | 83 | | |
| 23 | (structure) | 3.47 | 212.49 | 85.10 | 0, 100 | | 22.39 / 30.96 |
| 12 | (structure) | 3.34 | 314.22 | 103.34 | 43, 100 | | 37.27 / 18.6 |
| 20 | (structure) | 3.34 | 432.69 | 88.03 | 45, 100 | 78 | 19.27 / 35.97 |

TABLE 7-continued

AR Binding (K$_i$), Inhibition of AR Transactivation (IC$_{50}$), AR Degradation and Metabolic Stability of Indole Based SARDs.

| | | | Binding/Transactivation (wt AR) | | SARD Activity | | DMPK (MLM) |
|---|---|---|---|---|---|---|---|
| | | | | | Full | S.V. (22RV1) | |
| Compd ID | Structure | Log P (−0.4 to +5.6) | K$_i$ (nM) (DHT = 1 nM) | IC$_{50}$ (nM) | Length % inhibition at 1, 10 µM | % inhibition at 10 µM | T$_{1/2}$ (min) CL$_{int}$ (µl/min/mg) |
| 32 | [structure: NC-phenyl(CF3)-NH-C(=O)-C(CH3)(OH)-CH2-N(indole-6-NO2)] | 3.34 | 46.58 | 57.76 | 0, 100 | | 13.48 51.43 |
| 24 | [structure: NC-phenyl(CF3)-NH-C(=O)-C(CH3)(OH)-CH2-N(indole-6-Br)] | 4.14 | 315.84 | 917.68 | | 0 | 17.02 40.73 |
| 21 | [structure: NC-phenyl(CF3)-NH-C(=O)-C(CH3)(OH)-CH2-N(indole-I)] | 4.67 | 293.84 | 984.52 | | 13 | 20.37 34.02 |
| 18 | [structure: NC-phenyl(CF3)-NH-C(=O)-C(CH3)(OH)-CH2-N(indole-CF3)] | 4.23 | 416.03 | 335.98 | 74, 79 | 47 | 21.07 32.9 |
| 16 | [structure: NC-phenyl(CF3)-NH-C(=O)-C(CH3)(OH)-CH2-N(indole-OCH3)] | 3.18 | 489.88 | 2285.14 | | | |
| 13 | [structure: NC-phenyl(CF3)-NH-C(=O)-C(CH3)(OH)-CH2-N(indole-CH3)] | 3.80 | 625.01 | — | 52, 86 | | |
| 17 | [structure: NC-phenyl(CF3)-NH-C(=O)-C(CH3)(OH)-CH2-N(indole-Cl)] | 3.87 | 80.43 | 545.48 | 0, 0 | | |
| 14 | [structure: NC-phenyl(CF3)-NH-C(=O)-C(CH3)(OH)-CH2-N(indole-CN)] | 3.34 | 223.74 | 71.81 (partial antagonism) 1018.73 (agonist (EC$_{50}$)) | | | 15.97 43.4 |

TABLE 7-continued

AR Binding (K$_i$), Inhibition of AR Transactivation (IC$_{50}$), AR Degradation and Metabolic Stability of Indole Based SARDs.

| Compd ID | Structure | Log P (−0.4 to +5.6) | Binding/Transactivation (wt AR) K$_i$ (nM) (DHT = 1 nM) | IC$_{50}$ (nM) | SARD Activity Full Length % inhibition at 1, 10 μM | S.V. (22RV1) % inhibition at 10 μM | DMPK (MLM) T$_{1/2}$ (min) CL$_{int}$ (μl/min/mg) |
|---|---|---|---|---|---|---|---|
| 15 | | 2.87 | >10,000 | — | | | 29.79 23.28 |
| 19 | | 5.33 | | — | | | |
| | | 6.09 | | — | | | |
| 30 | | 3.47 | 995.23 | 971.78 (11 was 38 nM in the same exp) | | | 25.78 26.89 |
| 31 | | 3.95 | 547.27 | 157.41 | | | 21.77 31.84 |
| 70, 71 (mixture) | | 2.70 | 530.72 | 299.78 | 50 | | 48.58 14.27 |

TABLE 7-continued

AR Binding (K$_i$), Inhibition of AR Transactivation (IC$_{50}$), AR Degradation and Metabolic Stability of Indole Based SARDs.

Figure 69A:
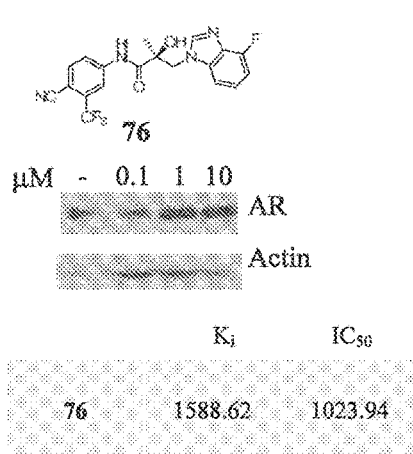
Figure 69B:
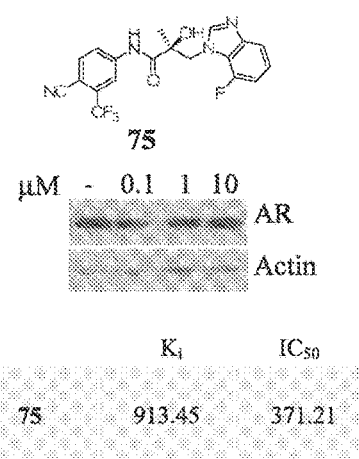

| | | | Binding/Transactivation (wt AR) | | SARD Activity | | DMPK (MLM) |
|---|---|---|---|---|---|---|---|
| | | | | | Full | S.V. (22RV1) | |
| Compd ID | Structure | Log P (−0.4 to +5.6) | K$_i$ (nM) (DHT = 1 nM) | IC$_{50}$ (nM) | Length % inhibition at 1, 10 μM | % inhibition at 10 μM | T$_{1/2}$ (min) CL$_{int}$ (μl/min/mg) |
| 72 | | 4.56 | — | 1016 | | | |
| 73 | | 2.86 | 724.07 | 998.56 | 7, 68 | | |
| 74 | | 3.50 | 1399.69 | 720.61 | 51 | 0 | |
| 75 | | 2.70 | >1000 | 973.15 | 14 (Figure 69B) | | |
| 76 | | 2.70 | 1588.62 | 1023.94 | (Figure 69A) | | |
| 77 | | 3.47 | 492.56 | >10,000 | 50 | | |
| 78 | | 3.47 | 474.38 | 3616 | 76 | | |
| 79 | | 2.34 | 882.75 | 1661.97 | | | |

TABLE 7-continued

AR Binding (K$_i$), Inhibition of AR Transactivation (IC$_{50}$), AR Degradation and Metabolic Stability of Indole Based SARDs.

| Compd ID | Structure | Log P (−0.4 to +5.6) | K$_i$ (nM) (DHT = 1 nM) | IC$_{50}$ (nM) | Full Length % inhibition at 1, 10 μM | S.V. (22RV1) % inhibition at 10 μM | DMPK (MLM) T$_{1/2}$ (min) CL$_{int}$ (μl/min/mg) |
|---|---|---|---|---|---|---|---|
| 80 | 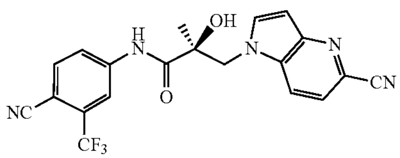 [SMILES: C[C@](O)(Cn1ccc2nc(C#N)ccc21)C(=O)Nc1ccc(C#N)c(C(F)(F)F)c1] | 2.85 | >10,000 | 684.64 | | | |
| 33 | 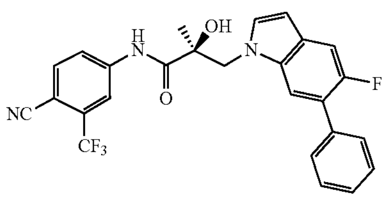 [SMILES: C[C@](O)(Cn1ccc2cc(F)c(-c3ccccc3)cc21)C(=O)Nc1ccc(C#N)c(C(F)(F)F)c1] | 5.14 | 124.66 | 214.66 | 54 | 22 | 15.43 44.94 |
| 34 | 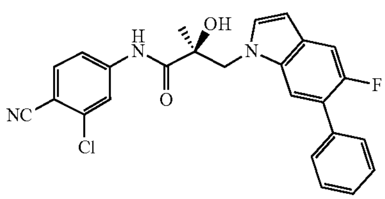 [SMILES: C[C@](O)(Cn1ccc2cc(F)c(-c3ccccc3)cc21)C(=O)Nc1ccc(C#N)c(Cl)c1] | 4.78 | 132.94 See Figure 65O | 202.67 See Figure 65O | 55 (Figure 65O) | 41 (Figure 65O) | 9.131 75.91 |
| 35 | 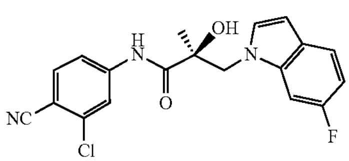 [SMILES: C[C@](O)(Cn1ccc2ccc(F)cc21)C(=O)Nc1ccc(C#N)c(Cl)c1] | 3.10 | 155.74 See Figure 65K | 98.47 | 65, 80 (Figure 65K) | 0 | |
| 36 | 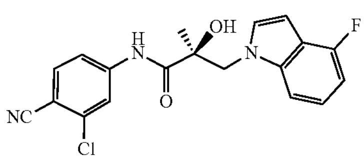 [SMILES: C[C@](O)(Cn1ccc2c(F)cccc21)C(=O)Nc1ccc(C#N)c(Cl)c1] | 3.10 | 315.32 See Figure 65I | 141.99 See Figure 65I | 71 (Figure 65I) | 41 | 11.77 58.8 |
| 37 | 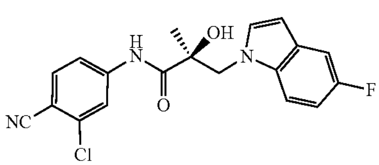 [SMILES: C[C@](O)(Cn1ccc2cc(F)ccc21)C(=O)Nc1ccc(C#N)c(Cl)c1] | 3.10 | 252.58 See Figure 65H | 94.33 See Figure 65H | 81 (Figure 65H) | 30 (Figure 65H) | |
| 38 | 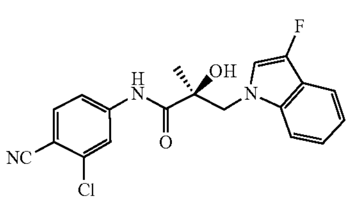 [SMILES: C[C@](O)(Cn1cc(F)c2ccccc21)C(=O)Nc1ccc(C#N)c(Cl)c1] | 3.10 | 331.79 (Figure 65G) | 44.50 (Figure 65G) | 68 (100 nM) (Figure 65G) | 62 (Figure 65G) | 9.291 74.6 |

TABLE 7-continued

AR Binding (K$_i$), Inhibition of AR Transactivation (IC$_{50}$), AR Degradation and Metabolic Stability of Indole Based SARDs.

Figure 69C:
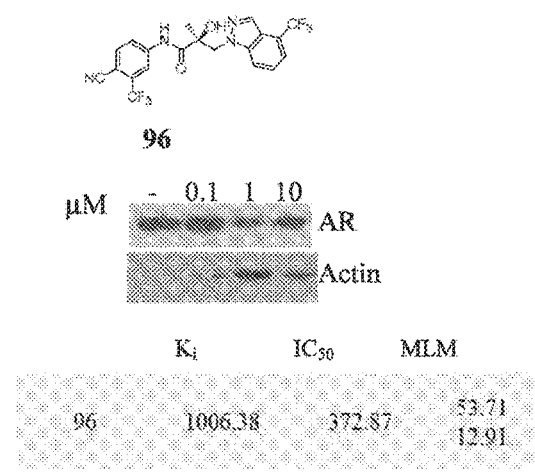

| | | | Binding/Transactivation (wt AR) | | SARD Activity | | DMPK (MLM) |
|---|---|---|---|---|---|---|---|
| | | | | | Full | S.V. (22RV1) | |
| Compd ID | Structure | Log P (−0.4 to +5.6) | K$_i$ (nM) (DHT = 1 nM) | IC$_{50}$ (nM) | Length % inhibition at 1, 10 μM | % inhibition at 10 μM | T$_{1/2}$ (min) CL$_{int}$ (μl/min/mg) |
| 39 | | 3.10 | 719.81 (Figure 65F) | 233.8 (Figure 65F) | 40 (Figure 65F) | 45 | |
| 90, 91 (mixture) | | 3.08, 3.45 | 806.67 | 851.94 | 0 | 8 | |
| 92, 93 (mixture) | | 2.72, 3.08 | No binding (Figure 65E) | 946.84 (Figure 65E) | 40 (Figure 65E) | 80 (Figure 65E) | |
| 94 | | 3.08 | 137.47 | 172.86 | 92 | 34 | 13.29 52.16 |
| 95 | | 3.45 | 171.84 | No effect | 0 | 0 | |
| 96 | | 3.84 | 1006.38 | 372.87 | 70 (Figure 69C) | | 53.71 12.91 |

TABLE 7-continued

AR Binding (K_i), Inhibition of AR Transactivation (IC_{50}), AR Degradation and Metabolic Stability of Indole Based SARDs.

Figure 69D:
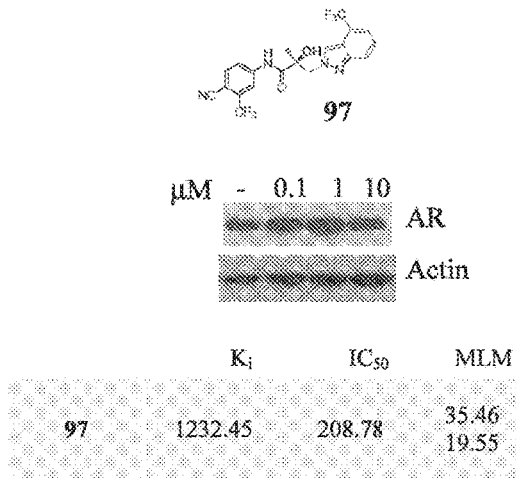

| Compd ID | Structure | Log P (−0.4 to +5.6) | $K_i$ (nM) (DHT = 1 nM) | $IC_{50}$ (nM) | SARD Activity Full Length % inhibition at 1, 10 μM | S.V. (22RV1) % inhibition at 10 μM | DMPK (MLM) $T_{1/2}$ (min) $CL_{int}$ (μl/min/mg) |
|---|---|---|---|---|---|---|---|
| | | | Binding/Transactivation (wt AR) | | | | |
| 97 | | 4.21 | 1232.45 | 208.78 | (Figure 69D) | | 35.46 19.55 |
| 98 | | 3.71 | | 182.1 | | | |
| 40 | | 4.78 | 134.88 See Figure 65D | 1032.14 See Figure 65D | 0 | 0 | |
| 41 | | 4.98 | 84.32 See Figure 65B | >10000 See Figure 65 | 0 | 0 | |
| 42 | | 5.14 | 86.18 See Figure 65A | 1015.12 See Figure 65A | 0 | 0 | |
| 43 | | 5.3 | 62.34 | 897.5 | 100 | | |
| 44 | | 3.63 | 317.64 | 274.3 | 72 | 84 | |

TABLE 7-continued

AR Binding (K_i), Inhibition of AR Transactivation (IC_50), AR Degradation and Metabolic Stability of Indole Based SARDs.

| Compd ID | Structure | Log P (−0.4 to +5.6) | Binding/Transactivation (wt AR) | | SARD Activity | | DMPK (MLM) |
| | | | $K_i$ (nM) (DHT = 1 nM) | IC$_{50}$ (nM) | Full Length % inhibition at 1, 10 µM | S.V. (22RV1) % inhibition at 10 µM | T$_{1/2}$ (min) CL$_{int}$ (µl/min/mg) |
|---|---|---|---|---|---|---|---|
| 45 | [structure] | 4.03 | 754.7 | 366.9 | 60 | 80 | |
| 46 | [structure] | 3.7 | 134.19 | 133.1 | 90 | 100 | |

TABLE 7A

AR Binding (K_i), Inhibition of AR Transactivation (IC_50), AR Degradation and in vitro Metabolic Stability of SARDs.

| Compd ID | Structure | Log P (−0.4 to +5.6) | Binding/Transactivation (wt AR) | | SARD Activity | | DMPK (MLM) |
| | | | $K_i$ (nM) (DHT = 1 nM) | IC$_{50}$ (nM) | Full Length % inhibition at 1, 10 µM | S.V. (22RV1) % inhibition at 10 µM | T$_{1/2}$ (min) CL$_{int}$ (µl/min/mg) |
|---|---|---|---|---|---|---|---|
| Enobosarm | [structure] | 3.44 | 20.21 | ~20 | | | |
| R-Bicalutamide | [structure] | 2.57 | 508.84 | 248.2 | | | |
| Enzalutamide | [structure] | 4.56 | 3641.29 | 216.3 | | | |

TABLE 7A-continued

AR Binding (K$_i$), Inhibition of AR Transactivation (IC$_{50}$), AR Degradation and in vitro Metabolic Stability of SARDs.

| Compd ID | Structure | Log P (−0.4 to +5.6) | Binding/ Transactivation (wt AR) | | SARD Activity | | DMPK (MLM) T$_{1/2}$ |
| --- | --- | --- | --- | --- | --- | --- | --- |
| | | | K$_i$ (nM) (DHT = 1 nM) | IC$_{50}$ (nM) | Full Length % inhibition at 1, 10 μM | S.V. (22RV1) % inhibition at 10 μM | (min) CL$_{int}$ (μl/min/ mg) |
| ARN-509 | | 3.47 | 1452.29 | | 0 | 0 | |
| | | 2.57 | 87.67 | — | | | |
| | | 1.86 | 407.08 | | | | |
| −300 | | 4.25 | No effect | | | | |
| −301 | | 3.87 | — | | | | |
| 302 | | 3.87 | — | | | | |
| 301/302 | | 3.87 | No effect | | | | |
| 303 | | 3.48 | 3615 | 277 | 70 | 0 | |

TABLE 7A-continued

AR Binding (K$_i$), Inhibition of AR Transactivation (IC$_{50}$), AR Degradation and in vitro Metabolic Stability of SARDs.

| Compd ID | Structure | Log P (−0.4 to +5.6) | Binding/ Transactivation (wt AR) | | SARD Activity | | DMPK (MLM) T$_{1/2}$ (min) CL$_{int}$ (μl/min/mg) |
|---|---|---|---|---|---|---|---|
| | | | K$_i$ (nM) (DHT = 1 nM) | IC$_{50}$ (nM) | Full Length % inhibition at 1, 10 μM | S.V. (22RV1) % inhibition at 10 μM | |
| 304 | 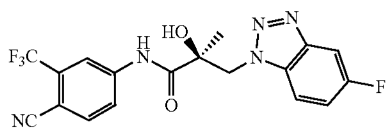 [SMILES: C[C@](O)(Cn1nnc2cc(F)ccc21)C(=O)Nc1ccc(C#N)c(C(F)(F)F)c1] | 3.11 | | 687 | 60 | 0 | |
| 305 | 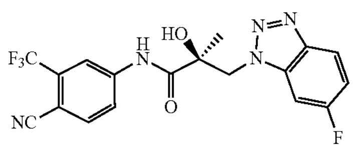 [SMILES: C[C@](O)(Cn1nnc2ccc(F)cc21)C(=O)Nc1ccc(C#N)c(C(F)(F)F)c1] | 3.11 | 1476 | 560 | 40 | 0 | |
| 307 | 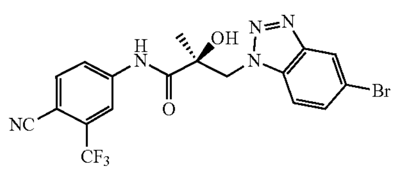 [SMILES: C[C@](O)(Cn1nnc2cc(Br)ccc21)C(=O)Nc1ccc(C#N)c(C(F)(F)F)c1] | 3.78 | | 2594 nM | | | |
| 308 | 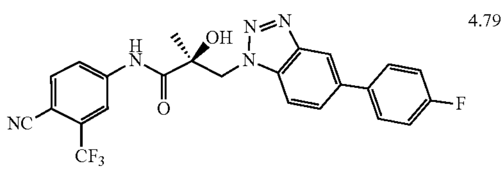 | 4.79 | | No effect | | | |

TABLE 8 4

Liver Microsome (LM) Data of Indole and Benzimidazole SARDs in Mouse LM (MLM), Human LM (HLM), Rat LM (RLM) and Dog LM (DLM).

| | MLM | | HLM | | RLM | | DLM | |
|---|---|---|---|---|---|---|---|---|
| Compd ID | T$_{1/2}$ (min) | CL$_{int}$ (μl/min/mg) | T$_{1/2}$ (min) | CL$_{int}$ (μl/min/mg) | T$_{1/2}$ (min) | CL$_{int}$ (μl/min/mg) | T$_{1/2}$ (min) | CL$_{int}$ (μl/min/mg) |
| 27 | 13.66 | 50.75 | | | | | | |
| 22 (4-F) | 36.32 | 19.08 | | | | | | |
| 11 (5-F) | 14.35 | 48.30 | 14.62 | 47.40 | | | | |
| 23 (6-F) | 22.39 | 30.96 | | | | | | |
| 12 (4-NO$_2$) | 37.27 | 18.60 | | | | | | |
| 20 (5-NO$_2$) | 19.27 | 35.97 | 17.97 | 38.57 | | | | |
| 32 (6-NO$_2$) | 13.48 | 51.43 | | | | | | |
| 24 (5-Br) | 17.02 | 40.73 | | | | | | |
| 21 (5-I) | 29.39 | 20.37 | | | | | | |
| 18 (5-CF$_3$) | 37.71 | 18.38 | | | | | | |
| 14 (5-CN) | 15.97 | 43.40 | | | | | | |
| 15 (3-CO$_2$H) | 29.78 | 23.28 | | | | | | |
| 30 | 25.78 | 26.89 | 13.77 | 0.05034 | | | | |
| 70, 71 | 48.58 | 14.27 | 16.36 | 42.37 | | | | |
| 31 | 21.77 | 31.84 | | | | | | |
| 33 | 15.43 | 44.94 | 7.31 | 94.82 | | | | |
| 34 | | | 9.131 | 75.91 | 15.50 | 58.87 | | |
| 38 | 9.291 | 74.6 | 6.611 | 104.9 | | | | |
| 36 | 11.77 | 58.8 | 12.66 | 54.7 | | | | |

Example 22

Androgen Receptor Binding and Transactivation, AR Degradation, and In Vitro Metabolism of Indoline, Quinolone and Isoquinoline Based SARDs (Tables 9-11)

Ligand Binding Assay

Objective: To determine SARDs binding affinity to the AR-LBD.

Method: hAR-LBD (633-919) was cloned into pGex4t.1. Large scale GST-tagged AR-LBD was prepared and purified using a GST column. Recombinant ARLBD was combined with [$^3$H]mibolerone (PerkinElmer, Waltham, Mass.) in buffer A (10 mM Tris, pH 7.4, 1.5 mM disodium EDTA, 0.25 M sucrose, 10 mM sodium molybdate, 1 mM PMSF) to determine the equilibrium dissociation constant ($K_d$) of [$^3$H]mibolerone. Protein was incubated with increasing concentrations of [$^3$H]mibolerone with and without a high concentration of unlabeled mibolerone at 4° C. for 18 h in order to determine total and non-specific binding. Non-specific binding was then subtracted from total binding to determine specific binding and non-linear regression for ligand binding curve with one site saturation to determine the $K_d$ of mibolerone.

Increasing concentrations of SARDs or DHT (range: $10^{-12}$ to $10^{-2}$M) were incubated with [$^3$H]mibolerone and AR LBD using the conditions described above. Following incubation, the ligand bound AR-LBD complex was isolated using Bio Gel HT® hydroxyapatite, washed and counted in a scintillation counter after adding scintillation cocktail. Values are expressed as $K_i$.

Transactivation Assay with wt AR

Objective: To determine the effect of SARDs on androgen-induced transactivation of AR wildtype (wt).

Method: HEK-293 cells were plated at 125,000 cells/well of a 24 well plate in DME+5% csFBS without phenol red. Cells were transfected with 0.25 ug GRE-LUC, 10 ng CMV-renilla LUC, and 50 ng CMV-hAR(wt) using Lipofectamine transfection reagent in optiMEM medium. Medium was changed 24 h after transfection to DME+5% csFBS without phenol red and treated with a dose response of various drugs (1 pM to 10 µM). SARDs and antagonists were treated in combination with 0.1 nM R1881. Luciferase assay was performed 24 h after treatment on a Biotek synergy 4 plate reader. Firefly luciferase values were normalized to renilla luciferase values. (Tables 9 and 10)

Plasmid Constructs and Transient Transfection.

Human AR cloned into CMV vector backbone was used for the transactivation study. HEK-293 cells were plated at 120,000 cells per well of a 24 well plate in DME+5% csFBS. The cells were transfected using Lipofectamine (Invitrogen, Carlsbad, Calif.) with 0.25 µg GRE-LUC, 0.01 µg CMV-LUC (renilla luciferase) and 25 ng of the AR. The cells were treated 24 hrs after transfection as indicated in the figures and the luciferase assay performed 48 hrs after transfection. Data are represented as $IC_{50}$ obtained from four parameter logistics curve.

LNCaP Gene Expression Assay.

Method: LNCaP cells were plated at 15,000 cells/well of a 96 well plate in RPMI+1% csFBS without phenol red. Forty-eight hours after plating, cells were treated with a dose response of SARDs. Twenty four hours after treatment, RNA was isolated using cells-to-ct reagent, cDNA synthesized, and expression of various genes was measured by realtime rtPCR (ABI 7900) using taqman primers and probes. Gene expression results were normalized to GAPDH.

LNCaP Growth Assay.

Method: LNCaP cells were plated at 10,000 cells/well of a 96 well plate in RPMI+1% csFBS without phenol red. Cells were treated with a dose response of SARDs. Three days after treatment, cells were treated again. Six days after treatment, cells were fixed and cell viability was measured by SRB assay.

LNCaP or AD1 Degradation.

Method: LNCaP or AD1 cells expressing full length AR were plated at 750,000-1,000,000 cells/well of a 6 well plate in growth medium (RPMI+10% FBS). Twenty four hours after plating, medium was changed to RPMI+1% csFBS without phenol red and maintained in this medium for 2 days. Medium was again changed to RPMI+1% csFBS without phenol red and cells were treated with SARDs (1 nM to 10 µM) in combination with 0.1 nM R1881. After 24 h of treatment, cells were washed with cold PBS and harvested. Protein was extracted using salt-containing lysis buffer with three free-thaw cycles. Protein concentration was estimated and five microgram of total protein was loaded on a SDS-PAGE, fractionated, and transferred to a PVDF membrane. The membrane was probed with AR N-20 antibody from SantaCruz and actin antibody from Sigma.

22RV1 and D567es Degradation.

Method: 22RV1 and D567es cells expressing AR splice variants were plated at 750,000-1,000,000 cells/well of a 6 well plate in growth medium (RPMI+10% FBS). Twenty four hours after plating, medium was changed and treated. After 24-30 h of treatment, cells were washed with cold PBS and harvested. Protein was extracted using salt-containing lysis buffer with three free-thaw cycles. Protein concentration was estimated and five microgram of total protein was loaded on a SDS-PAGE, fractionated, and transferred to a PVDF membrane. The membrane was probed with AR N-20 antibody from SantaCruz and actin antibody from Sigma.

22RV1 Growth and Gene Expression.

Methods: Cell growth was evaluated as described before by SRB assay. Cells were plated in a 96 well plate in full serum and treated for 6 days with medium change after day 3. Gene expression studies were performed in 22RV1 cells plated in 96 well plate at 10,000 cells/well in RPMI+10% FBS. Twenty four hours after plating, cells were treated for 3 days and gene expression studies were performed as described before.

Determination of Metabolic Stability (In Vitro $CL_{int}$) of Test Compounds (Table 11)

Phase I Metabolism

The assay was done in a final volume of 0.5 ml in duplicates (n=2). Test compound (1 µM) was pre-incubated for 10 minutes at 37° C. in 100 mM Tris-HCl, pH 7.5 containing 0.5 mg/ml liver microsomal protein. After pre-incubation, reaction was started by addition of 1 mM NADPH (pre-incubated at 37° C.). Incubations were carried out in triplicate and at various time-points (0, 5, 10, 15, 30 and 60 minutes) 100 µl aliquots were removed and quenched with 100 µl of acetonitrile containing internal standard. Samples were vortex mixed and centrifuged at 4000 rpm for 10 minutes. The supernatants were transferred to 96 well plates and submitted for LC-MS/MS analysis. As control, sample incubations done in absence of NADPH were included. From % PCR (% Parent Compound Remaining), rate of compound disappearance is determined (slope) and in vitro $CL_{int}$ (µl/min/mg protein) was calculated.

Metabolic Stability in Phase I & Phase II Pathways

In this assay, test compound was incubated with liver microsomes and disappearance of drug was determined using discovery grade LC-MS/MS. To stimulate Phase II metabolic pathway (glucuronidation), UDPGA and alamethicin was included in the assay.

LC-MS/MS Analysis:

The analysis of the compounds under investigation was performed using LC-MS/MS system consisting of Agilent 1100 HPLC with an MDS/Sciex 4000 Q-Trap™ mass spectrometer. The separation was achieved using a $C_{18}$ analytical column (Alltima™, 2.1×100 mm, 3 μm) protected by a $C_{18}$ guard cartridge system (SecurityGuard™ ULTRA Cartridges UHPLC for 4.6 mm ID columns, Phenomenex). Mobile phase was consisting of channel A (95% acetonitrile+5% water+0.1% formic acid) and channel C (95% water+5% acetonitrile+0.1% formic acid) and was delivered at a flow rate of 0.4 mL/min. The volume ratio of acetonitrile and water was optimized for each of the analytes. Multiple reaction monitoring (MRM) scans were made with curtain gas, collision gas, nebulizer gas, and auxiliary gas optimized for each compound, and source temperature at 550° C. Molecular ions were formed using an ion spray voltage of −4200 V (negative mode). Declustering potential, entrance potential, collision energy, product ion mass, and cell exit potential were optimized for each compound.

TABLE 9

AR Binding ($K_i$), Inhibition of AR Transactivation ($IC_{50}$), AR Degradation and in vitro Metabolic Stability of Indoline, Quinoline and Isoquinoline SARDs.

| Compd ID | Structure | Binding/Tranactivation (wtAR) $K_i$ (nM) | $IC_{50}$ (nM) | SARD activity (estimated median effect (nM)) | DMPK (MLM) $T_{1/2}$ (min) $CL_{int}$ (μl/min/mg) |
|---|---|---|---|---|---|
| Enobosarm | | 8.385 | ~20 | | |
| R-Bicalutamide | | 211.12 | 248.2 | — | |
| Enzalutamide | | 678.9 | 216.3 | — | |
| ARN-509 (apalutamide) | | >1000 | | + (Figure 54) | |
| 100 | | 23.17 34.16 | 530.95 | 10-100 (Figures 54 & 55) | 66.87 min 10.38 (μl/min/mg) |
| 101 | | 83.1 | 58.96 | 100-500 (Figure 61) | 25.06 27.67 μl/min/mg |

TABLE 9-continued

AR Binding ($K_i$), Inhibition of AR Transactivation ($IC_{50}$), AR Degradation and in vitro Metabolic Stability of Indoline, Quinoline and Isoquinoline SARDs.

| Compd ID | Structure | Binding/Tranactivation (wtAR) $K_i$ (nM) | $IC_{50}$ (nM) | SARD activity (estimated median effect (nM)) | DMPK (MLM) $T_{1/2}$ (min) $CL_{int}$ (µl/min/mg) |
|---|---|---|---|---|---|
| 102 | 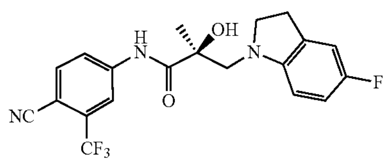 | 126.8 | 26.28 | 100-500 (Figures 55 & 57) | 55.14 min 12.57 µl/min/mg |
| 103 | 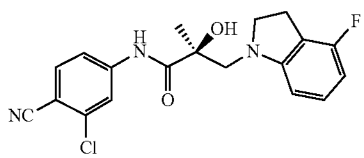 [SMILES: C[C@](O)(CN1CCc2c(F)cccc21)C(=O)Nc1ccc(C#N)c(Cl)c1] | 382.44 | 126.13 | 10000 (Figure 58) | |
| 104 | 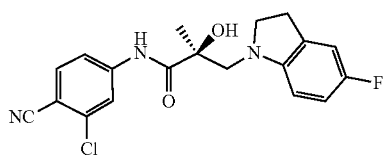 [SMILES: C[C@](O)(CN1CCc2cc(F)ccc21)C(=O)Nc1ccc(C#N)c(Cl)c1] | 326.14 | 130.37 | 10-100 (Figure 58) | 26.16 min 23.77 µl/min/mg |
| 105 | 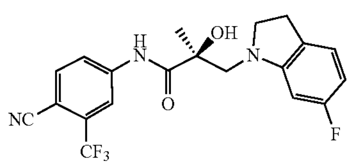 [SMILES: C[C@](O)(CN1CCc2ccc(F)cc21)C(=O)Nc1ccc(C#N)c(C(F)(F)F)c1] | 273.04 | 38.74 | (Figure 61) | |
| 106 | 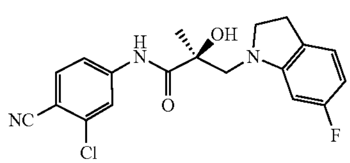 [SMILES: C[C@](O)(CN1CCc2ccc(F)cc21)C(=O)Nc1ccc(C#N)c(Cl)c1] | 489.95 | 36.45 | (Figure 61) | |
| 130 | 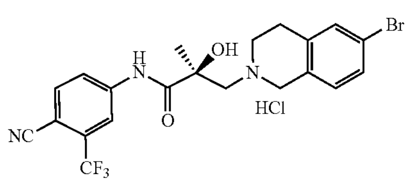 [SMILES: C[C@](O)(CN1CCc2cc(Br)ccc2C1)C(=O)Nc1ccc(C#N)c(C(F)(F)F)c1 ; Cl] | 1530.58 | 420.07 | 1000-5000 (Figures 55, 56, 59 & 60) | 161.7 min 4.286 µl/min/mg |
| 134 | 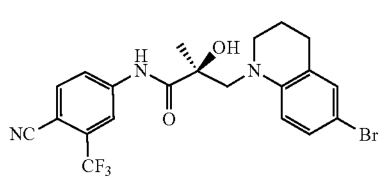 [SMILES: C[C@](O)(CN1CCCc2cc(Br)ccc21)C(=O)Nc1ccc(C#N)c(C(F)(F)F)c1] | 201.98 | 573.98 | 5000-10000 (Figure 60) | 38.25 min 18.12 µl/min/mg |
| 135 | 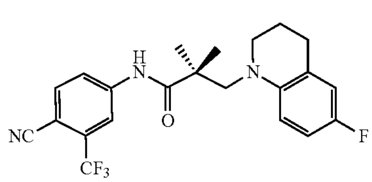 | 3112.73 | 867.48 | 10-100 nM (Figure 61) | 15.25 min 45.45 µl/min/mg |

TABLE 9-continued

AR Binding ($K_i$), Inhibition of AR Transactivation ($IC_{50}$), AR Degradation and in vitro Metabolic Stability of Indoline, Quinoline and Isoquinoline SARDs.

| Compd ID | Structure | Binding/Tranactivation (wtAR) $K_i$ (nM) | $IC_{50}$ (nM) | SARD activity (estimated median effect (nM)) | DMPK (MLM) $T_{1/2}$ (min) $CL_{int}$ (µl/min/mg) |
|---|---|---|---|---|---|
| 131 | 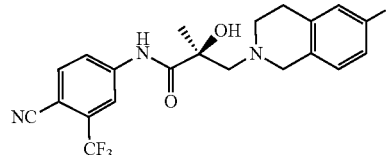 | 398.63 | 1002.73 | — | 25.42 min 27.27 µl/min/mg |
| 107 | 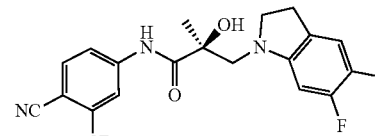 67 | 67.65 | 74.65 | (Figure 61) | |
| 108 | 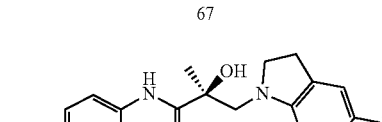 81 | 114.84 | 100.55 | (Figure 61) | |

The short half-lives ($t_{1/2}$) and high metabolic clearance ($CL_{int}$) values in vitro of some of the compounds of this invention suggest rapid plasma clearance for those compounds which could be favorable for topical treatment of androgenic dermatologic disorders as it would limit the risk of systemic side effects, even if the skin is penetrated. Other compounds demonstrate relatively long half-lives and low metabolic clearances values in vitro suggesting that these compounds may be able to achieve systemic exposures necessary to have systemic antiandrogen effects such as would be necessary to treat prostate cancer.

TABLE 10

AR Binding ($K_i$), Inhibition of AR Transactivation ($IC_{50}$), AR Degradation and Metabolic Stability of Indoline, Quinolin eand Isoquinoline SARDs.

| Compd ID | Structure | Log P (−0.4 to +5.6) | Binding/Transactivation (wt AR) $K_i$ (nM) (DHT = 1 nM) | $IC_{50}$ (nM) | SARD Activity Full Length % inhibition at 1, 10 µM | S.V. (22RV1) % inhibition at 10 µM | DMPK (MLM) $T_{1/2}$ (min) $CL_{int}$ (µl/min/mg) |
|---|---|---|---|---|---|---|---|
| Enobosarm | 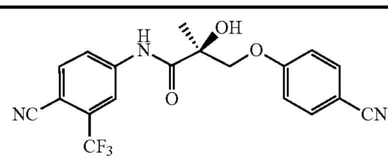 | 3.44 | 20.21 | ~20 | | | |
| R-Bicalutamide | 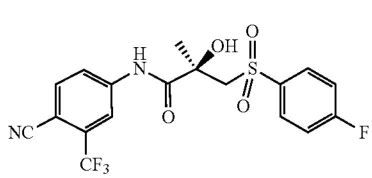 | 2.57 | 508.84 | 248.2 | | | |

TABLE 10-continued

AR Binding (K$_i$), Inhibition of AR Transactivation (IC$_{50}$), AR Degradation and Metabolic Stability of Indoline, Quinolin eand Isoquinoline SARDs.

| Compd ID | Structure | Log P (−0.4 to +5.6) | Binding/ Transactivation (wt AR) K$_i$ (nM) (DHT = 1 nM) | IC$_{50}$ (nM) | SARD Activity Full Length % inhibition at 1, 10 μM | SARD Activity S.V. (22RV1) % inhibition at 10 μM | DMPK (MLM) T$_{1/2}$ (min) CL$_{int}$ (μl/min/ mg) |
|---|---|---|---|---|---|---|---|
| Enzalutamide | | 4.56 | 3641.29 | 216.3 | | | |
| ARN-509 (apalutamide) | | 3.47 | 1452.29 | | 0 | 0 | |
| DJ-I-223 | | 2.57 | 87.67 | — | | | |
| DJ-VI-5E | | | 1.86 | 407.08 | | | |
| 100 | | 4.62 | 197.67 | 530.95 | 60 | 41 | 66.87 10.38 |
| 101 | | 3.95 | 169.86 | 58.96 | 61 | 5 | 25.06 27.67 |
| 102 | | 3.95 | 807.22 | 137.04 | 95 | 63 | 55.14 12.57 |

TABLE 10-continued

AR Binding (K$_i$), Inhibition of AR Transactivation (IC$_{50}$), AR Degradation and Metabolic Stability of Indoline, Quinolin eand Isoquinoline SARDs.

| Compd ID | Structure | Log P (−0.4 to +5.6) | Binding/Transactivation (wt AR) | | SARD Activity | | DMPK (MLM) T$_{1/2}$ (min) CL$_{int}$ (μl/min/mg) |
|---|---|---|---|---|---|---|---|
| | | | K$_i$ (nM) (DHT = 1 nM) | IC$_{50}$ (nM) | Full Length % inhibition at 1, 10 μM | S.V. (22RV1) % inhibition at 10 μM | |
| 103 | | 3.59 | 382.44 | 126.13 | 58 | 71 | 15 / 46.22 |
| 104 | | 3.59 | 326.14 | 130.37 | 47, 69 | 15 | 29.16 / 23.77 |
| 105 | | 3.95 | 273.04 | 38.74 | 60 | 30 | |
| 106 | | 3.59 | 489.95 | 36.45 | 99 | 12 | |
| 107 | | 4.51 | 67.65 | Agonist | 30-48 | 0 | |
| 108 | | 4.11 | 114.84 | 100.55 | 54 | 36 | |
| 109 | | 3.80 | >1000 | 142.13 | 84 | 45 | |
| 110 | | 3.75 | 251.94 | 31.71 | 79 | 40 | |

TABLE 10-continued

AR Binding ($K_i$), Inhibition of AR Transactivation ($IC_{50}$), AR Degradation and Metabolic Stability of Indoline, Quinolin eand Isoquinoline SARDs.

| | | | Binding/ Transactivation (wt AR) | | SARD Activity | | DMPK (MLM) $T_{1/2}$ (min) |
|---|---|---|---|---|---|---|---|
| | | | | | Full | S.V. | |
| Compd ID | Structure | Log P (−0.4 to +5.6) | $K_i$ (nM) (DHT = 1 nM) | $IC_{50}$ (nM) | Length % inhibition at 1, 10 μM | (22RV1) % inhibition at 10 μM | $CL_{int}$ (μl/min/mg) |
| 114 | | 4.25 | 204.36 See Figure 62M | 834.68 See Figure 62M | 37, 84 (Figure 65M) | 0 (Figure 65M) | 17.35 39.36 |
| 115 | | 5.27 | 71.48 See Figure 62J | 244.43 See Figure 62J | 93 (100 nM) (Figure 65J) | 90 (Figure 65J) | 21.37 32.44 |
| 130 | | 4.28 | 1530.58 | 420.07 | 70, 78 | 65 | 161.7 4.286 |
| 131 | | 3.61 | 398.63 | 1002.73 | | 24 | 25.42 27.27 |
| 132 | | 3.61 | 353.19 (Figure 65C legend) | 978.91 (Figure 65C) | 0 | 60 | |
| 134 | | 5.04 | 201.98 | 573.98 | | | 38.25 18.12 |
| 135 | | 4.37 | 3112.73 | 867.48 | | 21 | 15.25 45.45 |

TABLE 11

Liver Microsome (LM) Data for Indoline, Quinoline and Isoquinoline SARDs
in Mouse LM (MLM), Human LM (HLM), Rat LM (RLM), and Dog LM (DLM).

| | MLM | | HLM | | RLM | | DLM | |
|---|---|---|---|---|---|---|---|---|
| Compd ID | $T_{1/2}$ (min) | $CL_{int}$ (µl/min/mg) | $T_{1/2}$ (min) | $CL_{int}$ (µl/min/mg) | $T_{1/2}$ (min) | $CL_{int}$ (µl/min/mg) | $T_{1/2}$ (min) | $CL_{int}$ (µl/min/mg) |
| 102 (5F-indoline) | 55.14 | 0.01257 | | | | | | |
| 100 (5Br-indoline) | 66.87 | 10.38 | 64.84 | 0.01069 | | | | |
| 102 | 28.13 | 24.64 | 17.71 | 39.13 | | | | |
| 101 | 25.06 | 27.67 | | | | | | |
| 135 | 15.21 | 45.57 | 7.54 | 91.94 | | | | |
| 131 | 25.42 | 27.27 | 6.553 | 105.8 | | | | |
| 104 | 29.16 | 23.77 | 24.7 | 28.06 | 3.33 | 208 | 49.44 | 14 |
| 103 | 15 | 46.22 | 20.07 | 34.54 | 2.09 | 330 | 42.8 | 16.19 |
| 114 | | | 17.35 | 39.96 | 6.084 | 113.9 | | |
| 115 | 21.37 | 32.44 | 11.77 | 58.87 | | | | |

Example 23

AR Degradation Using Compounds of this Invention (Indoles, Benzimidazoles, Indazoles)

LNCaP Gene Expression Assay

Objective: To determine the effect of SARDs on AR-target gene expression in LNCaP cells.

Method: LNCaP cells were plated at 15,000 cells/well of a 96 well plate in RPMI+1% csFBS without phenol red. Forty-eight hours after plating, cells were treated with a dose response of SARDs. Sixteen-twenty four hours after treatment, RNA was isolated using cells-to-ct reagent, cDNA synthesized, and expression of various genes was measured by realtime rtPCR (ABI 7900) using taqman primers and probes. Gene expression results were normalized to GAPDH.

LNCaP Growth Assay

Objective: To determine the effect of SARDs on LNCaP cell growth.

Method: LNCaP cells were plated at 10,000 cells/well of a 96 well plate in RPMI+1% csFBS without phenol red. Cells were treated with a dose response of SARDs. Three days after treatment, cells were treated again. Six days after treatment, cells were fixed and cell viability was measured by SRB assay.

LNCaP Degradation Assay

Objective: To determine the effect of SARDs on AR expression in LNCaP cells.

Method: LNCaP cells were plated at 750,000-1,000,000 cells/well of a 6 well plate in growth medium (RPMI+10% FBS). Twenty four hours after plating, medium was changed to RPMI+1% csFBS without phenol red and maintained in this medium for 2 days. Medium was again changed to RPMI+1% csFBS without phenol red and cells were treated with SARDs (1 nM to 10 µM) in combination with 0.1 nM R1881. After 16-20 h of treatment, cells were washed with cold PBS and harvested. Protein was extracted using salt-containing lysis buffer with three free-thaw cycles. Protein concentration was estimated and five microgram of total protein was loaded on a SDS-PAGE, fractionated, and transferred to a PVDF membrane. The membrane was probed with AR N-20 antibody from SantaCruz and actin antibody from Sigma.

22RV-1 Degradation Assay

Objective: To determine the effect of SARDs on AR full length and splice variant expression in 22RV-1 cells.

Method: 22RV-1 cells were plated at 750,000-1,000,000 cells/well of a 6 well plate in growth medium (RPMI+10% FBS). Twenty four hours after plating, medium was changed and treated. After 16-20 h of treatment, cells were washed with cold PBS and harvested. Protein was extracted using salt-containing lysis buffer with three free-thaw cycles. Protein concentration was estimated and five microgram of total protein was loaded on a SDS-PAGE, fractionated, and transferred to a PVDF membrane. The membrane was probed with AR N-20 antibody from SantaCruz and actin antibody from Sigma.

AD1 Androgen Receptor Degradation (Full Length AR)

Objective: To determine the effect of compounds of this invention (SARDs) on full length AR protein expression in AD1 cells.

Method: AD1 cells expressing full length AR were plated at 750,000-1,000,000 cells/well of a 6 well plate in growth medium (RPMI+10% FBS). Twenty four hours after plating, the medium was changed to RPMI+1% csFBS without phenol red and maintained in this medium for 2 days. The medium again was changed to RPMI+1% csFBS without phenol red and cells were treated with SARDs (1 nM to 10 mM) in combination with 0.1 nM R1881. After 24 h of treatment, cells were washed with cold PBS and harvested. Protein was extracted using salt-containing lysis buffer with three freeze-thaw cycles. The protein concentration was estimated and five microgram of total protein was loaded on a SDS-PAGE, fractionated, and transferred to a PVDF membrane. The membrane was probed with AR N-20 antibody (SantaCruz Biotechnology, Inc., Dallas, Tex. 75220) and actin antibody (Sigma-Aldrich, St. Louis, Mo.). The results of this assay in AD1 cells were reported in FIGS. 69A (76), 69B (75), 69C (96) and 69D (97) as images of Western blot films (chemiluminescence exposed films). Also reported in FIGS. 69A-69D are results from wt AR binding ($K_i$), inhibition of transactivation ($IC_{50}$), and in vitro metabolic stability in mouse liver microsomes (MLM). One advantage of the indazole template is metabolic stability in vitro compared to indole and benzimidazole analogs. For example, 96 (4-$CF_3$ indazole) demonstrated a half-life of 53.7 minutes and intrinsic clearance of 12.91 µg/min/mg which is a two-fold improvement compared to 18 (5-$CF_3$ indole; 21 min and 32.9 µg/min/mg).

Figure 38A:
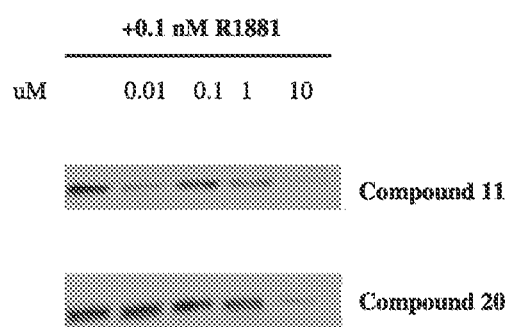
FIG. 38A demonstrates degradation in LNCaP cells using SARD compounds of this invention (11 and 20): LNCaP cells were plated in 6 well plates at 1 million cells/well. The cells were maintained in serum free conditions for 3 days. The cells were treated as indicated in the figure, harvested, protein extracted, and Western blotted for AR.

FIG. 38A presents degradation in LNCaP cells using 11 and 20. LNCaP cells were plated in 6 well plates at 1 million cells/well. The cells were maintained in serum free condition for 3 days. The cells were treated as indicated in the figure, harvested, protein extracted, and Western blotted for AR. 11 demonstrated selective degradation of AR (i.e., SARD activity) in the nM range, i.e., at concentrations comparable to its antagonist $IC_{50}$ value. LNCaP cells are known to express the AR mutant T877A, demonstrating the ability to degrade resistance conferring mutant androgen receptors.

Figure 38B:
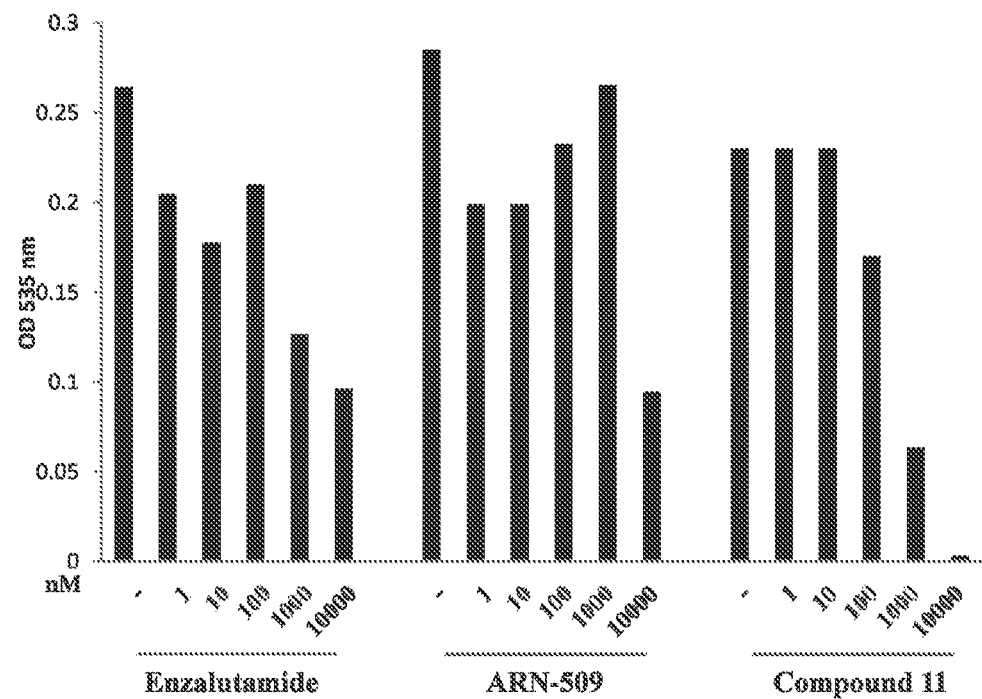
FIG. 38B presents the effect of AR antagonists and SARD 11 on LNCaP cell growth: LNCaP cells were plated in 96 well plates at 10,000 cells/well in RPMI+1% csFBS without phenol red. Cells were treated as indicated in the figure in combination with 0.1 nM R1881 for 6 days with medium change on day 3. At the end of 6 days, the cells were fixed and stained with sulphorhodamine blue stain. (Example 23)

FIG. 38B presents the effect of AR antagonists and SARDs on LNCaP cell growth: LNCaP cells were plated in 96 well plates at 10,000 cells/well in RPMI+1% csFBS without phenol red. Cells were treated as indicated in the figure in combination with 0.1 nM R1881 for 6 days with medium change on day 3. At the end of 6 days, the cells were fixed and stained with sulphorhodamine blue stain. 11 demonstrated more potent anti-proliferative activity in LNCaP cells at 1 and 10 μM when compared to enzalutamide and ARN-509.

Figure 39:
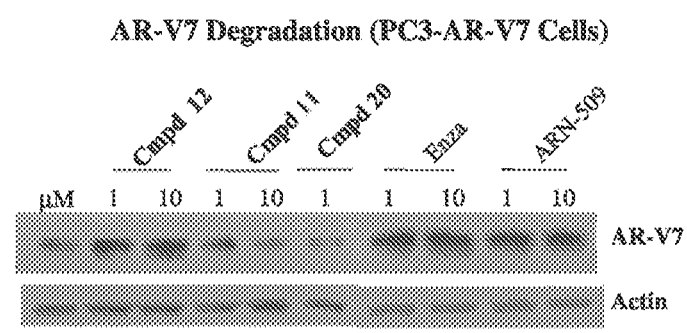
FIG. 39 presents AR-V7 degradation (PC3-AR-V7 cells) using SARD compounds of this invention (11, 12 and 20). PC-3 prostate cancer cells were serum stably transfected with a lentivirus construct for AR-V7. Once the stable cells were selected, the cells were plated in 6 well plates at 1 million cells/well. The cells were treated as indicated in the FIG. (μM) and Western blot performed for AR and actin. The results show that the SARDs have the potential to degrade truncated versions of AR such AR-V7, while enzalutamide or ARN-509 have no effect of the AR-V7 expression, suggesting that SARDs of this invention, unlike enzalutamide and ARN-509, can treat AR-V7 dependent CRPC. (Example 23)

FIG. 39 presents AR-V7 degradation (PC3-AR-V7 cells) using 11, 12 and 20 at 1 μM and 10 M. PC-3 prostate cancer cells were serum stably transfected with a lentivirus construct for AR-V7. Once the stable cells were selected, the cells were plated in 6 well plates at 1 million cells/well. The cells were treated as indicated in the figure and Western blot performed for AR and actin. The results show that the SARDs have the potential to degrade the truncated version of AR, while enzalutamide or ARN-509 had no effect of the AR-V7 expression.

SARD Compounds of this Invention Degrade AR-SV in 22RV-1 Cells

Figure 40:
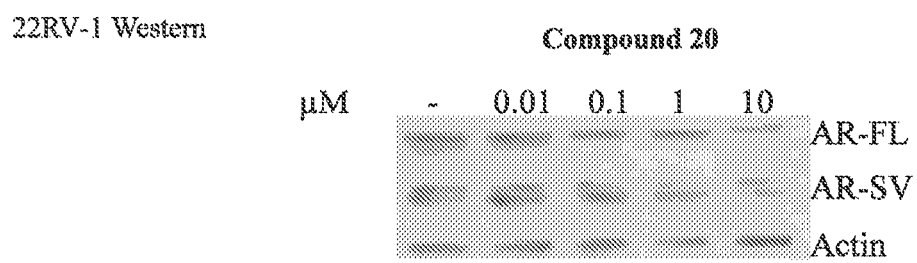
FIG. 40 demonstrates via Western blot that 20 degraded AR-FL and AR-SV in 22RV-1 cells, further supporting their use in the treatment of AR-SV-driven CRPC. (Example 23)
Figure 41:
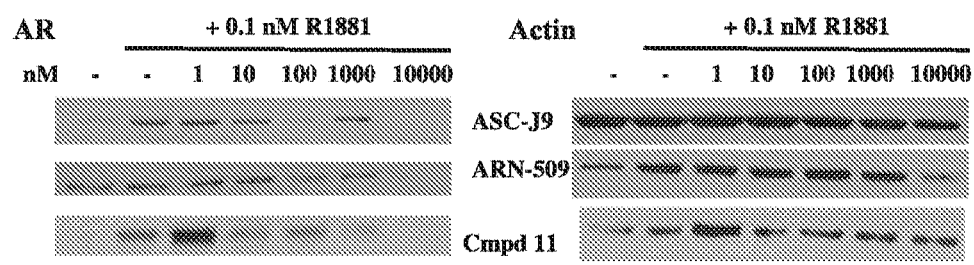
FIG. 41 presents SARD degradation of AR in LNCaP cells using 11. (Example 23)
Figure 42A:
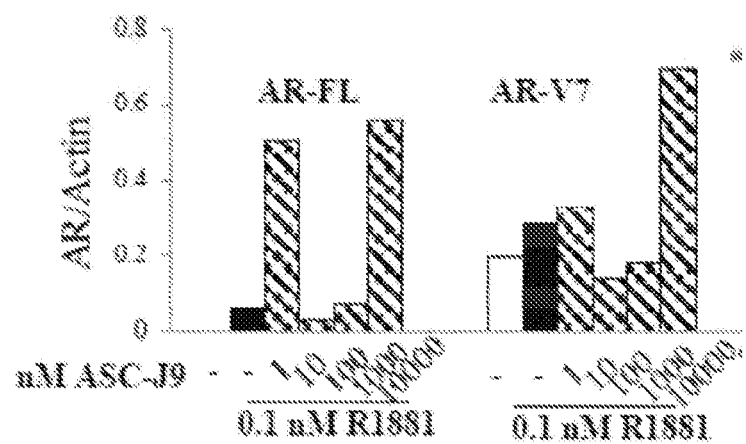
FIGS. 42A-42C present SARD degradation of AR-FL and AR-V7 in 22RV-1 cells using (FIG. 42A) ASC-J9, (FIG. 42B) ARN-509 and (FIG. 42C) 11. (Example 23)
Figure 42B:
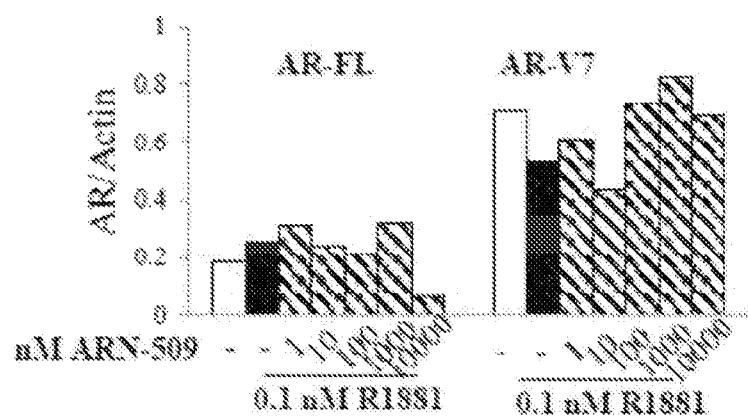
Figure 42C:
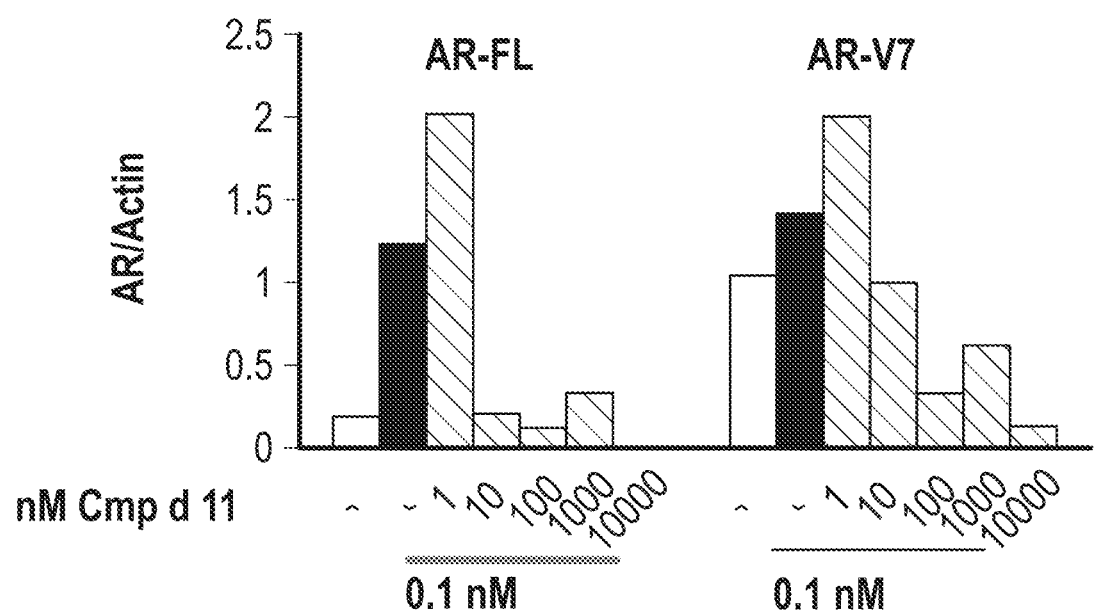

FIGS. 40—22RV-1 Western blot: 22RV-1 cells were plated in 6 well plate at 1-1.5 million cells/well in growth medium (RPMI+10% FBS). Next day, medium was changed and treated with vehicle or a dose response of 20. After overnight treatment (12-16 hrs), cells were washed in ice cold PBS and harvested by scrapping in 1 mL PBS. Cells were pelleted, protein extracted, quantified using BCA assay, and equal quantity of protein was fractionated on a SDS-PAGE. The proteins were transferred to nylon membrane and Western blotted with AR antibody (N20 from SCBT) and actin antibody. 20 was capable of degrading full length androgen receptor (AR-FL) and truncated AR (AR-SV) in 22RV-1 cells, suggesting that SARDs may be able to overcome AR-V7 dependent prostate cancers (e.g., CRPC). 11 degraded AR-FL but not actin in LNCaP cells (FIG. 41) and AR-FL and AR-SV in 22RV-1 cells (FIGS. 42A-42C). FIGS. 42A-42C show that 11 degraded AR-FL and AR-V7 at nM concentrations (FIG. 42C) whereas ARN-509 did not degrade either (FIG. 42B). Although ASC-J9 did exhibit some degradation in the nM range, μM concentrations failed to degrade AR (FIG. 42A). 11 also inhibited AR-dependent gene expression (PSA and TMPRSS2) in LNCaP cells, transactivation of AR in 22RV-1 cells and cellular growth in both the cell types (Table 12 and Table 13). Cumulatively, these observations suggest that SARDs of this invention may be useful in prostate cancers that are dependent on mutant ARs, AR-FL and/or AR-SV.

Figure 47:
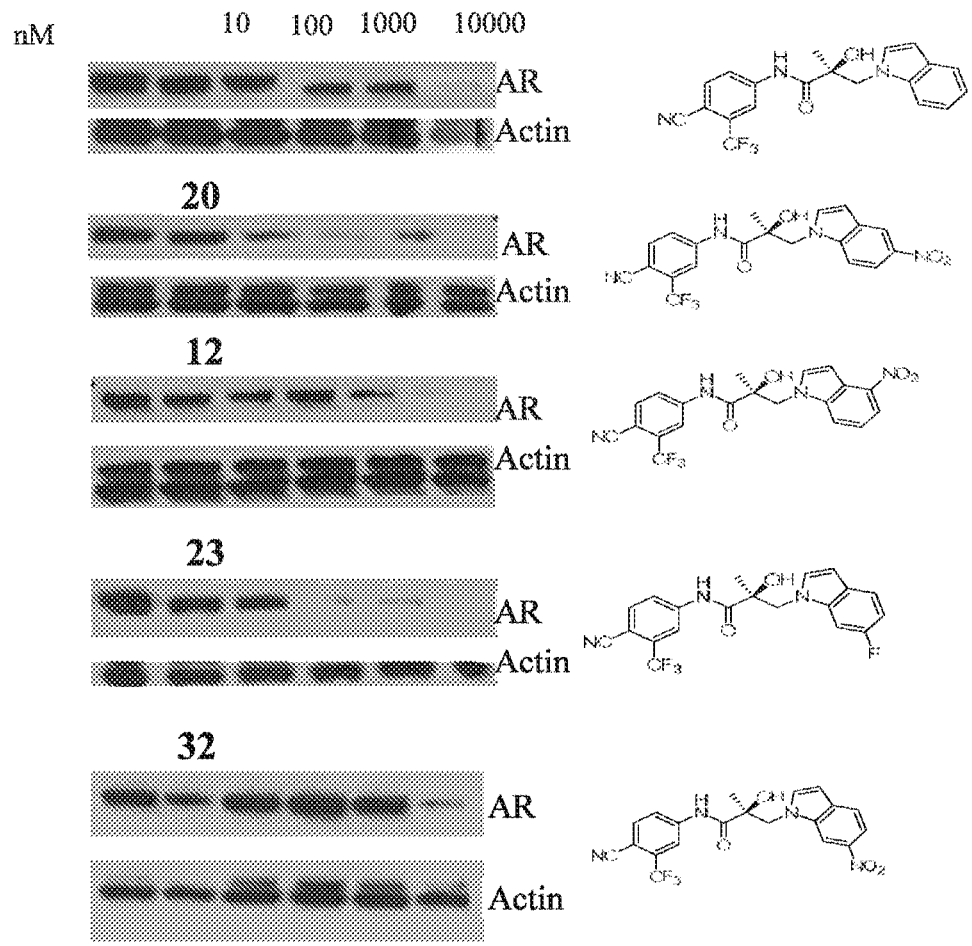
FIG. 47 presents degradation in LNCaP cells using 27, 20, 12, 23 and 32. LNCaP cells were plated in 6 well plates at 1 million cells/well. The cells were maintained in serum free conditions for 3 days. The cells were treated as indicated in the figure, harvested, protein extracted, and Western blotted for AR. SARDs demonstrated selective degradation of AR (i.e., SARD activity) in the nM range, i.e., at concentrations comparable to their antagonist $IC_{50}$ values. LNCaP cells are known to express the AR mutant T877A, demonstrating the ability to degrade resistance conferring mutant androgen receptors. (Example 23)

FIG. 47 presents degradation in LNCaP cells using 27, 20, 12, 23 and 32. LNCaP cells were plated in 6 well plates at 1 million cells/well. The cells were maintained in serum free conditions for 3 days. The cells were treated as indicated in the figure, harvested, protein extracted, and Western blotted for AR. All SARDs demonstrated selective degradation of AR (i.e., SARD activity) at concentrations comparable to their antagonist $IC_{50}$ values. LNCaP cells are known to express the AR mutant T877A, demonstrating the ability to degrade antiandrogen resistance conferring mutant androgen receptors (i.e., advanced prostate cancers and CRPC).

Figure 48:
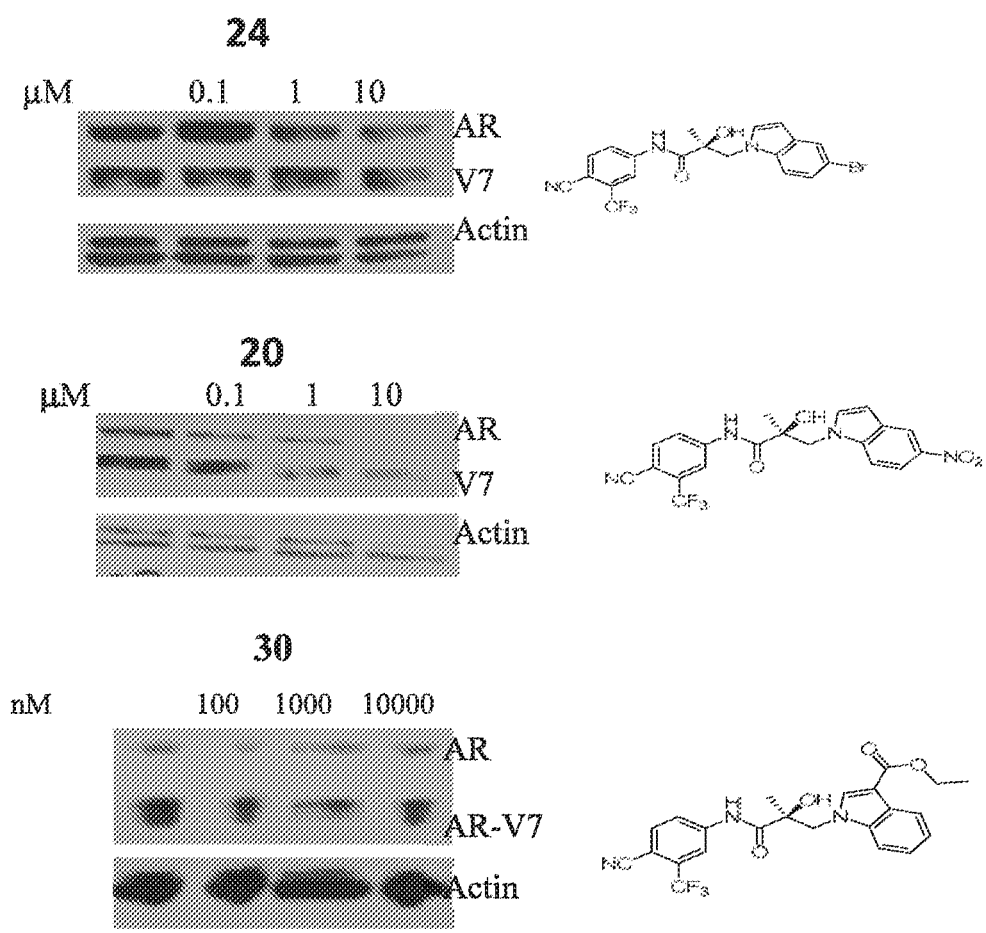
FIG. 48 presents 22RV-1 Western blots: 22RV-1 cells were plated in 6 well plates at 1-1.5 million cells/well in growth medium (RPMI+10% FBS). Next day, medium was changed and treated with vehicle or a dose response of compounds 20, 24 and 30. After overnight treatment (12-16 hrs), cells were washed in ice cold PBS and harvested by scrapping in 1 mL PBS. Cells were pelleted, protein extracted, quantified using BCA assay, and equal quantity of protein was fractionated on a SDS-PAGE. The proteins were transferred to nylon membrane and Western blotted with AR antibody (N20 from SCBT) and actin antibody. Compounds 20, 24 and 30 were capable of degrading full length androgen receptor (AR-FL) and truncated AR (AR-SV) in 22RV-1 cells, suggesting that SARDs may be able to overcome wildtype or AR-V7 dependent prostate cancers. (Example 23)

FIG. 48: 22RV-1 Western blot: 22RV-1 cells were plated in 6 well plates at 1-1.5 million cells/well in growth medium (RPMI+10% FBS). Next day, medium was changed and treated with vehicle or a dose response of 20, 24 and 30. After overnight treatment (12-16 hrs), cells were washed in ice cold PBS and harvested by scrapping in 1 mL PBS. Cells were pelleted, protein extracted, quantified using BCA assay, and equal quantity was fractionated on a SDS-PAGE. The proteins were transferred to nylon membrane and Western blotted with AR antibody (N20 from SCBT) and actin antibody. 20, 24 and 30 were capable of degrading full length androgen receptor (AR-FL) and truncated AR (AR-V7) in 22RV-1 cells, suggesting that SARDs may be able to overcome AR-V7 dependent prostate cancers (i.e., CRPC).

Figure 49:
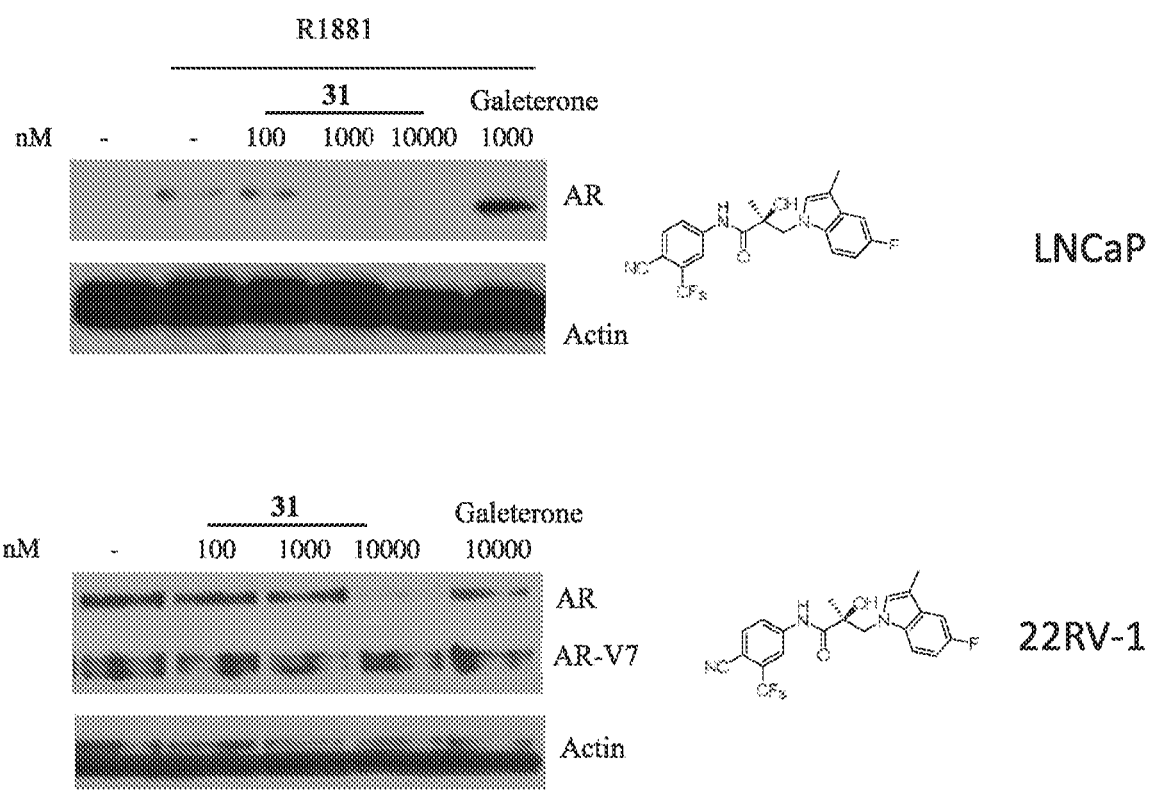
FIG. 49 presents degradation in LNCaP cells (top) and 22RV-1 cells (bottom) using 31 vs. galeterone. Using the methods described in the legends for FIG. 47 (LNCaP) and FIG. 48 (22RV-1), 31 was compared to galeterone (a clinical lead SARD). While 31 demonstrated SARD activity in both LNCaP (mutant AR harboring T877A mutation) and 22RV-1 (growth dependent on AR-SV lacking a LBD) cells, galeterone demonstrated little to no AR degradation in these models. (Example 23)

FIG. 49 presents degradation in LNCaP cells and 22RV-1 cells using 31 vs. galeterone. The experiments were performed by the methods cited above. A dose response of SARD 31 demonstrated the ability to degrade full length AR in LNCaP and 22RV-1 cell lines, whereas galeterone was not able to substantially degrade AR in either cell line.

Figure 50:
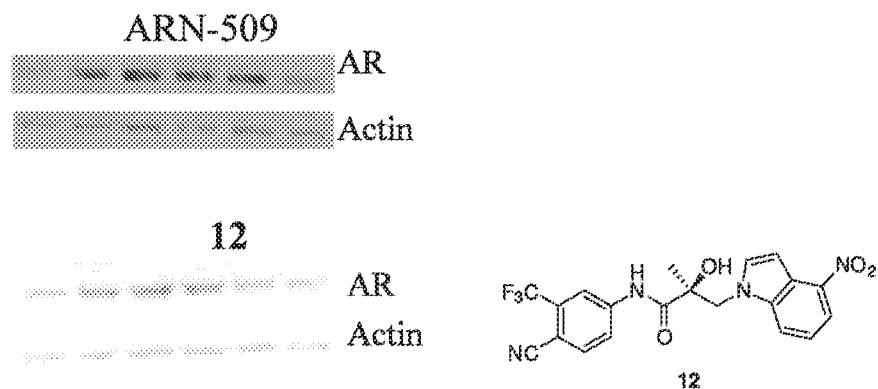
FIG. 50 presents degradation in LNCaP cells using a dose-response of 12 or ARN-509. Using the methods described in the legend for FIG. 47 (LNCaP), SARD activity for 12 was compared to known SARD ARN-509. 12 demonstrated activity in the nM range (100-1000 nM) whereas ARN-509 only had activity at 10,000 nM. (Example 23)

FIG. 50 presents degradation in LNCaP cells using 12 vs. ARN-509. 12 and ARN-509 both demonstrated the ability to degrade AR in LNCaP cells, however 12 demonstrated activity at 1 μM whereas ARN-509 only demonstrated activity at 10 μM.

Figure 12:
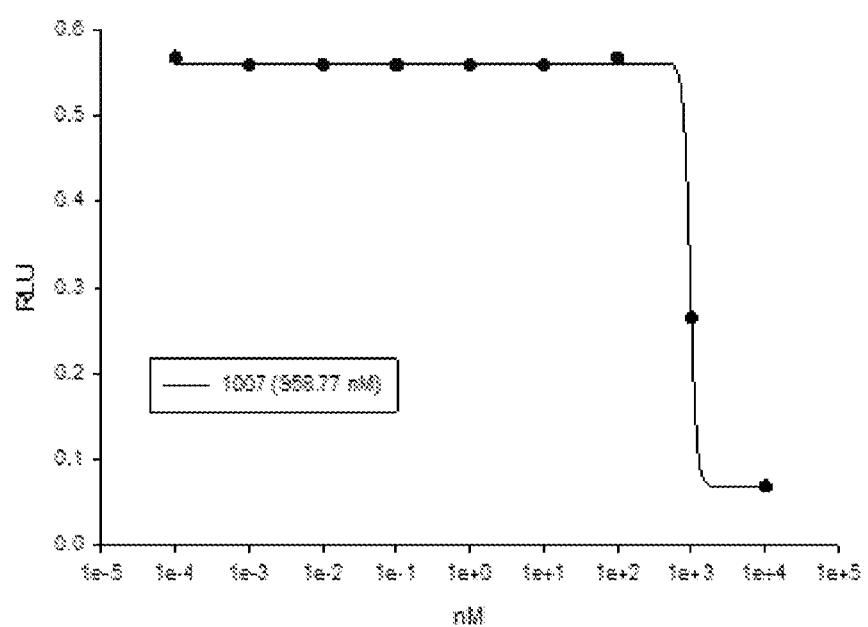
FIG. 12: The transactivation result of 1007 was reported based on measured luciferase light emissions and reported as relative light unit intensity (RLU).
Figure 13A:
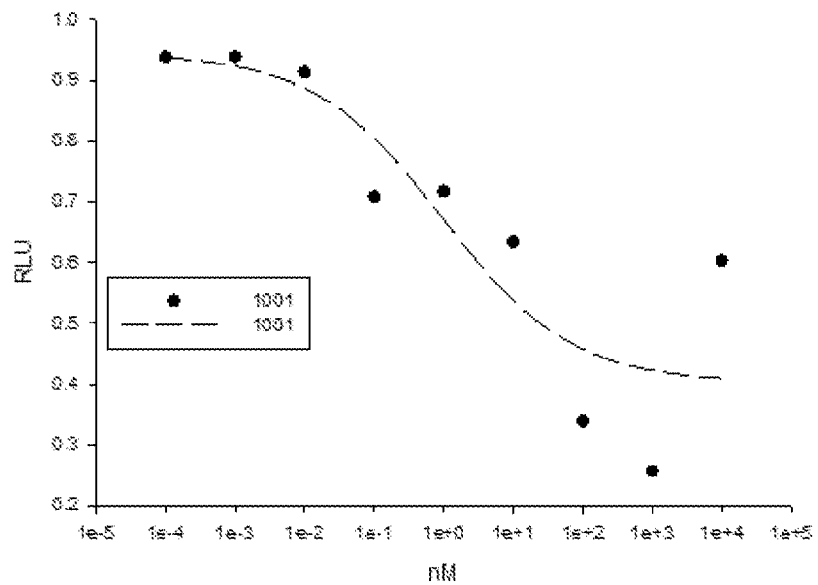
FIGS. 13A-13C: The transactivation result of 1001 was reported based on measured luciferase light emissions and reported as relative light unit intensity (RLU).
Figure 13B:
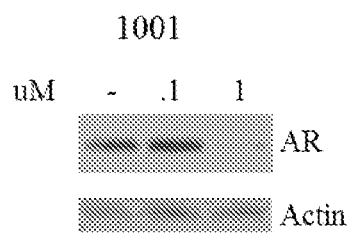
Figure 13C:
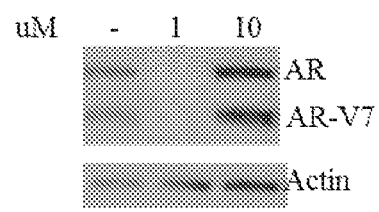
Figure 51:
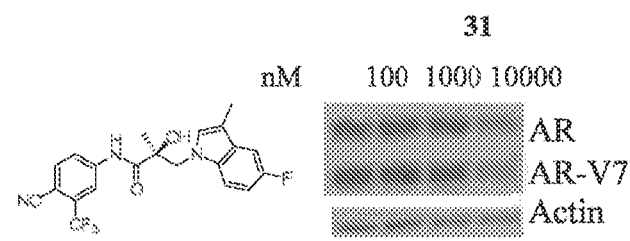
FIG. 51 presents degradation in 22RV-1 cells using 31. Using the methods described in the legend for FIG. 48 (22RV-1), SARD activity for 31 was demonstrated as degradation of full length (AR) and truncated splice variant (AR-V7) androgen receptor. (Example 23)

FIG. 51 presents degradation in 22RV-1 cells using 31. Using the methods described in the legend for FIG. 12 (22RV-1), SARD activity for 31 was demonstrated as degradation of full length (AR) and truncated splice variant (AR-V7) androgen receptor.

Figure 52:
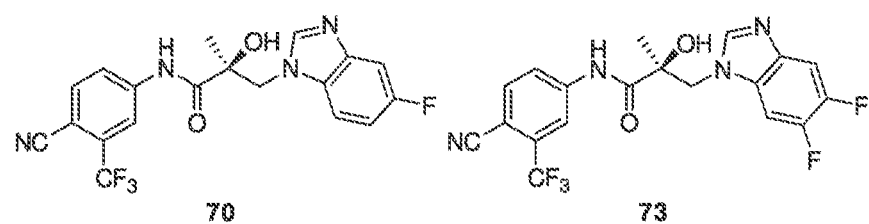
FIG. 52 presents degradation in LNCaP cells using 70 and 73. Using the methods described in the legend for FIG. 47 (LNCaP), SARD activity for 70 and 73 was demonstrated at concentrations as low as 100 nM. This demonstrates that benzimidazoles of this invention also demonstrate potent SARD activity. (Example 23)
Figure 52:
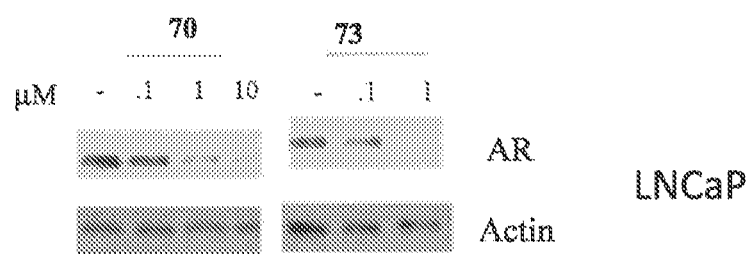

FIG. 52 presents degradation in LNCaP cells using benzimidazoles 70 and 73. Using the methods described in the legend for FIG. 47 (LNCaP), SARD activity for 70 and 73 was demonstrated at concentrations as low as 100 nM. This demonstrates that benzimidazoles of this invention also demonstrate potent SARD activity.

These selected SARD activity demonstrations as well of those reported in the tables suggest the compounds of this invention are able to degrade a variety of AR variants, and hence should provide the ability to inhibit the AR-axis activity whether it is androgen-dependent or androgen-independent. Degradation of the AR removes the possibility of promiscuous activation of mutant ARs, activation by intracellular processes such as signal transduction, kinase activation, and/or high levels of coactivators, etc.; and suggests that the SARDs should also degrade the polyQ polymorphisms in hyperandrogenic dermatologic disorders (shortened polyQ) or Kennedy's disease (extended polyQ), providing a rationale for treating either type of disease by destroying the AR in the affected tissues (skin and neuromuscular system, respectively).

TABLE 12

Inhibition of Growth and Gene Expression of LNCaP PCa Cells.

| Compound | Gene Expression $IC_{50}$ (nM) | | Growth $IC_{50}$ (nM) |
|---|---|---|---|
| | PSA | TMPRSS2 | |
| Bicalutamide | 783.7 | 831.4 | |
| Enzalutamide | 384.4 | 72.3 | 872 |
| Compound 11 | 5.0 | 13.1 | 271 |

TABLE 12-continued

Inhibition of Growth and Gene Expression of LNCaP PCa Cells.

| Compound | Gene Expression IC$_{50}$ (nM) | | Growth IC$_{50}$ (nM) |
|---|---|---|---|
| | PSA | TMPRSS2 | |
| ARN-509 | 169.7 | 517.1 | 994 |
| ASC-J9 | >10,000 | >10,000 | 1064 |

TABLE 13

Effects of SARDs on AR Transactivation and Growth of 22RV-1 Cells.

| Compound | Transactivation IC$_{50}$ (nM) | Growth IC$_{50}$ (nM) |
|---|---|---|
| Bicalutamide | 3133.52 | >10,000 |
| Enzalutamide | 101.87 | >10,000 |
| Compound 11 | 420.62 | 1041 |
| ARN-509 | 64.54 | >10,000 |
| ASC-J9 | 1026.91 | >10,000 |

Figure 74A:
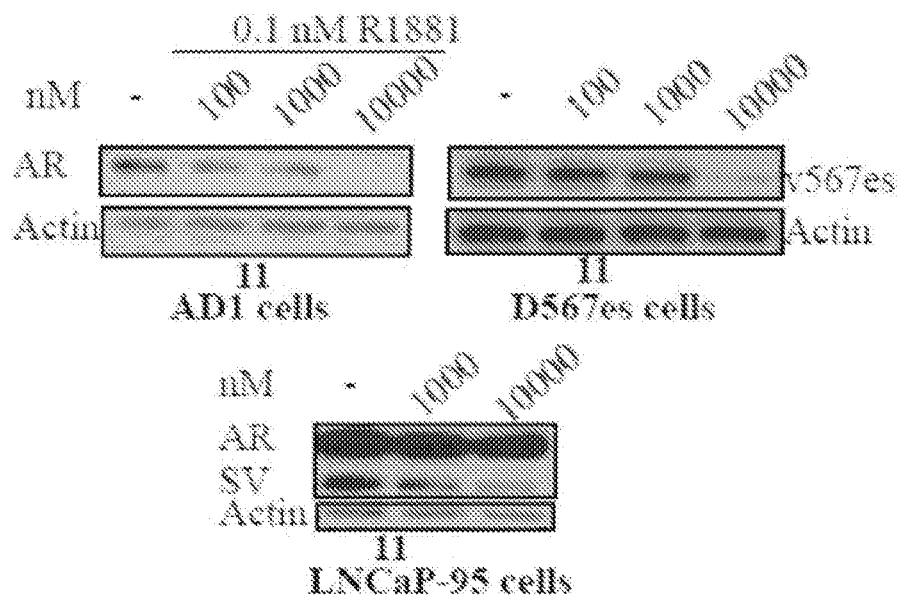
FIGS. 74A-74C: 11 degrades AR and splice variant ARs. 11 degrades AR full length in AD1 cells (left panel), AR-V567es in D567es cells (middle panel), and AR-SV in LNCaP-95 cells (lower panel). AD1 cells expressing AR were maintained in charcoal-stripped serum containing medium, while D567es cells expressing AR-v567es and LNCaP-95 cells expressing AR and AR-SV were maintained in growth medium for 2 days. Cells were treated for 24 hrs, protein extracted, and Western blot for AR and actin was performed (FIG. 74A). Inhibition of protein synthesis accelerates AR and AR-SV degradation by 11. 22RV1 cells (lower panel) and LNCaP cells (upper panel) were plated in growth medium and treated with 10 µM 11, 50 µM cycloheximide, or combination of 11 and cycloheximide for the indicated time-points. Cells were harvested, protein extracted, and Western blotted for AR and actin. Results from quantification of the blots are provided below (FIG. 74B). 11 promotes AR and ubiquitin interaction. LNCaP cells maintained in charcoal stripped serum containing medium were treated with vehicle or indicated concentrations of 11 for 4 hrs. Protein extracts were immunoprecipitated with AR antibody and Western blot for ubiquitin was performed (FIG. 74C).

To validate the results obtained in 22RV1 cells, AR degradation effect of 11 was tested in various PCa cell lines. AD-1 cells that express only AR-FL, D567es cells that express only AR-v567es, and LNCaP-95 cells that co-express AR-FL and AR-SV (FIG. 74A) were treated under various conditions with a dose response of 11. Cells were harvested 24 hrs after treatment and Western blot for the AR and its isoforms was performed. As indicated in the figures, 11 consistently degraded the AR and its SVs at concentrations ranging between 100 and 1000 nM, indicating that these SARDs degrade the AR and its SVs under various conditions and irrespective of the specific combination of the AR-FL and SV expressed. The D567es result was unexpected based on our hypothesis of SARD binding solely to the LBD, and earlier findings Watson, P. A., Chen, Y. F., Balbas, M. D., Wongvipat, J., Socci, N. D., Viale, A., Kim, K., and Sawyers, C. L. (2010) Constitutively active androgen receptor splice variants expressed in castration-resistant prostate cancer require full-length androgen receptor. Proceedings of the National Academy of Sciences of the United States of America 107, 16759-16765) that the AR-SV function depends on the AR. The D567es result argues for the direct interaction of the SARDS of this invention with AR-SV such as D567es which lacks themLBD.

Figure 74B:
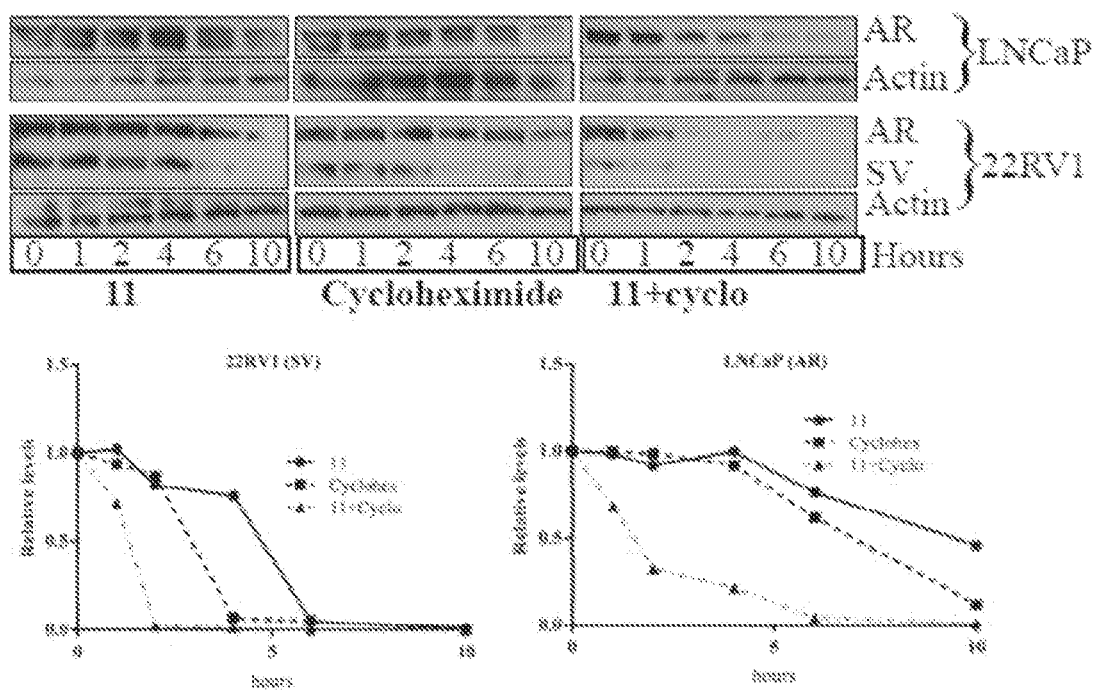
Figure 74C:
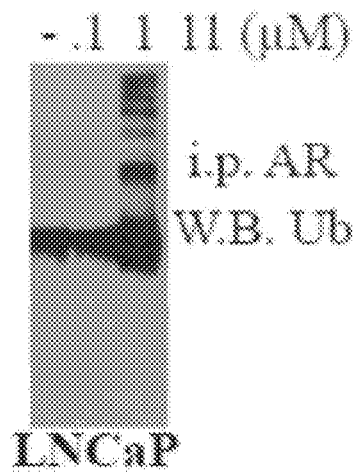

To determine if the degradation is a direct effect due to destabilization of already synthesized AR protein, LNCaP and 22RV1 cells were treated with 11, protein synthesis inhibitor cycloheximide, or a combination of cycloheximide and 11. While 11 degraded the AR and AR-V7 starting from 4-6 hrs, addition of cycloheximide accelerated the degradation, indicating that the 11-dependent AR and AR-SV degradation was not dependent on the expression of other proteins and that 11 destabilized the already synthesized AR and AR-SV (FIG. 74B) at the protein level. The graph below FIG. 74B shows the reduction in half-life of both the AR and AR-SV by 11.

Figure 75A:
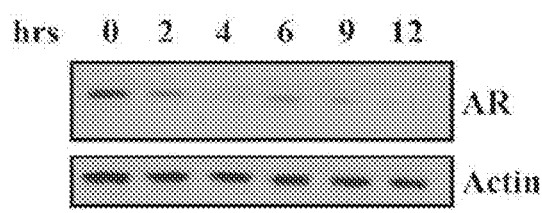
FIGS. 75A-75C: 11-dependent degradation is rapid and sustained. LNCaP cells were plated in charcoal stripped serum containing medium and treated with 10 µM 11 in combination with 0.1 nM R1881 for the indicated time-points. Western blot for the AR and actin was performed (FIG. 75A). LNCaP cells maintained in RPMI+1% csFBS w/o phenol red for 2 days were treated with 0.1 nM R1881 alone or in combination with 10 µM 11. Cells were harvested at the indicated time-points, RNA isolated, and expression of genes was measured and normalized to GAPDH (FIG. 75B). 11-induced degradation is sustained. 22RV1 cells were plated in growth medium containing 10% FBS and treated with 10 µM of 11 for 24 hrs. Twenty four hours after treatment, cells were washed with medium and fed with charcoal-stripped serum containing medium. One set of cells was immediately harvested (time point 0 hrs), while the remaining. Subsequently, cells were harvested 24 and 72 hrs after washing the SARD. Protein was extracted and Western blot for the AR and actin was performed (FIG. 75C).
Figure 75B:
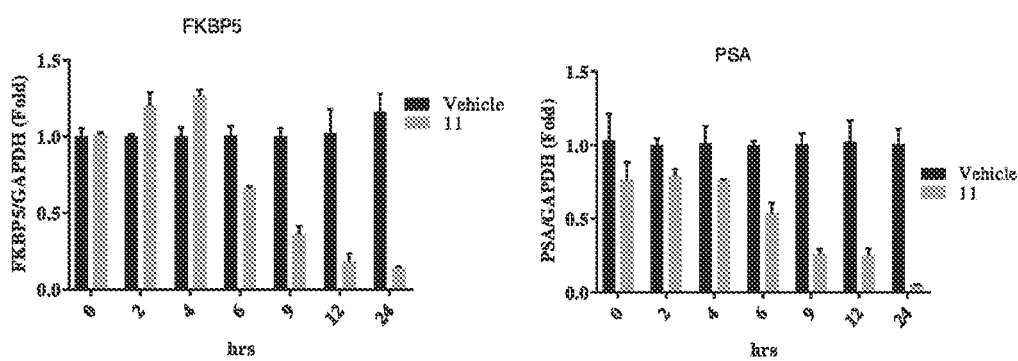
Figure 75C:
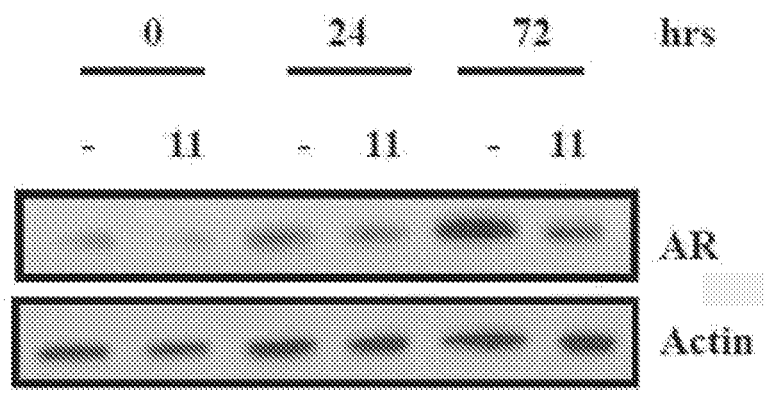

Degradation of the AR and AR-V7 by 11 was rapid and sustained. To evaluate the time-course of degradation, LNCaP cells were treated with 11 in combination with 0.1 nM R1881. Cells were harvested at different time-points and Western blot for AR and actin was performed. 11 degraded the AR starting at 4 hrs with complete degradation observed by 12 hrs (FIG. 75A). Almost comparable time-course was followed for the inhibition of AR function as measured by the expression of the AR-target genes PSA and FKBP5 (FIG. 75B). To determine the endurance of this degradation upon removal of 11, D567es cells were treated with vehicle or 11 for 24 hrs. Cells were washed and one set of plates was harvested immediately (time point 0 hrs), while the rest of the plates were harvested 24 or 72 hrs after the drug removal. Western blot for AR-V7 and actin was performed. AR was degraded by 11 by 24 hrs (time-point 0 hrs) and remained degraded up to 72 hrs after the 11 removal (FIG. 75C).

11 degraded the AR through ubiquitin-proteasome degradation machinery. To evaluate the role of ubiquitin-proteasome machinery in the SARD-dependent AR degradation, LNCaP cells were treated with 11 for 4 hrs, AR was immunoprecipitated, and a Western blot for ubiquitin was performed (FIG. 75C). AR co-immunoprecipitated with ubiquitin in the presence of 11, indicating that ubiquitination of the AR in response to these SARDs is a potential mechanism for AR degradation.

Figure 76A:
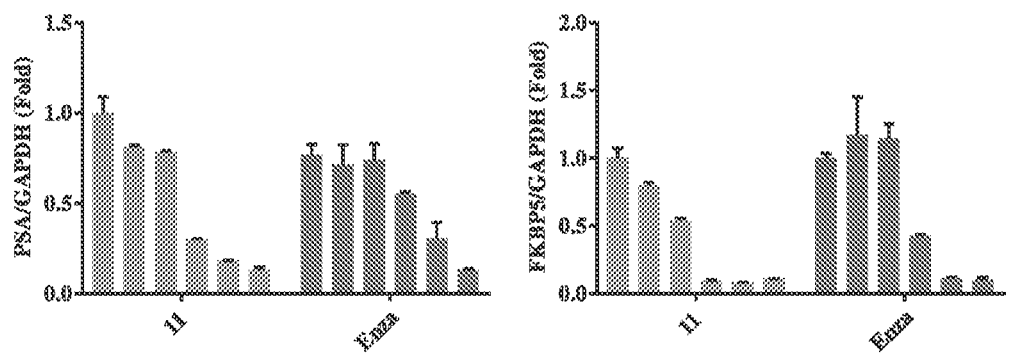
FIGS. 76A-76E: 11 inhibits the expression of AR-target genes and proliferation of prostate cancer cells. 11 potently inhibits the expression of AR-target genes in LNCaP cells. LNCaP cells were maintained in charcoal stripped serum containing medium for two days and treated with vehicle or indicated compounds (11 or enzalutamide with dose of 1, 10, 100, 1000, and 10,000 nM) in the presence of 0.1 nM R1881 for 24 hours. RNA was isolated and expression of PSA (left) or FKBP5 (right) was quantified and normalized to GAPDH by realtime PCR (FIG. 76A). 11 inhibits expression of a subset of genes induced by AR-V7 in PC3 cells. PC3 cells or PC3 cells stably transfected with AR-V7 (PC3-ARV7) were treated with vehicle or 10 µM 11 (n=3). RNA was isolated ~16 hrs after treatment and RNA-Sequencing was performed in Ion Torrent next-generation sequencer. Heatmap shows the top 50 genes differentially expressed in PC3-AR-V7 vehicle-treated but not in 11-treated cells compared to PC3 vehicle-treated cells. Bar graph on the right shows representative genes that were differentially expressed in RNA (FIG. 76B). 11 inhibits AR-target gene expression in 22RV1 cells. 22RV1 cells were plated in charcoal stripped serum, treated with vehicle (right-most bars of each chart) or indicated compounds (11 or enzalutamide with 10, 100, 1000, and 10,000 nM) for 3 days and the expression of AR-target genes was measured by realtime PCR (FIG. 76C). SARDs are potent inhibitors of prostate cancer cell proliferation. LNCaP cells maintained in charcoal stripped serum containing medium were treated with vehicle or indicated compounds (1 pM-10 µM) in the presence of 0.1 nM R1881. Cells were re-treated three days later and the cell viability was measured after 6 days of treatment using SRB assay. Castration-resistant prostate cancer (CRPC) cells 22RV1, LNCaP-abl, LNCaP-95, LNCaP-EnzR, and Hela cells were plated in charcoal-stripped serum containing medium and were treated as indicated for LNCaP cells in the absence of R1881 stimulation. SRB assay was performed 6 days after treatment (FIG. 76D). 11 inhibits enzalutamide-resistant AR-target gene expression and growth in enzalutamide-resistant (EnzR) prostate cancer cells. EnzR LNCaP cells were maintained in charcoal stripped serum containing medium for 2 days and treated with vehicle, enzalutamide, or 11 (1-10,000 nM) in the presence of 0.1 nM R1881 (FIG. 76E). Cells were harvested 24 hrs after treatment and expression of PSA was measured by realtime PCR. Cell proliferation in response to enzalutamide or SARDs and 0.1 nM R1881 was performed as described for LNCaP in panel 40D. Values in panels 40A-40C are represented as average ±S.E. with n=3.

11 inhibited AR-dependent gene expression and PCa cell proliferation. To evaluate whether the highly potent AR antagonism translates to inhibition of AR function and PCa cell proliferation, 11 was tested in LNCaP cells and compared to enzalutamide. Treatment of LNCaP cells with 11 inhibited 0.1 nM R1881-induced PSA and FKBP5 gene expression at low nanomolar concentrations with at least 10-fold better potency than enzalutamide (FIG. 76A).

Figure 76B:
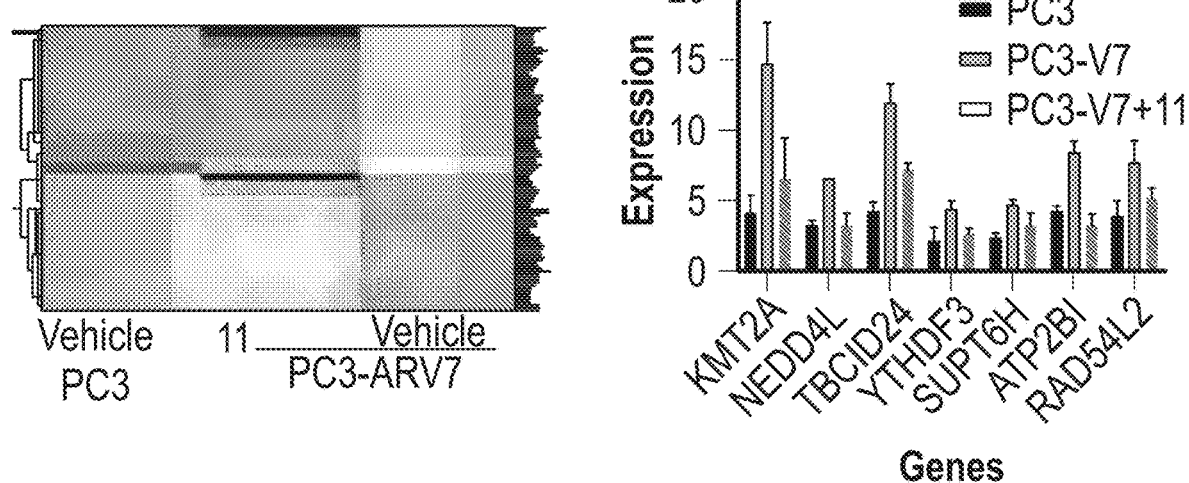
Figure 76C:
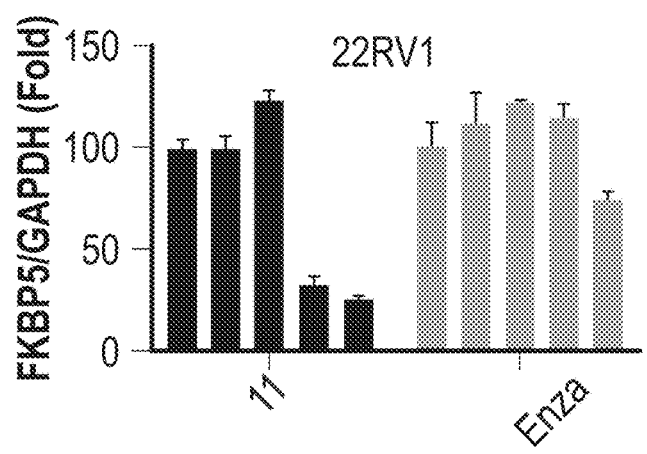

To determine the effect of 11 on AR-V7-dependent gene expression, PC-3 cells stably transfected with AR-V7 were treated with vehicle or 10 µM 11 for 24 hrs and RNA-sequencing was performed. Expression of several genes was altered by AR-V7, which were reversed back to PC-3-GFP cell levels by 11 (FIG. 76B left panel; selected genes from the list shown in FIG. 76B right panel). These results show that the genes induced by AR-V7 were inhibited by 11. The effect on AR-V7-dependent gene expression was confirmed in 22RV1 cells, where androgen-independent expression of FKBP5 was inhibited by 11, but not by enzalutamide (FIG. 76C).

Figure 76D:
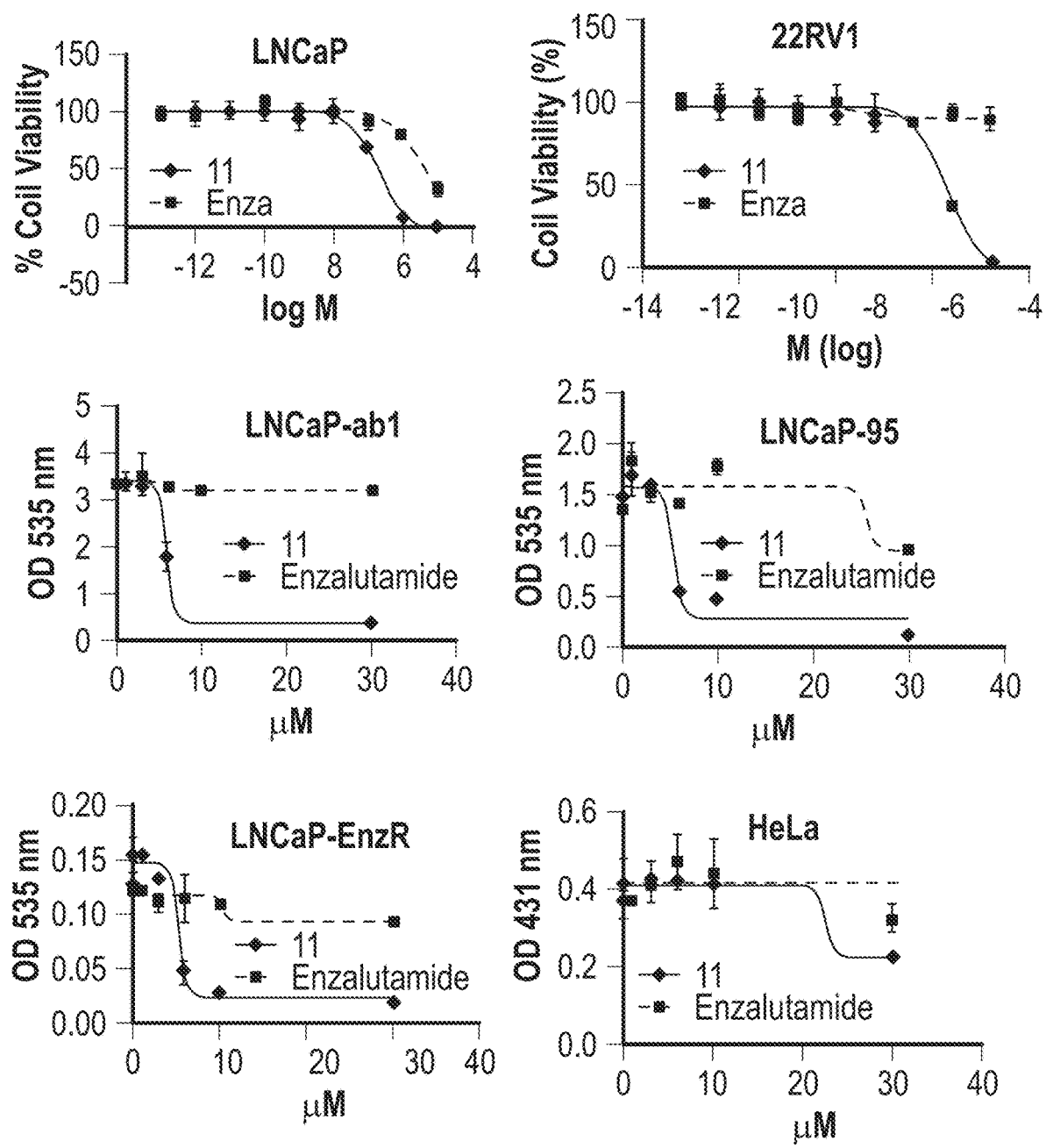
Figure 76E:
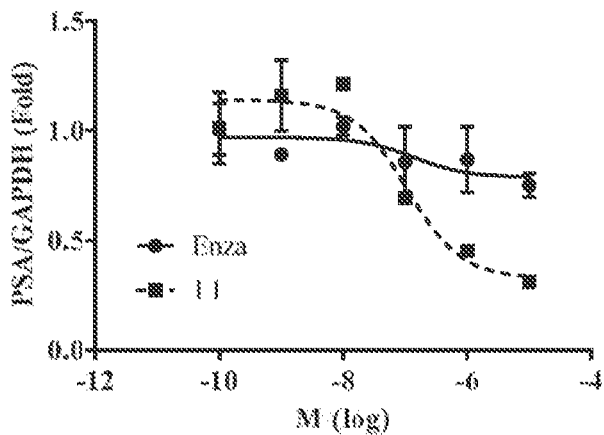
Figure 77A:
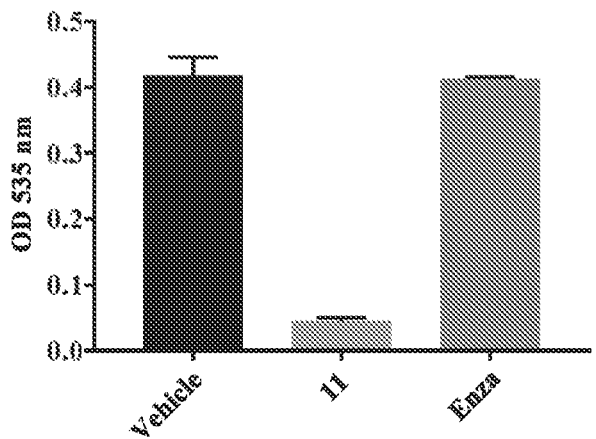
FIGS. 77A-77B: 11 inhibits transactivation of AD1 and D567es AR and cell proliferation. 11 inhibits AD1-AR-transactivation and cell growth. AR transactivation was performed by transfecting human GRE-LUC and CMV-renilla LUC into AD-1 cells. Cells were treated with vehicle, 0.1 nM R1881 alone or in combination with 10 µM 11 or enzalutamide 24 hrs after transfection and luciferase assay was performed 48 hrs after transfection (data not shown). AD1 cells maintained in charcoal stripped serum containing medium were treated with 10 µM UT-155 or enzalutamide in the presence of 0.1 nM R1881. Cells were re-treated three days later and the cell viability was measured after 6 days of treatment using SRB assay.
Figure 77B:
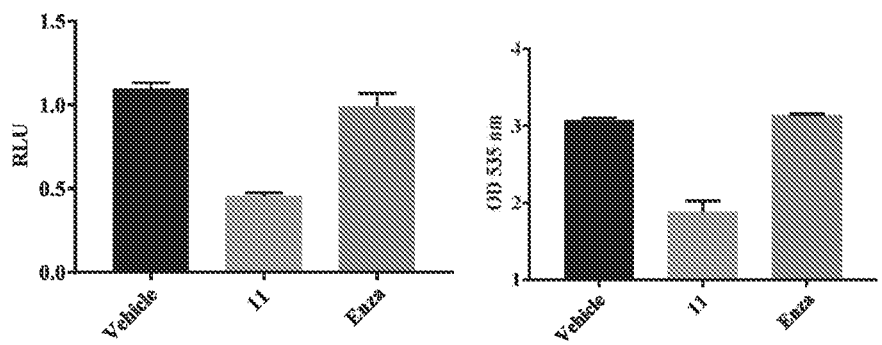

The effect of the SARD compounds of this invention on the proliferation of AR-FL- and AR-SV-expressing cell lines was evaluated. R1881-induced LNCaP proliferation was completely inhibited by 11 with nanomolar IC$_{50}$, while enzalutamide inhibited the proliferation at concentrations greater than 1 µM (FIG. 76D). 11 also inhibited the proliferation of 22RV1 cells at concentrations between 1 and 10 µM, while enzalutamide failed to inhibit the proliferation (FIG. 76D). These results were reproduced in various cell lines, including LNCaP-abl and LNCaP-EnzR, both containing enzalutamide-resistant AR, and in AR-SV-expressing LNCaP-95 cells. 11 modestly inhibited the proliferation of HeLa cells at 30 µM, demonstrating its specificity. In addition to these cells, 11 also inhibited the proliferation of AD-1 (FIG. 77A) and transactivation of v567es AR and proliferation of D567es cells that carry AR-v567es (FIG. 77B). 11, but not enzalutamide, inhibited the expression of PSA in LNCaP-EnzR, indicating that the F876L mutant that is resistant to enzalutamide is sensitive to 11 (FIG. 76E).

Figure 78A:
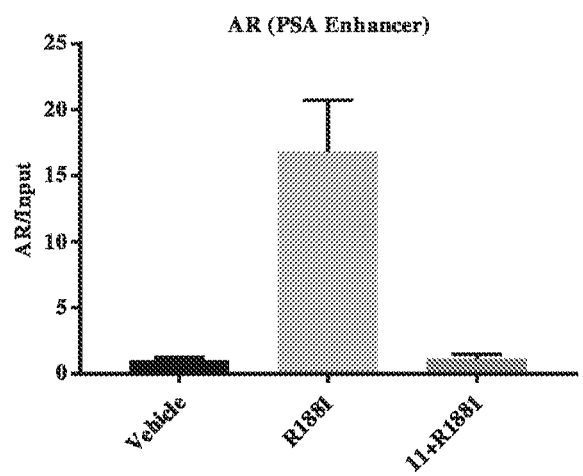
FIGS. 78A-78D: 11 inhibits nuclear translocation and DNA binding of the AR. 11 inhibits recruitment of AR to the androgen response element (ARE). LNCaP cells were serum starved for 2 days and were treated with 0.1 nM R1881 in the presence or absence of 10 µM 11 for 2 hrs. DNA-protein complex was cross-linked and AR was immunoprecipitated and its recruitment to PSA enhancer ARE was measured by realtime PCR. N=3. Values are expressed as average ±S.E.

The SARDs compounds of this invention inhibited the AR nuclear translocation and recruitment to PSA regulatory regions. To determine if the SARD compounds inhibit the recruitment of the AR to cis regulatory elements, LNCaP cells were treated with 11 in the presence of 0.1 nM R1881. Two hours after the treatment, cells were fixed to cross-link the protein to DNA, AR was immunoprecipitated, and recruitment to the PSA enhancer was quantified by realtime PCR. 11 inhibited the recruitment of the AR to PSA enhancer (FIG. 78A). These studies were performed at a time-point when no AR degradation could be detected.

Figure 78B:
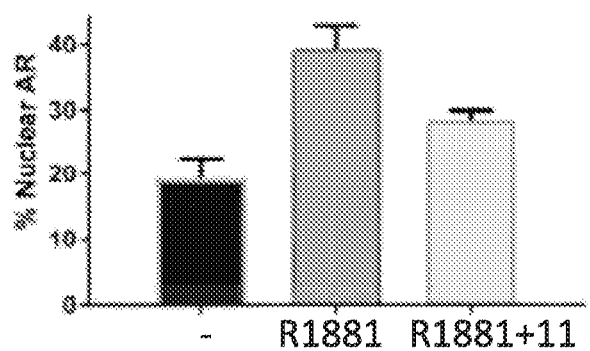

Inhibition of AR DNA binding could be a result of nuclear translocation inhibition. Microscopic evaluation of nuclear translocation shows that 11 inhibited the R1881-induced translocation of F876L enzalutamide-resistant AR (FIG. 78B).

Figure 78C:
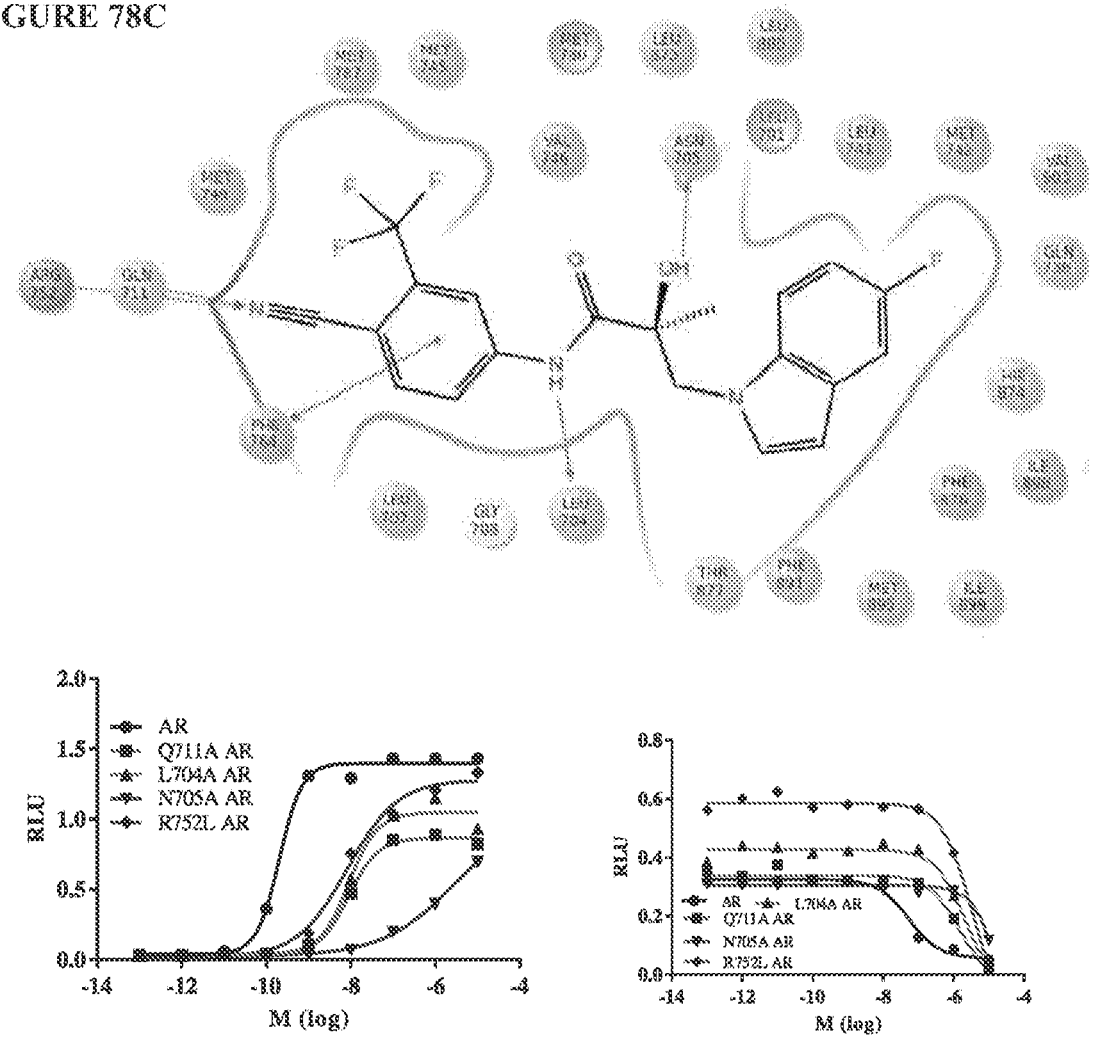

The SARD compounds of this invention did not require binding to the LBD to degrade the AR. As these SARDs bind to two domains and degrade the AR, they serve as a tool to probe into the role of each domain for degradation and proliferation. Molecular modeling was performed to determine the amino acids in the AR-LBD with which 11 interacted. 11 formed hydrogen bonds with Q711, R752, N705, and L704 (FIG. 78C). These sites were mutated and performed a transactivation assay. Mutating these amino acids individually compromised the ability of R1881 to activate the AR. While the $EC_{50}$ of R1881 for the wildtype AR was 0.11 nM, the $EC_{50}$ for the mutant ARs was 7.48 nM for Q711A, 8.72 nM for L704A, 15.41 nM for R752L, and 2037 nM for N705A (FIG. 78C; left panel).

The effect of 11 was determined on the transactivation of wildtype and mutants AR's. In these studies R1881 was used at the respective $EC_{50}$ for each mutant. While 11 effectively inhibited the wildtype AR transactivation at 63 nM, it inhibited the transactivation of the LBD mutants at concentrations greater than 1 µM. 11 failed to inhibit the function of N705A mutant AR (FIG. 78C; right panel). These studies show that mutating the interacting amino acids in the LBD weaken 11's ability to inhibit ligand-dependent AR transactivation and that 11's binding to LBD is important to antagonize androgen-dependent function of the AR.

Figure 78D:
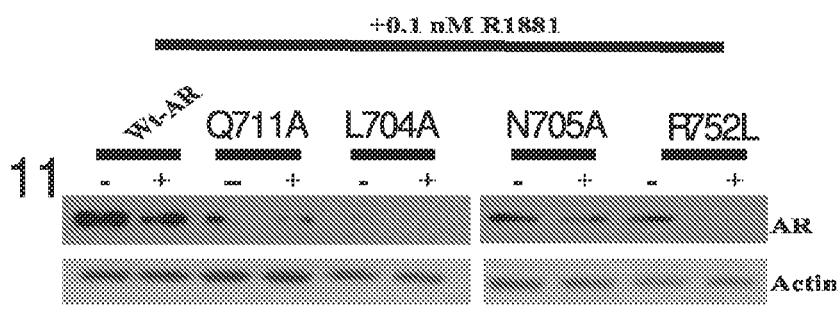

To determine if mutating the LBD will also impact 11's degradation role, HeLa cells transfected with wildtype or mutant ARs were treated with 11 and AR expression was evaluated by Western blot. These studies were performed under the same conditions as indicated for the transactivation. 11 degraded the wildtype and mutant ARs comparably (FIG. 78D), indicating that binding to LBD can be spared to retain the degradation activity.

Figure 79:
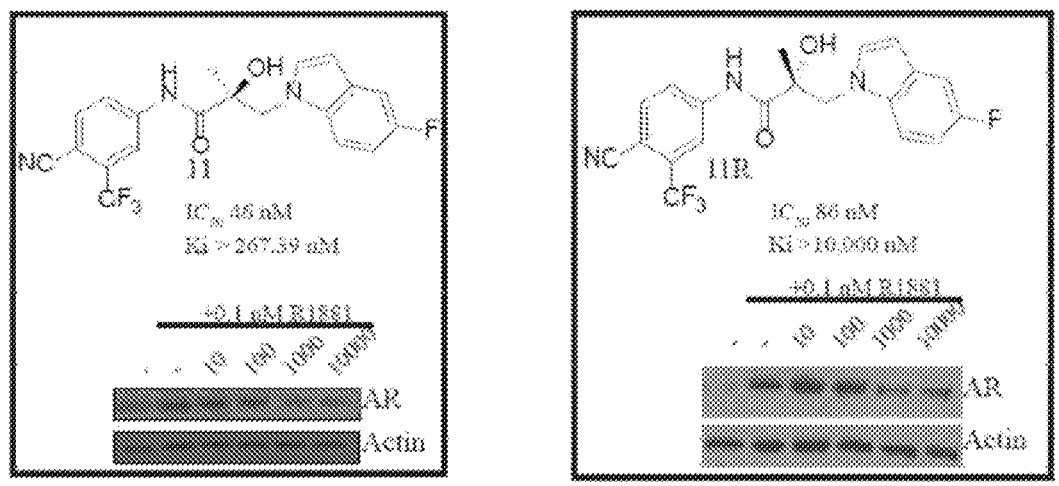
FIG. 79: The R-isomer of 11 (11R) was weaker in AR transactivation, but not in degradation. Structures of S- and R-isomers of 11 is shown. Transactivation $IC_{50}$ and Western blot for the AR are shown in the figure.

To confirm this observation the R-isomer of 11 was synthesized (11R). 11 has a chiral center and the active form is the S-isomer. Hence, an R-isomer is expected to be a weaker LBD binder than the S-isomer. We tested the effect of 11R on R1881-induced AR transactivation and AR expression. While the 11R was 10-fold weaker to inhibit the AR transactivation, no difference was observed between the S- and R-isomers of 11 in their ability to degrade the AR (FIG. 79).

Figure 80:
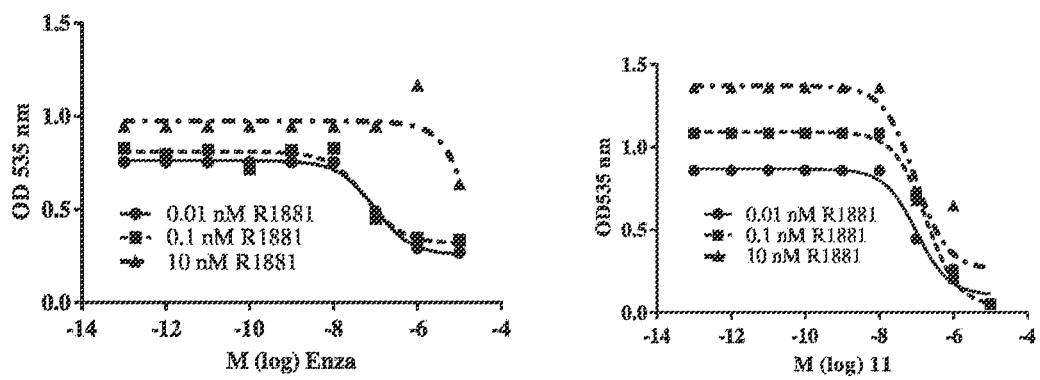
FIG. 80: Increasing concentrations of R1881 decreased enzalutamide's, but not 11's, potential to inhibit LNCaP cell proliferation. LNCaP cells were plated in charcoal stripped serum containing medium and treated with a dose response of 11 (left panel) or enzalutamide (right panel) in combination with 0.1 or 10 nM R1881. Medium was changed and the cells were re-treated after 3 days. At the end of 6 days of treatment, cells were fixed and SRB assay, a measure of cell viability, was performed.

To determine if 11's anti-proliferative effect is dependent on its competitive binding to the LBD, we performed proliferation assay in LNCaP cells in the presence of increasing concentrations of R1881. We expected that increasing concentration of R1881 will displace 11 from the ligand binding pocket, resulting in reduced or lack of anti-proliferative effects. Interestingly, increasing concentrations of R1881 weakened enzalutamide's effects, but failed to affect 11's effect on proliferation (FIG. 80) suggesting that anti-proliferative effects are not dependent of competitive binding to the LBD.

Collectively these studies provide compelling evidence to show that 11 elicits AR degradation and possibly anti-proliferative activity through its AF-1, while the antagonistic effect of ligand-dependent transactivation is through the LBD.

11 inhibited PCa xenografts growth. In vitro studies proved that 11 were extremely potent to inhibit and degrade both AR and AR-S Vs. 11 was tested in vivo in various xenograft models. In addition to LNCaP and 22RV1 xenografts, we developed a PDX, Pr-3001, from a CRPC patient specimen. Pr-3001 is a CRPC that expresses AR-FL and AR-SV and grows in castrated mice.

Figure 81:
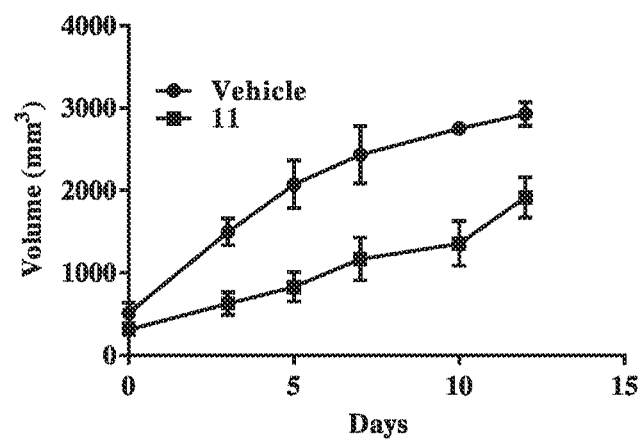
FIG. 81: 11 inhibited androgen-dependent and castration-resistant PCa growth in vivo. LNCaP cells (5 million/mouse) mixed with matrigel were implanted subcutaneously on the flanks of intact NSG mice (n=6-8 mice/group). Once tumors reached 100-200 mm$^3$, animals were randomized and treated with vehicle or 11 (50 mg/kg/day s.c.). Tumor volume was measured twice weekly. Tumor weights were recorded at sacrifice. 11 inhibited growth of patient-derived xenograft, Pr-3001. Pr-3001 was implanted as 1 mm$^3$ fragment subcutaneously in castrated NSG mice (n=8-10/group) and the study was performed as described above. Tumor volume was measured thrice weekly. At sacrifice tumor weights were recorded (not shown). * significance from vehicle-treated mice at p<0.05.

Pr-3001 is an aggressively growing patient-derived specimen. Typically, it is very hard to grow patient-derived PCa in mice due to their slow growing property. Pr-3001 developed tumors robustly and attained approximately 1000 mm$^3$ in less than 2 months. Pr-3001 expresses AR-FL and AR-SV and grows in castrated mice. Pr-3001 at 1 mm$^3$ piece were implanted on the flanks of mice and its growth was monitored. When Pr-3001 attained 100-200 mm$^3$, the animals were randomized and treated with vehicle or 11. Consistent with the observations made in 22RV1 xenograft, 11 inhibited the growth Pr-3001 by over 50% (FIG. 81).

Example 24

AR Degradation Using Indoline, Quinoline, or Isoquinoline SARD Compounds of this Invention Plasmid Constructs and Transient Transfection.

Human AR cloned into CMV vector backbone was used for the transactivation study. HEK-293 cells were plated at 120,000 cells per well of a 24 well plate in DME+5% csFBS. The cells were transfected using Lipofectamine (Invitrogen, Carlsbad, Calif.) with 0.25 µg GRE-LUC, 0.01 µg CMV-LUC (renilla luciferase) and 25 ng of the AR. The cells were treated 24 hrs after transfection as indicated in the figures and the luciferase assay performed 48 hrs after transfection. Data are represented as $IC_{50}$ obtained from four parameter logistics curve.

Ligand Binding Assay.

hAR-LBD (633-919) was cloned into pGex4t.1. Large scale GST-tagged AR-LBD was prepared and purified using a GST column. Recombinant ARLBD was combined with [$^3$H]mibolerone (PerkinElmer, Waltham, Mass.) in buffer A (10 mM Tris, pH 7.4, 1.5 mM disodium EDTA, 0.25 M sucrose, 10 mM sodium molybdate, 1 mM PMSF) to determine the equilibrium dissociation constant ($K_d$) of [$^3$H] mibolerone. Protein was incubated with increasing concentrations of [$^3$H]mibolerone with and without a high concentration of unlabeled mibolerone at 4° C. for 18 h in order to determine total and non-specific binding. Non-specific binding was then subtracted from total binding to determine specific binding and non-linear regression for ligand binding curve with one site saturation to determine the $K_d$ of mibolerone.

Increasing concentrations of SARDs or DHT (range: $10^{-12}$ to $10^{-4}$ M) were incubated with [$^3$H]mibolerone and AR LBD using the conditions described above. Following incubation, the ligand bound AR-LBD complex was isolated using biogelHT hydroxyapatite, washed and counted in a scintillation counter after adding scintillation cocktail. Values are expressed as $K_i$.

LNCaP Gene Expression Assay.

Method: LNCaP cells were plated at 15,000 cells/well of a 96 well plate in RPMI+1% csFBS without phenol red. Forty-eight hours after plating, cells were treated with a dose response of SARDs. Twenty four hours after treatment, RNA was isolated using cells-to-ct reagent, cDNA synthesized, and expression of various genes was measured by realtime rtPCR (ABI 7900) using taqman primers and probes. Gene expression results were normalized to GAPDH.

LNCaP Growth Assay.

Method: LNCaP cells were plated at 10,000 cells/well of a 96 well plate in RPMI+1% csFBS without phenol red. Cells were treated with a dose response of SARDs. Three days after treatment, cells were treated again. Six days after treatment, cells were fixed and cell viability was measured by SRB assay.

LNCaP or AD1 Degradation.

Method: LNCaP or AD1 cells expressing full length AR were plated at 750,000-1,000,000 cells/well of a 6 well plate in growth medium (RPMI+10% FBS). Twenty four hours after plating, medium was changed to RPMI+1% csFBS without phenol red and maintained in this medium for 2 days. Medium was again changed to RPMI+1% csFBS without phenol red and cells were treated with SARDs (1 nM to 10 µM) in combination with 0.1 nM R1881. After 24 h of treatment, cells were washed with cold PBS and harvested. Protein was extracted using salt-containing lysis buffer with three free-thaw cycles. Protein concentration was estimated and five microgram of total protein was loaded on a SDS-PAGE, fractionated, and transferred to a PVDF membrane. The membrane was probed with AR N-20 antibody from SantaCruz and actin antibody from Sigma.

22RV1 and D567es Degradation.

Method: 22RV1 and D567es cells expressing AR splice variants were plated at 750,000-1,000,000 cells/well of a 6 well plate in growth medium (RPMI+10% FBS). Twenty four hours after plating, medium was changed and treated. After 24-30 h of treatment, cells were washed with cold PBS and harvested. Protein was extracted using salt-containing lysis buffer with three free-thaw cycles. Protein concentration was estimated and five microgram of total protein was loaded on a SDS-PAGE, fractionated, and transferred to a PVDF membrane. The membrane was probed with AR N-20 antibody from SantaCruz and actin antibody from Sigma.

22RV1 Growth and Gene Expression.

Methods: Cell growth was evaluated as described before by SRB assay. Cells were plated in 96 well plate in full serum and treated for 6 days with medium change after day 3. Gene expression studies were performed in 22RV1 cells plated in 96 well plate at 10,000 cells/well in RPMI+10% FBS. Twenty four hours after plating, cells were treated for 3 days and gene expression studies were performed as described before.

Figure 54:
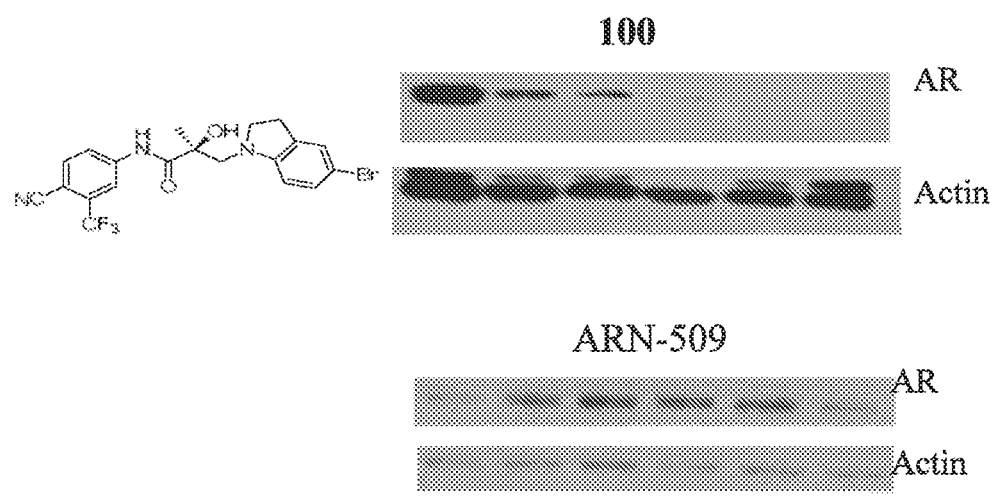
FIG. 54 demonstrates degradation in LNCaP cells using a SARD compound of this invention (100). LNCaP cells were plated in 6 well plates at 1 million cells/well. The cells were maintained in serum free conditions for 3 days. The cells were treated as indicated in the figure, harvested, protein extracted, and Western blotted for AR. (Example 24)

Results:

FIG. 54 presents degradation in LNCaP cells using 100 compared to ARN-509. LNCaP cells were plated in 6 well plates at 1 million cells/well. The cells were maintained in serum free conditions for 3 days. The cells were treated as indicated in the figure, harvested protein extracted, and Western blotted for AR. 100 demonstrated selective degradation of AR (i.e., SARD activity) in the nM range, i.e., at concentrations comparable to its antagonist $IC_{50}$ value whereas ARN-509 only demonstrated SARD activity at the highest concentration tested. LNCaP cells are known to express the AR mutant T877A, demonstrating the ability of compounds of this invention to degrade antiandrogen resistance conferring mutant androgen receptors.

Figure 55:
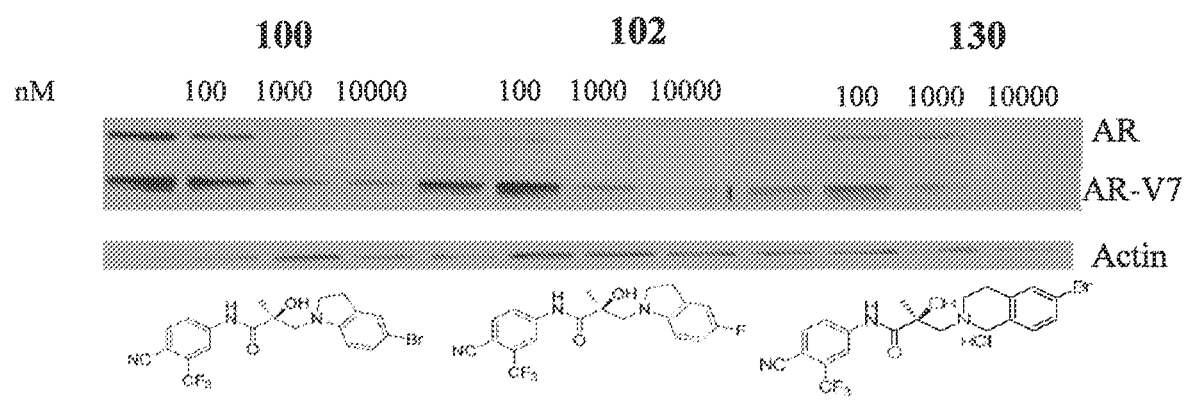
FIG. 55 demonstrates via Western blot as described above for FIG. 48, that 100, 102, and 130 degraded AR-FL and AR-SV in 22RV-1 cells. 100, 102, and 130 were capable of degrading full length androgen receptor (AR-FL) and truncated AR (AR-SV) in 22RV-1 cells, suggesting that SARDs of this invention may be able to overcome AR-V7 dependent prostate cancers. (Example 24)

FIG. 55 demonstrates via Western blot that 100, 102, and 130 degraded AR-FL and AR-SV in 22RV-1 cells. 22RV-1 cells were plated in 6 well plates at 1-1.5 million cells/well in growth medium (RPMI+10% FBS). Next day, medium was changed and treated with vehicle or a dose response of 100, 102, and 130. After overnight treatment (12-16 hrs), cells were washed in ice cold PBS and harvested by scrapping in 1 mL PBS. Cells were pelleted, protein extracted, quantified using BCA assay, and equal quantity of protein was fractionated on a SDS-PAGE. The proteins were transferred to nylon membrane and Western blotted with AR antibody (N20 from SCBT) and actin antibody. 100, 102, and 130 were capable of degrading full length androgen receptor (AR-FL) and truncated AR (AR-SV) in 22RV-1 cells, suggesting that SARDs may be able to overcome AR-V7 dependent prostate cancers.

Figure 56:
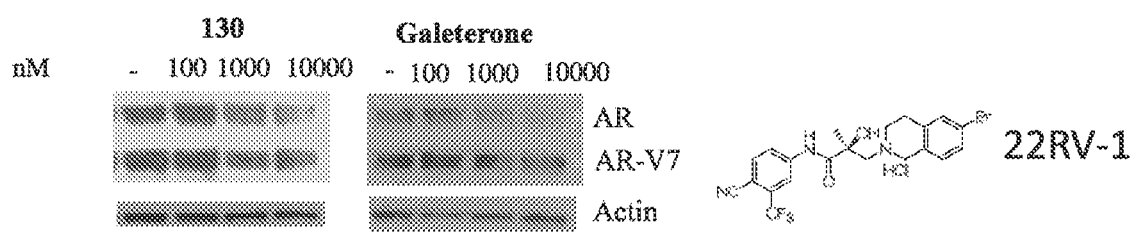
FIG. 56 presents degradation in 22RV-1 cells as described above for FIG. 48, using 130 vs. galeterone. 130 was compared to galeterone (a clinical lead SARD). 130 demonstrated SARD activity in 22RV-1 (growth dependent on AR-SV, an AR variant lacking a LBD) cells which was comparable to galeterone. (Example 24)

FIG. 56 presents degradation in 22RV-1 cells using 130 vs. galeterone. Using the methods described in the legend for FIG. 55 (22RV-1), 130 was compared to galeterone (a clinical lead SARD). 130 demonstrated SARD activity in 22RV-1 (growth dependent on AR-SV, an AR variant lacking a LBD) cells which was comparable to galeterone.

Figure 57:
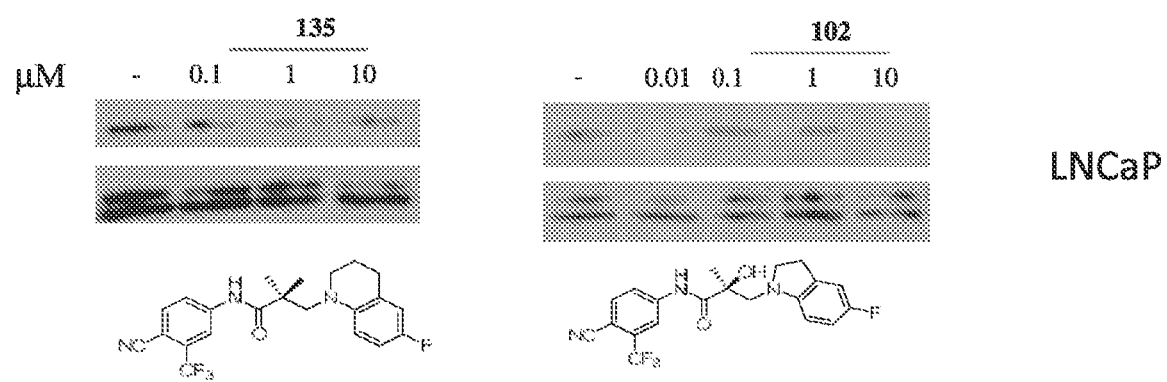
FIG. 57 presents degradation in LNCaP cells using 135 and 102. Using the methods described in the legend for FIG. 47, SARD activities for 135 and 102 were demonstrated. These compounds partially to fully degraded mutant AR (T877A), suggesting that SARDs of this invention such as these may be useful in advanced prostate cancer and/or CRPC. (Example 24)

FIG. 57 presents degradation in LNCaP cells using 135 and 102. Using the methods described in the legend for FIG. 54, SARD activities for 135 and 102 was demonstrated. These compounds partially and fully degraded mutant AR (T877A), suggesting that SARDs such as these may be useful in advanced prostate cancer and/or CRPC.

Figure 58:
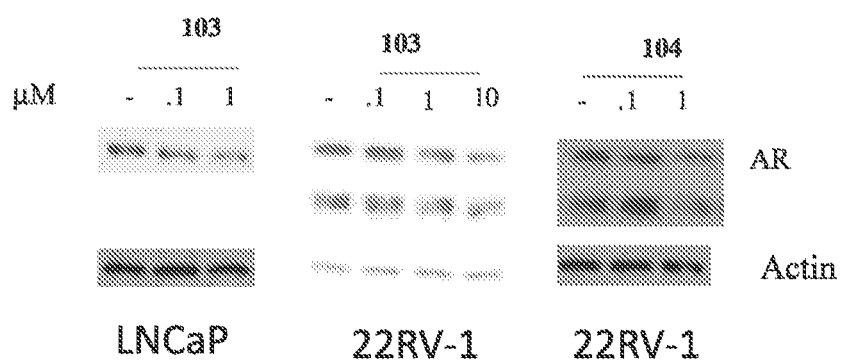
FIG. 58 presents degradation in LNCaP cells and 22RV-1 cells using 103 and 104. Using the methods described in the legends for FIG. 47 (LNCaP) and FIG. 48 (22RV-1), 103 and 104 demonstrated SARD activity in both LNCaP (mutant AR harboring T877A mutation) and 22RV-1 (growth dependent on AR-SV lacking a LBD) cells. (Example 24)
Figure 58:
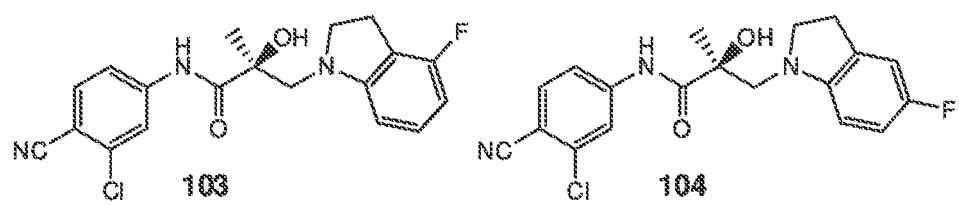

FIG. 58 presents degradation in LNCaP cells and 22RV-1 cells using 103 and 104. Using the methods described in the legends for FIG. 54 (LNCaP) and FIG. 55 (22RV-1), 103 and 104 demonstrated SARD activity in both LNCaP (mutant AR harboring T877A mutation) and 22RV-1 (growth dependent on AR-SV lacking a LBD) cells.

Figure 59:
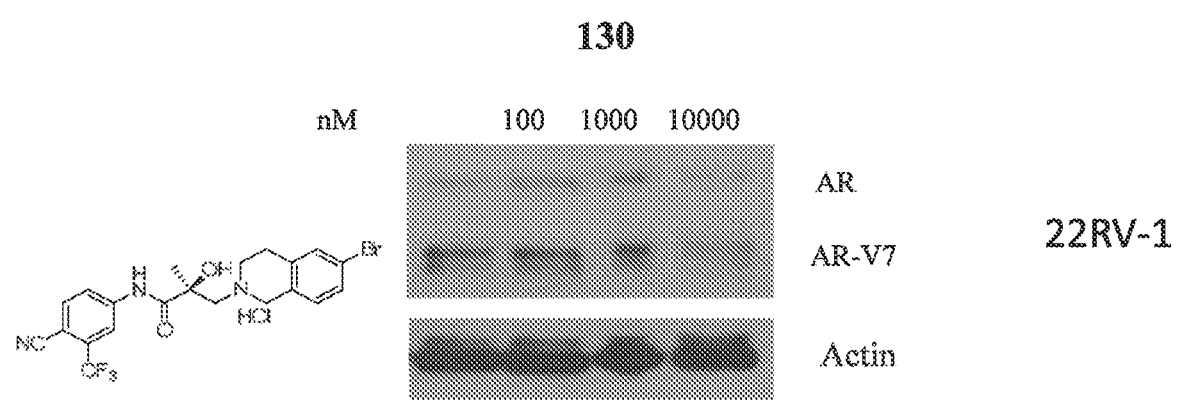
FIG. 59 presents degradation in 22RV-1 cells using 130. Using the methods described in the legend for FIG. 48, compound 130 demonstrated SARD activity at least at the 10 µM concentration. (Example 24)

FIG. 59 presents degradation in 22RV-1 cells using 130. Using the methods described in the legend for FIG. 55, compound 130 demonstrated SARD activity at least at the 10 µM concentration.

Figure 60:
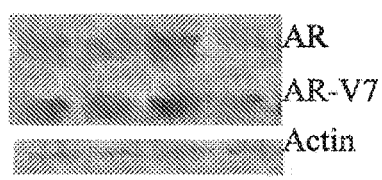
FIG. 60 presents degradation in 22RV-1 cells using 134 and 130. Using the methods described in the legend for FIG. 48, compounds 134 and 130 each demonstrated SARD activity at least at the 10 µM concentration. (Example 24)
Figure 60:
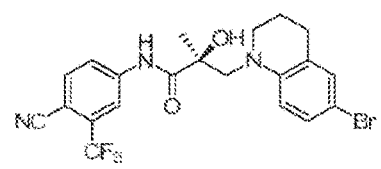
Figure 60:
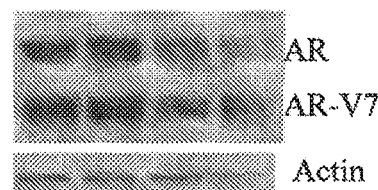
Figure 60:
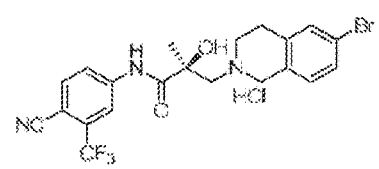

FIG. 60 presents degradation in 22RV-1 cells using 134 and 130. Using the methods described in the legend for FIG. 55, compounds 134 and 130 each demonstrated SARD activity at least at the 10 µM concentration.

Figure 61:
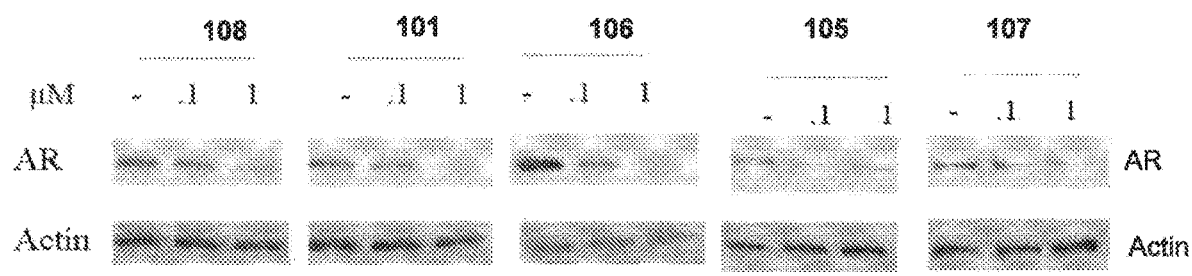
FIG. 61 presents degradation in LNCaP cells using 101, 105, 106, 107 and 108. Using the methods for FIG. 47 above, 101, 105, 106, 107 and 108 each demonstrated the ability to degrade the AR in the nM range. (Example 24)
Figure 61:
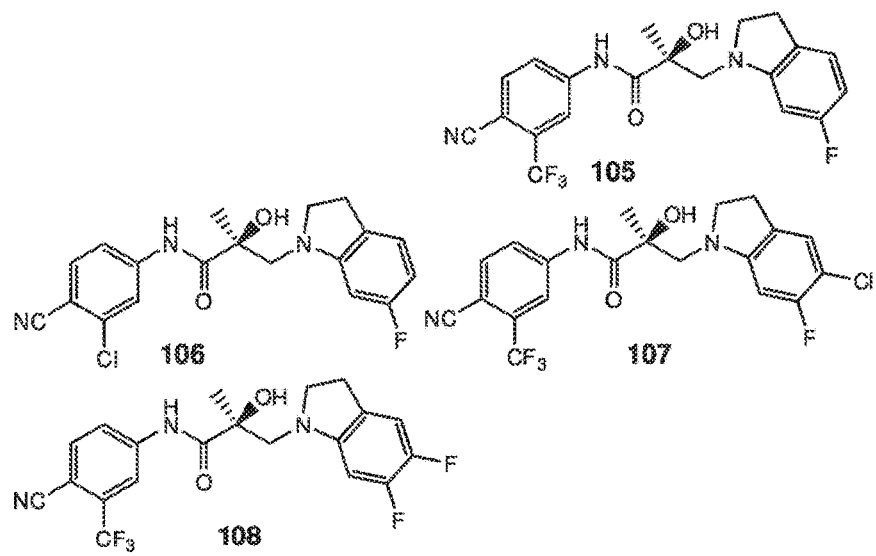

FIG. 61 presents degradation in LNCaP cells using –101, 105, 106, 107 and 108. LNCaP cells were plated in 6 well plates at 500,000 cells/well and maintained in RPMI+1% csFBS without phenol red for 2 days. Cells were treated as indicated above in combination with 0.1 nM R1881 for 24 hrs. Cells were harvested 24 hrs after treatment, protein extracted, Western blotted with AR antibody (SantaCruz antibody AR N-20) and actin antibody (Sigma). 101, 105, 106, 107 and 108 each demonstrated the ability to degrade the AR in the nM range.

Figure 85A:
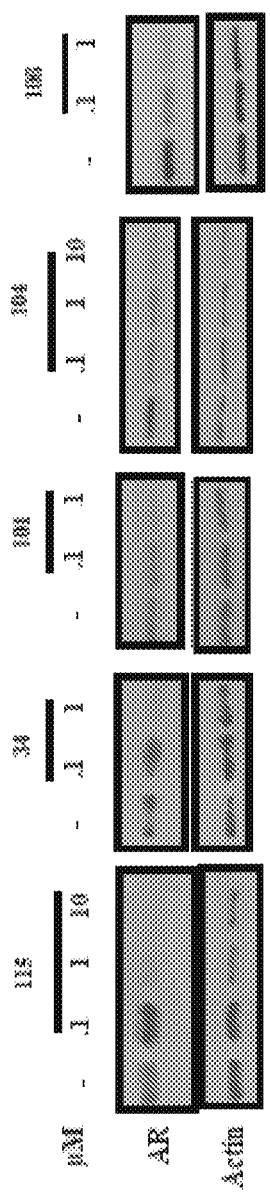
FIGS. 85A and 85B: Degradation of FL AR and AR SV by selected SARDs. LNCaP (FIG. 85A) or 22RV1 (FIG. 85B) cells were plated in full-serum containing medium. Medium was changed to 1% charcoal-stripped serum containing medium and maintained in this medium for 2 days. Medium was changed again and the cells were treated with 0.1 nM R1881 (agonist) and either vehicle or a titration of SARD as indicated in the figure. Twenty-four hours after treatment, cells were harvested, protein extracted, and the proteins were blotted with AR-N20 antibody. Blots were stripped and re-probed with an actin antibody. AR-full length androgen receptor; AR-SV-androgen receptor splice variant.
Figure 85B:
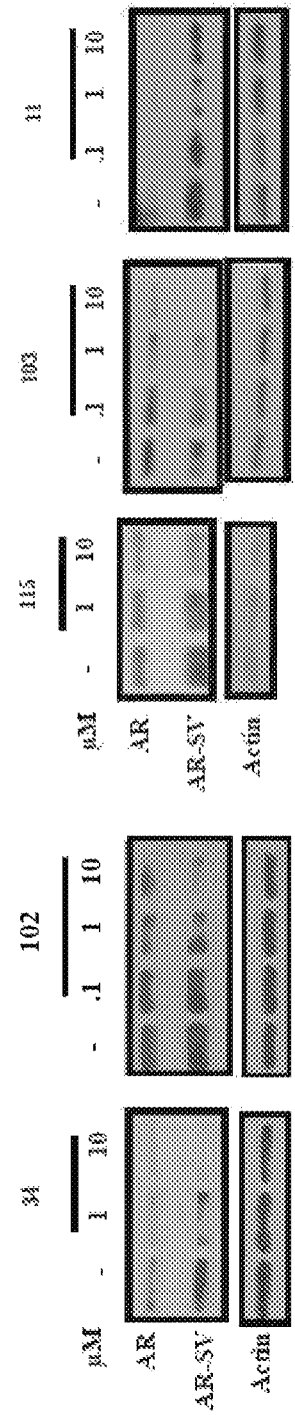

FIGS. 85A and 85B present degradation of FL AR and AR SV by selected SARDs. LNCaP (FIG. 85A) or 22RV1 (FIG. 85B) cells were plated in full-serum containing medium. Medium was changed to 1% charcoal-stripped serum containing medium and maintained in this medium for 2 days. Medium was changed again and the cells were treated with 0.1 nM R1881 (agonist) and either vehicle or a titration of SARD as indicated in the figure. Twenty-four hours after treatment, cells were harvested, protein extracted, and the proteins were blotted with AR-N20 antibody. Blots were stripped and re-probed with an actin antibody. AR-full length androgen receptor; AR-SV-androgen receptor splice variant. In FIGS. 85A and 85B, SARD activity was measured by treating cells with 0.1, 1.0 or 10 µM concentrations of SARDs in the presence of agonist (0.1 nM R1881). The Western blots were quantified densitometrically and the AR/Actin values are represented as fold change or percent change from vehicle-treated cells.

FIG. 85A showed the degradation of FL AR in LNCaP cells and FIG. 49B showed degradation of SV in 22RV1 cells, while actin in each lane serves as an internal standard to correct for variations in protein loading which complicate the visual interpretation of the immunoblots. The % degradation values reported in Tables 3 and 6 are normalized for variations in protein loading and are relied upon for relative efficacy determinations. Concentration-dependent degradation was seen in LNCaP cells for 115 (3'-Cl, 5-F, 6-Ph indoline), 34(3'-Cl, 5-F, 6-Ph indole), 101 (3'-CF$_3$, 4-F indoline), 104 (3'-Cl, 5-F indoline) and 106 (3'-Cl, 6-F indoline). From FIG. 49A, it is apparent that >50% of FL AR is already degraded at 1 μM of these SARDs, i.e. nM range SARD activity. SV AR degradation (the lower molecular weight band in FIG. 49B; upper band is disregarded in % degradation values) of 34 (3'-Cl, 5-F, 6-Ph indole), 102, 115 (3'-Cl, 5-F, 6-Ph indoline), 103 (3'-Cl, 4-F indoline), and 11 (3'-CF$_3$, 5-F indole) was observed to be dose-dependent and generally about 10-fold less potent (FIG. 49B) for selected SARDs, which is consistent with other SARDs. Some compounds degrade FL AR better than SV AR (e.g., 106) or vice versa (e.g., 32) (Tables 3 and 6), whereas the optimal SARD potently and completely (i.e., ++++) degrades both and has a high potency antagonism. 115 comes closest to displaying the perfect profile with complete/strong degradation of FL/SV and antagonism comparable to enzalutamide, 0.244 μM (115) vs. 0.216 μM (5).

These selected SARD activity demonstrations and well as other reported in the tables suggest the compounds of this invention are able to degrade a variety of AR variants, and hence the ability to inhibit the AR-axis activity whether it is androgen-dependent or androgen-independent. Degradation of the AR removes the possibility of promiscuous activation of mutant ARs, activation by intracellular processes such as signal transduction, kinase activation, high levels of coactivators, etc.; and suggests that the SARDs should also degrade the polyQ polymorphisms in hyperandrogenic dermatologic disorders (shortened polyQ) or Kennedy's disease (extended polyQ), providing a rationale for treating either type of diseases by destroying the AR in the affected tissues (skin and neuromuscular system, respectively). Further, a spectrum of in vitro metabolic stabilities were observed suggesting the possibility of either topical administration (short half-life such that systemic exposure are limited) or systemic (e.g., oral; requires relatively long half-lives) administration.

Example 25

SARDs Inhibit Ligand Independent AR Transcription

Compound 11 inhibited transactivation in the AR-NTD-DBD-hinge (A/BCD) AR construct which lacks the ligand binding domain (FIGS. 43A-43D). (A.) AR A/BCD increased GRE-LUC reporter activity. AR A/BCD construct that lacks the ligand binding domain (labeled as A/BCD) or empty vector (labeled as pCR3.1) was transfected into HEK-293 cells along with GRE-LUC and CMV-renilla LUC. Forty eight hours after transfection cells were harvested and luciferase assay performed. As expected, the empty vector did not produce a strong signal compared to the A/BCD construct. (B.-D.) AR A/BCD activity was inhibited by 11. AR A/BCD construct that lacks the ligand binding domain (LBD) was transfected along with GRE-LUC and CMV-LUC. Cells were treated 24 hrs after transfection as indicated in the figure and luciferase assay performed 48 hrs after transfection. 11 (a SARD) inhibited the activity of construct lacking LBD confirming the binding to an alternate site in addition to the LBD. Non-SARD antagonists ARN-509 and enzalutamide did not inhibit the activity of this AR construct lacking the LBD, suggesting that SARDs can inhibit ligand independent AR activity via an alternative binding and degradation domain (BDD) located outside of the LBD. Subsequently, experiments have indicated the NTD as the location of this binding site (see Example 28).

Example 26

Comparison of SARDs and Clinical Candidates in Binding and Transactivation

Plasmid Constructs and Transient Transfection. Human AR cloned into CMV vector backbone was used for the transactivation study. HEK-293 cells were plated at 120,000 cells per well of a 24 well plate in DME+5% csFBS. The cells were transfected using Lipofectamine (Invitrogen, Carlsbad, Calif.) with 0.25 mg GRE-LUC, 0.02 mg CMV-LUC (renilla luciferase) and 25 ng of the AR. The cells were treated 24 h after transfection as indicated in the figures and the luciferase assay performed 48 h after transfection. Data are represented as IC$_{50}$ obtained from a four parameter logistics curve.

Figure 44A:
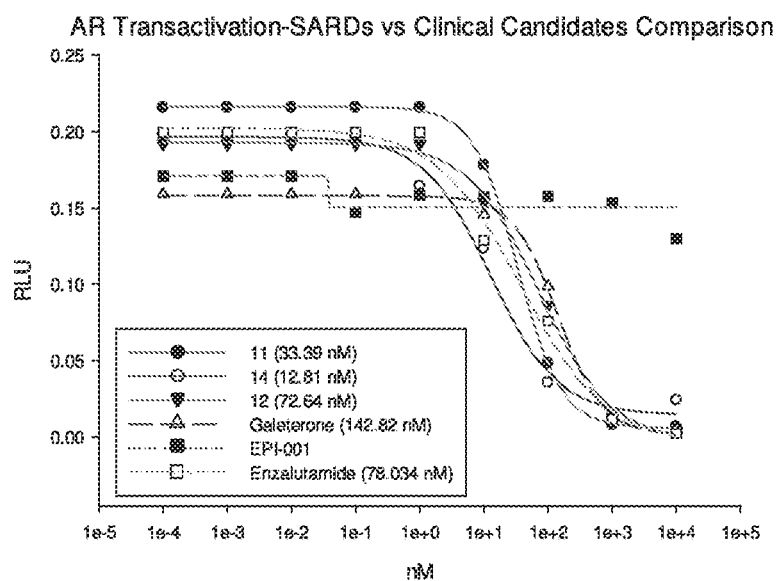
FIGS. 44A-44B present data comparing compounds 11, 12, and 14 with galeterone, EPI-001, and enzalutamide in AR transactivation studies.
Figure 44B:
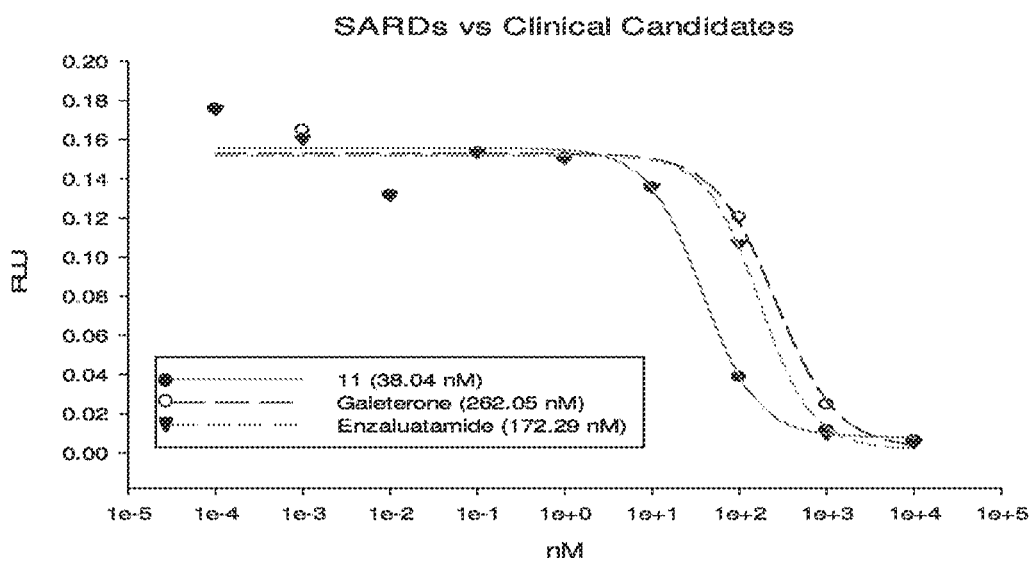

FIG. 44A presents the data comparing 11, 12, and 14 with galeterone, EPI-001, and enzalutamide, in the transactivation study. In general the SARDs of this invention were equipotent to more potent than enzalutamide which was the most potent known AR antagonist tested. EPI-001 did not demonstrate any inhibition in this assay. FIG. 44B shows the data comparing 11 with galeterone and enzalutamide in the transactivation study. The results show that the SARD compounds of the present invention were several-fold more potent than galeterone and enzalutamide in inhibition of DHT activated AR transactivation in vitro.

Figure 70:
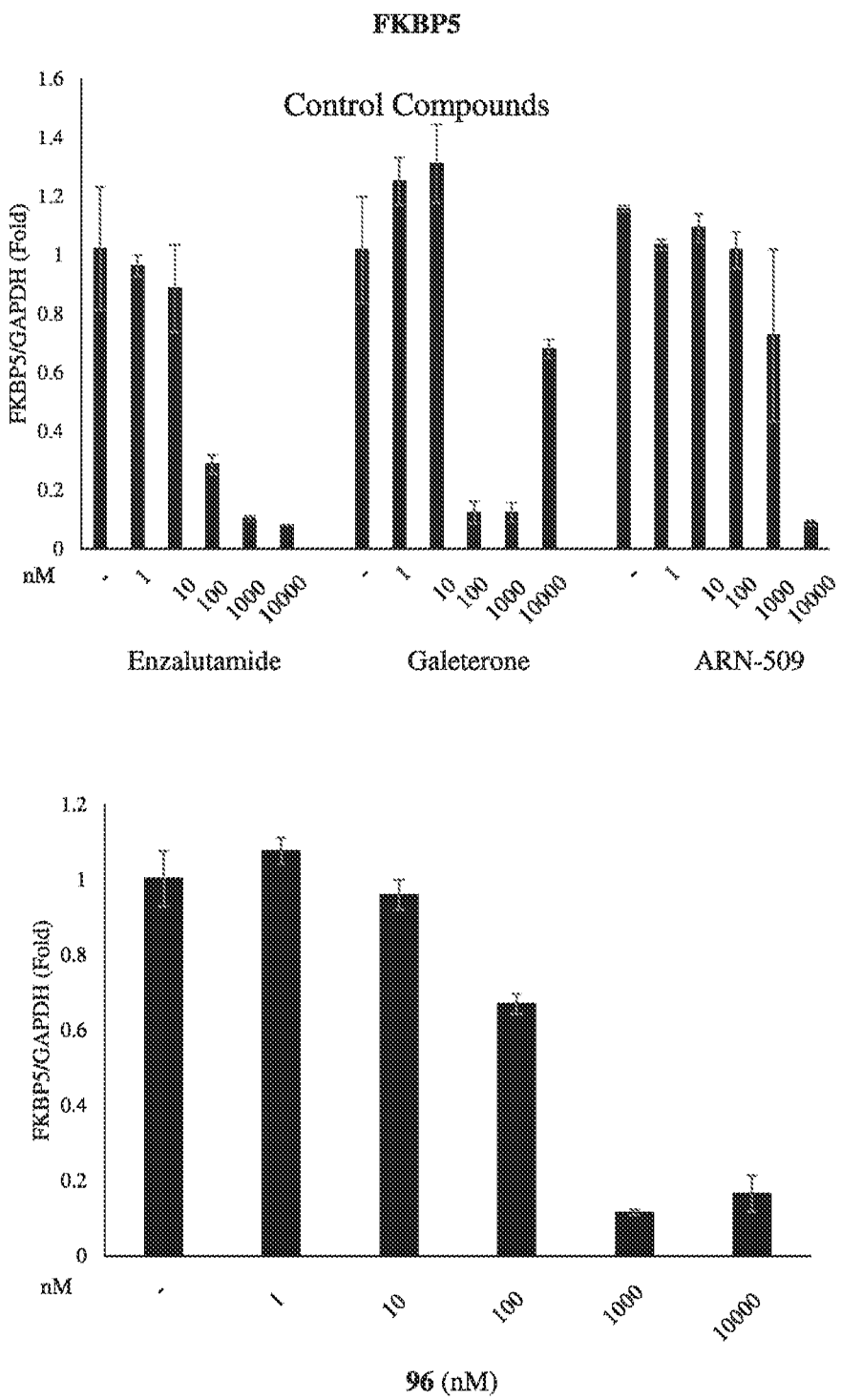
FIG. 70 presents the effect of known AR antagonists compared to SARD 96 on the AR-dependent gene FKBP5. 96 suppressed the AR-responsive gene FKBP5 to a comparable extent as did enzalutamide, galeterone, and ARN-509, demonstrating that 96 is a potent AR antagonist in vitro. (Example 26)
Figure 71:
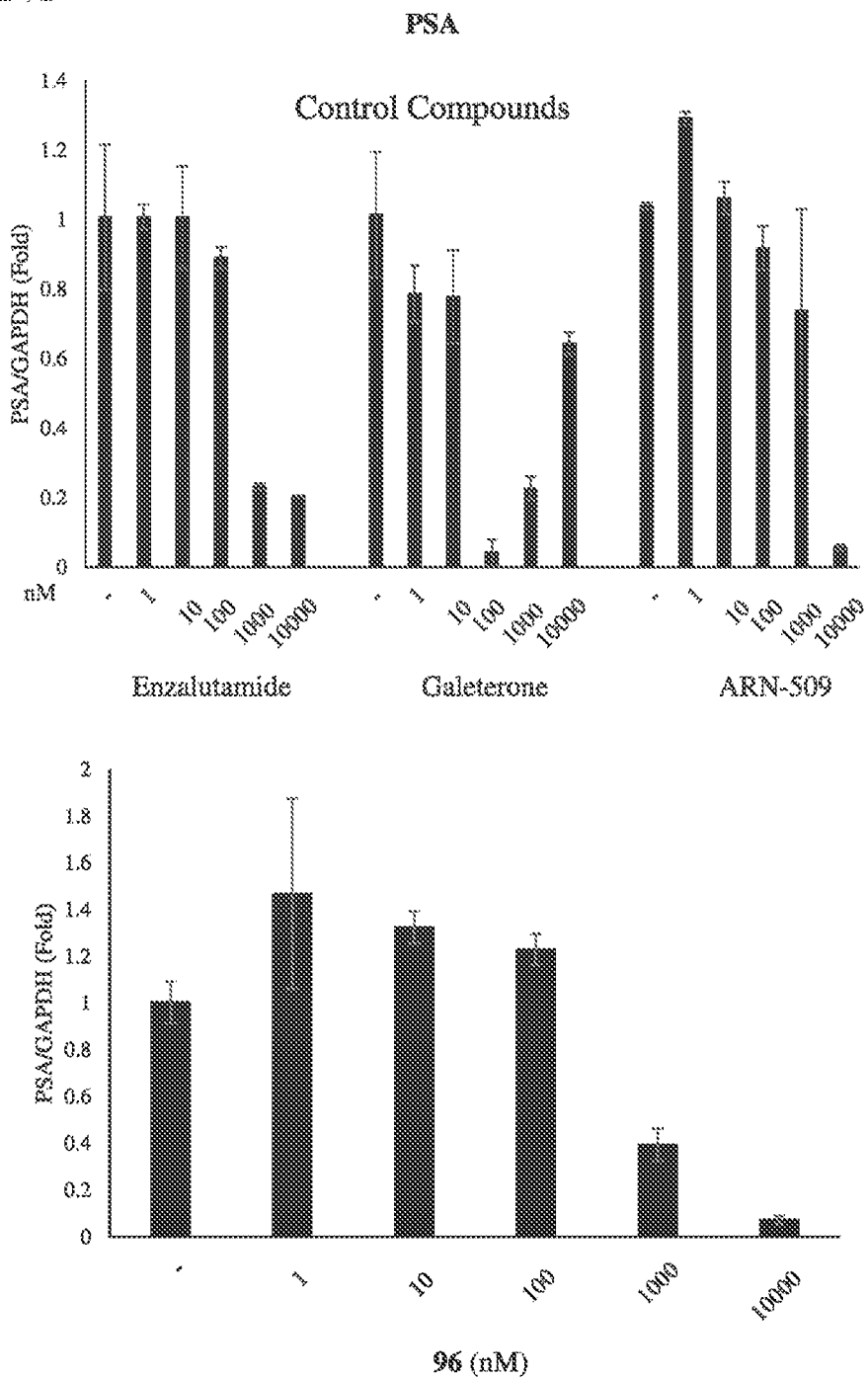
FIG. 71 presents the effect of known AR antagonists compared to SARD 96 on the AR-dependent gene PSA. 96 suppressed the AR-responsive gene PSA to a comparable extent as did enzalutamide and greater than ARN-509. In this case, galeterone potently suppressed at 100 nM but the effect was not dose responsive, reversing at higher doses. (Example 26)
Figure 72:
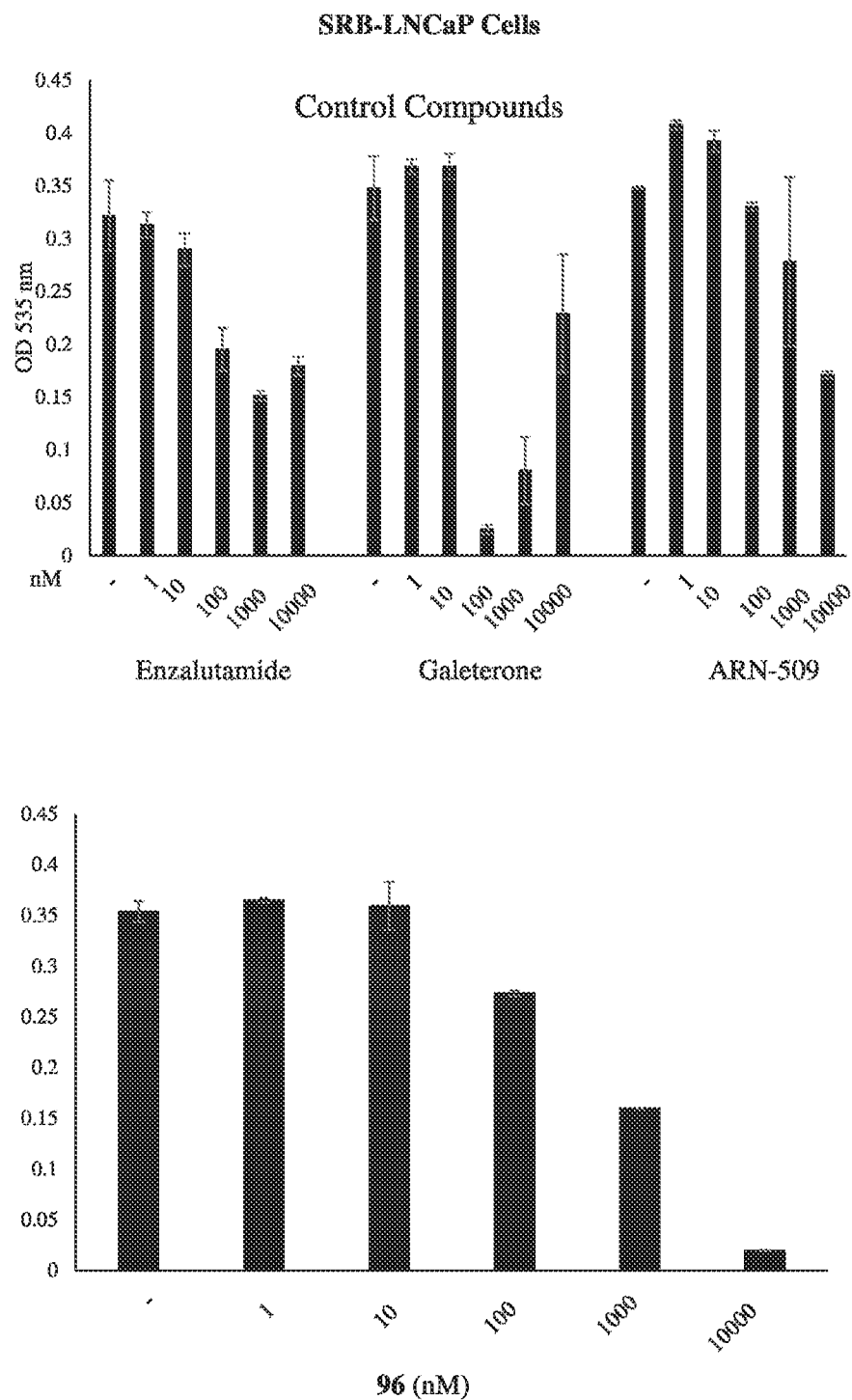
FIG. 72 presents the effect of known AR antagonists compared to SARD 96 on SRB-LNCaP cell growth: LNCaP cells were plated in 96 well plates at 10,000 cells/well in RPMI+1% csFBS without phenol red. Cells were treated as indicated in the figure in combination with 0.1 nM R1881 for 6 days with medium change on day 3. At the end of 6 days, the cells were fixed and stained with sulphorhodamine blue (SRB) stain. 96 demonstrated a robust and dose-dependent anti-proliferative effect whereas enzalutamide and ARN-509 only partially suppressed growth and galeterone did not exhibit dose-dependent effects. (Example 26).

FIGS. 70-72 present data comparing compound 96 with enzalutamide, galeterone and ARN-509. FIG. 70 presents the effect of known AR antagonists and SARD 96 on FKBP5. FIG. 71 presents the effect of known AR antagonists and SARD 96 on PSA. FIG. 72 presents the effect of AR antagonists and SARD 96 on SRB-LNCaP cell growth: LNCaP cells were plated in 96 well plates at 10,000 cells/well in RPMI+1% csFBS without phenol red. Cells were treated as indicated in the figure in combination with 0.1 nM R1881 for 6 days with medium change on day 3. At the end of 6 days, the cells were fixed and stained with sulphorhodamine blue stain. Table 14 summarizes the above and presents it as a panel of in vitro characterizations of 96 with regard to AR binding (K$_i$), nuclear hormone receptor transactivation including AR wt and mutant (IC$_{50}$), and inhibition of LNCaP cell growth and AR-dependent gene expression in LNCaP cells. 96 binds to the LBD of AR with relatively low affinity (~1 μM) but inhibits AR transactivation in wildtype (301 nM) and T877A (343 nM) and W741L (14 nM) mutants with greater potency suggesting that AR inhibition may not be mediated by the LBD. 96 demonstrates good nuclear receptor specificity with no inhibition of transactivation in the glucocorticoid receptor (GR) and mineralocorticoid receptor (MR), and inhibition in the progesterone receptor (PR) that is 3-fold less potent than inhibition of the AR (wt). The anti-androgenic activity of 96 is also evidenced in LNCaP cells, a prostate cancer cell line whose growth is dependent on mutant T877A AR. 96 was anti-proliferative (FIG. 72) and inhibited AR-dependent gene expression of FKBP5 (FIG. 70) and PSA (FIG. 71) in LNCaP cells demonstrating the potential for the treatment of prostate cancer with 96 and other SARDs of this invention based on their activity in well known models of prostate cancer such as LNCaP cells. This panel suggests that 96 is more potent in AR escape mutants than wt AR unlike the known AR antagonists tested, and more nuclear hormone receptor selective than the AR antagonists in use (enzalutamide) or advanced clinical testing (ARN-509 and galeterone).

TABLE 14

AR Binding ($K_i$), Inhibition of AR (wt and mutants), PR, GR, and MR Transactivation ($IC_{50}$), LNCaP Cell Growth Inhibition and Gene Expresssion of Compound 96 and Known AR Antagonists.

| | | Transactivation (IC50 nM) | | | | | | LNCaP | Gene Expression | |
|---|---|---|---|---|---|---|---|---|---|---|
| | Ki (nM) | AR | T877A | W741L | PR | GR | MR | Growth nM | PSA | FKBP5 |
| 96 | 1006.38 | 301.26 | 342.67 | 14.24 | 1057 | >=10 | >10 | 1015.23 | 980.74 | 105.28 |
| Galeterone | >1000 | 243.84 | 1530.74 | | 636.02 | N.I. | >10 | | | |
| Enzalutamide | >1000 | 183.41 | 54.91 | 619.73 | 196.97 | N.I. | >10 | 304.9 | 220.69 | 38.08 |
| ARN-509 | >1000 | 216.58 | 292.52 | 998.83 | 1195.9 | N.I. | >10 | 1907 | >=10 | >=10 |

Ligand binding assay. hAR-LBD (633-919) was cloned into pGex4t.1. Large scale GST-tagged AR-LBD was prepared and purified using a GST column. Recombinant AR-LBD was combined with [$^3$H]mibolerone (PerkinElmer, Waltham, Mass.) in buffer A (10 mM Tris, pH 7.4, 1.5 mM disodium EDTA, 0.25 M sucrose, 10 mM sodium molybdate, 1 mM PMSF) to determine the equilibrium dissociation constant ($K_d$) of [$^3$H]mibolerone. Protein was incubated with increasing concentrations of [$^3$H]mibolerone with and without a high concentration of unlabeled mibolerone at 4° C. for 18 h in order to determine total and non-specific binding. Non-specific binding was then subtracted from total binding to determine specific binding and non-linear regression for ligand binding curve with one site saturation to determine the $K_d$ of mibolerone.

Increasing concentrations of SARDs or DHT (range: $10^{-12}$ to $10^{-4}$ M) were incubated with [$^3$H]mibolerone and AR-LBD using the conditions described above. Following incubation, the ligand bound AR-LBD complex was isolated using BioGel HT hydroxyapatite, washed and counted in a scintillation counter after adding scintillation cocktail. Values are expressed as $K_i$. Table 15 shows that the SARD compounds of the present invention are at least approximately 8-10 fold more tightly bound than galeterone and enzalutamide in AR binding assay studies.

TABLE 15

Binding Assay Results.

| Compound | Binding ($K_i$) nM |
|---|---|
| 11 | 62.7 |
| 14 | 47.9 |
| 12 | 72.9 |
| Galeterone | 922.8 |
| Enzalutamide | 678.9 |
| EPI-001 | Does Not Bind |

Example 27

Compound 11 Inhibits Tumor Growth of an Aggressive Prostate Cancer Expressing AR Splice Variant Xenograft experiment. NOD SCID gamma (NSG) mice (n=8-10) were housed as five animals per cage and were allowed free access to tap water and commercial rat chow (Harlan Teklad 22/5 rodent diet—8640). Cell line xenografts were performed as previously published (Narayanan et al., 2010; Yepuru et al., 2013). LNCaP tumors were grown in intact mice, while 22RV-1 tumors were grown in castrated mice. Once tumor size reached 100 mm$^3$, the animals were randomized and treated with vehicle control (polyethylene glycol: DMSO 9:1 ratio) or 11 (50 mg/kg/day s.c.). Tumor volume was calculated using the formula length*width*width*0.5236. At the end of the experiment, animals were sacrificed, tumors were collected, weighed, and stored for further analysis. Blood was collected, serum separated, and serum PSA was measured using ELISA.

All experiments were performed thrice and each in vitro experiment was performed in triplicate. Statistical analysis was performed using JMP-Pro software (SAS; Cary, N.C.). Experiments containing only two groups were analyzed by simple t-test, while experiments containing more than two groups were analyzed by One Way ANOVA, followed by appropriate post-hoc test.

Figure 45A:
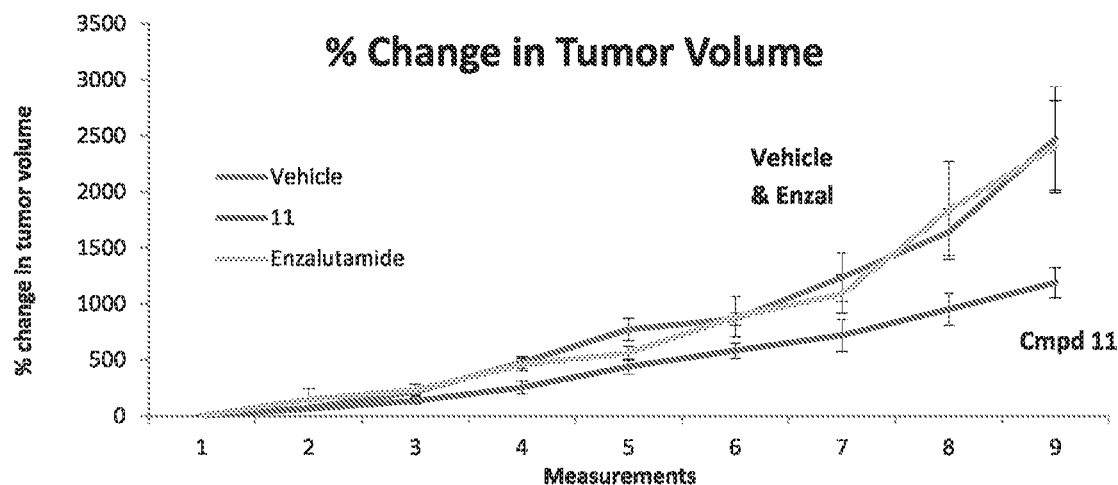
FIGS. 45A-45D demonstrate that 11 inhibited tumor growth of an aggressive prostate cancer (22RV-1) that expresses an AR splice variant (growth driven by AR-V7).
Figure 45B:
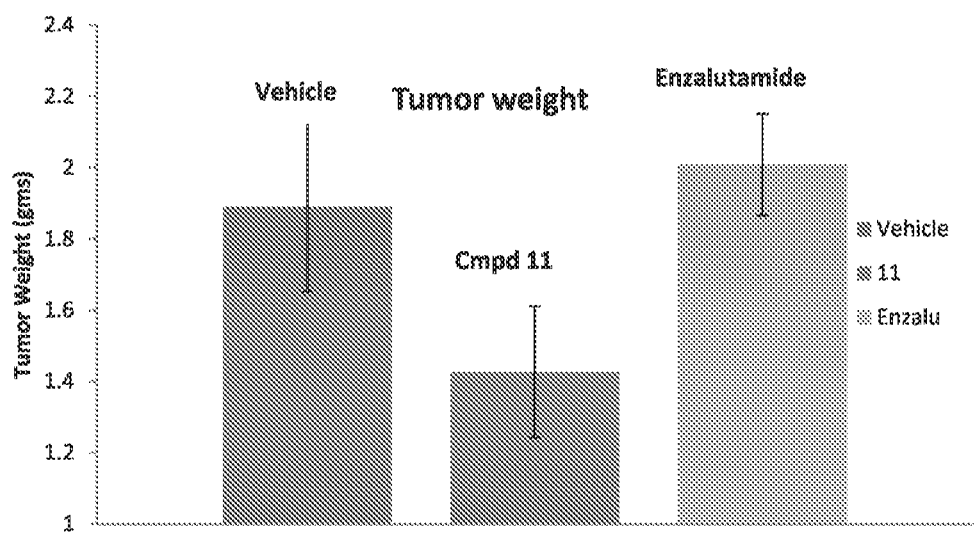
Figure 45C:
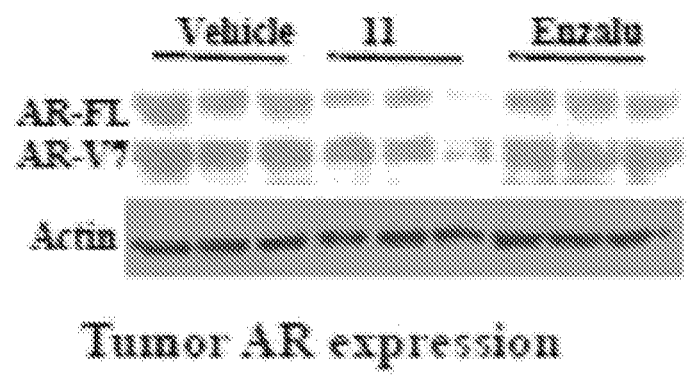
Figure 45D:
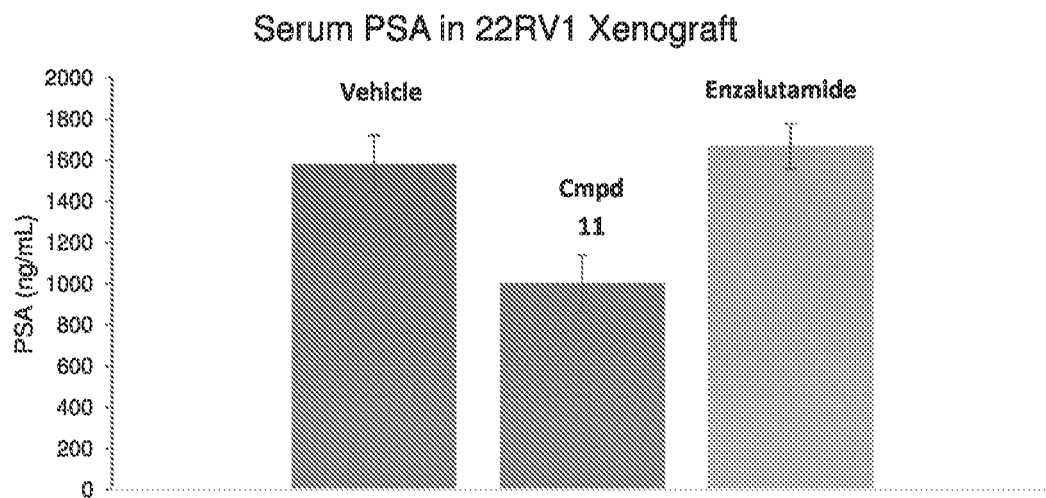

22RV-1 xenograft studies with Compound 11: Since 11 degraded both AR-FL and AR-SV in 22RV-1 and LNCaP cells, the molecule was evaluated in 22RV-1 (FIGS. 45A-45D) and LNCaP (FIGS. 46A-46C) xenograft studies described below. FIGS. 45A-45B show that 11 (100 mg/kg bid) inhibited tumor growth of a prostate cancer that expresses an AR splice variant (AR-V7) and full-length AR (AR-FL). 22RV-1 is a highly aggressive tumor model that is unresponsive to any current available treatments. A SARD compound of the present invention, 11, restricted its growth by approximately 50%, whereas enzalutamide (Enzal) was ineffective. No side-effects were observed in the 3-4 weeks study. FIG. 45C demonstrated that 11 degraded both AR-FL and AR-V7 in the 22RV-1 xenografts whereas enzalutamide (Enzalu) demonstrated no degradation of either AR in these xenografts. FIG. 45D demonstrated that 11 but not enzalutamide suppressed serum PSA in xenograft bearing animals, demonstrating that 11 suppressed AR gene expression in these tumors. This demonstrated that 11 but not enzalutamide can overcome the antiandrogen resistance present in 22RV-1 cells (e.g., AR-V7 dependent growth) by degrading the AR-V7 and AR-FL, resulting in significantly suppressing androgenic tone in these tumors. This provided a proof-of-concept that SARDs such as 11 would be of clinical benefit to CRPC patients, particularly if systemic exposures could be improved.

Figure 46A:
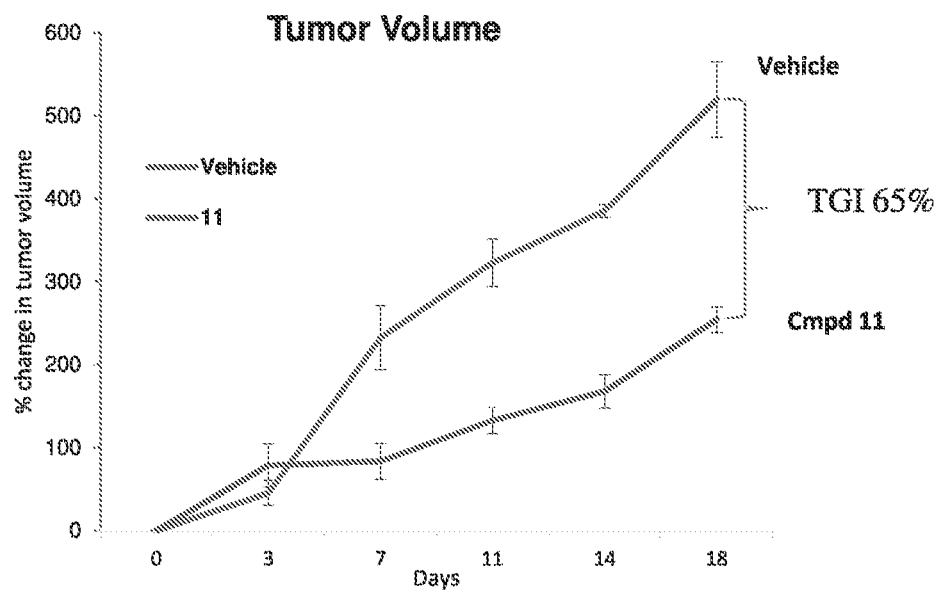
FIGS. 46A-46C demonstrate that 11 inhibited LNCaP tumor xenograft growth via (FIG. 46A) decreased tumor volume and (FIG. 46B) weights, and (FIG. 46C) serum PSA levels in animals treated with 11 when compared to vehicle. (Example 27)
Figure 46B:
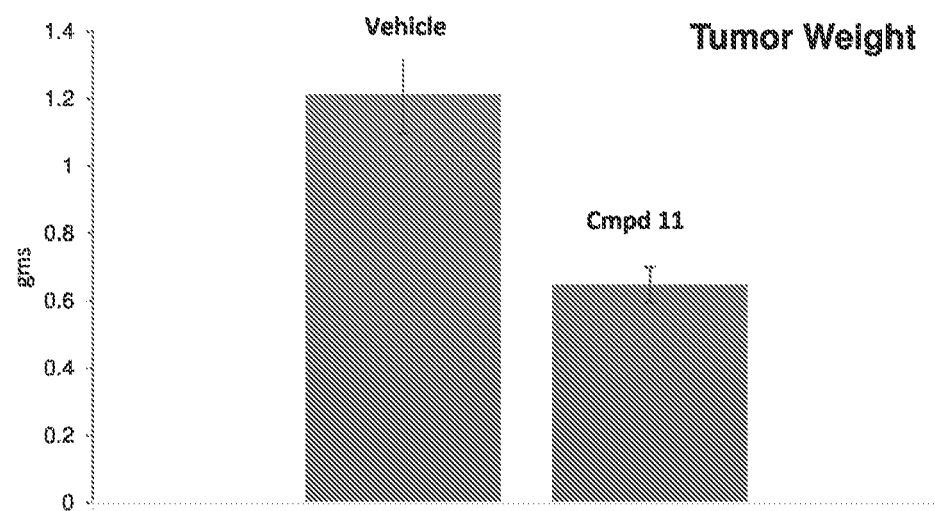
Figure 46C:
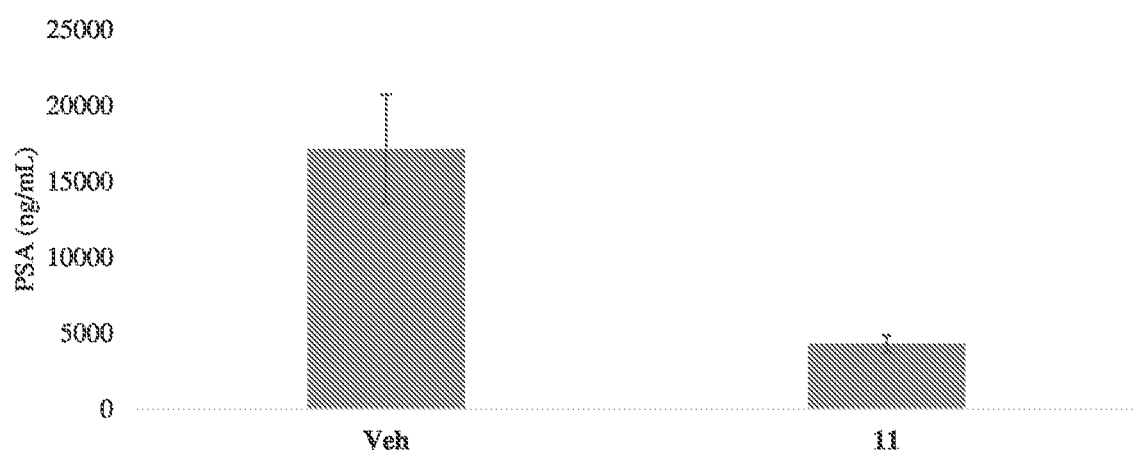

FIGS. 46A-46C show that 11 (100 mg/kg bid) inhibited LNCaP tumor xenograft growth with a % tumor growth inhibition (% TGI) of 65% (FIG. 46A) and inhibited tumor weight by about 50% (FIG. 46B). As shown in FIG. 46C, the serum PSA level was inhibited by >75%, indicating the AR-axis was suppressed in the xenograft as expected for a SARD. Cumulatively, these results indicated that SARDs should be effective in AR-driven prostate cancers regardless of whether the prostate cancers are driven by wt or mutant AR-FL and/or AR-SV such as AR-V7 which lack the LBD. As such SARDs, would be able to treat enzalutamide or abiraterone resistant prostate cancers.

Example 28

SARDs Bind to the AF1 of NTD of AR

Figure 53A:
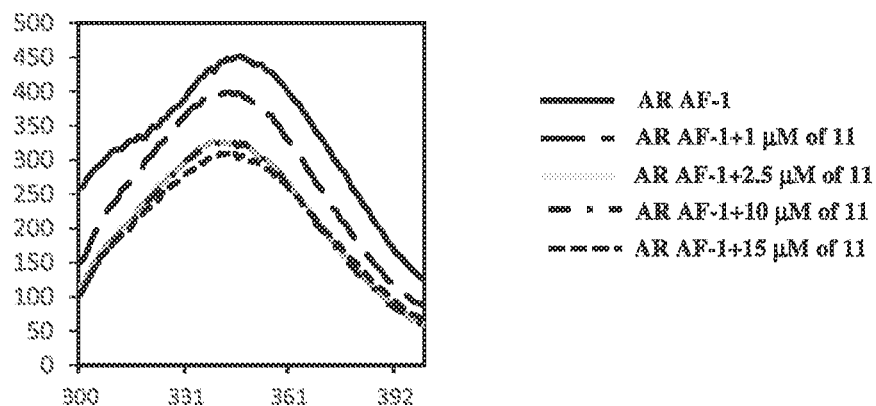
FIGS. 53A-53C present biophysical data that suggests that SARDs bind to the N-terminal domain of the AR (in addition to the LBD in the C-terminus).
Figure 53B:
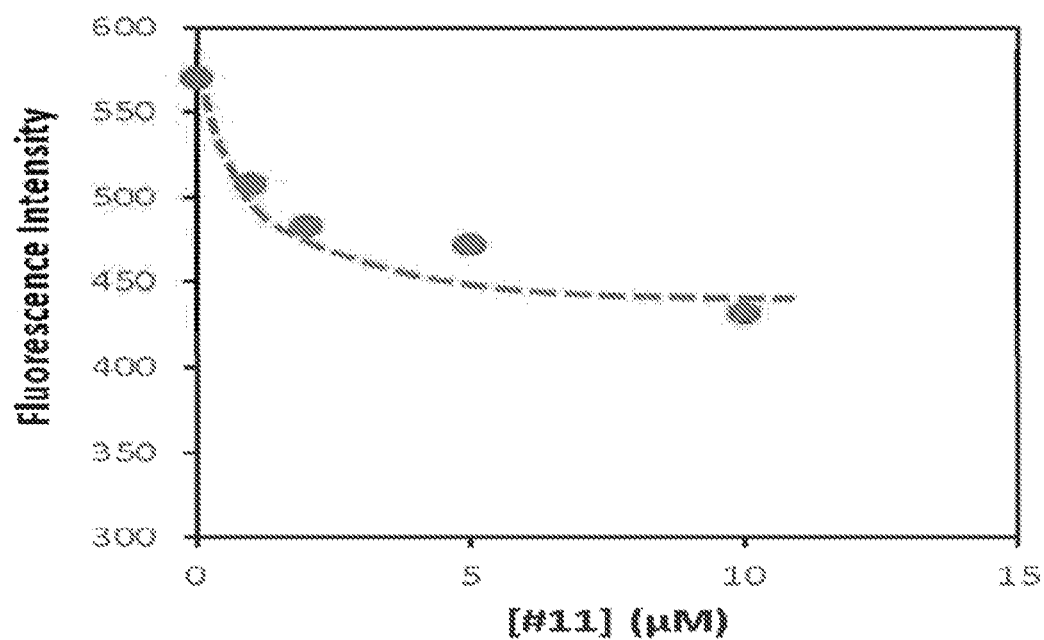
Figure 53C:
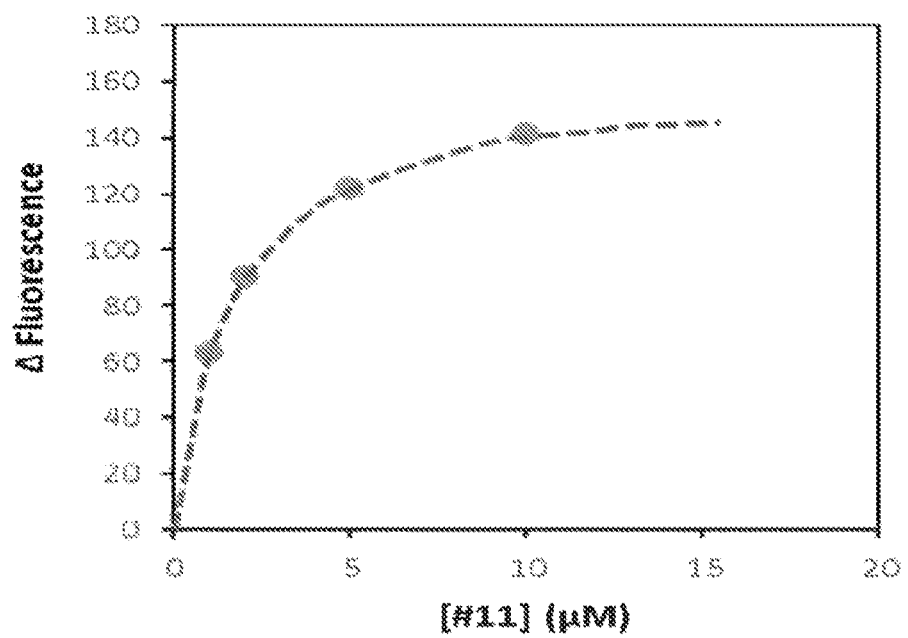

Fluorescent Polarization (FP): There are two tryptophan residues and up to 12 tyrosine residues in the AF1 of the AR which is located in the N-terminal domain (NTD) of AR. This has allowed the study of the folding properties of this domain using intrinsic steady state fluorescence emission spectra. Excitation at 287 nm excites both tyrosine and tryptophan residues. The emission maximum ($\lambda_{max}$) for the tryptophan is sensitive to the exposure to solvent. In the presence of the natural osmolyte TMAO there is a characteristic 'blue shift' consistent with the tryptophan residues being less solvent exposed and a loss of the shoulder (~307 nm) for tyrosine as there is increased energy transfer to tryptophan as the polypeptide folds. To test if the compounds (a nonsteroidal agonist enobosarm (negative control), and the SARD 11) interact with AF-1 and/or alter the folding of this domain the steady state fluorescence was measured for each compound with AR-AF1 alone or the presence of TMAO (3 M) or the denaturant urea (4 or 6 M). 1 µM of AR-AF1 and 5 µM of the individual compounds were used, and preincubated for at least 30 minutes prior to measuring the emission spectra. The emission spectra were all corrected for buffer alone or buffer with TMAO/urea/compounds as necessary. FIG. 53A-53C presents biophysical data that suggests that SARDs bind to the N-terminal domain of the AR (in addition to the LBD in the C-terminus reported as $K_i$ values herein). FIG. 53A: Dose-dependent shift in the fluorescence intensity by 11 when incubated with AR AF-1. The fluorescence shoulder observed at 307 nm, which corresponds to tyrosine residues in the AF-1, is shifted by 11. FIG. 53B: The overall fluorescence is also markedly altered by increasing concentrations of 11. FIG. 53C: Data shown in FIG. 53A was plotted as a difference in fluorescence between control and 11 treated samples (fluorescence in the absence of compound–fluorescence in the presence of compound), a dose dependent increase was observed in the presence of 11, consistent with binding to and stabilization of the intrinsically disordered AR-AF1 peptide derived from the NTD of AR. This data demonstrated binding of SARDs to the NTD domain. Only EPI-001 is reported to bind NTD but is not orally bioavailable. Enzalutamide and ARN-509 bind to the LBD only. This demonstrates the uniqueness of the compounds of this invention that are highly potent and selective androgen receptor degraders of a variety of full-length and splice-variant androgen receptors (Examples 21-24 and 29), potent inhibitors of LBD-dependent transactivation (Examples 21-24, 26, and 29), and inhibit NTD-dependent activity (Example 25) via binding to the NTD (Example 12). Based on their unique profile of AR antagonistic mechanisms, there is great expectation to expand the scope of diseases treatable with the androgen receptor antagonist compounds of this invention reported herein.

Based on half-maximum saturation for the change in fluorescence signal (at λmax 242 nm), the binding constant to AR-AF1 was calculated to be of KD=1.34±0.32 µM (n=3, mean±SEM).

1 µM AR-AF1 was pre-incubated without or with increasing concentrations of compound 11 (up to 15 µM) and steady-state fluorescence emission, after excitation at 287 nm, measured from 300 to 400 nm. Data was analysed as described by Epps et al (1999) *J. Pharm* 51, 41-48, Rawel et al (2006) *Mol. Nutr. Food Res.* 50, 705-713 and Wang et al (2011) *Mol. Endcor.* 25, 2041-2053 which are hereby incorporated by reference.

Figure 83:
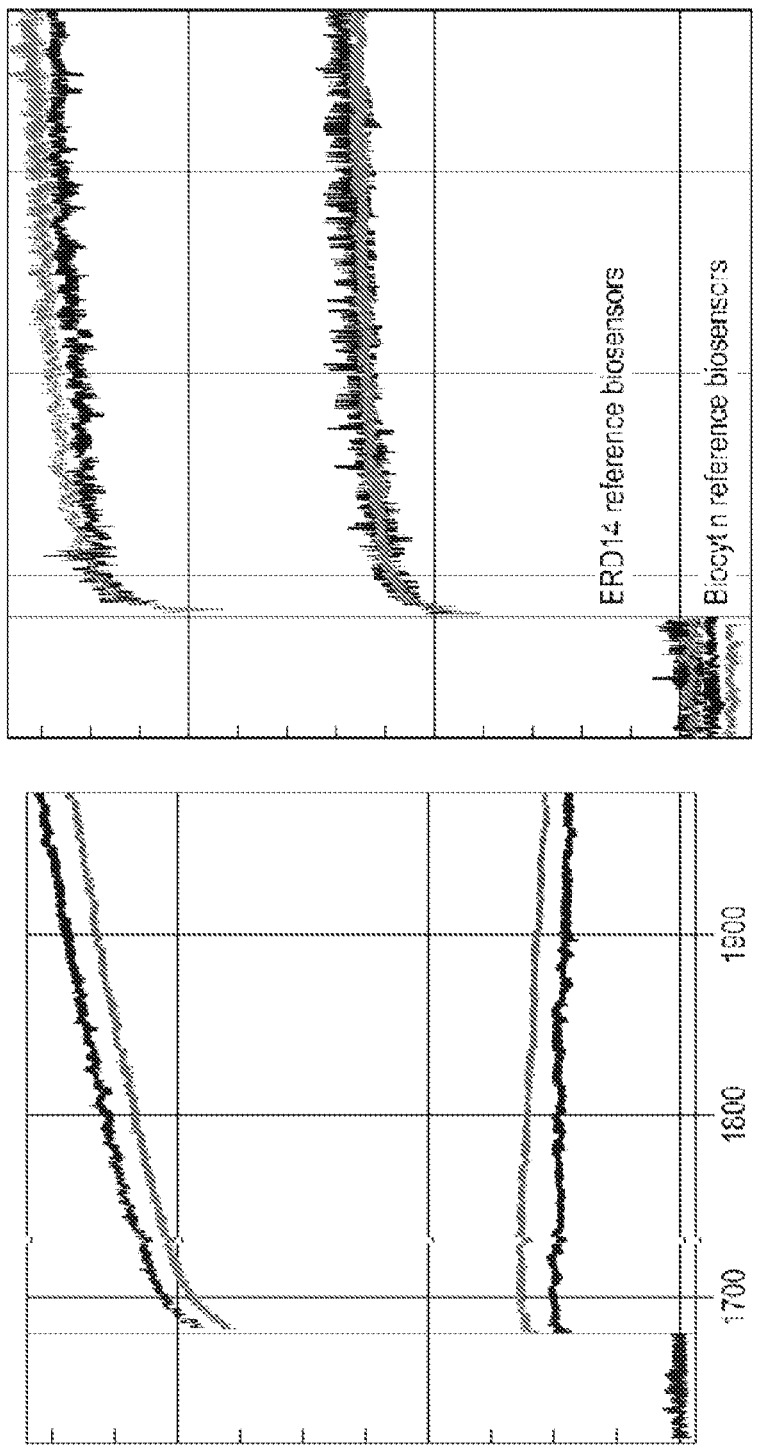
FIG. 83: 11 binds to AR AF-1 domain based on surface plasmon resonance. Biocore assay was performed with purified activation function domain 1 (AF-1) of the androgen receptor (AR) in the presence of 11.
Figure 84:
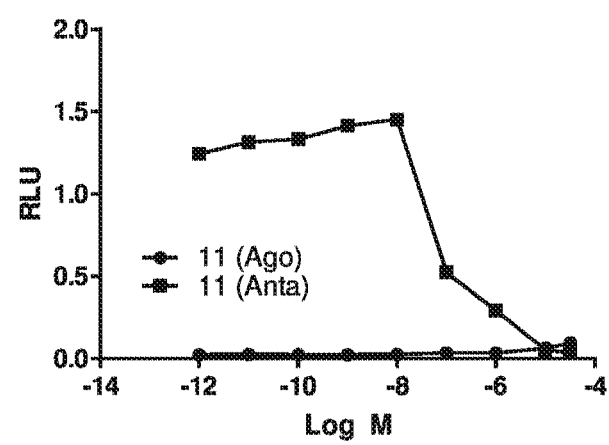
FIG. 84: 11 is a full antagonist with no agonist activity in transactivation studies.

Surface Plasmon Resonance (SPR): To confirm the results obtained by FP assay, a biotin labeled method using AF-1 was employed. Biacore assay uses surface plasmon resonance (SPR) to measure protein-protein interaction and protein-small molecule interaction. In this assay, AR AF-1 and 50 nM of 11 were added to a Biacore chip and SPR was measured. 11 demonstrated a change in the refraction index in the SPR, indicating an interaction with the AR AF-1 protein (FIG. 83).

NMR studies confirm the binding of 11 to AF-1 between amino acids 244-360. $^1$H NMR is consistently used in high-throughput screens to detect the binding of small molecules less than 500 Da to large proteins greater than 5 KDa [Dias, D. M., and Ciulli, A. (2014). NMR approaches in structure-based lead discovery: recent developments and new frontiers for targeting multi-protein complexes. Prog Biophys Mol Biol 116, 101-112; Shortridge, M. D., Hage, D. S., Harbison, G. S., and Powers, R. (2008). Estimating protein-ligand binding affinity using high-throughput screening by NMR. J Comb Chem 10, 948-958]. It is easier to use one-dimensional (1D) NMR to observe changes in line-width or line broadening as a high-throughput method to identify the binding of the molecules to proteins and then use two-dimensional (2D) NOE-based NMR techniques such as Water ligand-observed spectroscopy (Water-LOGSY) as confirmatory methodology [Dalvit, C., Pevarello, P., Tato, M., Veronesi, M., Vulpetti, A., and Sundstrom, M. (2000). Identification of compounds with binding affinity to proteins via magnetization transfer from bulk water. J Biomol NMR 18, 65-68; Shortridge et al., 2008].

All these experiments are based on the fact that NMR observables such as linewidths and NOE's vary dramatically between small molecules and heavy molecules. The decreased rotational correlation times upon binding of a small molecule ligand to a heavy target molecule produce an atypical heavy molecule NMR result characterized by broadened and weaker of ligand peaks in 1D NMR and negative NOE peaks in the waterLOGSY as compared to the free state. In the absence of any affinity, the small molecule NMR result is obtained (sharp peaks in 1D NMR and positive NOE's). This distinction provides the basis for NMR screening experiments.

Figure 82A:
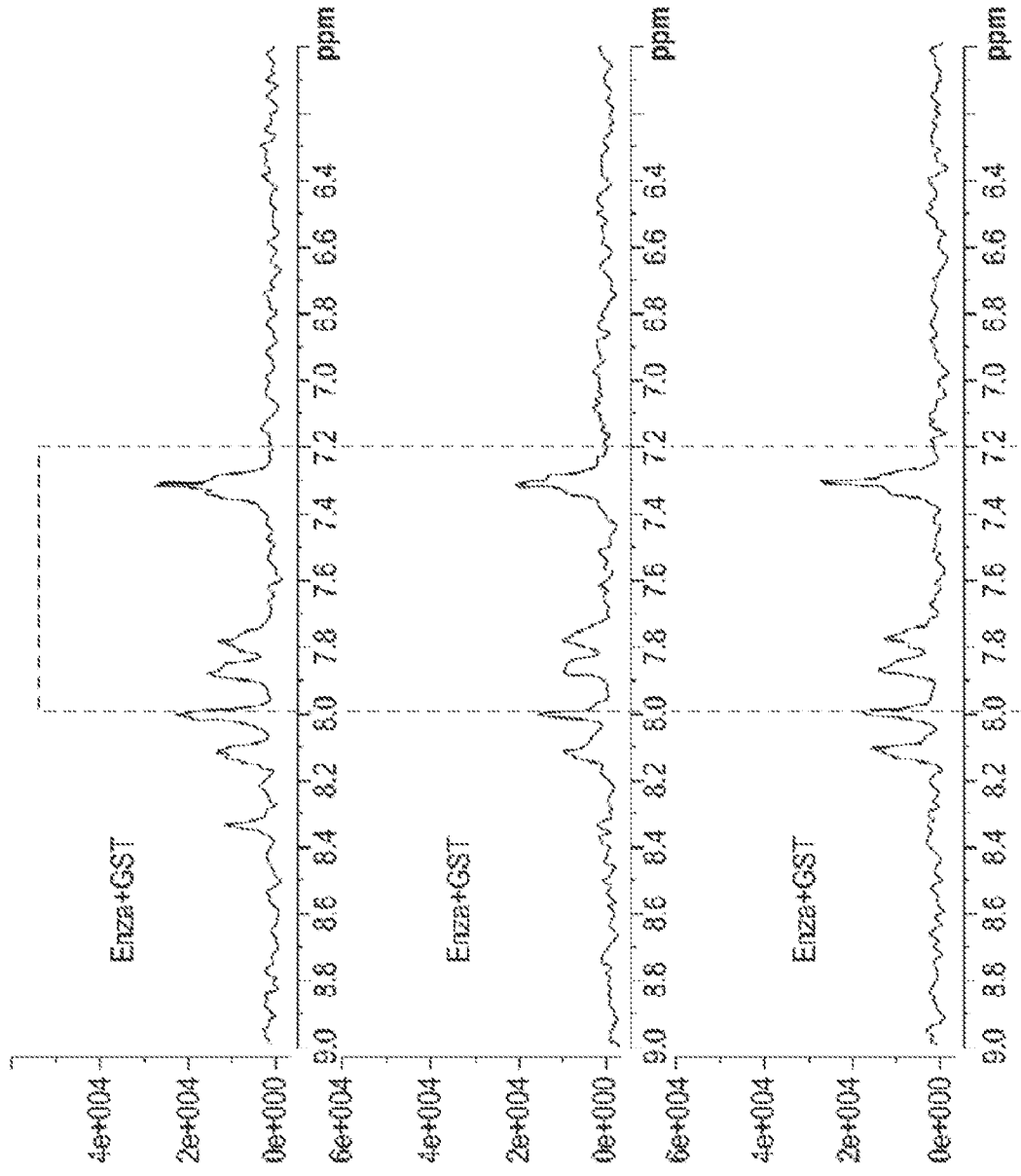

Using these principles $^1$H NMR was used to confirm the binding of 11 to AF-1 protein. In the first experiment, 11 or enzalutamide (500 µM) was dissolved in deuterated DMSO (DMSO-d$_6$) and was incubated alone or mixed with 5 µM GST-AF-1 or GST and the binding of the molecules to the protein was determined by NMR. While 11 alone or in combination with GST exhibited sharp peaks revealing that the ligand was present in the free state, 11 in combination with GST-AF-1 provided a broadened and weaker peaks (FIG. 82A; peaks in box) revealing that 11 has affinity for the AF-1 protein. Enzalutamide is a traditional AR antagonist known to competitively bind to the LBD. No line broadening was observed upon addition of enzalutamide to AF-1 revealing no affinity for AF-1. This result confirms that the 11, but not enzalutamide, binds to the AF-1 domain. To further confirm the 1D NMR results, we performed Water-LOGSY with 11 alone or in combination with AF-1. While the 11 alone gave a flat signal, i.e., no negative NOE's as expected for a free state small molecule, 11 in combination with AF-1 provided a negative signal characteristic of binding to the protein (FIG. 82B).

Figure 11:
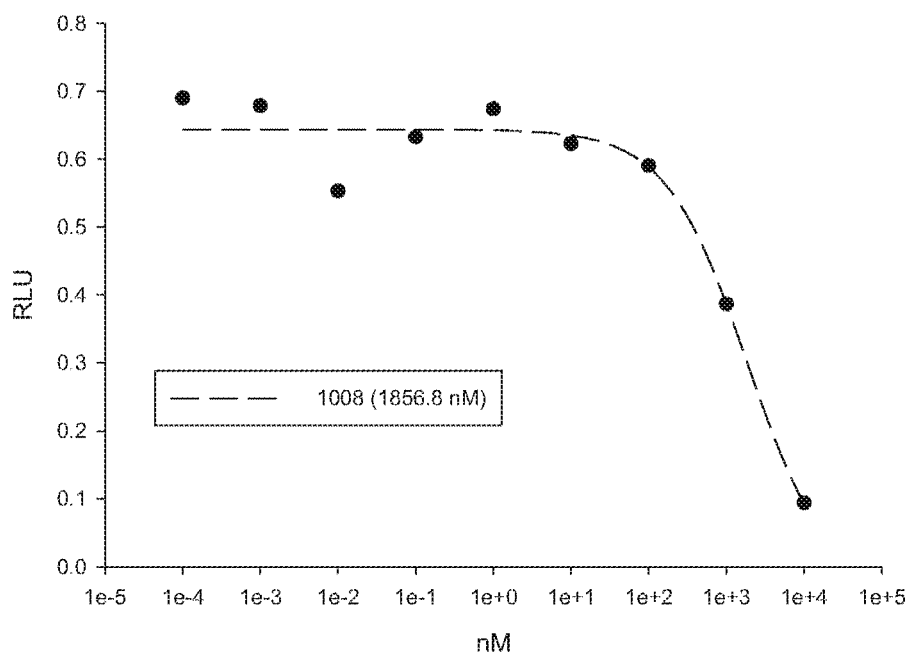
FIG. 11: The transactivation result of 1008 was reported based on measured luciferase light emissions and reported as relative light unit intensity (RLU).
Figure 82C:
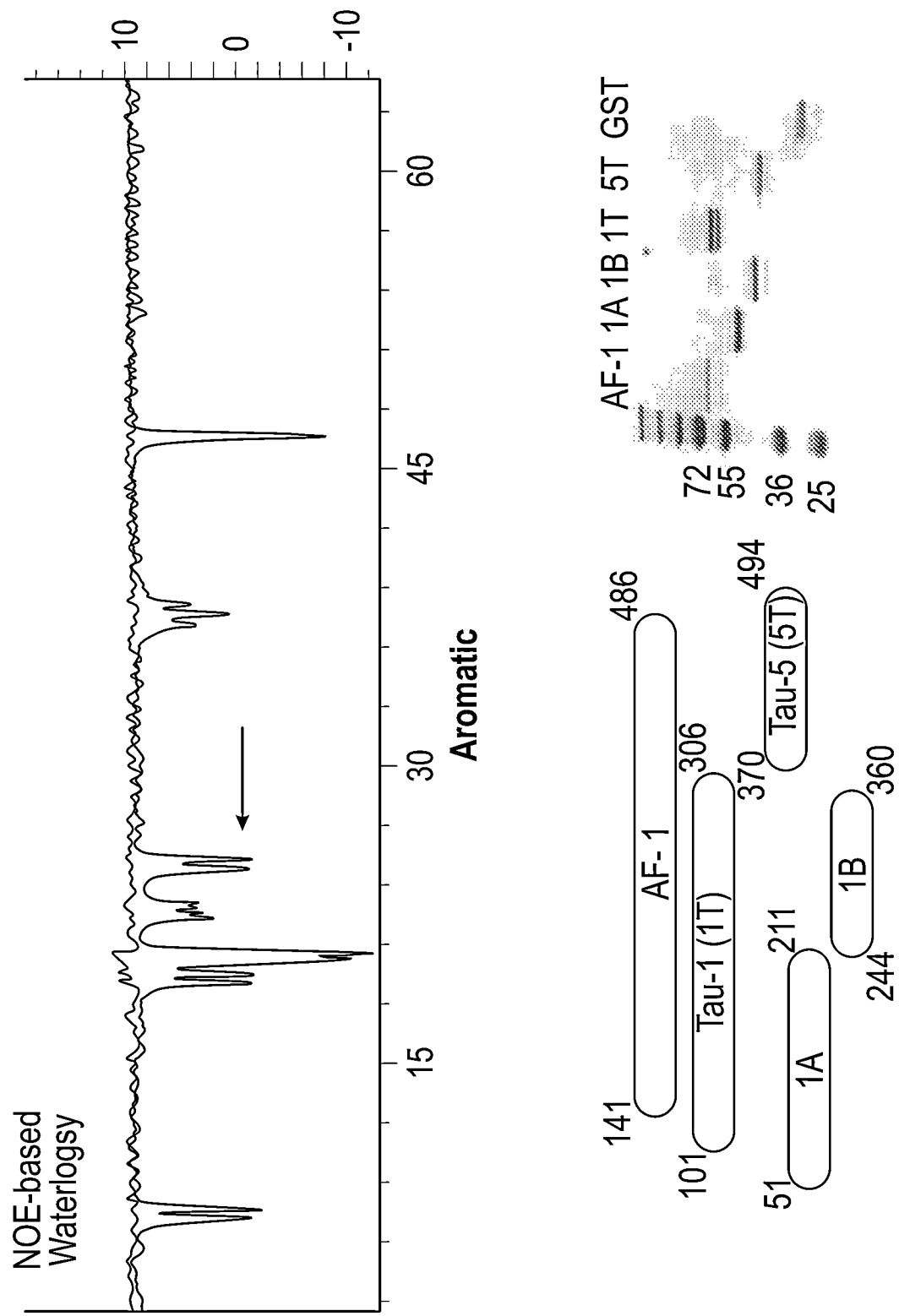

To determine precisely the region where 11 binds to the AF-1 region (since the AF-1 region is between 141 and 486 amino acids), we created smaller fragments of the AF-1 gene and purified the proteins coded for by fragments (FIG. 82C). 11 was incubated alone or in combination with GST, GST-AF-1 or with various fragments of the AF-1 region and 1D $^1$H NMR profile was obtained. Similar to the results shown in FIG. 82A, 11 provided a sharp signal by itself and when co-incubated with GST, but line broadening when incubated with the AF-1 (FIG. 82D). Similar to the unbound ligand, 11 in combination with fragments 1A and 5T produced spectra suggestive of free state. However, when 11 was incubated with fragment 1T, the signal was almost indistinguishable from line, indicating a strong binding affinity to this region. The profile of 11 in combination with 1B looked similar to that of the AF-1, confirming the binding to this region. Binding of 11 to 1T and 1B, but not to 1A, indicates that amino acids 51-211 could be excluded and that potentially the binding occurs between amino acids 244 and 360.

Three separate biophysical phenomena, FP, SPR, and NMR indicate that 11 and other SARDs of this invention have significant affinity for AF-1, suggestive of binding strong enough to mediate some of the unique characteristics of the AR antagonists reported herein.

Example 29

Androgen Receptor Binding and Transactivation of Carbazole Based SARDs

Ligand Binding Assay

Objective: To determine SARDs binding affinity to the AR-LBD.

Method: hAR-LBD (633-919) was cloned into pGex4t.1. Large scale GST-tagged AR-LBD was prepared and purified using a GST column. Recombinant ARLBD was combined with [$^3$H]mibolerone (PerkinElmer, Waltham, Mass.) in buffer A (10 mM Tris, pH 7.4, 1.5 mM disodium EDTA, 0.25 M sucrose, 10 mM sodium molybdate, 1 mM PMSF) to determine the equilibrium dissociation constant ($K_d$) of [$^3$H]mibolerone. Protein was incubated with increasing concentrations of [$^3$H]mibolerone with and without a high concentration of unlabeled mibolerone at 4° C. for 18 h in order to determine total and non-specific binding. Non-specific binding was then subtracted from total binding to determine specific binding and non-linear regression for ligand binding curve with one site saturation to determine the $K_d$ of mibolerone.

Increasing concentrations of SARDs or DHT (range: $10^{-12}$ to $10^{-2}$ M) were incubated with [$^3$H]mibolerone and AR LBD using the conditions described above. Following incubation, the ligand bound AR-LBD complex was isolated using BioGel HT® hydroxyapatite, washed and counted in a scintillation counter after adding scintillation cocktail. Values are expressed as $K_i$ (Table 16).

Transactivation Assay for wt and Mutant AR

Objective: To determine the effect of SARDs on androgen-induced transactivation of AR wildtype (wt) or AR carrying known AR-LB mutants (i.e., W741L or T877A).

Method: HEK-293 cells were plated at 125,000 cells/well of a 24 well plate in DME+5% csFBS without phenol red. Cells were transfected with 0.25 ug GRE-LUC, 10 ng CMV-renilla LUC, and 50 ng CMV-hAR(wt) or CMV-hAR (W741L) or CMV-hAR(T877A) using Lipofectamine transfection reagent in optiMEM medium. Medium was changed 24 h after transfection to DME+5% csFBS without phenol red and treated with a dose response of various drugs (Table 16: compounds 200-205) (1 pM to 10 □M). SARDs and antagonists were treated in combination with 0.1 nM R1881. Luciferase assay was performed 24 h after treatment on a Biotek synergy 4 plate reader. Firefly luciferase values were normalized to renilla luciferase values.

Transactivation Assay: wt and Mutant AR

Objective: To determine the effect of SARDs on androgen-induced transactivation of AR carrying known AR-LBD mutants.

Method: HEK-293 cells were plated at 125,000 cells/well of a 24 well plate in DME+5% csFBS without phenol red. Cells were transfected with 0.25 ug GRE-LUC, 10 ng CMV-renilla LUC, and 50 ng CMV-hAR/W741L-AR/T877A-AR using Lipofectamine transfection reagent in optiMEM medium. Medium was changed 24 h after transfection to DME+5% csFBS without phenol red and treated with a dose response of various drugs (1 pM to 10 □M). SARDs and antagonists were treated in combination with 0.1 nM R1881. Luciferase assay was performed 24 h after treatment on a Biotek synergy 4 plate reader. Firefly luciferase values were normalized to renilla luciferase values. (Table 16)

AR Degradation was Performed Using LNCaP, 22RV1, and AD1 Cells as Described Herein Above and in Example 29

Determination of Metabolic Stability (In Vitro $CL_{int}$) of Test Compounds:
Phase I Metabolism The assay was done in a final volume of 0.5 ml in duplicates (n=2). Test compound (1 µM) was pre-incubated for 10 minutes at 37° C. in 100 mM Tris-HCl, pH 7.5 containing 0.5 mg/ml liver microsomal protein. After pre-incubation, reaction was started by addition of 1 mM NADPH (pre-incubated at 37° C.). Incubations were carried out in triplicate and at various time-points (0, 5, 10, 15, 30 and 60 minutes) 100 µl aliquots were removed and quenched with 100 µl of acetonitrile containing internal standard. Samples were vortex mixed and centrifuged at 4000 rpm for 10 minutes. The supernatants were transferred to 96 well plates and submitted for LC-MS/MS analysis. As control, sample incubations done in absence of NADPH were included. From % PCR (% Parent Compound Remaining), rate of compound disappearance is determined (slope) and in vitro $CL_{int}$ (µl/min/mg protein) was calculated.
Metabolic Stability in Phase I & Phase II Pathways In this assay, test compound was incubated with liver microsomes and disappearance of drug was determined using discovery grade LC-MS/MS. To stimulate Phase II metabolic pathway (glucuronidation), UDPGA and alamethicin was included in the assay.
LC-MS/MS Analysis:

The analysis of the compounds under investigation was performed using LC-MS/MS system consisting of Agilent 1100 HPLC with an MDS/Sciex 4000 Q-Trap™ mass spectrometer. The separation was achieved using a $C_{18}$ analytical column (Alltima, 2.1×100 mm, 3 µm) protected by a $C_{18}$ guard cartridge system (SecurityGuard™ ULTRA Cartridges UHPLC for 4.6 mm ID columns, Phenomenex). Mobile phase was consisting of channel A (95% acetonitrile+5% water+0.1% formic acid) and channel C (95% water+5% acetonitrile+0.1% formic acid) and was delivered at a flow rate of 0.4 mL/min. The volume ratio of acetonitrile and water was optimized for each of the analytes. Multiple reaction monitoring (MRM) scans were made with curtain gas, collision gas, nebulizer gas, and auxiliary gas optimized for each compound, and source temperature at 550° C. Molecular ions were formed using an ion spray voltage of −4200 V (negative mode). Declustering potential, entrance potential, collision energy, product ion mass, and cell exit potential were optimized for each compound.

TABLE 16

AR Binding, Inhibition of wt and mutant AR Transactivation, AR degradation and in vitro metabolic stability of SARDs.

| Compound | Binding $K_i$ (nM) | Transcriptional Activation (+0.1 nM R1881; R1881 $EC_{50}$ = 0.11 nM | | | $T_{1/2}$ (min) $CL_{int}$ (µl/min/mg) |
|---|---|---|---|---|---|
| | | Wt. $IC_{50}$ (nM) | W741L $IC_{50}$ (nM) | T877A $IC_{50}$ (nM) | |
| DHT | 1 | — | — | — | |
| R-Bicalutamide | 545.5 | 248.2 | — | 557 | |
| Enzalutamide | 205.2 | 216.3 | 939 | 331.94 | |
| ARN-509 (apalutamide) | — | 297.0 | 1939.41 | 390.50 | |
| ASC-J9 | — | 1008.0 | 3487.68 | 2288.16 | |
| 200 | | 728.59 | 871.21 | | 41.77 min 16.6 µl/min/mg |
| 201 | | 506.94 | 237.91 | | 89.68 min 7.729 µl/min/mg |
| 202 | | | | | |

The relatively long half-lives ($T_{1/2}$) and low metabolic clearance ($CL_{int}$) values in vitro for compounds 200-202 of this invention suggest the possibility of oral bioavailability and stability in serum which would be favorable for systemic treatment of diseases of this invention such as prostate cancer, breast cancer, Kennedy's disease, and various androgen-dependent diseases. Similarly, indazoles such as 96 also demonstrated enhanced stability, as discussed herein above.

TABLE 17

AR Binding ($K_i$), Inhibition of AR Transactivation ($IC_{50}$), AR Degradation and in vitro Metabolic Stability of SARDs.

| Compd ID | Structure | Log P (−0.4 to +5.6) | Binding/Transactivation (wt AR) | | SARD Activity | | DMPK (MLM) |
|---|---|---|---|---|---|---|---|
| | | | $K_i$ (nM) (DHT = 1 nM) | $IC_{50}$ (nM) | Full Length % inhibition at 1, 10 µM | S.V. (22RV1) % inhibition at 10 µM | $T_{1/2}$ (min) $CL_{int}$ (µl/min/mg) |
| Enobosarm | 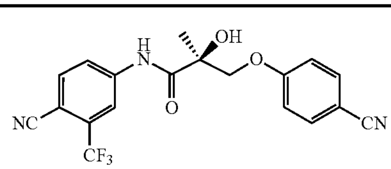 | 3.44 | 20.21 | ~20 | | | |
| R-Bicalutamide | 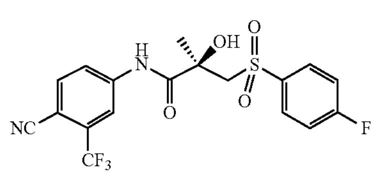 | 2.57 | 508.84 | 248.2 | | | |

TABLE 17-continued

AR Binding (K$_i$), Inhibition of AR Transactivation (IC$_{50}$), AR Degradation and in vitro Metabolic Stability of SARDs.

| Compd ID | Structure | Log P (−0.4 to +5.6) | K$_i$ (nM) (DHT = 1 nM) | IC$_{50}$ (nM) | Full Length % inhibition at 1, 10 μM | S.V. (22RV1) % inhibition at 10 μM | (MLM) T$_{1/2}$ (min) CL$_{int}$ (μl/min/mg) |
|---|---|---|---|---|---|---|---|
| Enzalutamide | 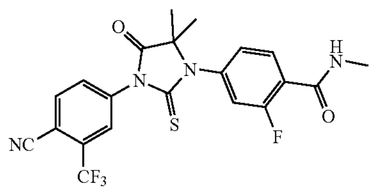 [SMILES: CNC(=O)c1ccc(N2C(=S)N(c3ccc(C#N)c(C(F)(F)F)c3)C(=O)C2(C)C)cc1F] | 4.56 | 3641.29 | 216.3 | | | |
| ARN-509 (apalutamide) | 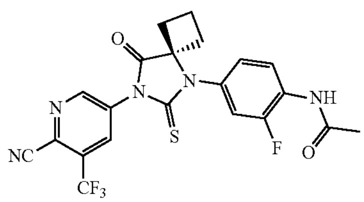 | 3.47 | 1452.29 | | 0 (Figure 62) | 0 | |
| | | 2.57 | 87.67 | — | | | |
| | | 1.86 | 407.08 | | | | |
| 200 | 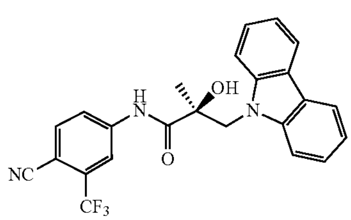 [SMILES: C[C@](O)(Cn1c2ccccc2c2ccccc21)C(=O)Nc1ccc(C#N)c(C(F)(F)F)c1] | 4.36 | 728.59 | 871.21 | 48 (Figures 62, 63) | 60 | 41.77 16.6 |
| 201 | 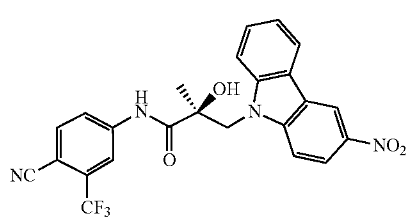 [SMILES: C[C@](O)(Cn1c2ccccc2c2cc([N+](=O)[O-])ccc21)C(=O)Nc1ccc(C#N)c(C(F)(F)F)c1] | 4.40 | 506.94 | 237.91 | 33 (Figures 63, 64) | | 89.68 7.729 |
| 202 | 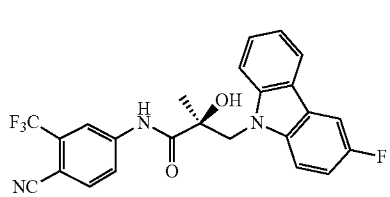 [SMILES: C[C@](O)(Cn1c2ccccc2c2cc(F)ccc21)C(=O)Nc1ccc(C#N)c(C(F)(F)F)c1] | 4.52 | 193.80 | 991.15 | 20 | 29 | 39.94 17.35 |

Header sub-grouping: "Binding/Transactivation (wt AR)" spans K$_i$ and IC$_{50}$ columns; "SARD Activity" spans Full Length and S.V. columns; "DMPK" covers the last column.

TABLE 17-continued

AR Binding (K_i), Inhibition of AR Transactivation (IC_50), AR Degradation and in vitro Metabolic Stability of SARDs.

| Compd ID | Structure | Log P (−0.4 to +5.6) | $K_i$ (nM) (DHT = 1 nM) | $IC_{50}$ (nM) | SARD Activity | | DMPK (MLM) $T_{1/2}$ (min) $CL_{int}$ (μl/min/mg) |
|---|---|---|---|---|---|---|---|
| | | | Binding/Transactivation (wt AR) | | Full Length % inhibition at 1, 10 μM | S.V. (22RV1) % inhibition at 10 μM | |
| 203 | | 4.16 | 248.54 | 1242.96 | 38 | 0 | |
| 204 | | 4.68 | 809.64 See Figure 65N | 1025.41 See Figure 65N | 51 | | |
| 205 | | 4.00 | 90.68 See Figure 65L | 1079.11 See Figure 65L | 19, 87 See Figure 65L | | 87 See Figure 65L |

TABLE 18

Liver Microsome (LM) Data for Carbazoles of this Invention using Mouse LM (MLM), Human LM (HLM), Rat LM (RLM), and Dog LM (DLM).

| | MLM | | HLM | | RLM | | DLM | |
|---|---|---|---|---|---|---|---|---|
| Compd ID | $T_{1/2}$ (min) | $CL_{int}$ (μl/min/mg) | $T_{1/2}$ (min) | $CL_{int}$ (μl/min/mg) | $T_{1/2}$ (min) | $CL_{int}$ (μl/min/mg) | $T_{1/2}$ (min) | $CL_{int}$ (μl/min/mg) |
| 200 (5-carbazole) | 95.9 | 0.72 | | | | | | |
| 201 | 89.68 | 7.729 | 61.38 | | | 0.01129 | | |
| 202 | 39.94 | 17.35 | 14.28 | | | 48.54 | | |

Example 30

AR Degradation Using Compounds of this Invention

LNCaP Degradation Assay

Objective: To determine the effect of SARDs on AR expression in LNCaP cells.

Plasmid Constructs and Transient Transfection.

Human AR cloned into CMV vector backbone was used for the transactivation study. HEK-293 cells were plated at 120,000 cells per well of a 24 well plate in DME+5% csFBS. The cells were transfected using Lipofectamine (Invitrogen, Carlsbad, Calif.) with 0.25 μg GRE-LUC, 0.01 μg CMV-LUC (renilla luciferase) and 25 ng of the AR. The cells were treated 24 hrs after transfection as indicated in the figures and the luciferase assay performed 48 hrs after transfection. Data are represented as $IC_{50}$ obtained from four parameter logistics curve.

Ligand Binding Assay.

hAR-LBD (633-919) was cloned into pGex4t.1. Large scale GST-tagged AR-LBD was prepared and purified using a GST column. Recombinant ARLBD was combined with [$^3$H]mibolerone (PerkinElmer, Waltham, Mass.) in buffer A (10 mM Tris, pH 7.4, 1.5 mM disodium EDTA, 0.25 M sucrose, 10 mM sodium molybdate, 1 mM PMSF) to determine the equilibrium dissociation constant ($K_d$) of [$^3$H] mibolerone. Protein was incubated with increasing concentrations of [$^3$H]mibolerone with and without a high concentration of unlabeled mibolerone at 4° C. for 18 h in order to determine total and non-specific binding. Non-specific binding was then subtracted from total binding to determine specific binding and non-linear regression for ligand binding curve with one site saturation to determine the $K_d$ of mibolerone.

Increasing concentrations of SARDs or DHT (range: $10^{-12}$ to $10^{-4}$ M) were incubated with [$^3$H]mibolerone and AR LBD using the conditions described above. Following incubation, the ligand bound AR-LBD complex was isolated using BioGel HT hydroxyapatite, washed and counted in a scintillation counter after adding scintillation cocktail. Values are expressed as K.

LNCaP Gene Expression Assay.

Method: LNCaP cells were plated at 15,000 cells/well of a 96 well plate in RPMI+1% csFBS without phenol red. Forty-eight hours after plating, cells were treated with a dose response of SARDs. Twenty four hours after treatment, RNA was isolated using cells-to-ct reagent, cDNA synthesized, and expression of various genes was measured by realtime rtPCR (ABI 7900) using taqman primers and probes. Gene expression results were normalized to GAPDH.

LNCaP Growth Assay.

Method: LNCaP cells were plated at 10,000 cells/well of a 96 well plate in RPMI+1% csFBS without phenol red. Cells were treated with a dose response of SARDs. Three days after treatment, cells were treated again. Six days after treatment, cells were fixed and cell viability was measured by SRB assay.

LNCaP or AD1 Degradation.

Method: LNCaP or AD1 cells expressing full length AR were plated at 750,000-1,000,000 cells/well of a 6 well plate in growth medium (RPMI+10% FBS). Twenty four hours after plating, medium was changed to RPMI+1% csFBS without phenol red and maintained in this medium for 2 days. Medium was again changed to RPMI+1% csFBS without phenol red and cells were treated with SARDs (1 nM to 10 µM) in combination with 0.1 nM R1881. After 24 h of treatment, cells were washed with cold PBS and harvested. Protein was extracted using salt-containing lysis buffer with three free-thaw cycles. Protein concentration was estimated and five microgram of total protein was loaded on a SDS-PAGE, fractionated, and transferred to a PVDF membrane. The membrane was probed with AR N-20 antibody from SantaCruz and actin antibody from Sigma.

22RV1 and D567es Degradation.

Method: 22RV1 and D567es cells expressing AR splice variants were plated at 750,000-1,000,000 cells/well of a 6 well plate in growth medium (RPMI+10% FBS). Twenty four hours after plating, medium was changed and treated. After 24-30 h of treatment, cells were washed with cold PBS and harvested. Protein was extracted using salt-containing lysis buffer with three free-thaw cycles. Protein concentration was estimated and five microgram of total protein was loaded on a SDS-PAGE, fractionated, and transferred to a PVDF membrane. The membrane was probed with AR N-20 antibody from SantaCruz and actin antibody from Sigma.

22RV1 Growth and Gene Expression.

Methods: Cell growth was evaluated as described before by SRB assay. Cells were plated in 96 well plate in full serum and treated for 6 days with medium change after day 3. Gene expression studies were performed in 22RV1 cells plated in 96 well plate at 10,000 cells/well in RPMI+10% FBS. Twenty four hours after plating, cells were treated for 3 days and gene expression studies were performed as described before.

Figure 62:
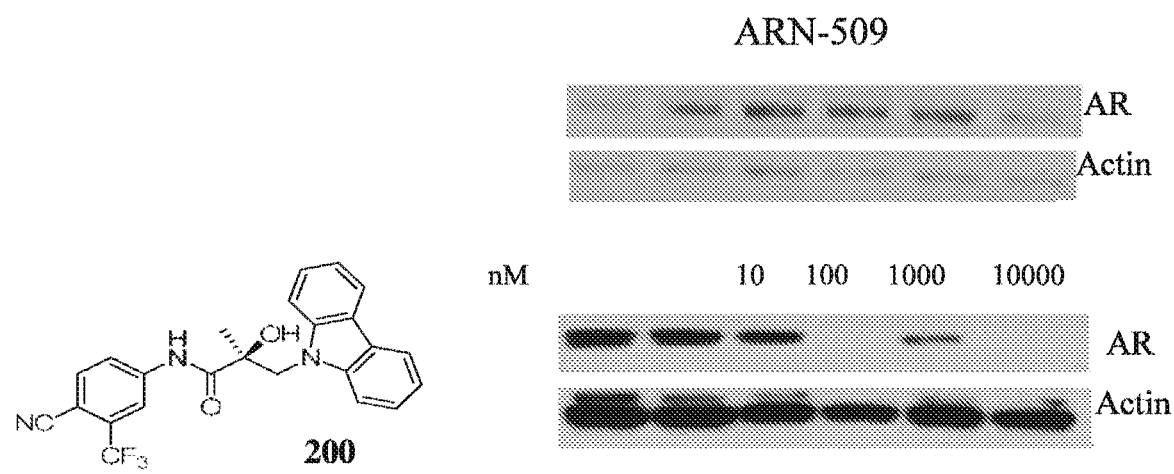
FIG. 62 depicts degradation in LNCaP cells using 200 and ARN-509. LNCaP cells treated with 200 were lysed and subjected to Western blot analysis, as described above. (Example 29 and 30)

Results:

FIG. 62 presents AR degradation by 200 vs. ARN-509 in LNCaP cells. Western blot analysis by the method described above demonstrated the ability of 200 to degrade a mutant AR (i.e., T877A) at 100 nM and 10 µM in LNCaP cells whereas ARN-509 only degraded at 10 µM, suggesting that SARDs such as 200 will have clinical utility in prostate cancers including those whose growth is driven by antiandrogen resistance-conferring mutant AR's (i.e., advanced prostate cancers and CRPC).

Figure 63:
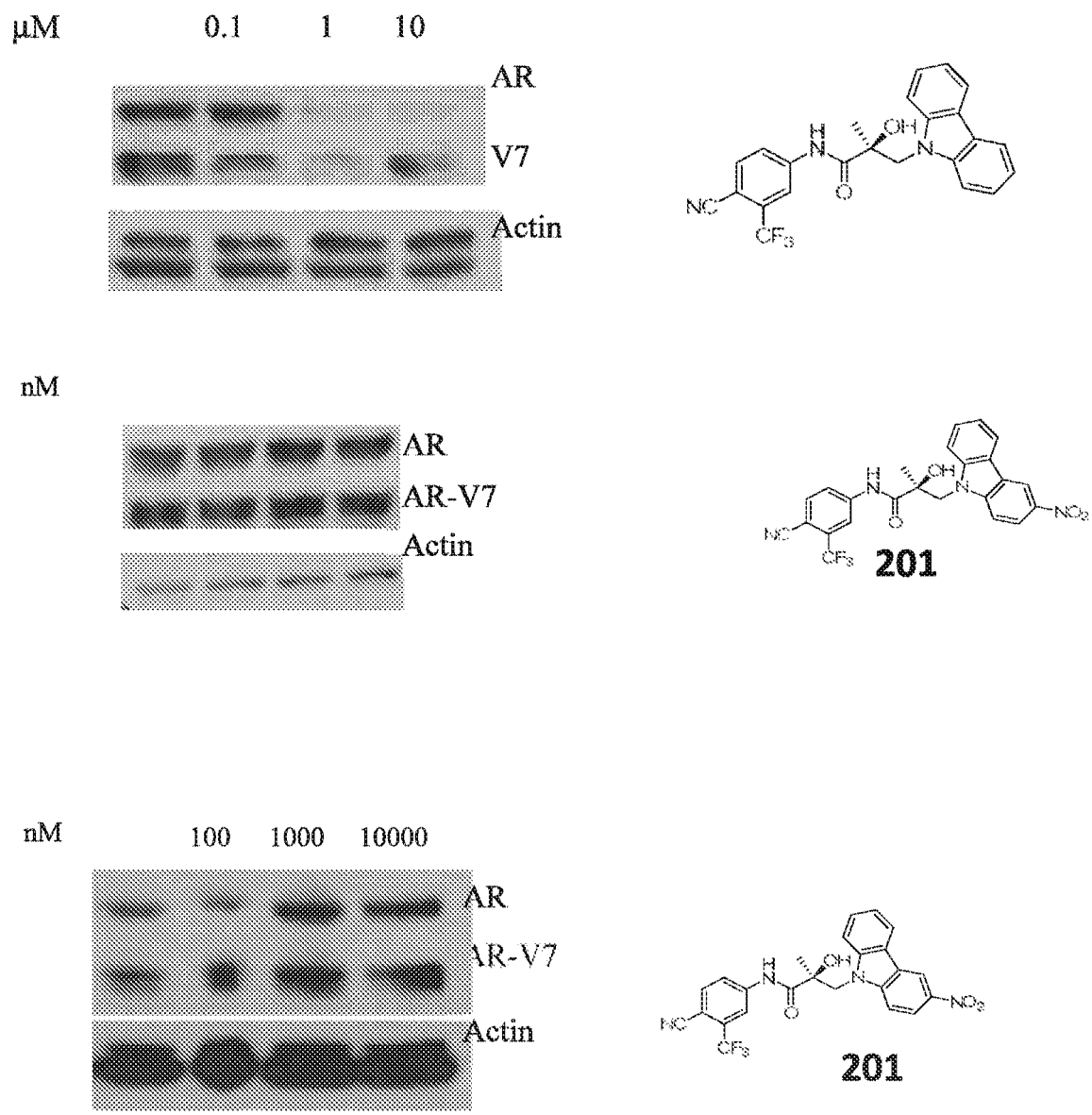
FIG. 63 depicts degradation in 22RV-1 cells using 200 and 201. 22RV-1 cells treated with 200 or 201 were lysed and subjected to Western blot analysis, as described above. (Example 29 and 30)
Figure 64:
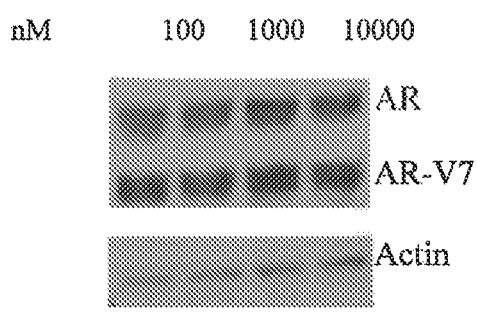
FIG. 64 depicts degradation in 22RV-1 cells using 201. 22RV-1 cells treated with 201 were lysed and subjected to Western blot analysis, as described above. (Example 29 and 30)
Figure 64:
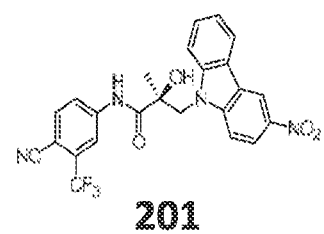
Figure 65A:
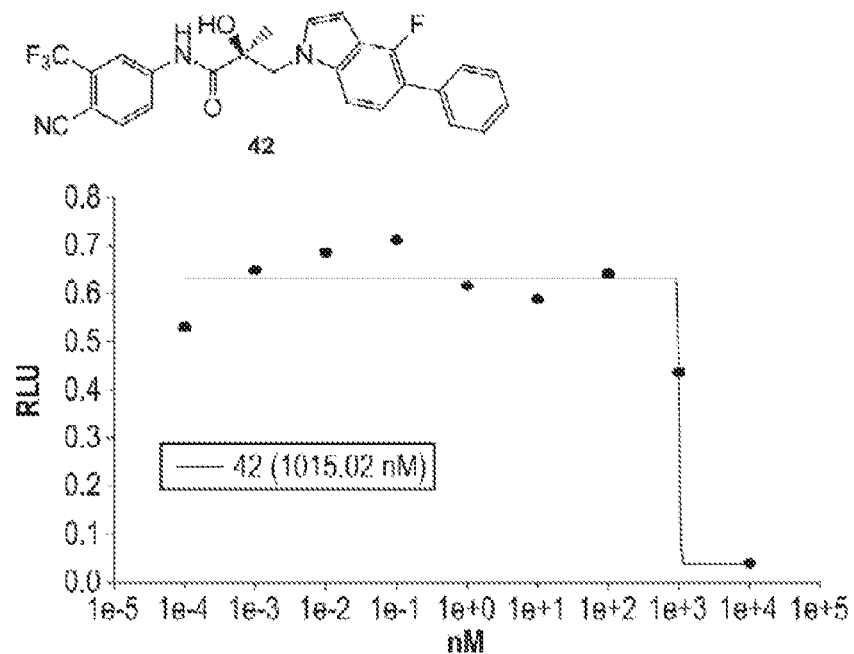
FIGS. 65A-65O depict transactivation data, binding, and AR-FL and AR-SV degradation for SARDs compounds of this invention.
Figure 65B:
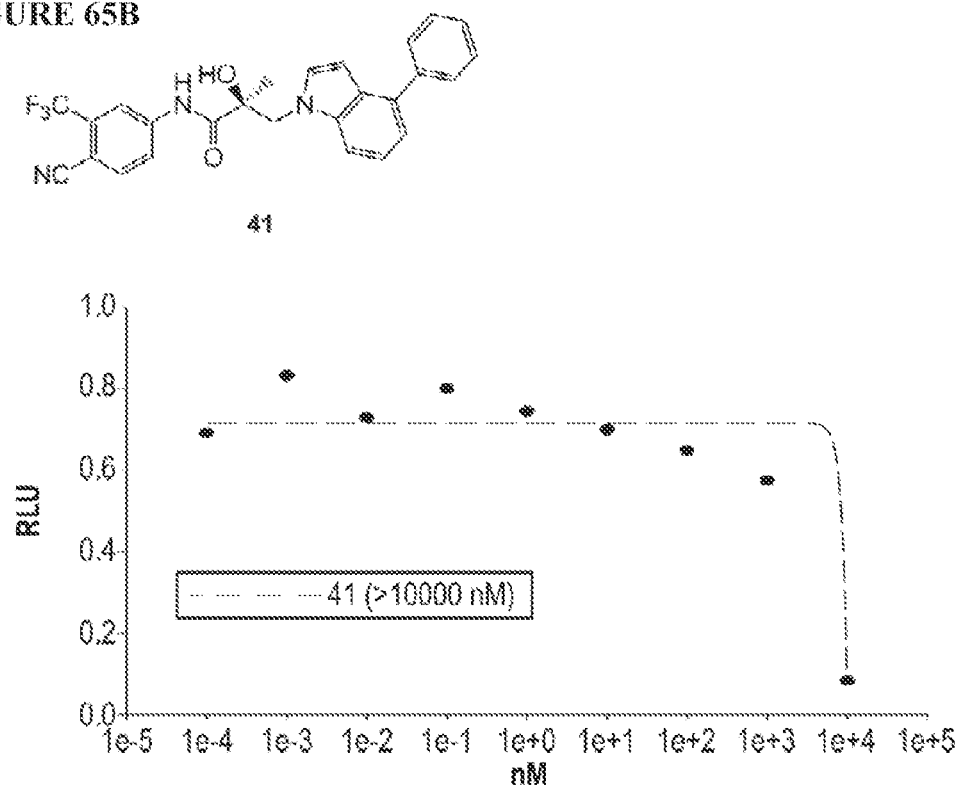
Figure 65C:
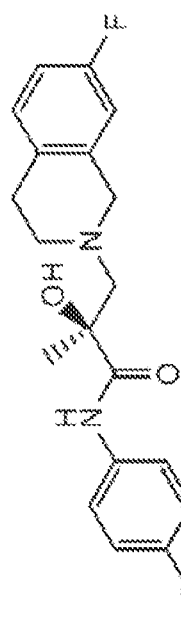
Figure 65C:
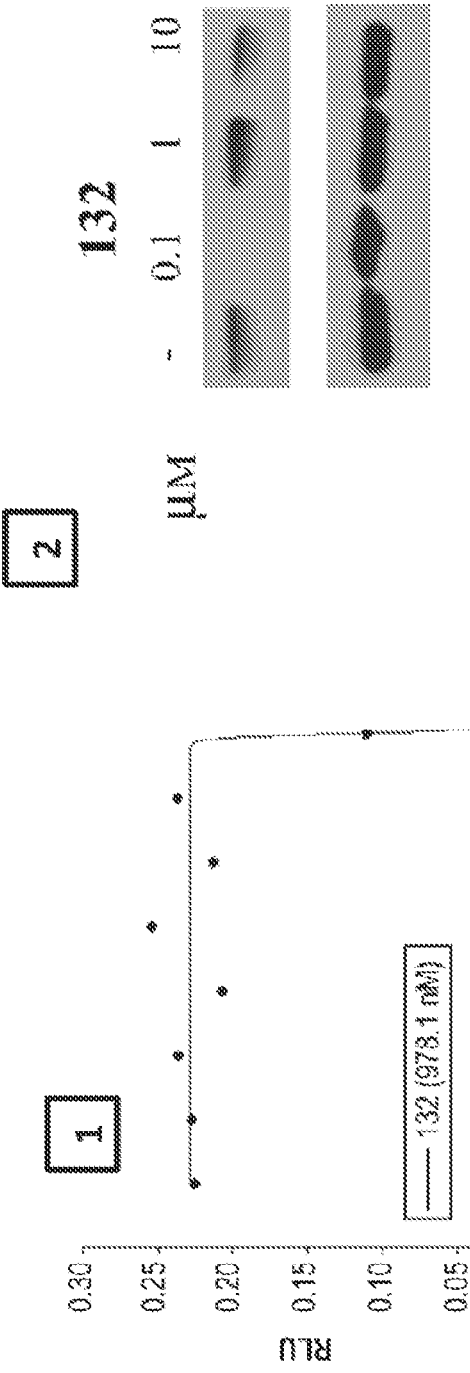
Figure 65C:
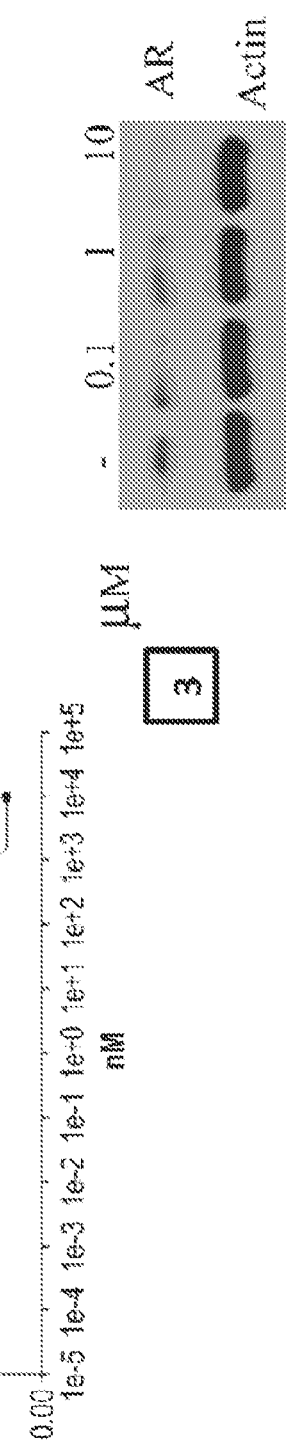
Figure 65D:
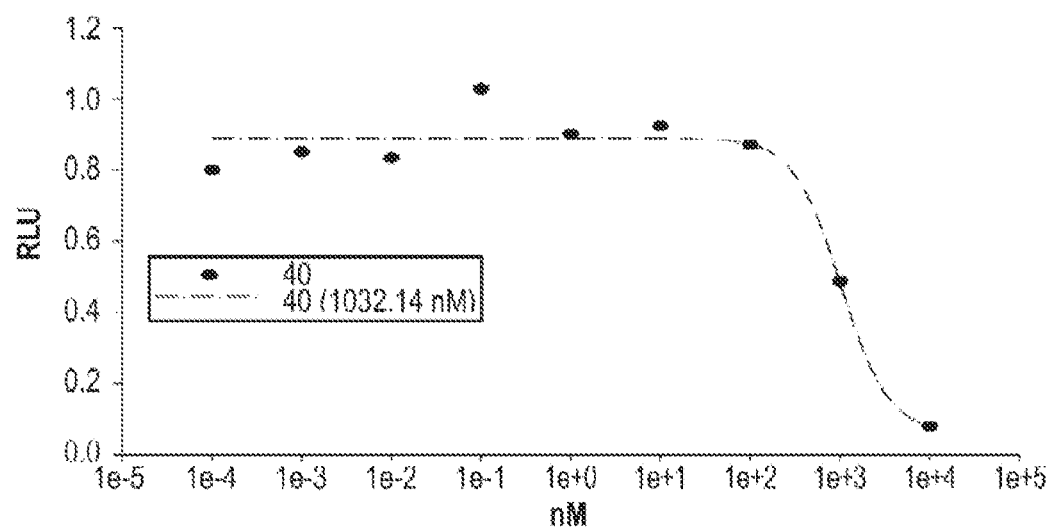
Figure 65D:
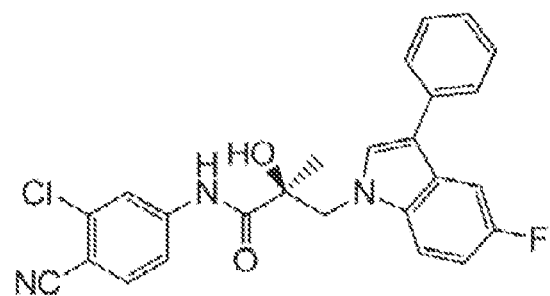
Figure 65E:
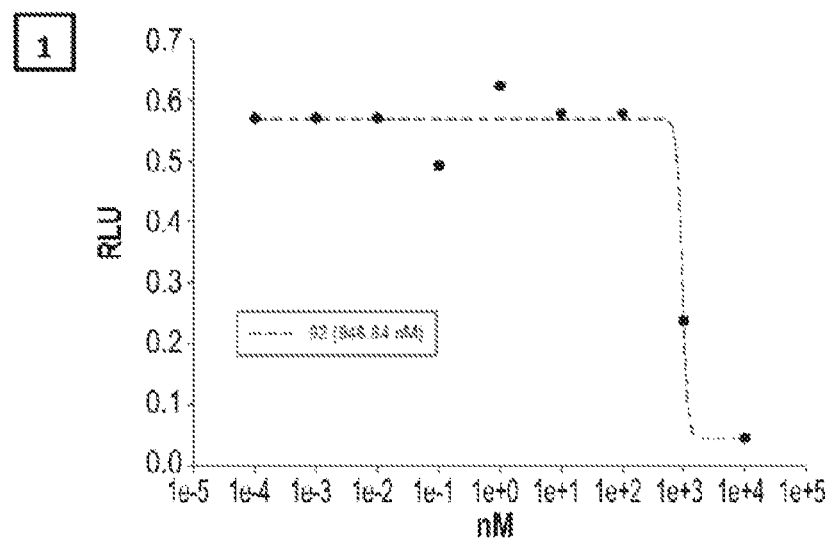
Figure 65E:
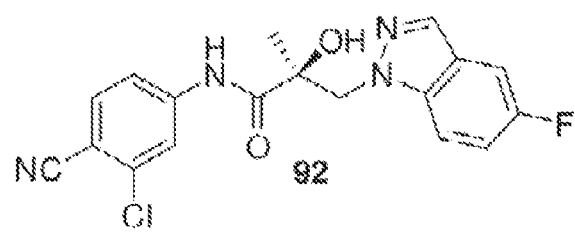
Figure 65E:
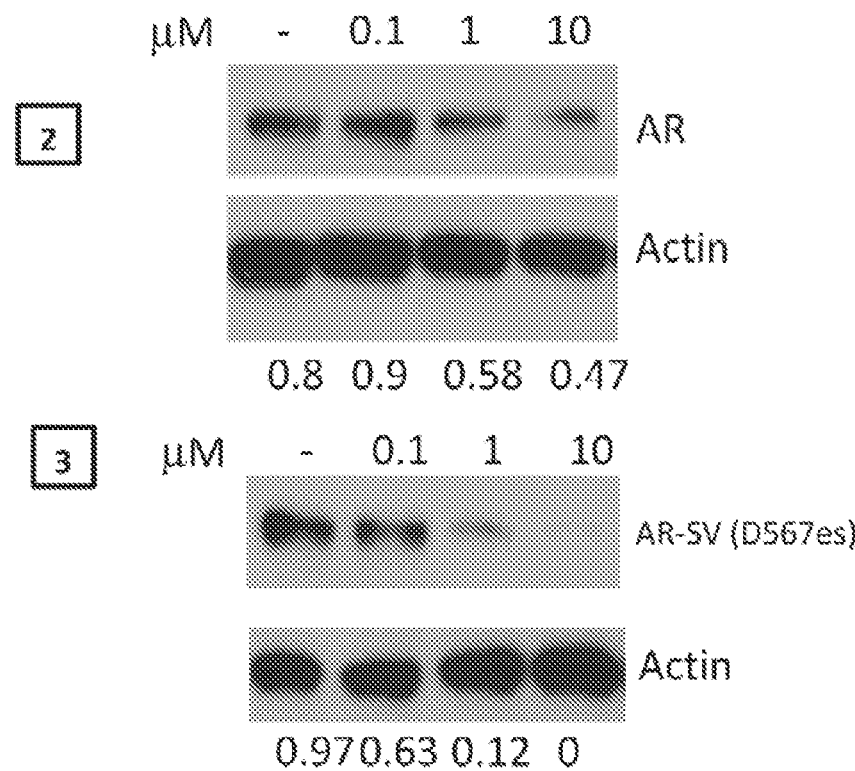
Figure 65F:
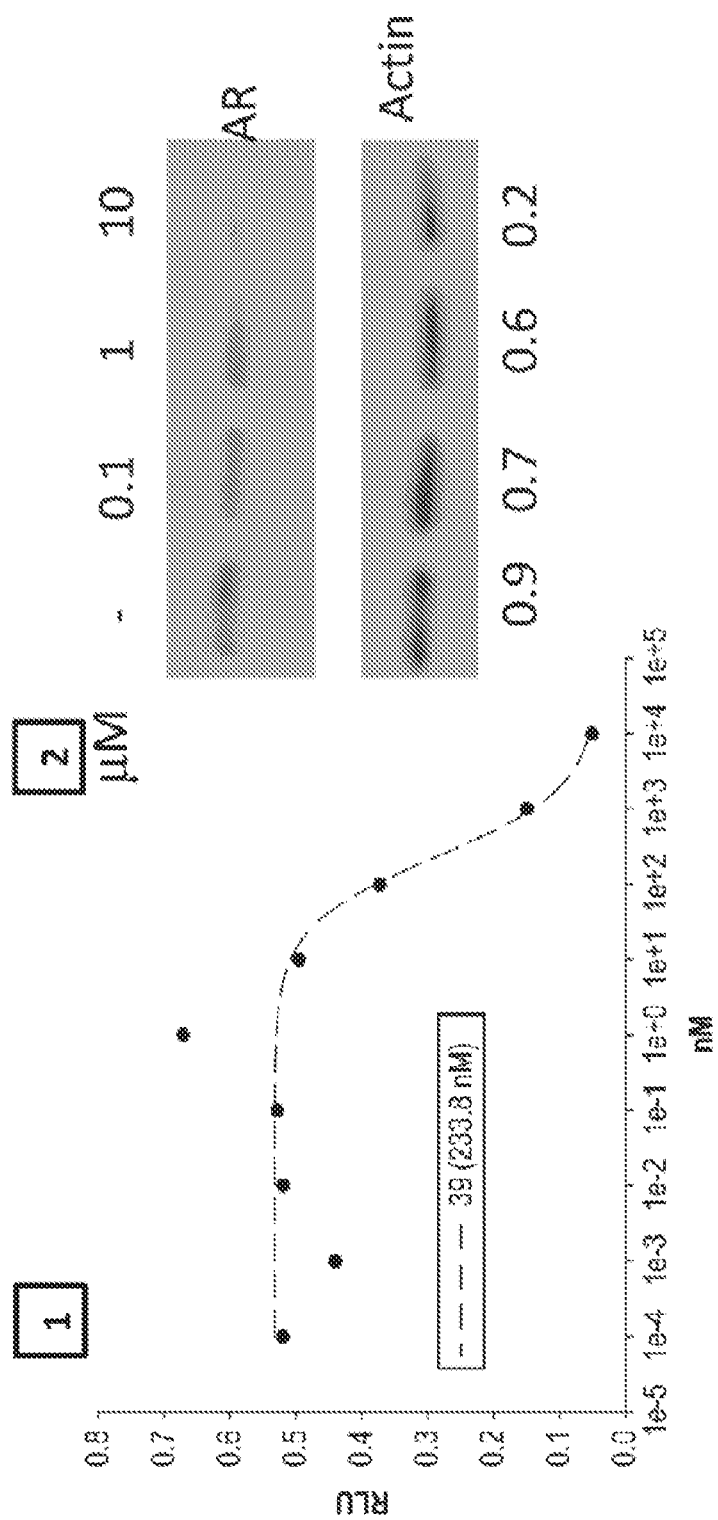
Figure 65G:
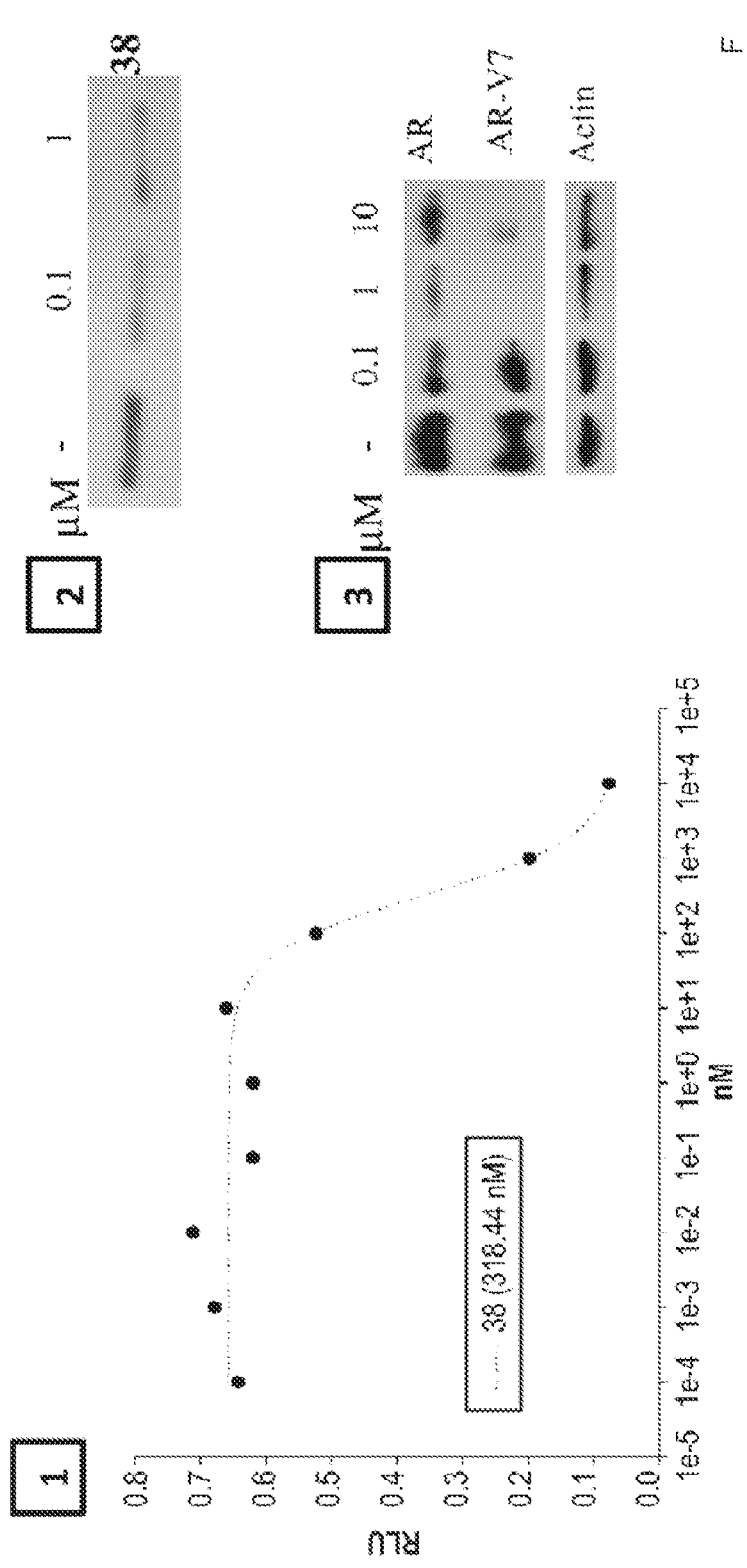
Figure 65G:
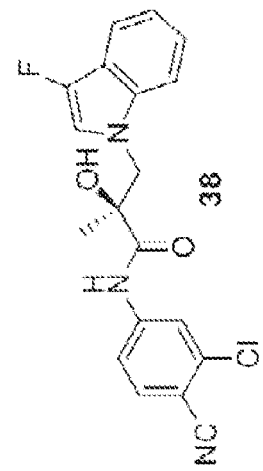
Figure 65I:
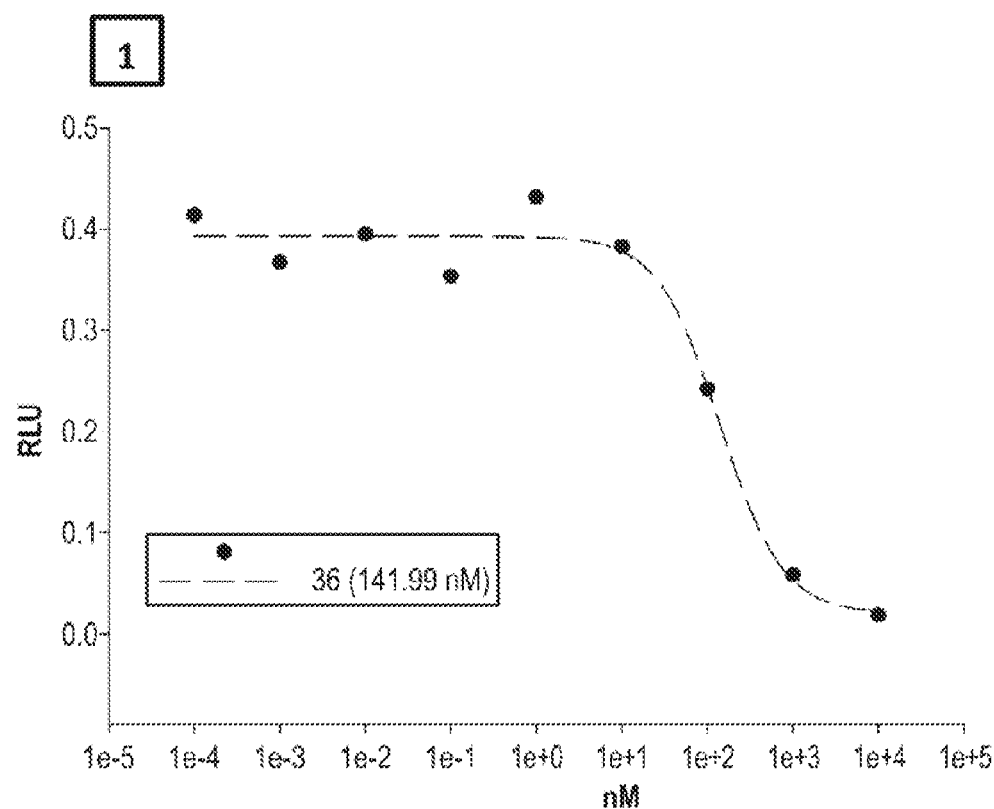
Figure 65I:
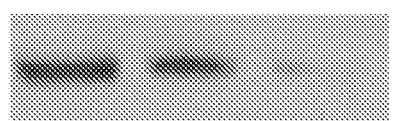
Figure 65I:
Figure 65I:
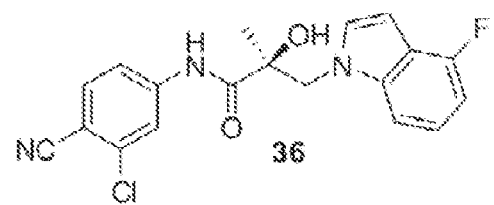
Figure 65J:
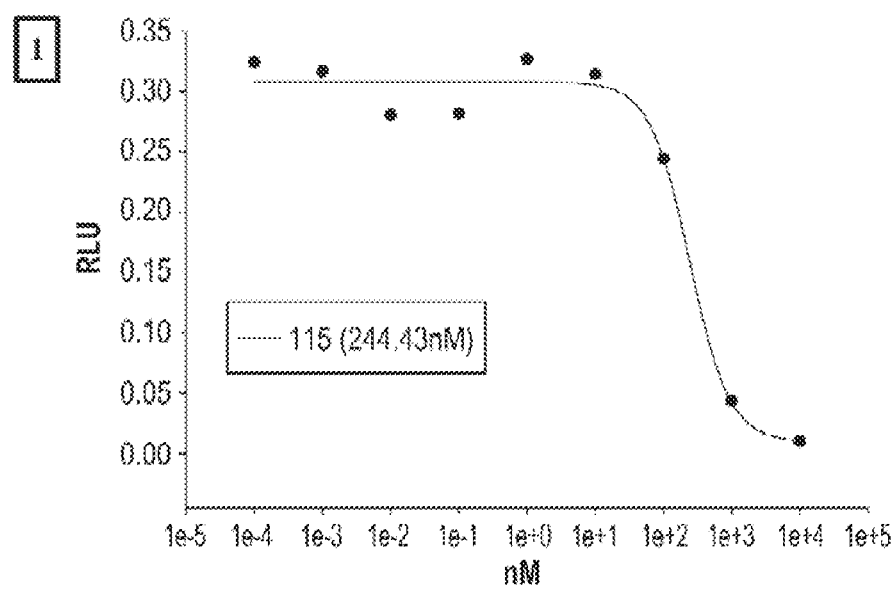
Figure 65J:
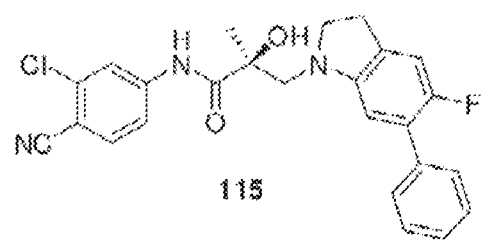
Figure 65J:
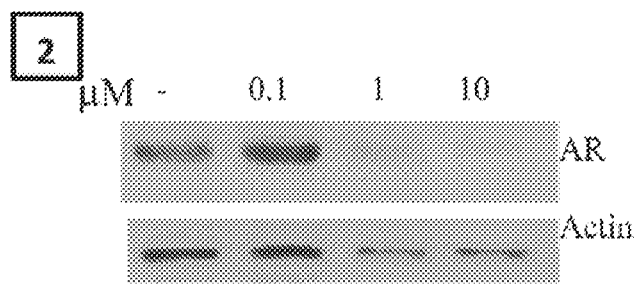
Figure 65J:
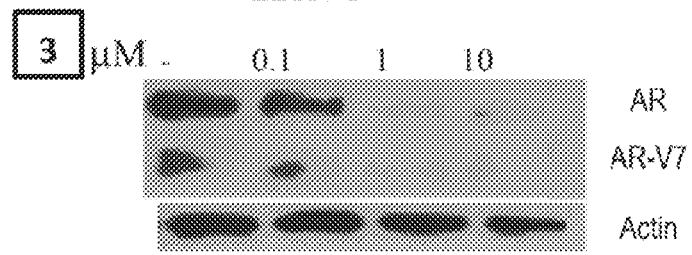
Figure 65K:
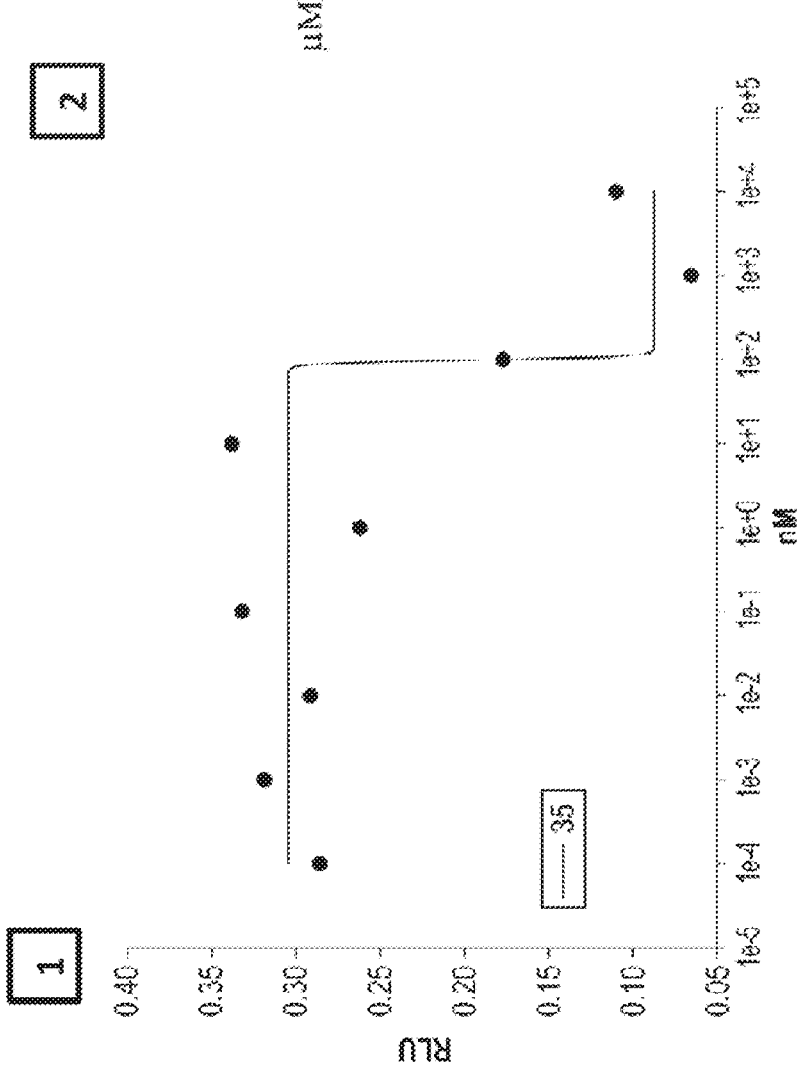
Figure 65K:
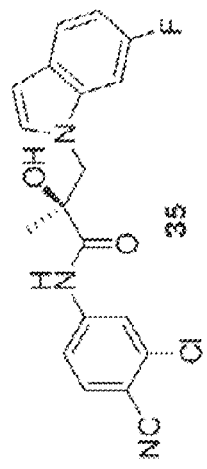
Figure 65L:
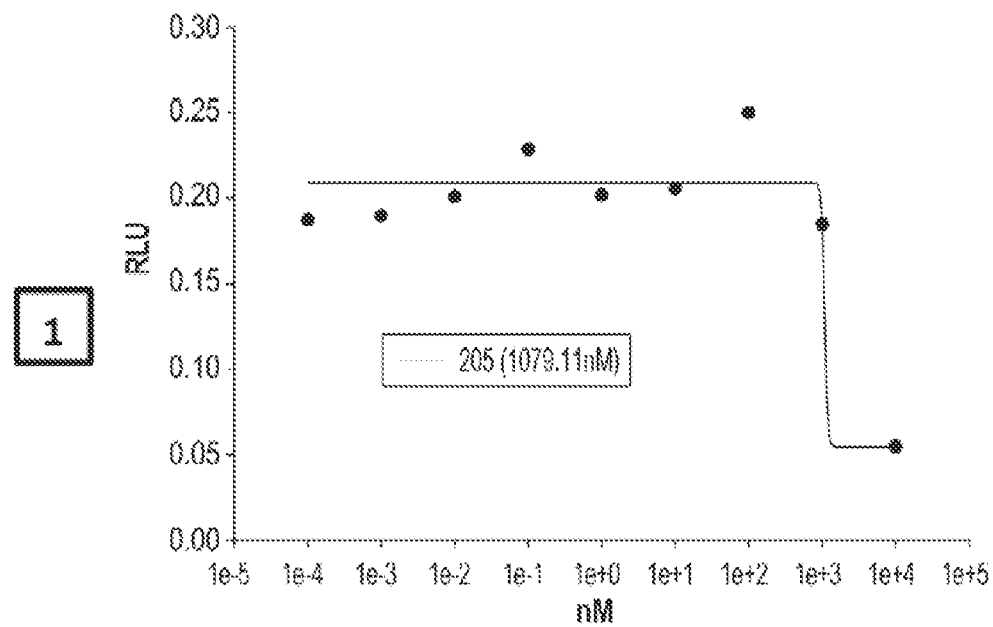
Figure 65L:
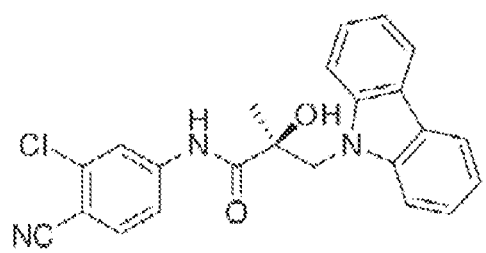
Figure 65L:
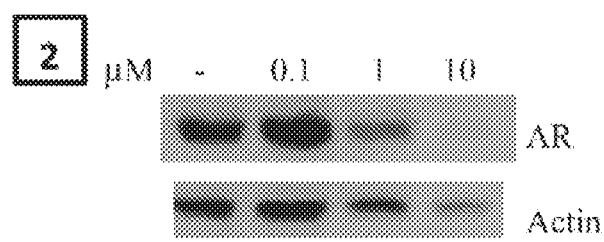
Figure 65L:
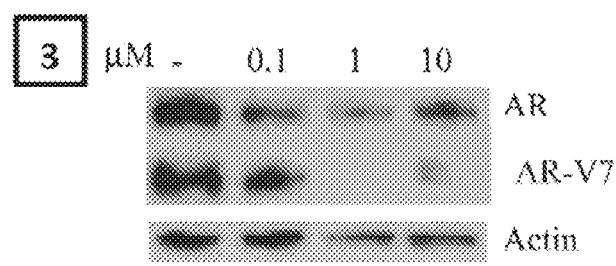
Figure 65M:
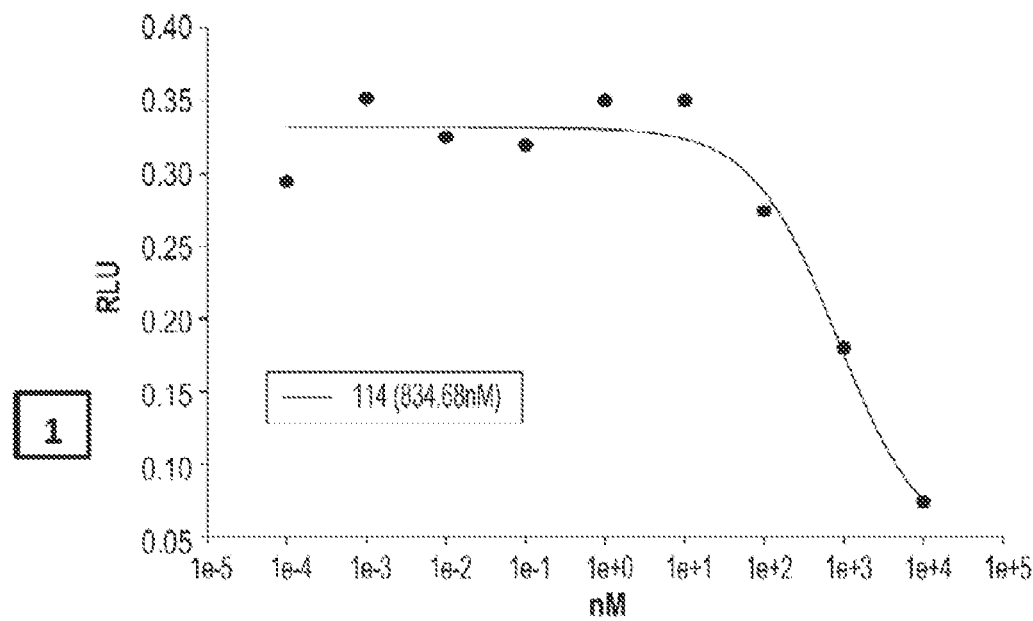
Figure 65M:
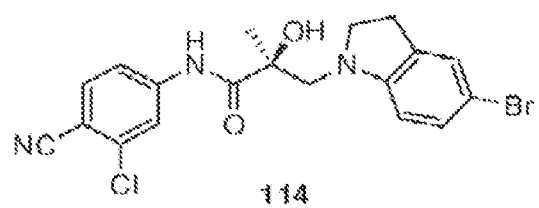
Figure 65M:
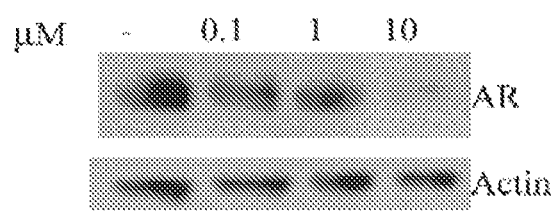
Figure 65M:
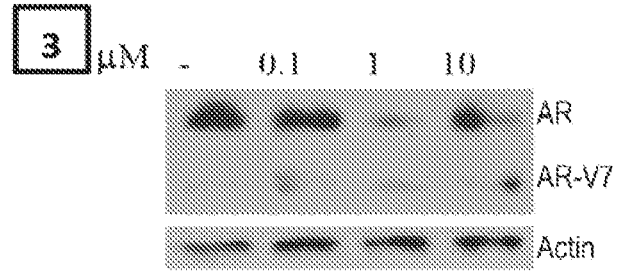
Figure 65N:
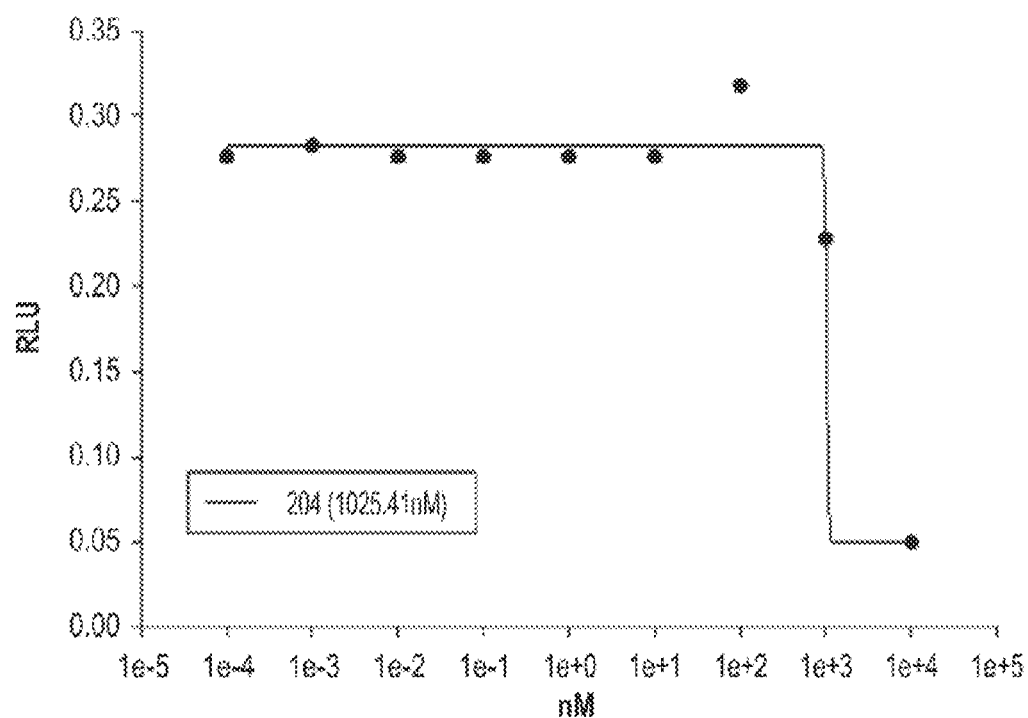
Figure 65N:
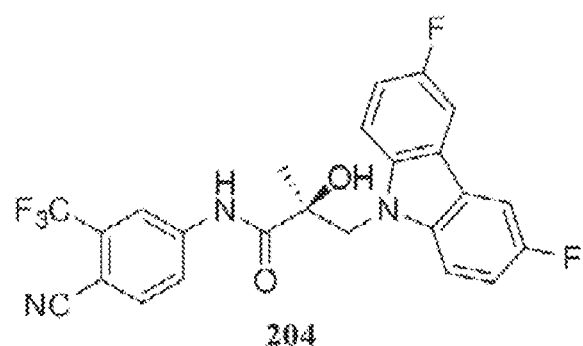
Figure 65O:
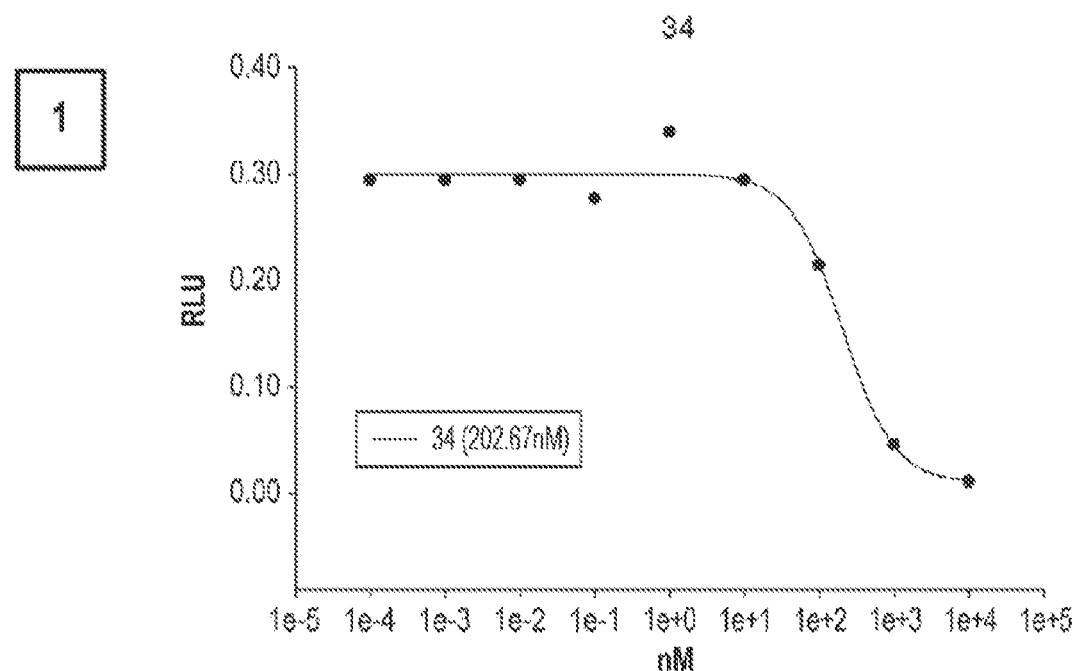
Figure 65O:
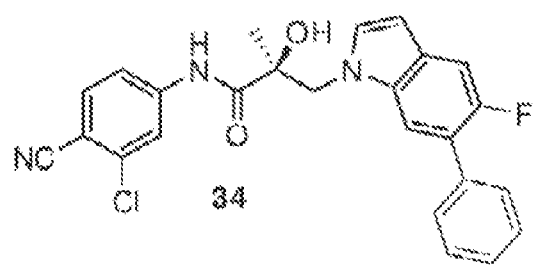
Figure 65O:
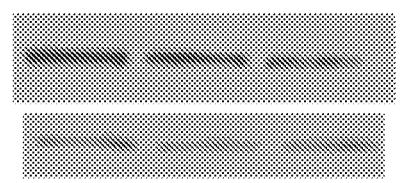
Figure 65O:
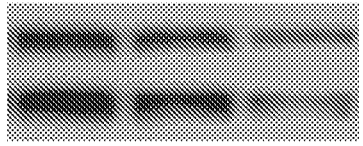
Figure 65O:

FIG. 63 and FIG. 64 present AR and AR-V7 degradation by 200 and 201 in 22RV-1 cells. 200 was capable of degrading full length androgen receptor (AR-FL) and truncated AR (AR-V7) in 22RV-1 cells, suggesting that SARDs may be able to overcome AR-V7 dependent prostate cancers (i.e., CRPC). By comparison, 201 demonstrated low levels of degradation in 22RV-1 cells.

These SARD activity demonstrations in FIGS. 62-64 as well as reported in the Tables suggest the compounds of this invention are able to degrade a variety of AR variants, and hence should provide the ability to inhibit the AR-axis activity whether it is androgen-dependent or androgen-independent. Degradation of the AR removes the possibility of promiscuous activation of mutant ARs, activation by intracellular processes such as signal transduction and kinase activation, etc.; and suggests that the SARDs should also degrade the polyQ polymorphism in hyperandrogenic dermatologic disorders (shortened polyQ) or Kennedy's disease (extended polyQ), providing a rationale for treating either type of diseases by destroying the AR in the affected tissues (skin and neuromuscular system, respectively).

Example 31

Further Studies with SARDs

PCa Gene Expression and Cell Growth:

PCa cells (LNCaP and 22RV1) will be plated at 10,000 cells per well of a 96 well plate in respective medium supplemented with 1% csFBS or in full serum. The cells will be maintained for 3 days and will be treated with SARDs or controls alone or in combination with 0.1 nM R1881 (1% csFBS). RNA will be isolated and cDNA prepared using cells-to-ct kits (Life Technologies). Expression of various androgen-regulated genes will be measured using TaqMan primer probe mix on an ABI 7900 realtime PCR machine. The expression of individual genes will be normalized to 18S rRNA levels.

PCa cells will be plated at 10,000 cells per well of a 96 well plate in respective medium supplemented with 1% csFBS or in full serum. The cells will be treated with SARDs alone or in combination with 0.1 nM R1881. The cell viability will be measured using Sulforhodamine blue reagent. As negative control, AR-negative PC3 cells will be treated similarly to ensure the absence of any non-specific growth inhibitory properties of SARDs.

Preclinical Rodent Pharmacokinetic (PK) Studies:

The PK parameters of SARDs in various formulations will be determined in rats and mice as appropriate. Approximately 250 gram Sprague-Dawley rats will be randomized into groups of 5 and a catheter surgically implanted into the jugular vein. After a recovery period the rats will be administered test compound and 250 µL of venous blood will be serially sampled from the catheter at 0, 10, 20, 30, 60, 120, 240, 480, 720, 1440 and 2880 minutes post administration for an intravenous dose or 0, 20, 40, 60, 90, 120, 150, 180, 210, 240, 480, 720, 1440, and 2880 minutes post administration for a non-intravenous dose. For mice, approximately 20 gram C57BL/6 mice will be grouped into three per time point per route of administration. Following administration of an intravenous dose mice will be sacrificed and blood collected by cardiac puncture at 0, 10, 20, 30, 60, 120, 240, 480, 720, 1440 and 2880 minutes after intravenous dosing or 0, 30, 60, 90, 120, 150, 180, 210, 240, 480, 720, 1440, 2880 minutes after dosing for a non-intravenous dose. Samples will be collected in appropriate anti-coagulant containing tubes and plasma prepared for LC-MS-MS analyses. Relevant PK parameters will be estimated via non-compartmental analyses using Phoenix WinNonlin.

PCa Xenograft Studies:

Nod Scid γ (NSG)/nude mice (6-8 weeks in age) will be used in the xenograft experiments. Briefly, a mixture of 1:1 LNCaP or 22RV-1 cells in medium (10% FBS supplemented medium):matrigel mixture will be implanted subcutaneously in male NSG mice. Cell number to be implanted will depend on the cell type. Tumors will be implanted in male nude mice that have high circulating androgens or in castrated animals supplemented with DHT to streamline the hormone circulation and to reduce variability between animals. For CRPC model, animals will be castrated when VCaP tumors reach 100 mm$^3$ and the tumors will be allowed to re-grow as CRPC. Animals will be randomized into groups once the tumors reach 200 mm$^3$ and will be treated daily with vehicle or respective SARD. Tumor volume will be measured thrice weekly and the animals will be sacrificed at the end of the study. At sacrifice, tumors will be weighed and stored for further histological and molecular biological analysis. Tumor volume will be calculated using the formula length×width×width×0.5236.

Example 32

In Vivo Studies of SARDs (Indoles and Indolines)

Hershberger assay: Mice (6-7 weeks old) were treated with vehicle or indicated SARDs (100 mg/kg/day twice daily) for 14 days orally. Animals were sacrificed and seminal vesicles (S.V.) weights were recorded and represented.

Figure 66A:
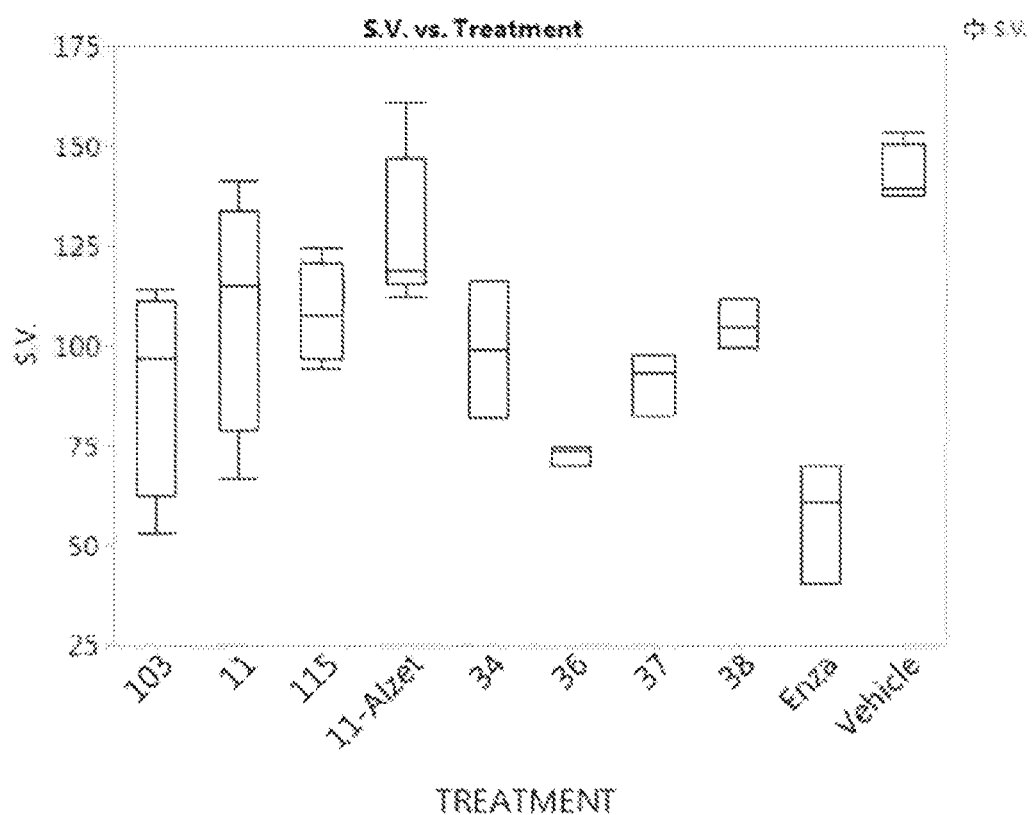
FIGS. 66A-66D present Hershberger assay: Mice (6-7 weeks old) were treated with vehicle or indicated SARDs (100 mg/kg/day twice daily) for 14 days orally. Animals were sacrificed and seminal vesicles weights were recorded and represented. Results.
Figure 66B:
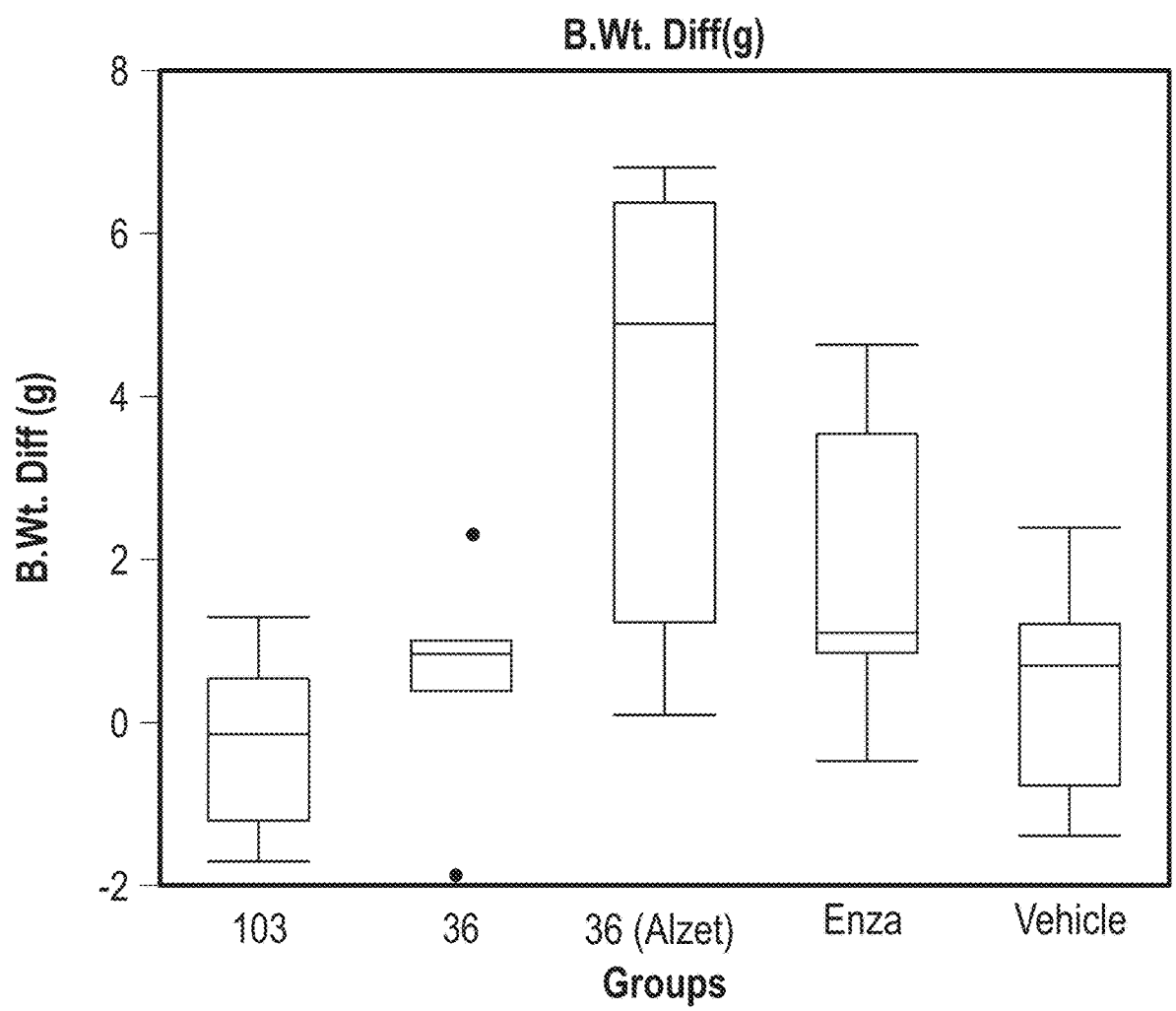
Figure 66C:
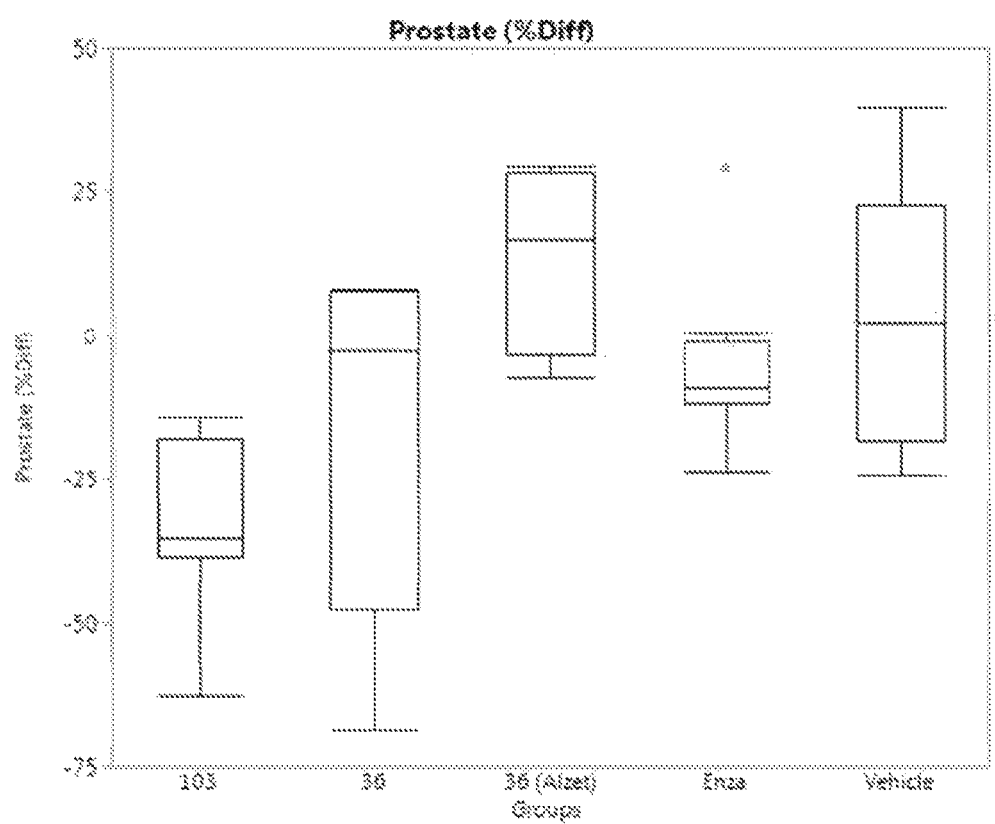
Figure 66D:
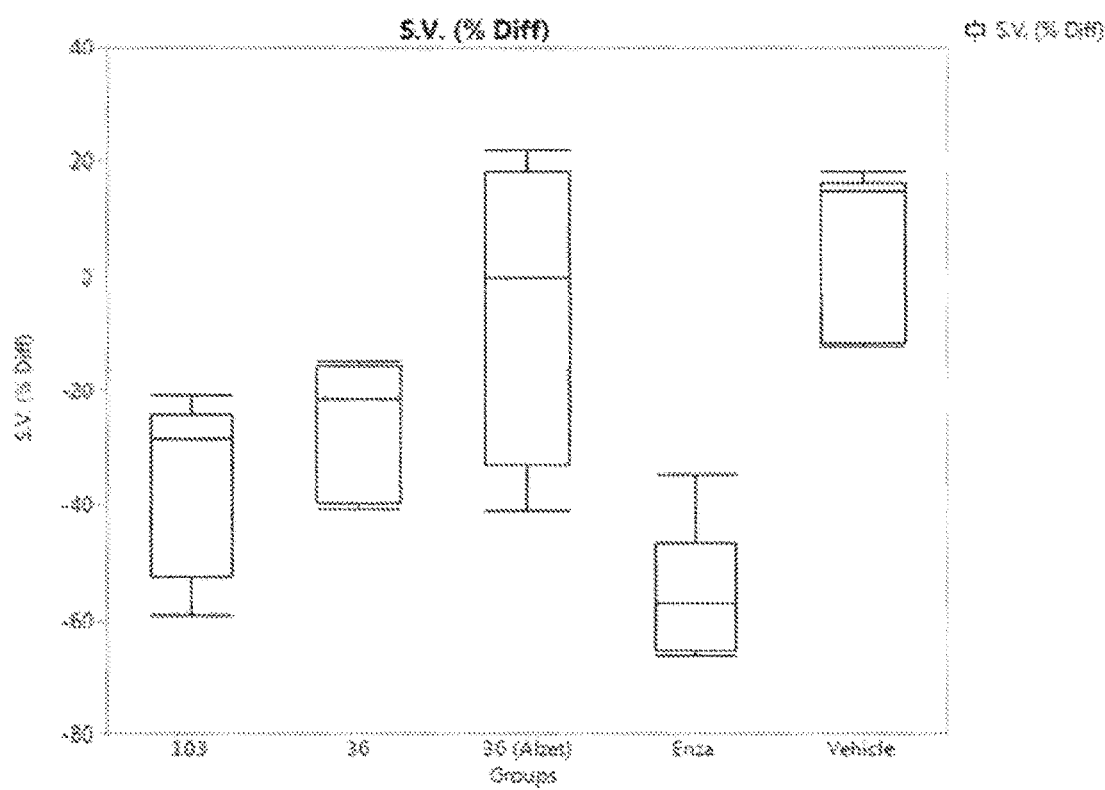

Results: SARDs 11, 34, 36, 37, 38, 103, and 115 demonstrated varying levels of inhibition of seminal vesicles (S.V.) growth. 103 and 36 had the greatest effect on suppressing S.V. growth (FIGS. 66A and 66D), prostate (FIG. 66C), and also had an effect of body weight (FIG. 66B). This suggests that these SARDs, despite low levels in the serum, were able to exert antiandrogenic effects on androgen dependent organs, supporting their potential use as treatments for prostate cancer and other diseases as described herein.

Figure 67:
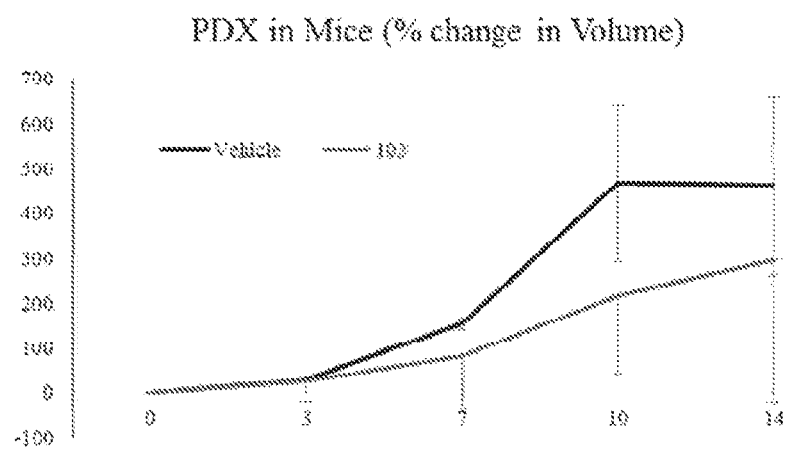
FIG. 67 demonstrates that 103 slowed prostate cancer tumor growth in patient-derived xenografts (PDX) despite low levels in the plasma. SARD 103 selectively accumulated in tumor. NSG mice were implanted with patient-derived prostate cancer xenografts (PDX). Animals were treated for 14 days and tumor volumes were measured twice weekly, as shown in the graph. Animals were sacrificed, 103 was extracted from the serum and tumor and measured using LC-MS/MS method. 103 selectively accumulated in tumor with almost 10 times more tumor accumulation than in plasma (see Example 32, Table 19), possibly providing an explanation for anti-tumor activity despite low levels of SARD in the plasma. (Example 32)
Figure 68:
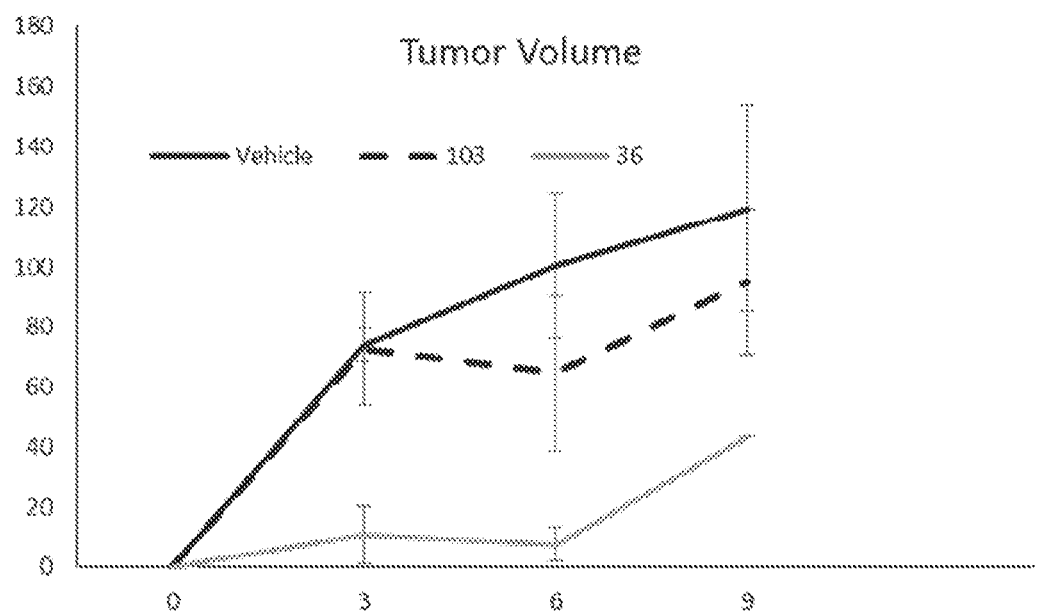
FIG. 68 presents data in a mouse xenograft model treated with 103 and 36. The % change in tumor volume is presented using 103 and 36. LNCaP cells were implanted (5 million cells/mouse) in NSG mice. Once tumors reach 70-200 mm$^3$, animals were randomized and treated with SARDs (100 mg/kg/twice daily). Tumor volume was measured at regular intervals and represented as % change from baseline. 36 significantly inhibited tumor growth. (Example 32)

SARDs were also investigated in xenograft studies. 103 demonstrated low levels of efficacy in patient derived (FIG. 67) and mouse (FIG. 68) xenografts despite very low levels in the plasma.

TABLE 19

SARDs are detected in plasma and patient derived tumor.

| | Conc of 103 (nM) |
|---|---|
| Plasma Sample #768 | 3.81 |
| Plasma Sample #769 | 18.4 |
| Tumor Sample #768 | 142 |
| Tumor Sample #769 | 282 |
| Calibration Curve | |
| Range | 1.95-2000 Nm |
| R$^2$ | 0.9957 |
| Regression | Quadratic |
| Weighting | 1/x$^2$ |

However, unexpectedly 103 was found to accumulate in the tumor (Table 19), possibly explaining its activity in the xenografts.

SARDs selectively accumulate in tumor: NSG mice were implanted with patient-derived prostate cancer xenograft. Animals were treated for 14 days and tumor volumes were measured twice weekly. Animals were sacrificed, 103 extracted from serum and tumor and measured using a LC-MS/MS method.

103 selectively accumulates in tumor with almost 10 times more tumor accumulation than in plasma. While 103 had weak activity in tumor xenografts, 36 demonstrated promising inhibition of tumor growth.

Example 33

SARDs Inhibit Transcriptional Activation of F876L

To validate that SARDs of the invention can antagonize the R1881-driven transcriptional activation of mutant AR F876L, COS cells were transfected with F876L AR with a GRE-driven luciferase reporter construct, and a Renilla reporter construct as a control for transfection efficiency. Cells were treated 24 h after transfection with 0.1 nM R1881 (AR agonist) and a dose response of SARDs. Luciferase (and Renilla) assays were performed 48 h after transfection and reported as relative light unit (RLU). COS is not a prostate cancer cell line, so transfection with F876L does not confer enzalutamide resistance (Enz-R). FIG. 50A (top middle panel) demonstrated potent (low nM) but not full efficacy antagonism by enzalutamide of R1881-driven F876L trans activation, whereas wt AR inhibition was less potent (low μM) and full efficacy. Importantly, at high concentrations (>1 μM), enzalutamide acts as an agonist of F876L transactivation (top right panel of FIG. 50A), which is not seen in wt AR. This is indicative that F876L acts like an agonist switch escape mutant of enzalutamide therapy. Given that SARDs of this invention were structurally novel high potency AR antagonists with a unique biological activity profile, representative compounds (i.e., 11 (5-F indole), 22 (4-F indole), 23 (6-F indole), 37 (5-F indole), 101 (4-F indoline), and 36 (4-F indole)) were tested for their ability to overcome the agonist switch behavior. Approximately equipotent nM range, full efficacy antagonism of R1881-driven transcriptional activation was observed in both F876L and wt. This suggested that SARDs of this invention would also exhibit activity in models of Enz-R (e.g., MR49F cells) and primary prostate cancer (PC) possessing wt AR.

Example 34

SARD Activity and Cellular Anti-Proliferation in a Model of Enz-R PC (MR49F)

Figure 86A:
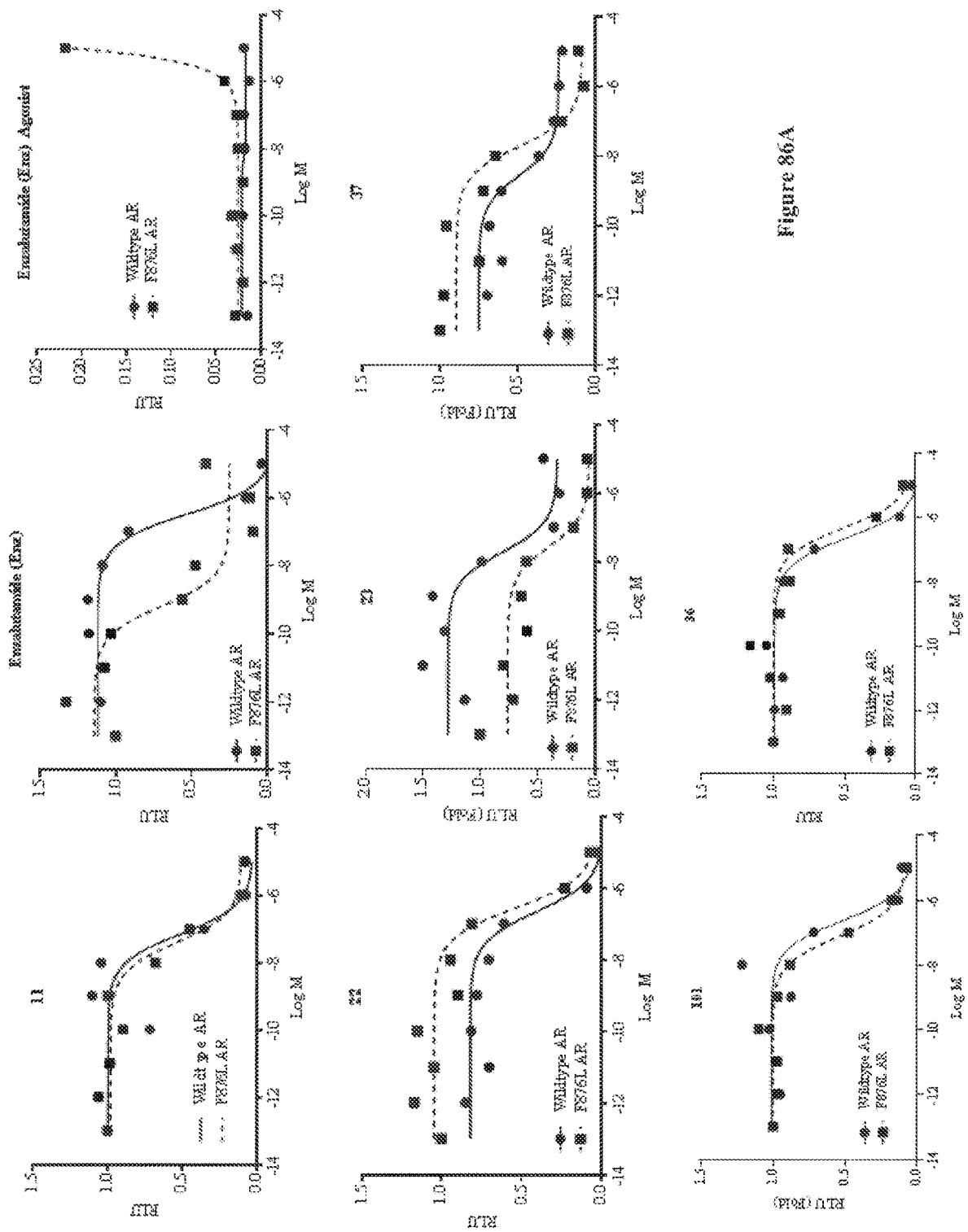
FIGS. 86A and 86B: SARDs antagonize transactivation and degrade Enz-R conferring escape mutant AR.
Figure 86B:
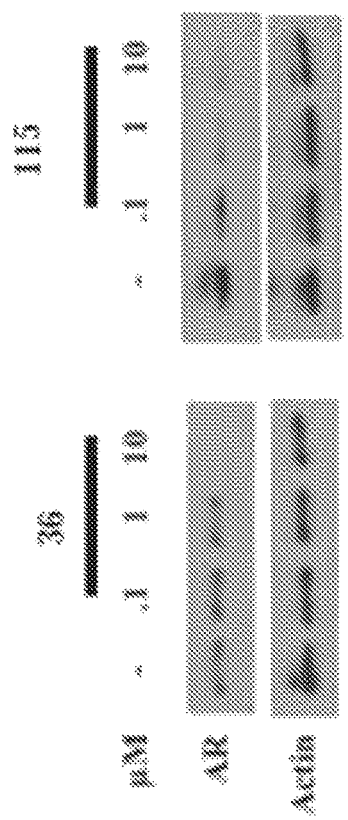

To ensure that SARD activity was also maintained in a Enz-R cell line, SARD assays were performed in MR49F LNCaP cells containing the F876L/T877A double mutant. As seen in FIG. 86B, 36 (4-F indole) and 115 (5-F, 6-Ph indoline) degraded this mutant FL AR in MR49F cells in the low μM and high nM range, respectively, consistent with the relative activities seen in Tables 3 and 6. Densitometric evaluation of the immunoblots suggests that 115 demonstrated similar to improved potency of SARD activities in the Enz-R LNCaP (FIG. 86A) when compared to the parental enzalutamide sensitive LNCaP shown supra (FIG. 85A). This suggests that the optimized activity profile for 115 reported in Table 6 was conserved in this model of Enz-R.

Enzalutamide was inactive in SARD activity assays in LNCaP (FL) and 22RV1 (SV) cells and was not tested in MR49F cells as it was not expected to be a SARD in this or any cellular context. The preservation of SARD activity for these representative compounds even in the Enz-R context suggested that SARDs of the invention may exhibit broad spectrum anti-proliferative and/or anti-tumor activities across many prostate cancers including enzalutamide-resistant prostate cancers.

Figure 87:
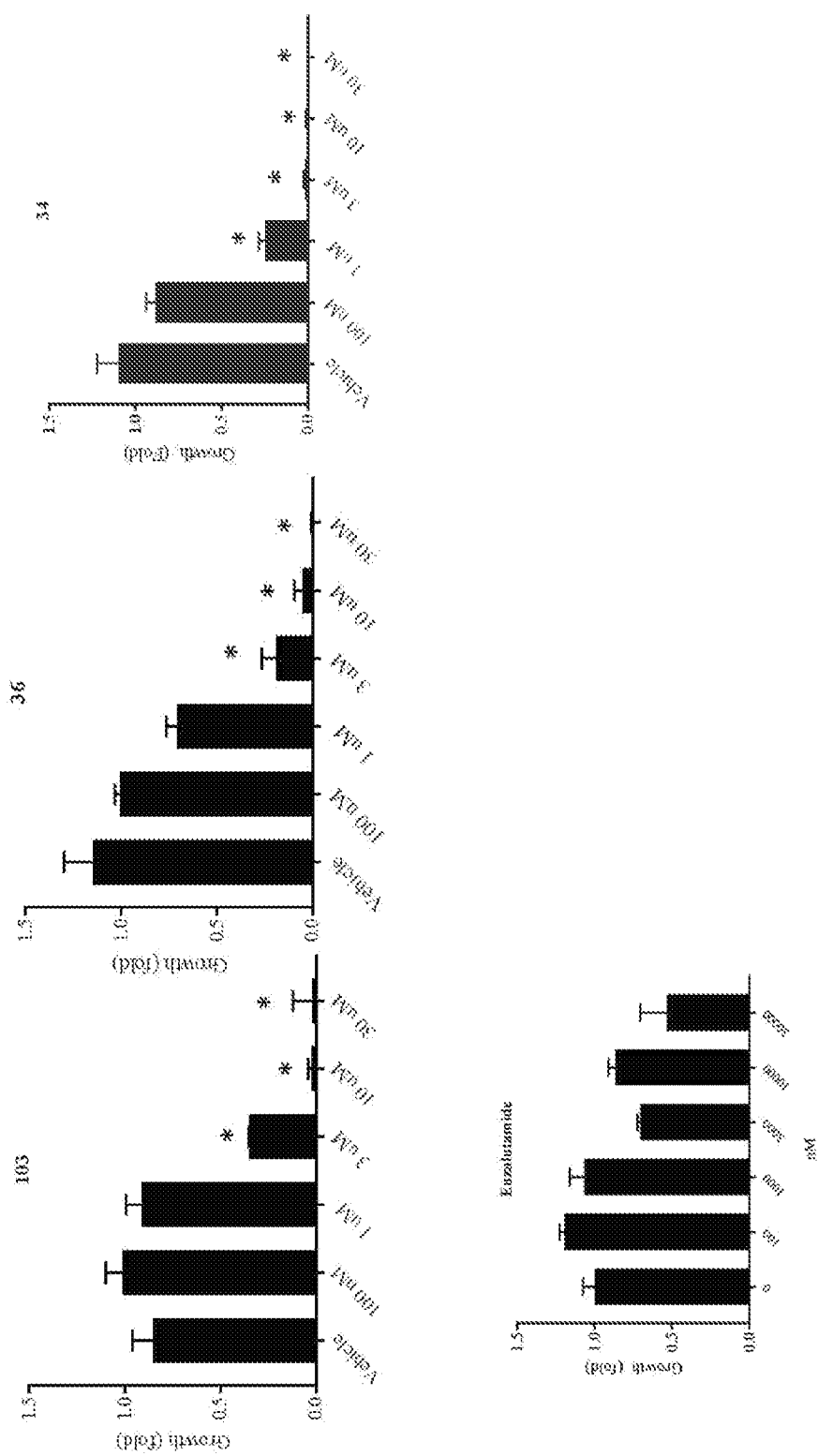
FIG. 87: Enzalutamide-resistant LNCaP (MR49F) cellular anti-proliferation: Enzalutamide-resistant LNCaP (MR49F) cells were plated in 1% charcoal-stripped, serum-containing medium and treated with 0.1 nM R1881 and titration of antagonist as indicated in the figure. Cells were re-treated 3 d after the first treatment and the number of viable cells measured by Cell-Titer Glo assay (Promega, Madison, Wis.). N=3. *=p<0.05.

Anti-proliferative assays in MR49F cells showed that 103 (4-F indoline), 36 (4-F indole), and 34 (5-F, 6-Ph indole) completely and dose-dependently inhibited cell growth with estimated $IC_{50}$ values of less than 3 µM for 103 and 36, and less than 1 µM for 34 (FIG. 87). For 36 at least, this correlates well with in vitro proliferative antagonism and SARD activity in MR49F cells (FIGS. 86A and 86B), suggesting that SARDs of this invention retained their unique biological profile in Enz-R PC. By comparison, enzalutamide demonstrated weak and incomplete efficacy as revealed by poor dose-dependence and only partial inhibition of growth. E.g., growth inhibitions at 3 µM, 10 µM and 30 µM were approximately 30%, 15% and 45%. This result demonstrated the enzalutamide resistant of these MR49F cells, and further affirmed our ability to overcome the Enz-R phenotype with representative examples of SARDs of this invention, supporting testing in MR49F xenografts.

Example 35

In Vivo Antagonism

Hershberger assays. Hershberger assays were performed on several SARDs of this invention in intact mice and rats. Surprisingly, despite poor mouse liver microsome (MLM) stabilities, the tested SARDs (103, 104, 23, 34, 11, 36, 37, 38 and 115) caused atrophy of AR-dependent seminal vesicles tissue in intact mice (FIG. 88A, left panels) whereas vehicle did not have any effect (0% change). Similar efficacy atrophy was also observed for 103 and 104 in rats (FIG. 88A, right panel) and was demonstrated to be dose-dependent in prostate and seminal vesicles, with up to ~40% change in organ weights relative to castrated control (100%). This confirms that orally administered compounds are being absorbed and distributed to the site of action in these organs and suggests that the compound should also distribute to tumors in xenograft models to exert anti-tumor effects in sensitive models.

MR49F Xenografts in mice: MR49F xenografts were established by implanting the Enz-R LNCaP cells (from University of British Columbia) mixed with Matrigel (BD Biosciences, San Jose, Calif.) at 1:1 ratio and injecting subcutaneously in NOD SCID gamma (NSG) mice. Once tumor sizes reached 100-200 mm$^3$, the mice were castrated and the tumors were allowed to regrow as CRPC. The animals were randomized once the tumors started to regrow and treated with vehicle (polyethylene glycol-300: DMSO 85:15 ratio) or 100 mg per kg of SARDs 34 or 36 for 14 d. In FIG. 88B, 34 and 36 significantly reduced the tumor volume with a 40-60% tumor growth inhibition (TGI).

Further, the significant levels of TGI activity indicated that the oral bioavailability demonstrated in Hershberger assays translated to adequate levels of 34 and 36 in tumor to reveal to some extent the pharmacodynamic behavior of the SARDs of this invention. \The proof-of-concept that the SARDs of the invention can overcome Enz-R CRPC in vivo was established through the susceptibility of these Enz-R xenografts to 34 and 36. This promising result is surprising given the poor metabolic stability of these SARDs as a whole in the same species (mice) as seen in MLM (Tables 8 and 10; $T_{1/2}$ for 34 and 36 were 9.13 min and 11.77 min). These experiments indicate that the SARDs of this invention with their unique biological profile could be used to overcome enzalutamide, and by extension apalutamide and abiraterone, resistances, in CRPC patients.

SARD compounds of the invention as described herein are potent AR antagonists and with a broad activity profile in models of prostate cancer, and in vivo AR antagonism when orally administered. For example, SARDs exhibited strong AR antagonistic activity in vitro in transcriptional activation and cellular proliferative assays including in models of enzalutamide sensitive and resistant PCs, and/or castration resistant PCs (CRPCs).

Additionally, SARDs of the invention showed selective AR [protein] degradation of full-length (FL AR; e.g., from LNCaP cells (T877A)) and splice variant (SV AR; e.g., from 22RV1 cells (AR-V7)) isoforms of AR, all at sub to low micromolar treatment levels, and in a variety of prostate cancer cell contexts including enzalutamide resistant PCs (e.g., MR49F). The ability to degrade SV AR in the study suggested the potential of SARDs of this invention to treat various currently untreatable advanced and refractory PCs, for example, those lacking the ligand binding domain (LBD) of AR such as AR-V7 and D567es AR truncations, which are not susceptible to androgen-deprivation therapy, abiraterone, or LBD-directed antiandrogens (e.g., enzalutamide, apalutamide, and bicalutamide), and are associated with short survival.

Further, in vivo investigation found that the SARDs of the invention overcome a variety of escape mutants including F876L and F876L/T877A (MR49F) that are known to emerge due to enzalutamide treatment. These mutations convert enzalutamide and apalutamide to agonists, conferring resistance to prostate cancer cells and tumors via an agonist switch mechanism as seen with other LBD-binding antiandrogens, e.g. W741L for bicalutamide and T877A for flutamide (N-(4-nitro-3-(trifluoromethyl)phenyl)isobutyramide). The intractability of truncation mutants and the frequency of the agonist switch mutations suggest that novel ways, potentially LBD-independent ways, of targeting the AR are needed. Moreover, these orally bioavailable SARDs are dual acting agents, i.e., potent inhibitors and degraders of AR, providing a higher evolutionary barrier to the development of resistance to SARDs. N-terminally directed SARDs such as the SARDs of this invention may provide a next generation of AR antagonists to treat a variety of refractory and/or advanced prostate cancers, including enzalutamide-resistant, castration resistant, and/or AR-V7 dependent PCs which are not amendable with current hormone therapies. As such, SARDs may delay the need to rely solely on chemotherapy.

Figure 88A:
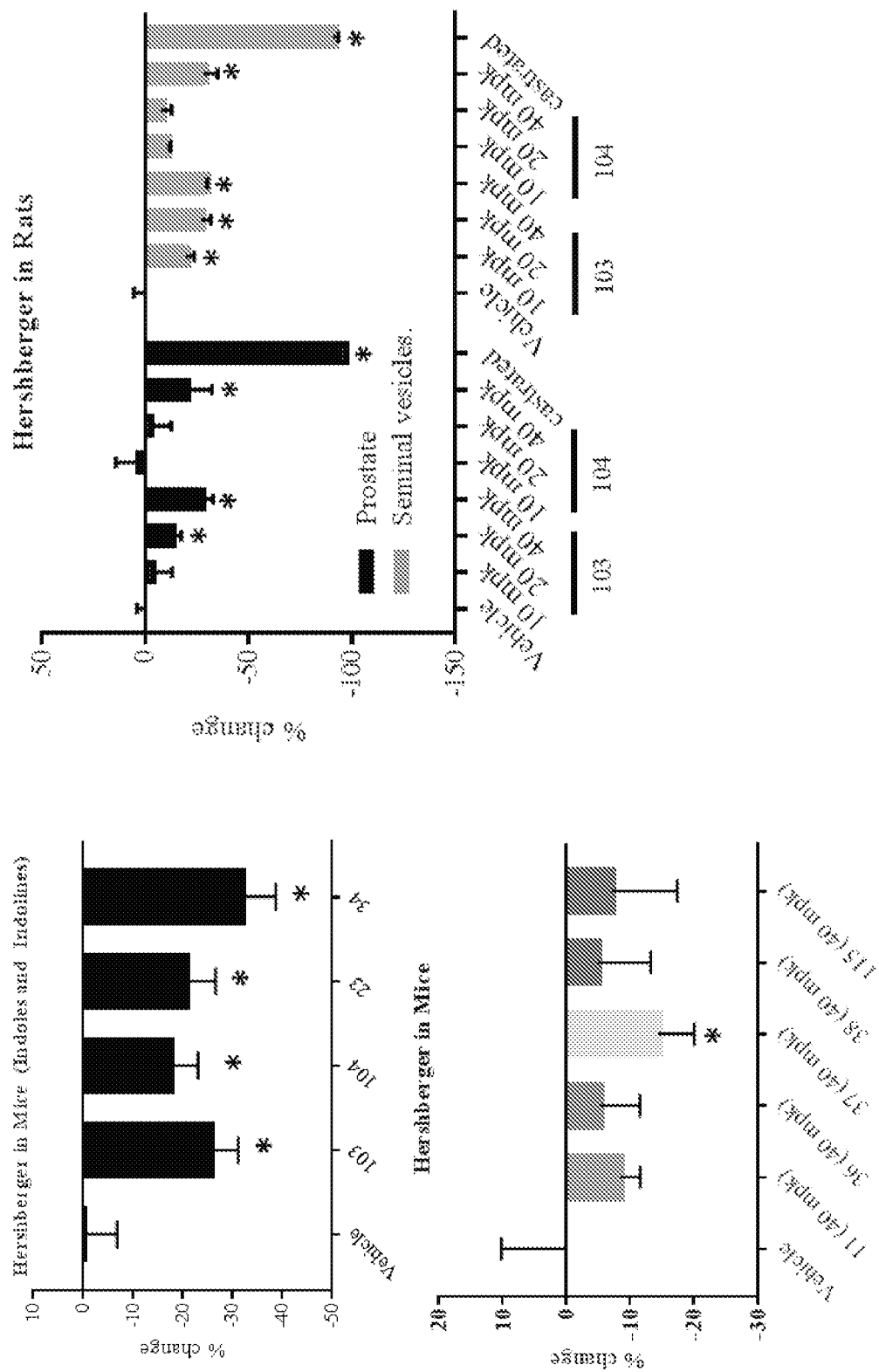
FIGS. 88A and 88B: SARDs inhibit androgen-dependent organs in mice and rats and inhibit growth of enzalutamide-resistant prostate cancer.
Figure 88B:
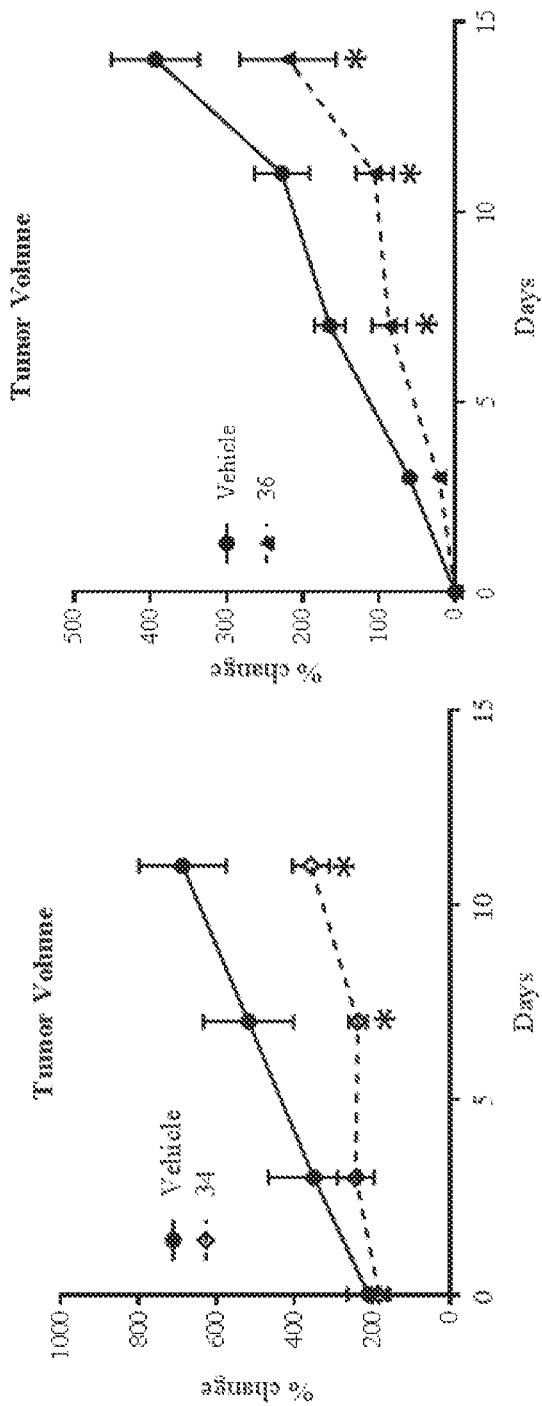

SARDs of the invention have a unique biological activity profile optimized to address Enz-R CPRC, including:
1) Generally bind to LBD of AR;
2) Inhibit transcriptional activation of wildtype AR, escape mutant ARs (T877A in Tables 7 and 10, F876L in FIG. 86A, and Q711A
3) Exert high efficacy and potency SARD activity against FL and SV AR whether wildtype or harboring point-mutations (LNCaP in Tables 7 and 10) or truncations (22RV1 in Tables 3 and 6), including an Enz-R cellular contexts (e.g., MR49F in FIG. 86B);
4) Exert AR antagonism in vivo when administered orally in intact animals (FIG. 88A);

5) Exert PC anti-proliferative activity in vitro (FIG. 87) and in vivo (see LNCaP, 22RV1) including in Enz-R CRPC (FIG. 88B); and
6) Bind to a secondary binding site in AF-1 believed to mediate SARD activity as demonstrated for 11 by steady fluorescence and NMR studies, as demonstrated herein.

Example 36

SBMA Method

Transgenic mice that express AR121Q (121 polyglutamine repeats instead of the usual 15-24 repeats) will be treated with vehicle or SARD orally. One group of mice will be castrated to serve as positive control as circulating androgens will worsen the SBMA (X-linked spinal-bulbar muscular atrophy) condition. Body weight, composition, and grip strength will be measured before the initiation of the experiment. Animals will be treated and weekly measurements will be performed. Animals will be treated and monitored until they die. AR121Q mice live only up to 60-80 days and hence evaluating the survival in the presence of SARD treatment is possible.

ALS Method

All experiments will be performed in male hSOD1-G93A mice (Jax labs; PMID: 26786249) as a model of anterior lateral sclerosis (ALS). Mice will be randomized and treated with either vehicle or SARD of this invention dissolved in DMSO+PEG-300 (15%+85%). Simultaneously, a group of mice will be castrated and used as positive control as castration has been shown to extend survival and disease duration in this model (PMID: 24630363). Mice will be treated orally every day until they reach morbidity. Weekly body weight and composition by magnetic resonance imaging (MRI) will be recorded. The mice performance will be measured each week by using a grip strength meter (Columbus instruments) or rotarod. Inability for the mice to move will be considered as a terminal disease state and the mice will be sacrificed.

Example 37

Synthesis of Benzotriazole SARD Compounds (S)—N-(4-Cyano-3-(trifluoromethyl)phenyl)-2-hydroxy-2-methyl-3-(5-(trifluoromethyl)-2H-benzo[d][1,2,3]triazol-2-yl)propanamide ($C_{19}H_{13}F_6N_5O_2$) (300)

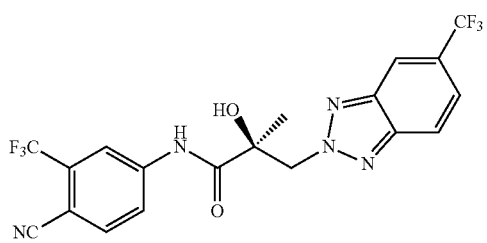 [SMILES: C[C@](O)(Cn1nc2ccc(C(F)(F)F)cc2n1)C(=O)Nc1ccc(C#N)c(C(F)(F)F)c1]

To a solution of 5-(trifluoromethyl)-1H-benzo[d][1,2,3]triazole (0.20 g, 0.0010688 mol) in anhydrous THF (5 mL), which was cooled in an ice water bath under an argon atmosphere, was added sodium hydride (60% dispersion in oil, 0.13 g, 0.0033134 mol). After addition, the resulting mixture was stirred for three hours. (R)-3-Bromo-N-(4-cyano-3-(trifluoromethyl)phenyl)-2-hydroxy-2-methylpropanamide (0.375 g, 0.0010688 mol) was added to above solution, and the resulting reaction mixture was allowed to stir overnight at room temperature under argon. The reaction was quenched by water, and extracted with ethyl acetate. The organic layer was washed with brine, dried with $MgSO_4$, filtered, and concentrated under vacuum. The product was purified by a silica gel column using DCM and ethyl acetate (9:1) as eluent to afford 0.044 g (9%) of the titled compound as yellowish solid.

$^1$H NMR (400 MHz, DMSO-$d_6$) δ 10.33 (s, 1H, NH), 8.40 (s, 1H, ArH), 8.38 (s, 1H, ArH), 8.23 (d, J=8.4 Hz, 1H, ArH), 8.11 (d, J=8.4 Hz, 2H, ArH), 7.67 (d, J=8.6 Hz, 1H, ArH), 6.67 (s, 1H, OH), 5.24 (d, J=14.0 Hz, 1H, CH), 4.99 (d, J=14.0 Hz, 1H, CH), 1.55 (s, 3H, $CH_3$).

Mass (ESI, Negative): 456.25 [M−H]$^-$; (ESI, Positive): 458.10 [M+H]$^+$.

(S)—N-(4-Cyano-3-(trifluoromethyl)phenyl)-2-hydroxy-2-methyl-3-(5-(trifluoromethyl)-1H-benzo[d][1,2,3]triazol-1-yl)propanamide ($C_{19}H_{13}F_6N_5O_2$) (301)

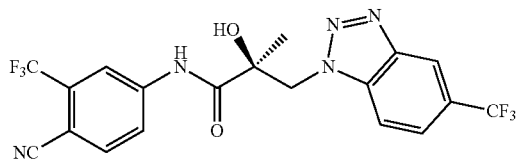 [SMILES: C[C@](O)(Cn1nnc2cc(C(F)(F)F)ccc21)C(=O)Nc1ccc(C#N)c(C(F)(F)F)c1]

To a solution of 5-(trifluoromethyl)-1H-benzo[d][1,2,3]triazole (0.20 g, 0.0010688 mol) in anhydrous THF (5 mL), which was cooled in an ice water bath under an argon atmosphere, was added sodium hydride (60% dispersion in oil, 0.13 g, 0.0033134 mol). After addition, the resulting mixture was stirred for three hours. (R)-3-Bromo-N-(4-cyano-3-(trifluoromethyl)phenyl)-2-hydroxy-2-methylpropanamide (0.375 g, 0.0010688 mol) was added to above solution, and the resulting reaction mixture was allowed to stir overnight at room temperature under argon. The reaction was quenched by water, and extracted with ethyl acetate. The organic layer was washed with brine, dried with $MgSO_4$, filtered, and concentrated under vacuum. The product was purified by a silica gel column using hexanes and ethyl acetate (3:1 to 2:1) as eluent to afford 0.025 g (5%) of the titled compound as yellowish solid.

$^1$H NMR (400 MHz, DMSO-$d_6$) δ 10.30 (s, 1H, NH), 8.39 (d, J=1.6 Hz, 1H, ArH), 8.33 (s, 1H, ArH), 8.25 (d, J=8.8 Hz, 1H, ArH), 8.12 (dd, J=8.8 Hz, J=2.0 Hz, 1H, ArH), 8.07 (d, J=8.4 Hz, 1H, ArH), 7.64 (dd, J=8.8 Hz, J=1.6 Hz, 1H, ArH), 6.64 (s, 1H, OH), 5.21 (d, J=14.4 Hz, 1H, CH), 5.01 (d, J=14.4 Hz, 1H, CH), 1.54 (s, 3H, $CH_3$).

Mass (ESI, Negative): 456.25 [M−H]$^-$; (ESI, Positive): 458.10 [M+H]$^+$.

(S)—N-(4-Cyano-3-(trifluoromethyl)phenyl)-2-hydroxy-2-methyl-3-(6-(trifluoromethyl)-1H-benzo[d][1,2,3]triazol-1-yl)propanamide ($C_{19}H_{13}F_6N_5O_2$) 302

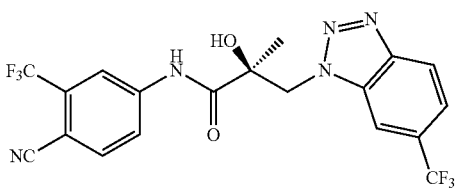 [SMILES: C[C@](O)(Cn1nnc2ccc(C(F)(F)F)cc21)C(=O)Nc1ccc(C#N)c(C(F)(F)F)c1]

To a solution of 5-(trifluoromethyl)-1H-benzo[d][1,2,3]triazole (0.20 g, 0.0010688 mol) in anhydrous THF (5 mL), which was cooled in an ice water bath under an argon atmosphere, was added sodium hydride (60% dispersion in oil, 0.13 g, 0.0033134 mol). After addition, the resulting mixture was stirred for three hours. (R)-3-Bromo-N-(4-cyano-3-(trifluoromethyl)phenyl)-2-hydroxy-2-methylpropanamide (0.375 g, 0.0010688 mol) was added to above solution, and the resulting reaction mixture was allowed to stir overnight at room temperature under argon. The reaction was quenched by water, and extracted with ethyl acetate. The organic layer was washed with brine, dried with MgSO$_4$, filtered, and concentrated under vacuum. The product was purified by a silica gel column using hexanes and ethyl acetate (3:1 to 2:1) as eluent to afford 0.023 g (5%) of the titled compound as yellowish solid.

$^1$H NMR (400 MHz, DMSO-d$_6$) δ 10.31 (s, 1H, NH), 8.50 (s, 1H, ArH), 8.34 (d, J=1.6 Hz, 1H, ArH), 8.18 (dd, J=8.8 Hz, J=2.0 Hz, 1H, ArH), 8.10 (d, J=8.8 Hz, 1H, ArH), 8.08 (d, J=8.4 Hz, 1H, ArH), 7.84 (dd, J=8.8 Hz, J=1.6 Hz, 1H, ArH), 6.49 (s, 1H, OH), 5.15 (d, J=14.4 Hz, 1H, CH), 4.97 (d, J=14.4 Hz, 1H, CH), 1.52 (s, 3H, CH$_3$).

Mass (ESI, Negative): 456.25 [M–H]$^-$; (ESI, Positive): 458.10 [M+H]$^+$.

(S)—N-(4-Cyano-3-(trifluoromethyl)phenyl)-2-hydroxy-2-methyl-3-(5-fluoro-2H-benzo[d][1,2,3]triazol-2-yl)propanamide ($C_{18}H_{13}F_4N_5O_2$) (303)

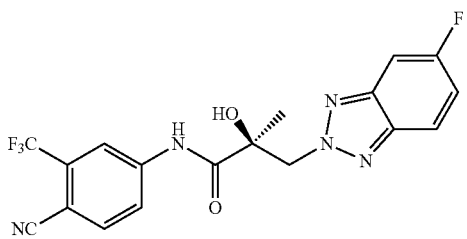 [SMILES: C[C@](O)(Cn1nc2ccc(F)cc2n1)C(=O)Nc1ccc(C#N)c(C(F)(F)F)c1]

To a solution of 5-fluoro-1H-benzo[d][1,2,3]triazole (0.20 g, 0.001459 mol) in anhydrous THF (5 mL), which was cooled in an ice water bath under an argon atmosphere, was added sodium hydride (60% dispersion in oil, 0.18 g, 0.004522 mol). After addition, the resulting mixture was stirred for three hours. (R)-3-Bromo-N-(4-cyano-3-(trifluoromethyl)phenyl)-2-hydroxy-2-methylpropanamide (0.51 g, 0.001459 mol) was added to above solution, and the resulting reaction mixture was allowed to stir overnight at room temperature under argon. The reaction was quenched by water, and extracted with ethyl acetate. The organic layer was washed with brine, dried with MgSO$_4$, filtered, and concentrated under vacuum. The product was purified by a silica gel column using hexanes and ethyl acetate (3:1 to 2:1) as eluent to afford 0.115 g (19.4%) of the titled compound as yellowish solid.

$^1$H NMR (400 MHz, DMSO-d$_6$) δ 10.35 (s, 1H, NH), 8.43 (s, 1H, ArH), 8.32 (d, J=8.2 Hz, 1H, ArH), 8.11 (d, J=8.2 Hz, 1H, ArH), 7.95-7.91 (m, 1H, ArH), 7.67 (d, J=8.8 Hz, 1H, ArH), 7.33-6-7.31 (m, 1H, ArH), 6.53 (s, 1H, OH), 5.14 (d, J=13.6 Hz, 1H, CH), 4.90 (d, J=13.6 Hz, 1H, CH), 1.53 (s, 3H, CH$_3$).

Mass (ESI, Positive): 430.09 [M+Na]$^+$.

(S)—N-(4-Cyano-3-(trifluoromethyl)phenyl)-2-hydroxy-2-methyl-3-(5-fluoro-1H-benzo[d][1,2,3]triazol-1-yl)propanamide ($C_{18}H_{13}F_4N_5O_2$) (304)

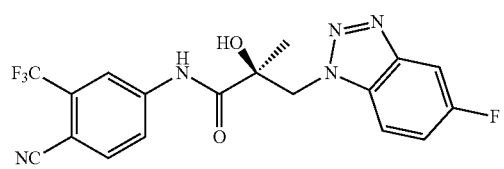 [SMILES: C[C@](O)(Cn1nnc2cc(F)ccc21)C(=O)Nc1ccc(C#N)c(C(F)(F)F)c1]

To a solution of 5-fluoro-1H-benzo[d][1,2,3]triazole (0.20 g, 0.001459 mol) in anhydrous THF (5 mL), which was cooled in an ice water bath under an argon atmosphere, was added sodium hydride (60% dispersion in oil, 0.18 g, 0.004522 mol). After addition, the resulting mixture was stirred for three hours. (R)-3-Bromo-N-(4-cyano-3-(trifluoromethyl)phenyl)-2-hydroxy-2-methylpropanamide (0.51 g, 0.001459 mol) was added to above solution, and the resulting reaction mixture was allowed to stir overnight at room temperature under argon. The reaction was quenched by water, and extracted with ethyl acetate. The organic layer was washed with brine, dried with MgSO$_4$, filtered, and concentrated under vacuum. The product was purified by a silica gel column using hexanes and ethyl acetate (3:1 to 2:1) as eluent to afford 0.075 g (12.6%) of the titled compound as yellowish solid.

$^1$H NMR (400 MHz, DMSO-d$_6$) δ 10.35 (s, 1H, NH), 8.40 (s, 1H, ArH), 8.19 (d, J=8.4 Hz, 1H, ArH), 8.10 (d, J=8.0 Hz, 1H, ArH), 8.07-8.04 (m, 1H, ArH), 7.70 (d, J=8.2 Hz, 1H, ArH), 7.28-6-7.23 (m, 1H, ArH), 6.45 (s, 1H, OH), 5.05 (d, J=14.4 Hz, 1H, CH), 4.87 (d, J=14.4 Hz, 1H, CH), 1.50 (s, 3H, CH$_3$).

Mass (ESI, Positive): 430.09 [M+Na]$^+$.

(S)—N-(4-Cyano-3-(trifluoromethyl)phenyl)-2-hydroxy-2-methyl-3-(6-fluoro-1H-benzo[d][1,2,3]triazol-1-yl)propanamide ($C_{18}H_{13}F_4N_5O_2$) (305)

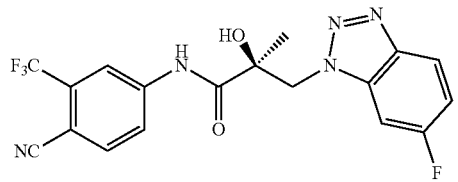 [SMILES: C[C@](O)(Cn1nnc2ccc(F)cc21)C(=O)Nc1ccc(C#N)c(C(F)(F)F)c1]

To a solution of 5-fluoro-1H-benzo[d][1,2,3]triazole (0.20 g, 0.001459 mol) in anhydrous THF (5 mL), which was cooled in an ice water bath under an argon atmosphere, was added sodium hydride (60% dispersion in oil, 0.18 g, 0.004522 mol). After addition, the resulting mixture was stirred for three hours. (R)-3-Bromo-N-(4-cyano-3-(trifluoromethyl)phenyl)-2-hydroxy-2-methylpropanamide (0.51 g, 0.001459 mol) was added to above solution, and the resulting reaction mixture was allowed to stir overnight at room temperature under argon. The reaction was quenched by water, and extracted with ethyl acetate. The organic layer was washed with brine, dried with MgSO$_4$, filtered, and concentrated under vacuum. The product was purified by a silica gel column using hexanes and ethyl acetate (3:1 to 2:1) as eluent to afford 0.052 g (8.8%) of the titled compound as yellowish solid.

$^1$H NMR (400 MHz, DMSO-d$_6$) δ 10.35 (s, 1H, NH), 8.38 (s, 1H, ArH), 8.20 (d, J=8.8 Hz, 1H, ArH), 8.10 (d, J=8.4 Hz, 1H, ArH), 7.92-7.89 (m, 1H, ArH), 7.84 (d, J=8.8 Hz, 1H, ArH), 7.46-7.42 (m, 1H, ArH), 6.46 (s, 1H, OH), 5.08 (d, J=14.4 Hz, 1H, CH), 4.90 (d, J=14.4 Hz, 1H, CH), 1.49 (s, 3H, CH$_3$).

Mass (ESI, Positive): 430.09 [M+Na]$^+$.

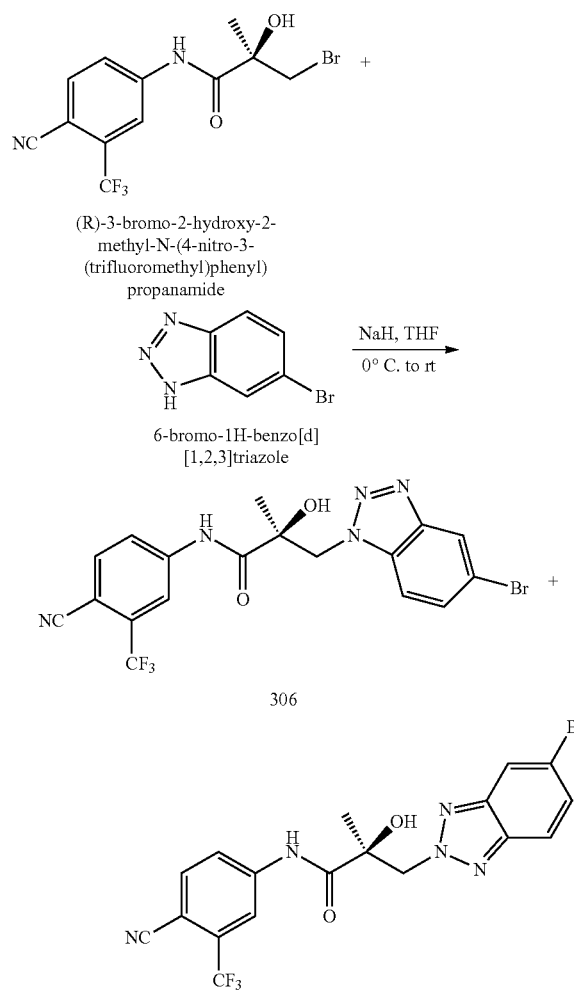

(S)-3-(5-Bromo-1H-benzo[d][1,2,3]triazol-1-yl)-N-(4-cyano-3-(trifluoromethyl)phenyl)-2-hydroxy-2-methylpropanamide (306)

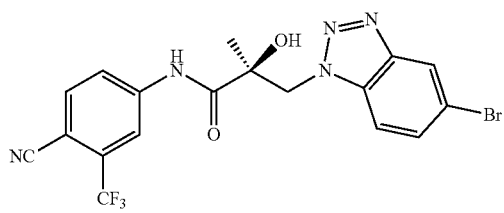 [SMILES: C[C@](O)(Cn1nnc2cc(Br)ccc21)C(=O)Nc1ccc(C#N)c(C(F)(F)F)c1]

To a dry, nitrogen-purged 100 mL round-bottom flask equipped with a dropping funnel under argon atmosphere, NaH of 60% dispersion in mineral oil (260 mg, 6.5 mmol) was added in 30 mL of anhydrous THF solvent in the flask at ice-water bath, and 6-bromo-1H-benzo[d][1,2,3]triazole (514 mg, 2.6 mmol) was stirred in over 30 min at the ice-water bath. Into the flask, the solution of (R)-3-bromo-2-hydroxy-2-methyl-N-(4-nitro-3-(trifluoromethyl)phenyl)propanamide (911 mg, 2.6 mmol) in 5 mL of anhydrous THF was added through dropping funnel under argon atmosphere at the ice-water bath and stirred overnight at room temperature. After adding 1 mL of H$_2$O, the reaction mixture was condensed under reduced pressure, and then dispersed into 50 mL of EtOAc, washed with 50 mL (×2) water, evaporated, dried over anhydrous MgSO$_4$, and evaporated to dryness. The mixture was purified with flash column chromatography as an eluent EtOAc/hexane=1/2 to produce designed compounds (Yield=65%: 42% for 306 and 23% of 307) as yellowish solid.

(S)-3-(5-Bromo-1H-benzo[d][1,2,3]triazol-1-yl)-N-(4-cyano-3-(trifluoromethyl)phenyl)-2-hydroxy-2-methylpropanamide (306)

MS (ESI) m/z 467.81 [M−H]$^−$; 492.00 [M+Na]$^+$;
$^1$H NMR (400 MHz, CDCl$_3$) δ 9.10 (bs, 1H, NH), 8.04 (s, 1H), 8.02 (s, 1H), 7.90 (d, J=8.0 Hz, 1H), 7.76 (d, J=8.0 Hz, 1H), 7.74 (d, J=8.8 Hz, 1H), 7.49 (d, J=8.8 Hz, 1H), 5.48 (s, 1H, OH), 5.26 (d, J=13.6 Hz, 1H), 4.94 (d, J=13.6 Hz, 1H), 1.54 (s, 3H);
$^{19}$F NMR (CDCl$_3$, decoupled) δ−62.19.

(S)-3-(5-Bromo-2H-benzo[d][1,2,3]triazol-2-yl)-N-(4-cyano-3-(trifluoromethyl)phenyl)-2-hydroxy-2-methylpropanamide (307))

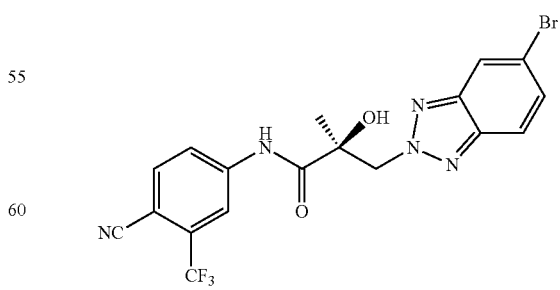

MS (ESI) m/z 467.84 [M−H]$^−$;
$^1$H NMR (400 MHz, CDCl$_3$) δ 8.97 (bs, 1H, NH), 8.15 (s, 1H), 7.92 (s, 1H), 7.75 (m, 2H), 7.62 (d, J=9.0 Hz, 1H), 7.53

(d, J=9.0 Hz, 1H), 5.16 (d, J=14.2 Hz, 1H), 4.79 (s, 1H, OH), 4.78 (d, J=14.2 Hz, 1H), 1.65 (s, 3H);

$^{19}$F NMR (CDCl$_3$, decoupled) δ −62.26.

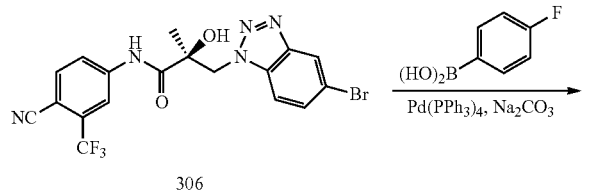

306

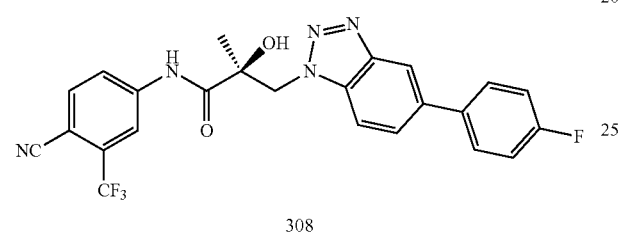

308

(S)—N-(4-Cyano-3-(trifluoromethyl)phenyl)-3-(5-(4-fluorophenyl)-1H-benzo[d][1,2,3]triazol-1-yl)-2-hydroxy-2-methylpropanamide (308)

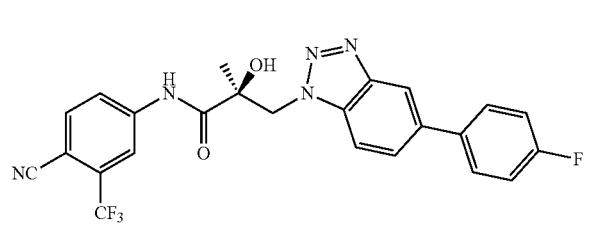 [SMILES: C[C@](O)(Cn1nnc2cc(-c3ccc(F)cc3)ccc21)C(=O)Nc1ccc(C#N)c(C(F)(F)F)c1]

A mixture of 306 (150 mg, 0.32 mmol), tetrakis(triphenylphosphine)palladium (0) (13 mg, 12 mmol) and trimethoxyboric acid (50 mg, 0.35 mmol) in THF/MeOH (1/1 mL) with sodium carbonate (82 mg, 7.69 mmol) in ethanol/water (5 mL/1 mL) were heated to reflux overnight. The mixture was cooled down to be concentrated under reduced pressure and poured into EtOAc, which was washed with water and dried over MgSO$_4$, concentrated, purified by silica gel chromatography (EtOAc/n-hexane=2:3) to afford 308 as a yellow solid.

Yield=90%;

MS (ESI) m/z 482.25 [M−H]$^−$;

$^1$H NMR (400 MHz, CDCl$_3$) δ 9.12 (bs, 1H, NH), 8.02 (s, 1H), 7.96 (s, 1H), 7.92 (d, J=9.2 Hz, 1H), 7.76 (d, J=8.4 Hz, 1H), 7.64 (d, J=9.2 Hz, 1H), 7.59 (dd, J=7.6, 5.2 Hz, 2H), 7.17 (t, J=8.4 Hz, 2H), 5.72 (s, 1H, OH), 5.28 (d, J=14.0 Hz, 1H), 4.97 (d, J=14.0 Hz, 1H), 1.55 (s, 3H); $^{19}$F NMR (CDCl$_3$, decoupled) δ −62.20, −114.49.

Example 38

Synthesis of (S)-3-(Substituted phenyl amino)-N-(4-nitro- or 4-cyano-3-(trifluoromethyl) phenyl)-2-hydroxy-2-methylpropanamides (Compounds 12-19)

Scheme 1. Synthesis of (S)-3-(substituted phenyl amino)-N-(4-nitro- or 4-cyano-3-(trifluoromethyl)phenyl)-2-hydroxy-2-methylpropanamides (12~19).

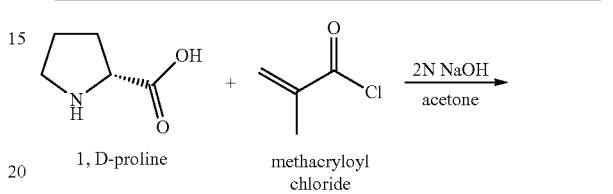

1, D-proline     methacryloyl chloride

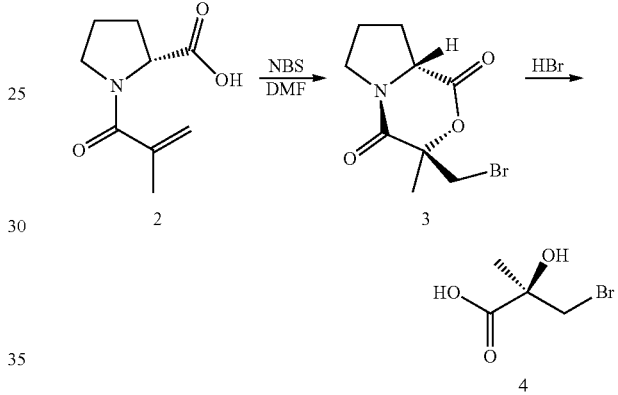

2     3     4

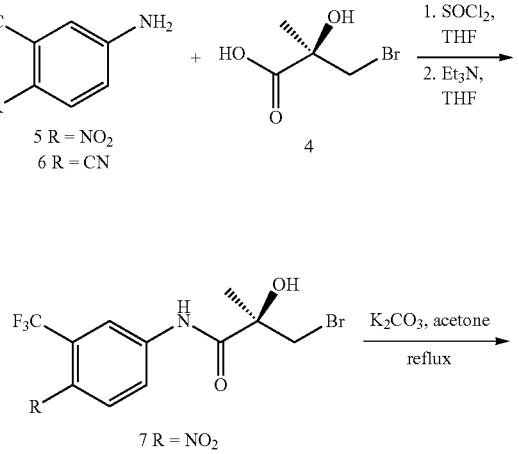

5 R = NO$_2$
6 R = CN

4

7 R = NO$_2$
8 R = CN

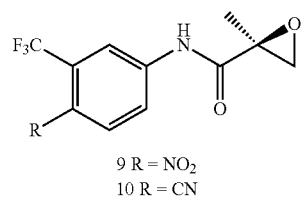

9 R = NO$_2$
10 R = CN

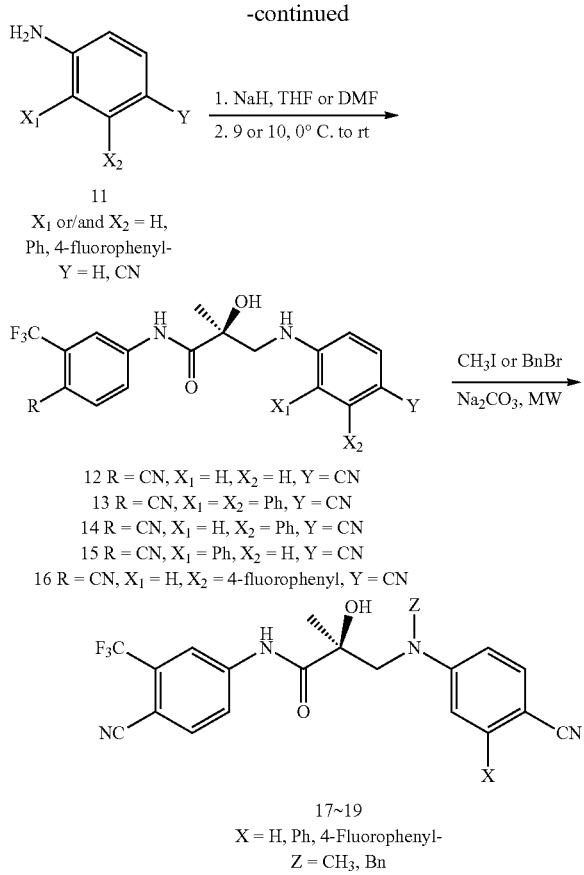

(2R)-1-Methacryloylpyrrolidin-2-carboxylic acid (2)

D-Proline (14.93 g, 0.13 mol) was dissolved in 71 mL of 2 N NaOH and cooled in an ice bath. The resulting alkaline solution was diluted with acetone (71 mL). An acetone solution (71 mL) of methacryloyl chloride (13.56 g, 0.13 mol) and 2 N NaOH solution (71 mL) were simultaneously added over 40 min to the aqueous solution of D-proline in an ice bath. The temperature of the mixture was kept at 10-11° C. during the addition of the methacryloyl chloride. After stirring (3 h, room temperature (RT)), the mixture was evaporated in vacuo at a temperature at 35-45° C. to remove acetone. The resulting solution was washed with ethyl ether and was acidified to pH 2 with concentrated HCl. The acidic mixture was saturated with NaCl and was extracted with EtOAc (100 mL×3). The combined extracts were dried over $Na_2SO_4$, filtered through Celite®, and evaporated in vacuo to give the crude product as a colorless oil. Recrystallization of the oil from ethyl ether and hexanes afforded 16.2 g (68%) of the desired compound as colorless crystals: mp 102.1-103.4° C. (lit. mp 102.5-103.5° C.); the NMR spectrum of this compound demonstrated the existence of two rotamers of the title compound.

$^1$H NMR (300 MHz, DMSO-$d_6$) δ 5.28 (s) and 5.15 (s) for the first rotamer, 5.15 (s) and 5.03 (s) for the second rotamer (totally 2H for both rotamers, vinyl $CH_2$), 4.48-4.44 for the first rotamer, 4.24-4.20 (m) for the second rotamer (totally 1H for both rotamers, CH at the chiral center), 3.57-3.38 (m, 2H, $CH_2$), 2.27-2.12 (1H, CH), 1.97-1.72 (m, 6H, $CH_2$, CH, Me); $^{13}$C NMR (75 MHz, DMSO-$d_6$) δ for major rotamer 173.3, 169.1, 140.9, 116.4, 58.3, 48.7, 28.9, 24.7, 19.5: for minor rotamer 174.0, 170.0, 141.6, 115.2, 60.3, 45.9, 31.0, 22.3, 19.7; IR (KBr) 3437 (OH), 1737 (C=O), 1647 (CO, COOH), 1584, 1508, 1459, 1369, 1348, 1178 cm$^{-1}$; $[α]_D^{26}$+80.8° (c=1, MeOH); Anal. Calcd. for $C_9H_{13}NO_3$: C, 59.00, H, 7.15, N, 7.65. Found: C, 59.13, H, 7.19, N, 7.61.

(3R,8aR)-3-Bromomethyl-3-methyl-tetrahydro-pyrrolo[2,1-c][1,4]oxazine-1,4-dione (3)

A solution of NBS (23.5 g, 0.132 mol) in 100 mL of DMF was added dropwise to a stirred solution of the (methylacryloyl)-pyrrolidine (16.1 g, 88 mmol) in 70 mL of DMF under argon at RT, and the resulting mixture was stirred 3 days. The solvent was removed in vacuo, and a yellow solid was precipitated. The solid was suspended in water, stirred overnight at RT, filtered, and dried to give 18.6 g (81%) (smaller weight when dried ~34%) of the title compound as a yellow solid: mp 158.1-160.3° C.;

$^1$H NMR (300 MHz, DMSO-$d_6$) δ 4.69 (dd, J=9.6 Hz, J=6.7 Hz, 1H, CH at the chiral center), 4.02 (d, J=11.4 Hz, 1H, CHH$_a$), 3.86 (d, J=11.4 Hz, 1H, CHH$_b$), 3.53-3.24 (m, 4H, $CH_2$), 2.30-2.20 (m, 1H, CH), 2.04-1.72 (m, 3H, $CH_2$ and CH), 1.56 (s, 2H, Me); $^{13}$C NMR (75 MHz, DMSO-$d_6$) δ 167.3, 163.1, 83.9, 57.2, 45.4, 37.8, 29.0, 22.9, 21.6; IR (KBr) 3474, 1745 (C=O), 1687 (C=O), 1448, 1377, 1360, 1308, 1227, 1159, 1062 cm$^{-1}$; $[α]_D^{26}$+124.5° (c=1.3, chloroform); Anal. Calcd. for $C_9H_{12}BrNO_3$: C, 41.24, H, 4.61, N, 5.34. Found: C, 41.46, H, 4.64, N, 5.32.

(2R)-3-Bromo-2-hydroxy-2-methylpropanoic acid (4)

A mixture of bromolactone (18.5 g, 71 mmol) in 300 mL of 24% HBr was heated at reflux for 1 h. The resulting solution was diluted with brine (200 mL), and was extracted with ethyl acetate (100 mL×4). The combined extracts were washed with saturated $NaHCO_3$ (100 mL×4). The aqueous solution was acidified with concentrated HCl to pH=1, which, in turn, was extracted with ethyl acetate (100 mL×4). The combined organic solution was dried over $Na_2SO_4$, filtered through Celite®, and evaporated in vacuo to dryness. Recrystallization from toluene afforded 10.2 g (86%) of the desired compound as colorless crystals: mp 110.3-113.8° C.;

$^1$H NMR (300 MHz, DMSO-$d_6$) δ 3.63 (d, J=10.1 Hz, 1H, CHH$_a$), 3.52 (d, J=10.1 Hz, 1H, CHH$_b$), 1.35 (s, 3H, Me); IR (KBr) 3434 (OH), 3300-2500 (COOH), 1730 (C=O), 1449, 1421, 1380, 1292, 1193, 1085 cm$^{-1}$; $[α]_D^{26}$+10.5° (c=2.6, MeOH); Anal. Calcd. for $C_4H_7BrO_3$: C, 26.25, H, 3.86. Found: C, 26.28, H, 3.75.

(2R)-3-Bromo-N-[4-cyano-3-(trifluoromethyl)phenyl]-2-hydroxy-2-methylpropanamide (8)

Thionyl chloride (46.02 g, 0.39 mol) was added dropwise to a cooled solution (less than 4° C.) of (R)-3-bromo-2-hydroxy-2-methylpropanoic acid (51.13 g, 0.28 mol) in 300 mL of THF under an argon atmosphere. The resulting mixture was stirred for 3 h under the same condition. To this was added Et$_3$N (39.14 g, 0.39 mol) and stirred for 20 min under the same condition. After 20 min, 5-amino-2-cyanobenzotrifluoride (40.0 g, 0.21 mol), 400 mL of THF were added and then the mixture was allowed to stir overnight at RT. The solvent was removed under reduced pressure to give a solid which was treated with 300 mL of $H_2O$, extracted with EtOAc (2×400 mL). The combined organic extracts were washed with saturated $NaHCO_3$ solution (2×300 mL)

and brine (300 mL). The organic layer was dried over MgSO₄ and concentrated under reduced pressure to give a solid which was purified from column chromatography using CH₂Cl₂/EtOAc (80:20) to give a solid. This solid was recrystallized from CH₂Cl₂/hexane to give 55.8 g (73.9%) of (2R)-3-bromo-N-[4-cyano-3-(trifluoromethyl)phenyl]-2-hydroxy-2-methylpropanamide as a light-yellow solid. Mp 134.0-136.5° C.;

¹H NMR (CDCl₃/TMS) δ 1.66 (s, 3H, CH₃), 3.11 (s, 1H, OH), 3.63 (d, J=10.8 Hz, 1H, CH₂), 4.05 (d, J=10.8 Hz, 1H, CH₂), 7.85 (d, J=8.4 Hz, 1H, ArH), 7.99 (dd, J=2.1, 8.4 Hz, 1H, ArH), 8.12 (d, J=2.1 Hz, 1H, ArH), 9.04 (bs, 1H, NH). MS (ESI) 349.0 [M−H]⁻; M.p.: 124-126° C.

Preparation of 4-Cyano 2,3-Substituted Anilines (26-28)

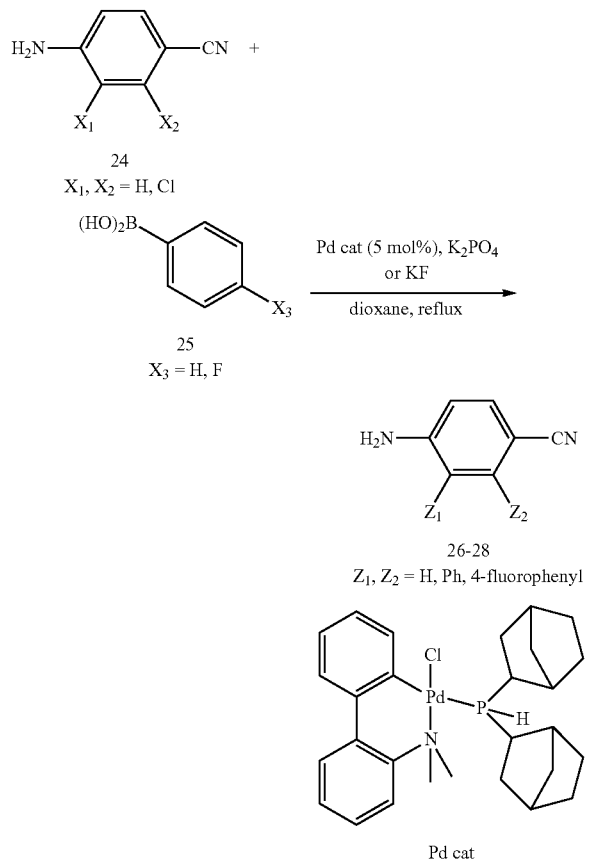

General procedure I: Arylaniline 24 (4.46 mmol), boric acid 25 (4.46 mmol), Pd cat (0.224 mmol, the structure as shown in Scheme 2) and K₂PO₄ (8.92 mmol) in 10 mL of 1,4-dioxane were heated to reflux under argon overnight. The mixture was cooled to RT and poured into DCM, which was washed with water, dried over anhydrous MgSO₄, and evaporated to dryness. The mixture was purified with flash column chromatography as an eluent EtOAc/hexane and then the condensed compounds were then recrystallized at EtOAc/hexane to give the target products (26~28).

5-Amino-[1,1'-biphenyl]-2-carbonitrile (26)

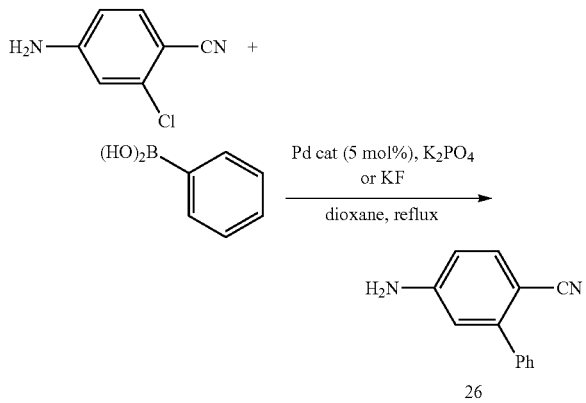

Yield 80%; Brown solid; MS (ESI) 192.8 [M−H]⁻; 217.1 [M+Na]⁺; ¹H NMR (CDCl₃, 400 MHz) δ 7.54-7.42 (m, 6H), 6.71 (d, J=3.2 Hz, 1H), 6.66 (dd, J=11.2, 3.2 Hz, 1H), 4.22 (bs, 2H, NH₂).

6-Amino-[1,1'-biphenyl]-3-carbonitrile (27)

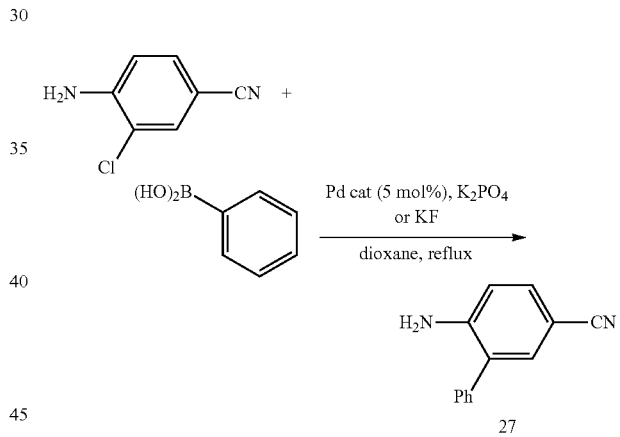

Yield 79%; Brown solid; MS (ESI) 192.8 [M−H]⁻; 217.1 [M+Na]⁺; ¹H NMR (CDCl₃, 400 MHz) δ 7.50-7.30 (m, 7H), 6.76 (dd, J=11.2, 6.0 Hz, 1H), 4.27 (bs, 2H, NH₂).

5-Amino-4'-fluoro-[1,1'-biphenyl]-2-carbonitrile (28)

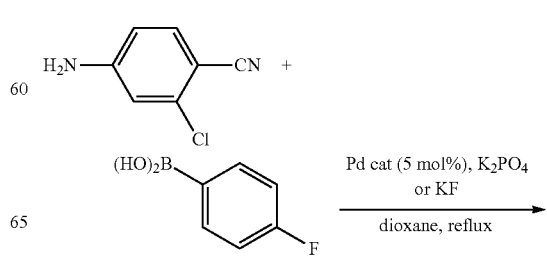

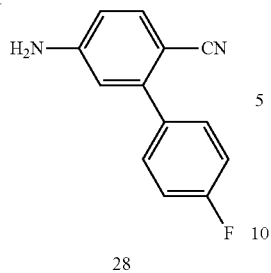

28

Yield 98%; Brown solid; MS (ESI) 200.8 [M–H]⁻; ¹H NMR (DMSO-d₆, 400 MHz) δ 7.50-7.48 (m, 3H), 7.34-7.30 (m, 2H), 6.63 (m, 2H), 6.26 (bs, 2H, NH₂).

Preparation of Several 2-hydroxy-2-methylpropanamides (12-19)

General Procedure II:

Step 1. Preparation of (S)—N-(4-cyano-3-(trifluoromethyl)phenyl)-2-methyloxirane-2-carboxamide (10) in THF: a mixture of hydroxylbromide 8 (1.0 g, 2.84 mmol) and potassium carbonate (790 mg, 5.70 mmol) in 60 mL acetone was heated to reflux for 30 min. After complete conversion of starting bromide 8 to desired epoxide 10 as monitored by TLC, the solvent was evaporated under reduced pressure to give yellowish residue, which was poured into 20 mL of anhydrous EtOAc. The solution was filtered through Celite® pad to remove K₂CO₃ residue and condensed under reduced pressure to give a yellowish solid of epoxide 10, which was dissolved in 5 mL of anhydrous THF to prepare a solution of epoxide 10 in THF. The resulting solution was directly used as next reactant without analysis.

Step 2. NaH of 60% dispersion in mineral oil (228 mg, 5.7 mmol) was added in 30 mL of anhydrous THF solvent in 100 mL dried two necked round bottom flask equipped with a dropping funnel. Substituted aniline 11 (2.84 mmol) was added to the solution under argon atmosphere at ice-water bath, and the resulting solution was stirred for 30 min at the ice-water bath. Into the flask, the prepared solution of epoxide 9 or 10 (2.84 mmol in THF) was added through dropping funnel under argon atmosphere at the ice-water bath and stirred overnight at RT. After adding 1 mL of H₂O, the reaction mixture was condensed under reduced pressure, and then dispersed into 50 mL of EtOAc, washed with 50 mL (×2) water, brine, dried over anhydrous MgSO₄, and evaporated to dryness. The mixture was purified with flash column chromatography with EtOAc/hexane as eluent, and then the condensed compounds were then recrystallized at EtOAc/hexane to give the respective target products 12-19. Preparation of SARDs 12-19:

Scheme 3. Preparation of SARDs 12-19.

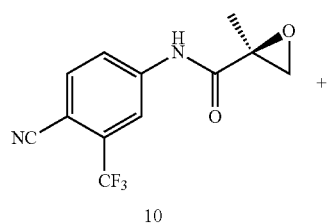

10

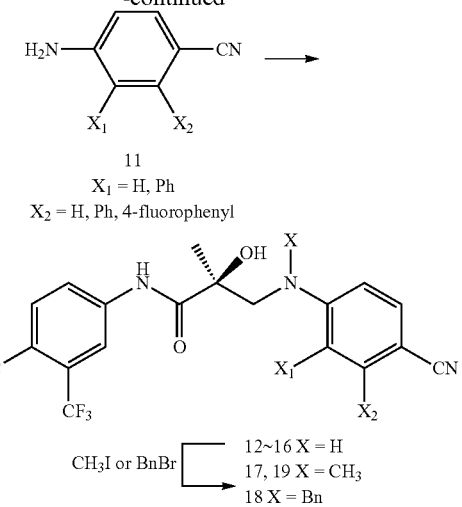

11
X₁ = H, Ph
X₂ = H, Ph, 4-fluorophenyl

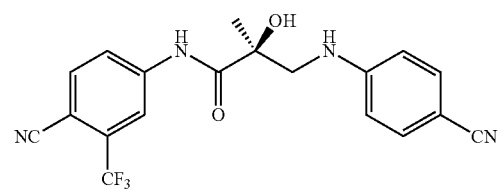 [SMILES: C[C@](O)(CNc1ccc(C#N)cc1)C(=O)Nc1ccc(C#N)c(C(F)(F)F)c1]

CH₃I or BnBr
12~16 X = H
17, 19 X = CH₃
18 X = Bn (S)—N-(4-Cyano-3-(trifluoromethyl)phenyl)-3-((4-cyanophenyl)amino)-2-hydroxy-2-methylpropanamide (12)

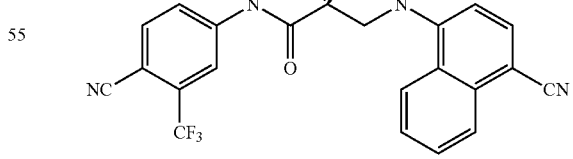

Yield 58%; Brown solid; MS (ESI) 387.2 [M–H]⁻; ¹H NMR (DMSO-d₆, 400 MHz) δ 10.42 (bs, 1H, NH), 8.11 (s, 1H), 8.21 (d, J=2.2 Hz, 1H), 8.01 (d, J=2.2 Hz, 1H), 7.38 (d, J=8.7, 2H), 6.75 (d, J=8.7 Hz, 2H), 6.12 (bs, 1H, NH), 3.61 (m, 1H), 3.25 (m, 1H), 2.29 (bs, 1H, OH), 1.42 (s, 3H); Anal. Calcd for C₁₉H₁₅F₃N₄O₂: C, H, N.

(S)—N-(4-Cyano-3-(trifluoromethyl)phenyl)-3-((4-cyanonaphthalen-1-yl)amino)-2-hydroxy-2-methylpropanamide (13)

Yield 39%; Brown solid; MS (ESI) 437.2 [M–H]⁻; ¹H NMR (CDCl₃, 400 MHz) δ 9.14 (bs, 1H, NH), 8.15 (d, J=8.3 Hz, 1H), 8.06 (d, J=1.8 Hz, 1H), 7.98 (dd, J=8.3, 1.8 Hz, 1H), 7.82-7.71 (m, 5H), 6.70 (d, J=8.1 Hz, 1H), 5.51 (bs, 1H, NH), 3.95 (m, 1H), 3.57 (m, 1H), 2.29 (bs, 1H, OH), 1.74 (s, 3H); Anal. Calcd for C₂₃H₁₇F₃N₄O₂: C, H, N.

(S)—N-(4-Cyano-3-(trifluoromethyl)phenyl)-3-((6-cyano-[1,1'-biphenyl]-3-yl)amino)-2-hydroxy-2-methylpropanamide (14)

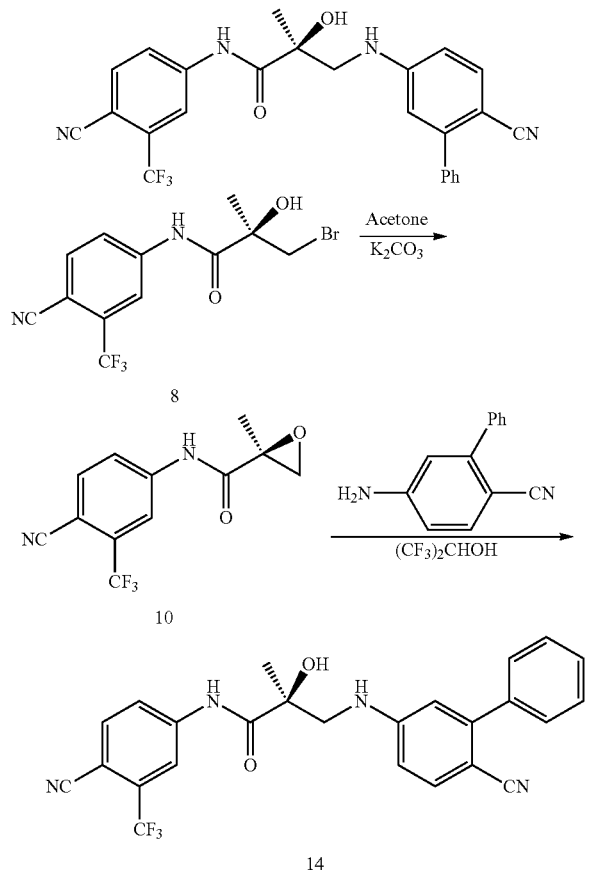

Yield 42%; Brown solid; MS (ESI) 463.0 [M–H]⁻; ¹H NMR (DMSO-d₆, 400 MHz) δ 10.50 (bs, 1H, NH), 8.46 (d, J=2.0 Hz, 1H), 8.17 (dd, J=8.4, 2.0 Hz, 1H), 8.08 (d, J=8.4 Hz, 1H), 7.47 (m, 6H), 6.75 (m, 1H), 6.58 (m, 1H), 6.13 (bs, 1H, NH), 3.67 (d, J=14.8 Hz, 1H), 3.31 (d, J=14.8 Hz, 1H), 2.49 (bs, 1H, OH), 1.24 (s, 3H); Anal. Calcd for C25H19F3N4O2: C, H, N.

(S)—N-(4-Cyano-3-(trifluoromethyl)phenyl)-3-((5-cyano-[1,1'-biphenyl]-2-yl)amino)-2-hydroxy-2-methylpropanamide (15)

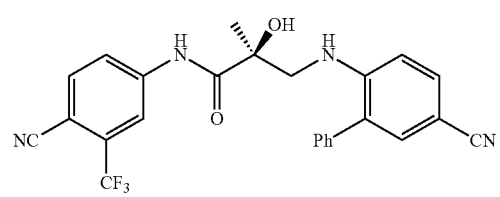 [SMILES: C[C@](O)(CNc1ccc(C#N)cc1-c1ccccc1)C(=O)Nc1ccc(C#N)c(C(F)(F)F)c1]

Yield 32%; Brown solid; MS (ESI) 462.9 [M–H]⁻; 487.1 [M+Na]⁺; ¹H NMR (CDCl₃, 400 MHz) δ 10.49 (bs, 1H, NH), 8.45 (m, 1H), 8.17-7.43 (m, 7H), 7.23 (m, 2H), 6.52 (m, 1H), 6.18 (bs, 1H, NH), 3.67 (d, J=14.8 Hz, 1H), 3.31 (d, J=14.8 Hz, 1H), 2.47 (bs, 1H, OH), 1.23 (s, 3H); Anal. Calcd for C₂₅H₁₉F₃N₄O₂: C, H, N.

Scheme 4. Preparation of SARDs 17-19 and 17a.

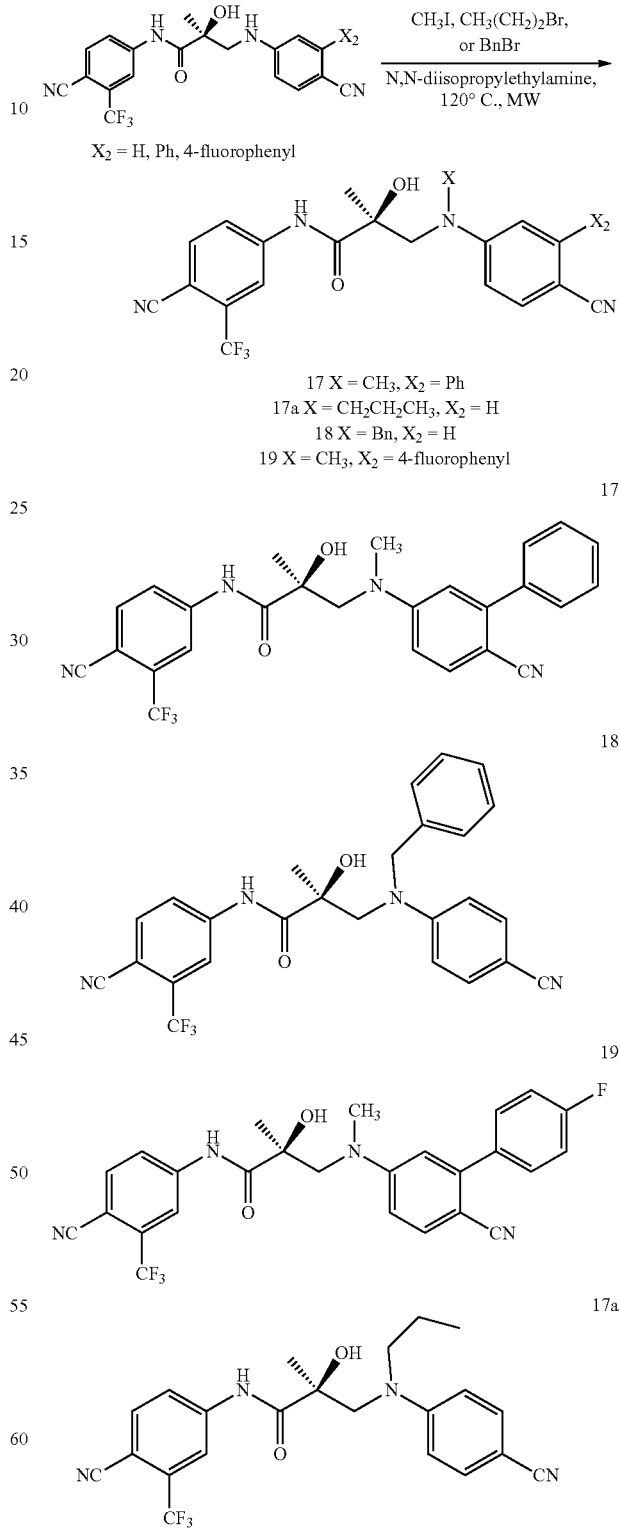

General Procedure III: A mixture of compounds 12 or 14 (0.15 mmol) and 0.5 mL of alkylhalide (methyl iodide, n-propylbromide or benzyl bromide) with 1 mL of N,N-diisopropylethylamine (DIPEA, Hünig's base) was loaded into a vessel with a cap. The reaction vessels were placed in a reactor block in the microwave. A programmable microwave irradiation cycle of 30 min on (300 W) at 150° C. and 25 min off (fan-cooled) was executed (irradiation time, 30 min). The mixture was transferred to round bottom flask to be concentrated under reduced pressure and poured into EtOAc, which was washed with water and dried over anhydrous MgSO$_4$, concentrated, purified by silica gel chromatography (EtOAc/n-hexane) to afford to desired products (17, 17a, 18 and 19).

(S)—N-(4-Cyano-3-(trifluoromethyl)phenyl)-3-((6-cyano-[1,1'-biphenyl]-3-yl)(methyl)amino)-2-hydroxy-2-methylpropanamide (17)

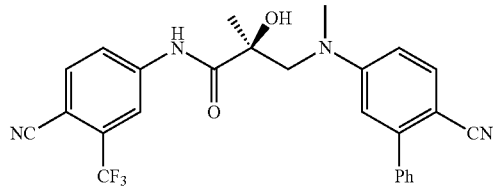 [SMILES: CN(C[C@](C)(O)C(=O)Nc1ccc(C#N)c(C(F)(F)F)c1)c1ccc(C#N)c(-c2ccccc2)c1]

Yield 42%; Yellowish solid; MS (ESI) 501.1 [M+Na]$^+$; $^1$H NMR (CDCl$_3$, 400 MHz) δ 9.09 (bs, 1H, NH), 8.06 (s, 1H), 7.93 (d, J=2.0 Hz, 1H), 7.90 (d, J=2.0 Hz, 1H), 7.79-7.28 (m, 7H), 6.88 (m, 2H), 3.98 (d, J=15.6 Hz, 1H), 3.75 (d, J=15.6 Hz, 1H), 3.01 (s, 3H), 2.06 (s, 1H, OH), 1.63 (s, 3H); Anal. Calcd for C$_{26}$H$_{21}$F$_3$N$_4$O$_2$: C, H, N.

(S)-3-(Benzyl(4-cyanophenyl)amino)-N-(4-cyano-3-(trifluoromethyl)phenyl)-2-hydroxy-2-methylpropanamide (18)

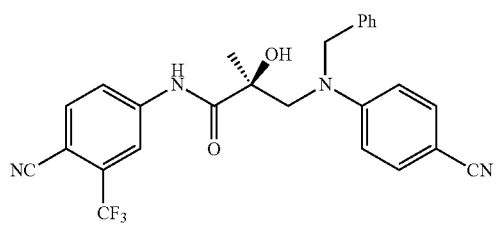 [SMILES: C[C@](O)(CN(Cc1ccccc1)c1ccc(C#N)cc1)C(=O)Nc1ccc(C#N)c(C(F)(F)F)c1]

Yield 32%; Brown solid; MS (ESI) 476.9 [M−H]$^-$; 501.1 [M+Na]$^+$; $^1$H NMR (CDCl$_3$, 400 MHz) δ 10.22 (bs, 1H, NH), 8.35 (s, 1H), 8.17 (d, J=8.2 Hz, 1H), 8.08 (d, J=8.2 Hz, 1H), 7.20-7.11 (m, 5H), 6.75 (m, 1H), 6.91 (m, 2H), 6.23 (s, 1H), 4.90 (s, 2H), 3.99 (d, J=14.8 Hz, 1H), 3.89 (d, J=14.8 Hz, 1H), 3.42 (bs, 1H, OH), 1.41 (s, 3H); Anal. Calcd for C$_{26}$H$_{21}$F$_3$N$_4$O$_2$: C, H, N.

(S)—N-(4-Cyano-3-(trifluoromethyl)phenyl)-3-((6-cyano-4'-fluoro-[1,1'-biphenyl]-3-yl)(methyl)amino)-2-hydroxy-2-methylpropanamide (19)

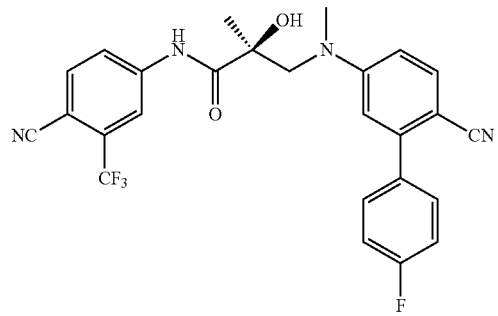 [SMILES: CN(C[C@](C)(O)C(=O)Nc1ccc(C#N)c(C(F)(F)F)c1)c1ccc(C#N)c(-c2ccc(F)cc2)c1]

Yield 38%; Brown solid; MS (ESI) 495.2 [M−H]$^-$; $^1$H NMR (CDCl$_3$, 400 MHz) δ 10.17 (bs, 1H, NH), 8.15 (s, 1H), 8.00 (d, J=2.0 Hz, 1H), 8.08 (d, J=2.0 Hz, 1H), 7.49-7.48 (m, 4H), 7.34-7.30 (m, 2H), 6.75 (m, 1H), 3.99 (d, J=14.8 Hz, 1H), 3.79 (d, J=14.8 Hz, 1H), 3.09 (s, 3H), 2.11 (bs, 1H, OH), 1.61 (s, 3H); Anal. Calcd for C$_{26}$H$_{20}$F$_4$N$_4$O$_2$: C, H, N.

Example 39

Synthesis of Compounds 14 and 17

Synthetic Scheme of SARDs 14 and 17

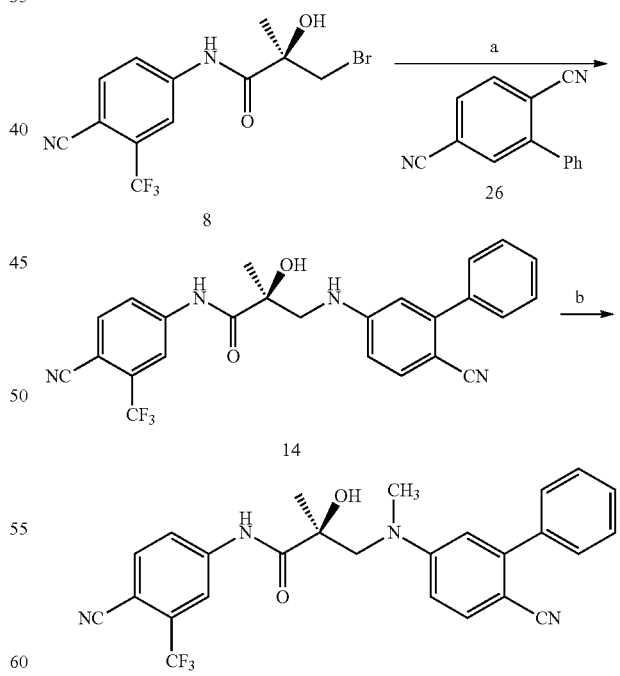

Reagents and conditions: (a) NaH, THF, 0° C.~RT; (b) CH$_3$I, N,N-diisopropylethylamine, 120° C., MW.

Hydroxybromide 8 was used as an important intermediate which was reacted with aniline 26 after activating by NaH in THF solvent to produce 14. N-Alkylation of 14 was a microwave assisted reaction and performed under a basic conditions in using N,N-diisopropylethylamine (Hunig's base) to generate 17.

Example 40

Synthesis of Compounds 49 and 50

General Procedure: Preparation of Compounds 49 and 50

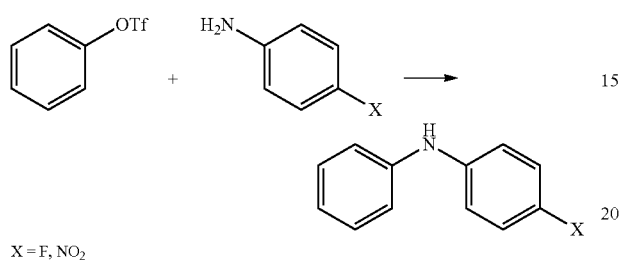

X = F, NO$_2$

A mixture of phenyl trifluoromethanesulfonate (500 mg, 2.21 mmol), palladium acetate (II) (50 mg, 0.22 mmol), (±) 2,2'-bis(diphenylphosphino)-1,1'-binaphthyl (317 mg, 0.66 mmol) and cesium carbonate (1.09 g, 3.31 mmol) in 50 mL of toluene were inertized with argon. Then, 4-nitroaniline (331 mg, 2.43 mmol) or 4-fluoroaniline (2.43 mmol) was added and the mixture was heated at 110° C. overnight. The reaction mixture was allowed to cool to room temperature and filtered through a pad of Celite®. The filtrate was diluted with CH$_2$Cl$_2$ and water. The phases were separated and the aqueous phase was re-extracted 2 times with CH$_2$Cl$_2$. The combined organic phases were dried over Na$_2$SO$_4$ and the resulting solution was dried over anhydrous Na$_2$SO$_4$ and purified with flash column chromatography as an eluent EtOAc/hexane (1/6, v/v) to give 4-nitro-N-phenylaniline or 4-fluoro-N-phenylaniline.

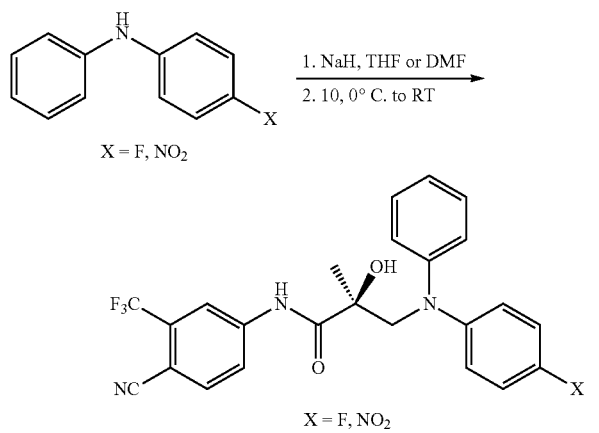

NaH of 60% dispersion in mineral oil (228 mg, 5.7 mmol) was added in 20 mL of anhydrous THF solvent into a 100 mL dried two necked round bottom flask equipped with a dropping funnel and NH(Ph)(Ar) [Ar=4-fluorophenyl; 4-nitrophenyl] (2.84 mmol) was added to the solution under argon atmosphere in ice-water bath, and the resulting solution was stirred for 30 min at the ice-water bath. Into the flask, epoxide 10 (2.84 mmol in THF) was added through dropping funnel under argon atmosphere at the ice-water bath and stirred overnight at room temperature. After adding 1 mL of H$_2$O, the reaction mixture was condensed under reduced pressure, and then dispersed into 50 mL of EtOAc, washed with 50 mL (×2) water, brine, dried over anhydrous MgSO$_4$, and evaporated to dryness. The mixture was purified with flash column chromatography as an eluent EtOAc/hexane, and then the condensed compounds were then recrystallized in EtOAc/hexane to give a target product 49 or 50.

(S)—N-(4-Cyano-3-(trifluoromethyl)phenyl)-3-((4-fluorophenyl)(phenyl)amino)-2-hydroxy-2-methylpropanamide (49): Yield; 67%; MS (ESI) m/z 456.1 [M−H]$^-$; $^1$H NMR (400 MHz, CDCl$_3$) δ 8.85 (bs, 1H, NH), 7.87 (m, 1H), 7.81-7.73 (m, 2H), 7.65 (dd, J=8.4, 1.8 Hz, 1H), 7.20 (m, 2H), 7.05-7.00 (m, 2H), 6.94-6.89 (m, 5H), 4.54 (d, J=15.2 Hz, 1H), 3.84 (d, J=15.2 Hz, 1H), 3.61 (s, 1H), 1.53 (s, 3H).

Example 41

Novel AR Antagonists

The target of this research is:
(a) To synthesize and optimize orally bioavailable SARDs, and deduce structure-activity relationship (SAR).
(b) Characterize SARDs in vitro in AR ligand binding, transactivation, and AR degradation and proliferation assays in PCa cells that are dependent on AR-FL and AR-SV for growth.
(c) Determine the pharmacokinetic (PK) properties, develop appropriate formulation, and characterize SARDs in vivo in LNCaP and 22RV-1 androgen-dependent and CRPC PCa xenografts, respectively.

The preliminary results are generated with two lead molecules, compounds 17 and 14, selected from a library.

Several molecules were synthesized and characterized with the intention to develop next generation AR antagonists. Interestingly, several of these AR antagonists exhibited degradation activity at concentrations comparable to their binding and antagonistic activity. These results provided an impetus to explore the degradation activity of these molecules.

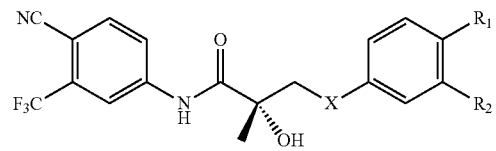

TABLE 20

SARDs of this invention, binding and AR antagonistic activities

| | X | R$_1$ | R$_2$ | K$_i$ (nM) |
|---|---|---|---|---|
| DHT | n/a | n/a | n/a | 6.62 |
| MDV-3100 | n/a | n/a | n/a | 1075.3 |
| bicalutamide | SO$_2$ | F | H | 545.5 |
| Cmpd 17 | N(CH$_3$) | CN | phenyl | 148.7 |
| Cmpd 14 | NH | CN | phenyl | 198.5 |

TABLE 20-continued

SARDs of this invention, binding and AR antagonistic activities

| | binding | Transcriptional Activation (Antagonist Mode) | | | |
|---|---|---|---|---|---|
| | | Wildtype | | W741L | |
| Compound | $K_i$ (nM) | $IC_{50}$ (nM) | % inhibition at 1 μM | $IC_{50}$ (nM) | % inhibition at 1 μM |
| DHT | 5.85 | | | | |
| bicalutamide | 545.5 | 420 | 91 | — | — |
| MDV-3100 | 1075.3 | 489 | 93 | 939 | 53 |
| ARN-509 | | 297 | | 1939.4 | |
| ASC-J9 | | 1008 | | 3487.6 | |
| 14 | 198.5 | 77 | 92 | >1000 | 48 |
| 17 | 270.7 | 95 | 98 | 101.7 | 87 |

TABLE 21

| | | Transcriptional Activation | | | DMPK (mouse liver microsomes) |
|---|---|---|---|---|---|
| Compound | Binding $K_i$ (nM) | Wt. $IC_{50}$ (nM) | W741L $IC_{50}$ (nM) | T877A $IC_{50}$ (nM) | $T_{1/2}$ (min) $CL_{int}$ (ml/min/kg) |
| DHT | 1 | | | | |
| Bicalutamide | 545.5 | 420 | — | 557 | |
| Enzalutamide | 1075.3 | 489 | 939 | 331.94 | |
| ARN-509 | | 297.0 | 1939.4 | 390.52 | |
| ASC-J9 | | 1008 | 3487.6 | | |
| 14 | 198.5 | 77 | >1000 | 48 | See Example 45 |
| 17 | 28.4 | 95 | 101.7 | 153.51 | See Example 45 |
| 49 | 275.41 | 172.22 | | | 5.069 min 136.8 ml/min/mg[#] |

[#]see MLM method below:

Metabolism Studies with Mouse Liver Microsomes (MLM)

Objective: To determine the relative stability of SARDs to metabolism by liver microsomal enzyme using MLM.

Method: Determination of metabolic stability (in vitro $CL_{int}$) of test compounds with regard to Phase I and Phase I+II metabolic pathways.

Metabolic stability to Phase I pathways: The assay was done in a final volume of 0.5 ml in duplicates (n=2). Test compound (1 μM) was pre-incubated for 10 minutes at 37° C. in 100 mM Tris-HCl, pH 7.5 containing 0.5 mg/ml liver microsomal protein. After pre-incubation, reaction was started by addition of 1 mM NADPH (pre-incubated at 37° C.). Incubations were carried out in triplicate and at various time-points (0, 5, 10, 15, 30 and 60 minutes), 100 μl aliquots were removed and quenched with 100 μl of acetonitrile containing internal standard. Samples were vortex mixed and centrifuged at 4000 rpm for 10 minutes. The supernatants were transferred to 96 well plates and submitted for LC-MS/MS analysis. As control, sample incubations done in absence of NADPH were also included. From % PCR (% Parent Compound Remaining), rate of compound disappearance is determined (slope) and in vitro $CL_{int}$ (μl/min/mg protein) was calculated.

Metabolic stability in Phase I & Phase II pathways: In this assay, test compound was incubated with liver microsomes and disappearance of drug was determined using discovery grade LC-MS/MS. To stimulate Phase II metabolic pathway (glucuronidation), UDPGA and alamethicin (a pore-forming peptide to increase microsomal activity) were included in the assay.

LC-MS/NIS analysis: The analysis of the compounds under investigation was performed using LC-MS/MS system consisting of Agilent 1100 HPLC with an MDS/Sciex 4000 Q-Trap™ mass spectrometer. The separation was achieved using a C18 analytical column (Alltima™, 2.1× 100 mm, 3 μm) protected by a C18 guard cartridge system (SecurityGuard™ ULTRA Cartridges UHPLC for 4.6 mm ID columns, Phenomenex). Mobile phase was consisting of channel A (95% acetonitrile+5% water+0.1% formic acid) and channel C (95% water+5% acetonitrile+0.1% formic acid) and was delivered at a flow rate of 0.4 mL/min. The volume ratio of acetonitrile and water was optimized for each of the analytes. Multiple reaction monitoring (MRM) scans were made with curtain gas, collision gas, nebulizer gas, and auxiliary gas optimized for each compound, and source temperature at 550° C. Molecular ions were formed using an ion spray voltage (IS) of −4200 V (negative mode). Declustering potential (DP), entrance potential (EP), collision energy (CE), product ion mass, and cell exit potential (CXP) were optimized for each compound.

As shown in Table 20, the first-generation SARDs were generated with amino linkers. Their binding and AR antagonistic activities were compared to standard molecules such as bicalutamide, enzalutamide (MDV3100), ARN-509, and ASC-J9.

As shown in Table 20 and Table 21, the SARDs of the invention bound to AR with higher affinity than the reference standards. Interestingly, two molecules in the list, compounds 14 and 17 robustly bound to AR by displacing the radiolabeled mibolerone from LBD in an AR-LBD binding assay. They bound at a much higher affinity than the reference standards. Consistent with potent binding, the two molecules effectively antagonized the R1881 stimulated wild type AR transcriptional activity by potencies at least five-fold greater than MDV-3100 and bicalutamide (77 nM and 95 nM for 14 and 17, respectively, compared to 420 nM and 489 nM for bicalutamide and MDV-3100, respectively) (Table 20 and Table 21).

Bicalutamide is a known agonist of AR containing W741L mutation, whereas MDV-3100 retains antagonist activity though its potency is somewhat reduced (939 nM). While 14 demonstrated reduced effectiveness in the W741L mutant (>1 μM), 17 retained the ability to antagonize agonist activated W741L AR (101.7 nM). The W741L mutation was selected due to the structural similarity of SARDs to bicalutamide (aryl propanamide). The antagonist activity of 17 was selective for the AR and did not cross-react with progesterone receptor (PR), mineralocorticoid receptor (MR) or glucocorticoid receptors (GR) (data not shown).

TABLE 22

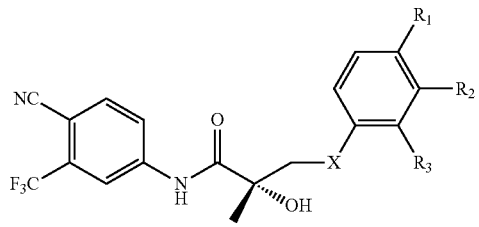

| Compound | X | R₁ | R₂ | R₃ | RBA | WT Agonist EC$_{50}$ (nM) | E$_{max}$ (nM) | WT Antagonist IC$_{50}$ (nM) | % inhibition at 1 μM |
|---|---|---|---|---|---|---|---|---|---|
| S-22 | O | CN | H | H | 5.8 ± 1.8 | 1.4 | 140 ± 15.1 | NA | NA |
| Bicalutamide | SO$_2$ | F | H | H | 0.62 ± 0.06 | NA | NA | 22.4 ± 6.7 | 90.9 ± 0.83 |
| 12 | NH | CN | H | H | 0.16 ± 0.01 | 626 | 156 ± 213.4 | 119 | 89.9 ± 0.4 |
| 13 | NH | CN | —(CH)$_4$— | | 1.5 ± 0.05 | >1000 | 48.3 ± 7.4 | 193 | 63.0 ± 1.2 |
| 14 | NH | CN | Ph | H | 0.56 ± 0.03 | NA | NA | 20.5 | 88.2 ± 1.1 |
| 15 | NH | CN | H | Ph | 0.65 ± 0.06 | >1000 | 22.6 ± 6.4 | 81.3 | 92.2 ± 1.0 |
| 18 | NCH$_2$(C$_6$H$_6$) | CN | H | H | ND | NA | NA | 118.6 | 92.7 ± 1.8 |
| 17 | NCH$_3$ | CH | Ph | H | | NA | NA | 6 | 94.8 |

TABLE 23

| Compound | X | R₁ | R₂ | R₃ | W741L Agonist EC$_{50}$ (nM) | E$_{max}$ (nM) | W741L Antagonist IC$_{50}$ (nM) | % inhibition at 1 μM | T877A Agonist EC$_{50}$ (nM) | E$_{max}$ (nM) | T877A Antagonist IC$_{50}$ (nM) | % inhibition at 1 μM |
|---|---|---|---|---|---|---|---|---|---|---|---|---|
| Bicalutamide | SO$_2$ | F | H | H | 1.1 ± 3.4 | 273 ± 37.9 | NA | NA | NA | NA | 229 | 73.7 ± 7.4 |
| 12 | NH | CN | H | H | >1000 | 24.8 ± 7.2 | >1000 | 20.9 ± 9.1 | 47 | 122 ± 26.4 | NA | NA |
| 13 | NH | CN | —(CH)$_4$— | | 2.4 | 93.1 ± 10.8 | NA | NA | 3.4 | 56.1 ± 9.9 | 784.4 | 60.5 ± 7.8 |
| 14 | NH | CN | Ph | H | >1000 | 26.8 ± 1.6 | >1000 | 48.3 ± 4.7 | >1000 | 20.6 ± 3.6 | 79.1 | 85.6 ± 2.0 |
| 15 | NH | CN | H | Ph | 1.9 | 76.7 ± 15.1 | 305 | 63.8 ± 13.8 | >1000 | 18.6 ±0.1 | 34.3 | 94.0 ± 0.7 |
| 18 | NCH$_2$(C$_6$H$_6$) | CN | H | H | >1000 | 26.1 ± 1.7 | >1000 | 47.6 ± 10.0 | >1000 | 17.4 ± 5.4 | 470 | 74.8 ± 8.7 |
| 17 | NCH$_3$ | CH | Ph | H | NA | NA | 101.7 | 87 | NA | NA | 33.1 | 95.6 |

In general, compounds 12-21 acted as antagonists of wildtype androgen receptor (wt-AR) with some residual agonism for 12, 13, and 15. Notably, 17 was the most potent antagonist with an IC$_{50}$ value of 6 nM (Table 22). Mutant AR's W741L and T877A confer resistance to bicalutamide and hydroxyflutamide, respectively. Most of the compounds 12-21 displayed mixed agonist/antagonist activity in in vitro transcriptional activation assays. However, 17 retains potent pure antagonism in wildtype and both mutations (Table 22 and Table 23), demonstrating potential to overcome resistance to bicalutamide and/or hydroxyflutamide, independent of its SARD activity (described below). 14 also demonstrated antagonist activity in wildtype and mutant AR's, but was not a potent antagonist in all the mutants tested.

Figure 101A:
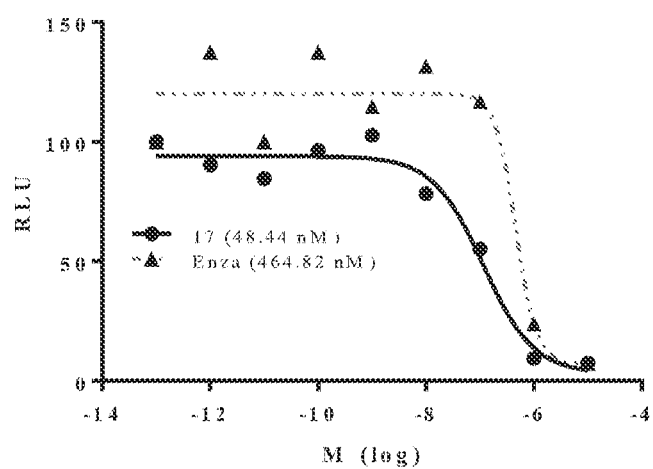
FIGS. 101A-101D depict inhibitory AR function of 17. 17 potently inhibited AR transactivation. AR transactivation was performed by transfecting human AR cDNA, GRE-LUC, and CMV-*renilla* LUC into HEK-293 cells. Cells were treated 24 hrs after transfection with a dose response of 17 and 0.1 nM R1881 and luciferase assay was performed 48 hrs after transfection. Values provided are $IC_{50}$.
Figure 101B:
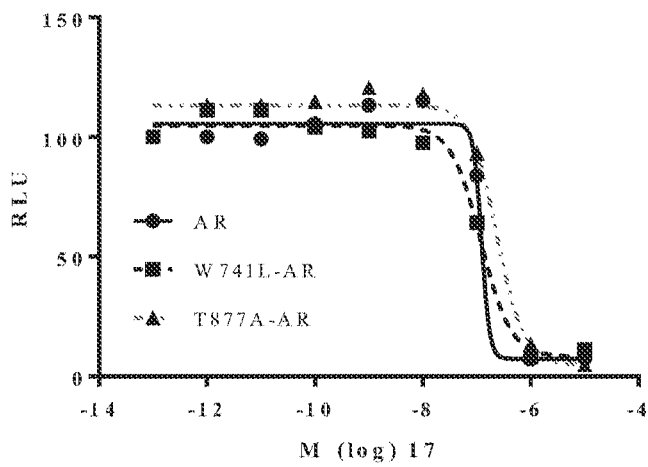
Figure 101C:
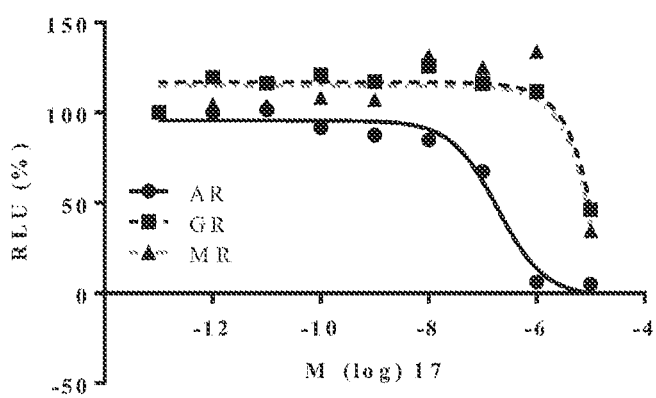
Figure 101D:
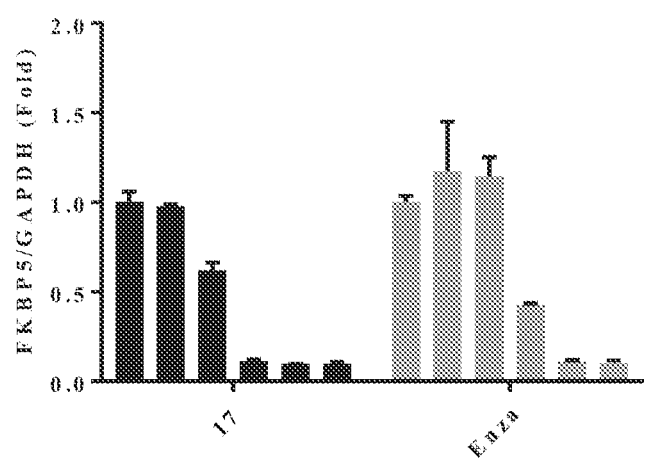

AR transactivation assay was performed with wildtype, W741L, and T877A AR constructs. W741 mutation to leucine or cysteine (L/C) confers resistance to bicalutamide (Hara, T., Miyazaki, J., Araki, H., Yamaoka, M., Kanzaki, N., Kusaka, M., and Miyamoto, M. (2003). Novel mutations of androgen receptor: a possible mechanism of bicalutamide withdrawal syndrome. Cancer research 63, 149-153), while T877 mutation results in resistance to hydroxyflutamide (Tan, J., Sharief, Y., Hamil, K. G., Gregory, C. W., Zang, D. Y., Sar, M., Gumerlock, P. H., deVere White, R. W., Pretlow, T. G., Harris, S. E., et al. (1997). Dehydroepiandrosterone activates mutant androgen receptors expressed in the androgen-dependent human prostate cancer xenograft CWR22 and LNCaP cells. Mol Endocrinol 11, 450-459). 17 potently inhibited the R1881-induced wildtype AR transactivation with much higher potency than enzalutamide (FIG. 101A). While 17 effectively antagonized both wildtype and mutant ARs comparably, (FIG. 101B). 17 inhibited glucocorticoid receptor (GR) and mineralocorticoid receptor (MR) transactivation only at ~10 μM (FIG. 101C).

Example 42

AR Degradation Activity

Figure 89:
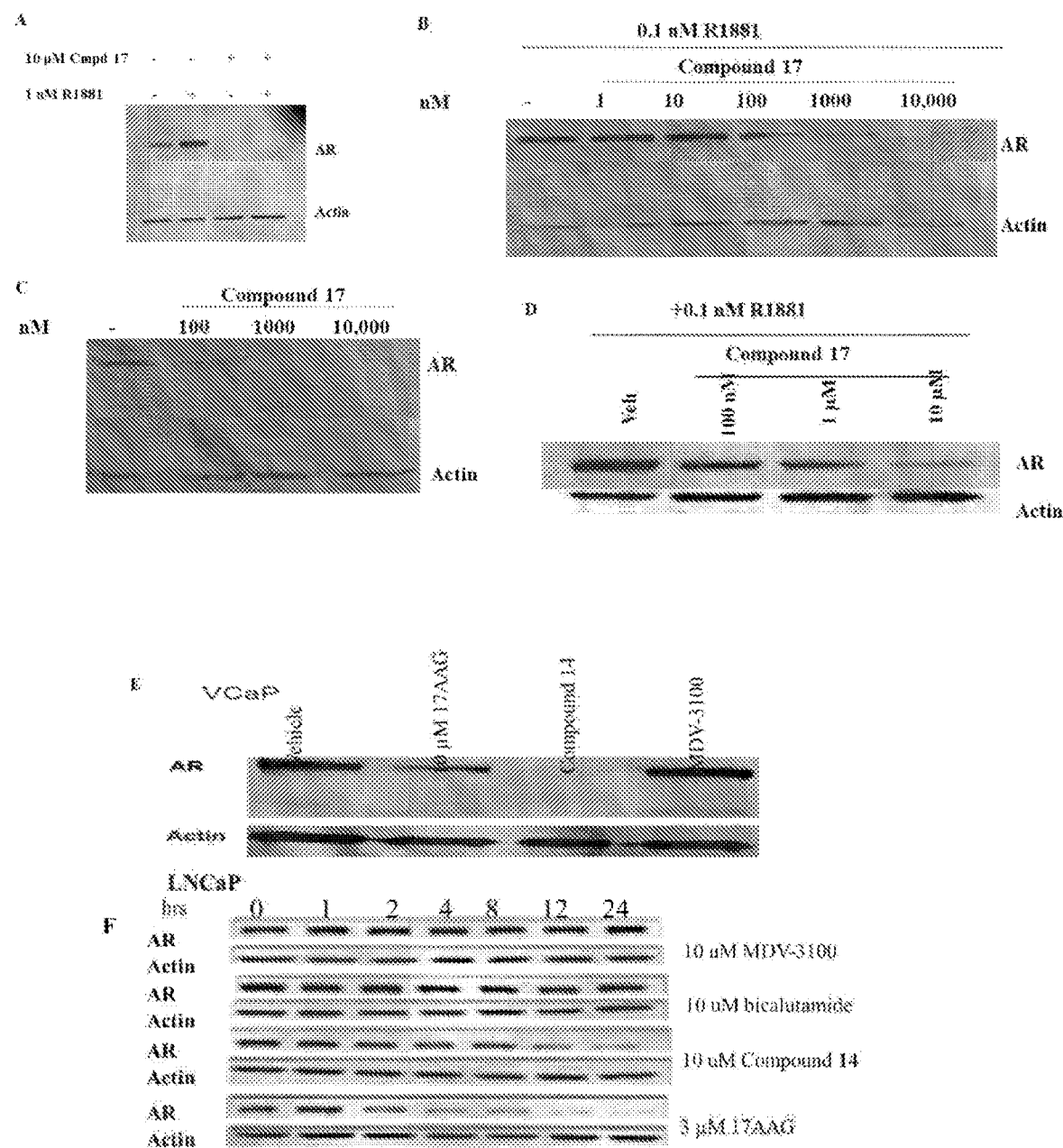
FIG. 89 depicts the effect of novel AR antagonists on AR protein levels (i.e. the SARD effect). (A) Serum-starved LNCaP cells treated with R1881 and SARD compound (17). (B) Dose response of 17 in the presence of 0.1 nM R1881 in LNCaP cells. (C) LNCaP cells were plated in full serum and treated with compound 17 (dose response). Cells were harvested, protein extracted, and Western blotted for AR and actin. (D) Effect of 17 on wild-type AR transfected into HeLa cells. (E) Effect of 14 on AR expression in VCaP. (F) Time-course response of AR to SARD (14) in LNCaP cells. 17-AAG—17-allylamino-17-demethoxygeldanamycin, a Hsp90 inhibitor. MDV-3100, an AR antagonist (antiandrogen) also known as enzalutamide. AR—androgen receptor; R1881—an AR agonist.
Figure 90A:
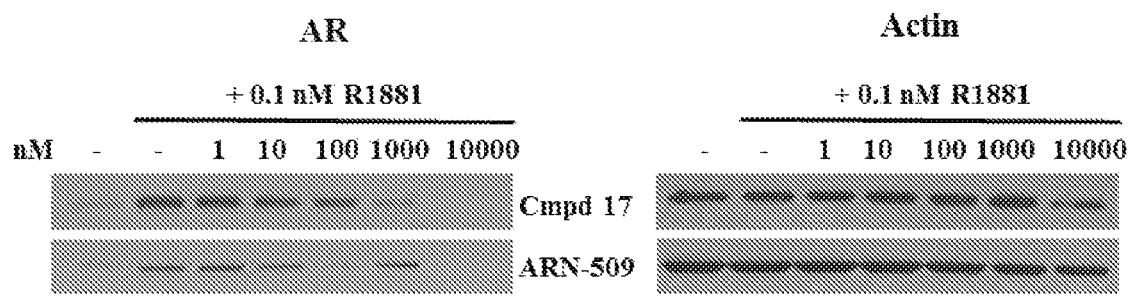
FIG. 90A and FIG. 90B depict the AR degradation by SARD compound 17 in LNCaP cells.
Figure 92:
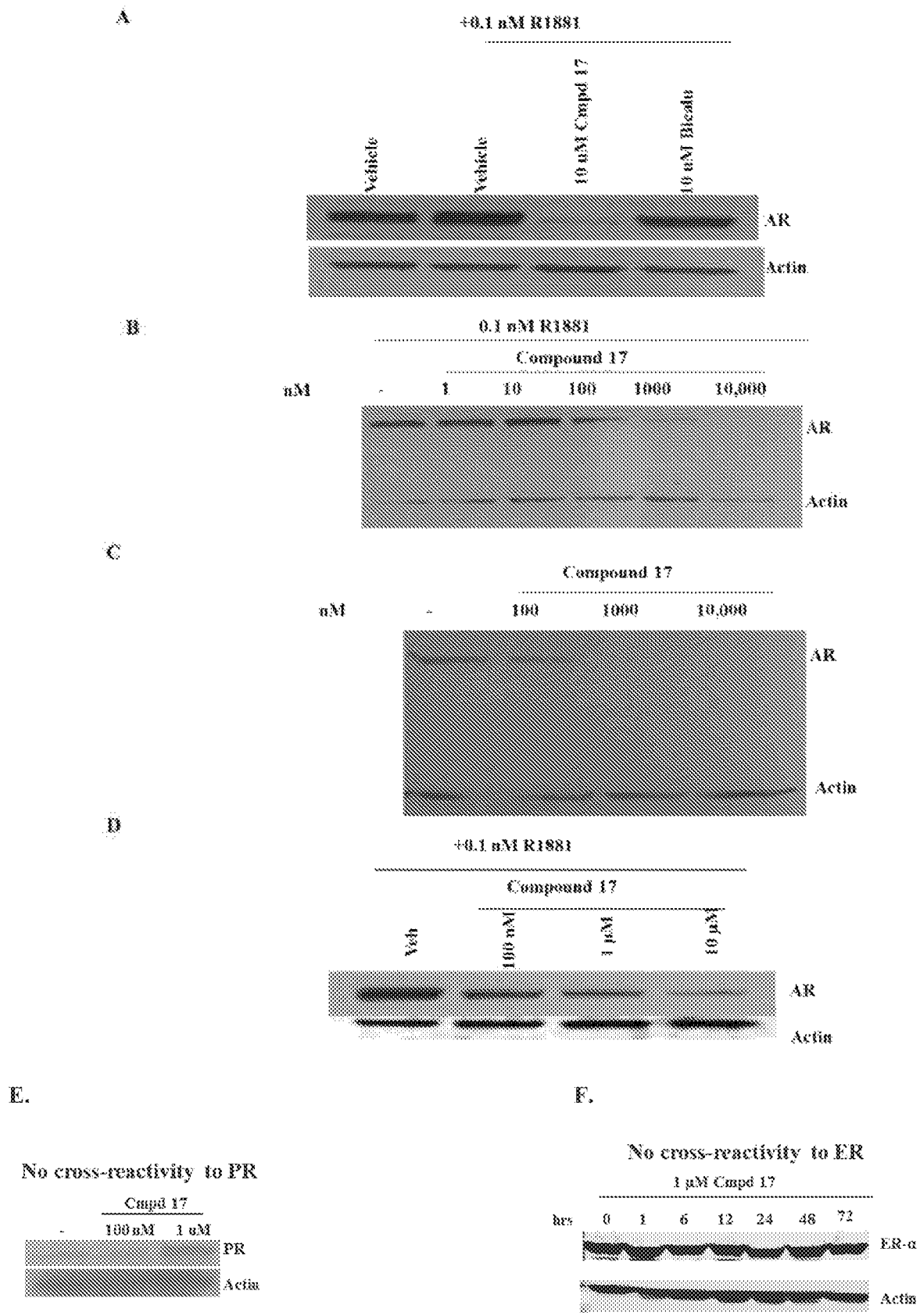
FIG. 92(A-F) depicts degradation of AR by SARDs under varying conditions (A-D), without degradation of other receptors (E-F). (A) and (B) LNCaP cells were serum starved and treated with compound 17 (10 uM in panel A and a dose response in panel B) in the presence or absence of R1881. Bicalutamide was used as a negative control. Cells were harvested, protein extracted, and Western blotted for AR and actin. (C) LNCaP cells were plated in full serum and treated with compound 17 (dose response). Cells were harvested, protein extracted, and Western blotted for AR and actin. (D) HeLa cells were infected with adenovirus containing AR and were treated with compound 17 in the presence or absence of R1881. Cells were harvested, protein extracted, and Western blotted for AR and actin. (E) and (F) SARDs do not degrade other nuclear receptors. T47D (left panel) and MCF-7 (right panel) cells were plated in full serum and treated with compound 17 (dose response). Cells were harvested, protein extracted, and Western blotted for PR (progesterone receptor) or ER-α (estrogen receptor-alpha) and actin.

Compounds 17 and 14 were tested for their effect on AR protein expression. While 17 drastically reduced the levels of AR protein following 24 hours of treatment in LNCaP cells (serum starved and treated with 0.1 nM R1881) as measured by Western blot (FIG. 89A), bicalutamide or enzalutamide (MDV-3100) had no effect at an equal concentration (FIGS. 89E (VCaP) and 89F (LNCaP)). Under identical conditions, the lowest concentration of 17 that was capable of reducing AR protein levels in LNCaP cells was 100 nM (FIG. 89B). Similar AR protein down-regulation was observed under hormone replete conditions in LNCaP (FIG. 89C), in HeLa cells infected with an adenovirus expressing high levels of wt-AR (FIG. 89D; suggesting activity in CPRC where AR gene has been activated) as well as in wt-AR expressing VCaP cells 14 (FIG. 89E). 14 also similarly reduced the AR levels in LNCaP cells, requiring as little as 2 hours of treatment and matching closely the time course of 17-AAG (FIG. 89F). Neither bicalutamide nor MDV-3100 (enzalutamide) had any effect on AR protein levels even after 24 hours of treatment. Likewise, 17 demonstrated more potent and complete AR degradation in LNCaP cells than the reported SARDs ASC-J9 (not shown) and ARN-509 (FIG. 90A), and AR antagonist enzalutamide (not shown) (FIG. 90A). 17 and 14 treatment in LNCaP cells resulted in small reductions in AR mRNA levels, but only at 10 μM and not at 1 μM. Unlike the HSP-90 inhibitor 17-AAG, 17 treatment did not affect PR (FIG. 92E), GR (not shown) and ERα (FIG. 92F) protein levels (FIG. 92).

Figure 97:
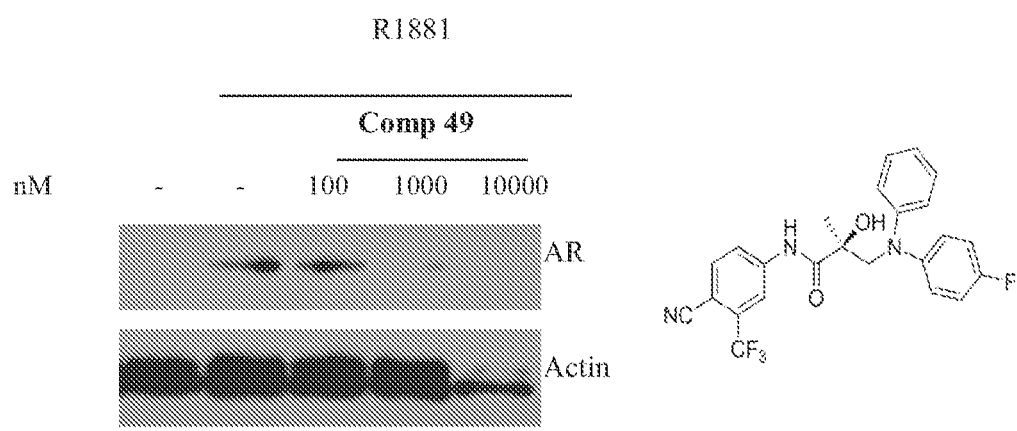
FIG. 97 depicts that 49 in the presence of R1881 degrades AR in LNCaP cells. LNCaP cells were plated in 6 well plates at 1 million cells/well. The cells were maintained in serum free conditions for 3 days. The cells were treated as indicated in the figure, harvested, protein extracted, and Western blotted for AR. 49 (and other SARDs disclosed herein) demonstrated selective degradation of AR (i.e., SARD activity) in the nM range, i.e., at concentrations comparable to their antagonist $IC_{50}$ values. LNCaP cells are known to express the AR mutant T877A, demonstrating the ability of SARDs of this invention to degrade antiandrogen resistance conferring mutant androgen receptors.

FIG. 97 depicts that 49 in the presence of R1881 degrades AR in LNCaP cells. LNCaP cells were plated in 6 well plates at 1 million cells/well. The cells were maintained in serum free conditions for 3 days. The cells were treated as indicated in the figure, harvested, protein extracted, and Western blotted for AR. 49 and other SARDs of this invention demonstrated selective degradation of AR (i.e., SARD activity) in the nM range, i.e., at concentrations comparable to their antagonist $IC_{50}$ values. LNCaP cells are known to express the AR mutant T877A, demonstrating the ability to degrade antiandrogen resistance conferring mutant androgen receptors.

Figure 98:
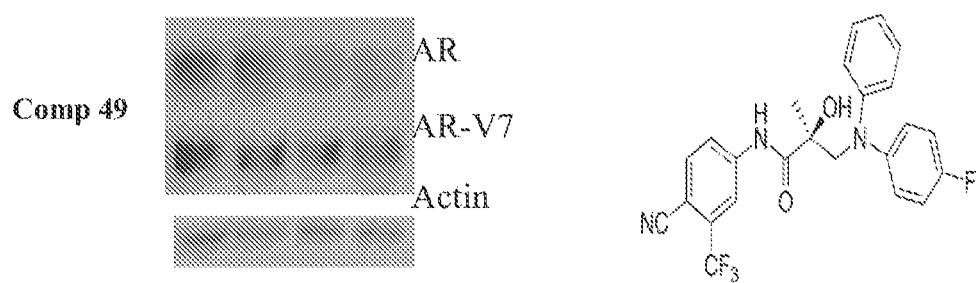
FIG. 98 depicts that 49 degrades AR in RV22-1 cells. 22RV-1 cells were plated in a 6 well plate at 1-1.5 million cells/well in growth medium (RPMI+10% FBS). Next day, medium was changed and treated with vehicle or a dose response of 49. After overnight treatment (12-16 hrs), cells were washed in ice cold PBS and harvested by scrapping in 1 mL PBS. Cells were pelleted, protein extracted, quantified using BCA assay, and equal quantity of protein was fractionated on a SDS-PAGE. The proteins were transferred to nylon membrane and Western blotted with AR antibody (N20 from SCBT) and actin antibody. 49 (and other SARDs disclosed herein) was capable of degrading full-length androgen receptor (AR-FL) and truncated AR (AR-SV) in 22RV-1 cells, suggesting that SARDs of this invention may be able to overcome AR-V7 dependent prostate cancers.

FIG. 98 depicts that 49 degrades AR in RV22-1 cells. 22RV-1 cells were plated in 6 well plate at 1-1.5 million cells/well in growth medium (RPMI+10% FBS). Next day, medium was changed and treated with vehicle or a dose response of 49. After overnight treatment (12-16 hrs), cells were washed in ice cold PBS and harvested by scrapping in 1 mL PBS. Cells were pelleted, protein extracted, quantified using BCA assay, and equal quantity of protein was fractionated on a SDS-PAGE. The proteins were transferred to nylon membrane and Western blotted with AR antibody (N20 from SCBT) and actin antibody. 49 was capable of degrading full-length androgen receptor (AR-FL) and truncated AR (AR-SV) in 22RV-1 cells, suggesting that SARDs will be able to overcome AR-V7 dependent prostate cancers.

LNCaP cells are known to express the AR mutant T877A, demonstrating the ability of the SARDs of this invention to degrade antiandrogen resistance conferring mutant androgen receptors (i.e., advanced prostate cancers and CRPC). 14, 17 and 49 were capable of degrading full-length androgen receptor (AR-FL) and truncated AR (AR-V7) in 22RV-1 cells, suggesting that SARDs will be able to overcome AR-V7 dependent prostate cancers (i.e., CRPC).

These SARD activity demonstrations suggest the compounds of this invention are able to degrade a variety of AR variants, and hence should provide the ability to inhibit the AR-axis activity whether it is androgen-dependent or androgen-independent. Degradation of the AR removes the possibility of promiscuous activation of mutant ARs, activation by intracellular processes such as signal transduction and kinase activation, etc.; and suggests that the SARDs should also degrade the polyQ polymorphism in hyperandrogenic dermatologic disorders (shortened polyQ) or Kennedy's disease (extended polyQ), providing a rationale for treating either type of diseases by destroying the AR in the affected tissues (skin and neuromuscular system, respectively).

Example 43

Effect on PCa Gene Expression and Cell Growth

The ability of these novel antagonists to inhibit AR-regulated gene expression was measured in LNCaP, a PCa cell line known to harbor a T877A mutation (Table 24).

TABLE 24

Effect of antagonists on AR-target gene expression and growth in LNCaP cells.

| | Gene Expression + 0.1 nM R1881 ($IC_{50}$ nM) | | |
|---|---|---|---|
| Gene | Bicalutamide | MDV-3100 | Cmpd 17 |
| PSA | 783.7 | 1,019.3 | 198.5 |
| NKx3.1 | 755.8 | 1,142.8 | 176.0 |
| FKBP51 | 270.9 | 76.8 | 51.8 |
| TMPRSS2 | 831.4 | 823.7 | 128.1 |
| Growth | | 872 | 469 |

Consistent with binding and transcriptional activation assays, 17 significantly inhibited agonist-stimulated expression of PSA, NKx3.1, FKBP51, and TMPRSS2 genes ($IC_{50}$ values of 198.5, 176.0, 51.8, and 128.1 nM, respectively).

TABLE 25

| Cell | Cmpd 17 7 Day Growth ($IC_{50}$, μM) | | | | 17-AAG 7 Day Growth ($IC_{50}$, μM) | | | | Enzalutamide 7 Day Growth ($IC_{50}$, μM) | | | |
|---|---|---|---|---|---|---|---|---|---|---|---|---|
| Line/R1881 | Veh | 0.01 | 0.1 | 10 | Veh | 0.01 | 0.1 | 10 | Veh | 0.01 | 0.1 | 10 |
| VCaP | 2.99 | 2.92 | 2.48 | 3.82 | 0.657 | 0.414 | 0.778 | 1.06 | 0.742 | 1.53 | >3 | >10 |
| LNCaP | 0.78 | 0.49 | 0.47 | — | 0.260 | 0.292 | 0.157 | — | 0.281 | 0.656 | 3.02 | — |
| PC-3 | >10 | >10 | >10 | >10 | 0.307 | 0.221 | 0.257 | 0.542 | >10 | >10 | >10 | >10 |

Figure 90B:
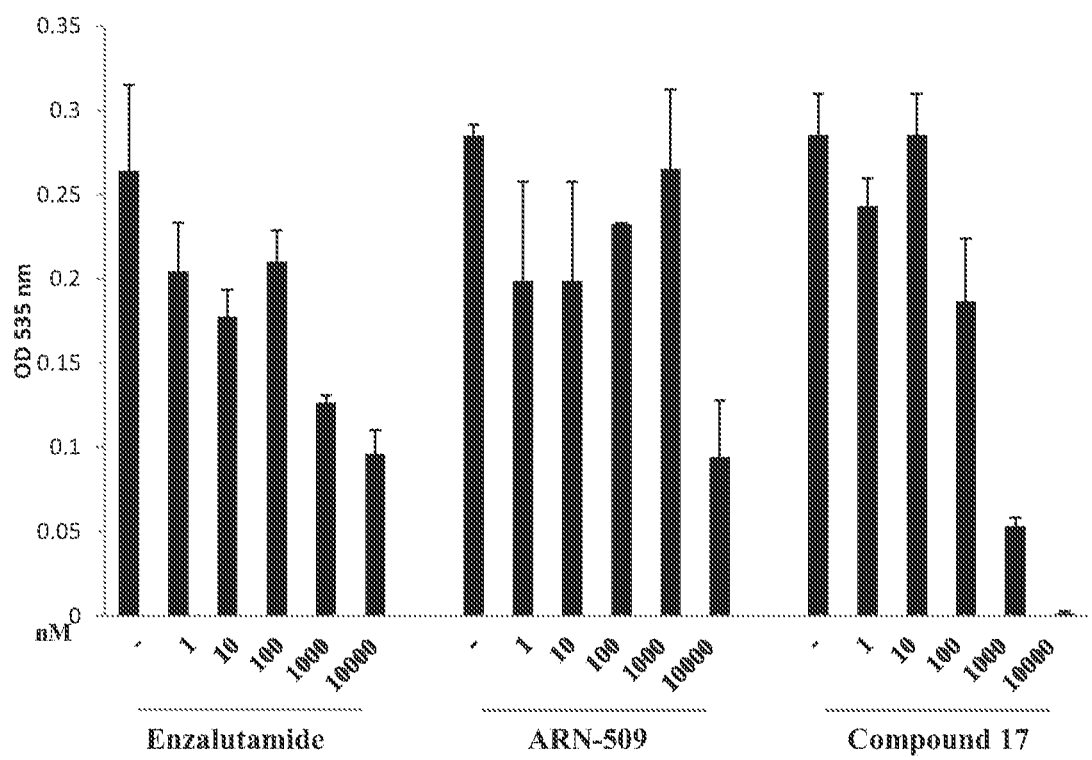

Similar activity was demonstrated in LNCaP cells with 14 (not shown). Consistent with inhibition of gene expression, 17 inhibited growth of AR-positive, androgen-dependent PCa cells (LNCaP and VCaP) in both the hormone-deplete and hormone-replete states (Table 25). Unlike the HSP-90 inhibitor 17-AAG, 17 had no effects in the AR negative PC cell line, PC-3 (Table 25). See also FIG. 90B for a bar graph that depicts that 17 inhibited growth of LNCaP cells with comparable efficacy and potency as enzalutamide and ARN-509.

Example 44

SARDs Degrade AR-SV in 22RV-1 Cells

Figure 91:
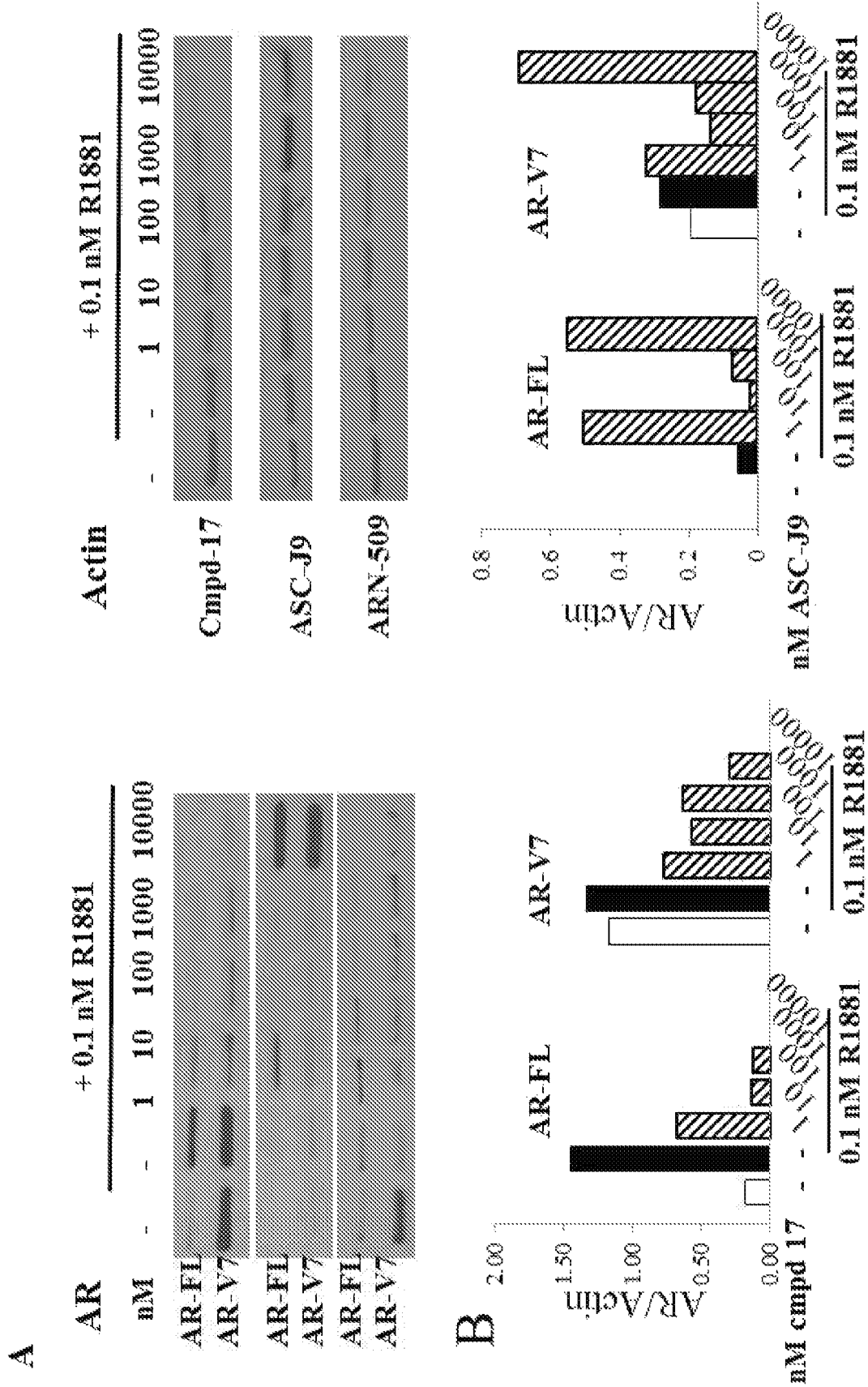
FIG. 91(A-C) depicts the effect of SARDs on AR-FL and AR-SV protein levels. (A) and (B) SARD 17 degrades AR full length and splice variant in 22RV-1 cells. 22RV-1 cells were plated in serum free medium and treated with the indicated concentrations of compound 17, ARN-509 or ASC-J9 in the presence or absence of R1881. Cells were harvested, protein extracted and Western blotted for AR and actin. Blots were quantified using Image-J (panel B). (C) Same experiment repeated with compound 14. AR-FL—androgen receptor-full length; AR-V7—androgen receptor splice variant 7 (lacks ligand binding domain); ARN-509 and ASC-J9 are other AR antagonists reported to degrade AR.
Figure 91:
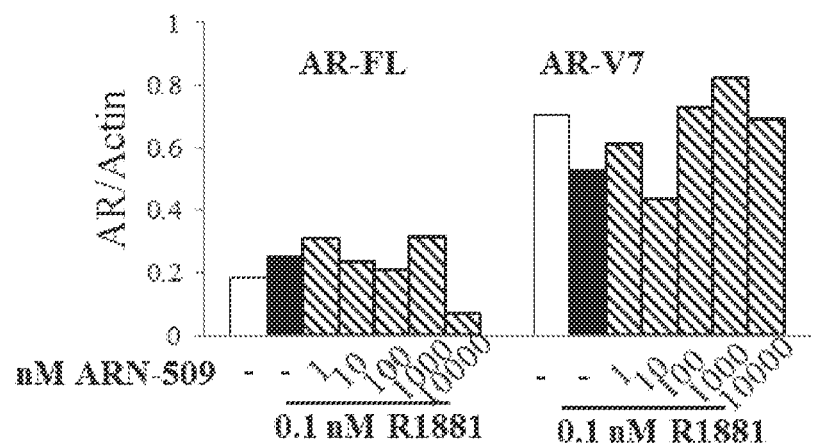
Figure 91:
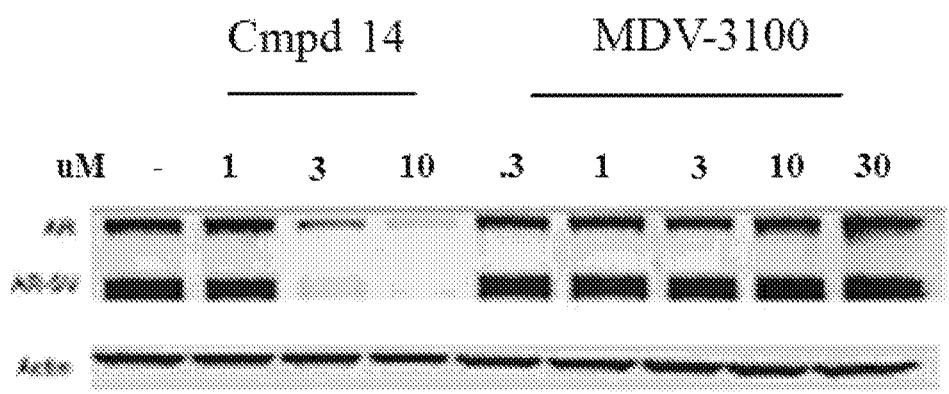

The effect of SARD treatment on the AR levels was also measured in androgen-refractory 22RV-1 PCa cells. These cells express both AR-FL and the low molecular weight splice variant species of the AR (AR-SV) and depend on the AR-SV for growth. 17 (FIGS. 91A and 91B) and 14 (FIG. 91C) completely down regulated both AR-FL and AR-SV species (FIG. 91) in contrast to the limited effects of 17-AAG only on AR-FL (not shown). MDV-3100 treatment did not affect levels of either AR species (FIG. 91C), and ASC-J9 and ARN-509 did not reduce AR-V7 levels. Growth assay performed in 22RV-1 cells treated with SARDs in the presence or absence of 0.1 nM R1881 demonstrated that SARDs, but not MDV-3100, bicalutamide, enzalutamide, or ARN-509, markedly suppressed the growth of 22RV-1 cells (Table 26). The AR-SV variant (e.g., AR-V7; Cancer Res. 2013 Jan. 15; 73(2): 483-489) lacks the LBD and so SARD activity against AR-SV must operate through an alternative binding and degradation domain (BDD).

TABLE 26

Effect of SARDs on AR transactivation and growth in 22RV-1 cells.

Figure 103:
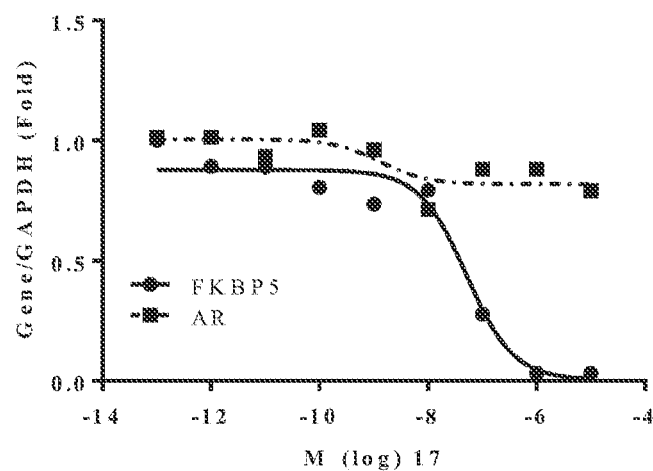
FIG. 103 shows that 17 does not inhibit AR mRNA. LNCaP cells were maintained in charcoal stripped serum containing medium for two days and treated for 24 hours with vehicle or 17 (0.001-10,000 nM) in the presence of 0.1 nM R1881. RNA was isolated and expression of AR or FKBP5 was quantified and normalized to GAPDH by real-time PCR.

| Compound | Transactivation $IC_{50}$ (nM) | Growth $IC_{50}$ (nM) |
|---|---|---|
| Bicalutamide | 3133.52 | >10,000 |
| Enzalutamide | 101.87 | >10,000 |
| Cmpd 17 | 56.36 | 2642 |
| ARN-509 | 64.54 | >10,000 |
| ASC-J9 | 1026.91 | >10,000 | in the presence of R1881 under conditions similar to that used for Western blot. 17 failed to alter the AR mRNA expression, while it robustly inhibited the expression of the AR-target gene, FKBP5 (FIG. 103).

Example 45

Liver Metabolism and Pharmacokinetic (PK) Properties of SARDs

To evaluate the metabolic stability parameters such as half-life and clearance, human, rat, and dog liver microsomes were incubated with 17 and 14 for 60 min. Both molecules had very short half-lives between 5 and 10 min and high clearance (Table 27).

TABLE 27

DMPK studies with SARDs of the invention.

| SARD | Rat PK CL_obs (mL/min/kg) | Rat PK IV AUC all (min*µg/mL) | PO_F % | Rat LM – P1 Half Life (min) | Rat LM – P1 CL (µL/min/mg) | Rat LM – P1 Half Life (min) | Rat LM – P1 CL (µL/min/mg) |
|---|---|---|---|---|---|---|---|
| 17 | 30.4 | 323.4 | 0.7 | 4.6 | 150.9 | 2.5 | 281.4 |
| 14 | 9.4 | 1067.9 | 0.4 | 7.0 | 99.5 | 2.6 | 266.0 |

FIG. 92 depicts degradation of AR by SARDs under varying conditions (A-D), without degradation of other receptors (E-F). (A.) and (B.) LNCaP cells were serum starved and treated with compound 17 (10 uM in panel A and a dose response in panel B) in the presence or absence of R1881. Bicalutamide was used as a negative control. Cells were harvested, protein extracted, and Western blotted for AR and actin. (C.) LNCaP cells were plated in full serum and treated with compound 17 (dose response). Cells were harvested, protein extracted, and Western blotted for AR and actin. (D.) HeLa cells were infected with adenovirus containing AR and were treated with compound 17 in the presence or absence of R1881. Cells were harvested, protein extracted, and Western blotted for AR and actin. (E.) and (F.) SARDs do not degrade other nuclear receptors. T47D (left panel) and MCF-7 (right panel) cells were plated in full serum and treated with compound 17 (dose response). Cells were harvested, protein extracted, and Western blotted for PR (progesterone receptor) or ER-α (estrogen receptor-alpha) and actin.

Figure 102A:
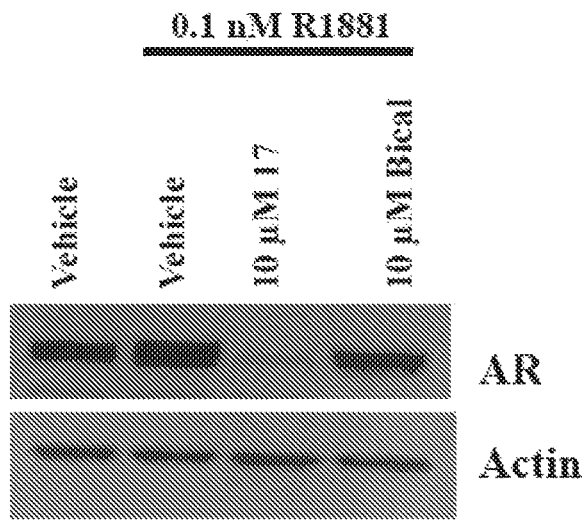
FIGS. 102A-102B depict degradation of AR using 17 under multiple conditions. LNCaP cells were maintained in charcoal stripped serum containing medium for 2 days and treated as indicated in the figure for 24 hrs. Western blot for the AR with N20 antibody and actin was performed (FIG. 102A). LNCaP cells were maintained in charcoal stripped serum containing medium for 2 days and treated with vehicle or 17 in the presence of 0.1 nM R1881. Western blot for the AR with AR C19 antibody and actin was performed (FIG. 102B).
Figure 102B:
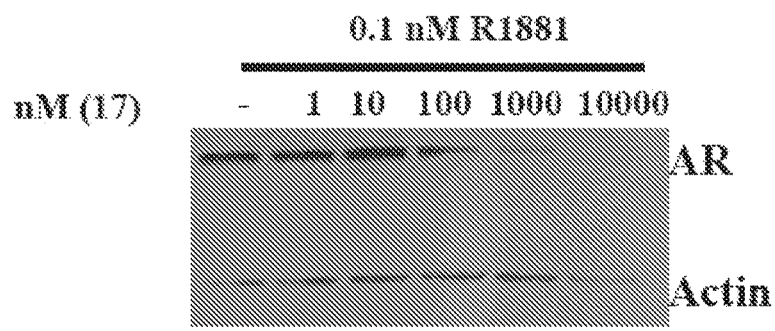

The reproducibility of the effect of the SARD compounds of this invention on the AR expression was evaluated under various experimental conditions (LNCaP cells in full serum, wildtype AR in HeLa cells, and others). 17 degradation effect was captured when the Western blot was performed for the AR with N20 antibody and actin (FIG. 102A). Western blot was performed with a different antibody targeting the C-terminus (AR C19; FIG. 102B), indicating that the degradation is not due to the masking of the antibody binding site by the SARDs.

To exclude that the degradation effects are not due to transcriptional inhibition, LNCaP cells were treated with 17

PK studies in rats to follow up the metabolism data also demonstrated that the SARDs have very low bioavailability and area under the curve (AUC) (Table 27), indicating that their PK properties need to be improved by structural modifications and optimal formulation in order to obtain systemic exposures necessary for oral administration and efficacy for, e.g., prostate cancer. However, the high potency and efficacy of the selective androgen receptor degradation coupled with the low half-lives and high metabolic clearances suggest that topical administration of the compounds of this invention could exert strong (high potency and high efficacy) antiandrogenic effects when applied topically directly to affected areas. E.g., topical administration to localized skin lesions such as in acne, seborrheic dermatitis, hirsutism, etc. could degrade the AR in these tissues, thereby countering the hyperandrogenism, without risk of significant systemic exposures that could result in untoward anti-anabolic or sexual side effects.

Example 46

Effects on Androgen-Dependent Tissues in Intact Male Rats

Figure 93:
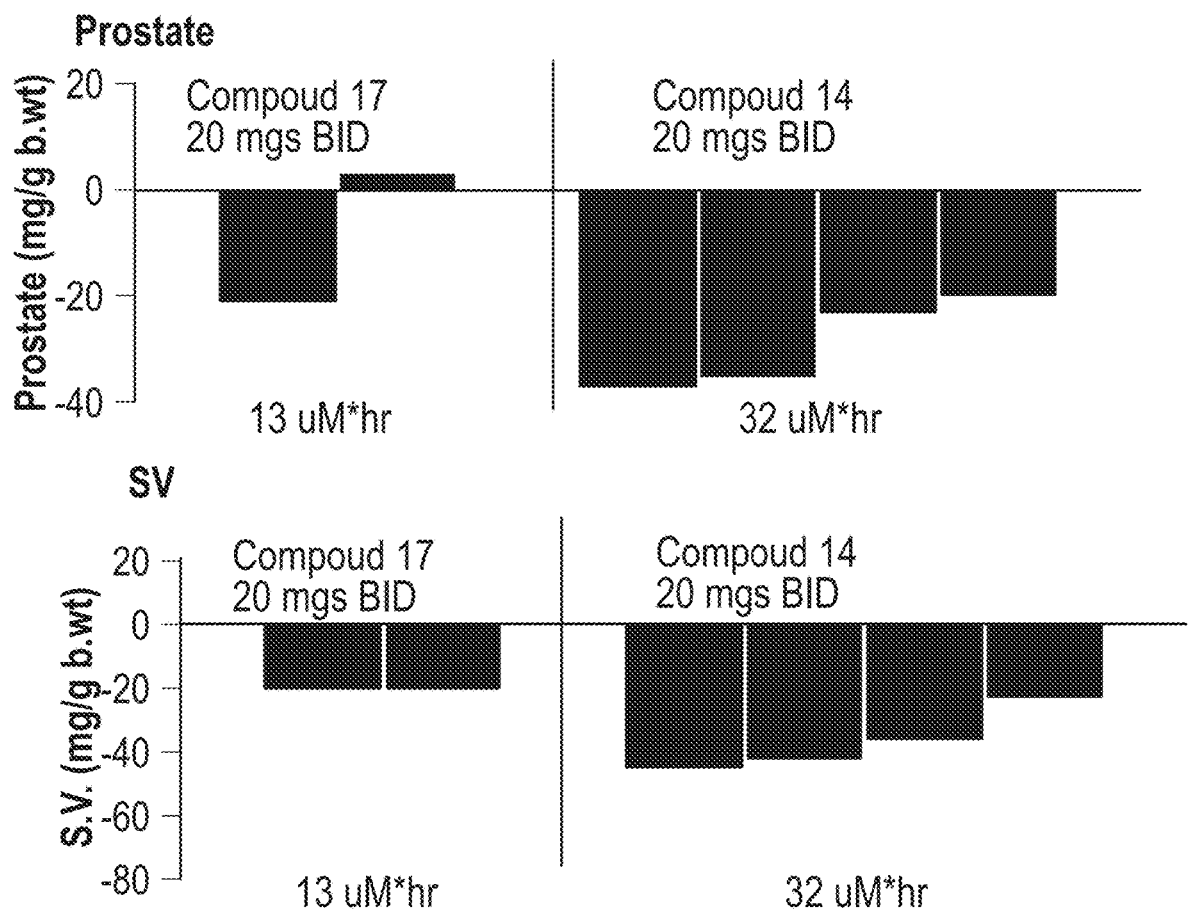
FIG. 93 depicts the effect of SARDs 17 and 14 on AR-target tissues (SV or S.V.—seminal vesicles and prostate) in the Hershberger assay. The numbers at the bottom of the graphs are the area under the curve (AUC) for drug concentration.

To measure in vivo antagonist activity, 17 and 14 were administered to intact male rats via intravenous (i.v.) bolus injection (FIG. 93). Due to high clearance, studies with oral administration of these molecules failed to significantly affect any androgen-dependent tissues such as prostate, seminal vesicles, or levator ani. Hence, the study was conducted with i.v. administration to derive evidence of in vivo activity. Following 3 days of therapy, reductions in prostate weight normalized to body weight were observed in 1 of 2 17-treated animals, and 3 of 4 14-treated animals as compared to vehicle-treated controls. Reductions of greater magnitude in seminal vesicle weight were observed in 4 of 4 animals treated with 14 with no changes in 17 animals. Both compounds tested varied greatly in the exposures following 23 mpk 14 and 23 mpk 17 doses resulting in 32 and 13 μM*hr exposures, respectively. These studies indicate the requirement for molecules with better bioavailability or formulation that will enhance the oral bioavailability and efficacy in achieving systemic antiandrogenic effects.

Example 47

SARDs do not Inhibit Transactivation of Other Receptors

Figure 94:
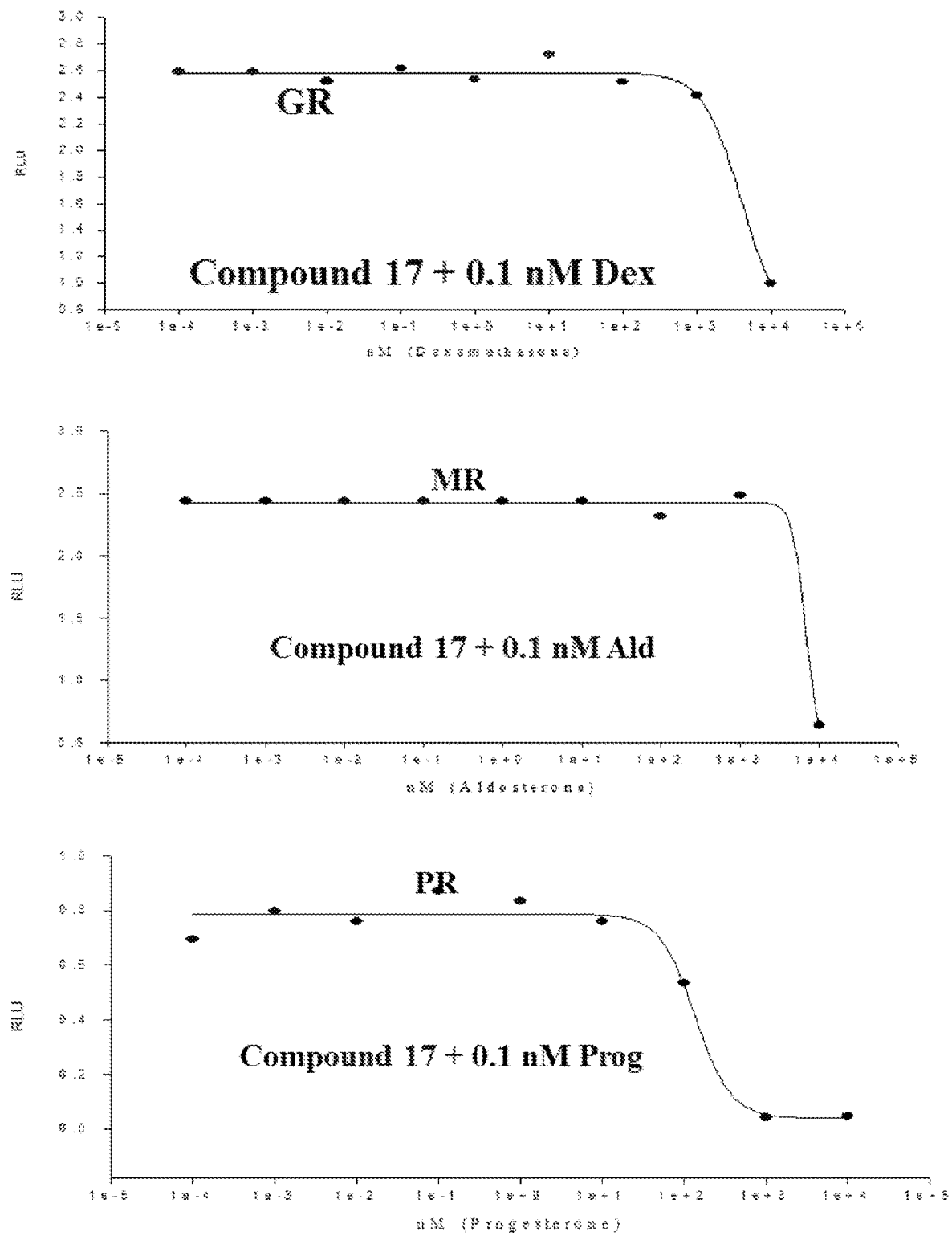
FIG. 94 depicts that SARDs do not inhibit transactivation of other receptors until 10 uM. HEK-293 cells were transfected with the indicated receptors and GRE-LUC and CMV-renilla luc. Cells were treated with 17 for 24 hrs after transfection and luciferase assay performed 48 hrs after transfection. GR—glucocorticoid receptor; Dex—dexamethasone; MR—mineralocorticoid receptor; Ald—aldosterone; PR—progesterone receptor; and Prog—progesterone.

HEK-293 cells were transfected with the indicated receptors and GRE-LUC and CMV-renilla luc. Cells were treated 24 hrs after transfection and luciferase assay performed 48 hrs after transfection. SARDs did not inhibit transactivation of other receptors until 10 uM (FIG. 94).

Example 48

Figure 95:
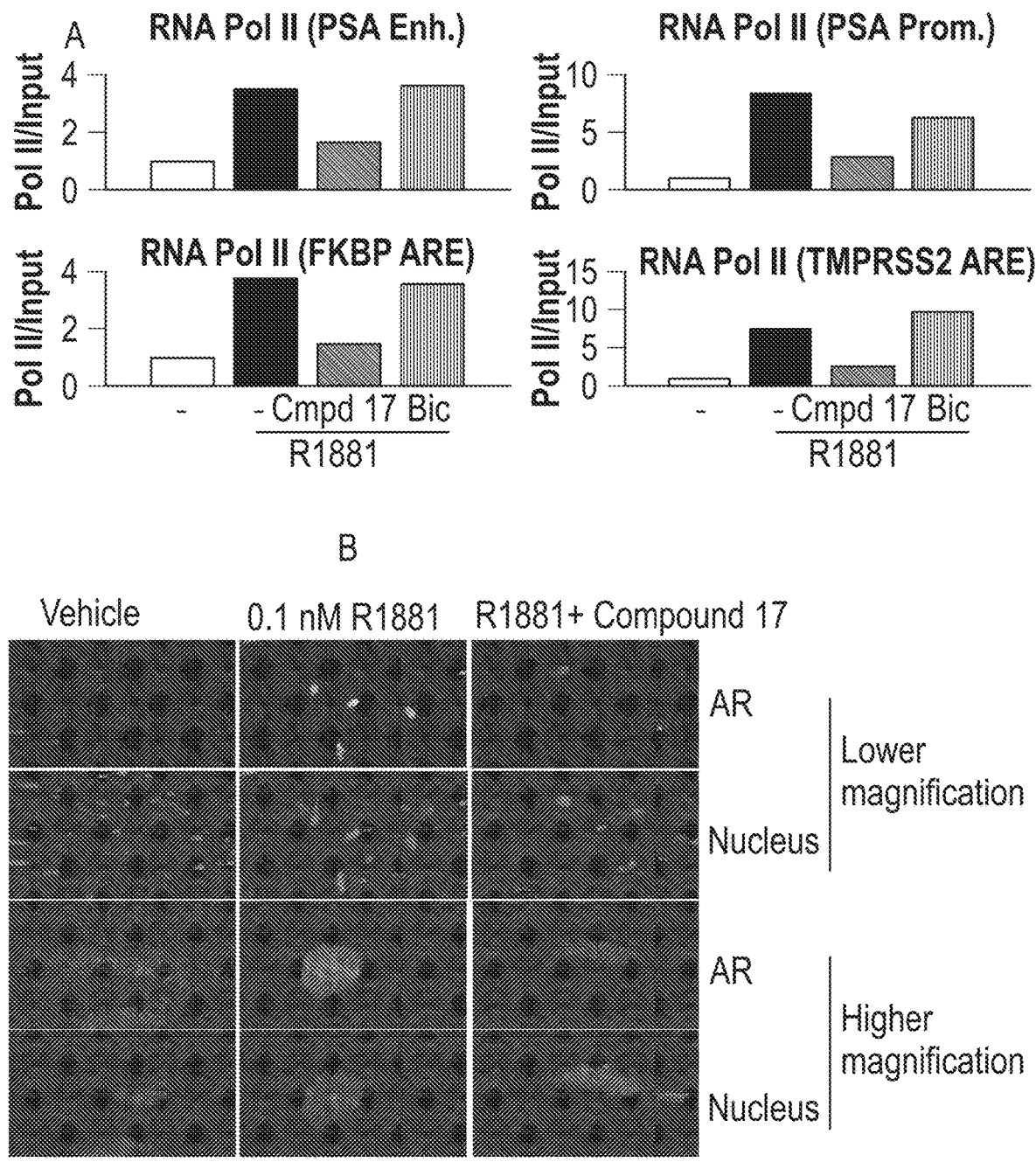
FIG. 95 (A-B) depicts that SARD treatment inhibited AR recruitment to the promoter of androgen responsive genes (PSA, FKBP, & TMPRSS2) and lowered AR levels in the nucleus in R1881 treated animals. (A) LNCaP cells were serum starved for 3 days and treated as indicated above with SARD (17) or bicalutamide at 10 uM in the presence or absence of 0.1 nM R1881. Proteins were cross-linked to DNA and chromatin immunoprecipitation studies were conducted with AR and RNA-Pol II antibodies. (B) SARDs degrade AR. LNCaP cells were serum starved for 3 days and treated as indicated above with SARD (17) at 10 uM in the presence or absence of 0.1 nM R1881. Cells were fixed and immunofluorescence for AR performed. Nucleus was stained with DAPI.

SARDs Inhibit Recruitment of AR to the Promoter and Enhancer Elements of Androgen Responsive Genes LNCaP cells were serum starved for 3 days and treated as indicated above with SARD (compound 17) or bicalutamide at 10 uM in the presence or absence of 0.1 nM R1881. Proteins were cross-linked to DNA and chromatin immunoprecipitation studies were conducted with AR and RNA-Pol II antibodies. 17 inhibited recruitment to the promoter or enhancer elements of androgen responsive genes such as PSA, FKBP, and TMPRSS2 (FIG. 95A). SARDs degrade AR. LNCaP cells were serum starved for 3 days and treated as indicated above with SARD (17) at 10 uM in the presence or absence of 0.1 nM R1881. Cells were fixed and immunofluorescence for AR performed. Nucleus was stained with DAPI. SARDs did not abrogate AR translocation to the nucleus but did decrease levels of AR in the nucleus upon treatment with an agonist R1881 (FIG. 95B).

Figure 104A:
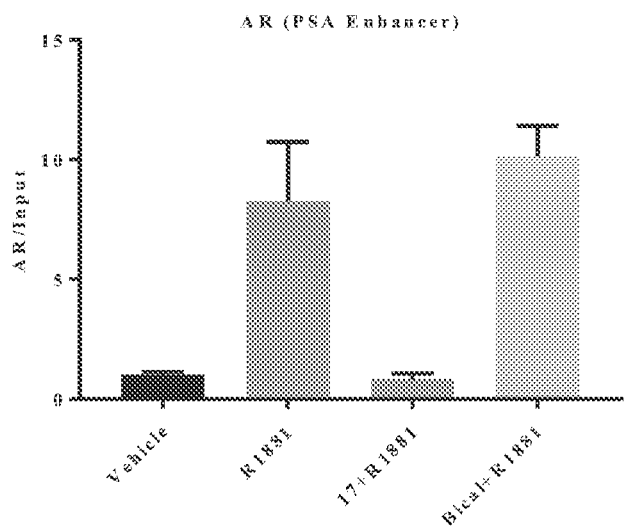
FIGS. 104A-104B depict inhibition of DNA binding of the AR and RNA Pol II using 17. LNCaP cells were serum starved for 2 days and were treated with 0.1 nM R1881 in the presence or absence of 10 µM 17 or bicalutamide (Bical) for 2 hrs. DNA-protein complex was cross-linked and AR (FIG. 104A) and RNA Pol II (FIG. 104B) were immunoprecipitated and their recruitment to PSA regulatory regions was measured by realtime PCR. N=3. Values are expressed as average ±S.E.
Figure 104B:
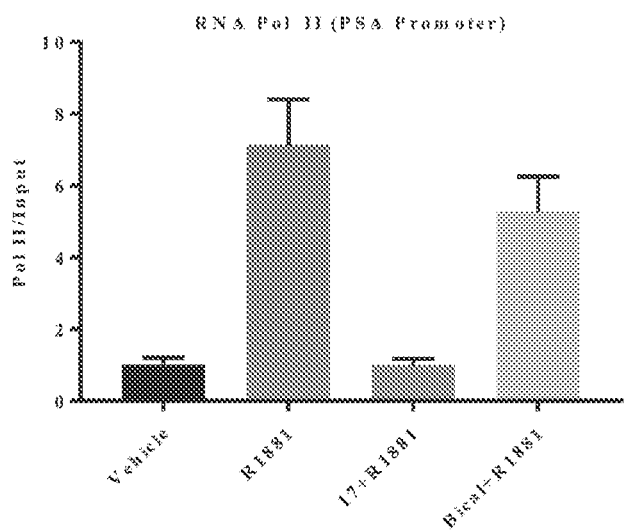
Figure 105:
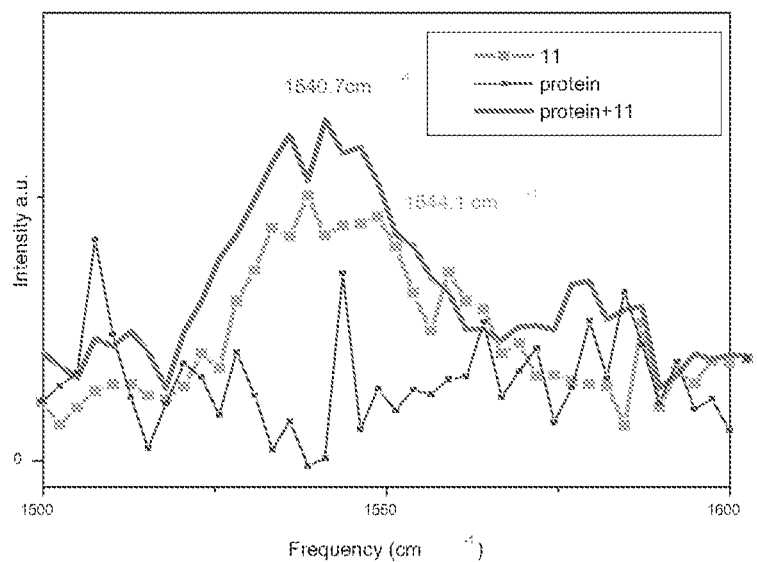
FIG. 105 provides tip-Enhanced Raman Spectroscopy (TERS) with compound 11.

Inhibition of AR recruitment to PSA enhancer and RNA Pol II recruitment to PSA promoter was also observed with 17 (FIGS. 104A, 104B).

Example 49

SARDs Inhibited LNCaP Cell Growth by Non-Competitive Binding to AR

Figure 96:
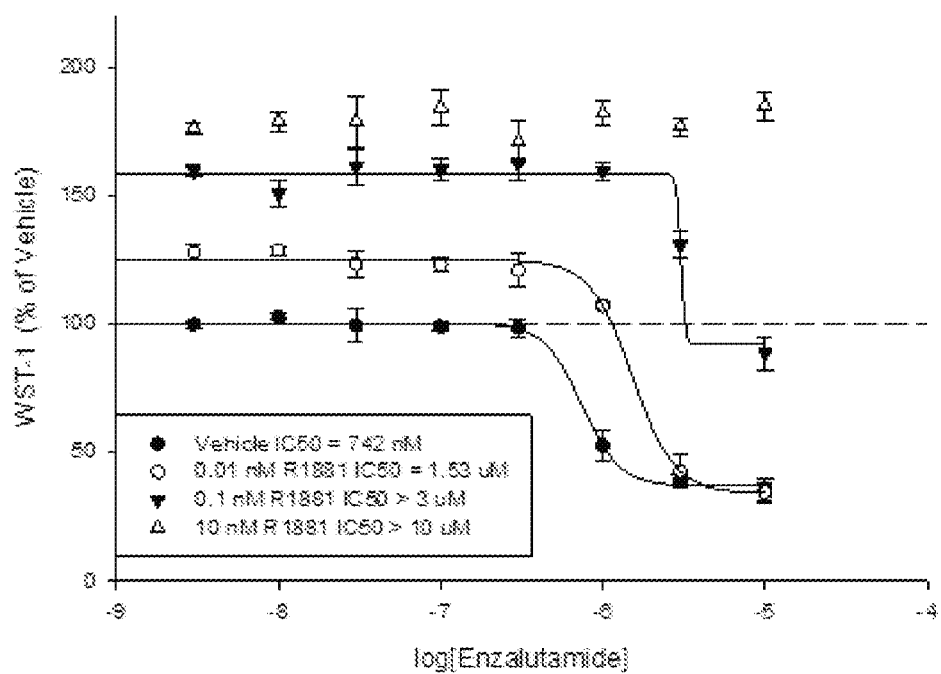
FIG. 96 depicts that SARDs inhibit LNCaP cell growth by non-competitive binding of AR. LNCaP cells were plated in serum free medium and were treated with increasing concentrations of enzalutamide or compound 17 in the presence of a dose range of R1881. Seven days after treatment, cells were fixed and growth measured by WST-1 assay.
Figure 96:
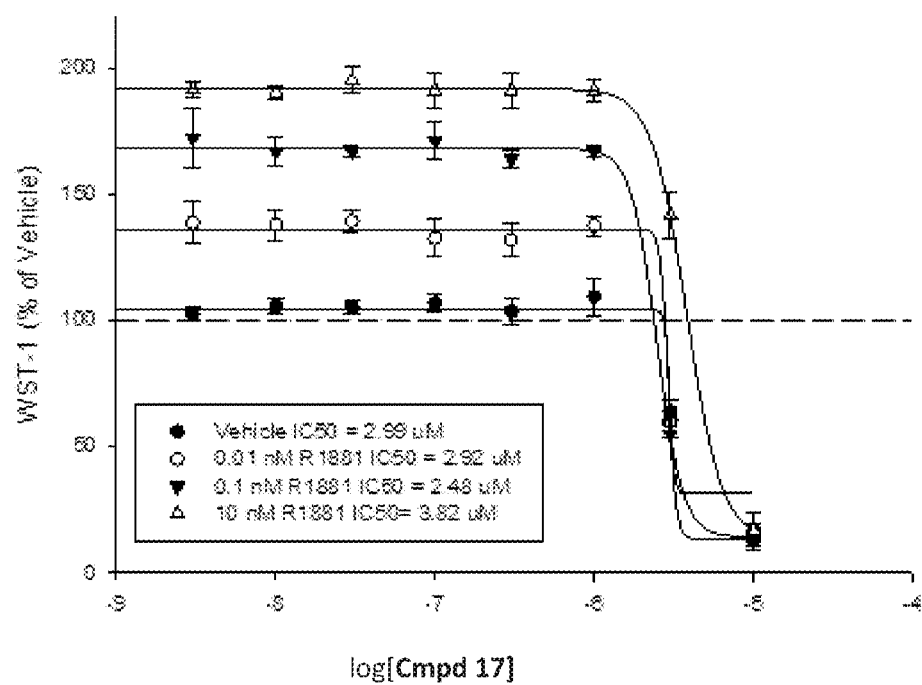

LNCaP cells were plated in serum free medium and were treated with increasing concentrations of enobosarm or 17 in the presence of a dose range of R1881. Seven days after treatment, cells were fixed and growth measured by WST-1 assay. SARDs inhibited LNCaP cell growth by an apparent non-competitive binding to AR (FIG. 96). As expected, enzalutamide $IC_{50}$ values for cell growth inhibition increased with increased amounts of R1881. However, the $IC_{50}$ values for cell growth inhibition for 17 did not increase with amounts of R1881, possibly indicating that R1881 and 17 were not competing for the same binding site on AR.

Example 50

SARDs Bind to the AR-AF1

There are two tryptophan residues and up to 12 tyrosine residues in the AF1 of the AR. This has allowed the study of the folding properties of this domain using intrinsic steady state fluorescence emission spectra. Excitation at 287 nm excites both tyrosine and tryptophan residues. The emission maximum (λmax) for the tryptophan is sensitive to the exposure to solvent. In the presence of the natural osmolyte TMAO there is a characteristic 'blue shift' consistent with the tryptophan residues being less solvent exposed and a loss of the shoulder (~307 nm) for tyrosine as there is increased energy transfer to tryptophan as the polypeptide folds. To test if the compounds, enobosarm (negative control), and 17 interact with AF-1 and/or alter the folding of this domain the steady state fluorescence was measured for each compound with AR-AF1 alone or the presence of TMAO (3 M) or urea (4 or 6 M). 1 μM of AR-AF1 and 5 μM of the individual compounds were used, and preincubated for at least 30 minutes prior to measuring the emission spectra. The emission spectra were all corrected for buffer alone or buffer with TMAO/urea/compounds as necessary.

Figure 99A:
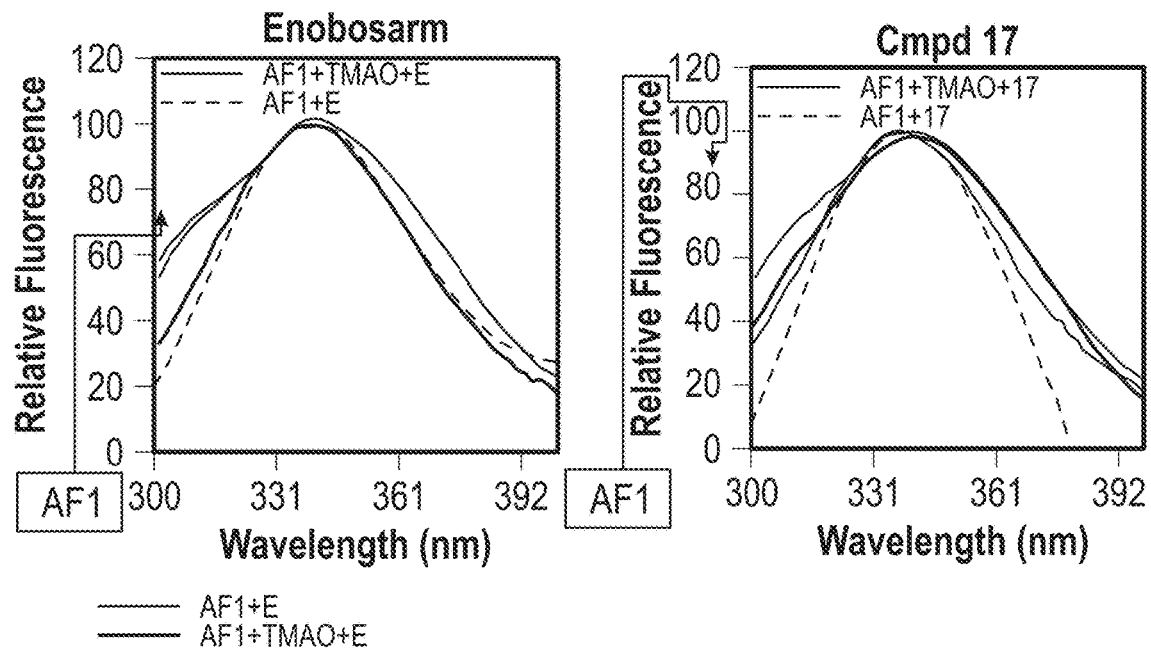
FIG. 99A-99B depicts that SARDs bind to the N-terminal activation function 1 of AR (AR-AF1) in addition to the C-terminal ligand binding domain (LBD) which contains the AR-AF2.
Figure 99B:
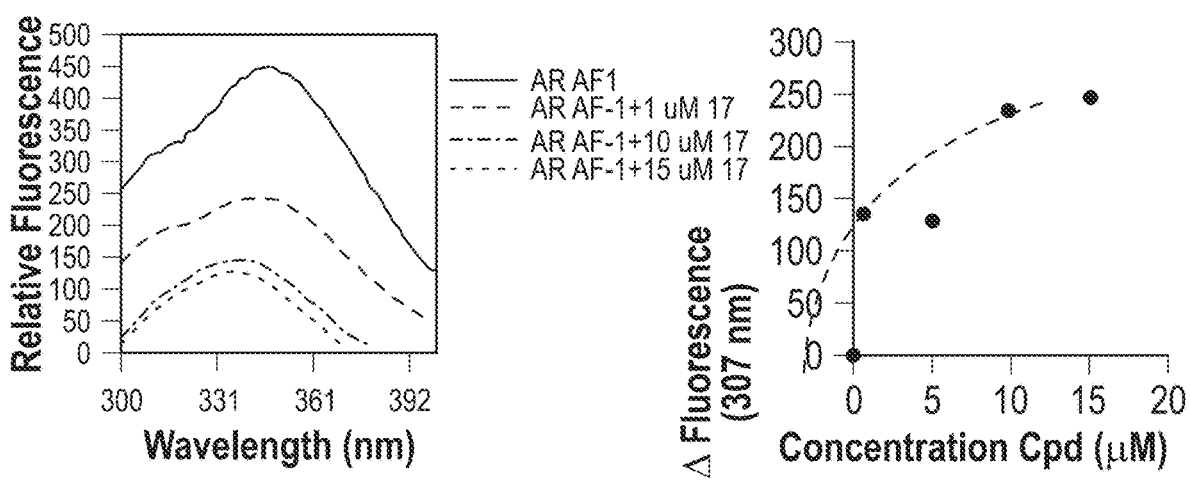

FIG. 99 depicts that SARDs bind to the AR-AF1. FIG. 99A: The emission spectra were all corrected for buffer alone or buffer with TMAO/urea/compounds as necessary. There was no dramatic effect of enobosarm (left panel) on the $\lambda_{max}$ for tryptophan, while 17 (right panel) reduces the wavelength (i.e., a 'blue shift'), indicating that 17 binds to the AF-1 and enobosarm does not bind to AF-1. FIG. 99B: Left Panel: Dose-dependent shift in the fluorescence intensity, i.e., fluorescent quenching, by 17 when incubated with AR AF-1. The fluorescence shoulder observed at 307 nm, which corresponds to tyrosine residues in the AF-1, is shifted by 17. The overall fluorescence is also markedly altered by 17.

Right Panel: Data shown in the left panel was plotted as difference in fluorescence between control and compound 17 treated samples (fluorescence in the absence of compound−fluorescence in the presence of compound). A dose dependent increase was observed in the presence of 17 indicating interaction between 17 and AF1.

Example 51

AF1 Binding-External Validation (VIB)

Figure 100:
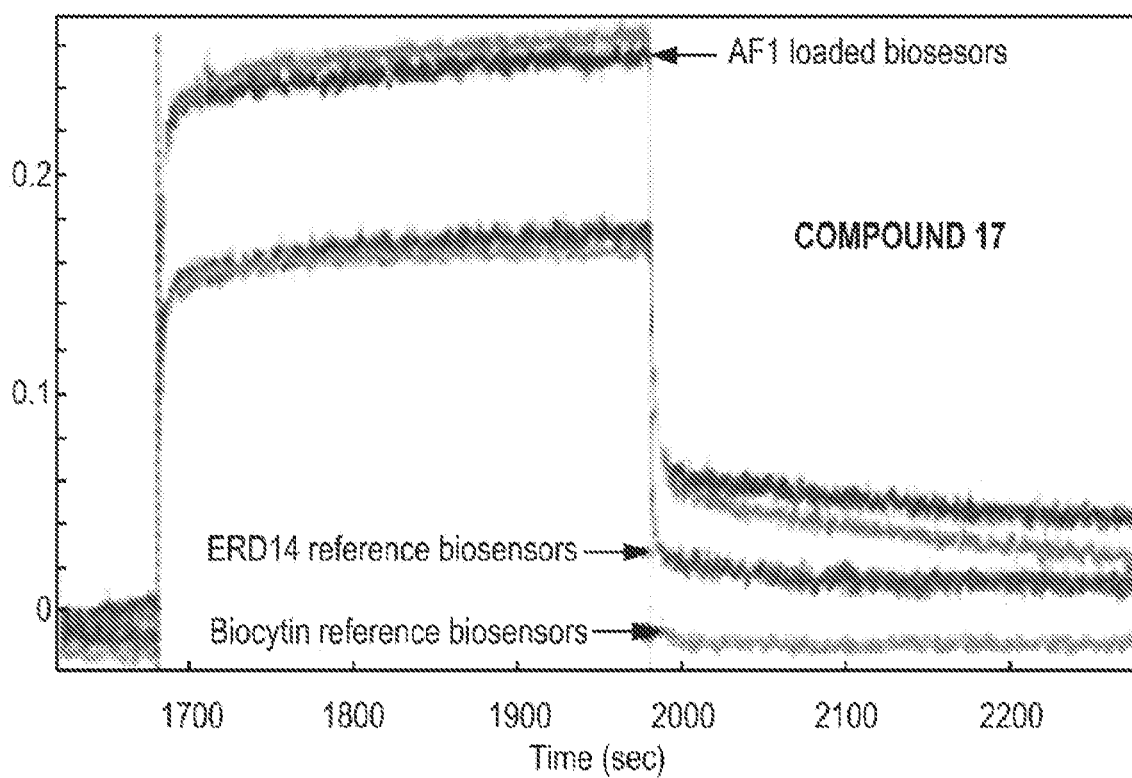
FIG. 100 depict biolayer-interferometry (BLI) raw data measurements of AF1 binding to compound 17 at the concentration of 50 nM. The first 60 seconds are baseline (does not start at 0), followed by 300 seconds of an association and dissociation phase (~1650-1950 on y-axis). AF1 loaded biosensors are the top two traces. Addition of 17 to AF-1 loaded sheets causes a stronger shift as compared to controls loaded with ERD14 and biocytin (bottom two traces) as reference sensors suggesting that 17 has a direct interaction with AF-1 at concentrations as low as 50 nM.

Target Molecule:
Compound 17 was delivered dissolved in DMSO at 10 μM.
Experimental Setup
Purified H6-AF1 was biotinylated with N-hydroxysuccinimide (NHS)-PEG4-biotin at an estimated protein-biotylation ratio of 1:1. Bio-layer interferometry (BLI) was used to screen for binding of small molecule to biotinylated protein using the Octet 96RED system (FortéBio®). Biotinylated H6-AF1 was immobilized on super streptavidin (SSA) biosensors at full saturation level in order to detect signals from binding of small molecule. Biosensors loaded with AF1 were used in parallel to screen for binding of 17.
Results
Raw data measurements from binding of Compound 17 to AF1 are shown in FIG. 100. The data shows the AF1 loaded biosensors gave a stronger signal than any of the reference sensors at 50 nM concentrations. At higher concentration measurements were not possible because of the solubility issue with the compound.

Example 52

SARDs for Early Treatment of Prostate Cancer

MDVR cells (enzalutamide resistant VCaP cells) were implanted (10 million/rat) subcutaneously in SRG rats. Once the tumors reached 1500-3000 mm3, the animals were castrated. The tumors were allowed to regress and regrow as CRPC. When the tumors showed growth in 3 consecutive readings, treatment (n=5-8/group) was initiated (Enza=30 mg/kg/day; compound 1002-60 mg/kg/day). Tumor volume was measured thrice weekly. Animals treated with 1002 had symptoms of gastric irritation. 1002-treated animals had loose stools and body weight loss. One set of animals was not castrated and treated as intact group (n=3/group).

Figure 109A:
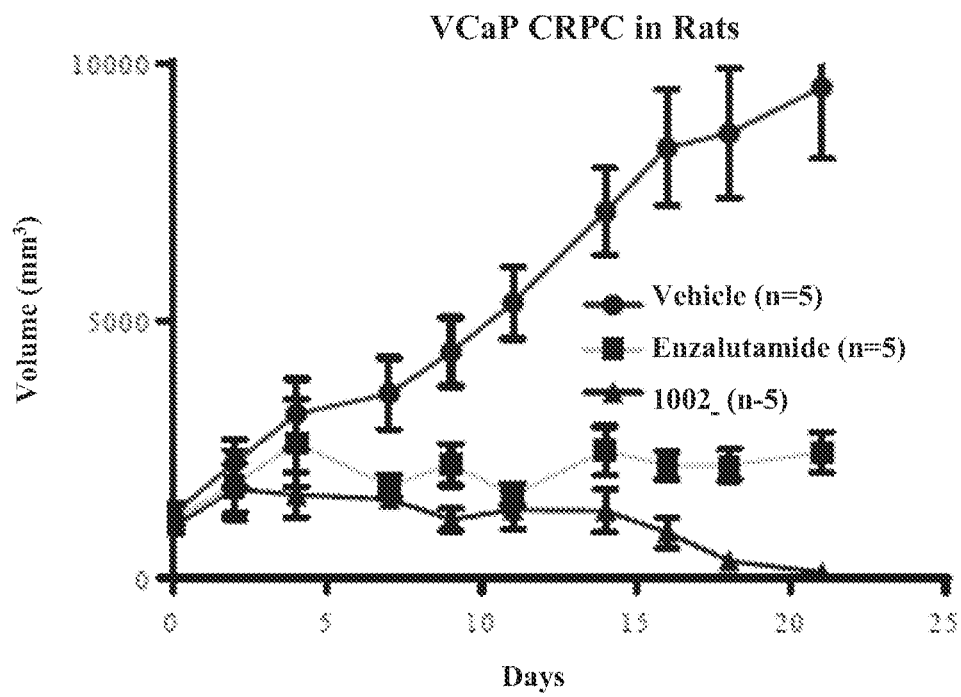
FIGS. 109A and 109B present VCaP CRPC data in castrated animals. Tumors of animals treated with 1002 showed complete tumor regression, while tumors of animals treated with enzalutamide showed tumor growth inhibition.
Figure 109B:
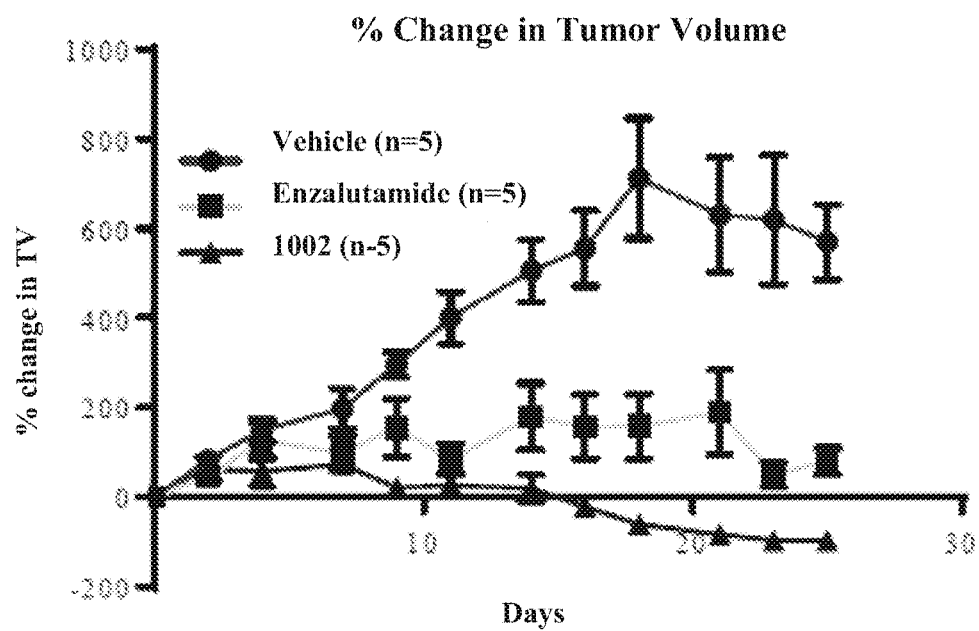
Figure 110:
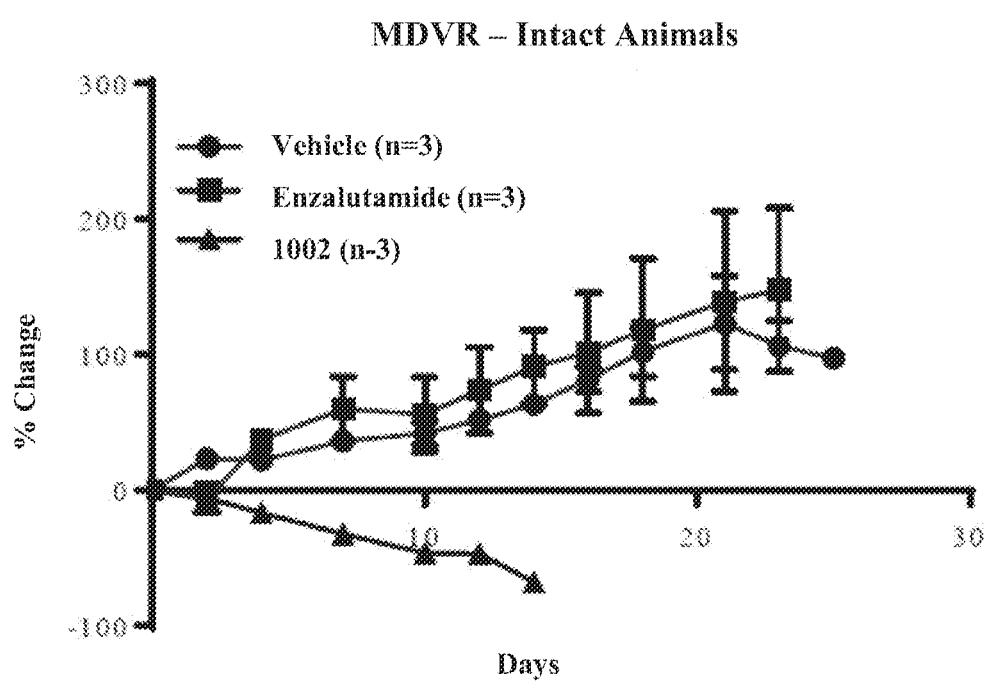
FIG. 110 demonstrate first evidence of an AR antagonist inhibiting tumor growth in intact animals.

When comparing the % change in tumor volume of MDVR xenografts in FIGS. 109A and 109B (CRPC—i.e., animals castrated and tumors allowed to re-grow before treatment) vs. FIG. 110 (animals left intact and treated) it can be seen that the tumors of animals treated with 1002 showed significantly slower growth, while tumors of animals treated with enzalutamide showed resistance. FIG. 110 demonstrated a first evidence of an AR antagonist inhibiting tumor growth in intact animals.

As can be seen, although the response was good in both castrated and intact animals, the regression only occurs after ~25 days in CRPC vs. immediately in intact animals. This makes no sense if the SARD compounds are competing for binding to AR with T/DHT in intact animals, as this should lessen or prevent efficacy. (Perhaps the allosteric binding site is higher affinity for 034 (and presumably other SARDs) in agonist conformation of the AR.

Example 53

Raman Studies for SARDs Binding to AF-1

Raman Spectroscopy

A Horiba system-Raman Spectrometer Xplore-coupled to 638 nm laser was used to measure Raman spectra of the samples. The samples were prepared on the aluminum mirrors through casting the solution of the materials and drying on the rotating (400 rpm) spin-coater for about 30 min. Next samples, we place in the vacuum oven to dry at room temperature. The recorded Raman spectra were fitted using a Gaussian function from where the peak position was determined.

Theoretical Predictions

Theoretical calculations are used to predict change in electron density to unravel type and strength of possible drug-amino acid interactions. The theoretical approach used is based on the density functional tight binding (DFTB) framework to describe the electronic structure. This is an approximate density functional theory in which only valence electrons are treated quantum mechanically while all core electrons and nuclei are treated via a pairwise interatomic repulsive potential $E_{rep}$.

$$E = \sum_i 2f_i \langle \phi_i | H_{core} | \phi_i \rangle + \frac{1}{2} \sum_{A,B}^{Atom} \gamma^{AB} \Delta q^A \Delta q^B + \sum_{A>B}^{Atom} E_{rep}^{AB}$$

where $f_i$ is an occupation number (typically 0 or 1) and i runs over all molecular orbitals. The first term describes interaction of valence electrons with core ions (nuclei and core electrons). The second term is responsible for electron-electron interaction. Symbols $\Delta q^A$ and $\gamma^{AB}$ are, respectively, a charge at center A and a chemical hardness' based parameter depending on interatomic distance that describes electron-electron interactions between centers A and B. The last term describes interaction between core ions obtained from a fit [1-2]. The DFTB method fills the gap between classical force fields and density functional theory. Importantly for the present project, is about 1000 times computationally cheaper than density functional theory. The main reason for low computational cost due facts that (a) only valence electrons are considered while core electrons are neglected, (b) a minimal basis set is used (Slater basis), (c) only pair-integrals are used in calculations. A consequence of (a) and (b) is that for a given molecular system all matrices are 5-10 times smaller. As a consequence of (c) the cost of formation of all matrices is significantly lower than in DFT. Overall this savings in computational time allows treating realistic sizes of systems as is required for the present study.

In the present study the interaction between 1002 or 11 and different amino acids was studied.

Results and Discussion

It is well-known that, establishing the interaction between the drug molecules and protein whether it is intramolecular hydrogen bonding or van der Waals interactions always leads to a change of electronic structure of reactants. The latter can be followed by Raman spectroscopy. Raman spectrum of protein contains very well pronounced peak at ~1650 cm$^{-1}$ which corresponds to in plane stretch of C=O bonds. This peak corresponds to so-called Amide I band due to the formation of secondary structure in protein. When 1002 were mixed with AF-1, we observed a red shift in the position of this peak. The obtained significant shift of ~10 cm$^{-1}$ suggests that an 1002 addition leads to a change in electron distribution in AF-1 which is likely due to their interaction. From literature, shift in band associated with the stretch of C=O bond is usually associated with formation of hydrogen bonds.

Figure 106:
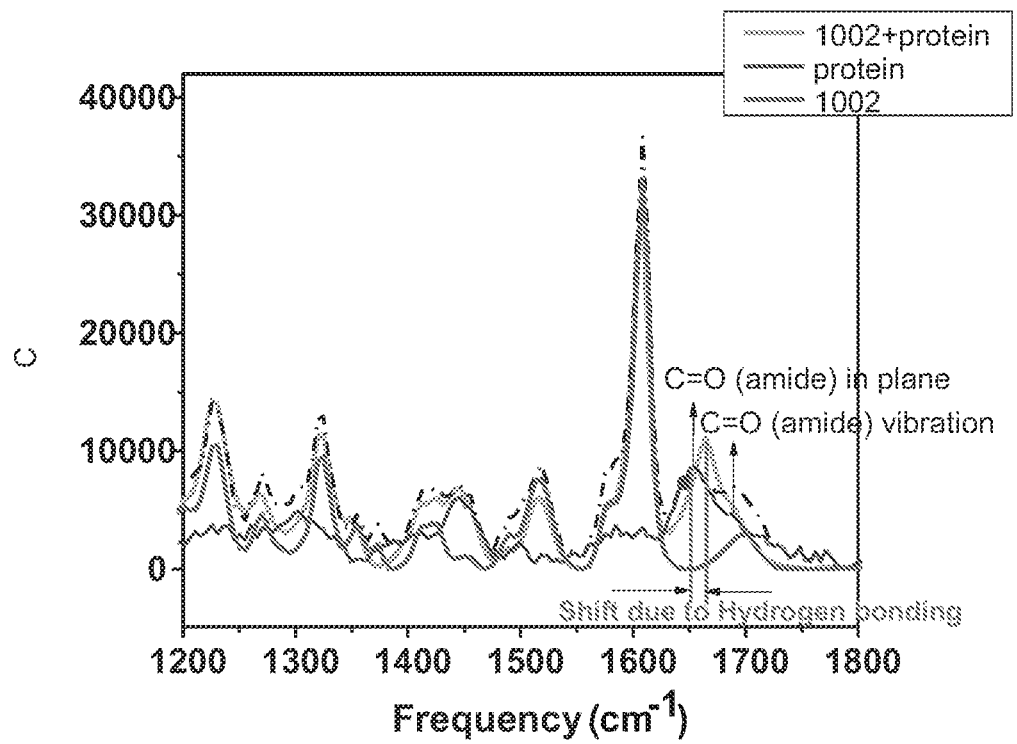
FIG. 106 provides tip-Enhanced Raman Spectroscopy (TERS) with compound 1002.
Figure 107A:
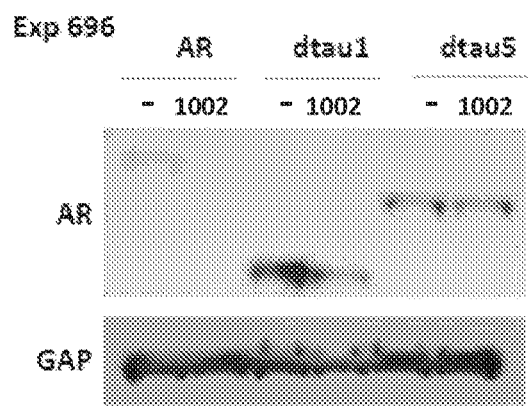
FIG. 107A-107D.
Figure 107B:
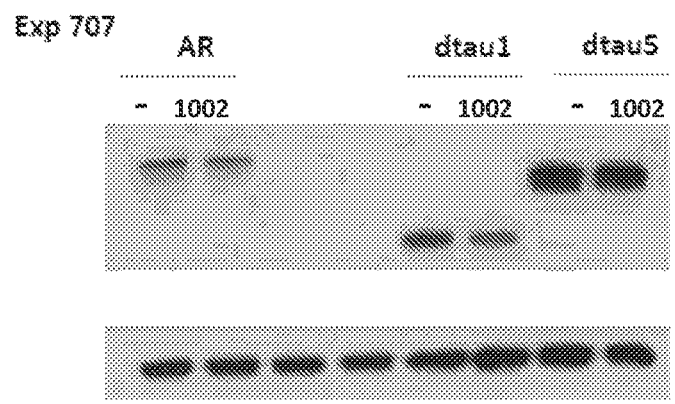
Figure 107C:
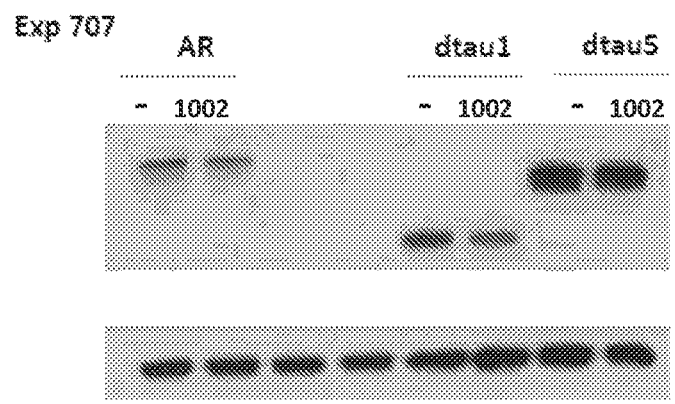
Figure 107D:
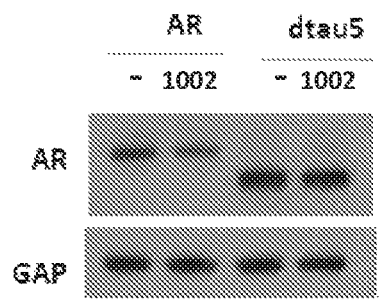
Figure 107E:
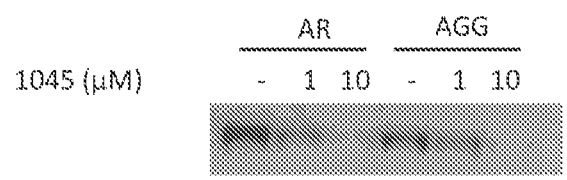
FIG. 107E is a chimeric domain experiment that demonstrates degradation with triazole SARD (monocyclic) 1045 in hAR (full length) and AGG chimeric constructs, demonstrating that the triazole template also relies on the NTD of AR to degrade AR.
Figure 107F:
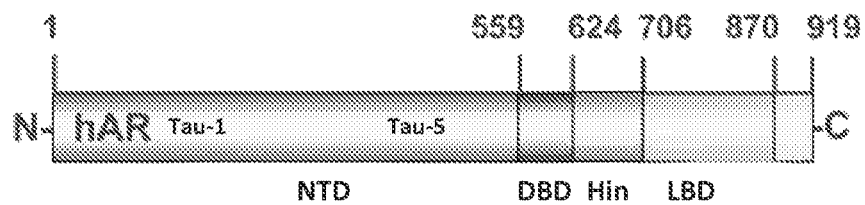
FIG. 107F is a domain map of the full length human androgen receptor (hAR). The relative locations of Tau-1 and Tau-5 in the N-terminal domain (NTD), the DNA binding domain (DBD), hinge region (Hin), and ligand binding domain (LBD) are indicated on the domain map. All FDA approved pharmacotherapeutics binding competitively with testosterone to the LBD. The SARDs of this invention in some cases bind to LBD but additionally appear to bind to a previously untargeted binding site in the NTD. Evidence suggests that Tau-5 is sufficient to bind the SARDs of this invention.
Figure 108:
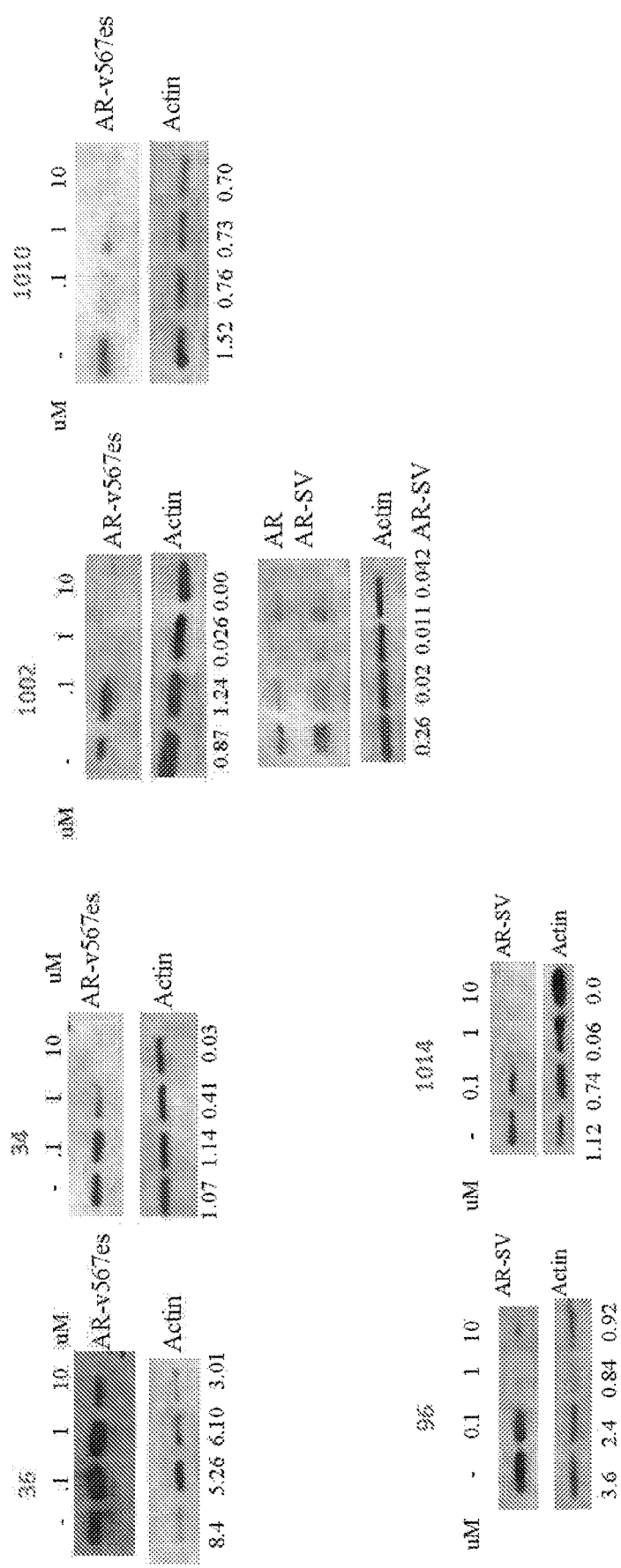
FIG. 108 demonstrates six example wherein AR SV degradation properties with diverse structure SARD compounds (at about 1 µM). Each of the compounds, degrade AR SV (which all lack LBD) when the AR SV is expressed alone, i.e., in the absence of the full length (FL) AR. When the AR SV is V567es as expressed in D567es cells, then the AR SV is expressed alone (whereas AR-SV in 22RV1 is expressed in combination with FL AR). This suggests that if we see AR SV degradation in D567es cells, then it is cannot be mediated by the binding of LBD in full-length (FL) AR via heterodimerization between FL and SV. Accordingly, NTD-dependent SARD activity and NTD-dependent ubiquitination of AR with the compounds of diverse structural templates, it is concluded that AR SV degradation is due to binding of the AR SV within the NTD.

To understand the nature and strength of this interaction further we performed DFTB theoretical calculations of electron density. DFTB calculations revealed that there are two possible isomeric structures of 1002 which is determined by cis or trans configurations of C=O and N—H groups in its structure. However, at room temperature the most stable configuration is trans and transition to cis configuration is unlikely due to the high energy barrier (~8 eV). In trans configuration 1002 can form one hydrogen bond with amino acids. Hydrogen bonds formed between C=O on 1002 site and —OH group of glycine. The same carbonyl group in 1002 structure participates in formation of hydrogen bonds with other amino acids. Since carbonyl group participates in formation of each hydrogen bonds its vibration should be the most affected. Thus, the selective red shift of C=O bond observed in the Raman experiment can be directly related to formation of hydrogen bond. To understand strength of interactions between 1002 and different amino acids, the binding energies for 1002 and individual amino acids were calculated and results are presented in the table in FIG. 106. From Table, among all amino acids 1002 strongly interacts with serine, tyrosine, and phenylalanine.

Figure 111A:
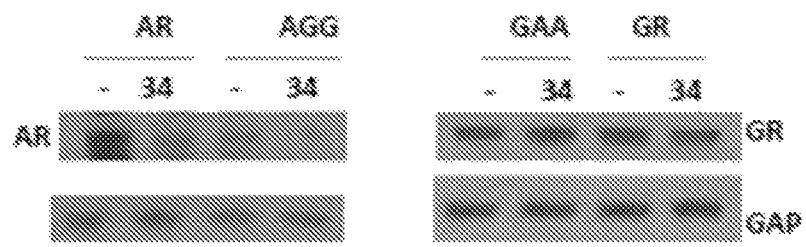
FIGS. 111A-111C demonstrate that NTD of AR is required for AR degradation by SARD. Compound 1002 (=compound 34 in Figures) downregulated AR and AGG.
Figure 111B:
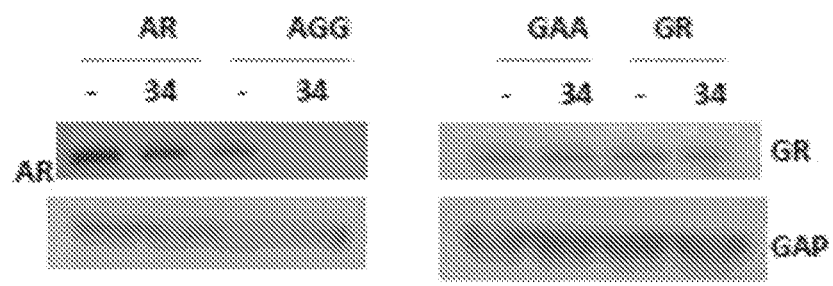
Figure 111C:
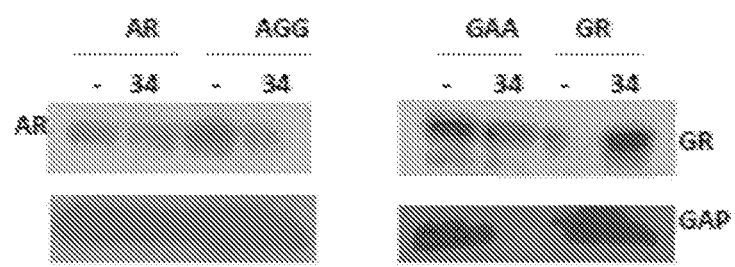
Figure 111D:
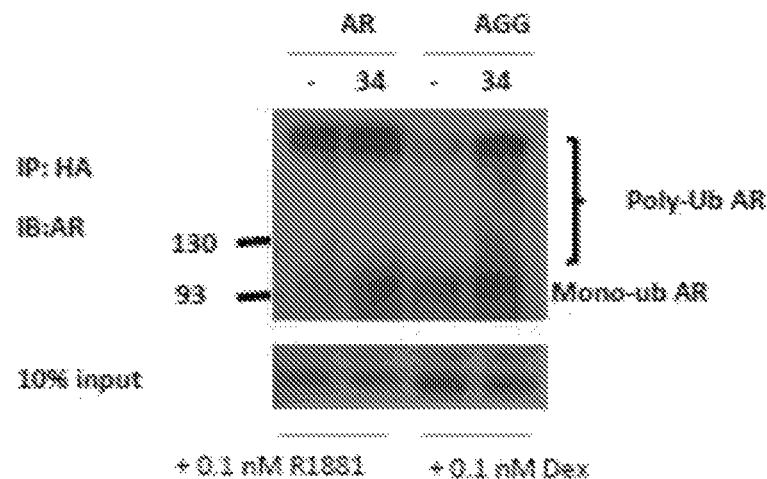
FIGS. 111D-111F demonstrate that AR-NTD is important for ubiquitination. COS cells were transfected with AR and GR, or the chimera and HA-tagged ubiquitin. Cells were treated 24 hours after transfection with 10 mM 1002 (=compound 34 in Figures) and 0.1 nM R1881. Two hours after the treatment, the cells were harvested, ubiquinon was Iped with HA tag and Western Bolot for AR or GR was performed.
Figure 111E:
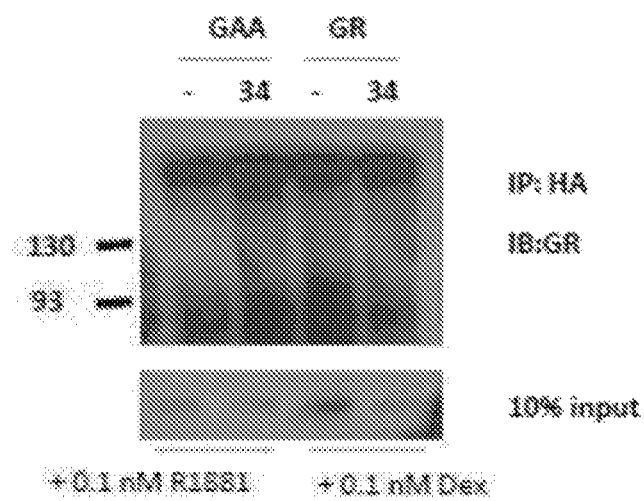
Figure 111F:
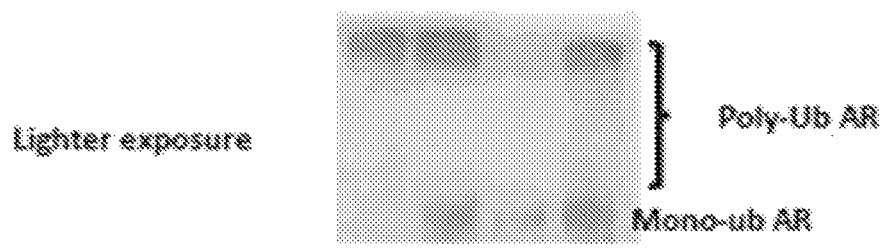
Figure 111G:
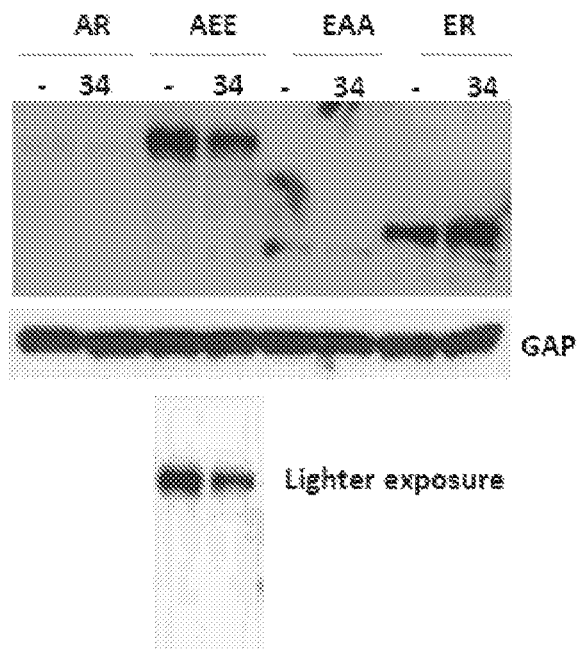
FIG. 111G: AR:ER Chimera confirms the observation made with AR:GR Chimera . . .
Figure 111H:
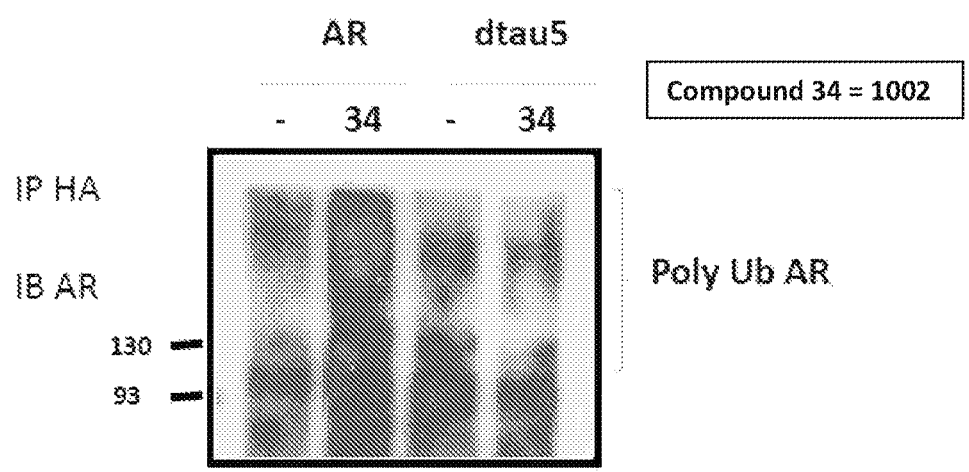
FIG. 111H: Tau 5 domain is important for ubiquitination with SARD.
Figure 112:
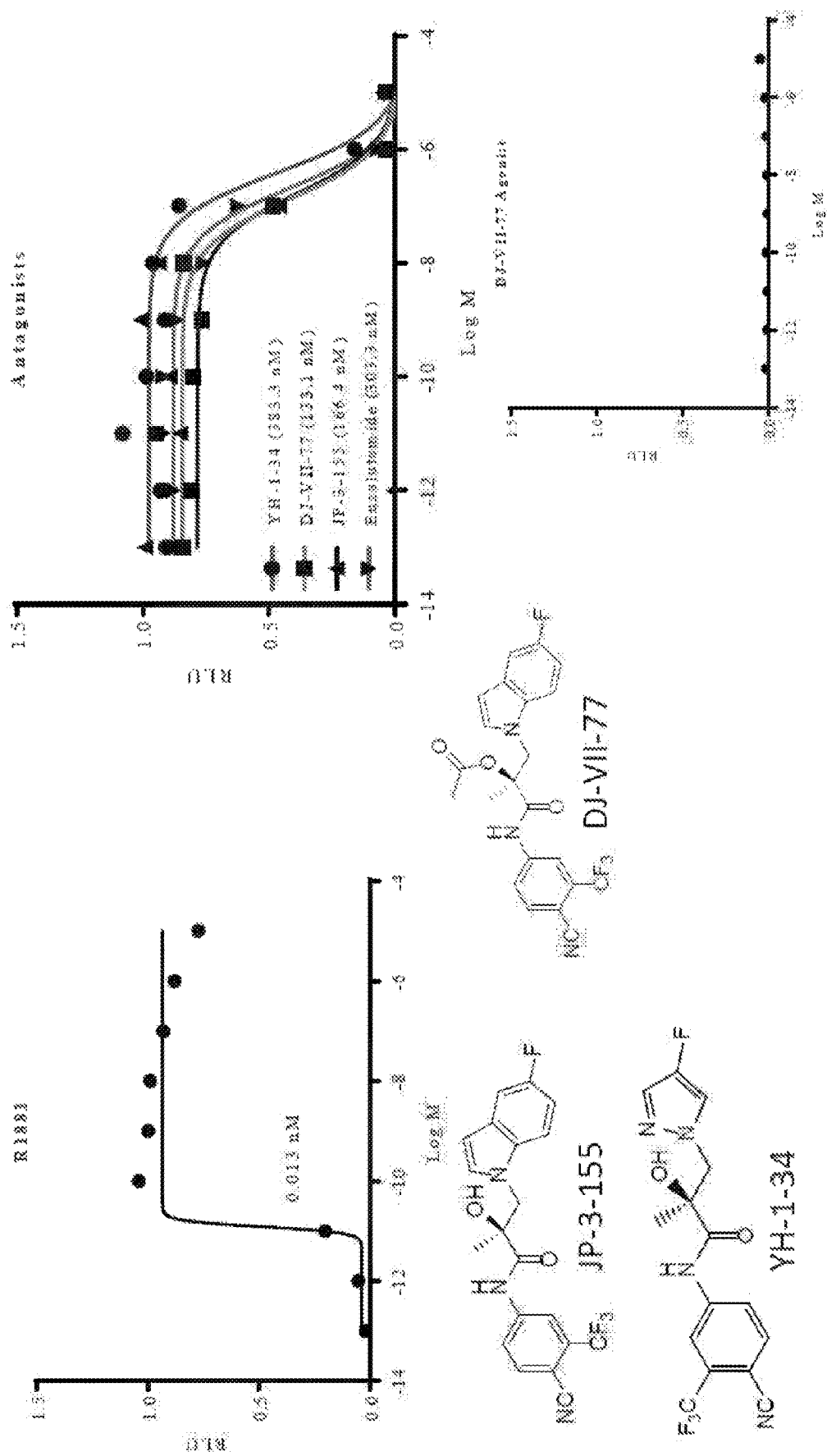
FIG. 112 demonstrates relative antagonist activity of SARD compounds.
Figure 113:
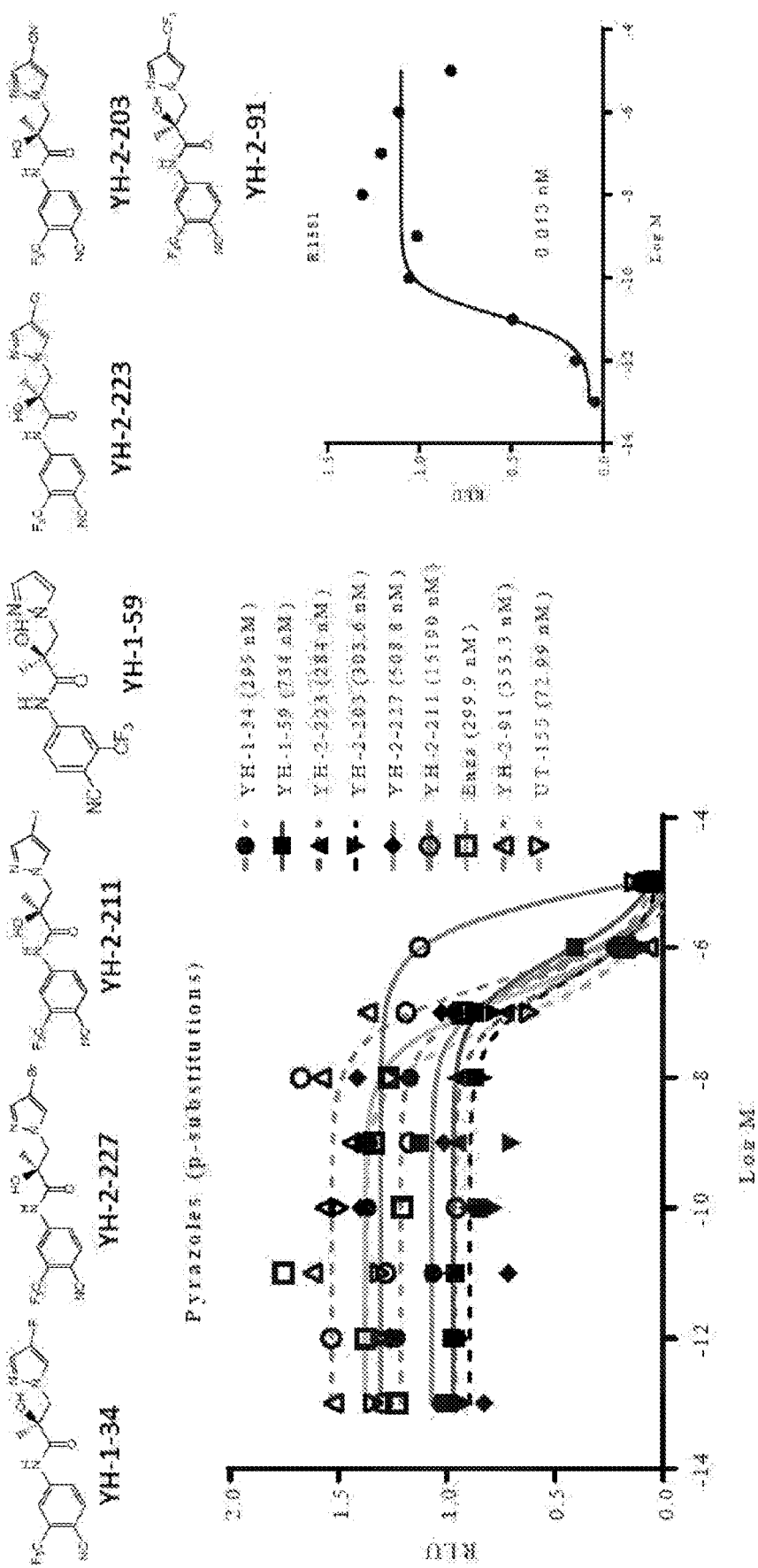
FIG. 113 demonstrates relative antagonist and SARD activity of SARD compounds.
Figure 114:
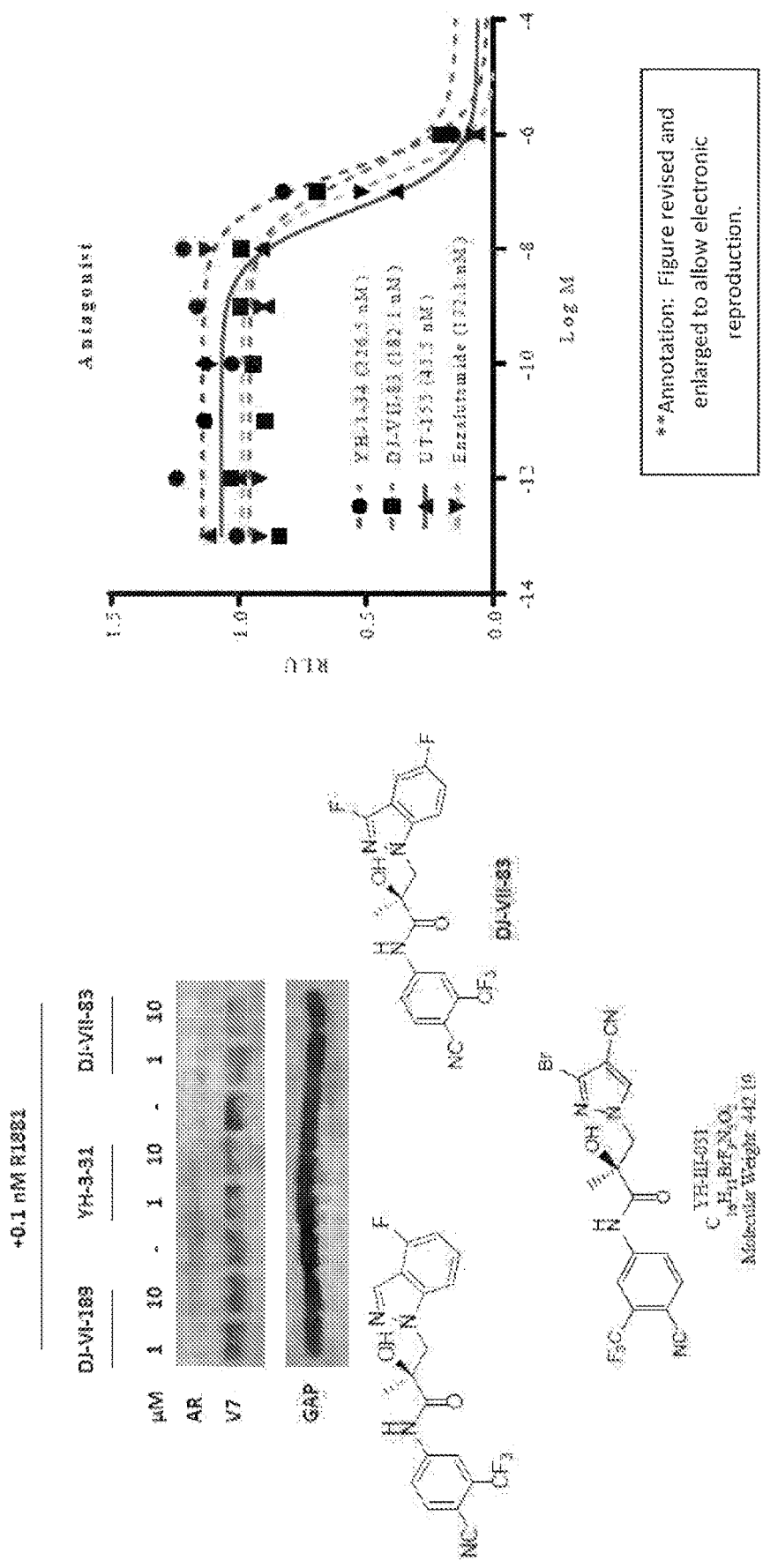
FIG. 114 demonstrates relative antagonist activity of SARD compounds.
Figure 115:
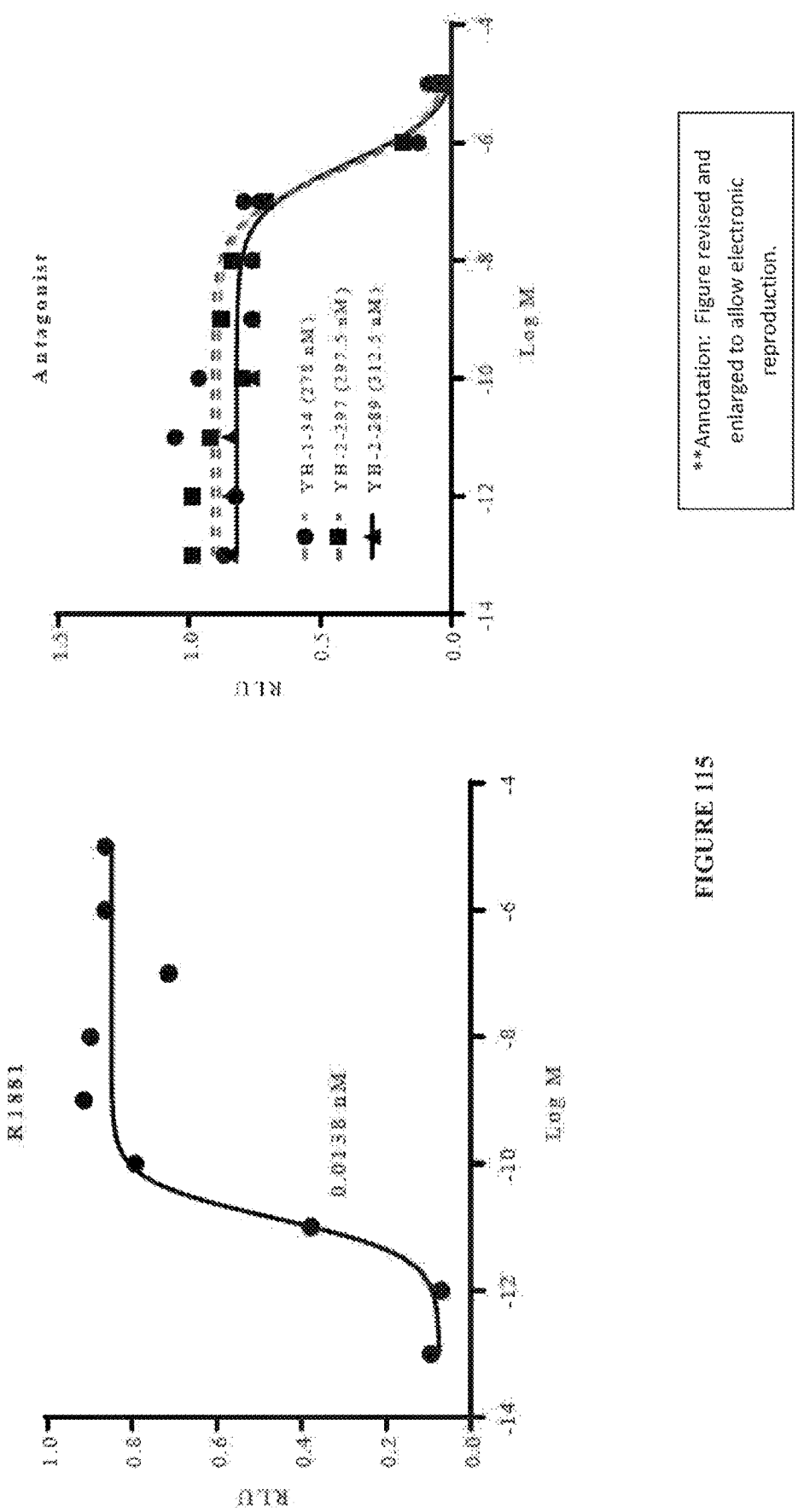
FIG. 115 demonstrates that S, R and racemate of 1002 (S isomer) and 1020 (R isomer) produce almost indistinguishable antagonist profiles, demonstrating that chirality of the tertiary chiral carbon is not significant and supportive of allosteric binding.

FIGS. 107A-107F and 111A-111G further establish the allosteric site in the NTD at the tau-5 domain of activation function-1 (AF-1), the selectivity of SARD activity for AR-NTD (FIGS. 111D-111F) constructs and the induction of ubiquitination of these constructs (AR/AGG) by 1002 treatment but no induction in GR (FIG. 111E) as confirmed using AR/ER chimera (see AEE lanes of FIG. 111G). Deletion mutations of AR were prepared in which Tau-1 and Tau-5 domains were removed. It was shown (FIG. 111H) that 1002 degrades hAR (no deletion) and hAR dtau 1 (Tau-1 deleted), but does not degrade hAR dtau5 in which the Tau-5 region of the NTD is deleted (see equivalent levels in right-most two lanes of each Western blot), indicating that Tau-5 is required for degradation of AR by 1002.

Another suggestion of non-competitive SARD activity is seen in in vitro experiments in which increasing R1881 does not decrease 1002 degradation, but may enhance it (slide 19).

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention

What is claimed is:

1. A method of treating prostate cancer in a subject in need thereof, comprising administering to the subject a therapeutically effective amount of a compound that binds to the N-terminal domain (NTD) of androgen receptor (AR), wherein the compound a selective androgen receptor degrader (SARD) compound represented by the structure of formula X(1):

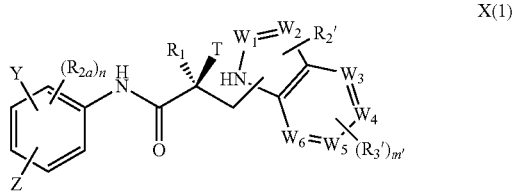

wherein $W_1$ and $W_2$ are each independently selected from N or CH;

W3, W4, W5 and $W_6$ are each independently selected from CH or N;

wherein if any one of $W_1$, $W_2$, $W_3$, $W_4$, $W_5$, and $W_6$ is CH, then the H is optionally replaced with $R_4$, Q or $R_3$ in the respective position, and if any one of $W_1$, $W_2$, $W_3$, $W_4$, $W_5$, and $W_6$ is not CH, then the respective position is unsubstituted;

T is H, OH, OR, OCOR, $CH_3$, $NHCOCH_3$, NHCOR or

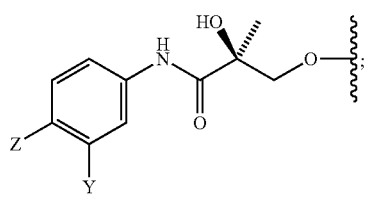

Z is H, $NO_2$, CN, halide, COOH, COR, NHCOR or CONHR;

Y is H, $CF_3$, F, I, Br, Cl, CN, $Sn(R)_3$, $C(R)_3$ or Y and Z form a 5 to 8 membered fused ring;

R is H, alkyl, haloalkyl, alcohol, $CH_2CH_2OH$, $CH_2F$, $CHF_2$, $CF_3$, $CF_2CF_3$, $CH_2Cl$, $CH_2CH_2Cl$, aryl, phenyl, F, Cl, Br, I, alkenyl or OH;

$R_1$ is H, $CH_3$, $CH_2F$, $CHF_2$, $CF_3$, $CH_2CH_3$, or $CF_2CF_3$;

$R_{2a}$, is hydrogen, halogen, CN, $NO_2$, COOH, COOR, COR, NHCOR, CONHR, OH, OR, SH, SR, $NH_2$, $NHR$, $NR_2$, $C_1$-$C_{12}$-alkyl, $C_1$-$C_{12}$-haloalkyl, O—$C_1$-$C_{12}$-alkyl, O—$C_1$-$C_{12}$-haloalkyl, $SO_2$-aryl, $SO_2$-phenyl, CO-aryl, arylalkyl, benzyl, aryl, or $C_3$-$C_7$-cycloalkyl;

Q is hydrogen, F, Cl, Br, I, $CF_3$, CN, $NO_2$, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;

$R_3$, and $R_4$, are independently selected from hydrogen, F, Cl, Br, I, $CF_3$, CN, $NO_2$, $NH_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, N(R)2, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;

n is an integer 1, 2, or 3; and m is an integer 1, 2, or 3;

or its isomer, pharmaceutically acceptable salt, pharmaceutical product, polymorph, hydrate or any combination thereof.

2. The method of claim 1, wherein the prostate cancer is advanced prostate cancer, castration resistant prostate cancer (CRPC), metastatic CRPC (mCRPC), nonmetastatic CRPC (nmCRPC), high-risk nmCRPC or any combination thereof.

3. The method of claim 1, wherein the compound is a selective androgen receptor degrader compound represented by the structure of formula XVIIIa or its optical isomers:

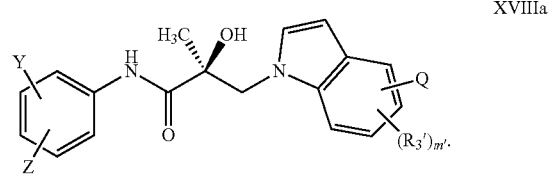

4. The method of claim 1, wherein the compound is a selective androgen receptor degrader compound represented by the following structure:

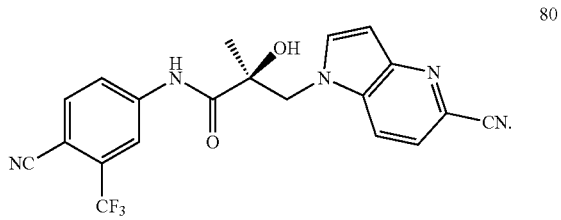 [SMILES: C[C@](O)(Cn1ccc2nc(C#N)ccc21)C(=O)Nc1ccc(C#N)c(C(F)(F)F)c1]

5. A method of adjuvant therapy of prostate cancer (PCa), and/or of neoadjuvant therapy of prostate cancer (PCa), and/or of treatment of early disease prostate cancer (PCa), and/or of treatment of prostate cancer (PCa) in intact males, and/or of treatment of prostate cancer (PCa) prior to androgen deprivation therapy (ADT) or castration, and/or of first line therapy of PCa, comprising administering to a subject in need thereof, a therapeutically effective amount of a compound that binds to the N-terminal domain (NTD) of androgen receptor (AR), wherein the compound a selective androgen receptor degrader (SARD) compound represented by the structure of formula XII or its optical isomers:

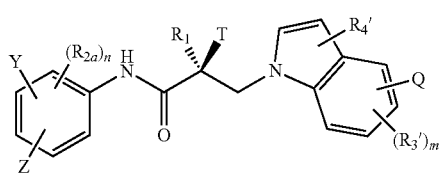

wherein

T is H, OH, OR, OCOR, $CH_3$, $NHCOCH_3$, or NHCOR;

Z is H, $NO_2$, CN, halide, COOH, COR, NHCOR or CONHR;

Y is H, $CF_3$, F, I, Br, Cl, CN, $Sn(R)_3$, $C(R)_3$ or Y and Z form a 5 to 8 membered fused ring;

R is H, alkyl, haloalkyl, alcohol, $CH_2CH_2OH$; $CH_2F$, $CHF_2$, $CF_3$, $CF_2CF_3$, $CH_2Cl$, $CH_2CH_2Cl$, aryl, phenyl, F, Cl, Br, I, alkenyl or OH;

$R_1$ is H, $CH_3$, $CH_2F$, $CHF_2$, $CF_3$, $CH_2CH_3$, or $CF_2CF_3$;

$R_2$, is hydrogen, halogen, CN, $NO_2$, COOH, COOR, COR, NHCOR, CONHR, OH, OR, SH, SR, $NH_2$, NHR, $NR_2$, $C_1$-$C_{12}$-alkyl, $C_1$-$C_{12}$-haloalkyl, O—$C_1$-$C_{12}$-alkyl, O—$C_1$-$C_{12}$-haloalkyl, $SO_2$ aryl, $SO_2$-phenyl, CO-aryl, arylalkyl, benzyl, aryl, or $C_3$-$C_7$-cycloalkyl;

Q is hydrogen, F, Cl, Br, I, $CF_3$, CN, $NO_2$, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;

$R_3$ is hydrogen, F, Cl, Br, I, $CF_3$, CN, $NO_2$, $NH_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;

$R_4$, is hydrogen, F, Cl, Br, I, $CF_3$, CN, $NO_2$, $NH_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;

n is an integer 1, 2, or 3; and m is an integer 1, 2, or 3;

or its isomer, pharmaceutically acceptable salt, pharmaceutical product, polymorph, hydrate or any combination thereof.

6. The method of claim 5, wherein the prostate cancer is advanced prostate cancer, castration resistant prostate cancer (CRPC), metastatic CRPC (mCRPC), nonmetastatic CRPC (nmCRPC), high-risk nmCRPC or any combination thereof.

7. A method of adjuvant therapy of prostate cancer (PCa), and/or of neoadjuvant therapy of prostate cancer (PCa), and/or of treatment of early disease prostate cancer (PCa), and/or of treatment of prostate cancer (PCa) in intact males, and/or of treatment of prostate cancer (PCa) prior to androgen deprivation therapy (ADT) or castration, and/or of first line therapy of PCa, comprising administering to a subject in need thereof, a therapeutically effective amount of a selective androgen receptor degrader (SARD) compound represented by the structure of formula XXa:

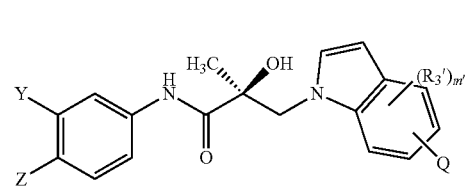

wherein

Y is H, $CF_3$, F, I, Br, Cl, CN, $C(R)_3$ or Y and Z form a 5 to 8 membered fused ring;

Z is H, $NO_2$, CN, halide, COOH, COR, NHCOR, CONHR;

R is H, alkyl, alkenyl, haloalkyl, alcohol, $CH_2CH_2OH$, $CF_3$, $CH_2Cl$, $CH_2CH_2Cl$, aryl, phenyl, F, Cl, Br, I, alkenyl or OH;

Q is hydrogen, F, Cl, Br, I, $CF_3$, CN, $NO_2$, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;

$R_{3'}$ is hydrogen, F, Cl, Br, I, $CF_3$, CN, $NO_2$, $NH_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, NHCSCF₃, NHCSR, NHSO₂CH₃, NHSO₂R, OR, COR, OCOR, OSO₂R, SO₂R, SR, NCS, SCN, NCO or OCN; and M' is an integer 1, 2, or 3;

or its isomer, pharmaceutically acceptable salt, pharmaceutical product, polymorph, hydrate or any combination thereof.

8. The method of claim 5, wherein the compound is:

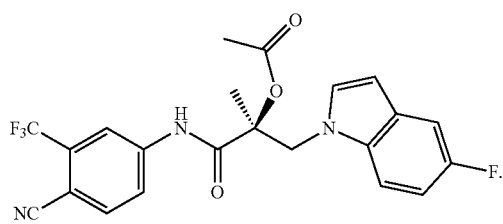

46

9. The method of claim 5, wherein the compound is selected from the group consisting of:

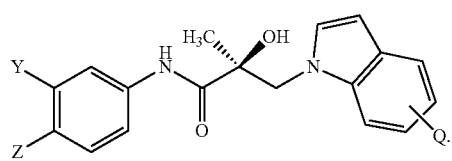

XXIIa

10. The method of claim 7, wherein the compound is a selective androgen receptor degrader compound represented by the following structures:

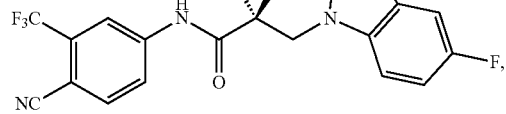

11

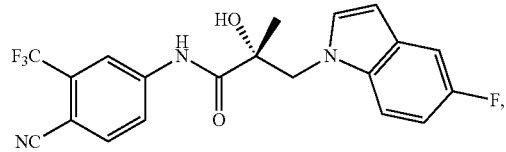

11R

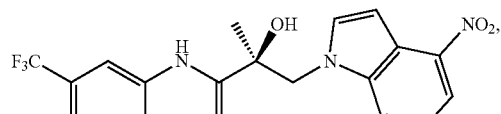

12

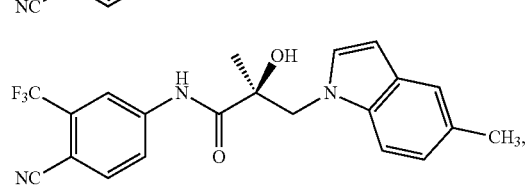

13

-continued

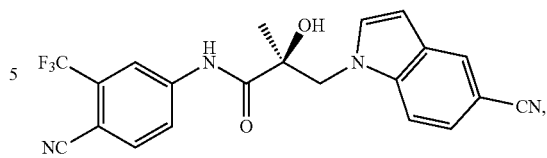

14

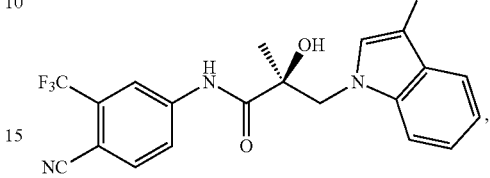

15

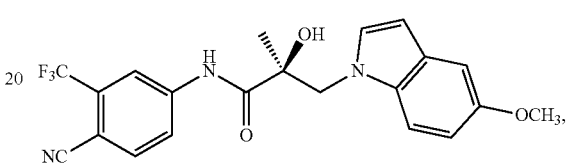

16

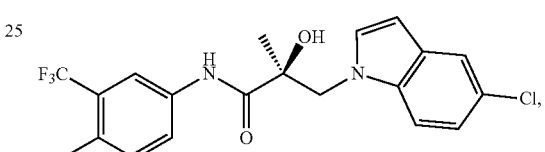

17

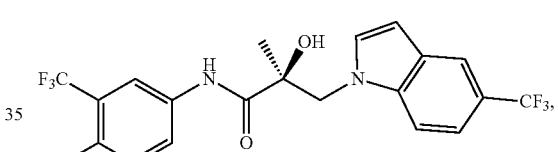

18

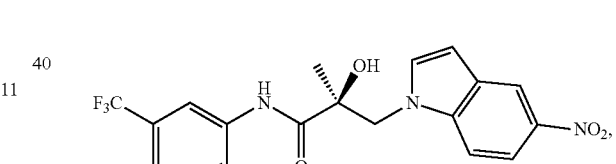

19

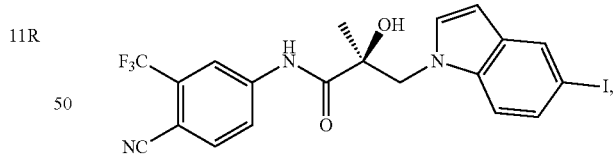

21

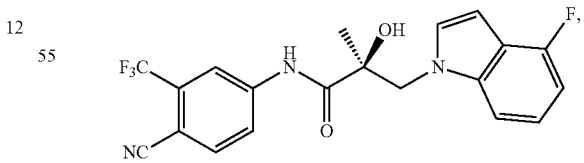

22

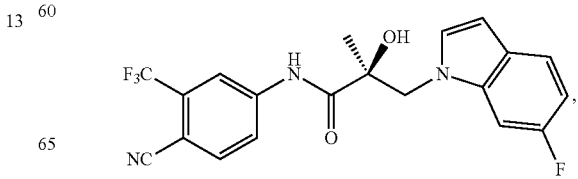

23

-continued

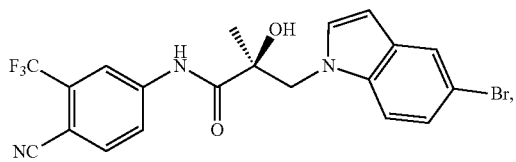
24

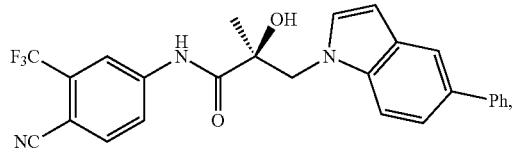
25

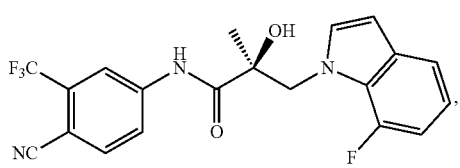
26

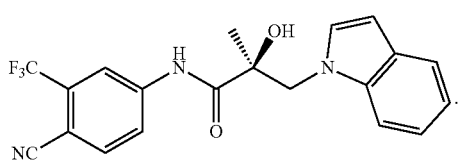
27

11. The method of claim 1, wherein the compound is selected from the group consisting of:

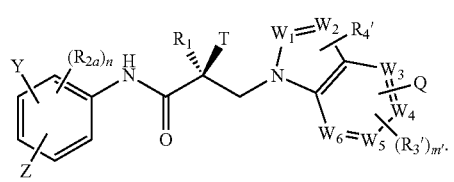
Xa(1)

12. The method of claim 1, wherein the compound is selected from the group consisting of:

Xb(1)

13. The method of claim 1, wherein the compound is selected from the group consisting of:

Xd(1)

14. The method of claim 1, wherein the compound is selected from the group consisting of:

Xe(1)

15. The method of claim 1, wherein the compound is:

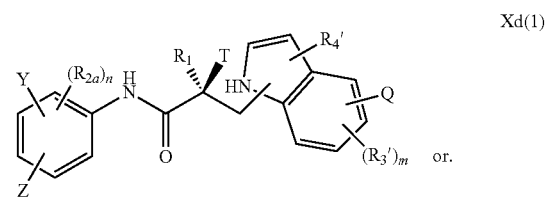

* * * * *